United States Patent
Adolfsson et al.

(10) Patent No.: US 10,836,817 B2
(45) Date of Patent: Nov. 17, 2020

(54) ANTI-TAU ANTIBODIES AND METHODS OF USE

(71) Applicants: AC Immune SA, Lausanne (CH); Genentech, Inc., South San Francisco, CA (US)

(72) Inventors: Oskar Adolfsson, Bercher (CH); Kristin Ruth Wildsmith, Half Moon Bay, CA (US); Marcel Van Der Brug, Daly City, CA (US); Andreas Muhs, Cugy (CH)

(73) Assignees: AC Immune SA, Lausanne (CH); Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/420,678

(22) Filed: May 23, 2019

(65) Prior Publication Data

US 2019/0367592 A1    Dec. 5, 2019

Related U.S. Application Data

(63) Continuation of application No. PCT/US2017/064855, filed on Dec. 6, 2017.

(60) Provisional application No. 62/431,183, filed on Dec. 7, 2016.

(51) Int. Cl.
*C07K 16/18* (2006.01)
*A61K 45/06* (2006.01)

(52) U.S. Cl.
CPC .............. *C07K 16/18* (2013.01); *A61K 45/06* (2013.01); *C07K 2317/24* (2013.01); *C07K 2317/31* (2013.01); *C07K 2317/56* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,926,974 B2 | 1/2015 | Griswold-Prenner et al. | |
| 8,940,272 B2 | 1/2015 | Nitsch et al. | |
| 8,980,270 B2 | 3/2015 | Griswold-Prenner et al. | |
| 8,980,271 B2 | 3/2015 | Griswold-Prenner et al. | |
| 9,051,367 B2 | 6/2015 | Griswold-Prenner et al. | |
| 9,447,179 B2 | 9/2016 | Winderickx et al. | |
| 9,447,180 B2 | 9/2016 | Griswold-Prenner et al. | |
| 9,505,826 B2 | 11/2016 | Wilson et al. | |
| 9,567,395 B2 | 2/2017 | Griswold-Prenner et al. | |
| 9,598,484 B2 | 3/2017 | Weinreb et al. | |
| 9,605,059 B2 | 3/2017 | Nitsch et al. | |
| 9,777,058 B2 | 10/2017 | Griswold-Prenner et al. | |
| 2014/0056901 A1 | 2/2014 | Agadjanyan et al. | |
| 2014/0086921 A1 | 3/2014 | Griswold-Prenner et al. | |
| 2015/0183855 A1 | 7/2015 | Diamond et al. | |
| 2016/0031976 A1 | 2/2016 | Seubert et al. | |
| 2016/0102138 A1 | 4/2016 | Iqbal et al. | |
| 2016/0289309 A1 | 10/2016 | Griswold-Prenner et al. | |
| 2016/0347804 A1 | 12/2016 | Griswold-Prenner et al. | |
| 2017/0058024 A1 | 3/2017 | West et al. | |
| 2017/0355756 A1* | 12/2017 | Julien ................... C07K 16/18 |

FOREIGN PATENT DOCUMENTS

| | | |
|---|---|---|
| RU | 2299889 C2 | 5/2007 |
| WO | WO 96/20218 A1 | 7/1996 |
| WO | WO 02/062851 A1 | 8/2002 |
| WO | WO 2002/060919 A2 | 8/2002 |
| WO | WO 2008068048 * | 6/2008 |
| WO | WO 2010/115843 A2 | 10/2010 |
| WO | WO 2010/142423 A2 | 12/2010 |
| WO | WO 2012/045882 A2 | 4/2012 |
| WO | WO 2012/049570 A1 | 4/2012 |
| WO | WO 2012/083370 A1 | 6/2012 |
| WO | WO 2012/106363 A2 | 8/2012 |
| WO | WO 2013/007839 A1 | 1/2013 |
| WO | WO 2013/041962 A1 | 3/2013 |
| WO | WO 2013/050567 A1 | 4/2013 |
| WO | WO 2013/096380 A2 | 6/2013 |
| WO | WO 2013/151762 A1 | 10/2013 |
| WO | WO 2014/008404 A1 | 1/2014 |
| WO | WO 2014/028777 A2 | 2/2014 |
| WO | WO 2014/031694 A2 | 2/2014 |
| WO | WO 2014/031697 A2 | 2/2014 |
| WO | WO 2014/059442 A2 | 4/2014 |
| WO | WO 2014/100600 A2 | 6/2014 |
| WO | WO 2014/105271 A1 | 7/2014 |
| WO | WO 2014/150877 A2 | 9/2014 |
| WO | WO 2014/165271 A2 | 10/2014 |
| WO | WO 2014/200921 A1 | 12/2014 |
| WO | WO 2015/081085 A2 | 6/2015 |
| WO | WO 2015/091656 A1 | 6/2015 |
| WO | WO 2015/122922 A1 | 8/2015 |
| WO | WO 2015/200806 A2 | 12/2015 |
| WO | WO 2016/055941 A1 | 4/2016 |
| WO | WO 2016/137811 A1 | 9/2016 |

(Continued)

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
Castillo-Carranza et al., "Tau aggregates as immunotherapeutic targets," Frontiers in Bioscience, Scholar, 5: 426-438 (2013).
Castillo-Carranza et al., "Passive Immunization with Tau Oligomer Monoclonal Antibody Reverses Tauopathy Phenotypes without Affecting Hyperphosphorylated Neurofibrillary Tangles," J. Neurosci., 34(12): 4260-4272 (2014).

(Continued)

*Primary Examiner* — Adam Weidner
(74) *Attorney, Agent, or Firm* — McNeill Baur PLLC

(57) ABSTRACT

The invention provides anti-Tau antibodies and methods of using the same.

22 Claims, 40 Drawing Sheets
Specification includes a Sequence Listing.

(56) References Cited

FOREIGN PATENT DOCUMENTS

| WO | WO 2016/137950 A1 | 9/2016 |
|---|---|---|
| WO | WO 2016/196726 A1 | 12/2016 |
| WO | WO 2016/201434 A2 | 12/2016 |
| WO | WO 2017/005732 A1 | 1/2017 |
| WO | WO 2017/005734 A1 | 1/2017 |
| WO | WO 2017/009308 A2 | 1/2017 |
| WO | WO 2017/191560 A1 | 11/2017 |
| WO | WO 2018/011073 A1 | 1/2018 |
| WO | WO 2018/106776 A2 | 6/2018 |
| WO | WO 2018/106781 A1 | 6/2018 |
| WO | WO 2018/183175 A1 | 10/2018 |

OTHER PUBLICATIONS

Chen et al., "Enhancement and destruction of antibody function by somatic mutation: unequal occurrence is controlled by V gene combinatorial associations," EMBO J., 14(12): 2784-2794 (1995).
Davidowitz et al., "Targeting tau oligomers for therapeutic development for Alzheimer's disease and tauopathies," Current Topics Biotech., 4: 47-64 (2008).
Esteves-Villanueva et al., "Electrochemical detection of anti-tau antibodies binding to tau protein and inhibition of GSK-3β-catalyzed phosphorylation," Analytical Biochemistry, 496: 55-62 (2015).
Garcia-Sierra et al., "Conformational changes and truncation of tau protein during tangle evolution in Alzheimer's disease," J. Alzheimer's Dis., 5: 65-77 (2003).
Ghoshal et al., "Conformational Changes Correspond to Impairments of Episodic Memory in Mild Cognitive Impairment and Alzheimer's Disease," Experimental Neurology, 177: 475-493 (2002).
Horowitz et al., "Early N-Terminal Changes and Caspase-6 Cleavage of Tau in Alzheimer's Disease," J. Neurosci., 24(36): 7895-7902 (2004).
Lee et al., "Antibody-Mediated Targeting of Tau In Vivo Does Not Require Effector Function and Microglial Engagement," Cell Reports, 16(6): 1690-1700 (2016).
Liu et al., "Profiling Murine Tau with 0N, 1N and 2N Isoform-Specific Antibodies in Brain and Peripheral Organs Reveals Distinct Subcellular Localization, with the 1N Isoform Being Enriched in the Nucleus," PLOS ONE, 8(12): e84849 (2013).
Notification of Transmittal of the International Search Report and the Written Opinion of the International Searching Authority, or the Declaration, for PCT/US2017/064869, dated Mar. 13, 2018 (15 pages).
Notification of Transmittal of the International Search Report and the Written Opinion of the International Searching Authority, or the Declaration, for PCT/US2017/064855, dated Aug. 20, 2018 (32 pages).
Notification of Transmittal of the International Search Report and the Written Opinion of the International Searching Authority, or the Declaration, for PCT/US2016/035409, dated Sep. 1, 2016 (14 pages).
Patterson et al., "Characterization of Prefibrillar Tau Oligomers in Vitro and in Alzheimer Disease," J. Biol. Chem., 286: 23063-23076 (2011).
Petry et al., "Specificity of Anti-Tau Antibodies when Analyzing Mice Models of Alzheimer's Disease: Problems and Solutions," PLOS ONE, 9(5) e94251 (2014).
Rosseels et al., "Tau Monoclonal Antibody Generation Based on Humanized Yeast Models," J. Biol. Chem., 290(7): 4059-4074 (2015).
Yanamandra et al., "Anti-Tau Antibodies that Block Tau Aggregate Seeding In Vitro Markedly Decrease Pathology and Improve Cognition In Vivo," Neuron, 80(2): 402-414 (2013).
C2n Diagnostics, "Press Releases: C2N Diagnostics Reports Phase 1 Study Results of C2N-8E12 (ABBV-8E12)—Anti-Tau Antibody—in Subjects with Progressive Supranuclear Palsy," retrieved from www.c2ndiagnostics.com/2016/12/c2n-diagnostics-reports-phase-1-study-results-of-c2n-8e12-abbv-8e12-anti-tau-antibody-in-subjects-with-progressive-supranuclear-palsy/, Dec. 9, 2016, 4 pages.
Colman, "Effects of amino acid sequence changes on antibody-antigen interactions," Research in Immunology, 145(1): 33-36 (1994).
Mariuzza et al., "The Structural Basis of Antigen-Antibody Recognition," Ann. Rev. Biophys. Biophys. Chem., 16: 139-159 (1987).
Notification of Transmittal of the International Search Report and the Written Opinion of the International Searching Authority, or the Declaration, for PCT/US2018/024300, dated Jun. 29, 2018 (15 pages).
Roitt et al., "Immunology" [in Russian], Moscow, "Mir", pp. 110-111 (2000), with translation (5 pages).
Rudikoff et al., "Single amino acid substitution altering antigen-binding specificity," Proc. Natl. Acad. Sci. USA, 78: 1979-1983 (1982).
Sakahara et al. "Effect of DTPA Conjugation on the Antigen Binding Activity and Biodistribution of Monoclonal Antibodies Against α-Fetoprotein," J Nucl Med, 26: 750-755 (1985).
Schroeder et al. "Tau-Directed Immunotherapy: A Promising Strategy for Treating Alzheimer's Disease and Other Tauopathies," J. Neuroimmune Pharmacol., 11(1): 9-25 (2015).
Singer et al., "Genes and Genomes" [in Russian], Moscow, "Mir", 1:63-64 (1998).
West et al.. "Preclinical and Clinical Development of ABBV-8E12, a Humanized Anti-Tau Antibody, for Treatment of Alzheimer's Disease and Other Tauopathies", J Prev. Alz. Dis., 4(4): 236-241 (2017).
Yu et al., "Developing Therapeutic Antibodies for Neurodegenerative Disease," Neurotherapeutics, 10(3): 459-472 (2013).

* cited by examiner

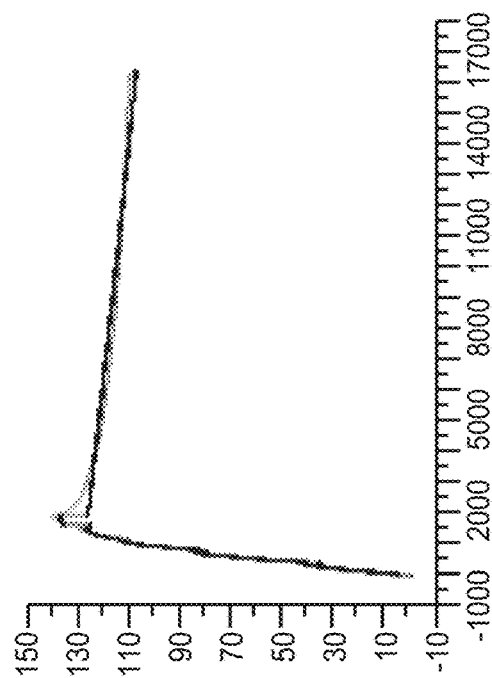
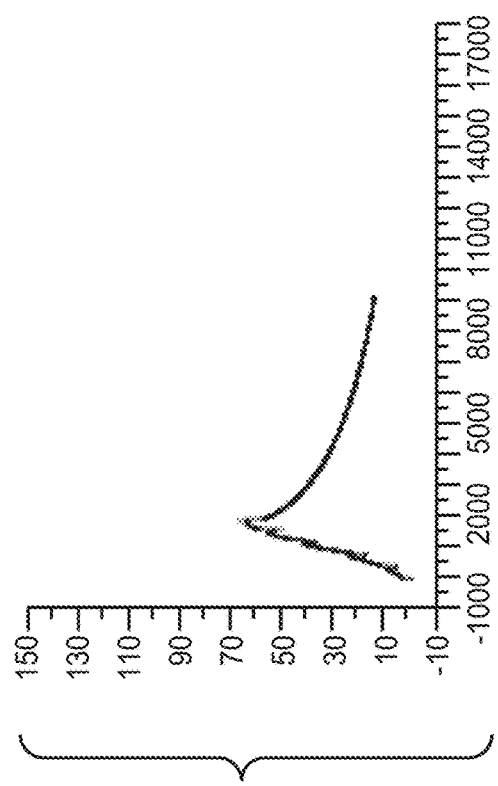
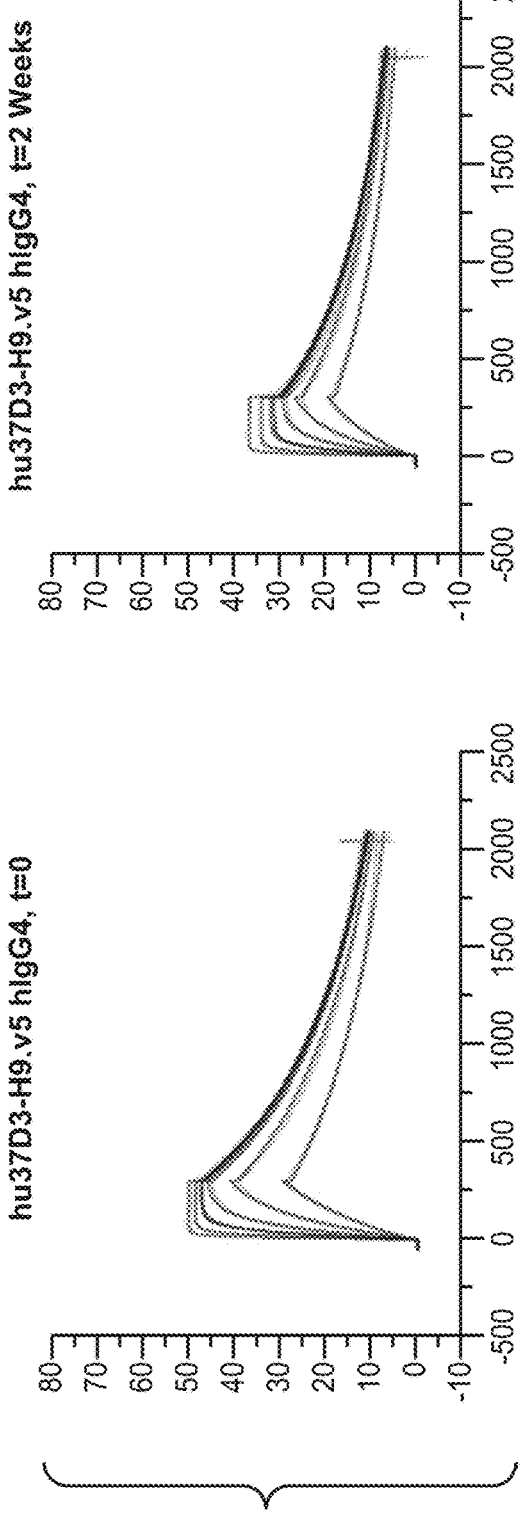
FIG. 5
FIG. 6

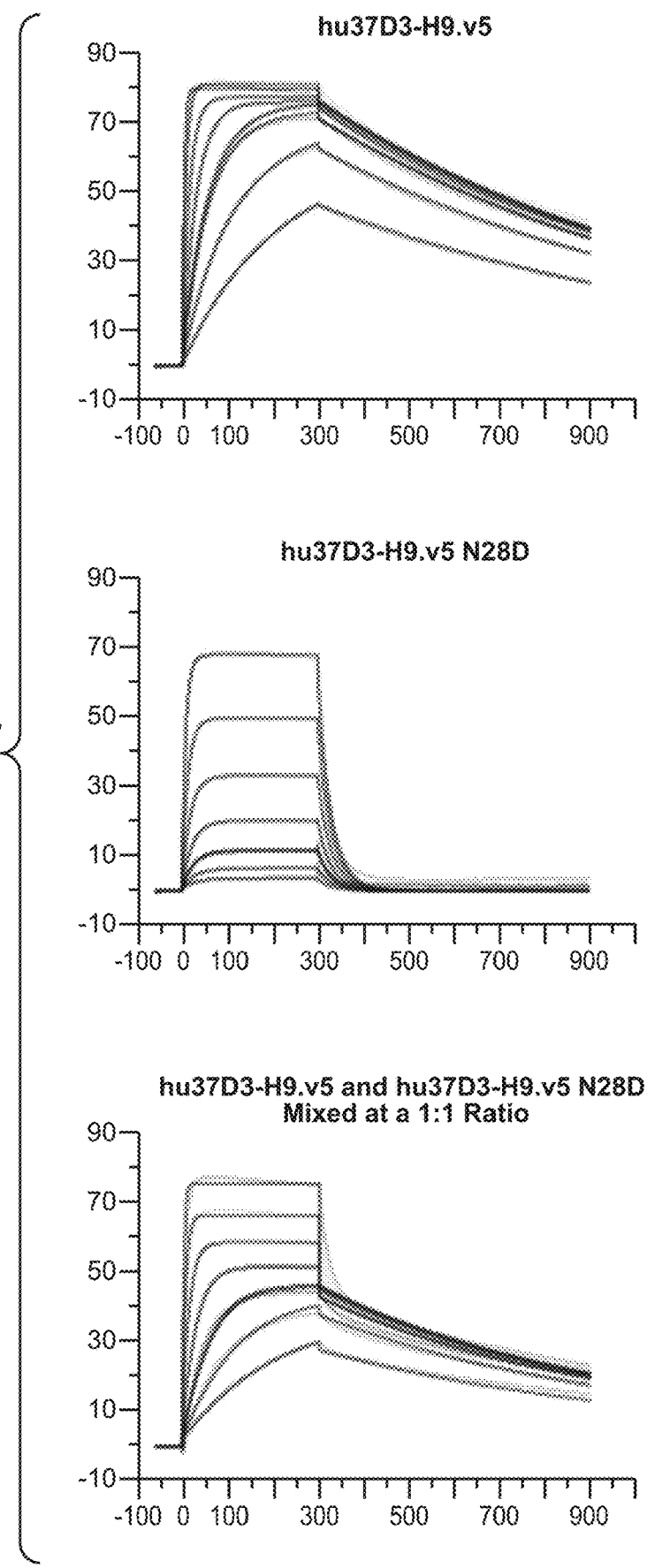

FIG. 8

| | |
|---|---|
| FIG. 8A | |
| FIG. 8B | |
| FIG. 8C | |
| FIG. 8D | |

FIG. 8A

| Antibody | KD (nM) | Stability Index | Chi2 < 10% Rmax and Normalized Rmax (Pre-stress) > 0.1? | 1 | 2 | 4 | 27D | 27E | 28 | 29 | 30 | 31 | 32 | 33 | 93 | SEQ ID: |
|---|---|---|---|---|---|---|---|---|---|---|---|---|---|---|---|---|
| Unstressed Control (mean, n=9) | 1.0 | 106% | Yes | E | D | L | H | S | N | G | N | T | Y | F | L | 350 |
| hu37D3-H9.v5 | 0.9 | 73% | Yes | E | D | L | H | S | N | G | N | T | Y | F | L | 351 |
| hu37D3-H9.v5.1 | 4.0 | 72% | Yes | E | D | L | H | S | N | A | N | T | Y | F | L | 352 |
| hu37D3-H9.v5.2 | 10.9 | 97% | Yes | E | D | L | H | S | S | G | N | T | Y | F | L | 353 |
| hu37D3-H9.v5.3 | 73.2 | 70% | - | E | D | L | H | S | D | G | N | T | Y | F | L | 354 |
| hu37D3-H9.v5.4 | 36.1 | 78% | - | E | D | L | H | S | Q | G | N | T | Y | F | L | 355 |
| hu37D3-H9.v5.5 | 64.5 | 75% | Yes | E | D | L | H | S | E | G | N | T | Y | F | L | 356 |
| hu37D3-H9.v5.6 | 36.6 | 67% | Yes | E | D | L | H | S | A | G | N | T | Y | F | L | 357 |
| hu37D3-H9.v5.7 | 13.0 | 67% | Yes | E | D | L | H | S | N | G | D | T | Y | F | L | 358 |
| hu37D3-H9.v5.8 | 2.2 | 90% | Yes | E | D | L | H | S | N | G | Q | T | Y | F | L | 359 |
| hu37D3-H9.v5.9 | 5.3 | 95% | Yes | E | D | L | H | S | N | G | E | T | Y | F | L | 360 |
| hu37D3-H9.v5.10 | 4.7 | 78% | Yes | E | D | L | H | S | N | G | A | T | Y | F | L | 361 |
| hu37D3-H9.v5.11 | 97.7 | 71% | Yes | E | D | L | H | S | N | G | S | T | Y | F | L | 362 |
| hu37D3.v28 | 0.9 | 78% | Yes | E | D | L | H | S | N | G | N | T | Y | F | L | 363 |
| hu37D3.v28.A2 | 32.6 | 72% | Yes | D | D | L | H | S | N | G | N | T | Y | F | H | 364 |
| hu37D3.v28.A4 | 1.2 | 96% | Yes | D | D | L | H | S | N | G | N | T | Y | L | L | 365 |
| hu37D3.v28.A6 | 38.3 | 82% | Yes | D | D | M | H | S | N | G | N | T | Y | L | H | 366 |
| hu37D3.v28.A8 | 1.8 | 57% | Yes | D | D | L | H | S | N | G | N | T | Y | F | L | 367 |

VL Residues at Selected Locations (Kabat Numbering)

| Name | Value | % | Binding | | | | | | | | | | | | | SEQ ID: |
|---|---|---|---|---|---|---|---|---|---|---|---|---|---|---|---|---|
| hu37D3.v28.A10 | 41.8 | 37% | Yes | D | D | M | H | S | N | G | N | T | Y | F | L | 368 |
| hu37D3.v28.A12 | 1.8 | 88% | Yes | D | D | M | H | S | N | G | N | T | Y | F | L | 369 |
| hu37D3.v28.A14 | 51.4 | 70% | Yes | D | D | M | H | S | N | G | N | T | Y | F | L | 370 |
| hu37D3.v28.A16 | 3.9 | 89% | Yes | D | V | L | H | S | N | G | N | T | Y | F | L | 371 |
| hu37D3.v28.A18 | 17.3 | 83% | Yes | D | V | L | H | S | N | G | N | T | Y | F | L | 372 |
| hu37D3.v28.A20 | 7.1 | 93% | Yes | D | V | L | H | S | N | G | N | T | Y | F | L | 373 |
| hu37D3.v28.A22 | 27.8 | 70% | Yes | D | V | M | H | S | N | G | N | T | Y | F | L | 374 |
| hu37D3.v28.A24 | 4.7 | 95% | Yes | D | V | M | H | S | N | G | N | T | Y | F | L | 375 |
| hu37D3.v28.A26 | 22.5 | 78% | Yes | D | V | M | H | S | N | G | N | T | Y | F | L | 376 |
| hu37D3.v28.A28 | 11.4 | 89% | Yes | D | V | M | H | S | N | G | N | T | Y | F | L | 377 |
| hu37D3.v28.A30 | 34.4 | 77% | - | D | D | L | H | S | I | G | N | T | F | F | L | 378 |
| hu37D3.v28.B1 | 24.3 | 101% | Yes | D | D | L | H | S | M | G | N | T | F | F | L | 379 |
| hu37D3.v28.B2 | 31.8 | 83% | Yes | D | D | L | H | S | Q | G | N | T | W | F | L | 380 |
| hu37D3.v28.B3 | 0.4 | 208% | - | D | D | L | H | S | Q | G | N | T | H | F | L | 381 |
| hu37D3.v28.B4 | 10.5 | 288% | - | D | D | L | H | S | D | G | N | T | R | F | L | 382 |
| hu37D3.v28.B6 | 85.6 | 46% | Yes | D | D | L | H | S | D | G | N | T | K | F | L | 383 |
| hu37D3.v28.B7 | 4.1 | 607% | - | D | D | L | H | S | E | G | N | T | R | F | L | 384 |
| hu37D3.v28.B8 | 1.8 | 456% | - | D | D | L | H | S | N | N | N | T | Y | F | L | 385 |
| hu37D3.v28.C1 | 1.4 | 77% | Yes | D | D | L | H | S | N | D | N | T | Y | F | L | 386 |
| hu37D3.v28.C2 | 9.6 | 75% | Yes | D | D | L | H | A | N | G | N | T | Y | F | L | 387 |
| hu37D3.v28.D1 | 5.7 | 73% | Yes | D | D | L | H | S | N | G | N | T | Y | F | L | 388 |

FIG. 8B

| Antibody | KD (nM) | Stability Index | Chi2 < 10% Rmax and Normalized Rmax (Pre-stress) > 0.1? | 1 | 2 | 4 | 27D | 27E | 28 | 29 | 30 | 31 | 32 | 33 | 93 | SEQ ID: |
|---|---|---|---|---|---|---|---|---|---|---|---|---|---|---|---|---|
| Unstressed Control (mean, n=9) | 1.0 | 106% | Yes | E | D | L | H | S | N | G | N | T | Y | F | L | 389 |
| hu37D3.v28.E1 | 20.1 | 46% | Yes | D | D | L | H | S | N | G | N | T | Y | F | L | 390 |
| hu37D3.v28.E2 | 22.5 | 28% | Yes | D | D | L | N | S | N | G | N | T | Y | F | L | 391 |
| hu37D3.v28.E3 | 1.1 | 364% | - | D | D | L | Q | S | N | G | N | T | Y | F | L | 392 |
| hu37D3.v28.F1 | 2.1 | 81% | Yes | D | D | L | D | S | D | G | N | T | Y | F | L | 393 |
| hu37D3.v28.F2 | 1.9 | 51% | Yes | D | D | L | H | T | N | T | N | T | Y | F | L | 394 |
| hu37D3.v28.F3 | 9.5 | 70% | - | D | D | L | H | T | N | A | N | T | Y | F | L | 395 |
| hu37D3.v28.51 | 35.6 | 74% | Yes | E | D | L | H | S | N | G | N | T | Y | F | L | 396 |
| hu37D3.v28.52 | 17.6 | 80% | Yes | E | D | L | H | S | H | G | N | T | Y | F | L | 397 |
| hu37D3.v28.53 | 22.9 | 76% | Yes | E | D | L | H | S | K | G | N | T | Y | F | L | 398 |
| hu37D3.v28.54 | 24.8 | 82% | Yes | E | D | L | H | S | R | G | N | T | Y | F | L | 399 |
| hu37D3.v28.55 | 2.6 | 82% | Yes | E | D | L | H | S | L | G | N | T | Y | F | L | 400 |
| hu37D3.v28.56 | 5.4 | 76% | Yes | D | D | L | H | S | N | Q | N | T | Y | F | L | 401 |
| hu37D3.v28.57 | 4.4 | 88% | Yes | D | D | L | H | S | N | Y | N | T | Y | F | L | 402 |
| hu37D3.v29.1 | 13.5 | 70% | Yes | E | D | L | H | S | N | F | N | T | Y | F | L | 403 |
| hu37D3.v29.2 | 2.6 | 88% | Yes | E | D | L | H | S | N | G | D | T | Y | F | L | 404 |
| hu37D3.v29.3 | 5.6 | 93% | Yes | E | D | L | H | S | N | G | Q | T | Y | F | L | 405 |
| hu37D3.v29.4 | 4.9 | 76% | Yes | E | D | L | H | S | N | G | E | T | Y | F | L | 406 |
| hu37D3.v29.5 | 1.4 | 64% | Yes | E | D | L | H | S | N | G | A | T | Y | F | L | 407 |
| hu37D3.v29.6 | 1.4 | 62% | Yes | E | D | L | H | S | N | G | H | T | Y | F | L | 408 |
| hu37D3.v29.7 | 4.6 | 90% | Yes | E | D | L | H | S | N | G | K | T | Y | F | L | 409 |
| hu37D3.v29.8 | 40.9 | 77% | - | E | D | L | H | S | N | A | L | T | Y | F | L | 410 |
| hu37D3.v29.9 | 7.3 | 86% | Yes | E | D | L | H | S | N | A | D | T | Y | F | L | 411 |
| hu37D3.v29.10 | 17.4 | 100% | Yes | E | D | L | H | S | N | A | E | T | Y | F | L | 412 |

FIG. 8C

| Name | | | | | | | | | | | | | | | | | SEQ ID: |
|---|---|---|---|---|---|---|---|---|---|---|---|---|---|---|---|---|---|
| hu37D3.v29.11 | 27.9 | 67% | Yes | E | D | L | H | S | N | A | A | T | Y | F | L | 413 |
| hu37D3.v29.12 | 7.0 | 50% | Yes | E | D | L | H | S | N | H | A | T | Y | F | L | 414 |
| hu37D3.v29.13 | 6.7 | 79% | Yes | E | D | L | H | S | N | K | A | T | Y | F | L | 415 |
| hu37D3.v29.14 | 22.0 | 92% | Yes | E | D | L | H | S | N | L | A | T | Y | F | L | 416 |
| hu37D3-H9.v30.1 | 23.5 | 87% | Yes | D | D | L | H | S | G | N | G | T | Y | F | L | 417 |
| hu37D3-H9.v30.2 | 4.2 | 96% | Yes | D | D | L | H | S | T | N | G | T | Y | F | L | 418 |
| hu37D3-H9.v30.3 | 38.1 | 83% | Yes | D | D | L | H | S | V | N | G | T | Y | F | L | 419 |
| hu37D3-H9.v30.4 | 22.0 | 87% | Yes | D | D | L | H | S | L | N | G | T | Y | F | L | 420 |
| hu37D3-H9.v30.5 | 29.1 | 80% | Yes | D | D | L | H | S | I | N | G | T | Y | F | L | 421 |
| hu37D3-H9.v30.6 | 19.1 | 270% | Yes | D | D | L | H | S | P | N | G | T | Y | F | L | 422 |
| hu37D3-H9.v30.7 | 34.9 | 93% | - | D | D | L | H | S | F | N | G | T | Y | F | L | 423 |
| hu37D3-H9.v30.8 | 31.4 | 105% | - | D | D | L | H | S | Y | N | G | T | Y | F | L | 424 |
| hu37D3-H9.v30.9 | 36.4 | 63% | - | D | D | L | H | S | H | N | G | T | Y | F | L | 425 |
| hu37D3-H9.v30.10 | 16.1 | 84% | - | D | D | L | H | S | K | N | G | T | Y | F | L | 426 |
| hu37D3-H9.v30.11 | 20.9 | 86% | Yes | D | D | L | H | S | R | N | G | T | Y | F | L | 427 |
| hu37D3-H9.v31.1 | 41.2 | 72% | Yes | D | D | L | H | S | N | N | A | T | Y | F | L | 428 |
| hu37D3-H9.v31.2 | 10.6 | 90% | - | D | D | L | H | S | N | N | V | T | Y | F | L | 429 |
| hu37D3-H9.v31.3 | 9.8 | 93% | Yes | D | D | L | H | S | N | N | I | T | Y | F | L | 430 |
| hu37D3-H9.v31.4 | 0.8 | 533% | - | D | D | L | H | S | N | N | P | T | Y | F | L | 431 |
| hu37D3-H9.v31.5 | 15.2 | 85% | Yes | D | D | L | H | S | N | N | F | T | Y | F | L | 432 |
| hu37D3-H9.v31.6 | 15.5 | 90% | Yes | D | D | L | H | S | N | N | Y | T | Y | F | L | 433 |
| hu37D3-H9.v31.7 | 6.9 | 83% | - | D | D | L | H | S | N | N | R | T | Y | F | L | 434 |
| hu37D3-H9.v31.8 | 10.9 | 78% | Yes | D | D | L | H | S | N | N | A | V | Y | F | L | 435 |
| hu37D3-H9.v31.9 | 7.5 | 81% | Yes | D | D | L | H | S | N | N | A | I | Y | F | L | 436 |
| hu37D3-H9.v31.10 | 5.5 | 261% | - | D | D | L | H | S | N | N | A | P | Y | F | L | 437 |
| hu37D3-H9.v31.11 | 22.7 | 126% | - | D | D | L | H | S | N | N | A | F | Y | F | L | 438 |
| hu37D3-H9.v31.12 | 41.6 | 99% | - | D | D | L | H | S | N | N | A | Y | Y | F | L | 439 |
| hu37D3-H9.v31.13 | 48.1 | 83% | - | D | D | L | H | S | N | N | A | N | Y | F | L | 440 |
| hu37D3-H9.v31.14 | 35.5 | 86% | - | D | D | L | H | S | N | N | A | R | Y | F | L | 441 |

FIG. 8D

```
Native Tau Position 2
         ↓              37D3 Epitope (2-24)
PRO364486.HU    1 MHHHHHHGENLYFQGSAEPRQEFEVMEDHAGTYGLGDRKDQGGYTMHQDQ  50
PRO378546.CYNO  1 MHHHHHHGENLYFQGSAEPRQEFDVMEDHAGTYGLGDRKDQEGYTMLQDQ  50

PRO364486.HU   51 EGDTDAGLKESPLQTPTEDGSEETSDAKSTPTAEDVTAPLVDEGAP      100
PRO378546.CYNO 51 EGDTDAGLKESPLQTPAEDGSEELGSETSDAKSTPTAEDVTAPLVDERAP  100

PRO364486.HU  101 GKQAAAQPHTEIPEGTTAEEAGIGDTPSLEDEAAGHVTQARMVSKSKDGT  150
PRO378546.CYNO 101 GEQAAAQPHMEIPEGTTAEEAGIGDTPSLEDEAAGHVTQARMVSKSKDGT  150

PRO364486.HU  151 GSDDKKAKGADGKTKIATPRGAAPPGQKGQANATRIPAKTPPAPKTPPSS  200
PRO378546.CYNO 151 GSDDKKAKGADGKTKIATPRGAAPPGQKGQANATRIPAKTPPAPKTPPSS  200

PRO364486.HU  201 GEPPKSGDRSGYSSPGSPGTPGSRSRTPSLPTPPTREPKKVAVVRTPPKS  250
PRO378546.CYNO 201 GEPPKSGDRSGYSSPGSPGTPGSRSRTPSLPTPPAREPKKVAVVRTPPKS  250

PRO364486.HU  251 PSSAKSRLQTAPVPMPDLKNVKSKIGSTENLKHQPGGGKVQIINKKLDLS  300
PRO378546.CYNO 251 PSSAKSRLQTAPVPMPDLKNVKSKIGSTENLKHQPGGGKVQIINKKLDLS  300

PRO364486.HU  301 NVQSKCGSKDNIKHVPGGGSVQIVYKPVDLSKVTSKCGSLGNIHHKPGGG  350
PRO378546.CYNO 301 NVQSKCGSKDNIKHVPGGGSVQIVYKPVDLSKVTSKCGSLGNIHHKPGGG  350

PRO364486.HU  351 QVEVKSEKLDFKDRVQSKIGSLDNITHVPGGGNKKIETHKLTFRENAKAK  400
PRO378546.CYNO 351 QVEVKSEKLDFKDRVQSKIGSLDNITHVPGGGNKKIETHKLTFRENAKAK  400

PRO364486.HU  401 TDHGAEIVYKSPVVSGDTSPRHLSNVSSTGSIDMVDSPQLATLADEVSAS  450
PRO378546.CYNO 401 TDHGAEIVYKSPVVSGDTSPRHLSNVSSTGSIDMVDSPQLATLADEVSAS  450

PRO364486.HU  451 LAKQGL 456  SEQ ID NO: 1
PRO378546.CYNO 451 LAKQGL 456  SEQ ID NO: 3
```

| Antibody | Tau isoform selectivity | Vaccine used |
|---|---|---|
| 12A10-E8 | 1N- and 2N-Tau | oligoTau vaccine |
| 55E7-B12 | 1N- and 2N-Tau | oligoTau vaccine |
| 55E7-F11 | 1N- and 2N-Tau | oligoTau vaccine |
| 72E12-H9 | 1N- and 2N-Tau | oligoTau vaccine |
| 30D12-B5 | 2N-Tau | oligoTau vaccine |
| 30D12-F6 | 2N-Tau | oligoTau vaccine |
| 21C1-D8 | 2N-Tau | oligoTau vaccine |
| 21C1-G6 | 2N-Tau | oligoTau vaccine |
| 31A3-A4 | 2N-Tau | oligoTau vaccine |
| 31A3-A7 | 2N-Tau | oligoTau vaccine |
| 77D1-D2 | 2N-Tau | oligoTau vaccine |
| 77D1-E6 | 2N-Tau | oligoTau vaccine |
| 30A1-C9 | 2N-Tau | oligoTau vaccine |
| 30A1-D11 | 2N-Tau | oligoTau vaccine |
| 28F5-G8 | 2N-Tau | oligoTau vaccine |
| 211G6-86 | 2N-Tau | flTau Liposomal vaccine |

*FIG. 25*

SEQUENCE LISTING

<160> NUMBER OF SEQ ID NOS: 698

<210> SEQ ID NO 1
<211> LENGTH: 456
<212> TYPE: PRT
<213> ORGANISM: Homo sapiens -continued

```
<220> FEATURE:
<221> NAME/KEY: misc_feature
<223> OTHER INFORMATION: Human Tau sequence

<400> SEQUENCE: 1

Met His His His His His Gly Glu Asn Leu Tyr Phe Gln Gly Ser
1               5                   10                  15

Ala Glu Pro Arg Gln Glu Phe Glu Val Met Glu Asp His Ala Gly Thr
            20                  25                  30

Tyr Gly Leu Gly Asp Arg Lys Asp Gln Gly Gly Tyr Thr Met His Gln
            35                  40                  45

Asp Gln Glu Gly Asp Thr Asp Ala Gly Leu Lys Glu Ser Pro Leu Gln
50                  55                  60

Thr Pro Thr Glu Asp Gly Ser Glu Glu Pro Gly Ser Glu Thr Ser Asp
65                  70                  75                  80

Ala Lys Ser Thr Pro Thr Ala Glu Asp Val Thr Ala Pro Leu Val Asp
            85                  90                  95

Glu Gly Ala Pro Gly Lys Gln Ala Ala Ala Gln Pro His Thr Glu Ile
            100                 105                 110

Pro Glu Gly Thr Thr Ala Glu Glu Ala Gly Ile Gly Asp Thr Pro Ser
            115                 120                 125

Leu Glu Asp Glu Ala Ala Gly His Val Thr Gln Ala Arg Met Val Ser
130                 135                 140

Lys Ser Lys Asp Gly Thr Gly Ser Asp Asp Lys Lys Ala Lys Gly Ala
145                 150                 155                 160

Asp Gly Lys Thr Lys Ile Ala Thr Pro Arg Gly Ala Ala Pro Pro Gly
            165                 170                 175

Gln Lys Gly Gln Ala Asn Ala Thr Arg Ile Pro Ala Lys Thr Pro Pro
            180                 185                 190

Ala Pro Lys Thr Pro Pro Ser Ser Gly Glu Pro Pro Lys Ser Gly Asp
            195                 200                 205

Arg Ser Gly Tyr Ser Ser Pro Gly Ser Pro Gly Thr Pro Gly Ser Arg
210                 215                 220

Ser Arg Thr Pro Ser Leu Pro Thr Pro Pro Thr Arg Glu Pro Lys Lys
225                 230                 235                 240

Val Ala Val Val Arg Thr Pro Pro Lys Ser Pro Ser Ser Ala Lys Ser
            245                 250                 255

Arg Leu Gln Thr Ala Pro Val Pro Met Pro Asp Leu Lys Asn Val Lys
            260                 265                 270

Ser Lys Ile Gly Ser Thr Glu Asn Leu Lys His Gln Pro Gly Gly Gly
            275                 280                 285

Lys Val Gln Ile Ile Asn Lys Lys Leu Asp Leu Ser Asn Val Gln Ser
290                 295                 300

Lys Cys Gly Ser Lys Asp Asn Ile Lys His Val Pro Gly Gly Gly Ser
305                 310                 315                 320

Val Gln Ile Val Tyr Lys Pro Val Asp Leu Ser Lys Val Thr Ser Lys
            325                 330                 335

Cys Gly Ser Leu Gly Asn Ile His His Lys Pro Gly Gly Gly Gln Val
            340                 345                 350

Glu Val Lys Ser Glu Lys Leu Asp Phe Lys Asp Arg Val Gln Ser Lys
            355                 360                 365

Ile Gly Ser Leu Asp Asn Ile Thr His Val Pro Gly Gly Gly Asn Lys
370                 375                 380

Lys Ile Glu Thr His Lys Leu Thr Phe Arg Glu Asn Ala Lys Ala Lys
```

```
385                 390                 395                 400
Thr Asp His Gly Ala Glu Ile Val Tyr Lys Ser Pro Val Ser Gly
                405                 410                 415

Asp Thr Ser Pro Arg His Leu Ser Asn Val Ser Ser Thr Gly Ser Ile
                420                 425                 430

Asp Met Val Asp Ser Pro Gln Leu Ala Thr Leu Ala Asp Glu Val Ser
                435                 440                 445

Ala Ser Leu Ala Lys Gln Gly Leu
    450                 455

<210> SEQ ID NO 2
<211> LENGTH: 23
<212> TYPE: PRT
<213> ORGANISM: Homo sapiens
<220> FEATURE:
<221> NAME/KEY: misc_feature
<223> OTHER INFORMATION: Human Tau epitope (2-24)

<400> SEQUENCE: 2

Ala Glu Pro Arg Gln Glu Phe Glu Val Met Glu Asp His Ala Gly Thr
1               5                   10                  15

Tyr Gly Leu Gly Asp Arg Lys
            20

<210> SEQ ID NO 3
<211> LENGTH: 456
<212> TYPE: PRT
<213> ORGANISM: Macaca fascicularis
<220> FEATURE:
<221> NAME/KEY: misc_feature
<223> OTHER INFORMATION: Cynomolgus monkey Tau sequence

<400> SEQUENCE: 3

Met His His His His His Gly Glu Asn Leu Tyr Phe Gln Gly Ser
1               5                   10                  15

Ala Glu Pro Arg Gln Glu Phe Asp Val Met Glu Asp His Ala Gly Thr
                20                  25                  30

Tyr Gly Leu Gly Asp Arg Lys Asp Gln Glu Gly Tyr Thr Met Leu Gln
            35                  40                  45

Asp Gln Glu Gly Asp Thr Asp Ala Gly Leu Lys Glu Ser Pro Leu Gln
    50                  55                  60

Thr Pro Ala Glu Asp Gly Ser Glu Glu Leu Gly Ser Glu Thr Ser Asp
65                  70                  75                  80

Ala Lys Ser Thr Pro Thr Ala Glu Asp Val Thr Ala Pro Leu Val Asp
                85                  90                  95

Glu Arg Ala Pro Gly Glu Gln Ala Ala Ala Gln Pro His Met Glu Ile
                100                 105                 110

Pro Glu Gly Thr Thr Ala Glu Glu Ala Gly Ile Gly Asp Thr Pro Ser
            115                 120                 125

Leu Glu Asp Glu Ala Ala Gly His Val Thr Gln Ala Arg Met Val Ser
    130                 135                 140

Lys Ser Lys Asp Gly Thr Gly Ser Asp Asp Lys Lys Ala Lys Gly Ala
145                 150                 155                 160

Asp Gly Lys Thr Lys Ile Ala Thr Pro Arg Gly Ala Ala Pro Pro Gly
                165                 170                 175

Gln Lys Gly Gln Ala Asn Ala Thr Arg Ile Pro Ala Lys Thr Pro Pro
            180                 185                 190

Ala Pro Lys Thr Pro Pro Ser Ser Gly Glu Pro Pro Lys Ser Gly Asp
```

```
                195                 200                 205
Arg Ser Gly Tyr Ser Ser Pro Gly Ser Pro Gly Thr Pro Gly Ser Arg
    210                 215                 220

Ser Arg Thr Pro Ser Leu Pro Thr Pro Pro Ala Arg Glu Pro Lys Lys
225                 230                 235                 240

Val Ala Val Val Arg Thr Pro Pro Lys Ser Pro Ser Ser Ala Lys Ser
                245                 250                 255

Arg Leu Gln Thr Ala Pro Val Pro Met Pro Asp Leu Lys Asn Val Lys
            260                 265                 270

Ser Lys Ile Gly Ser Thr Glu Asn Leu Lys His Gln Pro Gly Gly Gly
        275                 280                 285

Lys Val Gln Ile Ile Asn Lys Lys Leu Asp Leu Ser Asn Val Gln Ser
    290                 295                 300

Lys Cys Gly Ser Lys Asp Asn Ile Lys His Val Pro Gly Gly Gly Ser
305                 310                 315                 320

Val Gln Ile Val Tyr Lys Pro Val Asp Leu Ser Lys Val Thr Ser Lys
                325                 330                 335

Cys Gly Ser Leu Gly Asn Ile His His Lys Pro Gly Gly Gly Gln Val
            340                 345                 350

Glu Val Lys Ser Glu Lys Leu Asp Phe Lys Asp Arg Val Gln Ser Lys
        355                 360                 365

Ile Gly Ser Leu Asp Asn Ile Thr His Val Pro Gly Gly Gly Asn Lys
    370                 375                 380

Lys Ile Glu Thr His Lys Leu Thr Phe Arg Glu Asn Ala Lys Ala Lys
385                 390                 395                 400

Thr Asp His Gly Ala Glu Ile Val Tyr Lys Ser Pro Val Val Ser Gly
                405                 410                 415

Asp Thr Ser Pro Arg His Leu Ser Asn Val Ser Ser Thr Gly Ser Ile
            420                 425                 430

Asp Met Val Asp Ser Pro Gln Leu Ala Thr Leu Ala Asp Glu Val Ser
        435                 440                 445

Ala Ser Leu Ala Lys Gln Gly Leu
    450                 455

<210> SEQ ID NO 4
<211> LENGTH: 23
<212> TYPE: PRT
<213> ORGANISM: Macaca fascicularis
<220> FEATURE:
<221> NAME/KEY: misc_feature
<223> OTHER INFORMATION: Cynomolgus monkey Tau epitope (2-24)

<400> SEQUENCE: 4

Ala Glu Pro Arg Gln Glu Phe Asp Val Met Glu Asp His Ala Gly Thr
1               5                   10                  15

Tyr Gly Leu Gly Asp Arg Lys
            20

<210> SEQ ID NO 5

<400> SEQUENCE: 5

000

<210> SEQ ID NO 6

<400> SEQUENCE: 6
```

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 117
<212> TYPE: PRT
<213> ORGANISM: Artificial Sequence
<220> FEATURE:
<223> OTHER INFORMATION: Synthetic: 37D3-H9 heavy chain variable region
      (VH)

<400> SEQUENCE: 10

```
Glu Val Gln Leu Val Glu Ser Gly Gly Asp Leu Ala Lys Pro Gly Gly
1               5                   10                  15

Ser Leu Lys Leu Ser Cys Thr Ala Ser Gly Leu Ile Phe Arg Ser Tyr
            20                  25                  30

Gly Met Ser Trp Val Arg Gln Thr Pro Asp Lys Arg Leu Glu Trp Val
        35                  40                  45

Ala Thr Ile Asn Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Asn Ser Tyr Ser Gly Ala Met Asp Tyr Trp Gly Gln Gly Thr Ser
            100                 105                 110

Val Thr Val Ser Ser
        115
```

<210> SEQ ID NO 11
<211> LENGTH: 112
<212> TYPE: PRT
<213> ORGANISM: Artificial Sequence
<220> FEATURE:
<223> OTHER INFORMATION: Synthetic: 37D3-H9 light chain variable region
      (VL)

<400> SEQUENCE: 11

```
Asp Asp Leu Leu Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Gly Asn Thr Tyr Phe Glu Trp Tyr Leu Gln Lys Pro Gly Gln Ser
        35                  40                  45

Pro Lys Leu Leu Ile Tyr Lys Val Ser Asn Arg Phe Ser Gly Val Pro
```

```
                50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser Leu Val Pro Trp Thr Phe Gly Gly Gly Thr Lys Leu Glu Ile Lys
            100                 105                 110
```

```
<210> SEQ ID NO 12
<211> LENGTH: 5
<212> TYPE: PRT
<213> ORGANISM: Artificial Sequence
<220> FEATURE:
<223> OTHER INFORMATION: Synthetic: 37D3-H9 HVR-H1

<400> SEQUENCE: 12

Ser Tyr Gly Met Ser
1               5
```

```
<210> SEQ ID NO 13
<211> LENGTH: 17
<212> TYPE: PRT
<213> ORGANISM: Artificial Sequence
<220> FEATURE:
<223> OTHER INFORMATION: Synthetic: 37D3-H9 HVR-H2

<400> SEQUENCE: 13

Thr Ile Asn Ser Gly Gly Thr Tyr Thr Tyr Tyr Pro Asp Ser Val Lys
1               5                  10                  15
Gly
```

```
<210> SEQ ID NO 14
<211> LENGTH: 8
<212> TYPE: PRT
<213> ORGANISM: Artificial Sequence
<220> FEATURE:
<223> OTHER INFORMATION: Synthetic: 37D3-H9 HVR-H3

<400> SEQUENCE: 14

Ser Tyr Ser Gly Ala Met Asp Tyr
1               5
```

```
<210> SEQ ID NO 15
<211> LENGTH: 16
<212> TYPE: PRT
<213> ORGANISM: Artificial Sequence
<220> FEATURE:
<223> OTHER INFORMATION: Synthetic: 37D3-H9 HVR-L1

<400> SEQUENCE: 15

Arg Ser Ser Gln Ser Ile Val His Ser Asn Gly Asn Thr Tyr Phe Glu
1               5                  10                  15
```

```
<210> SEQ ID NO 16
<211> LENGTH: 7
<212> TYPE: PRT
<213> ORGANISM: Artificial Sequence
<220> FEATURE:
<223> OTHER INFORMATION: Synthetic: 37D3-H9 HVR-L2

<400> SEQUENCE: 16

Lys Val Ser Asn Arg Phe Ser
1               5
```

```
<210> SEQ ID NO 17
<211> LENGTH: 9
<212> TYPE: PRT
<213> ORGANISM: Artificial Sequence
<220> FEATURE:
<223> OTHER INFORMATION: Synthetic: 37D3-H9 HVR-L3

<400> SEQUENCE: 17

Phe Gln Gly Ser Leu Val Pro Trp Thr
1               5

<210> SEQ ID NO 18

<400> SEQUENCE: 18

000

<210> SEQ ID NO 19

<400> SEQUENCE: 19

000

<210> SEQ ID NO 20
<211> LENGTH: 117
<212> TYPE: PRT
<213> ORGANISM: Artificial Sequence
<220> FEATURE:
<223> OTHER INFORMATION: Synthetic: 37D3-H9b heavy chain variable region
      (VH)

<400> SEQUENCE: 20

Glu Val Gln Leu Val Glu Ser Gly Gly Asp Leu Ala Lys Pro Gly Gly
1               5                   10                  15

Ser Leu Lys Leu Ser Cys Thr Ala Ser Gly Leu Ile Phe Arg Ser Tyr
            20                  25                  30

Gly Met Ser Trp Val Arg Gln Thr Pro Asp Lys Arg Leu Glu Trp Val
        35                  40                  45

Ala Thr Ile Asn Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Asn Ser Tyr Ser Gly Ala Met Asp Tyr Trp Gly Gln Gly Thr Ser
            100                 105                 110

Val Thr Val Ser Ser
        115

<210> SEQ ID NO 21
<211> LENGTH: 112
<212> TYPE: PRT
<213> ORGANISM: Artificial Sequence
<220> FEATURE:
<223> OTHER INFORMATION: Synthetic: 37D3-H9b light chain variable region
      (VL)

<400> SEQUENCE: 21

Glu Asp Leu Leu Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Gly Asn Thr Tyr Phe Glu Trp Tyr Leu Gln Lys Pro Gly Gln Ser
```

-continued

```
                35                  40                  45
Pro Lys Leu Leu Ile Tyr Lys Val Ser Asn Arg Phe Ser Gly Val Pro
                50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                    85                  90                  95

Ser Leu Val Pro Trp Thr Phe Gly Gly Gly Thr Lys Leu Glu Ile Lys
                100                 105                 110
```

<210> SEQ ID NO 22
<211> LENGTH: 5
<212> TYPE: PRT
<213> ORGANISM: Artificial Sequence
<220> FEATURE:
<223> OTHER INFORMATION: Synthetic: 37D3-H9b HVR-H1

<400> SEQUENCE: 22

```
Ser Tyr Gly Met Ser
 1               5
```

<210> SEQ ID NO 23
<211> LENGTH: 17
<212> TYPE: PRT
<213> ORGANISM: Artificial Sequence
<220> FEATURE:
<223> OTHER INFORMATION: Synthetic: 37D3-H9b HVR-H2

<400> SEQUENCE: 23

```
Thr Ile Asn Ser Gly Gly Thr Tyr Thr Tyr Tyr Pro Asp Ser Val Lys
 1               5                  10                  15

Gly
```

<210> SEQ ID NO 24
<211> LENGTH: 8
<212> TYPE: PRT
<213> ORGANISM: Artificial Sequence
<220> FEATURE:
<223> OTHER INFORMATION: Synthetic: 37D3-H9b HVR-H3

<400> SEQUENCE: 24

```
Ser Tyr Ser Gly Ala Met Asp Tyr
 1               5
```

<210> SEQ ID NO 25
<211> LENGTH: 16
<212> TYPE: PRT
<213> ORGANISM: Artificial Sequence
<220> FEATURE:
<223> OTHER INFORMATION: Synthetic: 37D3-H9b HVR-L1

<400> SEQUENCE: 25

```
Arg Ser Ser Gln Ser Ile Val His Ser Asn Gly Asn Thr Tyr Phe Glu
 1               5                  10                  15
```

<210> SEQ ID NO 26
<211> LENGTH: 7
<212> TYPE: PRT
<213> ORGANISM: Artificial Sequence
<220> FEATURE:
<223> OTHER INFORMATION: Synthetic: 37D3-H9b HVR-L2

<400> SEQUENCE: 26

```
Lys Val Ser Asn Arg Phe Ser
```

-continued

<210> SEQ ID NO 27
<211> LENGTH: 9
<212> TYPE: PRT
<213> ORGANISM: Artificial Sequence
<220> FEATURE:
<223> OTHER INFORMATION: Synthetic: 37D3-H9b HVR-L3

<400> SEQUENCE: 27

```
Phe Gln Gly Ser Leu Val Pro Trp Thr
1               5
```

<210> SEQ ID NO 28

<400> SEQUENCE: 28

000

<210> SEQ ID NO 29

<400> SEQUENCE: 29

000

<210> SEQ ID NO 30
<211> LENGTH: 117
<212> TYPE: PRT
<213> ORGANISM: Artificial Sequence
<220> FEATURE:
<223> OTHER INFORMATION: Synthetic: 11E10-B8 heavy chain variable region
      (VH)

<400> SEQUENCE: 30

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Arg Ser Tyr
            20                  25                  30

Gly Met Ser Trp Val Arg Gln Thr Pro Asp Lys Arg Leu Glu Trp Val
        35                  40                  45

Ala Thr Ile Ser Gly Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Val Ser Tyr Asp Gly Ala Met Asp Tyr Trp Gly Gln Gly Thr Ser
            100                 105                 110

Val Thr Val Ser Ser
        115
```

<210> SEQ ID NO 31
<211> LENGTH: 112
<212> TYPE: PRT
<213> ORGANISM: Artificial Sequence
<220> FEATURE:
<223> OTHER INFORMATION: Synthetic: 11E10-B8 light chain variable region
      (VL)

<400> SEQUENCE: 31

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
```

```
                    20                  25                  30
Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 32
<211> LENGTH: 5
<212> TYPE: PRT
<213> ORGANISM: Artificial Sequence
<220> FEATURE:
<223> OTHER INFORMATION: Synthetic: 11E10-B8 HVR-H1

<400> SEQUENCE: 32

```
Ser Tyr Gly Met Ser
1               5
```

<210> SEQ ID NO 33
<211> LENGTH: 17
<212> TYPE: PRT
<213> ORGANISM: Artificial Sequence
<220> FEATURE:
<223> OTHER INFORMATION: Synthetic: 11E10-B8 HVR-H2

<400> SEQUENCE: 33

```
Thr Ile Ser Gly Gly Gly Ser Tyr Thr Tyr Tyr Pro Asp Ser Val Lys
1               5                   10                  15

Gly
```

<210> SEQ ID NO 34
<211> LENGTH: 8
<212> TYPE: PRT
<213> ORGANISM: Artificial Sequence
<220> FEATURE:
<223> OTHER INFORMATION: Synthetic: 11E10-B8 HVR-H3

<400> SEQUENCE: 34

```
Ser Tyr Asp Gly Ala Met Asp Tyr
1               5
```

<210> SEQ ID NO 35
<211> LENGTH: 16
<212> TYPE: PRT
<213> ORGANISM: Artificial Sequence
<220> FEATURE:
<223> OTHER INFORMATION: Synthetic: 11E10-B8 HVR-L1

<400> SEQUENCE: 35

```
Arg Ser Ser Gln Ser Ile Val His Ser Asn Gly Asn Thr Tyr Leu Glu
1               5                   10                  15
```

<210> SEQ ID NO 36
<211> LENGTH: 7
<212> TYPE: PRT
<213> ORGANISM: Artificial Sequence
<220> FEATURE:
<223> OTHER INFORMATION: Synthetic: 11E10-B8 HVR-L2

```
<400> SEQUENCE: 36

Lys Val Ser Asn Arg Phe Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic: 11E10-B8 HVR-L3

<400> SEQUENCE: 37

Phe Gln Gly Ser His Val Pro Trp Thr
1               5

<210> SEQ ID NO 38

<400> SEQUENCE: 38

000

<210> SEQ ID NO 39

<400> SEQUENCE: 39

000

<210> SEQ ID NO 40
<211> LENGTH: 117
<212> TYPE: PRT
<213> ORGANISM: Artificial Sequence
<220> FEATURE:
<223> OTHER INFORMATION: Synthetic: 54C1-H11 and 61E7-C4 heavy chain
      variable region (VH)

<400> SEQUENCE: 40

Glu Val Gln Leu Val Glu Ser Gly Gly Asp Leu Val Lys Pro Gly Gly
1               5                   10                  15

Ser Leu Lys Val Ser Cys Val Ala Ser Gly Phe Thr Phe Arg Ser Tyr
            20                  25                  30

Gly Met Ser Trp Val Arg Gln Thr Pro Asp Lys Arg Leu Asp Trp Val
        35                  40                  45

Ala Thr Ile Ser Ser Gly Gly Asn Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Ser Ser Tyr Ser Gly Ala Met Asp Tyr Trp Gly Gln Gly Thr Ser
            100                 105                 110

Val Thr Val Ser Ser
        115

<210> SEQ ID NO 41
<211> LENGTH: 112
<212> TYPE: PRT
<213> ORGANISM: Artificial Sequence
<220> FEATURE:
<223> OTHER INFORMATION: Synthetic: 54C1-H11 and 61E7-C4 light chain
      variable region (VL)

<400> SEQUENCE: 41

Asp Thr Val Met Thr Gln Ser Pro Leu Ser Leu Pro Val Ser Leu Gly
```

```
1               5                   10                  15
Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
                100                 105                 110
```

<210> SEQ ID NO 42
<211> LENGTH: 5
<212> TYPE: PRT
<213> ORGANISM: Artificial Sequence
<220> FEATURE:
<223> OTHER INFORMATION: Synthetic: 54C1-H11 and 61E7-C4 HVR-H1

<400> SEQUENCE: 42

```
Ser Tyr Gly Met Ser
1               5
```

<210> SEQ ID NO 43
<211> LENGTH: 17
<212> TYPE: PRT
<213> ORGANISM: Artificial Sequence
<220> FEATURE:
<223> OTHER INFORMATION: Synthetic: 54C1-H11 and 61E7-C4 HVR-H2

<400> SEQUENCE: 43

```
Thr Ile Ser Ser Gly Gly Asn Tyr Thr Tyr Tyr Pro Asp Ser Val Lys
1               5                   10                  15
Gly
```

<210> SEQ ID NO 44
<211> LENGTH: 8
<212> TYPE: PRT
<213> ORGANISM: Artificial Sequence
<220> FEATURE:
<223> OTHER INFORMATION: Synthetic: 54C1-H11 and 61E7-C4 HVR-H3

<400> SEQUENCE: 44

```
Ser Tyr Ser Gly Ala Met Asp Tyr
1               5
```

<210> SEQ ID NO 45
<211> LENGTH: 16
<212> TYPE: PRT
<213> ORGANISM: Artificial Sequence
<220> FEATURE:
<223> OTHER INFORMATION: Synthetic: 54C1-H11 and 61E7-C4 HVR-L1

<400> SEQUENCE: 45

```
Arg Ser Ser Gln Ser Ile Val His Ser Asn Gly Asn Thr Tyr Leu Glu
1               5                   10                  15
```

<210> SEQ ID NO 46
<211> LENGTH: 7
<212> TYPE: PRT
<213> ORGANISM: Artificial Sequence
<220> FEATURE:
<223> OTHER INFORMATION: Synthetic: 54C1-H11 and 61E7-C4 HVR-L2

<400> SEQUENCE: 46

Thr Val Ser Asn Arg Phe Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic: 54C1-H11 and 61E7-C4 HVR-L3

<400> SEQUENCE: 47

Phe Gln Gly Ser His Val Pro Trp Thr
1               5

<210> SEQ ID NO 48

<400> SEQUENCE: 48

000

<210> SEQ ID NO 49

<400> SEQUENCE: 49

000

<210> SEQ ID NO 50
<211> LENGTH: 117
<212> TYPE: PRT
<213> ORGANISM: Artificial Sequence
<220> FEATURE:
<223> OTHER INFORMATION: Synthetic: 3A4-H4 heavy chain variable region
      (VH)

<400> SEQUENCE: 50

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Phe Cys
                85                  90                  95

Ala Thr Ser Tyr Asp Gly Ala Met Asp Tyr Trp Gly Gln Gly Thr Ser
            100                 105                 110

Val Thr Val Ser Ser
        115

<210> SEQ ID NO 51
<211> LENGTH: 112
<212> TYPE: PRT
<213> ORGANISM: Artificial Sequence
<220> FEATURE:
<223> OTHER INFORMATION: Synthetic: 3A4-H4 light chain variable region
      (VL)

<400> SEQUENCE: 51

Asp Val Leu Met Thr Gln Thr Pro Leu Ser Leu Pro Val Ser Leu Gly
1               5                   10                  15

Asp Gln Ala Ser Ile Ser Cys Arg Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Thr Leu Val Pro Trp Thr Phe Gly Gly Gly Thr Lys Leu Glu Ile Lys
            100                 105                 110

<210> SEQ ID NO 52
<211> LENGTH: 5
<212> TYPE: PRT
<213> ORGANISM: Artificial Sequence
<220> FEATURE:
<223> OTHER INFORMATION: Synthetic: 3A4-H4 HVR-H1

<400> SEQUENCE: 52

Ser Tyr Gly Met Ser
1               5

<210> SEQ ID NO 53
<211> LENGTH: 17
<212> TYPE: PRT
<213> ORGANISM: Artificial Sequence
<220> FEATURE:
<223> OTHER INFORMATION: Synthetic: 3A4-H4 HVR-H2

<400> SEQUENCE: 53

Thr Ile Ser Ser Gly Gly Thr Tyr Thr Tyr Tyr Pro Asp Ser Val Lys
1               5                   10                  15

Gly

<210> SEQ ID NO 54
<211> LENGTH: 8
<212> TYPE: PRT
<213> ORGANISM: Artificial Sequence
<220> FEATURE:
<223> OTHER INFORMATION: Synthetic: 3A4-H4 HVR-H3

<400> SEQUENCE: 54

Ser Tyr Asp Gly Ala Met Asp Tyr
1               5

<210> SEQ ID NO 55
<211> LENGTH: 16
<212> TYPE: PRT
<213> ORGANISM: Artificial Sequence
<220> FEATURE:
<223> OTHER INFORMATION: Synthetic: 3A4-H4 HVR-L1

<400> SEQUENCE: 55

Arg Ser Ser Gln Asn Ile Val His Ser Asn Gly Asn Thr Tyr Leu Glu
1               5                   10                  15

<210> SEQ ID NO 56

```
<211> LENGTH: 7
<212> TYPE: PRT
<213> ORGANISM: Artificial Sequence
<220> FEATURE:
<223> OTHER INFORMATION: Synthetic: 3A4-H4 HVR-L2

<400> SEQUENCE: 56

Lys Val Ser Asn Arg Phe Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic: 3A4-H4 HVR-L3

<400> SEQUENCE: 57

Phe Gln Gly Thr Leu Val Pro Trp Thr
1               5

<210> SEQ ID NO 58

<400> SEQUENCE: 58

000

<210> SEQ ID NO 59

<400> SEQUENCE: 59

000

<210> SEQ ID NO 60
<211> LENGTH: 117
<212> TYPE: PRT
<213> ORGANISM: Artificial Sequence
<220> FEATURE:
<223> OTHER INFORMATION: Synthetic: 19H6-F7 heavy chain variable region
      (VH)

<400> SEQUENCE: 60

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Pro Ser Tyr Asp Gly Ala Met Asp Tyr Trp Gly Gln Gly Thr Ser
            100                 105                 110

Val Thr Val Ser Ser
        115

<210> SEQ ID NO 61
<211> LENGTH: 112
<212> TYPE: PRT
<213> ORGANISM: Artificial Sequence
<220> FEATURE:
```

<223> OTHER INFORMATION: Synthetic: 19H6-F7 light chain variable region
      (VL)

<400> SEQUENCE: 61

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Leu Val Pro Trp Thr Phe Gly Gly Gly Thr Lys Leu Glu Ile Lys
            100                 105                 110

<210> SEQ ID NO 62
<211> LENGTH: 5
<212> TYPE: PRT
<213> ORGANISM: Artificial Sequence
<220> FEATURE:
<223> OTHER INFORMATION: Synthetic: 19H6-F7 HVR-H1

<400> SEQUENCE: 62

Ser Tyr Gly Met Ser
1               5

<210> SEQ ID NO 63
<211> LENGTH: 17
<212> TYPE: PRT
<213> ORGANISM: Artificial Sequence
<220> FEATURE:
<223> OTHER INFORMATION: Synthetic: 19H6-F7 HVR-H2

<400> SEQUENCE: 63

Thr Ile Ser Ser Gly Gly Thr Tyr Thr Tyr Tyr Pro Asp Ser Val Lys
1               5                   10                  15

Gly

<210> SEQ ID NO 64
<211> LENGTH: 8
<212> TYPE: PRT
<213> ORGANISM: Artificial Sequence
<220> FEATURE:
<223> OTHER INFORMATION: Synthetic: 19H6-F7 HVR-H3

<400> SEQUENCE: 64

Ser Tyr Asp Gly Ala Met Asp Tyr
1               5

<210> SEQ ID NO 65
<211> LENGTH: 16
<212> TYPE: PRT
<213> ORGANISM: Artificial Sequence
<220> FEATURE:
<223> OTHER INFORMATION: Synthetic: 19H6-F7 HVR-L1

<400> SEQUENCE: 65

Arg Ser Ser Gln Ser Ile Val His Ser Asn Gly Asn Thr Tyr Leu Glu
1               5                   10                  15

<210> SEQ ID NO 66
<211> LENGTH: 7
<212> TYPE: PRT
<213> ORGANISM: Artificial Sequence
<220> FEATURE:
<223> OTHER INFORMATION: Synthetic: 19H6-F7 HVR-L2

<400> SEQUENCE: 66

Lys Val Ser Asn Arg Phe Ser
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic: 19H6-F7 HVR-L3

<400> SEQUENCE: 67

Phe Gln Gly Ser Leu Val Pro Trp Thr
1               5

<210> SEQ ID NO 68

<400> SEQUENCE: 68

000

<210> SEQ ID NO 69

<400> SEQUENCE: 69

000

<210> SEQ ID NO 70
<211> LENGTH: 113
<212> TYPE: PRT
<213> ORGANISM: Artificial Sequence
<220> FEATURE:
<223> OTHER INFORMATION: Synthetic: 94B2-C1 heavy chain variable region
      (VH)

<400> SEQUENCE: 70

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Leu Thr Gly Tyr
            20                  25                  30

Thr Met Asn Trp Val Lys Gln Ser His Gly Lys Asn Leu Glu Trp Ile
        35                  40                  45

Gly Leu Ile Ser Pro Tyr Asn Gly Val Thr Ser Tyr Asn Gln Lys Phe
    50                  55                  60

Lys Gly Lys Ala Thr Leu Thr Val Asp Lys Ser Ser Asn Thr Ala Tyr
65                  70                  75                  80

Met Glu Leu Leu Ser Leu Thr Phe Glu Asp Ser Ala Val Tyr Tyr Cys
                85                  90                  95

Ala Arg Gln Gly Ala Tyr Trp Gly Gln Gly Thr Leu Val Thr Val Ser
            100                 105                 110

Ala

<210> SEQ ID NO 71
<211> LENGTH: 112
<212> TYPE: PRT

```
<213> ORGANISM: Artificial Sequence
<220> FEATURE:
<223> OTHER INFORMATION: Synthetic: 94B2-C1 light chain variable region
      (VL)

<400> SEQUENCE: 71

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Thr Lys Leu Glu Ile Lys
            100                 105                 110

<210> SEQ ID NO 72
<211> LENGTH: 5
<212> TYPE: PRT
<213> ORGANISM: Artificial Sequence
<220> FEATURE:
<223> OTHER INFORMATION: Synthetic: 94B2-C1 HVR-H1

<400> SEQUENCE: 72

Gly Tyr Thr Met Asn
1               5

<210> SEQ ID NO 73
<211> LENGTH: 17
<212> TYPE: PRT
<213> ORGANISM: Artificial Sequence
<220> FEATURE:
<223> OTHER INFORMATION: Synthetic: 94B2-C1 HVR-H2

<400> SEQUENCE: 73

Leu Ile Ser Pro Tyr Asn Gly Val Thr Ser Tyr Asn Gln Lys Phe Lys
1               5                   10                  15

Gly

<210> SEQ ID NO 74
<211> LENGTH: 4
<212> TYPE: PRT
<213> ORGANISM: Artificial Sequence
<220> FEATURE:
<223> OTHER INFORMATION: Synthetic: 94B2-C1 HVR-H3

<400> SEQUENCE: 74

Gln Gly Ala Tyr
1

<210> SEQ ID NO 75
<211> LENGTH: 16
<212> TYPE: PRT
<213> ORGANISM: Artificial Sequence
<220> FEATURE:
<223> OTHER INFORMATION: Synthetic: 94B2-C1 HVR-L1

<400> SEQUENCE: 75
```

```
Lys Ser Ser Gln Ser Leu Leu Asp Ser Asp Gly Lys Thr Tyr Leu Asn
1               5                   10                  15
```

<210> SEQ ID NO 76
<211> LENGTH: 7
<212> TYPE: PRT
<213> ORGANISM: Artificial Sequence
<220> FEATURE:
<223> OTHER INFORMATION: Synthetic: 94B2-C1 HVR-L2

<400> SEQUENCE: 76

```
Leu Val Ser Lys Leu Asp Ser
1               5
```

<210> SEQ ID NO 77
<211> LENGTH: 9
<212> TYPE: PRT
<213> ORGANISM: Artificial Sequence
<220> FEATURE:
<223> OTHER INFORMATION: Synthetic: 94B2-C1 HVR-L3

<400> SEQUENCE: 77

```
Trp Gln Gly Thr His Phe Pro Trp Thr
1               5
```

<210> SEQ ID NO 78

<400> SEQUENCE: 78

000

<210> SEQ ID NO 79

<400> SEQUENCE: 79

000

<210> SEQ ID NO 80
<211> LENGTH: 115
<212> TYPE: PRT
<213> ORGANISM: Artificial Sequence
<220> FEATURE:
<223> OTHER INFORMATION: Synthetic: 125B11-H3 heavy chain variable
    region (VH)

<400> SEQUENCE: 80

```
Glu Val Lys Leu Glu Glu Ser Gly Gly Gly Leu Val Gln Pro Gly Gly
1               5                   10                  15

Ser Met Lys Leu Ser Cys Val Ala Ser Arg Phe Ile Phe Ser Asn Tyr
            20                  25                  30

Trp Met Asn Trp Val Arg Gln Ser Pro Glu Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Gly Thr Thr Tyr Trp Gly Gln Gly Thr Thr Leu Thr
            100                 105                 110

Val Ser Ser
        115
```

<210> SEQ ID NO 81
<211> LENGTH: 107
<212> TYPE: PRT
<213> ORGANISM: Artificial Sequence
<220> FEATURE:
<223> OTHER INFORMATION: Synthetic: 125B11-H3 light chain variable region (VL)

<400> SEQUENCE: 81

Asp Ile Val Met Thr Gln Ser Gln Lys Phe Leu Ser Thr Ser Val Gly
1               5                   10                  15

Asp Arg Val Asn Ile Thr Cys Lys Ala Ser Gln Asn Val Gly Thr Ala
            20                  25                  30

Val Ala Trp Tyr Gln Gln Lys Pro Gly Gln Ser Pro Gly Leu Leu Ile
        35                  40                  45

Tyr Ser Ala Ser Ile Arg Tyr Thr Gly Val Pro Asp Arg Phe Thr Gly
50                  55                  60

Asn Gly Ser Gly Thr Asp Phe Thr Leu Thr Ile Ser Asp Met Gln Ser
65                  70                  75                  80

Glu Asp Leu Ala Asp Tyr Phe Cys Gln Gln Phe Arg Thr Tyr Pro Tyr
                85                  90                  95

Thr Phe Gly Gly Gly Thr Lys Leu Glu Ile Lys
            100                 105

<210> SEQ ID NO 82
<211> LENGTH: 5
<212> TYPE: PRT
<213> ORGANISM: Artificial Sequence
<220> FEATURE:
<223> OTHER INFORMATION: Synthetic: 125B11-H3 HVR-H1

<400> SEQUENCE: 82

Asn Tyr Trp Met Asn
1               5

<210> SEQ ID NO 83
<211> LENGTH: 19
<212> TYPE: PRT
<213> ORGANISM: Artificial Sequence
<220> FEATURE:
<223> OTHER INFORMATION: Synthetic: 125B11-H3 HVR-H2

<400> SEQUENCE: 83

Gln Ile Arg Leu Lys Ser Asp Asn Tyr Ala Thr His Tyr Ala Glu Ser
1               5                   10                  15

Val Lys Gly

<210> SEQ ID NO 84
<211> LENGTH: 4
<212> TYPE: PRT
<213> ORGANISM: Artificial Sequence
<220> FEATURE:
<223> OTHER INFORMATION: Synthetic: 125B11-H3 HVR-H3

<400> SEQUENCE: 84

Gly Thr Thr Tyr
1

<210> SEQ ID NO 85
<211> LENGTH: 11
<212> TYPE: PRT
<213> ORGANISM: Artificial Sequence
<220> FEATURE:
<223> OTHER INFORMATION: Synthetic: 125B11-H3 HVR-L1

```
<400> SEQUENCE: 85

Lys Ala Ser Gln Asn Val Gly Thr Ala Val Ala
1               5                   10

<210> SEQ ID NO 86
<211> LENGTH: 7
<212> TYPE: PRT
<213> ORGANISM: Artificial Sequence
<220> FEATURE:
<223> OTHER INFORMATION: Synthetic: 125B11-H3 HVR-L2

<400> SEQUENCE: 86

Ser Ala Ser Ile Arg Tyr Thr
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic: 125B11-H3 HVR-L3

<400> SEQUENCE: 87

Gln Gln Phe Arg Thr Tyr Pro Tyr Thr
1               5

<210> SEQ ID NO 88

<400> SEQUENCE: 88

000

<210> SEQ ID NO 89

<400> SEQUENCE: 89

000

<210> SEQ ID NO 90
<211> LENGTH: 115
<212> TYPE: PRT
<213> ORGANISM: Artificial Sequence
<220> FEATURE:
<223> OTHER INFORMATION: Synthetic: 113F5-F7 heavy chain variable region
      (VH)

<400> SEQUENCE: 90

Glu Val Lys Leu Glu Glu Ser Gly Gly Gly Leu Val Gln Pro Gly Gly
1               5                   10                  15

Ser Met Arg Leu Ser Cys Val Ala Ser Glu Phe Thr Phe Ser Asn Tyr
            20                  25                  30

Trp Met Asn Trp Ile Arg Gln Ser Pro Glu Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Ala Ser Asn Phe Ser
65                  70                  75                  80

Val Tyr Leu Gln Met Asn Asn Leu Arg Ala Glu Asp Thr Gly Ile Tyr
                85                  90                  95

Tyr Cys Thr Gly Gly Thr Ser Tyr Trp Gly Gln Gly Thr Thr Leu Thr
            100                 105                 110

Val Ser Ser
```

-continued

```
115

<210> SEQ ID NO 91
<211> LENGTH: 107
<212> TYPE: PRT
<213> ORGANISM: Artificial Sequence
<220> FEATURE:
<223> OTHER INFORMATION: Synthetic: 113F5-F7 light chain variable region
      (VL)

<400> SEQUENCE: 91

Asp Ile Val Met Thr Gln Ser Gln Lys Ile Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Arg Pro Gly His Ser Pro Lys Leu Leu Ile
        35                  40                  45

Tyr Ser Ala Ser Arg Arg Phe Ser Gly Val Pro Asp Arg Phe Thr Gly
    50                  55                  60

Ser Gly Ser Gly Thr Asp Phe Thr Leu Thr Ile Asn Val Gln Ser
65                  70                  75                  80

Glu Asp Leu Ala Asp Tyr Phe Cys Gln Gln Phe Ser Thr Tyr Pro Tyr
                85                  90                  95

Thr Phe Gly Val Gly Thr Lys Leu Glu Ile Lys
            100                 105

<210> SEQ ID NO 92
<211> LENGTH: 5
<212> TYPE: PRT
<213> ORGANISM: Artificial Sequence
<220> FEATURE:
<223> OTHER INFORMATION: Synthetic: 113F5-F7 HVR-H1

<400> SEQUENCE: 92

Asn Tyr Trp Met Asn
1               5

<210> SEQ ID NO 93
<211> LENGTH: 19
<212> TYPE: PRT
<213> ORGANISM: Artificial Sequence
<220> FEATURE:
<223> OTHER INFORMATION: Synthetic: 113F5-F7 HVR-H2

<400> SEQUENCE: 93

Gln Ile Arg Leu Lys Ser Asp Asn Tyr Ala Thr His Tyr Ala Glu Ser
1               5                   10                  15

Val Lys Gly

<210> SEQ ID NO 94
<211> LENGTH: 4
<212> TYPE: PRT
<213> ORGANISM: Artificial Sequence
<220> FEATURE:
<223> OTHER INFORMATION: Synthetic: 113F5-F7 HVR-H3

<400> SEQUENCE: 94

Gly Thr Ser Tyr
1

<210> SEQ ID NO 95
<211> LENGTH: 11
<212> TYPE: PRT
```

<213> ORGANISM: Artificial Sequence
<220> FEATURE:
<223> OTHER INFORMATION: Synthetic: 113F5-F7 HVR-L1

<400> SEQUENCE: 95

Lys Ala Ser Gln Asn Val Gly Thr Ala Val Ala
1               5                   10

<210> SEQ ID NO 96
<211> LENGTH: 7
<212> TYPE: PRT
<213> ORGANISM: Artificial Sequence
<220> FEATURE:
<223> OTHER INFORMATION: Synthetic: 113F5-F7 HVR-L2

<400> SEQUENCE: 96

Ser Ala Ser Arg Arg Phe Ser
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic: 113F5-F7 HVR-L3

<400> SEQUENCE: 97

Gln Gln Phe Ser Thr Tyr Pro Tyr Thr
1               5

<210> SEQ ID NO 98

<400> SEQUENCE: 98

000

<210> SEQ ID NO 99

<400> SEQUENCE: 99

000

<210> SEQ ID NO 100
<211> LENGTH: 121
<212> TYPE: PRT
<213> ORGANISM: Artificial Sequence
<220> FEATURE:
<223> OTHER INFORMATION: Synthetic: 26C1-B11 heavy chain variable region
      (VH)

<400> SEQUENCE: 100

Glu Val His Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met Tyr Trp Val Lys Gln Arg Pro Glu Gln Gly Leu Glu Trp Ile
        35                  40                  45

Gly Trp Ile Asp Pro Glu Asn Gly Asp Thr Glu Tyr Phe Pro Lys Phe
    50                  55                  60

Gln Gly Lys Ala Thr Met Thr Ala Asp Thr Ser Ser Lys Thr Ala Tyr
65                  70                  75                  80

Leu Gln Leu Ser Ser Leu Thr Ser Glu Asp Thr Ala Val Tyr Tyr Cys
                85                  90                  95

Asn Ala Trp Arg Ala Arg Ala Thr Asn Ser Ala Leu Asp Tyr Trp Gly

```
                100             105             110
Gln Gly Thr Ser Val Thr Val Ser Ser
        115             120

<210> SEQ ID NO 101
<211> LENGTH: 112
<212> TYPE: PRT
<213> ORGANISM: Artificial Sequence
<220> FEATURE:
<223> OTHER INFORMATION: Synthetic: 26C1-B11 light chain variable region
      (VL)

<400> SEQUENCE: 101

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Arg Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

<210> SEQ ID NO 102
<211> LENGTH: 5
<212> TYPE: PRT
<213> ORGANISM: Artificial Sequence
<220> FEATURE:
<223> OTHER INFORMATION: Synthetic: 26C1-B11 HVR-H1

<400> SEQUENCE: 102

Asp Tyr Tyr Met Tyr
1               5

<210> SEQ ID NO 103
<211> LENGTH: 17
<212> TYPE: PRT
<213> ORGANISM: Artificial Sequence
<220> FEATURE:
<223> OTHER INFORMATION: Synthetic: 26C1-B11 HVR-H2

<400> SEQUENCE: 103

Trp Ile Asp Pro Glu Asn Gly Asp Thr Glu Tyr Phe Pro Lys Phe Gln
1               5                   10                  15

Gly

<210> SEQ ID NO 104
<211> LENGTH: 12
<212> TYPE: PRT
<213> ORGANISM: Artificial Sequence
<220> FEATURE:
<223> OTHER INFORMATION: Synthetic: 26C1-B11 HVR-H3

<400> SEQUENCE: 104

Trp Arg Ala Arg Ala Thr Asn Ser Ala Leu Asp Tyr
1               5                   10
```

```
<210> SEQ ID NO 105
<211> LENGTH: 16
<212> TYPE: PRT
<213> ORGANISM: Artificial Sequence
<220> FEATURE:
<223> OTHER INFORMATION: Synthetic: 26C1-B11 HVR-L1

<400> SEQUENCE: 105

Lys Ser Ser Gln Ser Leu Leu Asp Ser Asp Gly Lys Thr Tyr Leu Asn
1               5                   10                  15

<210> SEQ ID NO 106
<211> LENGTH: 7
<212> TYPE: PRT
<213> ORGANISM: Artificial Sequence
<220> FEATURE:
<223> OTHER INFORMATION: Synthetic: 26C1-B11 HVR-L2

<400> SEQUENCE: 106

Leu Val Ser Lys Leu Asp Ser
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic: 26C1-B11 HVR-L3

<400> SEQUENCE: 107

Trp Gln Gly Thr His Phe Pro Trp Thr
1               5

<210> SEQ ID NO 108

<400> SEQUENCE: 108

000

<210> SEQ ID NO 109

<400> SEQUENCE: 109

000

<210> SEQ ID NO 110
<211> LENGTH: 121
<212> TYPE: PRT
<213> ORGANISM: Artificial Sequence
<220> FEATURE:
<223> OTHER INFORMATION: Synthetic: 26C1-C8 heavy chain variable region
      (VH)

<400> SEQUENCE: 110

Glu Val His Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met Tyr Trp Val Lys Gln Arg Pro Glu Gln Gly Leu Glu Trp Ile
        35                  40                  45

Gly Trp Ile Asp Pro Glu Asn Gly Asp Thr Glu Tyr Phe Pro Lys Phe
    50                  55                  60

Gln Gly Lys Ala Thr Met Thr Ala Asp Thr Ser Ser Lys Thr Ala Tyr
65                  70                  75                  80

Leu Gln Leu Ser Ser Leu Thr Ser Glu Asp Thr Ala Val Tyr Tyr Cys
```

-continued

```
                85                  90                  95
Asn Ala Trp Arg Ala Arg Ala Thr Asn Ser Ala Leu Asp Tyr Trp Gly
            100                 105                 110

Gln Gly Thr Ser Val Thr Val Ser Ser
            115                 120
```

<210> SEQ ID NO 111
<211> LENGTH: 112
<212> TYPE: PRT
<213> ORGANISM: Artificial Sequence
<220> FEATURE:
<223> OTHER INFORMATION: Synthetic: 26C1-C8 light chain variable region
      (VL)

<400> SEQUENCE: 111

```
Asp Val Val Met Thr Gln Thr Pro Leu Thr Leu Ser Val Thr Ile Gly
1               5                   10                  15

Gln Pro Ala Ser Ile Ser Cys Lys Ser Gln Ser Leu Leu Asp Ser
            20                  25                  30

Asp Gly Lys Thr Tyr Leu Asn Trp Leu Leu Arg Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110
```

<210> SEQ ID NO 112
<211> LENGTH: 5
<212> TYPE: PRT
<213> ORGANISM: Artificial Sequence
<220> FEATURE:
<223> OTHER INFORMATION: Synthetic: 26C1-C8 HVR-H1

<400> SEQUENCE: 112

```
Asp Tyr Tyr Met Tyr
1               5
```

<210> SEQ ID NO 113
<211> LENGTH: 17
<212> TYPE: PRT
<213> ORGANISM: Artificial Sequence
<220> FEATURE:
<223> OTHER INFORMATION: Synthetic: 26C1-C8 HVR-H2

<400> SEQUENCE: 113

```
Trp Ile Asp Pro Glu Asn Gly Asp Thr Glu Tyr Phe Pro Lys Phe Gln
1               5                   10                  15

Gly
```

<210> SEQ ID NO 114
<211> LENGTH: 12
<212> TYPE: PRT
<213> ORGANISM: Artificial Sequence
<220> FEATURE:
<223> OTHER INFORMATION: Synthetic: 26C1-C8 HVR-H3

<400> SEQUENCE: 114

Trp Arg Ala Arg Ala Thr Asn Ser Ala Leu Asp Tyr

```
1               5                   10
```

<210> SEQ ID NO 115
<211> LENGTH: 16
<212> TYPE: PRT
<213> ORGANISM: Artificial Sequence
<220> FEATURE:
<223> OTHER INFORMATION: Synthetic: 26C1-C8 HVR-L1

<400> SEQUENCE: 115

```
Lys Ser Ser Gln Ser Leu Leu Asp Ser Asp Gly Lys Thr Tyr Leu Asn
1               5                   10                  15
```

<210> SEQ ID NO 116
<211> LENGTH: 7
<212> TYPE: PRT
<213> ORGANISM: Artificial Sequence
<220> FEATURE:
<223> OTHER INFORMATION: Synthetic: 26C1-C8 HVR-L2

<400> SEQUENCE: 116

```
Leu Val Ser Lys Leu Asp Ser
1               5
```

<210> SEQ ID NO 117
<211> LENGTH: 9
<212> TYPE: PRT
<213> ORGANISM: Artificial Sequence
<220> FEATURE:
<223> OTHER INFORMATION: Synthetic: 26C1-C8 HVR-L3

<400> SEQUENCE: 117

```
Trp Gln Gly Thr His Phe Pro Trp Thr
1               5
```

<210> SEQ ID NO 118

<400> SEQUENCE: 118

000

<210> SEQ ID NO 119

<400> SEQUENCE: 119

000

<210> SEQ ID NO 120
<211> LENGTH: 117
<212> TYPE: PRT
<213> ORGANISM: Artificial Sequence
<220> FEATURE:
<223> OTHER INFORMATION: Synthetic: 30G1-B2 heavy chain variable region
      (VH)

<400> SEQUENCE: 120

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met Tyr Trp Val Lys Gln Thr Pro Val His Gly Leu Glu Trp Ile
        35                  40                  45

Gly Ala Ile Asp Pro Glu Thr Gly Asp Thr Ala Tyr Asn Gln Lys Phe
    50                  55                  60

Lys Gly Lys Ala Thr Leu Thr Ala Asp Lys Ser Ser Asn Thr Ala Tyr
```

```
                65                  70                  75                  80
Met Glu Leu Arg Ser Leu Thr Ser Glu Asp Ser Ala Val Tyr Tyr Cys
                        85                  90                  95

Ile Arg Gln Tyr Gly Asn Trp Phe Pro Tyr Trp Gly Gln Gly Thr Leu
                100                 105                 110

Val Thr Val Ser Ala
            115

<210> SEQ ID NO 121
<211> LENGTH: 112
<212> TYPE: PRT
<213> ORGANISM: Artificial Sequence
<220> FEATURE:
<223> OTHER INFORMATION: Synthetic: 30G1-B2 light chain variable region
      (VL)

<400> SEQUENCE: 121

Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ala
                20                  25                  30

Asn Gly Asn Thr Tyr Leu His Trp Phe Leu Gln Lys Pro Gly Leu Ser
                35                  40                  45

Pro Lys Leu Leu Ile Tyr Lys Val Ser Asn Arg Phe Ser Gly Val Pro
        50                  55                  60

Asp Arg Phe Ser Gly Gly Gly Ser Gly Thr Asp Phe Thr Leu Lys Ile
65                  70                  75                  80

Thr Arg Leu Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
                100                 105                 110

<210> SEQ ID NO 122
<211> LENGTH: 5
<212> TYPE: PRT
<213> ORGANISM: Artificial Sequence
<220> FEATURE:
<223> OTHER INFORMATION: Synthetic: 30G1-B2 HVR-H1

<400> SEQUENCE: 122

Asp Tyr Glu Met Tyr
1               5

<210> SEQ ID NO 123
<211> LENGTH: 17
<212> TYPE: PRT
<213> ORGANISM: Artificial Sequence
<220> FEATURE:
<223> OTHER INFORMATION: Synthetic: 30G1-B2 HVR-H2

<400> SEQUENCE: 123

Ala Ile Asp Pro Glu Thr Gly Asp Thr Ala Tyr Asn Gln Lys Phe Lys
1               5                   10                  15

Gly

<210> SEQ ID NO 124
<211> LENGTH: 8
<212> TYPE: PRT
<213> ORGANISM: Artificial Sequence
<220> FEATURE:
<223> OTHER INFORMATION: Synthetic: 30G1-B2 HVR-H3
```

```
<400> SEQUENCE: 124

Gln Tyr Gly Asn Trp Phe Pro Tyr
1               5

<210> SEQ ID NO 125
<211> LENGTH: 16
<212> TYPE: PRT
<213> ORGANISM: Artificial Sequence
<220> FEATURE:
<223> OTHER INFORMATION: Synthetic: 30G1-B2 HVR-L1

<400> SEQUENCE: 125

Arg Ser Ser Gln Ser Leu Val His Ala Asn Gly Asn Thr Tyr Leu His
1               5                   10                  15

<210> SEQ ID NO 126
<211> LENGTH: 7
<212> TYPE: PRT
<213> ORGANISM: Artificial Sequence
<220> FEATURE:
<223> OTHER INFORMATION: Synthetic: 30G1-B2 HVR-L2

<400> SEQUENCE: 126

Lys Val Ser Asn Arg Phe Ser
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic: 30G1-B2 HVR-L3

<400> SEQUENCE: 127

Ser Gln Ser Thr His Val Pro Phe Thr
1               5

<210> SEQ ID NO 128

<400> SEQUENCE: 128

000

<210> SEQ ID NO 129

<400> SEQUENCE: 129

000

<210> SEQ ID NO 130
<211> LENGTH: 114
<212> TYPE: PRT
<213> ORGANISM: Artificial Sequence
<220> FEATURE:
<223> OTHER INFORMATION: Synthetic: 66F5-A1 heavy chain variable region
      (VH)

<400> SEQUENCE: 130

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ile Asp Tyr
            20                  25                  30

Glu Met Asn Trp Val Lys Gln Thr Pro Val His Gly Leu Glu Trp Ile
        35                  40                  45

Gly Ala Ile Asp Pro Glu Asn Gly Gly Thr Ala Tyr Asn Gln Lys Phe
```

-continued

```
               50                  55                  60
Lys Gly Lys Ala Ile Val Thr Ala Asp Lys Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ser Gly Pro His Phe Asp Tyr Trp Gly Gln Gly Thr Thr Leu Thr Val
            100                 105                 110

Ser Ser

<210> SEQ ID NO 131
<211> LENGTH: 113
<212> TYPE: PRT
<213> ORGANISM: Artificial Sequence
<220> FEATURE:
<223> OTHER INFORMATION: Synthetic: 66F5-A1 light chain variable region
      (VL)

<400> SEQUENCE: 131

Asp Ile Val Met Thr Gln Ser Pro Ser Ser Leu Ala Met Ser Val Gly
 1               5                  10                  15

Gln Lys Val Thr Met Ser Cys Lys Ser Ser Gln Ser Leu Leu Asn Ser
             20                  25                  30

Ser Thr Gln Lys Asn Tyr Leu Ala Trp Tyr Gln Gln Lys Pro Gly Gln
         35                  40                  45

Ser Pro Lys Leu Leu Val Tyr Phe Ala Ser Thr Arg Glu Ser Gly Val
     50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                 85                  90                  95

His Tyr Ser Thr Pro Tyr Thr Phe Gly Gly Gly Thr Lys Leu Glu Ile
            100                 105                 110

Lys

<210> SEQ ID NO 132
<211> LENGTH: 5
<212> TYPE: PRT
<213> ORGANISM: Artificial Sequence
<220> FEATURE:
<223> OTHER INFORMATION: Synthetic: 66F5-A1 HVR-H1

<400> SEQUENCE: 132

Asp Tyr Glu Met Asn
 1               5

<210> SEQ ID NO 133
<211> LENGTH: 17
<212> TYPE: PRT
<213> ORGANISM: Artificial Sequence
<220> FEATURE:
<223> OTHER INFORMATION: Synthetic: 66F5-A1 HVR-H2

<400> SEQUENCE: 133

Ala Ile Asp Pro Glu Asn Gly Gly Thr Ala Tyr Asn Gln Lys Phe Lys
 1               5                  10                  15

Gly

<210> SEQ ID NO 134
<211> LENGTH: 5
<212> TYPE: PRT
```

<213> ORGANISM: Artificial Sequence
<220> FEATURE:
<223> OTHER INFORMATION: Synthetic: 66F5-A1 HVR-H3

<400> SEQUENCE: 134

Pro His Phe Asp Tyr
1               5

<210> SEQ ID NO 135
<211> LENGTH: 17
<212> TYPE: PRT
<213> ORGANISM: Artificial Sequence
<220> FEATURE:
<223> OTHER INFORMATION: Synthetic: 66F5-A1 HVR-L1

<400> SEQUENCE: 135

Lys Ser Ser Gln Ser Leu Leu Asn Ser Ser Thr Gln Lys Asn Tyr Leu
1               5                   10                  15

Ala

<210> SEQ ID NO 136
<211> LENGTH: 7
<212> TYPE: PRT
<213> ORGANISM: Artificial Sequence
<220> FEATURE:
<223> OTHER INFORMATION: Synthetic: 66F5-A1 HVR-L2

<400> SEQUENCE: 136

Phe Ala Ser Thr Arg Glu Ser
1               5

<210> SEQ ID NO 137
<211> LENGTH: 9
<212> TYPE: PRT
<213> ORGANISM: Artificial Sequence
<220> FEATURE:
<223> OTHER INFORMATION: Synthetic: 66F5-A1 HVR-L3

<400> SEQUENCE: 137

Gln Gln His Tyr Ser Thr Pro Tyr Thr
1               5

<210> SEQ ID NO 138

<400> SEQUENCE: 138

000

<210> SEQ ID NO 139

<400> SEQUENCE: 139

000

<210> SEQ ID NO 140
<211> LENGTH: 119
<212> TYPE: PRT
<213> ORGANISM: Artificial Sequence
<220> FEATURE:
<223> OTHER INFORMATION: Synthetic: 123E9-A1 heavy chain variable region
      (VH)

<400> SEQUENCE: 140

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr

```
                    20                  25                  30
Tyr Met Lys Trp Val Lys Gln Ser His Gly Lys Ser Leu Glu Trp Ile
            35                  40                  45

Gly Asp Ile Asp Pro Asn Asn Gly Gly Thr Ser Tyr Asn Gln Lys Phe
        50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Ala Gly Phe Gly Asp Ser Phe Ser Phe Trp Gly Leu Gly
                100                 105                 110

Thr Leu Val Thr Val Ser Ala
            115

<210> SEQ ID NO 141
<211> LENGTH: 112
<212> TYPE: PRT
<213> ORGANISM: Artificial Sequence
<220> FEATURE:
<223> OTHER INFORMATION: Synthetic: 123E9-A1 light chain variable region
      (VL)

<400> SEQUENCE: 141

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Phe Tyr Tyr Cys Phe Gln Gly
                85                  90                  95

Ser His Val Pro Pro Thr Phe Gly Gly Gly Thr Lys Leu Glu Ile Lys
                100                 105                 110

<210> SEQ ID NO 142
<211> LENGTH: 5
<212> TYPE: PRT
<213> ORGANISM: Artificial Sequence
<220> FEATURE:
<223> OTHER INFORMATION: Synthetic: 123E9-A1 HVR-H1

<400> SEQUENCE: 142

Asp Tyr Tyr Met Lys
1               5

<210> SEQ ID NO 143
<211> LENGTH: 17
<212> TYPE: PRT
<213> ORGANISM: Artificial Sequence
<220> FEATURE:
<223> OTHER INFORMATION: Synthetic: 123E9-A1 HVR-H2

<400> SEQUENCE: 143

Asp Ile Asp Pro Asn Asn Gly Gly Thr Ser Tyr Asn Gln Lys Phe Lys
1               5                   10                  15

Gly
```

<210> SEQ ID NO 144
<211> LENGTH: 10
<212> TYPE: PRT
<213> ORGANISM: Artificial Sequence
<220> FEATURE:
<223> OTHER INFORMATION: Synthetic: 123E9-A1 HVR-H3

<400> SEQUENCE: 144

Ser Ala Gly Phe Gly Asp Ser Phe Ser Phe
1               5                   10

<210> SEQ ID NO 145
<211> LENGTH: 16
<212> TYPE: PRT
<213> ORGANISM: Artificial Sequence
<220> FEATURE:
<223> OTHER INFORMATION: Synthetic: 123E9-A1 HVR-L1

<400> SEQUENCE: 145

Arg Ser Ser Gln Ser Ile Val His Ser Asn Gly Asn Thr Tyr Leu Glu
1               5                   10                  15

<210> SEQ ID NO 146
<211> LENGTH: 7
<212> TYPE: PRT
<213> ORGANISM: Artificial Sequence
<220> FEATURE:
<223> OTHER INFORMATION: Synthetic: 123E9-A1 HVR-L2

<400> SEQUENCE: 146

Lys Val Ser Asn Arg Phe Ser
1               5

<210> SEQ ID NO 147
<211> LENGTH: 9
<212> TYPE: PRT
<213> ORGANISM: Artificial Sequence
<220> FEATURE:
<223> OTHER INFORMATION: Synthetic: 123E9-A1 HVR-L3

<400> SEQUENCE: 147

Phe Gln Gly Ser His Val Pro Pro Thr
1               5

<210> SEQ ID NO 148

<400> SEQUENCE: 148

000

<210> SEQ ID NO 149

<400> SEQUENCE: 149

000

<210> SEQ ID NO 150
<211> LENGTH: 119
<212> TYPE: PRT
<213> ORGANISM: Artificial Sequence
<220> FEATURE:
<223> OTHER INFORMATION: Synthetic: 15C6-A7 heavy chain variable region
      (VH)

<400> SEQUENCE: 150

Glu Val Gln Leu Gln Gln Ser Gly Pro Glu Leu Val Lys Pro Gly Ala

```
                1               5                   10                  15
Ser Val Met Met Thr Cys Lys Ala Ser Gly Tyr Thr Phe Thr Asp Tyr
                20                  25                  30

Tyr Met Lys Trp Val Lys Gln Ser Asn Gly Lys Ser Leu Glu Trp Ile
                35                  40                  45

Gly Asp Leu Asp Pro Tyr Thr Gly Gly Ala Asn Tyr Asn Gln Lys Phe
        50                  55                  60

Lys Gly Lys Ala Thr Leu Thr Val Asp Lys Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Ser Arg Gly Tyr Gly Asp Ser Phe Ala Tyr Trp Gly Gln Gly
                100                 105                 110

Thr Leu Val Thr Val Ser Ala
        115
```

<210> SEQ ID NO 151
<211> LENGTH: 112
<212> TYPE: PRT
<213> ORGANISM: Artificial Sequence
<220> FEATURE:
<223> OTHER INFORMATION: Synthetic: 15C6-A7 light chain variable region
      (VL)

<400> SEQUENCE: 151

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
                20                  25                  30

Asn Gly Asn Thr Tyr Leu Glu Trp Tyr Leu Gln Lys Pro Gly Gln Ser
                35                  40                  45

Pro Lys Leu Leu Ile Tyr Lys Val Ser Asn Arg Phe Ser Gly Val Pro
        50                  55                  60

Asp Lys Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Ser His Val Pro Pro Thr Phe Gly Gly Gly Thr Lys Leu Glu Ile Lys
                100                 105                 110
```

<210> SEQ ID NO 152
<211> LENGTH: 5
<212> TYPE: PRT
<213> ORGANISM: Artificial Sequence
<220> FEATURE:
<223> OTHER INFORMATION: Synthetic: 15C6-A7 HVR-H1

<400> SEQUENCE: 152

```
Asp Tyr Tyr Met Lys
1               5
```

<210> SEQ ID NO 153
<211> LENGTH: 17
<212> TYPE: PRT
<213> ORGANISM: Artificial Sequence
<220> FEATURE:
<223> OTHER INFORMATION: Synthetic: 15C6-A7 HVR-H2

<400> SEQUENCE: 153

```
Asp Leu Asp Pro Tyr Thr Gly Gly Ala Asn Tyr Asn Gln Lys Phe Lys
```

Gly

<210> SEQ ID NO 154
<211> LENGTH: 10
<212> TYPE: PRT
<213> ORGANISM: Artificial Sequence
<220> FEATURE:
<223> OTHER INFORMATION: Synthetic: 15C6-A7 HVR-H3

<400> SEQUENCE: 154

Ser Arg Gly Tyr Gly Asp Ser Phe Ala Tyr
1               5                   10

<210> SEQ ID NO 155
<211> LENGTH: 16
<212> TYPE: PRT
<213> ORGANISM: Artificial Sequence
<220> FEATURE:
<223> OTHER INFORMATION: Synthetic: 15C6-A7 HVR-L1

<400> SEQUENCE: 155

Arg Ser Ser Gln Asn Ile Val His Ser Asn Gly Asn Thr Tyr Leu Glu
1               5                   10                  15

<210> SEQ ID NO 156
<211> LENGTH: 7
<212> TYPE: PRT
<213> ORGANISM: Artificial Sequence
<220> FEATURE:
<223> OTHER INFORMATION: Synthetic: 15C6-A7 HVR-L2

<400> SEQUENCE: 156

Lys Val Ser Asn Arg Phe Ser
1               5

<210> SEQ ID NO 157
<211> LENGTH: 9
<212> TYPE: PRT
<213> ORGANISM: Artificial Sequence
<220> FEATURE:
<223> OTHER INFORMATION: Synthetic: 15C6-A7 HVR-L3

<400> SEQUENCE: 157

Phe Gln Gly Ser His Val Pro Pro Thr
1               5

<210> SEQ ID NO 158

<400> SEQUENCE: 158

000

<210> SEQ ID NO 159

<400> SEQUENCE: 159

000

<210> SEQ ID NO 160
<211> LENGTH: 119
<212> TYPE: PRT
<213> ORGANISM: Artificial Sequence
<220> FEATURE:
<223> OTHER INFORMATION: Synthetic: 19F8-B1  heavy chain variable region
      (VH)

<400> SEQUENCE: 160

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Leu Asn Pro Asn Asn Gly Gly Thr Leu Tyr Asn Gln Lys Phe
    50                  55                  60

Lys Gly Gln Ala Thr Leu Thr Val Asp Lys Ser Ser Thr Ala Tyr
65                  70                  75                  80

Met Gln Phe Asn Ser Leu Thr Ser Glu Asp Ser Ala Val Tyr Tyr Cys
                85                  90                  95

Ala Arg Ser Ala Gly Tyr Gly Asp Ser Phe Ala Tyr Trp Gly Gln Gly
            100                 105                 110

Thr Leu Val Thr Val Ser Ala
        115

<210> SEQ ID NO 161
<211> LENGTH: 112
<212> TYPE: PRT
<213> ORGANISM: Artificial Sequence
<220> FEATURE:
<223> OTHER INFORMATION: Synthetic: 19F8-B1 light chain variable region
      (VL)

<400> SEQUENCE: 161

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Phe Gln Gly
                85                  90                  95

Ser His Val Pro Pro Thr Phe Gly Gly Gly Thr Lys Leu Glu Ile Lys
            100                 105                 110

<210> SEQ ID NO 162
<211> LENGTH: 5
<212> TYPE: PRT
<213> ORGANISM: Artificial Sequence
<220> FEATURE:
<223> OTHER INFORMATION: Synthetic: 19F8-B1 HVR-H1

<400> SEQUENCE: 162

Asp Tyr Tyr Met Lys
1               5

<210> SEQ ID NO 163
<211> LENGTH: 17
<212> TYPE: PRT
<213> ORGANISM: Artificial Sequence
<220> FEATURE:
<223> OTHER INFORMATION: Synthetic: 19F8-B1 HVR-H2

```
<400> SEQUENCE: 163

Asp Leu Asn Pro Asn Asn Gly Gly Thr Leu Tyr Asn Gln Lys Phe Lys
1               5                   10                  15

Gly

<210> SEQ ID NO 164
<211> LENGTH: 10
<212> TYPE: PRT
<213> ORGANISM: Artificial Sequence
<220> FEATURE:
<223> OTHER INFORMATION: Synthetic: 19F8-B1 HVR-H3

<400> SEQUENCE: 164

Ser Ala Gly Tyr Gly Asp Ser Phe Ala Tyr
1               5                   10

<210> SEQ ID NO 165
<211> LENGTH: 16
<212> TYPE: PRT
<213> ORGANISM: Artificial Sequence
<220> FEATURE:
<223> OTHER INFORMATION: Synthetic: 19F8-B1  HVR-L1

<400> SEQUENCE: 165

Arg Ser Ser Gln Asn Ile Val His Ser Asn Gly Asn Thr Tyr Leu Glu
1               5                   10                  15

<210> SEQ ID NO 166
<211> LENGTH: 7
<212> TYPE: PRT
<213> ORGANISM: Artificial Sequence
<220> FEATURE:
<223> OTHER INFORMATION: Synthetic: 19F8-B1  HVR-L2

<400> SEQUENCE: 166

Lys Val Ser Asn Arg Phe Ser
1               5

<210> SEQ ID NO 167
<211> LENGTH: 9
<212> TYPE: PRT
<213> ORGANISM: Artificial Sequence
<220> FEATURE:
<223> OTHER INFORMATION: Synthetic: 19F8-B1  HVR-L3

<400> SEQUENCE: 167

Phe Gln Gly Ser His Val Pro Pro Thr
1               5

<210> SEQ ID NO 168

<400> SEQUENCE: 168

000

<210> SEQ ID NO 169

<400> SEQUENCE: 169

000

<210> SEQ ID NO 170
<211> LENGTH: 119
<212> TYPE: PRT
<213> ORGANISM: Artificial Sequence
<220> FEATURE:
```

<223> OTHER INFORMATION: Synthetic: 24A11-D5 heavy chain variable region
      (VH)

<400> SEQUENCE: 170

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Leu Asn Pro Lys Asn Gly Ile Ile Tyr Asn Gln Lys Phe
    50                  55                  60

Lys Gly Gln Ala Thr Leu Thr Val Asp Lys Ser Ser Thr Ala Tyr
65                  70                  75                  80

Met Gln Leu Asn Ser Leu Thr Ser Glu Asp Ser Ala Val Phe Tyr Cys
                85                  90                  95

Ala Arg Ser Gly Gly Tyr Gly Asp Ser Phe Ala Tyr Trp Gly Gln Gly
            100                 105                 110

Thr Leu Val Thr Val Ser Ala
        115

<210> SEQ ID NO 171
<211> LENGTH: 112
<212> TYPE: PRT
<213> ORGANISM: Artificial Sequence
<220> FEATURE:
<223> OTHER INFORMATION: Synthetic: 24A11-D5 light chain variable region
      (VL)

<400> SEQUENCE: 171

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Phe Gln Gly
                85                  90                  95

Ser His Val Pro Pro Thr Phe Gly Gly Gly Thr Lys Leu Glu Ile Lys
            100                 105                 110

<210> SEQ ID NO 172
<211> LENGTH: 5
<212> TYPE: PRT
<213> ORGANISM: Artificial Sequence
<220> FEATURE:
<223> OTHER INFORMATION: Synthetic: 24A11-D5 HVR-H1

<400> SEQUENCE: 172

Asp Tyr Tyr Met Lys
1               5

<210> SEQ ID NO 173
<211> LENGTH: 17
<212> TYPE: PRT
<213> ORGANISM: Artificial Sequence

```
<220> FEATURE:
<223> OTHER INFORMATION: Synthetic: 24A11-D5 HVR-H2

<400> SEQUENCE: 173

Asp Leu Asn Pro Lys Asn Gly Gly Ile Ile Tyr Asn Gln Lys Phe Lys
1               5                   10                  15
Gly

<210> SEQ ID NO 174
<211> LENGTH: 10
<212> TYPE: PRT
<213> ORGANISM: Artificial Sequence
<220> FEATURE:
<223> OTHER INFORMATION: Synthetic: 24A11-D5 HVR-H3

<400> SEQUENCE: 174

Ser Gly Gly Tyr Gly Asp Ser Phe Ala Tyr
1               5                   10

<210> SEQ ID NO 175
<211> LENGTH: 16
<212> TYPE: PRT
<213> ORGANISM: Artificial Sequence
<220> FEATURE:
<223> OTHER INFORMATION: Synthetic: 24A11-D5 HVR-L1

<400> SEQUENCE: 175

Arg Ser Ser Gln Asn Ile Val His Ser Asn Gly Asn Thr Tyr Leu Glu
1               5                   10                  15

<210> SEQ ID NO 176
<211> LENGTH: 7
<212> TYPE: PRT
<213> ORGANISM: Artificial Sequence
<220> FEATURE:
<223> OTHER INFORMATION: Synthetic: 24A11-D5 HVR-L2

<400> SEQUENCE: 176

Lys Val Ser Asn Arg Phe Ser
1               5

<210> SEQ ID NO 177
<211> LENGTH: 9
<212> TYPE: PRT
<213> ORGANISM: Artificial Sequence
<220> FEATURE:
<223> OTHER INFORMATION: Synthetic: 24A11-D5 HVR-L3

<400> SEQUENCE: 177

Phe Gln Gly Ser His Val Pro Pro Thr
1               5

<210> SEQ ID NO 178

<400> SEQUENCE: 178

000

<210> SEQ ID NO 179

<400> SEQUENCE: 179

000

<210> SEQ ID NO 180
<211> LENGTH: 114
```

<212> TYPE: PRT
<213> ORGANISM: Artificial Sequence
<220> FEATURE:
<223> OTHER INFORMATION: Synthetic: 126F11-G11 heavy chain variable
      region (VH)

<400> SEQUENCE: 180

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Ser Lys Phe
    50                  55                  60

Gln Gly Lys Ala Thr Ile Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Leu Asp Phe Ala Tyr Gly Tyr Trp Gly Gln Gly Thr Thr Leu Thr Val
            100                 105                 110

Ser Ser

<210> SEQ ID NO 181
<211> LENGTH: 112
<212> TYPE: PRT
<213> ORGANISM: Artificial Sequence
<220> FEATURE:
<223> OTHER INFORMATION: Synthetic: 126F11-G11 light chain variable
      region (VL)

<400> SEQUENCE: 181

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Ala Phe Gly Gly Gly Thr Lys Leu Glu Ile Lys
            100                 105                 110

<210> SEQ ID NO 182
<211> LENGTH: 5
<212> TYPE: PRT
<213> ORGANISM: Artificial Sequence
<220> FEATURE:
<223> OTHER INFORMATION: Synthetic: 126F11-G11 HVR-H1

<400> SEQUENCE: 182

Asp Asp Tyr Met His
1               5

<210> SEQ ID NO 183
<211> LENGTH: 17

```
<212> TYPE: PRT
<213> ORGANISM: Artificial Sequence
<220> FEATURE:
<223> OTHER INFORMATION: Synthetic: 126F11-G11 HVR-H2

<400> SEQUENCE: 183

Trp Ile Asp Pro Glu Asn Gly Asp Thr Glu Tyr Ala Ser Lys Phe Gln
1               5                   10                  15

Gly

<210> SEQ ID NO 184
<211> LENGTH: 5
<212> TYPE: PRT
<213> ORGANISM: Artificial Sequence
<220> FEATURE:
<223> OTHER INFORMATION: Synthetic: 126F11-G11 HVR-H3

<400> SEQUENCE: 184

Phe Ala Tyr Gly Tyr
1               5

<210> SEQ ID NO 185
<211> LENGTH: 16
<212> TYPE: PRT
<213> ORGANISM: Artificial Sequence
<220> FEATURE:
<223> OTHER INFORMATION: Synthetic: 126F11-G11 HVR-L1

<400> SEQUENCE: 185

Arg Ser Ser Gln Ser Ile Val His Ser Asn Gly Asn Thr Tyr Leu Glu
1               5                   10                  15

<210> SEQ ID NO 186
<211> LENGTH: 7
<212> TYPE: PRT
<213> ORGANISM: Artificial Sequence
<220> FEATURE:
<223> OTHER INFORMATION: Synthetic: 126F11-G11 HVR-L2

<400> SEQUENCE: 186

Lys Val Ser Asn Arg Phe Ser
1               5

<210> SEQ ID NO 187
<211> LENGTH: 9
<212> TYPE: PRT
<213> ORGANISM: Artificial Sequence
<220> FEATURE:
<223> OTHER INFORMATION: Synthetic: 126F11-G11 HVR-L3

<400> SEQUENCE: 187

Phe Gln Gly Ser His Val Pro Pro Ala
1               5

<210> SEQ ID NO 188

<400> SEQUENCE: 188

000

<210> SEQ ID NO 189

<400> SEQUENCE: 189

000
```

```
<210> SEQ ID NO 190
<211> LENGTH: 120
<212> TYPE: PRT
<213> ORGANISM: Artificial Sequence
<220> FEATURE:
<223> OTHER INFORMATION: Synthetic: 89F4-A1 heavy chain variable region
      (VH)

<400> SEQUENCE: 190

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Ala Tyr Phe Ala Asp
    50                  55                  60

Ser Val Lys Asp Arg Phe Thr Ile Ser Arg Asp Asp Ser Gln Thr Met
65                  70                  75                  80

Leu Tyr Leu Gln Met Asn Asn Leu Lys Ser Glu Asp Thr Ala Met Tyr
                85                  90                  95

Tyr Cys Val Ser Gly Gly Asn Tyr Val Pro Phe Ala Tyr Trp Gly Gln
            100                 105                 110

Gly Thr Leu Val Thr Val Ser Ala
        115                 120

<210> SEQ ID NO 191
<211> LENGTH: 112
<212> TYPE: PRT
<213> ORGANISM: Artificial Sequence
<220> FEATURE:
<223> OTHER INFORMATION: Synthetic: 89F4-A1 light chain variable region
      (VL)

<400> SEQUENCE: 191

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Phe Tyr Ser
            20                  25                  30

Ser Glu Gln Arg Asn Tyr Leu Ala Trp Tyr Gln Gln Lys Pro Gly Gln
        35                  40                  45

Ser Pro Lys Leu Leu Ile Ser Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Gly Glu Asp Leu Ala Val Tyr Tyr Cys His Gln
                85                  90                  95

Tyr Leu Ser Ser Phe Thr Phe Gly Ser Gly Thr Lys Leu Glu Ile Lys
            100                 105                 110

<210> SEQ ID NO 192
<211> LENGTH: 5
<212> TYPE: PRT
<213> ORGANISM: Artificial Sequence
<220> FEATURE:
<223> OTHER INFORMATION: Synthetic: 89F4-A1 HVR-H1

<400> SEQUENCE: 192

Thr Tyr Ala Met Asn
1               5
```

<210> SEQ ID NO 193
<211> LENGTH: 19
<212> TYPE: PRT
<213> ORGANISM: Artificial Sequence
<220> FEATURE:
<223> OTHER INFORMATION: Synthetic: 89F4-A1 HVR-H2

<400> SEQUENCE: 193

Arg Ile Arg Ser Lys Ser Asn Asn Tyr Ala Ala Tyr Phe Ala Asp Ser
1               5                   10                  15

Val Lys Asp

<210> SEQ ID NO 194
<211> LENGTH: 9
<212> TYPE: PRT
<213> ORGANISM: Artificial Sequence
<220> FEATURE:
<223> OTHER INFORMATION: Synthetic: 89F4-A1 HVR-H3

<400> SEQUENCE: 194

Gly Gly Asn Tyr Val Pro Phe Ala Tyr
1               5

<210> SEQ ID NO 195
<211> LENGTH: 17
<212> TYPE: PRT
<213> ORGANISM: Artificial Sequence
<220> FEATURE:
<223> OTHER INFORMATION: Synthetic: 89F4-A1 HVR-L1

<400> SEQUENCE: 195

Lys Ser Ser Gln Ser Val Phe Tyr Ser Ser Glu Gln Arg Asn Tyr Leu
1               5                   10                  15

Ala

<210> SEQ ID NO 196
<211> LENGTH: 7
<212> TYPE: PRT
<213> ORGANISM: Artificial Sequence
<220> FEATURE:
<223> OTHER INFORMATION: Synthetic: 89F4-A1 HVR-L2

<400> SEQUENCE: 196

Trp Ala Ser Thr Arg Glu Ser
1               5

<210> SEQ ID NO 197
<211> LENGTH: 8
<212> TYPE: PRT
<213> ORGANISM: Artificial Sequence
<220> FEATURE:
<223> OTHER INFORMATION: Synthetic: 89F4-A1 HVR-L3

<400> SEQUENCE: 197

His Gln Tyr Leu Ser Ser Phe Thr
1               5

<210> SEQ ID NO 198

<400> SEQUENCE: 198

000

<210> SEQ ID NO 199

<400> SEQUENCE: 199

000

<210> SEQ ID NO 200
<211> LENGTH: 115
<212> TYPE: PRT
<213> ORGANISM: Artificial Sequence
<220> FEATURE:
<223> OTHER INFORMATION: Synthetic: 93A8-D2 heavy chain variable region
      (VH)

<400> SEQUENCE: 200

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Val Asn Trp Val Lys Gln Ser His Gly Lys Gly Leu Glu Trp Ile
        35                  40                  45

Gly Leu Ile Asn Pro Asn Asn Gly Arg Thr Ser Tyr Asn Gln Asn Phe
    50                  55                  60

Asn Asp Lys Ala Thr Leu Thr Val Asp Lys Ser Ser Thr Ala Phe
65                  70                  75                  80

Met Asp Leu Asn Ser Leu Thr Ser Glu Asp Ser Ala Val Tyr Tyr Cys
                85                  90                  95

Thr Arg Glu Gly Gly Thr Gly Tyr Trp Gly Gln Gly Thr Thr Leu Ser
            100                 105                 110

Val Ser Ser
        115

<210> SEQ ID NO 201
<211> LENGTH: 112
<212> TYPE: PRT
<213> ORGANISM: Artificial Sequence
<220> FEATURE:
<223> OTHER INFORMATION: Synthetic: 93A8-D2 light chain variable region
      (VL)

<400> SEQUENCE: 201

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Ala Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 202
<211> LENGTH: 5
<212> TYPE: PRT
<213> ORGANISM: Artificial Sequence
<220> FEATURE:
<223> OTHER INFORMATION: Synthetic: 93A8-D2 HVR-H1

```
<400> SEQUENCE: 202

Asp Tyr Tyr Val Asn
1               5

<210> SEQ ID NO 203
<211> LENGTH: 17
<212> TYPE: PRT
<213> ORGANISM: Artificial Sequence
<220> FEATURE:
<223> OTHER INFORMATION: Synthetic: 93A8-D2 HVR-H2

<400> SEQUENCE: 203

Leu Ile Asn Pro Asn Asn Gly Arg Thr Ser Tyr Asn Gln Asn Phe Asn
1               5                   10                  15

Asp

<210> SEQ ID NO 204
<211> LENGTH: 6
<212> TYPE: PRT
<213> ORGANISM: Artificial Sequence
<220> FEATURE:
<223> OTHER INFORMATION: Synthetic: 93A8-D2 HVR-H3

<400> SEQUENCE: 204

Glu Gly Gly Thr Gly Tyr
1               5

<210> SEQ ID NO 205
<211> LENGTH: 16
<212> TYPE: PRT
<213> ORGANISM: Artificial Sequence
<220> FEATURE:
<223> OTHER INFORMATION: Synthetic: 93A8-D2 HVR-L1

<400> SEQUENCE: 205

Lys Ser Ser Gln Ser Leu Leu Asp Ser Asp Gly Lys Thr Tyr Leu Asn
1               5                   10                  15

<210> SEQ ID NO 206
<211> LENGTH: 7
<212> TYPE: PRT
<213> ORGANISM: Artificial Sequence
<220> FEATURE:
<223> OTHER INFORMATION: Synthetic: 93A8-D2 HVR-L2

<400> SEQUENCE: 206

Leu Val Ser Lys Leu Asp Ser
1               5

<210> SEQ ID NO 207
<211> LENGTH: 9
<212> TYPE: PRT
<213> ORGANISM: Artificial Sequence
<220> FEATURE:
<223> OTHER INFORMATION: Synthetic: 93A8-D2 HVR-L3

<400> SEQUENCE: 207

Trp Gln Gly Thr His Phe Pro Arg Thr
1               5

<210> SEQ ID NO 208

<400> SEQUENCE: 208

000
```

<210> SEQ ID NO 209

<400> SEQUENCE: 209

000

<210> SEQ ID NO 210
<211> LENGTH: 120
<212> TYPE: PRT
<213> ORGANISM: Artificial Sequence
<220> FEATURE:
<223> OTHER INFORMATION: Synthetic: 14F5-D9 heavy chain variable region (VH)

<400> SEQUENCE: 210

```
Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Ser Pro Gly Lys Arg Leu Glu Trp Ile
        35                  40                  45

Ala Ala Ser Lys Asn Lys Ala Asn Asp Tyr Thr Thr Glu Tyr Asn Ala
    50                  55                  60

Ser Val Lys Asp Arg Phe Phe Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Ala Leu Gly Thr Val Phe Ala Tyr Trp Gly Gln
            100                 105                 110

Gly Thr Leu Val Thr Val Ser Ala
        115                 120
```

<210> SEQ ID NO 211
<211> LENGTH: 112
<212> TYPE: PRT
<213> ORGANISM: Artificial Sequence
<220> FEATURE:
<223> OTHER INFORMATION: Synthetic: 14F5-D9 light chain variable region (VL)

<400> SEQUENCE: 211

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Phe Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr Leu Val Pro Leu Thr Phe Gly Ala Gly Thr Lys Leu Glu Leu Lys
            100                 105                 110
```

<210> SEQ ID NO 212
<211> LENGTH: 5
<212> TYPE: PRT
<213> ORGANISM: Artificial Sequence

```
<220> FEATURE:
<223> OTHER INFORMATION: Synthetic: 14F5-D9 HVR-H1

<400> SEQUENCE: 212

Asp Phe Tyr Met Glu
1               5

<210> SEQ ID NO 213
<211> LENGTH: 19
<212> TYPE: PRT
<213> ORGANISM: Artificial Sequence
<220> FEATURE:
<223> OTHER INFORMATION: Synthetic: 14F5-D9 HVR-H2

<400> SEQUENCE: 213

Ala Ser Lys Asn Lys Ala Asn Asp Tyr Thr Thr Glu Tyr Asn Ala Ser
1               5                   10                  15

Val Lys Asp

<210> SEQ ID NO 214
<211> LENGTH: 9
<212> TYPE: PRT
<213> ORGANISM: Artificial Sequence
<220> FEATURE:
<223> OTHER INFORMATION: Synthetic: 14F5-D9 HVR-H3

<400> SEQUENCE: 214

Asp Ala Leu Gly Thr Val Phe Ala Tyr
1               5

<210> SEQ ID NO 215
<211> LENGTH: 16
<212> TYPE: PRT
<213> ORGANISM: Artificial Sequence
<220> FEATURE:
<223> OTHER INFORMATION: Synthetic: 14F5-D9 HVR-L1

<400> SEQUENCE: 215

Arg Ser Ser Gln Ser Leu Val His Ser Asn Gly Asn Thr Tyr Leu His
1               5                   10                  15

<210> SEQ ID NO 216
<211> LENGTH: 7
<212> TYPE: PRT
<213> ORGANISM: Artificial Sequence
<220> FEATURE:
<223> OTHER INFORMATION: Synthetic: 14F5-D9 HVR-L2

<400> SEQUENCE: 216

Lys Val Phe Asn Arg Phe Ser
1               5

<210> SEQ ID NO 217
<211> LENGTH: 9
<212> TYPE: PRT
<213> ORGANISM: Artificial Sequence
<220> FEATURE:
<223> OTHER INFORMATION: Synthetic: 14F5-D9 HVR-L3

<400> SEQUENCE: 217

Ser Gln Ser Thr Leu Val Pro Leu Thr
1               5

<210> SEQ ID NO 218

<400> SEQUENCE: 218
```

000

<210> SEQ ID NO 219
<400> SEQUENCE: 219

000

<210> SEQ ID NO 220
<211> LENGTH: 122
<212> TYPE: PRT
<213> ORGANISM: Artificial Sequence
<220> FEATURE:
<223> OTHER INFORMATION: Synthetic: 73H6-B8 heavy chain variable region
      (VH)

<400> SEQUENCE: 220

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Thr Thr Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Gln Gly Gly Phe Ile Thr Thr Ala Tyr Tyr Ala Met Asp Tyr Trp
            100                 105                 110

Gly Gln Gly Thr Ser Val Thr Val Ser Ser
        115                 120

<210> SEQ ID NO 221
<211> LENGTH: 112
<212> TYPE: PRT
<213> ORGANISM: Artificial Sequence
<220> FEATURE:
<223> OTHER INFORMATION: Synthetic: 73H6-B8 light chain variable region
      (VL)

<400> SEQUENCE: 221

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

<210> SEQ ID NO 222

```
<211> LENGTH: 5
<212> TYPE: PRT
<213> ORGANISM: Artificial Sequence
<220> FEATURE:
<223> OTHER INFORMATION: Synthetic: 73H6-B8 HVR-H1

<400> SEQUENCE: 222

Ser Tyr Gly Val His
1               5

<210> SEQ ID NO 223
<211> LENGTH: 16
<212> TYPE: PRT
<213> ORGANISM: Artificial Sequence
<220> FEATURE:
<223> OTHER INFORMATION: Synthetic: 73H6-B8 HVR-H2

<400> SEQUENCE: 223

Val Ile Trp Ser Asp Gly Ser Thr Thr Tyr Asn Ser Ala Leu Lys Ser
1               5                   10                  15

<210> SEQ ID NO 224
<211> LENGTH: 14
<212> TYPE: PRT
<213> ORGANISM: Artificial Sequence
<220> FEATURE:
<223> OTHER INFORMATION: Synthetic: 73H6-B8 HVR-H3

<400> SEQUENCE: 224

Gln Gly Gly Phe Ile Thr Thr Ala Tyr Tyr Ala Met Asp Tyr
1               5                   10

<210> SEQ ID NO 225
<211> LENGTH: 17
<212> TYPE: PRT
<213> ORGANISM: Artificial Sequence
<220> FEATURE:
<223> OTHER INFORMATION: Synthetic: 73H6-B8 HVR-L1

<400> SEQUENCE: 225

Lys Ser Ser Gln Ser Leu Leu Asn Ser Arg Thr Arg Lys Asn Tyr Leu
1               5                   10                  15

Ala

<210> SEQ ID NO 226
<211> LENGTH: 7
<212> TYPE: PRT
<213> ORGANISM: Artificial Sequence
<220> FEATURE:
<223> OTHER INFORMATION: Synthetic: 73H6-B8 HVR-L2

<400> SEQUENCE: 226

Trp Ala Ser Thr Arg Glu Ser
1               5

<210> SEQ ID NO 227
<211> LENGTH: 8
<212> TYPE: PRT
<213> ORGANISM: Artificial Sequence
<220> FEATURE:
<223> OTHER INFORMATION: Synthetic: 73H6-B8 HVR-L3

<400> SEQUENCE: 227

Lys Gln Ser Tyr Asn Leu Tyr Thr
1               5
```

<210> SEQ ID NO 228

<400> SEQUENCE: 228

000

<210> SEQ ID NO 229

<400> SEQUENCE: 229

000

<210> SEQ ID NO 230
<211> LENGTH: 120
<212> TYPE: PRT
<213> ORGANISM: Artificial Sequence
<220> FEATURE:
<223> OTHER INFORMATION: Synthetic: 22G7-C9 heavy chain variable region (VH)

<400> SEQUENCE: 230

```
Gln Ile Gln Leu Val Gln Ser Gly Pro Glu Leu Lys Lys Pro Gly Glu
1               5                  10                  15

Thr Val Lys Ile Ser Cys Lys Ala Ser Gly Tyr Thr Phe Thr Asp Cys
            20                  25                  30

Ser Ile His Trp Val Lys Gln Ala Pro Gly Glu Gly Leu Lys Trp Met
        35                  40                  45

Gly Trp Ile Asn Thr Glu Thr Gly Glu Pro Ser Tyr Ala Asp Asp Phe
    50                  55                  60

Lys Gly Arg Phe Ala Phe Ser Leu Glu Thr Ser Ala Ser Thr Ala Phe
65                  70                  75                  80

Leu Gln Ile Asn Asn Leu Lys Ser Glu Asp Thr Ala Ser Tyr Phe Cys
                85                  90                  95

Gly Thr Ala Tyr Tyr Arg Tyr Asp Gly Ala Leu Asp Tyr Trp Gly Gln
            100                 105                 110

Gly Thr Ser Val Thr Val Ser Ser
        115                 120
```

<210> SEQ ID NO 231
<211> LENGTH: 111
<212> TYPE: PRT
<213> ORGANISM: Artificial Sequence
<220> FEATURE:
<223> OTHER INFORMATION: Synthetic: 22G7-C9 light chain variable region (VL)

<400> SEQUENCE: 231

```
Asp Ile Val Leu Thr Gln Ser Pro Ala Ser Leu Ala Val Ser Leu Gly
1               5                  10                  15

Gln Arg Ala Thr Ile Ser Cys Arg Ala Ser Gln Ser Val Ser Thr Ser
            20                  25                  30

Ser Tyr Ser Tyr Met His Trp Phe Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Leu Pro Trp Thr Phe Gly Gly Gly Thr Lys Leu Glu Ile Lys
            100                 105                 110
```

<210> SEQ ID NO 232
<211> LENGTH: 5
<212> TYPE: PRT
<213> ORGANISM: Artificial Sequence
<220> FEATURE:
<223> OTHER INFORMATION: Synthetic: 22G7-C9 HVR-H1

<400> SEQUENCE: 232

Asp Cys Ser Ile His
1               5

<210> SEQ ID NO 233
<211> LENGTH: 17
<212> TYPE: PRT
<213> ORGANISM: Artificial Sequence
<220> FEATURE:
<223> OTHER INFORMATION: Synthetic: 22G7-C9 HVR-H2

<400> SEQUENCE: 233

Trp Ile Asn Thr Glu Thr Gly Glu Pro Ser Tyr Ala Asp Asp Phe Lys
1               5                   10                  15

Gly

<210> SEQ ID NO 234
<211> LENGTH: 11
<212> TYPE: PRT
<213> ORGANISM: Artificial Sequence
<220> FEATURE:
<223> OTHER INFORMATION: Synthetic: 22G7-C9 HVR-H3

<400> SEQUENCE: 234

Ala Tyr Tyr Arg Tyr Asp Gly Ala Leu Asp Tyr
1               5                   10

<210> SEQ ID NO 235
<211> LENGTH: 15
<212> TYPE: PRT
<213> ORGANISM: Artificial Sequence
<220> FEATURE:
<223> OTHER INFORMATION: Synthetic: 22G7-C9 HVR-L1

<400> SEQUENCE: 235

Arg Ala Ser Gln Ser Val Ser Thr Ser Ser Tyr Ser Tyr Met His
1               5                   10                  15

<210> SEQ ID NO 236
<211> LENGTH: 7
<212> TYPE: PRT
<213> ORGANISM: Artificial Sequence
<220> FEATURE:
<223> OTHER INFORMATION: Synthetic: 22G7-C9 HVR-L2

<400> SEQUENCE: 236

Tyr Ala Ser Asn Leu Glu Ser
1               5

<210> SEQ ID NO 237
<211> LENGTH: 9
<212> TYPE: PRT
<213> ORGANISM: Artificial Sequence
<220> FEATURE:
<223> OTHER INFORMATION: Synthetic: 22G7-C9 HVR-L3

<400> SEQUENCE: 237

Gln His Ser Trp Glu Leu Pro Trp Thr

<210> SEQ ID NO 238

<400> SEQUENCE: 238

000

<210> SEQ ID NO 239

<400> SEQUENCE: 239

000

<210> SEQ ID NO 240
<211> LENGTH: 116
<212> TYPE: PRT
<213> ORGANISM: Artificial Sequence
<220> FEATURE:
<223> OTHER INFORMATION: Synthetic: 7A11-C12 heavy chain variable region
      (VH)

<400> SEQUENCE: 240

```
Gln Ile Gln Leu Val Gln Ser Gly Pro Asp Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asp Asn Leu Lys Asn Glu Asp Thr Ala Thr Tyr Phe Cys
                85                  90                  95

Ala Arg Gly Thr Val Ser Phe Pro Tyr Trp Gly Gln Gly Thr Leu Val
            100                 105                 110

Thr Val Ser Ala
        115
```

<210> SEQ ID NO 241
<211> LENGTH: 112
<212> TYPE: PRT
<213> ORGANISM: Artificial Sequence
<220> FEATURE:
<223> OTHER INFORMATION: Synthetic: 7A11-C12 light chain variable region
      (VL)

<400> SEQUENCE: 241

```
Asp Val Val Met Ser Gln Thr Pro Leu Ser Leu Pro Val Ser Leu Gly
1               5                   10                  15

Asp His Ala Ser Ile Ser Cys Arg Ser Ser Gln Asn Leu Val His Ser
            20                  25                  30

Asp Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95
```

Thr His Val Ile Phe Thr Phe Gly Ser Gly Thr Lys Leu Glu Ile Lys
                100                 105                 110

<210> SEQ ID NO 242
<211> LENGTH: 5
<212> TYPE: PRT
<213> ORGANISM: Artificial Sequence
<220> FEATURE:
<223> OTHER INFORMATION: Synthetic: 7A11-C12 HVR-H1

<400> SEQUENCE: 242

Asn Tyr Gly Met Asn
1               5

<210> SEQ ID NO 243
<211> LENGTH: 17
<212> TYPE: PRT
<213> ORGANISM: Artificial Sequence
<220> FEATURE:
<223> OTHER INFORMATION: Synthetic: 7A11-C12 HVR-H2

<400> SEQUENCE: 243

Trp Ile Asn Thr Asn Thr Gly Glu Pro Thr Tyr Ala Glu Glu Phe Lys
1               5                   10                  15

Gly

<210> SEQ ID NO 244
<211> LENGTH: 7
<212> TYPE: PRT
<213> ORGANISM: Artificial Sequence
<220> FEATURE:
<223> OTHER INFORMATION: Synthetic: 7A11-C12 HVR-H3

<400> SEQUENCE: 244

Gly Thr Val Ser Phe Pro Tyr
1               5

<210> SEQ ID NO 245
<211> LENGTH: 16
<212> TYPE: PRT
<213> ORGANISM: Artificial Sequence
<220> FEATURE:
<223> OTHER INFORMATION: Synthetic: 7A11-C12 HVR-L1

<400> SEQUENCE: 245

Arg Ser Ser Gln Asn Leu Val His Ser Asp Gly Asn Thr Tyr Leu His
1               5                   10                  15

<210> SEQ ID NO 246
<211> LENGTH: 7
<212> TYPE: PRT
<213> ORGANISM: Artificial Sequence
<220> FEATURE:
<223> OTHER INFORMATION: Synthetic: 7A11-C12 HVR-L2

<400> SEQUENCE: 246

Lys Val Ser Asn Arg Phe Ser
1               5

<210> SEQ ID NO 247
<211> LENGTH: 9
<212> TYPE: PRT
<213> ORGANISM: Artificial Sequence
<220> FEATURE:
<223> OTHER INFORMATION: Synthetic: 7A11-C12 HVR-L3

```
<400> SEQUENCE: 247

Ser Gln Ser Thr His Val Ile Phe Thr
1               5

<210> SEQ ID NO 248

<400> SEQUENCE: 248

000

<210> SEQ ID NO 249

<400> SEQUENCE: 249

000

<210> SEQ ID NO 250
<211> LENGTH: 115
<212> TYPE: PRT
<213> ORGANISM: Artificial Sequence
<220> FEATURE:
<223> OTHER INFORMATION: Synthetic: 12A10-E8 heavy chain variable region
      (VH)

<400> SEQUENCE: 250

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Met Tyr Thr Gly Glu Pro Thr Tyr Gly Asp Asp Phe
    50                  55                  60

Lys Gly Arg Phe Val Phe Ser Leu Glu Thr Ser Val Ser Thr Val Tyr
65                  70                  75                  80

Leu Gln Ile Asn Asn Leu Lys Lys Glu Asp Thr Ala Thr Phe Phe Cys
                85                  90                  95

Ala Arg Gly Gly Arg Pro Asp Tyr Trp Gly Gln Gly Thr Ser Val Thr
            100                 105                 110

Val Ser Ser
        115

<210> SEQ ID NO 251
<211> LENGTH: 112
<212> TYPE: PRT
<213> ORGANISM: Artificial Sequence
<220> FEATURE:
<223> OTHER INFORMATION: Synthetic: 12A10-E8 light chain variable region
      (VL)

<400> SEQUENCE: 251

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Phe Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

-continued

Asn Arg Val Glu Ala Glu Asp Leu Gly Val Tyr Tyr Cys Leu Gln Gly
            85                  90                  95

Ser His Val Pro Tyr Thr Phe Gly Gly Thr Lys Leu Glu Ile Lys
        100                 105                 110

<210> SEQ ID NO 252
<211> LENGTH: 5
<212> TYPE: PRT
<213> ORGANISM: Artificial Sequence
<220> FEATURE:
<223> OTHER INFORMATION: Synthetic: 12A10-E8 HVR-H1

<400> SEQUENCE: 252

Asn Tyr Gly Met Asn
1               5

<210> SEQ ID NO 253
<211> LENGTH: 17
<212> TYPE: PRT
<213> ORGANISM: Artificial Sequence
<220> FEATURE:
<223> OTHER INFORMATION: Synthetic: 12A10-E8 HVR-H2

<400> SEQUENCE: 253

Trp Ile Asn Met Tyr Thr Gly Glu Pro Thr Tyr Gly Asp Asp Phe Lys
1               5                   10                  15
Gly

<210> SEQ ID NO 254
<211> LENGTH: 6
<212> TYPE: PRT
<213> ORGANISM: Artificial Sequence
<220> FEATURE:
<223> OTHER INFORMATION: Synthetic: 12A10-E8 HVR-H3

<400> SEQUENCE: 254

Gly Gly Arg Pro Asp Tyr
1               5

<210> SEQ ID NO 255
<211> LENGTH: 16
<212> TYPE: PRT
<213> ORGANISM: Artificial Sequence
<220> FEATURE:
<223> OTHER INFORMATION: Synthetic: 12A10-E8 HVR-L1

<400> SEQUENCE: 255

Arg Ser Ser Gln Ser Ile Val His Ser Asn Gly Asn Thr Tyr Leu Glu
1               5                   10                  15

<210> SEQ ID NO 256
<211> LENGTH: 7
<212> TYPE: PRT
<213> ORGANISM: Artificial Sequence
<220> FEATURE:
<223> OTHER INFORMATION: Synthetic: 1 2A10-E8 HVR-L2

<400> SEQUENCE: 256

Lys Val Phe Asn Arg Phe Ser
1               5

<210> SEQ ID NO 257
<211> LENGTH: 9
<212> TYPE: PRT
<213> ORGANISM: Artificial Sequence -continued

```
<220> FEATURE:
<223> OTHER INFORMATION: Synthetic: 12A10-E8 HVR-L3

<400> SEQUENCE: 257

Leu Gln Gly Ser His Val Pro Tyr Thr
1               5

<210> SEQ ID NO 258

<400> SEQUENCE: 258

000

<210> SEQ ID NO 259

<400> SEQUENCE: 259

000

<210> SEQ ID NO 260
<211> LENGTH: 120
<212> TYPE: PRT
<213> ORGANISM: Artificial Sequence
<220> FEATURE:
<223> OTHER INFORMATION: Synthetic: 55E7-F11 heavy chain variable region
      (VH)

<400> SEQUENCE: 260

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Ala Gly Tyr Phe Tyr Gly Tyr Phe Asp Val Trp Gly Thr
            100                 105                 110

Gly Thr Thr Val Thr Val Ser Ser
        115                 120

<210> SEQ ID NO 261
<211> LENGTH: 108
<212> TYPE: PRT
<213> ORGANISM: Artificial Sequence
<220> FEATURE:
<223> OTHER INFORMATION: Synthetic: 55E7-F11 light chain variable region
      (VL)

<400> SEQUENCE: 261

Glu Leu Val Leu Thr Gln Ser Pro Thr Thr Met Ala Ala Ser Pro Gly
1               5                   10                  15

Lys Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60
```

```
Gly Ser Gly Ser Gly Thr Ser Tyr Ser Leu Thr Ile Gly Thr Met Glu
 65                  70                  75                  80

Ala Glu Asp Val Ala Thr Tyr Tyr Cys Gln Gln Gly Ser Ser Leu Pro
                 85                  90                  95

Phe Thr Phe Gly Ser Gly Thr Lys Leu Glu Ile Lys
            100                 105

<210> SEQ ID NO 262
<211> LENGTH: 5
<212> TYPE: PRT
<213> ORGANISM: Artificial Sequence
<220> FEATURE:
<223> OTHER INFORMATION: Synthetic: 55E7-F11 HVR-H1

<400> SEQUENCE: 262

Asn Tyr Trp Met Asn
1               5

<210> SEQ ID NO 263
<211> LENGTH: 19
<212> TYPE: PRT
<213> ORGANISM: Artificial Sequence
<220> FEATURE:
<223> OTHER INFORMATION: Synthetic: 55E7-F11 HVR-H2

<400> SEQUENCE: 263

Gln Ile Arg Leu Lys Ser Asp Asn Tyr Ala Thr His Tyr Ala Glu Ser
1               5                   10                  15

Val Lys Gly

<210> SEQ ID NO 264
<211> LENGTH: 9
<212> TYPE: PRT
<213> ORGANISM: Artificial Sequence
<220> FEATURE:
<223> OTHER INFORMATION: Synthetic: 55E7-F11 HVR-H3

<400> SEQUENCE: 264

Tyr Phe Tyr Gly Gly Tyr Phe Asp Val
1               5

<210> SEQ ID NO 265
<211> LENGTH: 12
<212> TYPE: PRT
<213> ORGANISM: Artificial Sequence
<220> FEATURE:
<223> OTHER INFORMATION: Synthetic: 55E7-F11 HVR-L1

<400> SEQUENCE: 265

Ser Ala Ser Ser Ser Ile Ser Ser Asn Tyr Leu His
1               5                   10

<210> SEQ ID NO 266
<211> LENGTH: 7
<212> TYPE: PRT
<213> ORGANISM: Artificial Sequence
<220> FEATURE:
<223> OTHER INFORMATION: Synthetic: 55E7-F11 HVR-L2

<400> SEQUENCE: 266

Arg Thr Ser Asn Leu Ala Ser
1               5

<210> SEQ ID NO 267
```

-continued

```
<211> LENGTH: 9
<212> TYPE: PRT
<213> ORGANISM: Artificial Sequence
<220> FEATURE:
<223> OTHER INFORMATION: Synthetic: 55E7-F11 HVR-L3

<400> SEQUENCE: 267

Gln Gln Gly Ser Ser Leu Pro Phe Thr
1               5

<210> SEQ ID NO 268

<400> SEQUENCE: 268

000

<210> SEQ ID NO 269

<400> SEQUENCE: 269

000

<210> SEQ ID NO 270
<211> LENGTH: 117
<212> TYPE: PRT
<213> ORGANISM: Artificial Sequence
<220> FEATURE:
<223> OTHER INFORMATION: Synthetic: 52F6-F11 heavy chain variable region
      (VH)

<400> SEQUENCE: 270

Gln Val Gln Leu Gln Gln Ser Gly Thr Glu Leu Ala Lys Pro Gly Ala
1               5                   10                  15

Ser Val Lys Leu Ser Cys Lys Ala Ser Gly Tyr Thr Phe Thr His Tyr
            20                  25                  30

Trp Met His Trp Ile Lys Gln Arg Pro Gly Gln Gly Leu Glu Trp Ile
        35                  40                  45

Gly Tyr Ile Tyr Pro Thr Asn Asp Tyr Thr Lys Tyr Asn Gln Asn Phe
    50                  55                  60

Arg Asp Lys Ala Thr Leu Thr Ala Asp Glu Ser Ser Asn Ser Ala Tyr
65                  70                  75                  80

Met Gln Leu Asn Ser Leu Thr Tyr Glu Asp Ser Ala Val Tyr Tyr Cys
                85                  90                  95

Ala Arg Ala Gly Asn Arg Val Phe Asp Phe Trp Gly Gln Gly Thr Thr
            100                 105                 110

Leu Thr Val Ser Ser
        115

<210> SEQ ID NO 271
<211> LENGTH: 109
<212> TYPE: PRT
<213> ORGANISM: Artificial Sequence
<220> FEATURE:
<223> OTHER INFORMATION: Synthetic: 52F6-F11 light chain variable region
      (VL)

<400> SEQUENCE: 271

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Phe Ala Asn Trp Val Gln Glu Lys Pro Asp His Leu Phe Thr Gly
        35                  40                  45
```

```
Leu Ile Gly Gly Thr Asn Asn Arg Ala Pro Gly Val Pro Ala Arg Phe
         50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

Leu Trp Val Phe Gly Gly Gly Thr Lys Leu Thr Val Leu
                100                 105

<210> SEQ ID NO 272
<211> LENGTH: 5
<212> TYPE: PRT
<213> ORGANISM: Artificial Sequence
<220> FEATURE:
<223> OTHER INFORMATION: Synthetic: 52F6-F11 HVR-H1

<400> SEQUENCE: 272

His Tyr Trp Met His
 1               5

<210> SEQ ID NO 273
<211> LENGTH: 17
<212> TYPE: PRT
<213> ORGANISM: Artificial Sequence
<220> FEATURE:
<223> OTHER INFORMATION: Synthetic: 52F6-F11 HVR-H2

<400> SEQUENCE: 273

Tyr Ile Tyr Pro Thr Asn Asp Tyr Thr Lys Tyr Asn Gln Asn Phe Arg
 1               5                  10                  15

Asp

<210> SEQ ID NO 274
<211> LENGTH: 8
<212> TYPE: PRT
<213> ORGANISM: Artificial Sequence
<220> FEATURE:
<223> OTHER INFORMATION: Synthetic: 52F6-F11 HVR-H3

<400> SEQUENCE: 274

Ala Gly Asn Arg Val Phe Asp Phe
 1               5

<210> SEQ ID NO 275
<211> LENGTH: 14
<212> TYPE: PRT
<213> ORGANISM: Artificial Sequence
<220> FEATURE:
<223> OTHER INFORMATION: Synthetic: 52F6-F11 HVR-L1

<400> SEQUENCE: 275

Arg Ser Ser Thr Gly Ala Val Thr Thr Ser Asn Phe Ala Asn
 1               5                  10

<210> SEQ ID NO 276
<211> LENGTH: 7
<212> TYPE: PRT
<213> ORGANISM: Artificial Sequence
<220> FEATURE:
<223> OTHER INFORMATION: Synthetic: 52F6-F11 HVR-L2

<400> SEQUENCE: 276

Gly Thr Asn Asn Arg Ala Pro
 1               5
```

<210> SEQ ID NO 277
<211> LENGTH: 9
<212> TYPE: PRT
<213> ORGANISM: Artificial Sequence
<220> FEATURE:
<223> OTHER INFORMATION: Synthetic: 52F6-F11 HVR-L3

<400> SEQUENCE: 277

Ala Leu Trp Tyr Ser Asn Leu Trp Val
1               5

<210> SEQ ID NO 278

<400> SEQUENCE: 278

000

<210> SEQ ID NO 279

<400> SEQUENCE: 279

000

<210> SEQ ID NO 280
<211> LENGTH: 117
<212> TYPE: PRT
<213> ORGANISM: Artificial Sequence
<220> FEATURE:
<223> OTHER INFORMATION: Synthetic: Hu37D3-H9.v1 heavy chain variable
      region (VH)

<400> SEQUENCE: 280

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Arg Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ser Tyr Ser Gly Ala Met Asp Tyr Trp Gly Gln Gly Thr Leu
            100                 105                 110

Val Thr Val Ser Ser
        115

<210> SEQ ID NO 281
<211> LENGTH: 112
<212> TYPE: PRT
<213> ORGANISM: Artificial Sequence
<220> FEATURE:
<223> OTHER INFORMATION: Synthetic: Hu37D3-H9.v1 light chain variable
      region (VL)

<400> SEQUENCE: 281

Glu Asp Gln Leu Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

```
Asn Gly Asn Thr Tyr Phe Glu Trp Tyr Gln Gln Lys Pro Gly Lys Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Leu Val Pro Trp Thr Phe Gly Gln Gly Thr Lys Val Glu Ile Lys
            100                 105                 110

<210> SEQ ID NO 282
<211> LENGTH: 5
<212> TYPE: PRT
<213> ORGANISM: Artificial Sequence
<220> FEATURE:
<223> OTHER INFORMATION: Synthetic: Hu37D3-H9.v1 HVR-H1

<400> SEQUENCE: 282

Ser Tyr Gly Met Ser
1               5

<210> SEQ ID NO 283
<211> LENGTH: 17
<212> TYPE: PRT
<213> ORGANISM: Artificial Sequence
<220> FEATURE:
<223> OTHER INFORMATION: Synthetic: Hu37D3-H9.v1 HVR-H2

<400> SEQUENCE: 283

Thr Ile Asn Ser Gly Gly Thr Tyr Thr Tyr Tyr Pro Asp Ser Val Lys
1               5                   10                  15

Gly

<210> SEQ ID NO 284
<211> LENGTH: 8
<212> TYPE: PRT
<213> ORGANISM: Artificial Sequence
<220> FEATURE:
<223> OTHER INFORMATION: Synthetic: Hu37D3-H9.v1 HVR-H3

<400> SEQUENCE: 284

Ser Tyr Ser Gly Ala Met Asp Tyr
1               5

<210> SEQ ID NO 285
<211> LENGTH: 16
<212> TYPE: PRT
<213> ORGANISM: Artificial Sequence
<220> FEATURE:
<223> OTHER INFORMATION: Synthetic: Hu37D3-H9.v1 HVR-L1

<400> SEQUENCE: 285

Arg Ser Ser Gln Ser Ile Val His Ser Asn Gly Asn Thr Tyr Phe Glu
1               5                   10                  15

<210> SEQ ID NO 286
<211> LENGTH: 7
<212> TYPE: PRT
<213> ORGANISM: Artificial Sequence
<220> FEATURE:
<223> OTHER INFORMATION: Synthetic: Hu37D3-H9.v1 HVR-L2

<400> SEQUENCE: 286
```

```
Lys Val Ser Asn Arg Phe Ser
1               5
```

<210> SEQ ID NO 287
<211> LENGTH: 9
<212> TYPE: PRT
<213> ORGANISM: Artificial Sequence
<220> FEATURE:
<223> OTHER INFORMATION: Synthetic: Hu37D3-H9.v1 HVR-L3

<400> SEQUENCE: 287

```
Phe Gln Gly Ser Leu Val Pro Trp Thr
1               5
```

<210> SEQ ID NO 288
<211> LENGTH: 447
<212> TYPE: PRT
<213> ORGANISM: Artificial Sequence
<220> FEATURE:
<223> OTHER INFORMATION: Synthetic: Hu37D3-H9.v1 IgG1 heavy chain

<400> SEQUENCE: 288

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Arg Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ser Tyr Ser Gly Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
```

```
                275                 280                 285
Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 289
<211> LENGTH: 219
<212> TYPE: PRT
<213> ORGANISM: Artificial Sequence
<220> FEATURE:
<223> OTHER INFORMATION: Synthetic: Hu37D3-H9.v1 IgG1 light chain

<400> SEQUENCE: 289

Glu Asp Gln Leu Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
                20                  25                  30

Asn Gly Asn Thr Tyr Phe Glu Trp Tyr Gln Gln Lys Pro Gly Lys Ser
                35                  40                  45

Pro Lys Leu Leu Ile Tyr Lys Val Ser Asn Arg Phe Ser Gly Val Pro
50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Leu Val Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
```

```
                195                 200                 205
Pro Val Thr Lys Ser Phe Asn Arg Gly Glu Cys
    210                 215

<210> SEQ ID NO 290
<211> LENGTH: 117
<212> TYPE: PRT
<213> ORGANISM: Artificial Sequence
<220> FEATURE:
<223> OTHER INFORMATION: Synthetic: Hu37D3-H9.v5 heavy chain variable
      region (VH)

<400> SEQUENCE: 290

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Arg Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ser Tyr Ser Gly Ala Met Asp Tyr Trp Gly Gln Gly Thr Leu
            100                 105                 110

Val Thr Val Ser Ser
        115

<210> SEQ ID NO 291
<211> LENGTH: 112
<212> TYPE: PRT
<213> ORGANISM: Artificial Sequence
<220> FEATURE:
<223> OTHER INFORMATION: Synthetic: Hu37D3-H9.v5 light chain variable
      region (VL)

<400> SEQUENCE: 291

Glu Asp Val Leu Thr Gln Thr Pro Leu Ser Leu Pro Val Thr Pro Gly
1               5                   10                  15

Gln Pro Ala Ser Ile Ser Cys Arg Ser Ser Gln Ser Ile Val His Ser
            20                  25                  30

Asn Gly Asn Thr Tyr Phe Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Leu Val Pro Trp Thr Phe Gly Gln Gly Thr Lys Val Glu Ile Lys
            100                 105                 110

<210> SEQ ID NO 292
<211> LENGTH: 5
<212> TYPE: PRT
<213> ORGANISM: Artificial Sequence
<220> FEATURE:
<223> OTHER INFORMATION: Synthetic: Hu37D3-H9.v5 HVR-H1
```

```
<400> SEQUENCE: 292

Ser Tyr Gly Met Ser
1               5

<210> SEQ ID NO 293
<211> LENGTH: 17
<212> TYPE: PRT
<213> ORGANISM: Artificial Sequence
<220> FEATURE:
<223> OTHER INFORMATION: Synthetic: Hu37D3-H9.v5 HVR-H2

<400> SEQUENCE: 293

Thr Ile Asn Ser Gly Gly Thr Tyr Thr Tyr Tyr Pro Asp Ser Val Lys
1               5                   10                  15
Gly

<210> SEQ ID NO 294
<211> LENGTH: 8
<212> TYPE: PRT
<213> ORGANISM: Artificial Sequence
<220> FEATURE:
<223> OTHER INFORMATION: Synthetic: Hu37D3-H9.v5 HVR-H3

<400> SEQUENCE: 294

Ser Tyr Ser Gly Ala Met Asp Tyr
1               5

<210> SEQ ID NO 295
<211> LENGTH: 16
<212> TYPE: PRT
<213> ORGANISM: Artificial Sequence
<220> FEATURE:
<223> OTHER INFORMATION: Synthetic: Hu37D3-H9.v5 HVR-L1

<400> SEQUENCE: 295

Arg Ser Ser Gln Ser Ile Val His Ser Asn Gly Asn Thr Tyr Phe Glu
1               5                   10                  15

<210> SEQ ID NO 296
<211> LENGTH: 7
<212> TYPE: PRT
<213> ORGANISM: Artificial Sequence
<220> FEATURE:
<223> OTHER INFORMATION: Synthetic: Hu37D3-H9.v5 HVR-L2

<400> SEQUENCE: 296

Lys Val Ser Asn Arg Phe Ser
1               5

<210> SEQ ID NO 297
<211> LENGTH: 9
<212> TYPE: PRT
<213> ORGANISM: Artificial Sequence
<220> FEATURE:
<223> OTHER INFORMATION: Synthetic: Hu37D3-H9.v5 HVR-L3

<400> SEQUENCE: 297

Phe Gln Gly Ser Leu Val Pro Trp Thr
1               5

<210> SEQ ID NO 298

<400> SEQUENCE: 298

000
```

<210> SEQ ID NO 299

<400> SEQUENCE: 299

000

<210> SEQ ID NO 300
<211> LENGTH: 113
<212> TYPE: PRT
<213> ORGANISM: Artificial Sequence
<220> FEATURE:
<223> OTHER INFORMATION: Synthetic: Hu94B2.v105 heavy chain variable
      region (VH)

<400> SEQUENCE: 300

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Gly Tyr
                20                  25                  30

Thr Met Asn Trp Val Arg Gln Ala Pro Gly Gln Gly Leu Glu Trp Ile
            35                  40                  45

Gly Leu Ile Ser Pro Tyr Asn Gly Val Thr Ser Tyr Asn Gln Lys Phe
    50                  55                  60

Lys Gly Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gln Gly Ala Tyr Trp Gly Gln Gly Thr Leu Val Thr Val Ser
                100                 105                 110

Ser

<210> SEQ ID NO 301
<211> LENGTH: 112
<212> TYPE: PRT
<213> ORGANISM: Artificial Sequence
<220> FEATURE:
<223> OTHER INFORMATION: Synthetic: Hu94B2.v105 light chain variable
      region (VL)

<400> SEQUENCE: 301

Asp Ile Val Met Thr Gln Thr Pro Leu Ser Leu Pro Val Thr Pro Gly
1               5                   10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Lys Pro Gly Gln Ser
            35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gln Gly Thr Lys Val Glu Ile Lys
                100                 105                 110

<210> SEQ ID NO 302
<211> LENGTH: 5
<212> TYPE: PRT
<213> ORGANISM: Artificial Sequence

```
<220> FEATURE:
<223> OTHER INFORMATION: Synthetic: Hu94B2.v105 HVR-H1

<400> SEQUENCE: 302

Gly Tyr Thr Met Asn
1               5

<210> SEQ ID NO 303
<211> LENGTH: 17
<212> TYPE: PRT
<213> ORGANISM: Artificial Sequence
<220> FEATURE:
<223> OTHER INFORMATION: Synthetic: Hu94B2.v105 HVR-H2

<400> SEQUENCE: 303

Leu Ile Ser Pro Tyr Asn Gly Val Thr Ser Tyr Asn Gln Lys Phe Lys
1               5                   10                  15

Gly

<210> SEQ ID NO 304
<211> LENGTH: 4
<212> TYPE: PRT
<213> ORGANISM: Artificial Sequence
<220> FEATURE:
<223> OTHER INFORMATION: Synthetic: Hu94B2.v105 HVR-H3

<400> SEQUENCE: 304

Gln Gly Ala Tyr
1

<210> SEQ ID NO 305
<211> LENGTH: 16
<212> TYPE: PRT
<213> ORGANISM: Artificial Sequence
<220> FEATURE:
<223> OTHER INFORMATION: Synthetic: Hu94B2.v105 HVR-L1

<400> SEQUENCE: 305

Lys Ser Ser Gln Ser Leu Leu Asp Ser Asp Gly Lys Thr Tyr Leu Asn
1               5                   10                  15

<210> SEQ ID NO 306
<211> LENGTH: 7
<212> TYPE: PRT
<213> ORGANISM: Artificial Sequence
<220> FEATURE:
<223> OTHER INFORMATION: Synthetic: Hu94B2.v105 HVR-L2

<400> SEQUENCE: 306

Leu Val Ser Lys Leu Asp Ser
1               5

<210> SEQ ID NO 307
<211> LENGTH: 9
<212> TYPE: PRT
<213> ORGANISM: Artificial Sequence
<220> FEATURE:
<223> OTHER INFORMATION: Synthetic: Hu94B2.v105 HVR-L3

<400> SEQUENCE: 307

Trp Gln Gly Thr His Phe Pro Trp Thr
1               5

<210> SEQ ID NO 308

<400> SEQUENCE: 308
```

000

<210> SEQ ID NO 309

<400> SEQUENCE: 309

000

<210> SEQ ID NO 310
<211> LENGTH: 115
<212> TYPE: PRT
<213> ORGANISM: Artificial Sequence
<220> FEATURE:
<223> OTHER INFORMATION: Synthetic: hu125B11.v17 heavy chain variable
      region (VH)

<400> SEQUENCE: 310

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Ile Phe Ser Asn Tyr
            20                  25                  30

Trp Met Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Thr Gly Gly Thr Thr Tyr Trp Gly Gln Gly Thr Leu Val Thr
            100                 105                 110

Val Ser Ser
        115

<210> SEQ ID NO 311
<211> LENGTH: 107
<212> TYPE: PRT
<213> ORGANISM: Artificial Sequence
<220> FEATURE:
<223> OTHER INFORMATION: Synthetic: hu125B11.v17 light chain variable
      region (VL)

<400> SEQUENCE: 311

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ser Pro Lys Leu Leu Ile
        35                  40                  45

Tyr Ser Ala Ser Ile Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Phe Arg Thr Tyr Pro Tyr
                85                  90                  95

Thr Phe Gly Gln Gly Thr Lys Val Glu Ile Lys
            100                 105

<210> SEQ ID NO 312

```
<211> LENGTH: 5
<212> TYPE: PRT
<213> ORGANISM: Artificial Sequence
<220> FEATURE:
<223> OTHER INFORMATION: Synthetic: hu125B11.v17 HVR-H1

<400> SEQUENCE: 312

Asn Tyr Trp Met Asn
1               5

<210> SEQ ID NO 313
<211> LENGTH: 19
<212> TYPE: PRT
<213> ORGANISM: Artificial Sequence
<220> FEATURE:
<223> OTHER INFORMATION: Synthetic: hu125B11.v17 HVR-H2

<400> SEQUENCE: 313

Gln Ile Arg Leu Lys Ser Asp Asn Tyr Ala Thr His Tyr Ala Glu Ser
1               5                   10                  15

Val Lys Gly

<210> SEQ ID NO 314
<211> LENGTH: 4
<212> TYPE: PRT
<213> ORGANISM: Artificial Sequence
<220> FEATURE:
<223> OTHER INFORMATION: Synthetic: hu125B11.v17 HVR-H3

<400> SEQUENCE: 314

Gly Thr Thr Tyr
1

<210> SEQ ID NO 315
<211> LENGTH: 11
<212> TYPE: PRT
<213> ORGANISM: Artificial Sequence
<220> FEATURE:
<223> OTHER INFORMATION: Synthetic: hu125B11.v17 HVR-L1

<400> SEQUENCE: 315

Lys Ala Ser Gln Asn Val Gly Thr Ala Val Ala
1               5                   10

<210> SEQ ID NO 316
<211> LENGTH: 7
<212> TYPE: PRT
<213> ORGANISM: Artificial Sequence
<220> FEATURE:
<223> OTHER INFORMATION: Synthetic: hu125B11.v17 HVR-L2

<400> SEQUENCE: 316

Ser Ala Ser Ile Arg Tyr Thr
1               5

<210> SEQ ID NO 317
<211> LENGTH: 9
<212> TYPE: PRT
<213> ORGANISM: Artificial Sequence
<220> FEATURE:
<223> OTHER INFORMATION: Synthetic: hu125B11.v17 HVR-L3

<400> SEQUENCE: 317

Gln Gln Phe Arg Thr Tyr Pro Tyr Thr
1               5
```

<210> SEQ ID NO 318

<400> SEQUENCE: 318

000

<210> SEQ ID NO 319

<400> SEQUENCE: 319

000

<210> SEQ ID NO 320
<211> LENGTH: 115
<212> TYPE: PRT
<213> ORGANISM: Artificial Sequence
<220> FEATURE:
<223> OTHER INFORMATION: Synthetic: hu125B11.v26 heavy chain variable region (VH)

<400> SEQUENCE: 320

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Ile Phe Ser Asn Tyr
            20                  25                  30

Trp Met Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Thr Gly Gly Thr Thr Tyr Trp Gly Gln Gly Thr Leu Val Thr
            100                 105                 110

Val Ser Ser
        115

<210> SEQ ID NO 321
<211> LENGTH: 107
<212> TYPE: PRT
<213> ORGANISM: Artificial Sequence
<220> FEATURE:
<223> OTHER INFORMATION: Synthetic: hu125B11.v26 light chain variable region (VL)

<400> SEQUENCE: 321

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Ile Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Phe Arg Thr Tyr Pro Tyr
                85                  90                  95

Thr Phe Gly Gln Gly Thr Lys Val Glu Ile Lys
            100                 105

<210> SEQ ID NO 322
<211> LENGTH: 5
<212> TYPE: PRT
<213> ORGANISM: Artificial Sequence
<220> FEATURE:
<223> OTHER INFORMATION: Synthetic: hu125B11.v26 HVR-H1

<400> SEQUENCE: 322

Asn Tyr Trp Met Asn
1               5

<210> SEQ ID NO 323
<211> LENGTH: 19
<212> TYPE: PRT
<213> ORGANISM: Artificial Sequence
<220> FEATURE:
<223> OTHER INFORMATION: Synthetic: hu125B11.v26 HVR-H2

<400> SEQUENCE: 323

Gln Ile Arg Leu Lys Ser Asp Asn Tyr Ala Thr His Tyr Ala Glu Ser
1               5                   10                  15

Val Lys Gly

<210> SEQ ID NO 324
<211> LENGTH: 4
<212> TYPE: PRT
<213> ORGANISM: Artificial Sequence
<220> FEATURE:
<223> OTHER INFORMATION: Synthetic: hu125B11.v26 HVR-H3

<400> SEQUENCE: 324

Gly Thr Thr Tyr
1

<210> SEQ ID NO 325
<211> LENGTH: 11
<212> TYPE: PRT
<213> ORGANISM: Artificial Sequence
<220> FEATURE:
<223> OTHER INFORMATION: Synthetic: hu125B11.v26 HVR-L1

<400> SEQUENCE: 325

Lys Ala Ser Gln Asn Val Gly Thr Ala Val Ala
1               5                   10

<210> SEQ ID NO 326
<211> LENGTH: 7
<212> TYPE: PRT
<213> ORGANISM: Artificial Sequence
<220> FEATURE:
<223> OTHER INFORMATION: Synthetic: hu125B11.v26 HVR-L2

<400> SEQUENCE: 326

Ser Ala Ser Ile Arg Tyr Thr
1               5

<210> SEQ ID NO 327
<211> LENGTH: 9
<212> TYPE: PRT
<213> ORGANISM: Artificial Sequence
<220> FEATURE:
<223> OTHER INFORMATION: Synthetic: hu125B11.v26 HVR-L3

<400> SEQUENCE: 327

Gln Gln Phe Arg Thr Tyr Pro Tyr Thr

<210> SEQ ID NO 328

<400> SEQUENCE: 328

000

<210> SEQ ID NO 329

<400> SEQUENCE: 329

000

<210> SEQ ID NO 330
<211> LENGTH: 115
<212> TYPE: PRT
<213> ORGANISM: Artificial Sequence
<220> FEATURE:
<223> OTHER INFORMATION: Synthetic: hu125B11.v28 heavy chain variable
      region (VH)

<400> SEQUENCE: 330

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Ile Phe Ser Asn Tyr
            20                  25                  30

Trp Met Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Thr Gly Gly Thr Thr Tyr Trp Gly Gln Gly Thr Leu Val Thr
            100                 105                 110

Val Ser Ser
        115

<210> SEQ ID NO 331
<211> LENGTH: 107
<212> TYPE: PRT
<213> ORGANISM: Artificial Sequence
<220> FEATURE:
<223> OTHER INFORMATION: Synthetic: hu125B11.v28 light chain variable
      region (VL)

<400> SEQUENCE: 331

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Ile Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Arg Thr Tyr Pro Tyr
                85                  90                  95

Thr Phe Gly Gln Gly Thr Lys Val Glu Ile Lys
            100                 105

<210> SEQ ID NO 332
<211> LENGTH: 5
<212> TYPE: PRT
<213> ORGANISM: Artificial Sequence
<220> FEATURE:
<223> OTHER INFORMATION: Synthetic: hu125B11.v28 HVR-H1

<400> SEQUENCE: 332

Asn Tyr Trp Met Asn
1               5

<210> SEQ ID NO 333
<211> LENGTH: 19
<212> TYPE: PRT
<213> ORGANISM: Artificial Sequence
<220> FEATURE:
<223> OTHER INFORMATION: Synthetic: hu125B11.v28 HVR-H2

<400> SEQUENCE: 333

Gln Ile Arg Leu Lys Ser Asp Asn Tyr Ala Thr His Tyr Ala Glu Ser
1               5                   10                  15

Val Lys Gly

<210> SEQ ID NO 334
<211> LENGTH: 4
<212> TYPE: PRT
<213> ORGANISM: Artificial Sequence
<220> FEATURE:
<223> OTHER INFORMATION: Synthetic: hu125B11.v28 HVR-H3

<400> SEQUENCE: 334

Gly Thr Thr Tyr
1

<210> SEQ ID NO 335
<211> LENGTH: 11
<212> TYPE: PRT
<213> ORGANISM: Artificial Sequence
<220> FEATURE:
<223> OTHER INFORMATION: Synthetic: hu125B11.v28 HVR-L1

<400> SEQUENCE: 335

Lys Ala Ser Gln Asn Val Gly Thr Ala Val Ala
1               5                   10

<210> SEQ ID NO 336
<211> LENGTH: 7
<212> TYPE: PRT
<213> ORGANISM: Artificial Sequence
<220> FEATURE:
<223> OTHER INFORMATION: Synthetic: hu125B11.v28 HVR-L2

<400> SEQUENCE: 336

Ser Ala Ser Ile Arg Tyr Thr
1               5

<210> SEQ ID NO 337
<211> LENGTH: 9
<212> TYPE: PRT
<213> ORGANISM: Artificial Sequence
<220> FEATURE:
<223> OTHER INFORMATION: Synthetic: hu125B11.v28 HVR-L3

-continued

<400> SEQUENCE: 337

Gln Gln Phe Arg Thr Tyr Pro Tyr Thr
1               5

<210> SEQ ID NO 338

<400> SEQUENCE: 338

000

<210> SEQ ID NO 339

<400> SEQUENCE: 339

000

<210> SEQ ID NO 340
<211> LENGTH: 117
<212> TYPE: PRT
<213> ORGANISM: Artificial Sequence
<220> FEATURE:
<223> OTHER INFORMATION: Synthetic: Hu37D3-H9.v28.A4 heavy chain
      variable region (VH)

<400> SEQUENCE: 340

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Arg Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ser Tyr Ser Gly Ala Met Asp Tyr Trp Gly Gln Gly Thr Leu
            100                 105                 110

Val Thr Val Ser Ser
        115

<210> SEQ ID NO 341
<211> LENGTH: 112
<212> TYPE: PRT
<213> ORGANISM: Artificial Sequence
<220> FEATURE:
<223> OTHER INFORMATION: Synthetic: Hu37D3-H9.v28.A4 light chain
      variable region (VL)

<400> SEQUENCE: 341

Asp Asp Val Leu Thr Gln Thr Pro Leu Ser Leu Pro Val Thr Pro Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
            85                  90                  95

Ser Leu Val Pro Trp Thr Phe Gly Gln Gly Thr Lys Val Glu Ile Lys
            100                 105                 110

<210> SEQ ID NO 342
<211> LENGTH: 5
<212> TYPE: PRT
<213> ORGANISM: Artificial Sequence
<220> FEATURE:
<223> OTHER INFORMATION: Synthetic: Hu37D3-H9.v28.A4 HVR-H1

<400> SEQUENCE: 342

Ser Tyr Gly Met Ser
1               5

<210> SEQ ID NO 343
<211> LENGTH: 17
<212> TYPE: PRT
<213> ORGANISM: Artificial Sequence
<220> FEATURE:
<223> OTHER INFORMATION: Synthetic: Hu37D3-H9.v28.A4 HVR-H2

<400> SEQUENCE: 343

Thr Ile Asn Ser Gly Gly Thr Tyr Thr Tyr Tyr Pro Asp Ser Val Lys
1               5                   10                  15

Gly

<210> SEQ ID NO 344
<211> LENGTH: 8
<212> TYPE: PRT
<213> ORGANISM: Artificial Sequence
<220> FEATURE:
<223> OTHER INFORMATION: Synthetic: Hu37D3-H9.v28.A4 HVR-H3

<400> SEQUENCE: 344

Ser Tyr Ser Gly Ala Met Asp Tyr
1               5

<210> SEQ ID NO 345
<211> LENGTH: 16
<212> TYPE: PRT
<213> ORGANISM: Artificial Sequence
<220> FEATURE:
<223> OTHER INFORMATION: Synthetic: Hu37D3-H9.v28.A4 HVR-L1

<400> SEQUENCE: 345

Arg Ser Ser Gln Ser Ile Val His Ser Asn Gly Asn Thr Tyr Leu Glu
1               5                   10                  15

<210> SEQ ID NO 346
<211> LENGTH: 7
<212> TYPE: PRT
<213> ORGANISM: Artificial Sequence
<220> FEATURE:
<223> OTHER INFORMATION: Synthetic: Hu37D3-H9.v28.A4 HVR-L2

<400> SEQUENCE: 346

Lys Val Ser Asn Arg Phe Ser
1               5

<210> SEQ ID NO 347
<211> LENGTH: 9
<212> TYPE: PRT
<213> ORGANISM: Artificial Sequence
<220> FEATURE:
<223> OTHER INFORMATION: Synthetic: Hu37D3-H9.v28.A4 HVR-L3

<400> SEQUENCE: 347

Phe Gln Gly Ser Leu Val Pro Trp Thr
1               5

<210> SEQ ID NO 348
<211> LENGTH: 444
<212> TYPE: PRT
<213> ORGANISM: Artificial Sequence
<220> FEATURE:
<223> OTHER INFORMATION: Synthetic: Hu37D3-H9.v28.A4 IgG4-S228P.YTE
      heavy chain

<400> SEQUENCE: 348

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Arg Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ser Tyr Ser Gly Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Tyr Ile Thr Arg Glu Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

```
Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
                435                 440

<210> SEQ ID NO 349
<211> LENGTH: 219
<212> TYPE: PRT
<213> ORGANISM: Artificial Sequence
<220> FEATURE:
<223> OTHER INFORMATION: Synthetic: Hu37D3-H9.v28.A4 IgG4-S228P.YTE
      light chain

<400> SEQUENCE: 349

Asp Asp Val Leu Thr Gln Thr Pro Leu Ser Leu Pro Val Thr Pro Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Leu Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 350
```

```
<211> LENGTH: 12
<212> TYPE: PRT
<213> ORGANISM: Artificial Sequence
<220> FEATURE:
<223> OTHER INFORMATION: Synthetic: Unstressed control (mean, n=9)

<400> SEQUENCE: 350

Glu Asp Leu His Ser Asn Gly Asn Thr Tyr Phe Leu
1               5                   10

<210> SEQ ID NO 351
<211> LENGTH: 12
<212> TYPE: PRT
<213> ORGANISM: Artificial Sequence
<220> FEATURE:
<223> OTHER INFORMATION: Synthetic: hu37D3-H9.v5

<400> SEQUENCE: 351

Glu Asp Leu His Ser Asn Gly Asn Thr Tyr Phe Leu
1               5                   10

<210> SEQ ID NO 352
<211> LENGTH: 12
<212> TYPE: PRT
<213> ORGANISM: Artificial Sequence
<220> FEATURE:
<223> OTHER INFORMATION: Synthetic: hu37D3-H9.v5.1

<400> SEQUENCE: 352

Glu Asp Leu His Ser Asn Ala Asn Thr Tyr Phe Leu
1               5                   10

<210> SEQ ID NO 353
<211> LENGTH: 12
<212> TYPE: PRT
<213> ORGANISM: Artificial Sequence
<220> FEATURE:
<223> OTHER INFORMATION: Synthetic: hu37D3-H9.v5.2

<400> SEQUENCE: 353

Glu Asp Leu His Ser Ser Gly Asn Thr Tyr Phe Leu
1               5                   10

<210> SEQ ID NO 354
<211> LENGTH: 12
<212> TYPE: PRT
<213> ORGANISM: Artificial Sequence
<220> FEATURE:
<223> OTHER INFORMATION: Synthetic: hu37D3-H9.v5.3

<400> SEQUENCE: 354

Glu Asp Leu His Ser Asp Gly Asn Thr Tyr Phe Leu
1               5                   10

<210> SEQ ID NO 355
<211> LENGTH: 12
<212> TYPE: PRT
<213> ORGANISM: Artificial Sequence
<220> FEATURE:
<223> OTHER INFORMATION: Synthetic: hu37D3-H9.v5.4

<400> SEQUENCE: 355

Glu Asp Leu His Ser Gln Gly Asn Thr Tyr Phe Leu
1               5                   10

<210> SEQ ID NO 356
<211> LENGTH: 12
```

```
<212> TYPE: PRT
<213> ORGANISM: Artificial Sequence
<220> FEATURE:
<223> OTHER INFORMATION: Synthetic: hu37D3-H9.v5.5

<400> SEQUENCE: 356

Glu Asp Leu His Ser Glu Gly Asn Thr Tyr Phe Leu
1               5                   10

<210> SEQ ID NO 357
<211> LENGTH: 12
<212> TYPE: PRT
<213> ORGANISM: Artificial Sequence
<220> FEATURE:
<223> OTHER INFORMATION: Synthetic: hu37D3-H9.v5.6

<400> SEQUENCE: 357

Glu Asp Leu His Ser Ala Gly Asn Thr Tyr Phe Leu
1               5                   10

<210> SEQ ID NO 358
<211> LENGTH: 12
<212> TYPE: PRT
<213> ORGANISM: Artificial Sequence
<220> FEATURE:
<223> OTHER INFORMATION: Synthetic: hu37D3-H9.v5.7

<400> SEQUENCE: 358

Glu Asp Leu His Ser Asn Gly Asp Thr Tyr Phe Leu
1               5                   10

<210> SEQ ID NO 359
<211> LENGTH: 12
<212> TYPE: PRT
<213> ORGANISM: Artificial Sequence
<220> FEATURE:
<223> OTHER INFORMATION: Synthetic: hu37D3-H9.v5.8

<400> SEQUENCE: 359

Glu Asp Leu His Ser Asn Gly Gln Thr Tyr Phe Leu
1               5                   10

<210> SEQ ID NO 360
<211> LENGTH: 12
<212> TYPE: PRT
<213> ORGANISM: Artificial Sequence
<220> FEATURE:
<223> OTHER INFORMATION: Synthetic: hu37D3-H9.v5.9

<400> SEQUENCE: 360

Glu Asp Leu His Ser Asn Gly Glu Thr Tyr Phe Leu
1               5                   10

<210> SEQ ID NO 361
<211> LENGTH: 12
<212> TYPE: PRT
<213> ORGANISM: Artificial Sequence
<220> FEATURE:
<223> OTHER INFORMATION: Synthetic: hu37D3-H9.v5.10

<400> SEQUENCE: 361

Glu Asp Leu His Ser Asn Gly Ala Thr Tyr Phe Leu
1               5                   10

<210> SEQ ID NO 362
<211> LENGTH: 12
<212> TYPE: PRT
```

```
<213> ORGANISM: Artificial Sequence
<220> FEATURE:
<223> OTHER INFORMATION: Synthetic: hu37D3-H9.v5.11

<400> SEQUENCE: 362

Glu Asp Leu His Ser Asn Gly Ser Thr Tyr Phe Leu
1               5                   10

<210> SEQ ID NO 363
<211> LENGTH: 12
<212> TYPE: PRT
<213> ORGANISM: Artificial Sequence
<220> FEATURE:
<223> OTHER INFORMATION: Synthetic: hu37D3.v28

<400> SEQUENCE: 363

Asp Asp Leu His Ser Asn Gly Asn Thr Tyr Phe Leu
1               5                   10

<210> SEQ ID NO 364
<211> LENGTH: 12
<212> TYPE: PRT
<213> ORGANISM: Artificial Sequence
<220> FEATURE:
<223> OTHER INFORMATION: Synthetic: hu37D3.v28.A2

<400> SEQUENCE: 364

Asp Asp Leu His Ser Asn Gly Asn Thr Tyr Phe His
1               5                   10

<210> SEQ ID NO 365
<211> LENGTH: 12
<212> TYPE: PRT
<213> ORGANISM: Artificial Sequence
<220> FEATURE:
<223> OTHER INFORMATION: Synthetic: hu37D3.v28.A4

<400> SEQUENCE: 365

Asp Asp Leu His Ser Asn Gly Asn Thr Tyr Leu Leu
1               5                   10

<210> SEQ ID NO 366
<211> LENGTH: 12
<212> TYPE: PRT
<213> ORGANISM: Artificial Sequence
<220> FEATURE:
<223> OTHER INFORMATION: Synthetic: hu37D3.v28.A6

<400> SEQUENCE: 366

Asp Asp Leu His Ser Asn Gly Asn Thr Tyr Leu His
1               5                   10

<210> SEQ ID NO 367
<211> LENGTH: 12
<212> TYPE: PRT
<213> ORGANISM: Artificial Sequence
<220> FEATURE:
<223> OTHER INFORMATION: Synthetic: hu37D3.v28.A8

<400> SEQUENCE: 367

Asp Asp Met His Ser Asn Gly Asn Thr Tyr Phe Leu
1               5                   10

<210> SEQ ID NO 368
<211> LENGTH: 12
<212> TYPE: PRT
<213> ORGANISM: Artificial Sequence
```

```
<220> FEATURE:
<223> OTHER INFORMATION: Synthetic: hu37D3.v28.A10

<400> SEQUENCE: 368

Asp Asp Met His Ser Asn Gly Asn Thr Tyr Phe His
1               5                   10

<210> SEQ ID NO 369
<211> LENGTH: 12
<212> TYPE: PRT
<213> ORGANISM: Artificial Sequence
<220> FEATURE:
<223> OTHER INFORMATION: Synthetic: hu37D3.v28.A12

<400> SEQUENCE: 369

Asp Asp Met His Ser Asn Gly Asn Thr Tyr Leu Leu
1               5                   10

<210> SEQ ID NO 370
<211> LENGTH: 12
<212> TYPE: PRT
<213> ORGANISM: Artificial Sequence
<220> FEATURE:
<223> OTHER INFORMATION: Synthetic: hu37D3.v28.A14

<400> SEQUENCE: 370

Asp Asp Met His Ser Asn Gly Asn Thr Tyr Leu His
1               5                   10

<210> SEQ ID NO 371
<211> LENGTH: 12
<212> TYPE: PRT
<213> ORGANISM: Artificial Sequence
<220> FEATURE:
<223> OTHER INFORMATION: Synthetic: hu37D3.v28.A16

<400> SEQUENCE: 371

Asp Val Leu His Ser Asn Gly Asn Thr Tyr Phe Leu
1               5                   10

<210> SEQ ID NO 372
<211> LENGTH: 12
<212> TYPE: PRT
<213> ORGANISM: Artificial Sequence
<220> FEATURE:
<223> OTHER INFORMATION: Synthetic: hu37D3.v28.A18

<400> SEQUENCE: 372

Asp Val Leu His Ser Asn Gly Asn Thr Tyr Phe His
1               5                   10

<210> SEQ ID NO 373
<211> LENGTH: 12
<212> TYPE: PRT
<213> ORGANISM: Artificial Sequence
<220> FEATURE:
<223> OTHER INFORMATION: Synthetic: hu37D3.v28.A20

<400> SEQUENCE: 373

Asp Val Leu His Ser Asn Gly Asn Thr Tyr Leu Leu
1               5                   10

<210> SEQ ID NO 374
<211> LENGTH: 12
<212> TYPE: PRT
<213> ORGANISM: Artificial Sequence
<220> FEATURE:
```

<223> OTHER INFORMATION: Synthetic: hu37D3.v28.A22

<400> SEQUENCE: 374

Asp Val Leu His Ser Asn Gly Asn Thr Tyr Leu His
1               5                   10

<210> SEQ ID NO 375
<211> LENGTH: 12
<212> TYPE: PRT
<213> ORGANISM: Artificial Sequence
<220> FEATURE:
<223> OTHER INFORMATION: Synthetic: hu37D3.v28.A24

<400> SEQUENCE: 375

Asp Val Met His Ser Asn Gly Asn Thr Tyr Phe Leu
1               5                   10

<210> SEQ ID NO 376
<211> LENGTH: 12
<212> TYPE: PRT
<213> ORGANISM: Artificial Sequence
<220> FEATURE:
<223> OTHER INFORMATION: Synthetic: hu37D3.v28.A26

<400> SEQUENCE: 376

Asp Val Met His Ser Asn Gly Asn Thr Tyr Phe His
1               5                   10

<210> SEQ ID NO 377
<211> LENGTH: 12
<212> TYPE: PRT
<213> ORGANISM: Artificial Sequence
<220> FEATURE:
<223> OTHER INFORMATION: Synthetic: hu37D3.v28.A28

<400> SEQUENCE: 377

Asp Val Met His Ser Asn Gly Asn Thr Tyr Leu Leu
1               5                   10

<210> SEQ ID NO 378
<211> LENGTH: 12
<212> TYPE: PRT
<213> ORGANISM: Artificial Sequence
<220> FEATURE:
<223> OTHER INFORMATION: Synthetic: hu37D3.v28.A30

<400> SEQUENCE: 378

Asp Val Met His Ser Asn Gly Asn Thr Tyr Leu His
1               5                   10

<210> SEQ ID NO 379
<211> LENGTH: 12
<212> TYPE: PRT
<213> ORGANISM: Artificial Sequence
<220> FEATURE:
<223> OTHER INFORMATION: Synthetic: hu37D3.v28.B1

<400> SEQUENCE: 379

Asp Asp Leu His Ser Ile Gly Asn Thr Phe Phe Leu
1               5                   10

<210> SEQ ID NO 380
<211> LENGTH: 12
<212> TYPE: PRT
<213> ORGANISM: Artificial Sequence
<220> FEATURE:
<223> OTHER INFORMATION: Synthetic: hu37D3.v28.B2

```
<400> SEQUENCE: 380

Asp Asp Leu His Ser Met Gly Asn Thr Phe Phe Leu
1               5                   10

<210> SEQ ID NO 381
<211> LENGTH: 12
<212> TYPE: PRT
<213> ORGANISM: Artificial Sequence
<220> FEATURE:
<223> OTHER INFORMATION: Synthetic: hu37D3.v28.B3

<400> SEQUENCE: 381

Asp Asp Leu His Ser Gln Gly Asn Thr Trp Phe Leu
1               5                   10

<210> SEQ ID NO 382
<211> LENGTH: 12
<212> TYPE: PRT
<213> ORGANISM: Artificial Sequence
<220> FEATURE:
<223> OTHER INFORMATION: Synthetic: hu37D3.v28.B4

<400> SEQUENCE: 382

Asp Asp Leu His Ser Gln Gly Asn Thr His Phe Leu
1               5                   10

<210> SEQ ID NO 383
<211> LENGTH: 12
<212> TYPE: PRT
<213> ORGANISM: Artificial Sequence
<220> FEATURE:
<223> OTHER INFORMATION: Synthetic: hu37D3.v28.B6

<400> SEQUENCE: 383

Asp Asp Leu His Ser Asp Gly Asn Thr Arg Phe Leu
1               5                   10

<210> SEQ ID NO 384
<211> LENGTH: 12
<212> TYPE: PRT
<213> ORGANISM: Artificial Sequence
<220> FEATURE:
<223> OTHER INFORMATION: Synthetic: hu37D3.v28.B7

<400> SEQUENCE: 384

Asp Asp Leu His Ser Asp Gly Asn Thr Lys Phe Leu
1               5                   10

<210> SEQ ID NO 385
<211> LENGTH: 12
<212> TYPE: PRT
<213> ORGANISM: Artificial Sequence
<220> FEATURE:
<223> OTHER INFORMATION: Synthetic: hu37D3.v28.B8

<400> SEQUENCE: 385

Asp Asp Leu His Ser Glu Gly Asn Thr Arg Phe Leu
1               5                   10

<210> SEQ ID NO 386
<211> LENGTH: 12
<212> TYPE: PRT
<213> ORGANISM: Artificial Sequence
<220> FEATURE:
<223> OTHER INFORMATION: Synthetic: hu37D3.v28.C1
```

-continued

<400> SEQUENCE: 386

Asp Asp Leu His Ser Asn Asn Asn Thr Tyr Phe Leu
1               5                   10

<210> SEQ ID NO 387
<211> LENGTH: 12
<212> TYPE: PRT
<213> ORGANISM: Artificial Sequence
<220> FEATURE:
<223> OTHER INFORMATION: Synthetic: hu37D3.v28.C2

<400> SEQUENCE: 387

Asp Asp Leu His Ser Asn Asp Asn Thr Tyr Phe Leu
1               5                   10

<210> SEQ ID NO 388
<211> LENGTH: 12
<212> TYPE: PRT
<213> ORGANISM: Artificial Sequence
<220> FEATURE:
<223> OTHER INFORMATION: Synthetic: hu37D3.v28.D1

<400> SEQUENCE: 388

Asp Asp Leu His Ala Asn Gly Asn Thr Tyr Phe Leu
1               5                   10

<210> SEQ ID NO 389
<211> LENGTH: 12
<212> TYPE: PRT
<213> ORGANISM: Artificial Sequence
<220> FEATURE:
<223> OTHER INFORMATION: Synthetic: Unstressed control (mean, n=9)

<400> SEQUENCE: 389

Glu Asp Leu His Ser Asn Gly Asn Thr Tyr Phe Leu
1               5                   10

<210> SEQ ID NO 390
<211> LENGTH: 12
<212> TYPE: PRT
<213> ORGANISM: Artificial Sequence
<220> FEATURE:
<223> OTHER INFORMATION: Synthetic: hu37D3.v28.E1

<400> SEQUENCE: 390

Asp Asp Leu Asn Ser Asn Gly Asn Thr Tyr Phe Leu
1               5                   10

<210> SEQ ID NO 391
<211> LENGTH: 12
<212> TYPE: PRT
<213> ORGANISM: Artificial Sequence
<220> FEATURE:
<223> OTHER INFORMATION: Synthetic: hu37D3.v28.E2

<400> SEQUENCE: 391

Asp Asp Leu Gln Ser Asn Gly Asn Thr Tyr Phe Leu
1               5                   10

<210> SEQ ID NO 392
<211> LENGTH: 12
<212> TYPE: PRT
<213> ORGANISM: Artificial Sequence
<220> FEATURE:
<223> OTHER INFORMATION: Synthetic: hu37D3.v28.E3

<400> SEQUENCE: 392

```
Asp Asp Leu Asp Ser Asp Gly Asn Thr Tyr Phe Leu
1               5                   10
```

<210> SEQ ID NO 393
<211> LENGTH: 12
<212> TYPE: PRT
<213> ORGANISM: Artificial Sequence
<220> FEATURE:
<223> OTHER INFORMATION: Synthetic: hu37D3.v28.F1

<400> SEQUENCE: 393

```
Asp Asp Leu His Ser Asn Thr Asn Thr Tyr Phe Leu
1               5                   10
```

<210> SEQ ID NO 394
<211> LENGTH: 12
<212> TYPE: PRT
<213> ORGANISM: Artificial Sequence
<220> FEATURE:
<223> OTHER INFORMATION: Synthetic: hu37D3.v28.F2

<400> SEQUENCE: 394

```
Asp Asp Leu His Thr Asn Gly Asn Thr Tyr Phe Leu
1               5                   10
```

<210> SEQ ID NO 395
<211> LENGTH: 12
<212> TYPE: PRT
<213> ORGANISM: Artificial Sequence
<220> FEATURE:
<223> OTHER INFORMATION: Synthetic: hu37D3.v28.F3

<400> SEQUENCE: 395

```
Asp Asp Leu His Thr Asn Ala Asn Thr Tyr Phe Leu
1               5                   10
```

<210> SEQ ID NO 396
<211> LENGTH: 12
<212> TYPE: PRT
<213> ORGANISM: Artificial Sequence
<220> FEATURE:
<223> OTHER INFORMATION: Synthetic: hu37D3.v28.51

<400> SEQUENCE: 396

```
Glu Asp Leu His Ser His Gly Asn Thr Tyr Phe Leu
1               5                   10
```

<210> SEQ ID NO 397
<211> LENGTH: 12
<212> TYPE: PRT
<213> ORGANISM: Artificial Sequence
<220> FEATURE:
<223> OTHER INFORMATION: Synthetic: hu37D3.v28.52

<400> SEQUENCE: 397

```
Glu Asp Leu His Ser Lys Gly Asn Thr Tyr Phe Leu
1               5                   10
```

<210> SEQ ID NO 398
<211> LENGTH: 12
<212> TYPE: PRT
<213> ORGANISM: Artificial Sequence
<220> FEATURE:
<223> OTHER INFORMATION: Synthetic: hu37D3.v28.53

<400> SEQUENCE: 398

Glu Asp Leu His Ser Arg Gly Asn Thr Tyr Phe Leu
1               5                   10

<210> SEQ ID NO 399
<211> LENGTH: 12
<212> TYPE: PRT
<213> ORGANISM: Artificial Sequence
<220> FEATURE:
<223> OTHER INFORMATION: Synthetic: hu37D3.v28.54

<400> SEQUENCE: 399

Glu Asp Leu His Ser Leu Gly Asn Thr Tyr Phe Leu
1               5                   10

<210> SEQ ID NO 400
<211> LENGTH: 12
<212> TYPE: PRT
<213> ORGANISM: Artificial Sequence
<220> FEATURE:
<223> OTHER INFORMATION: Synthetic: hu37D3.v28.55

<400> SEQUENCE: 400

Asp Asp Leu His Ser Asn Gln Asn Thr Tyr Phe Leu
1               5                   10

<210> SEQ ID NO 401
<211> LENGTH: 12
<212> TYPE: PRT
<213> ORGANISM: Artificial Sequence
<220> FEATURE:
<223> OTHER INFORMATION: Synthetic: hu37D3.v28.56

<400> SEQUENCE: 401

Asp Asp Leu His Ser Asn Tyr Asn Thr Tyr Phe Leu
1               5                   10

<210> SEQ ID NO 402
<211> LENGTH: 12
<212> TYPE: PRT
<213> ORGANISM: Artificial Sequence
<220> FEATURE:
<223> OTHER INFORMATION: Synthetic: hu37D3.v28.57

<400> SEQUENCE: 402

Asp Asp Leu His Ser Asn Phe Asn Thr Tyr Phe Leu
1               5                   10

<210> SEQ ID NO 403
<211> LENGTH: 12
<212> TYPE: PRT
<213> ORGANISM: Artificial Sequence
<220> FEATURE:
<223> OTHER INFORMATION: Synthetic: hu37D3.v29.1

<400> SEQUENCE: 403

Glu Asp Leu His Ser Asn Gly Asp Thr Tyr Phe Leu
1               5                   10

<210> SEQ ID NO 404
<211> LENGTH: 12
<212> TYPE: PRT
<213> ORGANISM: Artificial Sequence
<220> FEATURE:
<223> OTHER INFORMATION: Synthetic: hu37D3.v29.2

<400> SEQUENCE: 404

Glu Asp Leu His Ser Asn Gly Gln Thr Tyr Phe Leu

```
1               5               10

<210> SEQ ID NO 405
<211> LENGTH: 12
<212> TYPE: PRT
<213> ORGANISM: Artificial Sequence
<220> FEATURE:
<223> OTHER INFORMATION: Synthetic: hu37D3.v29.3

<400> SEQUENCE: 405

Glu Asp Leu His Ser Asn Gly Glu Thr Tyr Phe Leu
1               5                   10

<210> SEQ ID NO 406
<211> LENGTH: 12
<212> TYPE: PRT
<213> ORGANISM: Artificial Sequence
<220> FEATURE:
<223> OTHER INFORMATION: Synthetic: hu37D3.v29.4

<400> SEQUENCE: 406

Glu Asp Leu His Ser Asn Gly Ala Thr Tyr Phe Leu
1               5                   10

<210> SEQ ID NO 407
<211> LENGTH: 12
<212> TYPE: PRT
<213> ORGANISM: Artificial Sequence
<220> FEATURE:
<223> OTHER INFORMATION: Synthetic: hu37D3.v29.5

<400> SEQUENCE: 407

Glu Asp Leu His Ser Asn Gly His Thr Tyr Phe Leu
1               5                   10

<210> SEQ ID NO 408
<211> LENGTH: 12
<212> TYPE: PRT
<213> ORGANISM: Artificial Sequence
<220> FEATURE:
<223> OTHER INFORMATION: Synthetic: hu37D3.v29.6

<400> SEQUENCE: 408

Glu Asp Leu His Ser Asn Gly Lys Thr Tyr Phe Leu
1               5                   10

<210> SEQ ID NO 409
<211> LENGTH: 12
<212> TYPE: PRT
<213> ORGANISM: Artificial Sequence
<220> FEATURE:
<223> OTHER INFORMATION: Synthetic: hu37D3.v29.7

<400> SEQUENCE: 409

Glu Asp Leu His Ser Asn Gly Leu Thr Tyr Phe Leu
1               5                   10

<210> SEQ ID NO 410
<211> LENGTH: 12
<212> TYPE: PRT
<213> ORGANISM: Artificial Sequence
<220> FEATURE:
<223> OTHER INFORMATION: Synthetic: hu37D3.v29.8

<400> SEQUENCE: 410

Glu Asp Leu His Ser Asn Ala Asp Thr Tyr Phe Leu
1               5                   10
```

```
<210> SEQ ID NO 411
<211> LENGTH: 12
<212> TYPE: PRT
<213> ORGANISM: Artificial Sequence
<220> FEATURE:
<223> OTHER INFORMATION: Synthetic: hu37D3.v29.9

<400> SEQUENCE: 411

Glu Asp Leu His Ser Asn Ala Gln Thr Tyr Phe Leu
1               5                   10

<210> SEQ ID NO 412
<211> LENGTH: 12
<212> TYPE: PRT
<213> ORGANISM: Artificial Sequence
<220> FEATURE:
<223> OTHER INFORMATION: Synthetic: hu37D3.v29.10

<400> SEQUENCE: 412

Glu Asp Leu His Ser Asn Ala Glu Thr Tyr Phe Leu
1               5                   10

<210> SEQ ID NO 413
<211> LENGTH: 12
<212> TYPE: PRT
<213> ORGANISM: Artificial Sequence
<220> FEATURE:
<223> OTHER INFORMATION: Synthetic: hu37D3.v29.11

<400> SEQUENCE: 413

Glu Asp Leu His Ser Asn Ala Ala Thr Tyr Phe Leu
1               5                   10

<210> SEQ ID NO 414
<211> LENGTH: 12
<212> TYPE: PRT
<213> ORGANISM: Artificial Sequence
<220> FEATURE:
<223> OTHER INFORMATION: Synthetic: hu37D3.v29.12

<400> SEQUENCE: 414

Glu Asp Leu His Ser Asn Ala His Thr Tyr Phe Leu
1               5                   10

<210> SEQ ID NO 415
<211> LENGTH: 12
<212> TYPE: PRT
<213> ORGANISM: Artificial Sequence
<220> FEATURE:
<223> OTHER INFORMATION: Synthetic: hu37D3.v29.13

<400> SEQUENCE: 415

Glu Asp Leu His Ser Asn Ala Lys Thr Tyr Phe Leu
1               5                   10

<210> SEQ ID NO 416
<211> LENGTH: 12
<212> TYPE: PRT
<213> ORGANISM: Artificial Sequence
<220> FEATURE:
<223> OTHER INFORMATION: Synthetic: hu37D3.v29.14

<400> SEQUENCE: 416

Glu Asp Leu His Ser Asn Ala Leu Thr Tyr Phe Leu
1               5                   10
```

<210> SEQ ID NO 417
<211> LENGTH: 12
<212> TYPE: PRT
<213> ORGANISM: Artificial Sequence
<220> FEATURE:
<223> OTHER INFORMATION: Synthetic: hu37D3-H9.v30.1

<400> SEQUENCE: 417

Asp Asp Leu His Ser Gly Gly Asn Thr Tyr Phe Leu
1               5                   10

<210> SEQ ID NO 418
<211> LENGTH: 12
<212> TYPE: PRT
<213> ORGANISM: Artificial Sequence
<220> FEATURE:
<223> OTHER INFORMATION: Synthetic: hu37D3-H9.v30.2

<400> SEQUENCE: 418

Asp Asp Leu His Ser Thr Gly Asn Thr Tyr Phe Leu
1               5                   10

<210> SEQ ID NO 419
<211> LENGTH: 12
<212> TYPE: PRT
<213> ORGANISM: Artificial Sequence
<220> FEATURE:
<223> OTHER INFORMATION: Synthetic: hu37D3-H9.v30.3

<400> SEQUENCE: 419

Asp Asp Leu His Ser Val Gly Asn Thr Tyr Phe Leu
1               5                   10

<210> SEQ ID NO 420
<211> LENGTH: 12
<212> TYPE: PRT
<213> ORGANISM: Artificial Sequence
<220> FEATURE:
<223> OTHER INFORMATION: Synthetic: hu37D3-H9.v30.4

<400> SEQUENCE: 420

Asp Asp Leu His Ser Leu Gly Asn Thr Tyr Phe Leu
1               5                   10

<210> SEQ ID NO 421
<211> LENGTH: 12
<212> TYPE: PRT
<213> ORGANISM: Artificial Sequence
<220> FEATURE:
<223> OTHER INFORMATION: Synthetic: hu37D3-H9.v30.5

<400> SEQUENCE: 421

Asp Asp Leu His Ser Ile Gly Asn Thr Tyr Phe Leu
1               5                   10

<210> SEQ ID NO 422
<211> LENGTH: 12
<212> TYPE: PRT
<213> ORGANISM: Artificial Sequence
<220> FEATURE:
<223> OTHER INFORMATION: Synthetic: hu37D3-H9.v30.6

<400> SEQUENCE: 422

Asp Asp Leu His Ser Pro Gly Asn Thr Tyr Phe Leu
1               5                   10

```
<210> SEQ ID NO 423
<211> LENGTH: 12
<212> TYPE: PRT
<213> ORGANISM: Artificial Sequence
<220> FEATURE:
<223> OTHER INFORMATION: Synthetic: hu37D3-H9.v30.7

<400> SEQUENCE: 423

Asp Asp Leu His Ser Phe Gly Asn Thr Tyr Phe Leu
1               5                   10

<210> SEQ ID NO 424
<211> LENGTH: 12
<212> TYPE: PRT
<213> ORGANISM: Artificial Sequence
<220> FEATURE:
<223> OTHER INFORMATION: Synthetic: hu37D3-H9.v30.8

<400> SEQUENCE: 424

Asp Asp Leu His Ser Tyr Gly Asn Thr Tyr Phe Leu
1               5                   10

<210> SEQ ID NO 425
<211> LENGTH: 12
<212> TYPE: PRT
<213> ORGANISM: Artificial Sequence
<220> FEATURE:
<223> OTHER INFORMATION: Synthetic: hu37D3-H9.v30.9

<400> SEQUENCE: 425

Asp Asp Leu His Ser His Gly Asn Thr Tyr Phe Leu
1               5                   10

<210> SEQ ID NO 426
<211> LENGTH: 12
<212> TYPE: PRT
<213> ORGANISM: Artificial Sequence
<220> FEATURE:
<223> OTHER INFORMATION: Synthetic: hu37D3-H9.v30.10

<400> SEQUENCE: 426

Asp Asp Leu His Ser Lys Gly Asn Thr Tyr Phe Leu
1               5                   10

<210> SEQ ID NO 427
<211> LENGTH: 12
<212> TYPE: PRT
<213> ORGANISM: Artificial Sequence
<220> FEATURE:
<223> OTHER INFORMATION: Synthetic: hu37D3-H9.v30.11

<400> SEQUENCE: 427

Asp Asp Leu His Ser Arg Gly Asn Thr Tyr Phe Leu
1               5                   10

<210> SEQ ID NO 428
<211> LENGTH: 12
<212> TYPE: PRT
<213> ORGANISM: Artificial Sequence
<220> FEATURE:
<223> OTHER INFORMATION: Synthetic: hu37D3-H9.v31.1

<400> SEQUENCE: 428

Asp Asp Leu His Ser Asn Ala Gly Thr Tyr Phe Leu
1               5                   10

<210> SEQ ID NO 429
```

```
<211> LENGTH: 12
<212> TYPE: PRT
<213> ORGANISM: Artificial Sequence
<220> FEATURE:
<223> OTHER INFORMATION: Synthetic: hu37D3-H9.v31.2

<400> SEQUENCE: 429

Asp Asp Leu His Ser Asn Ala Val Thr Tyr Phe Leu
1               5                   10

<210> SEQ ID NO 430
<211> LENGTH: 12
<212> TYPE: PRT
<213> ORGANISM: Artificial Sequence
<220> FEATURE:
<223> OTHER INFORMATION: Synthetic: hu37D3-H9.v31.3

<400> SEQUENCE: 430

Asp Asp Leu His Ser Asn Ala Ile Thr Tyr Phe Leu
1               5                   10

<210> SEQ ID NO 431
<211> LENGTH: 12
<212> TYPE: PRT
<213> ORGANISM: Artificial Sequence
<220> FEATURE:
<223> OTHER INFORMATION: Synthetic: hu37D3-H9.v31.4

<400> SEQUENCE: 431

Asp Asp Leu His Ser Asn Ala Pro Thr Tyr Phe Leu
1               5                   10

<210> SEQ ID NO 432
<211> LENGTH: 12
<212> TYPE: PRT
<213> ORGANISM: Artificial Sequence
<220> FEATURE:
<223> OTHER INFORMATION: Synthetic: hu37D3-H9.v31.5

<400> SEQUENCE: 432

Asp Asp Leu His Ser Asn Ala Phe Thr Tyr Phe Leu
1               5                   10

<210> SEQ ID NO 433
<211> LENGTH: 12
<212> TYPE: PRT
<213> ORGANISM: Artificial Sequence
<220> FEATURE:
<223> OTHER INFORMATION: Synthetic: hu37D3-H9.v31.6

<400> SEQUENCE: 433

Asp Asp Leu His Ser Asn Ala Tyr Thr Tyr Phe Leu
1               5                   10

<210> SEQ ID NO 434
<211> LENGTH: 12
<212> TYPE: PRT
<213> ORGANISM: Artificial Sequence
<220> FEATURE:
<223> OTHER INFORMATION: Synthetic: hu37D3-H9.v31.7

<400> SEQUENCE: 434

Asp Asp Leu His Ser Asn Ala Arg Thr Tyr Phe Leu
1               5                   10

<210> SEQ ID NO 435
<211> LENGTH: 12
```

```
<212> TYPE: PRT
<213> ORGANISM: Artificial Sequence
<220> FEATURE:
<223> OTHER INFORMATION: Synthetic: hu37D3-H9.v31.8

<400> SEQUENCE: 435

Asp Asp Leu His Ser Asn Ala Asn Val Tyr Phe Leu
1               5                   10

<210> SEQ ID NO 436
<211> LENGTH: 12
<212> TYPE: PRT
<213> ORGANISM: Artificial Sequence
<220> FEATURE:
<223> OTHER INFORMATION: Synthetic: hu37D3-H9.v31.9

<400> SEQUENCE: 436

Asp Asp Leu His Ser Asn Ala Asn Ile Tyr Phe Leu
1               5                   10

<210> SEQ ID NO 437
<211> LENGTH: 12
<212> TYPE: PRT
<213> ORGANISM: Artificial Sequence
<220> FEATURE:
<223> OTHER INFORMATION: Synthetic: hu37D3-H9.v31.10

<400> SEQUENCE: 437

Asp Asp Leu His Ser Asn Ala Asn Pro Tyr Phe Leu
1               5                   10

<210> SEQ ID NO 438
<211> LENGTH: 12
<212> TYPE: PRT
<213> ORGANISM: Artificial Sequence
<220> FEATURE:
<223> OTHER INFORMATION: Synthetic: hu37D3-H9.v31.11

<400> SEQUENCE: 438

Asp Asp Leu His Ser Asn Ala Asn Phe Tyr Phe Leu
1               5                   10

<210> SEQ ID NO 439
<211> LENGTH: 12
<212> TYPE: PRT
<213> ORGANISM: Artificial Sequence
<220> FEATURE:
<223> OTHER INFORMATION: Synthetic: hu37D3-H9.v31.12

<400> SEQUENCE: 439

Asp Asp Leu His Ser Asn Ala Asn Tyr Tyr Phe Leu
1               5                   10

<210> SEQ ID NO 440
<211> LENGTH: 12
<212> TYPE: PRT
<213> ORGANISM: Artificial Sequence
<220> FEATURE:
<223> OTHER INFORMATION: Synthetic: hu37D3-H9.v31.13

<400> SEQUENCE: 440

Asp Asp Leu His Ser Asn Ala Asn Asn Tyr Phe Leu
1               5                   10

<210> SEQ ID NO 441
<211> LENGTH: 12
<212> TYPE: PRT
```

<213> ORGANISM: Artificial Sequence
<220> FEATURE:
<223> OTHER INFORMATION: Synthetic: hu37D3-H9.v31.14

<400> SEQUENCE: 441

Asp Asp Leu His Ser Asn Ala Asn Arg Tyr Phe Leu
1               5                   10

<210> SEQ ID NO 442
<211> LENGTH: 107
<212> TYPE: PRT
<213> ORGANISM: Artificial Sequence
<220> FEATURE:
<223> OTHER INFORMATION: Synthetic: hu125B11-H3.LC1

<400> SEQUENCE: 442

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
                20                  25                  30

Val Ala Trp Tyr Gln Gln Lys Pro Gly Lys Ser Pro Lys Leu Leu Ile
            35                  40                  45

Tyr Ser Ala Ser Ile Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Phe Arg Thr Tyr Pro Tyr
                85                  90                  95

Thr Phe Gly Gln Gly Thr Lys Val Glu Ile Lys
                100                 105

<210> SEQ ID NO 443
<211> LENGTH: 107
<212> TYPE: PRT
<213> ORGANISM: Artificial Sequence
<220> FEATURE:
<223> OTHER INFORMATION: Synthetic: hu125B11-H3.LC2

<400> SEQUENCE: 443

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
                20                  25                  30

Val Ala Trp Tyr Gln Gln Lys Pro Gly Lys Ala Pro Lys Leu Leu Ile
            35                  40                  45

Tyr Ser Ala Ser Ile Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Phe Arg Thr Tyr Pro Tyr
                85                  90                  95

Thr Phe Gly Gln Gly Thr Lys Val Glu Ile Lys
                100                 105

<210> SEQ ID NO 444
<211> LENGTH: 107
<212> TYPE: PRT
<213> ORGANISM: Artificial Sequence
<220> FEATURE:
<223> OTHER INFORMATION: Synthetic: hu125B11-H3.LC3

<400> SEQUENCE: 444

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ser Pro Lys Leu Leu Ile
        35                  40                  45

Tyr Ser Ala Ser Ile Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Arg Thr Tyr Pro Tyr
                85                  90                  95

Thr Phe Gly Gln Gly Thr Lys Val Glu Ile Lys
            100                 105

<210> SEQ ID NO 445
<211> LENGTH: 107
<212> TYPE: PRT
<213> ORGANISM: Artificial Sequence
<220> FEATURE:
<223> OTHER INFORMATION: Synthetic: hu125B11-H3.LC4

<400> SEQUENCE: 445

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Ile Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Arg Thr Tyr Pro Tyr
                85                  90                  95

Thr Phe Gly Gln Gly Thr Lys Val Glu Ile Lys
            100                 105

<210> SEQ ID NO 446
<211> LENGTH: 115
<212> TYPE: PRT
<213> ORGANISM: Artificial Sequence
<220> FEATURE:
<223> OTHER INFORMATION: Synthetic: hu125B11-H3.HC1

<400> SEQUENCE: 446

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Ile Phe Ser Asn Tyr
            20                  25                  30

Trp Met Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Ala Val Tyr
                85                  90                  95

Tyr Cys Thr Gly Gly Thr Thr Tyr Trp Gly Gln Gly Thr Leu Val Thr
            100                 105                 110

Val Ser Ser
        115

<210> SEQ ID NO 447
<211> LENGTH: 115
<212> TYPE: PRT
<213> ORGANISM: Artificial Sequence
<220> FEATURE:
<223> OTHER INFORMATION: Synthetic: hu125B11-H3.HC2

<400> SEQUENCE: 447

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Ile Phe Ser Asn Tyr
            20                  25                  30

Trp Met Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Thr Gly Gly Thr Thr Tyr Trp Gly Gln Gly Thr Leu Val Thr
            100                 105                 110

Val Ser Ser
        115

<210> SEQ ID NO 448
<211> LENGTH: 115
<212> TYPE: PRT
<213> ORGANISM: Artificial Sequence
<220> FEATURE:
<223> OTHER INFORMATION: Synthetic: hu125B11-H3.HC3

<400> SEQUENCE: 448

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Ile Phe Ser Asn Tyr
            20                  25                  30

Trp Met Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Thr Gly Gly Thr Thr Tyr Trp Gly Gln Gly Thr Leu Val Thr
            100                 105                 110

Val Ser Ser
        115

<210> SEQ ID NO 449

```
<211> LENGTH: 115
<212> TYPE: PRT
<213> ORGANISM: Artificial Sequence
<220> FEATURE:
<223> OTHER INFORMATION: Synthetic: hu125B11-H3.HC4

<400> SEQUENCE: 449

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Ile Phe Ser Asn Tyr
            20                  25                  30

Trp Met Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Thr Gly Gly Thr Thr Tyr Trp Gly Gln Gly Thr Leu Val Thr
            100                 105                 110

Val Ser Ser
        115

<210> SEQ ID NO 450
<211> LENGTH: 115
<212> TYPE: PRT
<213> ORGANISM: Artificial Sequence
<220> FEATURE:
<223> OTHER INFORMATION: Synthetic: hu125B11-H3.HC5

<400> SEQUENCE: 450

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Ile Phe Ser Asn Tyr
            20                  25                  30

Tyr Met Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Ala Val Tyr
                85                  90                  95

Tyr Cys Thr Gly Gly Thr Thr Tyr Trp Gly Gln Gly Thr Leu Val Thr
            100                 105                 110

Val Ser Ser
        115

<210> SEQ ID NO 451
<211> LENGTH: 115
<212> TYPE: PRT
<213> ORGANISM: Artificial Sequence
<220> FEATURE:
<223> OTHER INFORMATION: Synthetic: hu125B11-H3.HC6

<400> SEQUENCE: 451

Glu Val Gln Leu Val Glu Ser Gly Gly Gly Leu Val Gln Pro Gly Gly
1               5                   10                  15
```

Ser Leu Arg Leu Ser Cys Ala Ala Ser Arg Phe Ile Phe Ser Asn Tyr
            20                  25                  30

Phe Met Asn Trp Val Arg Gln Ala Pro Gly Lys Gly Leu Glu Trp Val
            35                  40                  45

Ala Gln Ile Arg Leu Lys Ser Asp Asn Tyr Ala Thr His Tyr Ala Glu
50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Ala Val Tyr
                85                  90                  95

Tyr Cys Thr Gly Gly Thr Thr Tyr Trp Gly Gln Gly Thr Leu Val Thr
            100                 105                 110

Val Ser Ser
        115

<210> SEQ ID NO 452
<211> LENGTH: 113
<212> TYPE: PRT
<213> ORGANISM: Artificial Sequence
<220> FEATURE:
<223> OTHER INFORMATION: Synthetic: Hu94B2.HC1

<400> SEQUENCE: 452

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Gly Tyr
            20                  25                  30

Thr Met Asn Trp Val Arg Gln Ala Pro Gly Gln Gly Leu Glu Trp Ile
            35                  40                  45

Gly Leu Ile Ser Pro Tyr Asn Gly Val Thr Ser Tyr Asn Gln Lys Phe
        50                  55                  60

Lys Gly Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gln Gly Ala Tyr Trp Gly Gln Gly Thr Leu Val Thr Val Ser
            100                 105                 110

Ser

<210> SEQ ID NO 453
<211> LENGTH: 113
<212> TYPE: PRT
<213> ORGANISM: Artificial Sequence
<220> FEATURE:
<223> OTHER INFORMATION: Synthetic: Hu94B2.HC2

<400> SEQUENCE: 453

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Gly Tyr
            20                  25                  30

Thr Met Asn Trp Val Arg Gln Ala Pro Gly Gln Gly Leu Glu Trp Ile
            35                  40                  45

Gly Leu Ile Ser Pro Tyr Asn Gly Val Thr Ser Tyr Asn Gln Lys Phe
        50                  55                  60

Lys Gly Arg Val Thr Leu Thr Val Asp Lys Ser Thr Ser Thr Ala Tyr
65                  70                  75                  80

```
Leu Glu Leu Ser Ser Leu Arg Ser Glu Asp Thr Ala Val Tyr Tyr Cys
                85                  90                  95

Ala Arg Gln Gly Ala Tyr Trp Gly Gln Gly Thr Leu Val Thr Val Ser
            100                 105                 110

Ser
```

<210> SEQ ID NO 454
<211> LENGTH: 113
<212> TYPE: PRT
<213> ORGANISM: Artificial Sequence
<220> FEATURE:
<223> OTHER INFORMATION: Synthetic: Hu94B2.HC3

<400> SEQUENCE: 454

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Gly Tyr
                20                  25                  30

Thr Met Asn Trp Val Arg Gln Ala Pro Gly Gln Gly Leu Glu Trp Ile
            35                  40                  45

Gly Leu Ile Ser Pro Tyr Asn Gly Val Thr Ser Tyr Asn Gln Lys Phe
50                  55                  60

Lys Gly Arg Ala Thr Ile Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gln Gly Ala Tyr Trp Gly Gln Gly Thr Leu Val Thr Val Ser
            100                 105                 110

Ser
```

<210> SEQ ID NO 455
<211> LENGTH: 113
<212> TYPE: PRT
<213> ORGANISM: Artificial Sequence
<220> FEATURE:
<223> OTHER INFORMATION: Synthetic: Hu94B2.HC4

<400> SEQUENCE: 455

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Gly Tyr
                20                  25                  30

Thr Met Asn Trp Val Arg Gln Ala Pro Gly Gln Gly Leu Glu Trp Ile
            35                  40                  45

Gly Leu Ile Ser Pro Tyr Asn Gly Val Thr Ser Tyr Asn Gln Lys Phe
50                  55                  60

Lys Gly Arg Ala Thr Leu Thr Arg Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gln Gly Ala Tyr Trp Gly Gln Gly Thr Leu Val Thr Val Ser
            100                 105                 110

Ser
```

<210> SEQ ID NO 456
<211> LENGTH: 113
<212> TYPE: PRT
<213> ORGANISM: Artificial Sequence
<220> FEATURE:
<223> OTHER INFORMATION: Synthetic: Hu94B2.HC5

<400> SEQUENCE: 456

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Gly Tyr
            20                  25                  30

Thr Met Asn Trp Val Arg Gln Ala Pro Gly Gln Gly Leu Glu Trp Ile
        35                  40                  45

Gly Leu Ile Ser Pro Tyr Asn Gly Val Thr Ser Tyr Asn Gln Lys Phe
    50                  55                  60

Lys Gly Arg Ala Thr Leu Thr Val Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gln Gly Ala Tyr Trp Gly Gln Gly Thr Leu Val Thr Val Ser
            100                 105                 110

Ser

<210> SEQ ID NO 457
<211> LENGTH: 113
<212> TYPE: PRT
<213> ORGANISM: Artificial Sequence
<220> FEATURE:
<223> OTHER INFORMATION: Synthetic: Hu94B2.HC6

<400> SEQUENCE: 457

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Gly Tyr
            20                  25                  30

Thr Met Asn Trp Val Arg Gln Ala Pro Gly Gln Gly Leu Glu Trp Ile
        35                  40                  45

Gly Leu Ile Ser Pro Tyr Asn Gly Val Thr Ser Tyr Asn Gln Lys Phe
    50                  55                  60

Lys Gly Arg Val Thr Ile Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gln Gly Ala Tyr Trp Gly Gln Gly Thr Leu Val Thr Val Ser
            100                 105                 110

Ser

<210> SEQ ID NO 458
<211> LENGTH: 113
<212> TYPE: PRT
<213> ORGANISM: Artificial Sequence
<220> FEATURE:
<223> OTHER INFORMATION: Synthetic: Hu94B2.HC7

<400> SEQUENCE: 458

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Gly Tyr
            20                  25                  30

Thr Met Asn Trp Val Arg Gln Ala Pro Gly Gln Gly Leu Glu Trp Ile
        35                  40                  45

Gly Leu Ile Ser Pro Tyr Asn Gly Val Thr Ser Tyr Asn Gln Lys Phe
            50                  55                  60

Lys Gly Arg Val Thr Ile Thr Arg Asp Lys Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Gln Gly Ala Tyr Trp Gly Gln Gly Thr Leu Val Thr Val Ser
            100                 105                 110

Ser

<210> SEQ ID NO 459
<211> LENGTH: 113
<212> TYPE: PRT
<213> ORGANISM: Artificial Sequence
<220> FEATURE:
<223> OTHER INFORMATION: Synthetic: Hu94B2.HC8

<400> SEQUENCE: 459

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Leu Thr Gly Tyr
            20                  25                  30

Thr Met Asn Trp Val Arg Gln Ala Pro Gly Gln Gly Leu Glu Trp Ile
            35                  40                  45

Gly Leu Ile Ser Pro Tyr Asn Gly Val Thr Ser Tyr Asn Gln Lys Phe
            50                  55                  60

Lys Gly Arg Val Thr Ile Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Gln Gly Ala Tyr Trp Gly Gln Gly Thr Leu Val Thr Val Ser
            100                 105                 110

Ser

<210> SEQ ID NO 460
<211> LENGTH: 112
<212> TYPE: PRT
<213> ORGANISM: Artificial Sequence
<220> FEATURE:
<223> OTHER INFORMATION: Synthetic: Hu94B2.LC9

<400> SEQUENCE: 460

Asp Val Val Met Thr Gln Thr Pro Leu Ser Leu Pro Val Thr Pro Gly
 1               5                  10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
            35                  40                  45

Pro Gln Arg Leu Ile Tyr Leu Val Ser Lys Leu Asp Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Trp Thr Phe Gly Gln Gly Thr Lys Val Glu Ile Lys
            100                 105                 110

<210> SEQ ID NO 461
<211> LENGTH: 112
<212> TYPE: PRT
<213> ORGANISM: Artificial Sequence
<220> FEATURE:
<223> OTHER INFORMATION: Synthetic: Hu94B2.LC10

<400> SEQUENCE: 461

```
Asp Val Val Met Thr Gln Thr Pro Leu Ser Leu Pro Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gln Gly Thr Lys Val Glu Ile Lys
            100                 105                 110
```

<210> SEQ ID NO 462
<211> LENGTH: 112
<212> TYPE: PRT
<213> ORGANISM: Artificial Sequence
<220> FEATURE:
<223> OTHER INFORMATION: Synthetic: Hu94B2.LC11

<400> SEQUENCE: 462

```
Asp Val Val Met Thr Gln Thr Pro Leu Ser Leu Pro Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Tyr Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gln Gly Thr Lys Val Glu Ile Lys
            100                 105                 110
```

<210> SEQ ID NO 463
<211> LENGTH: 112
<212> TYPE: PRT
<213> ORGANISM: Artificial Sequence
<220> FEATURE:
<223> OTHER INFORMATION: Synthetic: Hu94B2.LC12

<400> SEQUENCE: 463

```
Asp Val Val Met Thr Gln Thr Pro Leu Ser Leu Pro Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Tyr Leu Gln Lys Pro Gly Gln Ser
```

```
                35                  40                  45
Pro Gln Leu Leu Ile Tyr Leu Val Ser Lys Leu Asp Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Trp Gln Gly
                85                  90                  95
Thr His Phe Pro Trp Thr Phe Gly Gln Gly Thr Lys Val Glu Ile Lys
            100                 105                 110
```

<210> SEQ ID NO 464
<211> LENGTH: 112
<212> TYPE: PRT
<213> ORGANISM: Artificial Sequence
<220> FEATURE:
<223> OTHER INFORMATION: Synthetic: Hu94B2.LC13

<400> SEQUENCE: 464

```
Asp Ile Val Met Thr Gln Thr Pro Leu Ser Leu Pro Val Thr Pro Gly
1               5                   10                  15
Gln Pro Ala Ser Ile Ser Cys Lys Ser Ser Gln Ser Leu Leu Asp Ser
            20                  25                  30
Asp Gly Lys Thr Tyr Leu Asn Trp Leu Leu Gln Lys Pro Gly Gln Ser
        35                  40                  45
Pro Gln Arg Leu Ile Tyr Leu Val Ser Lys Leu Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Trp Gln Gly
                85                  90                  95
Thr His Phe Pro Trp Thr Phe Gly Gln Gly Thr Lys Val Glu Ile Lys
            100                 105                 110
```

<210> SEQ ID NO 465
<211> LENGTH: 112
<212> TYPE: PRT
<213> ORGANISM: Artificial Sequence
<220> FEATURE:
<223> OTHER INFORMATION: Synthetic: Hu94B2.LC14

<400> SEQUENCE: 465

```
Asp Ile Val Met Thr Gln Thr Pro Leu Ser Leu Pro Val Thr Pro Gly
1               5                   10                  15
Gln Pro Ala Ser Ile Ser Cys Lys Ser Ser Gln Ser Leu Leu Asp Ser
            20                  25                  30
Asp Gly Lys Thr Tyr Leu Asn Trp Leu Leu Gln Lys Pro Gly Gln Ser
        35                  40                  45
Pro Gln Leu Leu Ile Tyr Leu Val Ser Lys Leu Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Trp Gln Gly
                85                  90                  95
Thr His Phe Pro Trp Thr Phe Gly Gln Gly Thr Lys Val Glu Ile Lys
            100                 105                 110
```

<210> SEQ ID NO 466
<211> LENGTH: 112

<212> TYPE: PRT
<213> ORGANISM: Artificial Sequence
<220> FEATURE:
<223> OTHER INFORMATION: Synthetic: Hu94B2.LC15

<400> SEQUENCE: 466

Asp Ile Val Met Thr Gln Thr Pro Leu Ser Leu Pro Val Thr Pro Gly
1               5                   10                  15

Gln Pro Ala Ser Ile Ser Cys Lys Ser Gln Ser Leu Leu Asp Ser
            20                  25                  30

Asp Gly Lys Thr Tyr Leu Asn Trp Tyr Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gln Gly Thr Lys Val Glu Ile Lys
            100                 105                 110

<210> SEQ ID NO 467
<211> LENGTH: 112
<212> TYPE: PRT
<213> ORGANISM: Artificial Sequence
<220> FEATURE:
<223> OTHER INFORMATION: Synthetic: Hu94B2.LC16

<400> SEQUENCE: 467

Asp Ile Val Met Thr Gln Thr Pro Leu Ser Leu Pro Val Thr Pro Gly
1               5                   10                  15

Gln Pro Ala Ser Ile Ser Cys Lys Ser Gln Ser Leu Leu Asp Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gln Gly Thr Lys Val Glu Ile Lys
            100                 105                 110

<210> SEQ ID NO 468
<211> LENGTH: 16
<212> TYPE: PRT
<213> ORGANISM: Artificial Sequence
<220> FEATURE:
<223> OTHER INFORMATION: Synthetic: Hu37D3-H9.v5.1 HVR-L1

<400> SEQUENCE: 468

Arg Ser Ser Gln Ser Ile Val His Ser Asn Ala Asn Thr Tyr Phe Glu
1               5                   10                  15

<210> SEQ ID NO 469
<211> LENGTH: 16
<212> TYPE: PRT
<213> ORGANISM: Artificial Sequence
<220> FEATURE:
<223> OTHER INFORMATION: Synthetic: Hu37D3-H9.v5.2 HVR-L1

```
<400> SEQUENCE: 469

Arg Ser Ser Gln Ser Ile Val His Ser Ser Gly Asn Thr Tyr Phe Glu
1               5                   10                  15

<210> SEQ ID NO 470
<211> LENGTH: 16
<212> TYPE: PRT
<213> ORGANISM: Artificial Sequence
<220> FEATURE:
<223> OTHER INFORMATION: Synthetic: Hu37D3-H9.v5.3 HVR-L1

<400> SEQUENCE: 470

Arg Ser Ser Gln Ser Ile Val His Ser Asp Gly Asn Thr Tyr Phe Glu
1               5                   10                  15

<210> SEQ ID NO 471
<211> LENGTH: 16
<212> TYPE: PRT
<213> ORGANISM: Artificial Sequence
<220> FEATURE:
<223> OTHER INFORMATION: Synthetic: Hu37D3-H9.v5.4 HVR-L1

<400> SEQUENCE: 471

Arg Ser Ser Gln Ser Ile Val His Ser Gln Gly Asn Thr Tyr Phe Glu
1               5                   10                  15

<210> SEQ ID NO 472
<211> LENGTH: 16
<212> TYPE: PRT
<213> ORGANISM: Artificial Sequence
<220> FEATURE:
<223> OTHER INFORMATION: Synthetic: Hu37D3-H9.v5.5 HVR-L1

<400> SEQUENCE: 472

Arg Ser Ser Gln Ser Ile Val His Ser Glu Gly Asn Thr Tyr Phe Glu
1               5                   10                  15

<210> SEQ ID NO 473
<211> LENGTH: 16
<212> TYPE: PRT
<213> ORGANISM: Artificial Sequence
<220> FEATURE:
<223> OTHER INFORMATION: Synthetic: Hu37D3-H9.v5.6 HVR-L1

<400> SEQUENCE: 473

Arg Ser Ser Gln Ser Ile Val His Ser Ala Gly Asn Thr Tyr Phe Glu
1               5                   10                  15

<210> SEQ ID NO 474
<211> LENGTH: 16
<212> TYPE: PRT
<213> ORGANISM: Artificial Sequence
<220> FEATURE:
<223> OTHER INFORMATION: Synthetic: Hu37D3-H9.v5.7 HVR-L1

<400> SEQUENCE: 474

Arg Ser Ser Gln Ser Ile Val His Ser Asn Gly Asp Thr Tyr Phe Glu
1               5                   10                  15

<210> SEQ ID NO 475
<211> LENGTH: 16
<212> TYPE: PRT
<213> ORGANISM: Artificial Sequence
<220> FEATURE:
<223> OTHER INFORMATION: Synthetic: Hu37D3-H9.v5.8 HVR-L1
```

<400> SEQUENCE: 475

Arg Ser Ser Gln Ser Ile Val His Ser Asn Gly Gln Thr Tyr Phe Glu
1               5                   10                  15

<210> SEQ ID NO 476
<211> LENGTH: 16
<212> TYPE: PRT
<213> ORGANISM: Artificial Sequence
<220> FEATURE:
<223> OTHER INFORMATION: Synthetic: Hu37D3-H9.v5.9 HVR-L1

<400> SEQUENCE: 476

Arg Ser Ser Gln Ser Ile Val His Ser Asn Gly Glu Thr Tyr Phe Glu
1               5                   10                  15

<210> SEQ ID NO 477
<211> LENGTH: 16
<212> TYPE: PRT
<213> ORGANISM: Artificial Sequence
<220> FEATURE:
<223> OTHER INFORMATION: Synthetic: Hu37D3-H9.v5.10 HVR-L1

<400> SEQUENCE: 477

Arg Ser Ser Gln Ser Ile Val His Ser Asn Gly Ala Thr Tyr Phe Glu
1               5                   10                  15

<210> SEQ ID NO 478
<211> LENGTH: 16
<212> TYPE: PRT
<213> ORGANISM: Artificial Sequence
<220> FEATURE:
<223> OTHER INFORMATION: Synthetic: Hu37D3-H9.v5.11 HVR-L1

<400> SEQUENCE: 478

Arg Ser Ser Gln Ser Ile Val His Ser Asn Gly Ser Thr Tyr Phe Glu
1               5                   10                  15

<210> SEQ ID NO 479
<211> LENGTH: 16
<212> TYPE: PRT
<213> ORGANISM: Artificial Sequence
<220> FEATURE:
<223> OTHER INFORMATION: Synthetic: Hu37D3.v28 HVR-L1

<400> SEQUENCE: 479

Arg Ser Ser Gln Ser Ile Val His Ser Asn Gly Asn Thr Tyr Phe Glu
1               5                   10                  15

<210> SEQ ID NO 480
<211> LENGTH: 16
<212> TYPE: PRT
<213> ORGANISM: Artificial Sequence
<220> FEATURE:
<223> OTHER INFORMATION: Synthetic: Hu37D3.v28.A2 HVR-L1

<400> SEQUENCE: 480

Arg Ser Ser Gln Ser Ile Val His Ser Asn Gly Asn Thr Tyr Phe Glu
1               5                   10                  15

<210> SEQ ID NO 481
<211> LENGTH: 16
<212> TYPE: PRT
<213> ORGANISM: Artificial Sequence
<220> FEATURE:
<223> OTHER INFORMATION: Synthetic: Hu37D3.v28.A4 HVR-L1

<400> SEQUENCE: 481

Arg Ser Ser Gln Ser Ile Val His Ser Asn Gly Asn Thr Tyr Leu Glu
1               5                   10                  15

<210> SEQ ID NO 482
<211> LENGTH: 16
<212> TYPE: PRT
<213> ORGANISM: Artificial Sequence
<220> FEATURE:
<223> OTHER INFORMATION: Synthetic: Hu37D3.v28.A6 HVR-L1

<400> SEQUENCE: 482

Arg Ser Ser Gln Ser Ile Val His Ser Asn Gly Asn Thr Tyr Leu Glu
1               5                   10                  15

<210> SEQ ID NO 483
<211> LENGTH: 16
<212> TYPE: PRT
<213> ORGANISM: Artificial Sequence
<220> FEATURE:
<223> OTHER INFORMATION: Synthetic: Hu37D3.v28.A8 HVR-L1

<400> SEQUENCE: 483

Arg Ser Ser Gln Ser Ile Val His Ser Asn Gly Asn Thr Tyr Phe Glu
1               5                   10                  15

<210> SEQ ID NO 484
<211> LENGTH: 16
<212> TYPE: PRT
<213> ORGANISM: Artificial Sequence
<220> FEATURE:
<223> OTHER INFORMATION: Synthetic: Hu37D3.v28.A10 HVR-L1

<400> SEQUENCE: 484

Arg Ser Ser Gln Ser Ile Val His Ser Asn Gly Asn Thr Tyr Phe Glu
1               5                   10                  15

<210> SEQ ID NO 485
<211> LENGTH: 16
<212> TYPE: PRT
<213> ORGANISM: Artificial Sequence
<220> FEATURE:
<223> OTHER INFORMATION: Synthetic: Hu37D3.v28.A12 HVR-L1

<400> SEQUENCE: 485

Arg Ser Ser Gln Ser Ile Val His Ser Asn Gly Asn Thr Tyr Leu Glu
1               5                   10                  15

<210> SEQ ID NO 486
<211> LENGTH: 16
<212> TYPE: PRT
<213> ORGANISM: Artificial Sequence
<220> FEATURE:
<223> OTHER INFORMATION: Synthetic: Hu37D3.v28.A14 HVR-L1

<400> SEQUENCE: 486

Arg Ser Ser Gln Ser Ile Val His Ser Asn Gly Asn Thr Tyr Leu Glu
1               5                   10                  15

<210> SEQ ID NO 487
<211> LENGTH: 16
<212> TYPE: PRT
<213> ORGANISM: Artificial Sequence
<220> FEATURE:
<223> OTHER INFORMATION: Synthetic: Hu37D3.v28.A16 HVR-L1

<400> SEQUENCE: 487

Arg Ser Ser Gln Ser Ile Val His Ser Asn Gly Asn Thr Tyr Phe Glu
1               5                   10                  15

<210> SEQ ID NO 488
<211> LENGTH: 16
<212> TYPE: PRT
<213> ORGANISM: Artificial Sequence
<220> FEATURE:
<223> OTHER INFORMATION: Synthetic: Hu37D3.v28.A18 HVR-L1

<400> SEQUENCE: 488

Arg Ser Ser Gln Ser Ile Val His Ser Asn Gly Asn Thr Tyr Phe Glu
1               5                   10                  15

<210> SEQ ID NO 489
<211> LENGTH: 16
<212> TYPE: PRT
<213> ORGANISM: Artificial Sequence
<220> FEATURE:
<223> OTHER INFORMATION: Synthetic: Hu37D3.v28.A20 HVR-L1

<400> SEQUENCE: 489

Arg Ser Ser Gln Ser Ile Val His Ser Asn Gly Asn Thr Tyr Leu Glu
1               5                   10                  15

<210> SEQ ID NO 490
<211> LENGTH: 16
<212> TYPE: PRT
<213> ORGANISM: Artificial Sequence
<220> FEATURE:
<223> OTHER INFORMATION: Synthetic: Hu37D3.v28.A22 HVR-L1

<400> SEQUENCE: 490

Arg Ser Ser Gln Ser Ile Val His Ser Asn Gly Asn Thr Tyr Leu Glu
1               5                   10                  15

<210> SEQ ID NO 491
<211> LENGTH: 16
<212> TYPE: PRT
<213> ORGANISM: Artificial Sequence
<220> FEATURE:
<223> OTHER INFORMATION: Synthetic: Hu37D3.v28.A24 HVR-L1

<400> SEQUENCE: 491

Arg Ser Ser Gln Ser Ile Val His Ser Asn Gly Asn Thr Tyr Phe Glu
1               5                   10                  15

<210> SEQ ID NO 492
<211> LENGTH: 16
<212> TYPE: PRT
<213> ORGANISM: Artificial Sequence
<220> FEATURE:
<223> OTHER INFORMATION: Synthetic: Hu37D3.v28.A26 HVR-L1

<400> SEQUENCE: 492

Arg Ser Ser Gln Ser Ile Val His Ser Asn Gly Asn Thr Tyr Phe Glu
1               5                   10                  15

<210> SEQ ID NO 493
<211> LENGTH: 16
<212> TYPE: PRT
<213> ORGANISM: Artificial Sequence
<220> FEATURE:
<223> OTHER INFORMATION: Synthetic: Hu37D3.v28.A28 HVR-L1

<400> SEQUENCE: 493

Arg Ser Ser Gln Ser Ile Val His Ser Asn Gly Asn Thr Tyr Leu Glu

<210> SEQ ID NO 494
<211> LENGTH: 16
<212> TYPE: PRT
<213> ORGANISM: Artificial Sequence
<220> FEATURE:
<223> OTHER INFORMATION: Synthetic: Hu37D3.v28.A30 HVR-L1

<400> SEQUENCE: 494

Arg Ser Ser Gln Ser Ile Val His Ser Asn Gly Asn Thr Tyr Leu Glu
1               5                   10                  15

<210> SEQ ID NO 495
<211> LENGTH: 16
<212> TYPE: PRT
<213> ORGANISM: Artificial Sequence
<220> FEATURE:
<223> OTHER INFORMATION: Synthetic: Hu37D3.v28.B1 HVR-L1

<400> SEQUENCE: 495

Arg Ser Ser Gln Ser Ile Val His Ser Ile Gly Asn Thr Phe Phe Glu
1               5                   10                  15

<210> SEQ ID NO 496
<211> LENGTH: 16
<212> TYPE: PRT
<213> ORGANISM: Artificial Sequence
<220> FEATURE:
<223> OTHER INFORMATION: Synthetic: Hu37D3.v28.B2 HVR-L1

<400> SEQUENCE: 496

Arg Ser Ser Gln Ser Ile Val His Ser Met Gly Asn Thr Phe Phe Glu
1               5                   10                  15

<210> SEQ ID NO 497
<211> LENGTH: 16
<212> TYPE: PRT
<213> ORGANISM: Artificial Sequence
<220> FEATURE:
<223> OTHER INFORMATION: Synthetic: Hu37D3.v28.B3 HVR-L1

<400> SEQUENCE: 497

Arg Ser Ser Gln Ser Ile Val His Ser Gln Gly Asn Thr Trp Phe Glu
1               5                   10                  15

<210> SEQ ID NO 498
<211> LENGTH: 16
<212> TYPE: PRT
<213> ORGANISM: Artificial Sequence
<220> FEATURE:
<223> OTHER INFORMATION: Synthetic: Hu37D3.v28.B4 HVR-L1

<400> SEQUENCE: 498

Arg Ser Ser Gln Ser Ile Val His Ser Gln Gly Asn Thr His Phe Glu
1               5                   10                  15

<210> SEQ ID NO 499
<211> LENGTH: 16
<212> TYPE: PRT
<213> ORGANISM: Artificial Sequence
<220> FEATURE:
<223> OTHER INFORMATION: Synthetic: Hu37D3.v28.B6 HVR-L1

<400> SEQUENCE: 499

Arg Ser Ser Gln Ser Ile Val His Ser Asp Gly Asn Thr Arg Phe Glu
1               5                   10                  15

```
<210> SEQ ID NO 500
<211> LENGTH: 16
<212> TYPE: PRT
<213> ORGANISM: Artificial Sequence
<220> FEATURE:
<223> OTHER INFORMATION: Synthetic: Hu37D3.v28.B7 HVR-L1

<400> SEQUENCE: 500

Arg Ser Ser Gln Ser Ile Val His Ser Asp Gly Asn Thr Lys Phe Glu
1               5                   10                  15

<210> SEQ ID NO 501
<211> LENGTH: 16
<212> TYPE: PRT
<213> ORGANISM: Artificial Sequence
<220> FEATURE:
<223> OTHER INFORMATION: Synthetic: Hu37D3.v28.B8 HVR-L1

<400> SEQUENCE: 501

Arg Ser Ser Gln Ser Ile Val His Ser Glu Gly Asn Thr Arg Phe Glu
1               5                   10                  15

<210> SEQ ID NO 502
<211> LENGTH: 16
<212> TYPE: PRT
<213> ORGANISM: Artificial Sequence
<220> FEATURE:
<223> OTHER INFORMATION: Synthetic: Hu37D3.v28.C1 HVR-L1

<400> SEQUENCE: 502

Arg Ser Ser Gln Ser Ile Val His Ser Asn Asn Asn Thr Tyr Phe Glu
1               5                   10                  15

<210> SEQ ID NO 503
<211> LENGTH: 16
<212> TYPE: PRT
<213> ORGANISM: Artificial Sequence
<220> FEATURE:
<223> OTHER INFORMATION: Synthetic: Hu37D3.v28.C2 HVR-L1

<400> SEQUENCE: 503

Arg Ser Ser Gln Ser Ile Val His Ser Asn Asp Asn Thr Tyr Phe Glu
1               5                   10                  15

<210> SEQ ID NO 504
<211> LENGTH: 16
<212> TYPE: PRT
<213> ORGANISM: Artificial Sequence
<220> FEATURE:
<223> OTHER INFORMATION: Synthetic: Hu37D3.v28.D1 HVR-L1

<400> SEQUENCE: 504

Arg Ser Ser Gln Ser Ile Val His Ala Asn Gly Asn Thr Tyr Phe Glu
1               5                   10                  15

<210> SEQ ID NO 505
<211> LENGTH: 16
<212> TYPE: PRT
<213> ORGANISM: Artificial Sequence
<220> FEATURE:
<223> OTHER INFORMATION: Synthetic: Hu37D3.v28.E1 HVR-L1

<400> SEQUENCE: 505

Arg Ser Ser Gln Ser Ile Val Asn Ser Asn Gly Asn Thr Tyr Phe Glu
1               5                   10                  15
```

<210> SEQ ID NO 506
<211> LENGTH: 16
<212> TYPE: PRT
<213> ORGANISM: Artificial Sequence
<220> FEATURE:
<223> OTHER INFORMATION: Synthetic: Hu37D3.v28.E2 HVR-L1

<400> SEQUENCE: 506

Arg Ser Ser Gln Ser Ile Val Gln Ser Asn Gly Asn Thr Tyr Phe Glu
1               5                   10                  15

<210> SEQ ID NO 507
<211> LENGTH: 16
<212> TYPE: PRT
<213> ORGANISM: Artificial Sequence
<220> FEATURE:
<223> OTHER INFORMATION: Synthetic: Hu37D3.v28.E3 HVR-L1

<400> SEQUENCE: 507

Arg Ser Ser Gln Ser Ile Val Asp Ser Asp Gly Asn Thr Tyr Phe Glu
1               5                   10                  15

<210> SEQ ID NO 508
<211> LENGTH: 16
<212> TYPE: PRT
<213> ORGANISM: Artificial Sequence
<220> FEATURE:
<223> OTHER INFORMATION: Synthetic: Hu37D3.v28.F1 HVR-L1

<400> SEQUENCE: 508

Arg Ser Ser Gln Ser Ile Val His Ser Asn Thr Asn Thr Tyr Phe Glu
1               5                   10                  15

<210> SEQ ID NO 509
<211> LENGTH: 16
<212> TYPE: PRT
<213> ORGANISM: Artificial Sequence
<220> FEATURE:
<223> OTHER INFORMATION: Synthetic: Hu37D3.v28.F2 HVR-L1

<400> SEQUENCE: 509

Arg Ser Ser Gln Ser Ile Val His Thr Asn Gly Asn Thr Tyr Phe Glu
1               5                   10                  15

<210> SEQ ID NO 510
<211> LENGTH: 16
<212> TYPE: PRT
<213> ORGANISM: Artificial Sequence
<220> FEATURE:
<223> OTHER INFORMATION: Synthetic: Hu37D3.v28.F3 HVR-L1

<400> SEQUENCE: 510

Arg Ser Ser Gln Ser Ile Val His Thr Asn Ala Asn Thr Tyr Phe Glu
1               5                   10                  15

<210> SEQ ID NO 511
<211> LENGTH: 16
<212> TYPE: PRT
<213> ORGANISM: Artificial Sequence
<220> FEATURE:
<223> OTHER INFORMATION: Synthetic: Hu37D3.v28.51 HVR-L1

<400> SEQUENCE: 511

Arg Ser Ser Gln Ser Ile Val His Ser His Gly Asn Thr Tyr Phe Glu
1               5                   10                  15

```
<210> SEQ ID NO 512
<211> LENGTH: 16
<212> TYPE: PRT
<213> ORGANISM: Artificial Sequence
<220> FEATURE:
<223> OTHER INFORMATION: Synthetic: Hu37D3.v28.52 HVR-L1

<400> SEQUENCE: 512

Arg Ser Ser Gln Ser Ile Val His Ser Lys Gly Asn Thr Tyr Phe Glu
1               5                   10                  15

<210> SEQ ID NO 513
<211> LENGTH: 16
<212> TYPE: PRT
<213> ORGANISM: Artificial Sequence
<220> FEATURE:
<223> OTHER INFORMATION: Synthetic: Hu37D3.v28.53 HVR-L1

<400> SEQUENCE: 513

Arg Ser Ser Gln Ser Ile Val His Ser Arg Gly Asn Thr Tyr Phe Glu
1               5                   10                  15

<210> SEQ ID NO 514
<211> LENGTH: 16
<212> TYPE: PRT
<213> ORGANISM: Artificial Sequence
<220> FEATURE:
<223> OTHER INFORMATION: Synthetic: Hu37D3.v28.54 HVR-L1

<400> SEQUENCE: 514

Arg Ser Ser Gln Ser Ile Val His Ser Leu Gly Asn Thr Tyr Phe Glu
1               5                   10                  15

<210> SEQ ID NO 515
<211> LENGTH: 16
<212> TYPE: PRT
<213> ORGANISM: Artificial Sequence
<220> FEATURE:
<223> OTHER INFORMATION: Synthetic: Hu37D3.v28.55 HVR-L1

<400> SEQUENCE: 515

Arg Ser Ser Gln Ser Ile Val His Ser Asn Gln Asn Thr Tyr Phe Glu
1               5                   10                  15

<210> SEQ ID NO 516
<211> LENGTH: 16
<212> TYPE: PRT
<213> ORGANISM: Artificial Sequence
<220> FEATURE:
<223> OTHER INFORMATION: Synthetic: Hu37D3.v28.56 HVR-L1

<400> SEQUENCE: 516

Arg Ser Ser Gln Ser Ile Val His Ser Asn Tyr Asn Thr Tyr Phe Glu
1               5                   10                  15

<210> SEQ ID NO 517
<211> LENGTH: 16
<212> TYPE: PRT
<213> ORGANISM: Artificial Sequence
<220> FEATURE:
<223> OTHER INFORMATION: Synthetic: Hu37D3.v28.57 HVR-L1

<400> SEQUENCE: 517

Arg Ser Ser Gln Ser Ile Val His Ser Asn Phe Asn Thr Tyr Phe Glu
1               5                   10                  15

<210> SEQ ID NO 518
```

```
<211> LENGTH: 16
<212> TYPE: PRT
<213> ORGANISM: Artificial Sequence
<220> FEATURE:
<223> OTHER INFORMATION: Synthetic: Hu37D3.v29.1 HVR-L1

<400> SEQUENCE: 518

Arg Ser Ser Gln Ser Ile Val His Ser Asn Gly Asp Thr Tyr Phe Glu
1               5                   10                  15

<210> SEQ ID NO 519
<211> LENGTH: 16
<212> TYPE: PRT
<213> ORGANISM: Artificial Sequence
<220> FEATURE:
<223> OTHER INFORMATION: Synthetic: Hu37D3.v29.2 HVR-L1

<400> SEQUENCE: 519

Arg Ser Ser Gln Ser Ile Val His Ser Asn Gly Gln Thr Tyr Phe Glu
1               5                   10                  15

<210> SEQ ID NO 520
<211> LENGTH: 16
<212> TYPE: PRT
<213> ORGANISM: Artificial Sequence
<220> FEATURE:
<223> OTHER INFORMATION: Synthetic: Hu37D3.v29.3 HVR-L1

<400> SEQUENCE: 520

Arg Ser Ser Gln Ser Ile Val His Ser Asn Gly Glu Thr Tyr Phe Glu
1               5                   10                  15

<210> SEQ ID NO 521
<211> LENGTH: 16
<212> TYPE: PRT
<213> ORGANISM: Artificial Sequence
<220> FEATURE:
<223> OTHER INFORMATION: Synthetic: Hu37D3.v29.4 HVR-L1

<400> SEQUENCE: 521

Arg Ser Ser Gln Ser Ile Val His Ser Asn Gly Ala Thr Tyr Phe Glu
1               5                   10                  15

<210> SEQ ID NO 522
<211> LENGTH: 16
<212> TYPE: PRT
<213> ORGANISM: Artificial Sequence
<220> FEATURE:
<223> OTHER INFORMATION: Synthetic: Hu37D3.v29.5 HVR-L1

<400> SEQUENCE: 522

Arg Ser Ser Gln Ser Ile Val His Ser Asn Gly His Thr Tyr Phe Glu
1               5                   10                  15

<210> SEQ ID NO 523
<211> LENGTH: 16
<212> TYPE: PRT
<213> ORGANISM: Artificial Sequence
<220> FEATURE:
<223> OTHER INFORMATION: Synthetic: Hu37D3.v29.6 HVR-L1

<400> SEQUENCE: 523

Arg Ser Ser Gln Ser Ile Val His Ser Asn Gly Lys Thr Tyr Phe Glu
1               5                   10                  15

<210> SEQ ID NO 524
<211> LENGTH: 16
```

<212> TYPE: PRT
<213> ORGANISM: Artificial Sequence
<220> FEATURE:
<223> OTHER INFORMATION: Synthetic: Hu37D3.v29.7 HVR-L1

<400> SEQUENCE: 524

Arg Ser Ser Gln Ser Ile Val His Ser Asn Gly Leu Thr Tyr Phe Glu
1               5                   10                  15

<210> SEQ ID NO 525
<211> LENGTH: 16
<212> TYPE: PRT
<213> ORGANISM: Artificial Sequence
<220> FEATURE:
<223> OTHER INFORMATION: Synthetic: Hu37D3.v29.8 HVR-L1

<400> SEQUENCE: 525

Arg Ser Ser Gln Ser Ile Val His Ser Asn Ala Asp Thr Tyr Phe Glu
1               5                   10                  15

<210> SEQ ID NO 526
<211> LENGTH: 16
<212> TYPE: PRT
<213> ORGANISM: Artificial Sequence
<220> FEATURE:
<223> OTHER INFORMATION: Synthetic: Hu37D3.v29.9 HVR-L1

<400> SEQUENCE: 526

Arg Ser Ser Gln Ser Ile Val His Ser Asn Ala Gln Thr Tyr Phe Glu
1               5                   10                  15

<210> SEQ ID NO 527
<211> LENGTH: 16
<212> TYPE: PRT
<213> ORGANISM: Artificial Sequence
<220> FEATURE:
<223> OTHER INFORMATION: Synthetic: Hu37D3.v29.10 HVR-L1

<400> SEQUENCE: 527

Arg Ser Ser Gln Ser Ile Val His Ser Asn Ala Glu Thr Tyr Phe Glu
1               5                   10                  15

<210> SEQ ID NO 528
<211> LENGTH: 16
<212> TYPE: PRT
<213> ORGANISM: Artificial Sequence
<220> FEATURE:
<223> OTHER INFORMATION: Synthetic: Hu37D3.v29.11 HVR-L1

<400> SEQUENCE: 528

Arg Ser Ser Gln Ser Ile Val His Ser Asn Ala Ala Thr Tyr Phe Glu
1               5                   10                  15

<210> SEQ ID NO 529
<211> LENGTH: 16
<212> TYPE: PRT
<213> ORGANISM: Artificial Sequence
<220> FEATURE:
<223> OTHER INFORMATION: Synthetic: Hu37D3.v29.12 HVR-L1

<400> SEQUENCE: 529

Arg Ser Ser Gln Ser Ile Val His Ser Asn Ala His Thr Tyr Phe Glu
1               5                   10                  15

<210> SEQ ID NO 530
<211> LENGTH: 16
<212> TYPE: PRT

<213> ORGANISM: Artificial Sequence
<220> FEATURE:
<223> OTHER INFORMATION: Synthetic: Hu37D3.v29.13 HVR-L1

<400> SEQUENCE: 530

Arg Ser Ser Gln Ser Ile Val His Ser Asn Ala Lys Thr Tyr Phe Glu
1               5                   10                  15

<210> SEQ ID NO 531
<211> LENGTH: 16
<212> TYPE: PRT
<213> ORGANISM: Artificial Sequence
<220> FEATURE:
<223> OTHER INFORMATION: Synthetic: Hu37D3.v29.14 HVR-L1

<400> SEQUENCE: 531

Arg Ser Ser Gln Ser Ile Val His Ser Asn Ala Leu Thr Tyr Phe Glu
1               5                   10                  15

<210> SEQ ID NO 532
<211> LENGTH: 16
<212> TYPE: PRT
<213> ORGANISM: Artificial Sequence
<220> FEATURE:
<223> OTHER INFORMATION: Synthetic: Hu37D3-H9.v30.1 HVR-L1

<400> SEQUENCE: 532

Arg Ser Ser Gln Ser Ile Val His Ser Gly Gly Asn Thr Tyr Phe Glu
1               5                   10                  15

<210> SEQ ID NO 533
<211> LENGTH: 16
<212> TYPE: PRT
<213> ORGANISM: Artificial Sequence
<220> FEATURE:
<223> OTHER INFORMATION: Synthetic: Hu37D3-H9.v30.2 HVR-L1

<400> SEQUENCE: 533

Arg Ser Ser Gln Ser Ile Val His Ser Thr Gly Asn Thr Tyr Phe Glu
1               5                   10                  15

<210> SEQ ID NO 534
<211> LENGTH: 16
<212> TYPE: PRT
<213> ORGANISM: Artificial Sequence
<220> FEATURE:
<223> OTHER INFORMATION: Synthetic: Hu37D3-H9.v30.3 HVR-L1

<400> SEQUENCE: 534

Arg Ser Ser Gln Ser Ile Val His Ser Val Gly Asn Thr Tyr Phe Glu
1               5                   10                  15

<210> SEQ ID NO 535
<211> LENGTH: 16
<212> TYPE: PRT
<213> ORGANISM: Artificial Sequence
<220> FEATURE:
<223> OTHER INFORMATION: Synthetic: Hu37D3-H9.v30.4 HVR-L1

<400> SEQUENCE: 535

Arg Ser Ser Gln Ser Ile Val His Ser Leu Gly Asn Thr Tyr Phe Glu
1               5                   10                  15

<210> SEQ ID NO 536
<211> LENGTH: 16
<212> TYPE: PRT
<213> ORGANISM: Artificial Sequence

```
<220> FEATURE:
<223> OTHER INFORMATION: Synthetic: Hu37D3-H9.v30.5 HVR-L1

<400> SEQUENCE: 536

Arg Ser Ser Gln Ser Ile Val His Ser Ile Gly Asn Thr Tyr Phe Glu
1               5                   10                  15

<210> SEQ ID NO 537
<211> LENGTH: 16
<212> TYPE: PRT
<213> ORGANISM: Artificial Sequence
<220> FEATURE:
<223> OTHER INFORMATION: Synthetic: Hu37D3-H9.v30.6 HVR-L1

<400> SEQUENCE: 537

Arg Ser Ser Gln Ser Ile Val His Ser Pro Gly Asn Thr Tyr Phe Glu
1               5                   10                  15

<210> SEQ ID NO 538
<211> LENGTH: 16
<212> TYPE: PRT
<213> ORGANISM: Artificial Sequence
<220> FEATURE:
<223> OTHER INFORMATION: Synthetic: Hu37D3-H9.v30.7 HVR-L1

<400> SEQUENCE: 538

Arg Ser Ser Gln Ser Ile Val His Ser Phe Gly Asn Thr Tyr Phe Glu
1               5                   10                  15

<210> SEQ ID NO 539
<211> LENGTH: 16
<212> TYPE: PRT
<213> ORGANISM: Artificial Sequence
<220> FEATURE:
<223> OTHER INFORMATION: Synthetic: Hu37D3-H9.v30.8 HVR-L1

<400> SEQUENCE: 539

Arg Ser Ser Gln Ser Ile Val His Ser Tyr Gly Asn Thr Tyr Phe Glu
1               5                   10                  15

<210> SEQ ID NO 540
<211> LENGTH: 16
<212> TYPE: PRT
<213> ORGANISM: Artificial Sequence
<220> FEATURE:
<223> OTHER INFORMATION: Synthetic: Hu37D3-H9.v30.9 HVR-L1

<400> SEQUENCE: 540

Arg Ser Ser Gln Ser Ile Val His Ser His Gly Asn Thr Tyr Phe Glu
1               5                   10                  15

<210> SEQ ID NO 541
<211> LENGTH: 16
<212> TYPE: PRT
<213> ORGANISM: Artificial Sequence
<220> FEATURE:
<223> OTHER INFORMATION: Synthetic: Hu37D3-H9.v30.10 HVR-L1

<400> SEQUENCE: 541

Arg Ser Ser Gln Ser Ile Val His Ser Lys Gly Asn Thr Tyr Phe Glu
1               5                   10                  15

<210> SEQ ID NO 542
<211> LENGTH: 16
<212> TYPE: PRT
<213> ORGANISM: Artificial Sequence
<220> FEATURE:
```

<223> OTHER INFORMATION: Synthetic: Hu37D3-H9.v30.11 HVR-L1

<400> SEQUENCE: 542

Arg Ser Ser Gln Ser Ile Val His Ser Arg Gly Asn Thr Tyr Phe Glu
1               5                   10                  15

<210> SEQ ID NO 543
<211> LENGTH: 16
<212> TYPE: PRT
<213> ORGANISM: Artificial Sequence
<220> FEATURE:
<223> OTHER INFORMATION: Synthetic: Hu37D3-H9.v31.1 HVR-L1

<400> SEQUENCE: 543

Arg Ser Ser Gln Ser Ile Val His Ser Asn Ala Gly Thr Tyr Phe Glu
1               5                   10                  15

<210> SEQ ID NO 544
<211> LENGTH: 16
<212> TYPE: PRT
<213> ORGANISM: Artificial Sequence
<220> FEATURE:
<223> OTHER INFORMATION: Synthetic: Hu37D3-H9.v31.2 HVR-L1

<400> SEQUENCE: 544

Arg Ser Ser Gln Ser Ile Val His Ser Asn Ala Val Thr Tyr Phe Glu
1               5                   10                  15

<210> SEQ ID NO 545
<211> LENGTH: 16
<212> TYPE: PRT
<213> ORGANISM: Artificial Sequence
<220> FEATURE:
<223> OTHER INFORMATION: Synthetic: Hu37D3-H9.v31.3 HVR-L1

<400> SEQUENCE: 545

Arg Ser Ser Gln Ser Ile Val His Ser Asn Ala Ile Thr Tyr Phe Glu
1               5                   10                  15

<210> SEQ ID NO 546
<211> LENGTH: 16
<212> TYPE: PRT
<213> ORGANISM: Artificial Sequence
<220> FEATURE:
<223> OTHER INFORMATION: Synthetic: Hu37D3-H9.v31.4 HVR-L1

<400> SEQUENCE: 546

Arg Ser Ser Gln Ser Ile Val His Ser Asn Ala Pro Thr Tyr Phe Glu
1               5                   10                  15

<210> SEQ ID NO 547
<211> LENGTH: 16
<212> TYPE: PRT
<213> ORGANISM: Artificial Sequence
<220> FEATURE:
<223> OTHER INFORMATION: Synthetic: Hu37D3-H9.v31.5 HVR-L1

<400> SEQUENCE: 547

Arg Ser Ser Gln Ser Ile Val His Ser Asn Ala Phe Thr Tyr Phe Glu
1               5                   10                  15

<210> SEQ ID NO 548
<211> LENGTH: 16
<212> TYPE: PRT
<213> ORGANISM: Artificial Sequence
<220> FEATURE:
<223> OTHER INFORMATION: Synthetic: Hu37D3-H9.v31.6 HVR-L1

```
<400> SEQUENCE: 548

Arg Ser Ser Gln Ser Ile Val His Ser Asn Ala Tyr Thr Tyr Phe Glu
1               5                   10                  15

<210> SEQ ID NO 549
<211> LENGTH: 16
<212> TYPE: PRT
<213> ORGANISM: Artificial Sequence
<220> FEATURE:
<223> OTHER INFORMATION: Synthetic: Hu37D3-H9.v31.7 HVR-L1

<400> SEQUENCE: 549

Arg Ser Ser Gln Ser Ile Val His Ser Asn Ala Arg Thr Tyr Phe Glu
1               5                   10                  15

<210> SEQ ID NO 550
<211> LENGTH: 16
<212> TYPE: PRT
<213> ORGANISM: Artificial Sequence
<220> FEATURE:
<223> OTHER INFORMATION: Synthetic: Hu37D3-H9.v31.8 HVR-L1

<400> SEQUENCE: 550

Arg Ser Ser Gln Ser Ile Val His Ser Asn Ala Asn Val Tyr Phe Glu
1               5                   10                  15

<210> SEQ ID NO 551
<211> LENGTH: 16
<212> TYPE: PRT
<213> ORGANISM: Artificial Sequence
<220> FEATURE:
<223> OTHER INFORMATION: Synthetic: Hu37D3-H9.v31.9 HVR-L1

<400> SEQUENCE: 551

Arg Ser Ser Gln Ser Ile Val His Ser Asn Ala Asn Ile Tyr Phe Glu
1               5                   10                  15

<210> SEQ ID NO 552
<211> LENGTH: 16
<212> TYPE: PRT
<213> ORGANISM: Artificial Sequence
<220> FEATURE:
<223> OTHER INFORMATION: Synthetic: Hu37D3-H9.v31.10 HVR-L1

<400> SEQUENCE: 552

Arg Ser Ser Gln Ser Ile Val His Ser Asn Ala Asn Pro Tyr Phe Glu
1               5                   10                  15

<210> SEQ ID NO 553
<211> LENGTH: 16
<212> TYPE: PRT
<213> ORGANISM: Artificial Sequence
<220> FEATURE:
<223> OTHER INFORMATION: Synthetic: Hu37D3-H9.v31.11 HVR-L1

<400> SEQUENCE: 553

Arg Ser Ser Gln Ser Ile Val His Ser Asn Ala Asn Phe Tyr Phe Glu
1               5                   10                  15

<210> SEQ ID NO 554
<211> LENGTH: 16
<212> TYPE: PRT
<213> ORGANISM: Artificial Sequence
<220> FEATURE:
<223> OTHER INFORMATION: Synthetic: Hu37D3-H9.v31.12 HVR-L1
```

```
<400> SEQUENCE: 554

Arg Ser Ser Gln Ser Ile Val His Ser Asn Ala Asn Tyr Tyr Phe Glu
1               5                   10                  15

<210> SEQ ID NO 555
<211> LENGTH: 16
<212> TYPE: PRT
<213> ORGANISM: Artificial Sequence
<220> FEATURE:
<223> OTHER INFORMATION: Synthetic: Hu37D3-H9.v31.13 HVR-L1

<400> SEQUENCE: 555

Arg Ser Ser Gln Ser Ile Val His Ser Asn Ala Asn Asn Tyr Phe Glu
1               5                   10                  15

<210> SEQ ID NO 556
<211> LENGTH: 16
<212> TYPE: PRT
<213> ORGANISM: Artificial Sequence
<220> FEATURE:
<223> OTHER INFORMATION: Synthetic: Hu37D3-H9.v31.14 HVR-L1

<400> SEQUENCE: 556

Arg Ser Ser Gln Ser Ile Val His Ser Asn Ala Asn Arg Tyr Phe Glu
1               5                   10                  15

<210> SEQ ID NO 557
<211> LENGTH: 18
<212> TYPE: PRT
<213> ORGANISM: Artificial Sequence
<220> FEATURE:
<223> OTHER INFORMATION: Synthetic: Human Tau 7-24 peptide

<400> SEQUENCE: 557

Glu Phe Glu Val Met Glu Asp His Ala Gly Thr Tyr Gly Leu Gly Asp
1               5                   10                  15

Arg Lys

<210> SEQ ID NO 558
<211> LENGTH: 14
<212> TYPE: PRT
<213> ORGANISM: Artificial Sequence
<220> FEATURE:
<223> OTHER INFORMATION: Synthetic: Human Tau 7-20 peptide

<400> SEQUENCE: 558

Glu Phe Glu Val Met Glu Asp His Ala Gly Thr Tyr Gly Leu
1               5                   10

<210> SEQ ID NO 559

<400> SEQUENCE: 559

000

<210> SEQ ID NO 560
<211> LENGTH: 117
<212> TYPE: PRT
<213> ORGANISM: Artificial Sequence
<220> FEATURE:
<223> OTHER INFORMATION: Synthetic: Hu37D3.v39 heavy chain variable
      region (VH)

<400> SEQUENCE: 560

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Leu Ile Phe Arg Ser Tyr
         20                  25                  30

Gly Met Ser Trp Val Arg Gln Ala Pro Gly Lys Gly Leu Glu Trp Val
         35                  40                  45

Ala Thr Ile Asn Ser Gly Gly Thr Tyr Thr Tyr Tyr Pro Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Asn Ser Tyr Ser Gly Ala Met Asp Tyr Trp Gly Gln Gly Thr Leu
             100                 105                 110

Val Thr Val Ser Ser
             115

<210> SEQ ID NO 561
<211> LENGTH: 112
<212> TYPE: PRT
<213> ORGANISM: Artificial Sequence
<220> FEATURE:
<223> OTHER INFORMATION: Synthetic: Hu37D3.v39 light chain variable
      region (VL)

<400> SEQUENCE: 561

Glu Asp Gln Leu Thr Gln Ser Pro Ser Ser Leu Ser Ala Ser Val Gly
 1               5                  10                  15

Asp Arg Val Thr Ile Thr Cys Arg Ser Ser Gln Ser Ile Val His Ser
             20                  25                  30

Asn Gly Asn Thr Tyr Leu Glu Trp Tyr Gln Gln Lys Pro Gly Lys Ser
         35                  40                  45

Pro Lys Leu Leu Ile Tyr Lys Val Ser Asn Arg Phe Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Phe Gln Gly
                 85                  90                  95

Ser Leu Val Pro Trp Thr Phe Gly Gln Gly Thr Lys Val Glu Ile Lys
             100                 105                 110

<210> SEQ ID NO 562
<211> LENGTH: 5
<212> TYPE: PRT
<213> ORGANISM: Artificial Sequence
<220> FEATURE:
<223> OTHER INFORMATION: Synthetic: Hu37D3.v39 HVR-H1

<400> SEQUENCE: 562

Ser Tyr Gly Met Ser
 1               5

<210> SEQ ID NO 563
<211> LENGTH: 17
<212> TYPE: PRT
<213> ORGANISM: Artificial Sequence
<220> FEATURE:
<223> OTHER INFORMATION: Synthetic: Hu37D3.v39 HVR-H2

<400> SEQUENCE: 563

Thr Ile Asn Ser Gly Gly Thr Tyr Thr Tyr Tyr Pro Asp Ser Val Lys
 1               5                  10                  15
```

Gly

<210> SEQ ID NO 564
<211> LENGTH: 8
<212> TYPE: PRT
<213> ORGANISM: Artificial Sequence
<220> FEATURE:
<223> OTHER INFORMATION: Synthetic: Hu37D3.v39 HVR-H3

<400> SEQUENCE: 564

Ser Tyr Ser Gly Ala Met Asp Tyr
1               5

<210> SEQ ID NO 565
<211> LENGTH: 16
<212> TYPE: PRT
<213> ORGANISM: Artificial Sequence
<220> FEATURE:
<223> OTHER INFORMATION: Synthetic: Hu37D3.v39 HVR-L1

<400> SEQUENCE: 565

Arg Ser Ser Gln Ser Ile Val His Ser Asn Gly Asn Thr Tyr Leu Glu
1               5                   10                  15

<210> SEQ ID NO 566
<211> LENGTH: 7
<212> TYPE: PRT
<213> ORGANISM: Artificial Sequence
<220> FEATURE:
<223> OTHER INFORMATION: Synthetic: Hu37D3.v39 HVR-L2

<400> SEQUENCE: 566

Lys Val Ser Asn Arg Phe Ser
1               5

<210> SEQ ID NO 567
<211> LENGTH: 9
<212> TYPE: PRT
<213> ORGANISM: Artificial Sequence
<220> FEATURE:
<223> OTHER INFORMATION: Synthetic: Hu37D3.v39 HVR-L3

<400> SEQUENCE: 567

Phe Gln Gly Ser Leu Val Pro Trp Thr
1               5

<210> SEQ ID NO 568
<211> LENGTH: 444
<212> TYPE: PRT
<213> ORGANISM: Artificial Sequence
<220> FEATURE:
<223> OTHER INFORMATION: Synthetic: Hu37D3.v39 IgG4-S228P.YTE heavy
    chain

<400> SEQUENCE: 568

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Arg Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr

```
            65                  70                  75                  80
Leu Gln Met Asn Ser Leu Arg Ala Glu Asp Thr Ala Val Tyr Tyr Cys
                    85                  90                  95
Ala Asn Ser Tyr Ser Gly Ala Met Asp Tyr Trp Gly Gln Gly Thr Leu
                    100                 105                 110
Val Thr Val Ser Ser Ala Ser Thr Lys Gly Pro Ser Val Phe Pro Leu
                    115                 120                 125
Ala Pro Cys Ser Arg Ser Thr Ser Glu Ser Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                    165                 170                 175
Ser Gly Leu Tyr Ser Leu Ser Ser Val Val Thr Val Pro Ser Ser Ser
                    180                 185                 190
Leu Gly Thr Lys Thr Tyr Thr Cys Asn Val Asp His Lys Pro Ser Asn
                    195                 200                 205
Thr Lys Val Asp Lys Arg Val Glu Ser Lys Tyr Gly Pro Pro Cys Pro
            210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Tyr Ile Thr Arg Glu Pro Glu Val
                    245                 250                 255
Thr Cys Val Val Val Asp Val Ser Gln Glu Asp Pro Glu Val Gln Phe
                    260                 265                 270
Asn Trp Tyr Val Asp Gly Val Glu Val His Asn Ala Lys Thr Lys Pro
                    275                 280                 285
Arg Glu Glu Gln Phe Asn Ser Thr Tyr Arg Val Val Ser Val Leu Thr
            290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                    325                 330                 335
Lys Gly Gln Pro Arg Glu Pro Gln Val Tyr Thr Leu Pro Pro Ser Gln
                    340                 345                 350
Glu Glu Met Thr Lys Asn Gln Val Ser Leu Thr Cys Leu Val Lys Gly
                    355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                    405                 410                 415
Gly Asn Val Phe Ser Cys Ser Val Met His Glu Ala Leu His Asn His
                    420                 425                 430
Tyr Thr Gln Lys Ser Leu Ser Leu Ser Leu Gly Lys
            435                 440

<210> SEQ ID NO 569
<211> LENGTH: 219
<212> TYPE: PRT
<213> ORGANISM: Artificial Sequence
<220> FEATURE:
<223> OTHER INFORMATION: Synthetic: Hu37D3.v39 IgG4-S228P.YTE light
      chain
```

<400> SEQUENCE: 569

```
Glu Asp Gln Leu Thr Gln Ser Pro Ser Ser Leu Ser Ala Ser Val Gly
1               5                   10                  15

Asp Arg Val Thr Ile Thr Cys Arg Ser Gln Ser Ile Val His Ser
            20                  25                  30

Asn Gly Asn Thr Tyr Leu Glu Trp Tyr Gln Gln Lys Pro Gly Lys Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Leu Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 570
<211> LENGTH: 117
<212> TYPE: PRT
<213> ORGANISM: Artificial Sequence
<220> FEATURE:
<223> OTHER INFORMATION: Synthetic: Hu37D3.v40 heavy chain variable
      region (VH)

<400> SEQUENCE: 570

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Arg Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Thr Tyr Thr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ser Tyr Ser Gly Ala Met Asp Tyr Trp Gly Gln Gly Thr Leu
            100                 105                 110

Val Thr Val Ser Ser
            115
```

<210> SEQ ID NO 571
<211> LENGTH: 112
<212> TYPE: PRT
<213> ORGANISM: Artificial Sequence
<220> FEATURE:
<223> OTHER INFORMATION: Synthetic: Hu37D3.v40 light chain variable
      region (VL)

<400> SEQUENCE: 571

Glu Asp Gln Leu Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Asn Thr Asn Thr Tyr Phe Glu Trp Tyr Gln Gln Lys Pro Gly Lys Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Leu Val Pro Trp Thr Phe Gly Gln Gly Thr Lys Val Glu Ile Lys
            100                 105                 110

<210> SEQ ID NO 572
<211> LENGTH: 5
<212> TYPE: PRT
<213> ORGANISM: Artificial Sequence
<220> FEATURE:
<223> OTHER INFORMATION: Synthetic: Hu37D3.v40 HVR-H1

<400> SEQUENCE: 572

Ser Tyr Gly Met Ser
1               5

<210> SEQ ID NO 573
<211> LENGTH: 17
<212> TYPE: PRT
<213> ORGANISM: Artificial Sequence
<220> FEATURE:
<223> OTHER INFORMATION: Synthetic: Hu37D3.v40 HVR-H2

<400> SEQUENCE: 573

Thr Ile Asn Ser Gly Gly Thr Tyr Thr Tyr Tyr Pro Asp Ser Val Lys
1               5                   10                  15

Gly

<210> SEQ ID NO 574
<211> LENGTH: 8
<212> TYPE: PRT
<213> ORGANISM: Artificial Sequence
<220> FEATURE:
<223> OTHER INFORMATION: Synthetic: Hu37D3.v40 HVR-H3

<400> SEQUENCE: 574

Ser Tyr Ser Gly Ala Met Asp Tyr
1               5

<210> SEQ ID NO 575
<211> LENGTH: 16
<212> TYPE: PRT
<213> ORGANISM: Artificial Sequence
<220> FEATURE:
<223> OTHER INFORMATION: Synthetic: Hu37D3.v40 HVR-L1

<400> SEQUENCE: 575

Arg Ser Ser Gln Ser Ile Val His Ser Asn Thr Asn Thr Tyr Phe Glu
1               5                   10                  15

<210> SEQ ID NO 576
<211> LENGTH: 7
<212> TYPE: PRT
<213> ORGANISM: Artificial Sequence
<220> FEATURE:
<223> OTHER INFORMATION: Synthetic: Hu37D3.v40 HVR-L2

<400> SEQUENCE: 576

Lys Val Ser Asn Arg Phe Ser
1               5

<210> SEQ ID NO 577
<211> LENGTH: 9
<212> TYPE: PRT
<213> ORGANISM: Artificial Sequence
<220> FEATURE:
<223> OTHER INFORMATION: Synthetic: Hu37D3.v40 HVR-L3

<400> SEQUENCE: 577

Phe Gln Gly Ser Leu Val Pro Trp Thr
1               5

<210> SEQ ID NO 578
<211> LENGTH: 444
<212> TYPE: PRT
<213> ORGANISM: Artificial Sequence
<220> FEATURE:
<223> OTHER INFORMATION: Synthetic: Hu37D3.v40 IgG4-S228P.YTE heavy
      chain

<400> SEQUENCE: 578

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Arg Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ser Tyr Ser Gly Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser

```
            180                 185                 190
Leu Gly Thr Lys Thr Tyr Thr Cys Asn Val Asp His Lys Pro Ser Asn
            195                 200                 205
Thr Lys Val Asp Lys Arg Val Glu Ser Lys Tyr Gly Pro Pro Cys Pro
            210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Tyr Ile Thr Arg Glu Pro Glu Val
            245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
            275                 280                 285
Arg Glu Glu Gln Phe Asn Ser Thr Tyr Arg Val Val Ser Val Leu Thr
            290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
            325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
            355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
            405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly Lys
            435                 440

<210> SEQ ID NO 579
<211> LENGTH: 219
<212> TYPE: PRT
<213> ORGANISM: Artificial Sequence
<220> FEATURE:
<223> OTHER INFORMATION: Synthetic: Hu37D3.v40 IgG4-S228P.YTE light
      chain

<400> SEQUENCE: 579

Glu Asp Gln Leu Thr Gln Ser Pro Ser Ser Leu Ser Ala Ser Val Gly
1               5                   10                  15
Asp Arg Val Thr Ile Thr Cys Arg Ser Ser Gln Ser Ile Val His Ser
            20                  25                  30
Asn Thr Asn Thr Tyr Phe Glu Trp Tyr Gln Gln Lys Pro Gly Lys Ser
            35                  40                  45
Pro Lys Leu Leu Ile Tyr Lys Val Ser Asn Arg Phe Ser Gly Val Pro
        50                  55                  60
Ser Arg Phe Ser Gly Ser Gly Ser Gly Thr Asp Phe Thr Leu Thr Ile
65                  70                  75                  80
Ser Ser Leu Gln Pro Glu Asp Phe Ala Thr Tyr Tyr Cys Phe Gln Gly
            85                  90                  95
```

```
Ser Leu Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 580
<211> LENGTH: 117
<212> TYPE: PRT
<213> ORGANISM: Artificial Sequence
<220> FEATURE:
<223> OTHER INFORMATION: Synthetic: Hu37D3.v41 heavy chain variable
      region (VH)

<400> SEQUENCE: 580

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Arg Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ser Tyr Ser Gly Ala Met Asp Tyr Trp Gly Gln Gly Thr Leu
            100                 105                 110

Val Thr Val Ser Ser
        115

<210> SEQ ID NO 581
<211> LENGTH: 112
<212> TYPE: PRT
<213> ORGANISM: Artificial Sequence
<220> FEATURE:
<223> OTHER INFORMATION: Synthetic: Hu37D3.v41 light chain variable
      region (VL)

<400> SEQUENCE: 581

Glu Asp Gln Leu Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Asn Gly Gln Thr Tyr Phe Glu Trp Tyr Gln Gln Lys Pro Gly Lys Ser
        35                  40                  45
```

```
Pro Lys Leu Leu Ile Tyr Lys Val Ser Asn Arg Phe Ser Gly Val Pro
     50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Phe Gln Gly
                 85                  90                  95

Ser Leu Val Pro Trp Thr Phe Gly Gln Gly Thr Lys Val Glu Ile Lys
            100                 105                 110
```

<210> SEQ ID NO 582
<211> LENGTH: 5
<212> TYPE: PRT
<213> ORGANISM: Artificial Sequence
<220> FEATURE:
<223> OTHER INFORMATION: Synthetic: Hu37D3.v41 HVR-H1

<400> SEQUENCE: 582

```
Ser Tyr Gly Met Ser
 1               5
```

<210> SEQ ID NO 583
<211> LENGTH: 17
<212> TYPE: PRT
<213> ORGANISM: Artificial Sequence
<220> FEATURE:
<223> OTHER INFORMATION: Synthetic: Hu37D3.v41 HVR-H2

<400> SEQUENCE: 583

```
Thr Ile Asn Ser Gly Gly Thr Tyr Thr Tyr Tyr Pro Asp Ser Val Lys
 1               5                  10                  15

Gly
```

<210> SEQ ID NO 584
<211> LENGTH: 8
<212> TYPE: PRT
<213> ORGANISM: Artificial Sequence
<220> FEATURE:
<223> OTHER INFORMATION: Synthetic: Hu37D3.v41 HVR-H3

<400> SEQUENCE: 584

```
Ser Tyr Ser Gly Ala Met Asp Tyr
 1               5
```

<210> SEQ ID NO 585
<211> LENGTH: 16
<212> TYPE: PRT
<213> ORGANISM: Artificial Sequence
<220> FEATURE:
<223> OTHER INFORMATION: Synthetic: Hu37D3.v41 HVR-L1

<400> SEQUENCE: 585

```
Arg Ser Ser Gln Ser Ile Val His Ser Asn Gly Gln Thr Tyr Phe Glu
 1               5                  10                  15
```

<210> SEQ ID NO 586
<211> LENGTH: 7
<212> TYPE: PRT
<213> ORGANISM: Artificial Sequence
<220> FEATURE:
<223> OTHER INFORMATION: Synthetic: Hu37D3.v41 HVR-L2

<400> SEQUENCE: 586

```
Lys Val Ser Asn Arg Phe Ser
 1               5
```

<210> SEQ ID NO 587
<211> LENGTH: 9
<212> TYPE: PRT
<213> ORGANISM: Artificial Sequence
<220> FEATURE:
<223> OTHER INFORMATION: Synthetic: Hu37D3.v41 HVR-L3

<400> SEQUENCE: 587

Phe Gln Gly Ser Leu Val Pro Trp Thr
1               5

<210> SEQ ID NO 588
<211> LENGTH: 444
<212> TYPE: PRT
<213> ORGANISM: Artificial Sequence
<220> FEATURE:
<223> OTHER INFORMATION: Synthetic: Hu37D3.v41 IgG4-S228P.YTE heavy
      chain

<400> SEQUENCE: 588

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Arg Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ser Tyr Ser Gly Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Tyr Ile Thr Arg Glu Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr

```
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440

<210> SEQ ID NO 589
<211> LENGTH: 219
<212> TYPE: PRT
<213> ORGANISM: Artificial Sequence
<220> FEATURE:
<223> OTHER INFORMATION: Synthetic: Hu37D3.v41 IgG4-S228P.YTE light
      chain

<400> SEQUENCE: 589

Glu Asp Gln Leu Thr Gln Ser Pro Ser Ser Leu Ser Ala Ser Val Gly
1               5                   10                  15

Asp Arg Val Thr Ile Thr Cys Arg Ser Gln Ser Ile Val His Ser
                20                  25                  30

Asn Gly Gln Thr Tyr Phe Glu Trp Tyr Gln Gln Lys Pro Gly Lys Ser
            35                  40                  45

Pro Lys Leu Leu Ile Tyr Lys Val Ser Asn Arg Phe Ser Gly Val Pro
        50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Leu Val Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

```
Pro Val Thr Lys Ser Phe Asn Arg Gly Glu Cys
    210                 215
```

<210> SEQ ID NO 590
<211> LENGTH: 444
<212> TYPE: PRT
<213> ORGANISM: Artificial Sequence
<220> FEATURE:
<223> OTHER INFORMATION: Synthetic: Hu37D3-H9.v1 IgG4 heavy chain

<400> SEQUENCE: 590

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Arg Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ser Tyr Ser Gly Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350
```

```
Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440
```

<210> SEQ ID NO 591
<211> LENGTH: 219
<212> TYPE: PRT
<213> ORGANISM: Artificial Sequence
<220> FEATURE:
<223> OTHER INFORMATION: Synthetic: Hu37D3-H9.v1 IgG4 light chain

<400> SEQUENCE: 591

```
Glu Asp Gln Leu Thr Gln Ser Pro Ser Ser Leu Ser Ala Ser Val Gly
1               5                   10                  15

Asp Arg Val Thr Ile Thr Cys Arg Ser Gln Ser Ile Val His Ser
            20                  25                  30

Asn Gly Asn Thr Tyr Phe Glu Trp Tyr Gln Gln Lys Pro Gly Lys Ser
        35                  40                  45

Pro Lys Leu Leu Ile Tyr Lys Val Ser Asn Arg Phe Ser Gly Val Pro
50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Leu Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215
```

<210> SEQ ID NO 592
<211> LENGTH: 15
<212> TYPE: PRT
<213> ORGANISM: Artificial Sequence
<220> FEATURE:
<223> OTHER INFORMATION: Synthetic: MAPT(10-24)

<400> SEQUENCE: 592

Val Met Glu Asp His Ala Gly Thr Tyr Gly Leu Gly Asp Arg Lys
1               5                   10                  15

<210> SEQ ID NO 593
<211> LENGTH: 23
<212> TYPE: PRT
<213> ORGANISM: Artificial Sequence
<220> FEATURE:
<223> OTHER INFORMATION: Synthetic: MAPT(2-24)

<400> SEQUENCE: 593

Ala Glu Pro Arg Gln Glu Phe Glu Val Met Glu Asp His Ala Gly Thr
1               5                   10                  15

Tyr Gly Leu Gly Asp Arg Lys
            20

<210> SEQ ID NO 594
<211> LENGTH: 33
<212> TYPE: PRT
<213> ORGANISM: Artificial Sequence
<220> FEATURE:
<223> OTHER INFORMATION: Synthetic: MAPT(2-34)

<400> SEQUENCE: 594

Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp

<210> SEQ ID NO 595
<211> LENGTH: 35
<212> TYPE: PRT
<213> ORGANISM: Artificial Sequence
<220> FEATURE:
<223> OTHER INFORMATION: Synthetic: MAPT(10-44)

<400> SEQUENCE: 595

Val Met Glu Asp His Ala Gly Thr Tyr Gly Leu Gly Asp Arg Lys Asp
1               5                   10                  15

Gln Gly Gly Tyr Thr Met His Gln Asp Gln Glu Gly Asp Thr Asp Ala
            20                  25                  30

Gly Leu Lys
        35

<210> SEQ ID NO 596
<211> LENGTH: 23
<212> TYPE: PRT
<213> ORGANISM: Artificial Sequence
<220> FEATURE:
<223> OTHER INFORMATION: Synthetic: MAPT(2-24)Y18A

<400> SEQUENCE: 596

Ala Glu Pro Arg Gln Glu Phe Glu Val Met Glu Asp His Ala Gly Thr
1               5                   10                  15

Ala Gly Leu Gly Asp Arg Lys
            20

<210> SEQ ID NO 597
<211> LENGTH: 23
<212> TYPE: PRT
<213> ORGANISM: Artificial Sequence
<220> FEATURE:

<223> OTHER INFORMATION: Synthetic: MAPT(2-24)L20A

<400> SEQUENCE: 597

Ala Glu Pro Arg Gln Glu Phe Glu Val Met Glu Asp His Ala Gly Thr
1               5                   10                  15

Tyr Gly Ala Gly Asp Arg Lys
            20

<210> SEQ ID NO 598
<211> LENGTH: 107
<212> TYPE: PRT
<213> ORGANISM: Artificial Sequence
<220> FEATURE:
<223> OTHER INFORMATION: Synthetic: hu113F5-F7.LC1

<400> SEQUENCE: 598

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ser Pro Lys Leu Leu Ile
        35                  40                  45

Tyr Ser Ala Ser Arg Arg Phe Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Phe Ser Thr Tyr Pro Tyr
                85                  90                  95

Thr Phe Gly Gln Gly Thr Lys Val Glu Ile Lys
            100                 105

<210> SEQ ID NO 599
<211> LENGTH: 107
<212> TYPE: PRT
<213> ORGANISM: Artificial Sequence
<220> FEATURE:
<223> OTHER INFORMATION: Synthetic: hu113F5-F7.LC2

<400> SEQUENCE: 599

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Arg Arg Phe Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Phe Ser Thr Tyr Pro Tyr
                85                  90                  95

Thr Phe Gly Gln Gly Thr Lys Val Glu Ile Lys
            100                 105

<210> SEQ ID NO 600
<211> LENGTH: 107
<212> TYPE: PRT
<213> ORGANISM: Artificial Sequence
<220> FEATURE:
<223> OTHER INFORMATION: Synthetic: hu113F5-F7.LC3

-continued

<400> SEQUENCE: 600

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ser Pro Lys Leu Leu Ile
        35                  40                  45

Tyr Ser Ala Ser Arg Arg Phe Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Ser Thr Tyr Pro Tyr
                85                  90                  95

Thr Phe Gly Gln Gly Thr Lys Val Glu Ile Lys
            100                 105

<210> SEQ ID NO 601
<211> LENGTH: 107
<212> TYPE: PRT
<213> ORGANISM: Artificial Sequence
<220> FEATURE:
<223> OTHER INFORMATION: Synthetic: hu113F5-F7.LC4

<400> SEQUENCE: 601

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Arg Arg Phe Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Ser Thr Tyr Pro Tyr
                85                  90                  95

Thr Phe Gly Gln Gly Thr Lys Val Glu Ile Lys
            100                 105

<210> SEQ ID NO 602
<211> LENGTH: 443
<212> TYPE: PRT
<213> ORGANISM: Artificial Sequence
<220> FEATURE:
<223> OTHER INFORMATION: Synthetic: Hu37D3-H9.v28.A4 IgG4-S228P.YTE
    des-K heavy chain

<400> SEQUENCE: 602

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Arg Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95
Ala Asn Ser Tyr Ser Gly Ala Met Asp Tyr Trp Gly Gln Gly Thr Leu
                100                 105                 110
Val Thr Val Ser Ser Ala Ser Thr Lys Gly Pro Ser Val Phe Pro Leu
                115                 120                 125
Ala Pro Cys Ser Arg Ser Thr Ser Glu Ser Thr Ala Ala Leu Gly Cys
130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Lys Thr Tyr Thr Cys Asn Val Asp His Lys Pro Ser Asn
                195                 200                 205
Thr Lys Val Asp Lys Arg Val Glu Ser Lys Tyr Gly Pro Pro Cys Pro
210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Tyr Ile Thr Arg Glu Pro Glu Val
                245                 250                 255
Thr Cys Val Val Val Asp Val Ser Gln Glu Asp Pro Glu Val Gln Phe
                260                 265                 270
Asn Trp Tyr Val Asp Gly Val Glu Val His Asn Ala Lys Thr Lys Pro
                275                 280                 285
Arg Glu Glu Gln Phe Asn Ser Thr Tyr Arg Val Val Ser Val Leu Thr
                290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
                340                 345                 350
Glu Glu Met Thr Lys Asn Gln Val Ser Leu Thr Cys Leu Val Lys Gly
                355                 360                 365
Phe Tyr Pro Ser Asp Ile Ala Val Glu Trp Glu Ser Asn Gly Gln Pro
                370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
                420                 425                 430
Tyr Thr Gln Lys Ser Leu Ser Leu Ser Leu Gly
                435                 440

<210> SEQ ID NO 603
<211> LENGTH: 122
<212> TYPE: PRT
<213> ORGANISM: Artificial Sequences
<220> FEATURE:
<223> OTHER INFORMATION: 231G3F10 Heavy Chain Variable Region
```

<400> SEQUENCE: 603

Glu Val Arg Leu Val Glu Ser Gly Gly Gly Leu Val Gln Pro Lys Gly
1               5                   10                  15

Ser Leu Lys Leu Ser Cys Ala Ala Ser Gly Phe Ser Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Arg Asn Asn Phe Ala Thr Tyr Tyr Ala Asp
    50                  55                  60

Ser Val Lys Asp Arg Phe Thr Ile Ser Arg Asp Asp Ser Lys Ser Met
65                  70                  75                  80

Leu Tyr Leu Gln Met Asn Asn Leu Lys Thr Glu Asp Thr Ala Met Tyr
                85                  90                  95

Tyr Cys Val Arg Trp Gly Tyr Asp Pro Tyr Ala Met Asp Tyr Trp
            100                 105                 110

Gly Gln Gly Thr Ser Val Thr Val Ser Ser
        115                 120

<210> SEQ ID NO 604
<211> LENGTH: 112
<212> TYPE: PRT
<213> ORGANISM: Artificial Sequences
<220> FEATURE:
<223> OTHER INFORMATION: 231G3F10 Light Chain Variable Region

<400> SEQUENCE: 604

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Phe Ser Ser Phe Thr Phe Gly Ser Gly Thr Lys Leu Glu Ile Lys
            100                 105                 110

<210> SEQ ID NO 605
<211> LENGTH: 5
<212> TYPE: PRT
<213> ORGANISM: Artificial Sequences
<220> FEATURE:
<223> OTHER INFORMATION: 231G3F10 HVR-H1

<400> SEQUENCE: 605

Thr Tyr Ala Met Asn
1               5

<210> SEQ ID NO 606
<211> LENGTH: 19
<212> TYPE: PRT
<213> ORGANISM: Artificial Sequences
<220> FEATURE:
<223> OTHER INFORMATION: 231G3F10 HVR-H2

<400> SEQUENCE: 606

-continued

Arg Ile Arg Ser Lys Arg Asn Asn Phe Ala Thr Tyr Tyr Ala Asp Ser
1               5                   10                  15

Val Lys Asp

<210> SEQ ID NO 607
<211> LENGTH: 11
<212> TYPE: PRT
<213> ORGANISM: Artificial Sequences
<220> FEATURE:
<223> OTHER INFORMATION: 231G3F10 HVR-H3

<400> SEQUENCE: 607

Trp Gly Tyr Asp Asp Pro Tyr Ala Met Asp Tyr
1               5                   10

<210> SEQ ID NO 608
<211> LENGTH: 17
<212> TYPE: PRT
<213> ORGANISM: Artificial Sequences
<220> FEATURE:
<223> OTHER INFORMATION: 231G3F10 HVR-L1

<400> SEQUENCE: 608

Lys Ser Ser Gln Ser Val Leu Tyr Ser Ser Asn Gln Lys Asn Tyr Leu
1               5                   10                  15

Ala

<210> SEQ ID NO 609
<211> LENGTH: 7
<212> TYPE: PRT
<213> ORGANISM: Artificial Sequences
<220> FEATURE:
<223> OTHER INFORMATION: 231G3F10 HVR-L2

<400> SEQUENCE: 609

Trp Ala Ser Ala Arg Glu Ser
1               5

<210> SEQ ID NO 610
<211> LENGTH: 8
<212> TYPE: PRT
<213> ORGANISM: Artificial Sequences
<220> FEATURE:
<223> OTHER INFORMATION: 231G3F10 HVR-L3

<400> SEQUENCE: 610

His Gln Tyr Phe Ser Ser Phe Thr
1               5

<210> SEQ ID NO 611
<211> LENGTH: 112
<212> TYPE: PRT
<213> ORGANISM: Artificial Sequences
<220> FEATURE:
<223> OTHER INFORMATION: 30A1C9 Heavy Chain Variable Region

<400> SEQUENCE: 611

Gly Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Met Lys Gln Ser His Gly Lys Ser Leu Glu Trp Ile
            35                  40                  45

Gly Gly Ile Asp Pro Asn Thr Gly Asn Thr Asn Tyr Asn Gln Lys Phe
 50                  55                  60

Lys Gly Lys Ala Thr Leu Thr Val Asp Lys Ser Ser Thr Ala Tyr
 65                  70                  75                  80

Met Asp Leu Arg Ser Leu Thr Ser Glu Asp Ser Ala Val Tyr Tyr Phe
                 85                  90                  95

Tyr Gly Ser Gly Tyr Trp Gly Gln Gly Thr Ile Leu Thr Val Ser Ser
                100                 105                 110

<210> SEQ ID NO 612
<211> LENGTH: 112
<212> TYPE: PRT
<213> ORGANISM: Artificial Sequences
<220> FEATURE:
<223> OTHER INFORMATION: 30A1C9 Light Chain Variable Region

<400> SEQUENCE: 612

Asp Val Leu Met Thr Gln Ser Pro Leu Ser Leu Pro Val Ser Leu Gly
 1               5                  10                  15

Asp Gln Ala Ser Ile Ser Cys Arg Ser Ser Gln Ser Ile Val His Ser
                 20                  25                  30

Asn Gly Asn Thr Tyr Leu Glu Trp Phe Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Ala
                 85                  90                  95

Ser His Val Pro Arg Thr Phe Gly Gly Gly Thr Lys Leu Glu Ile Lys
                100                 105                 110

<210> SEQ ID NO 613
<211> LENGTH: 5
<212> TYPE: PRT
<213> ORGANISM: Artificial Sequences
<220> FEATURE:
<223> OTHER INFORMATION: 30A1C9 HVR-H1

<400> SEQUENCE: 613

Glu Tyr Thr Met His
 1               5

<210> SEQ ID NO 614
<211> LENGTH: 17
<212> TYPE: PRT
<213> ORGANISM: Artificial Sequences
<220> FEATURE:
<223> OTHER INFORMATION: 30A1C9 HVR-H2

<400> SEQUENCE: 614

Gly Ile Asp Pro Asn Thr Gly Asn Thr Asn Tyr Asn Gln Lys Phe Lys
 1               5                  10                  15

Gly

<210> SEQ ID NO 615
<211> LENGTH: 3
<212> TYPE: PRT
<213> ORGANISM: Artificial Sequences
<220> FEATURE:
<223> OTHER INFORMATION: 30A1C9 HVR-H3

```
<400> SEQUENCE: 615

Ser Gly Tyr
1

<210> SEQ ID NO 616
<211> LENGTH: 16
<212> TYPE: PRT
<213> ORGANISM: Artificial Sequences
<220> FEATURE:
<223> OTHER INFORMATION: 30A1C9 HVR-L1

<400> SEQUENCE: 616

Arg Ser Ser Gln Ser Ile Val His Ser Asn Gly Asn Thr Tyr Leu Glu
1               5                   10                  15

<210> SEQ ID NO 617
<211> LENGTH: 7
<212> TYPE: PRT
<213> ORGANISM: Artificial Sequences
<220> FEATURE:
<223> OTHER INFORMATION: 30A1C9 HVR-L2

<400> SEQUENCE: 617

Lys Val Ser Asn Arg Phe Ser
1               5

<210> SEQ ID NO 618
<211> LENGTH: 9
<212> TYPE: PRT
<213> ORGANISM: Artificial Sequences
<220> FEATURE:
<223> OTHER INFORMATION: 30A1C9 HVR-L3

<400> SEQUENCE: 618

Phe Gln Ala Ser His Val Pro Arg Thr
1               5

<210> SEQ ID NO 619
<211> LENGTH: 122
<212> TYPE: PRT
<213> ORGANISM: Artificial Sequences
<220> FEATURE:
<223> OTHER INFORMATION: 211G6-B6 Heavy Chain Variable Region

<400> SEQUENCE: 619

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Ala Ile Ser Trp Val Arg Gln Pro Pro Gly Lys Gly Leu Glu Trp Leu
        35                  40                  45

Gly Val Ile Trp Thr Gly Gly Thr Asn Tyr Asn Ser Ala Leu Lys
    50                  55                  60

Ser Arg Leu Ser Ile Thr Lys Asp Asn Ser Lys Asn Gln Val Phe Phe
65                  70                  75                  80

Arg Met Asn Ser Leu Gln Thr Asp Asp Thr Ala Arg Tyr Tyr Cys Ala
                85                  90                  95

Arg Lys Lys Leu Tyr Asp Tyr Asp Gly Tyr Phe Phe Asp Tyr Trp
            100                 105                 110

Gly Gln Gly Thr Thr Leu Thr Val Ser Ser
            115                 120
```

```
<210> SEQ ID NO 620
<211> LENGTH: 113
<212> TYPE: PRT
<213> ORGANISM: Artificial Sequences
<220> FEATURE:
<223> OTHER INFORMATION: 211G6-B6 Light Chain Variable Region

<400> SEQUENCE: 620
```

Asp Ile Val Met Ser Gln Ser Pro Ser Ser Leu Ala Met Ser Val Gly
1               5                   10                  15

Glu Lys Val Thr Met Ser Cys Lys Ser Asn Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys His Gln
                85                  90                  95

Tyr Tyr Ser Tyr Pro Trp Thr Phe Gly Gly Gly Thr Lys Leu Glu Ile
            100                 105                 110

Lys

```
<210> SEQ ID NO 621
<211> LENGTH: 5
<212> TYPE: PRT
<213> ORGANISM: Artificial Sequences
<220> FEATURE:
<223> OTHER INFORMATION: 211G6-B6 HVR-H1

<400> SEQUENCE: 621
```

Ser Tyr Ala Ile Ser
1               5

```
<210> SEQ ID NO 622
<211> LENGTH: 16
<212> TYPE: PRT
<213> ORGANISM: Artificial Sequences
<220> FEATURE:
<223> OTHER INFORMATION: 211G6-B6 HVR-H2

<400> SEQUENCE: 622
```

Val Ile Trp Thr Gly Gly Gly Thr Asn Tyr Asn Ser Ala Leu Lys Ser
1               5                   10                  15

```
<210> SEQ ID NO 623
<211> LENGTH: 14
<212> TYPE: PRT
<213> ORGANISM: Artificial Sequences
<220> FEATURE:
<223> OTHER INFORMATION: 211G6-B6 HVR-H3

<400> SEQUENCE: 623
```

Lys Lys Leu Tyr Asp Tyr Asp Gly Gly Tyr Phe Phe Asp Tyr
1               5                   10

```
<210> SEQ ID NO 624
<211> LENGTH: 17
<212> TYPE: PRT
<213> ORGANISM: Artificial Sequences
<220> FEATURE:
<223> OTHER INFORMATION: 211G6-B6 HVR-L1
```

```
<400> SEQUENCE: 624

Lys Ser Asn Gln Ser Leu Leu Tyr Ser Ser Asn Gln Lys Asn Tyr Leu
1               5                   10                  15
Ala

<210> SEQ ID NO 625
<211> LENGTH: 7
<212> TYPE: PRT
<213> ORGANISM: Artificial Sequences
<220> FEATURE:
<223> OTHER INFORMATION: 211G6-B6 HVR-L2

<400> SEQUENCE: 625

Trp Ala Ser Thr Arg Glu Ser
1               5

<210> SEQ ID NO 626
<211> LENGTH: 9
<212> TYPE: PRT
<213> ORGANISM: Artificial Sequences
<220> FEATURE:
<223> OTHER INFORMATION: 211G6-B6 HVR-L3

<400> SEQUENCE: 626

His Gln Tyr Tyr Ser Tyr Pro Trp Thr
1               5

<210> SEQ ID NO 627
<211> LENGTH: 114
<212> TYPE: PRT
<213> ORGANISM: Artificial Sequences
<220> FEATURE:
<223> OTHER INFORMATION: 77D1-D2 Heavy Chain Variable Region

<400> SEQUENCE: 627

Glu Val Gln Leu Gln Gln Ser Val Ala Glu Leu Val Arg Pro Gly Ala
1               5                   10                  15

Ser Val Thr Leu Ser Cys Thr Ser Ser Gly Phe Asn Ile Lys Asn Thr
                20                  25                  30

Tyr Met His Trp Val Ile Gln Arg Pro Glu Gln Gly Leu Glu Trp Ile
            35                  40                  45

Gly Lys Ile Asp Pro Ala Ile Val Asn Thr Lys Tyr Ala Pro Lys Phe
        50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Gly Ile Tyr Tyr Cys
                85                  90                  95

Ala Glu Gly Ala Leu Leu Tyr Trp Gly Leu Gly Thr Ser Val Thr Val
            100                 105                 110

Ser Ser

<210> SEQ ID NO 628
<211> LENGTH: 112
<212> TYPE: PRT
<213> ORGANISM: Artificial Sequences
<220> FEATURE:
<223> OTHER INFORMATION: 77D1-D2 Light Chain Variable Region

<400> SEQUENCE: 628

Asp Val Val Met Thr Gln Thr Pro Leu Ser Leu Ser Val Thr Ile Gly
1               5                   10                  15
```

```
Gln Pro Ala Ser Ile Ser Cys Lys Ser Ser Gln Ser Leu Leu His Ser
            20                  25                  30

Asn Gly Lys Thr Tyr Leu Asn Trp Leu Gln Gln Arg Pro Gly Gln Ala
        35                  40                  45

Pro Lys Leu Leu Met Tyr Leu Val Ser Lys Val Asp Pro Gly Ile Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Thr Tyr Tyr Pro His Thr Phe Gly Gly Gly Thr Lys Leu Glu Ile Lys
            100                 105                 110
```

<210> SEQ ID NO 629
<211> LENGTH: 5
<212> TYPE: PRT
<213> ORGANISM: Artificial Sequences
<220> FEATURE:
<223> OTHER INFORMATION: 77D1-D2 HVR-H1

<400> SEQUENCE: 629

```
Asn Thr Tyr Met His
1               5
```

<210> SEQ ID NO 630
<211> LENGTH: 17
<212> TYPE: PRT
<213> ORGANISM: Artificial Sequences
<220> FEATURE:
<223> OTHER INFORMATION: 77D1-D2 HVR-H2

<400> SEQUENCE: 630

```
Lys Ile Asp Pro Ala Ile Val Asn Thr Lys Tyr Ala Pro Lys Phe Gln
1               5                   10                  15

Gly
```

<210> SEQ ID NO 631
<211> LENGTH: 5
<212> TYPE: PRT
<213> ORGANISM: Artificial Sequences
<220> FEATURE:
<223> OTHER INFORMATION: 77D1-D2 HVR-H3

<400> SEQUENCE: 631

```
Gly Ala Leu Leu Tyr
1               5
```

<210> SEQ ID NO 632
<211> LENGTH: 16
<212> TYPE: PRT
<213> ORGANISM: Artificial Sequences
<220> FEATURE:
<223> OTHER INFORMATION: 77D1-D2 HVR-L1

<400> SEQUENCE: 632

```
Lys Ser Ser Gln Ser Leu Leu His Ser Asn Gly Lys Thr Tyr Leu Asn
1               5                   10                  15
```

<210> SEQ ID NO 633
<211> LENGTH: 7
<212> TYPE: PRT
<213> ORGANISM: Artificial Sequences
<220> FEATURE:
<223> OTHER INFORMATION: 77D1-D2 HVR-L2

<400> SEQUENCE: 633

Leu Val Ser Lys Val Asp Pro
1               5

<210> SEQ ID NO 634
<211> LENGTH: 9
<212> TYPE: PRT
<213> ORGANISM: Artificial Sequences
<220> FEATURE:
<223> OTHER INFORMATION: 77D1-D2 HVR-L3

<400> SEQUENCE: 634

Phe Gln Gly Thr Tyr Tyr Pro His Thr
1               5

<210> SEQ ID NO 635
<211> LENGTH: 113
<212> TYPE: PRT
<213> ORGANISM: Artificial Sequences
<220> FEATURE:
<223> OTHER INFORMATION: 71H8-D6 Heavy Chain Variable Region

<400> SEQUENCE: 635

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Ile Gln Trp Val Lys Gln Arg Pro Glu Gln Gly Leu Glu Trp Ile
        35                  40                  45

Gly Trp Ile Asp Pro Glu Asn Gly Asp Thr Asp Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Phe Ser Ser Leu Thr Ser Glu Asp Thr Ala Val Tyr Tyr Cys
                85                  90                  95

Asn Arg Gly Trp Gly Tyr Trp Gly Gln Gly Thr Thr Leu Thr Val Ser
            100                 105                 110

Ser

<210> SEQ ID NO 636
<211> LENGTH: 112
<212> TYPE: PRT
<213> ORGANISM: Artificial Sequences
<220> FEATURE:
<223> OTHER INFORMATION: 71H8-D6 Light Chain Variable Region

<400> SEQUENCE: 636

Asp Val Val Met Thr Gln Thr Pro Leu Thr Leu Pro Ile Thr Leu Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Ser Trp Leu Leu Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Leu Tyr Tyr Cys Trp Gln Gly
                85                  90                  95

```
Thr His Phe Pro Gln Thr Phe Gly Gly Gly Thr Lys Leu Glu Ile Lys
        100                 105                 110
```

<210> SEQ ID NO 637
<211> LENGTH: 5
<212> TYPE: PRT
<213> ORGANISM: Artificial Sequences
<220> FEATURE:
<223> OTHER INFORMATION: 71H8-D6 HVR-H1

<400> SEQUENCE: 637

```
Asp Tyr Tyr Ile Gln
1               5
```

<210> SEQ ID NO 638
<211> LENGTH: 17
<212> TYPE: PRT
<213> ORGANISM: Artificial Sequences
<220> FEATURE:
<223> OTHER INFORMATION: 71H8-D6 HVR-H2

<400> SEQUENCE: 638

```
Trp Ile Asp Pro Glu Asn Gly Asp Thr Asp Tyr Ala Pro Lys Phe Gln
1               5                   10                  15
Gly
```

<210> SEQ ID NO 639
<211> LENGTH: 4
<212> TYPE: PRT
<213> ORGANISM: Artificial Sequences
<220> FEATURE:
<223> OTHER INFORMATION: 71H8-D6 HVR-H3

<400> SEQUENCE: 639

```
Gly Trp Gly Tyr
1
```

<210> SEQ ID NO 640
<211> LENGTH: 16
<212> TYPE: PRT
<213> ORGANISM: Artificial Sequences
<220> FEATURE:
<223> OTHER INFORMATION: 71H8-D6 HVR-L1

<400> SEQUENCE: 640

```
Lys Ser Ser Gln Ser Leu Leu His Ser Asp Gly Lys Thr Tyr Leu Ser
1               5                   10                  15
```

<210> SEQ ID NO 641
<211> LENGTH: 7
<212> TYPE: PRT
<213> ORGANISM: Artificial Sequences
<220> FEATURE:
<223> OTHER INFORMATION: 71H8-D6 HVR-L2

<400> SEQUENCE: 641

```
Leu Val Ser Glu Leu Asp Ser
1               5
```

<210> SEQ ID NO 642
<211> LENGTH: 9
<212> TYPE: PRT
<213> ORGANISM: Artificial Sequences
<220> FEATURE:
<223> OTHER INFORMATION: 71H8-D6 HVR-L3

<400> SEQUENCE: 642

Trp Gln Gly Thr His Phe Pro Gln Thr
1               5

<210> SEQ ID NO 643
<211> LENGTH: 118
<212> TYPE: PRT
<213> ORGANISM: Artificial Sequences
<220> FEATURE:
<223> OTHER INFORMATION: 307H3E8 Heavy Chain Variable Region

<400> SEQUENCE: 643

Glu Val Lys Phe Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Gln Ile Arg Leu Lys Ser Asp Asn His Ala Thr His Tyr Ala Glu
    50                  55                  60

Ser Val Lys Gly Arg Phe Thr Ile Ser Arg Asp Asp Ser Lys Ser Thr
65                  70                  75                  80

Val Tyr Leu Gln Met Asn Asn Leu Gly Ala Glu Asp Thr Gly Ile Tyr
                85                  90                  95

Phe Cys Thr Glu Gly Gly Ala Tyr Phe Asp Tyr Trp Gly Gln Gly Thr
            100                 105                 110

Thr Leu Thr Val Ser Ser
        115

<210> SEQ ID NO 644
<211> LENGTH: 112
<212> TYPE: PRT
<213> ORGANISM: Artificial Sequences
<220> FEATURE:
<223> OTHER INFORMATION: 307H3E 8 Light Chain Variable Region

<400> SEQUENCE: 644

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Asn Leu Val His Ser
            20                  25                  30

Asn Gly Asn Thr Tyr Phe His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Val Cys Ser Gln Ser
                85                  90                  95

Thr His Val Pro Pro Thr Phe Gly Gly Gly Thr Lys Leu Glu Ile Lys
            100                 105                 110

<210> SEQ ID NO 645
<211> LENGTH: 5
<212> TYPE: PRT
<213> ORGANISM: Artificial Sequences
<220> FEATURE:
<223> OTHER INFORMATION: 307H3E8 HVR-H1

<400> SEQUENCE: 645

```
Asn Tyr Trp Met Asn
1               5

<210> SEQ ID NO 646
<211> LENGTH: 19
<212> TYPE: PRT
<213> ORGANISM: Artificial Sequences
<220> FEATURE:
<223> OTHER INFORMATION: 307H3E8 HVR-H2

<400> SEQUENCE: 646

Gln Ile Arg Leu Lys Ser Asp Asn His Ala Thr His Tyr Ala Glu Ser
1               5                   10                  15

Val Lys Gly

<210> SEQ ID NO 647
<211> LENGTH: 7
<212> TYPE: PRT
<213> ORGANISM: Artificial Sequences
<220> FEATURE:
<223> OTHER INFORMATION: 307H3E8 HVR-H3

<400> SEQUENCE: 647

Gly Gly Ala Tyr Phe Asp Tyr
1               5

<210> SEQ ID NO 648
<211> LENGTH: 16
<212> TYPE: PRT
<213> ORGANISM: Artificial Sequences
<220> FEATURE:
<223> OTHER INFORMATION: 307H3E8 HVR-L1

<400> SEQUENCE: 648

Arg Ser Ser Gln Asn Leu Val His Ser Asn Gly Asn Thr Tyr Phe His
1               5                   10                  15

<210> SEQ ID NO 649
<211> LENGTH: 7
<212> TYPE: PRT
<213> ORGANISM: Artificial Sequences
<220> FEATURE:
<223> OTHER INFORMATION: 307H3E8 HVR-L2

<400> SEQUENCE: 649

Lys Val Ser Asn Arg Phe Ser
1               5

<210> SEQ ID NO 650
<211> LENGTH: 9
<212> TYPE: PRT
<213> ORGANISM: Artificial Sequences
<220> FEATURE:
<223> OTHER INFORMATION: 307H3E8 HVR-L3

<400> SEQUENCE: 650

Ser Gln Ser Thr His Val Pro Pro Thr
1               5

<210> SEQ ID NO 651
<211> LENGTH: 117
<212> TYPE: PRT
<213> ORGANISM: Artificial Sequence
<220> FEATURE:
<223> OTHER INFORMATION: 63H3-D8 Heavy Chain Variable Region
```

<400> SEQUENCE: 651

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Ser His
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Ser Glu Leu Ser Trp Phe Ala Tyr Trp Gly Gln Gly Thr Leu
            100                 105                 110

Val Thr Val Ser Ala
            115

<210> SEQ ID NO 652
<211> LENGTH: 107
<212> TYPE: PRT
<213> ORGANISM: Artificial Sequence
<220> FEATURE:
<223> OTHER INFORMATION: 63H3-D8 Light Chain Variable Region

<400> SEQUENCE: 652

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys
            100                 105

<210> SEQ ID NO 653
<211> LENGTH: 5
<212> TYPE: PRT
<213> ORGANISM: Artificial Sequence
<220> FEATURE:
<223> OTHER INFORMATION: 63H3-D8 HVR-H1

<400> SEQUENCE: 653

Ser His Gly Met Ser
1               5

<210> SEQ ID NO 654
<211> LENGTH: 17
<212> TYPE: PRT
<213> ORGANISM: Artificial Sequence
<220> FEATURE:
<223> OTHER INFORMATION: 63H3-D8 HVR-H2

<400> SEQUENCE: 654

Trp Ile Asn Thr Tyr Ser Gly Val Pro Thr Tyr Ala Asp Asp Phe Lys
1               5                   10                  15

Gly

<210> SEQ ID NO 655
<211> LENGTH: 8
<212> TYPE: PRT
<213> ORGANISM: Artificial Sequence
<220> FEATURE:
<223> OTHER INFORMATION: 63H3-D8 HVR-H3

<400> SEQUENCE: 655

Ser Glu Leu Ser Trp Phe Ala Tyr
1               5

<210> SEQ ID NO 656
<211> LENGTH: 11
<212> TYPE: PRT
<213> ORGANISM: Artificial Sequence
<220> FEATURE:
<223> OTHER INFORMATION: 63H3-D8 HVR-L1

<400> SEQUENCE: 656

Arg Ala Ser Gln Ser Ile Ser Asp Tyr Leu His
1               5                   10

<210> SEQ ID NO 657
<211> LENGTH: 7
<212> TYPE: PRT
<213> ORGANISM: Artificial Sequence
<220> FEATURE:
<223> OTHER INFORMATION: 63H3-D8 HVR-L2

<400> SEQUENCE: 657

Tyr Ala Ser Gln Ser Ile Ser
1               5

<210> SEQ ID NO 658
<211> LENGTH: 9
<212> TYPE: PRT
<213> ORGANISM: Artificial Sequence
<220> FEATURE:
<223> OTHER INFORMATION: 63H3-D8 HVR-L3

<400> SEQUENCE: 658

Gln Asn Gly His Ser Phe Pro Tyr Thr
1               5

<210> SEQ ID NO 659
<211> LENGTH: 117
<212> TYPE: PRT
<213> ORGANISM: Artificial Sequence
<220> FEATURE:
<223> OTHER INFORMATION: 64B9-F12 Heavy Chain Variable Region (VH)

<400> SEQUENCE: 659

Gln Ile Gln Leu Val Gln Ser Gly Pro Glu Leu Arg Lys Pro Gly Glu
1               5                   10                  15

Thr Val Lys Ile Ser Cys Lys Ala Ser Gly Tyr Thr Phe Thr Thr Tyr
                20                  25                  30

Gly Met Ser Trp Val Lys Gln Ala Pro Gly Glu Gly Leu Lys Trp Met
            35                  40                  45

Gly Trp Ile Asn Thr Tyr Ser Gly Met Pro Thr Tyr Ala Asp Asp Phe
        50                  55                  60

Lys Gly Arg Phe Ala Phe Ser Leu Glu Thr Ser Ala Arg Thr Ala Tyr
65                  70                  75                  80

Leu Gln Ile Asn Asn Leu Lys Asn Glu Asp Thr Ala Thr Tyr Phe Cys
                85                  90                  95

Ala Arg Ser Glu Leu Ser Trp Phe Ala Tyr Trp Gly Gln Gly Thr Leu
            100                 105                 110

Val Thr Val Ser Ala
        115

<210> SEQ ID NO 660
<211> LENGTH: 107
<212> TYPE: PRT
<213> ORGANISM: Artificial Sequence
<220> FEATURE:
<223> OTHER INFORMATION: 64B9-F12 Light Chain Variable Region (VL)

<400> SEQUENCE: 660

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Asn Phe Pro Tyr
                85                  90                  95

Thr Phe Gly Gly Gly Thr Lys Leu Glu Ile Lys
            100                 105

<210> SEQ ID NO 661
<211> LENGTH: 5
<212> TYPE: PRT
<213> ORGANISM: Artificial Sequence
<220> FEATURE:
<223> OTHER INFORMATION: 64B9-F12 HVR-H1

<400> SEQUENCE: 661

Thr Tyr Gly Met Ser
1               5

<210> SEQ ID NO 662
<211> LENGTH: 17
<212> TYPE: PRT
<213> ORGANISM: Artificial Sequence
<220> FEATURE:
<223> OTHER INFORMATION: 64B9-F12 HVR-H2

<400> SEQUENCE: 662

Trp Ile Asn Thr Tyr Ser Gly Met Pro Thr Tyr Ala Asp Asp Phe Lys
1               5                   10                  15

Gly

<210> SEQ ID NO 663
<211> LENGTH: 8
<212> TYPE: PRT
<213> ORGANISM: Artificial Sequence
<220> FEATURE:
<223> OTHER INFORMATION: 64B9-F12 HVR-H3

```
<400> SEQUENCE: 663

Ser Glu Leu Ser Trp Phe Ala Tyr
1               5

<210> SEQ ID NO 664
<211> LENGTH: 11
<212> TYPE: PRT
<213> ORGANISM: Artificial Sequence
<220> FEATURE:
<223> OTHER INFORMATION: 64B9-F12 HVR-L1

<400> SEQUENCE: 664

Arg Ala Ser Gln Ser Ile Ser Asp Tyr Leu His
1               5                   10

<210> SEQ ID NO 665
<211> LENGTH: 7
<212> TYPE: PRT
<213> ORGANISM: Artificial Sequence
<220> FEATURE:
<223> OTHER INFORMATION: 64B9-F12 HVR-L2

<400> SEQUENCE: 665

Tyr Ala Ser Gln Ser Ile Ser
1               5

<210> SEQ ID NO 666
<211> LENGTH: 9
<212> TYPE: PRT
<213> ORGANISM: Artificial Sequence
<220> FEATURE:
<223> OTHER INFORMATION: 64B9-F12 HVR-L3

<400> SEQUENCE: 666

Gln Asn Gly His Asn Phe Pro Tyr Thr
1               5

<210> SEQ ID NO 667
<211> LENGTH: 120
<212> TYPE: PRT
<213> ORGANISM: Artificial Sequence
<220> FEATURE:
<223> OTHER INFORMATION: 72E12-H9 Heavy Chain Variable Region (VH)

<400> SEQUENCE: 667

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Ala Gly Tyr Phe Tyr Gly Gly Tyr Phe Asp Val Trp Gly Thr
                100                 105                 110

Gly Thr Thr Val Thr Val Ser Ser
            115                 120
```

<210> SEQ ID NO 668
<211> LENGTH: 108
<212> TYPE: PRT
<213> ORGANISM: Artificial Sequence
<220> FEATURE:
<223> OTHER INFORMATION: 72E12-H9 Light Chain Variable Region (VL)

<400> SEQUENCE: 668

Glu Leu Val Leu Thr Gln Ser Pro Thr Thr Met Ala Ala Ser Pro Gly
1               5                   10                  15

Lys Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Leu Pro
                85                  90                  95

Phe Thr Phe Gly Ser Gly Thr Lys Leu Glu Ile Lys
            100                 105

<210> SEQ ID NO 669
<211> LENGTH: 5
<212> TYPE: PRT
<213> ORGANISM: Artificial Sequence
<220> FEATURE:
<223> OTHER INFORMATION: 72E12-H9 HVR-H1

<400> SEQUENCE: 669

Asn Tyr Trp Met Asn
1               5

<210> SEQ ID NO 670
<211> LENGTH: 19
<212> TYPE: PRT
<213> ORGANISM: Artificial Sequence
<220> FEATURE:
<223> OTHER INFORMATION: 72E12-H9 HVR-H2

<400> SEQUENCE: 670

Gln Ile Arg Leu Lys Ser Asp Asn Tyr Ala Thr His Tyr Ala Glu Ser
1               5                   10                  15

Val Lys Gly

<210> SEQ ID NO 671
<211> LENGTH: 9
<212> TYPE: PRT
<213> ORGANISM: Artificial Sequence
<220> FEATURE:
<223> OTHER INFORMATION: 72E12-H9 HVR-H3

<400> SEQUENCE: 671

Tyr Phe Tyr Gly Gly Tyr Phe Asp Val
1               5

<210> SEQ ID NO 672
<211> LENGTH: 12
<212> TYPE: PRT
<213> ORGANISM: Artificial Sequence
<220> FEATURE:
<223> OTHER INFORMATION: 72E12-H9 HVR-L1

```
<400> SEQUENCE: 672

Ser Ala Ser Ser Ser Ile Ser Ser Asn Tyr Leu His
1               5                   10

<210> SEQ ID NO 673
<211> LENGTH: 7
<212> TYPE: PRT
<213> ORGANISM: Artificial Sequence
<220> FEATURE:
<223> OTHER INFORMATION: 72E12-H9 HVR-L2

<400> SEQUENCE: 673

Arg Thr Ser Asn Leu Ala Ser
1               5

<210> SEQ ID NO 674
<211> LENGTH: 9
<212> TYPE: PRT
<213> ORGANISM: Artificial Sequence
<220> FEATURE:
<223> OTHER INFORMATION: 72E12-H9 HVR-L3

<400> SEQUENCE: 674

Gln Gln Gly Ser Ser Leu Pro Phe Thr
1               5

<210> SEQ ID NO 675
<211> LENGTH: 114
<212> TYPE: PRT
<213> ORGANISM: Artificial Sequence
<220> FEATURE:
<223> OTHER INFORMATION: 30D12-B5 Heavy Chain Variable Region (VH)

<400> SEQUENCE: 675

Glu Val Gln Leu Gln Gln Ser Gly Ala Glu Leu Val Lys Pro Gly Ala
1               5                   10                  15

Ser Val Lys Leu Ser Cys Thr Thr Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Gly Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala His Gly Asn Phe Val Tyr Trp Gly Gln Gly Thr Leu Val Thr Val
            100                 105                 110

Ser Ala

<210> SEQ ID NO 676
<211> LENGTH: 112
<212> TYPE: PRT
<213> ORGANISM: Artificial Sequence
<220> FEATURE:
<223> OTHER INFORMATION: 30D12-B5 Light Chain Variable Region (VL)

<400> SEQUENCE: 676

Asp Val Val Met Thr Gln Thr Pro Leu Ser Leu Ser Val Thr Ile Gly
1               5                   10                  15

Gln Pro Ala Ser Ile Ser Cys Lys Ser Ser Gln Ser Leu Leu Tyr Ser
```

```
                    20                  25                  30

Asn Gly Lys Thr Tyr Leu Asn Trp Phe Gln Gln Arg Pro Gly Gln Ala
                35                  40                  45

Pro Lys His Leu Met Tyr Gln Val Ser Lys Leu Asp Pro Gly Ile Pro
        50                  55                  60

Asp Arg Phe Ser Gly Ser Gly Ser Glu Thr Asp Phe Thr Leu Lys Ile
65                  70                  75                  80

Ser Arg Val Glu Ala Glu Asp Leu Gly Val Tyr Tyr Cys Leu Gln Gly
                85                  90                  95

Thr Tyr Tyr Pro Leu Thr Phe Gly Ala Gly Thr Asn Leu Glu Leu Lys
            100                 105                 110
```

<210> SEQ ID NO 677
<211> LENGTH: 5
<212> TYPE: PRT
<213> ORGANISM: Artificial Sequence
<220> FEATURE:
<223> OTHER INFORMATION: 30D12-B5 HVR-H1

<400> SEQUENCE: 677

```
Asp Thr Tyr Met His
1               5
```

<210> SEQ ID NO 678
<211> LENGTH: 17
<212> TYPE: PRT
<213> ORGANISM: Artificial Sequence
<220> FEATURE:
<223> OTHER INFORMATION: 30D12-B5 HVR-H2

<400> SEQUENCE: 678

```
Gly Ile Asp Pro Ala Asn Gly Asn Thr Lys Tyr Asp Pro Lys Phe Gln
1               5                   10                  15

Gly
```

<210> SEQ ID NO 679
<211> LENGTH: 5
<212> TYPE: PRT
<213> ORGANISM: Artificial Sequence
<220> FEATURE:
<223> OTHER INFORMATION: 30D12-B5 HVR-H3

<400> SEQUENCE: 679

```
Gly Asn Phe Val Tyr
1               5
```

<210> SEQ ID NO 680
<211> LENGTH: 16
<212> TYPE: PRT
<213> ORGANISM: Artificial Sequence
<220> FEATURE:
<223> OTHER INFORMATION: 30D12-B5 HVR-L1

<400> SEQUENCE: 680

```
Lys Ser Ser Gln Ser Leu Leu Tyr Ser Asn Gly Lys Thr Tyr Leu Asn
1               5                   10                  15
```

<210> SEQ ID NO 681
<211> LENGTH: 7
<212> TYPE: PRT
<213> ORGANISM: Artificial Sequence
<220> FEATURE:
<223> OTHER INFORMATION: 30D12-B5 HVR-L2

<400> SEQUENCE: 681

Gln Val Ser Lys Leu Asp Pro
1               5

<210> SEQ ID NO 682
<211> LENGTH: 9
<212> TYPE: PRT
<213> ORGANISM: Artificial Sequence
<220> FEATURE:
<223> OTHER INFORMATION: 30D12-B5 HVR-L3

<400> SEQUENCE: 682

Leu Gln Gly Thr Tyr Tyr Pro Leu Thr
1               5

<210> SEQ ID NO 683
<211> LENGTH: 121
<212> TYPE: PRT
<213> ORGANISM: Artificial Sequence
<220> FEATURE:
<223> OTHER INFORMATION: 49G10-F4 Heavy Chain Variable Region (VH)

<400> SEQUENCE: 683

Gln Val Gln Leu Gln Gln Pro Gly Ala Glu Leu Val Gln Pro Gly Ala
1               5                   10                  15

Ser Val Lys Leu Ser Cys Lys Ala Ser Gly Tyr Thr Phe Thr Asn Tyr
            20                  25                  30

Trp Met Gln Trp Ile Lys Gln Arg Pro Gly Gln Gly Leu Glu Trp Ile
        35                  40                  45

Gly Glu Ile Asp Pro Ser Asp Ser Tyr Thr Asn Tyr Asn Gln Asn Phe
    50                  55                  60

Lys Asp Lys Ala Thr Leu Thr Val Asp Thr Ser Ser Arg Thr Ala Tyr
65                  70                  75                  80

Met Gln Leu Ser Ser Leu Thr Ser Glu Asp Ser Ala Val Tyr Tyr Cys
                85                  90                  95

Thr Arg Arg Trp Tyr Ile Asn Ser Val Arg Tyr Phe Asp Val Trp Gly
            100                 105                 110

Thr Gly Thr Thr Val Thr Val Ser Ala
        115                 120

<210> SEQ ID NO 684
<211> LENGTH: 112
<212> TYPE: PRT
<213> ORGANISM: Artificial Sequence
<220> FEATURE:
<223> OTHER INFORMATION: 49G10-F4 Light Chain Variable Region (VL)

<400> SEQUENCE: 684

Asp Val Leu Met Thr Gln Thr Pro Leu Ser Leu Ser Ala Ser Leu Gly
1               5                   10                  15

Asp Gln Ala Ser Ile Ser Cys Arg Ser Ser Gln Ser Ile Val His Ser
            20                  25                  30

Asn Gly Asn Ile Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Ser
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ala His Val Pro Phe Thr Phe Gly Ala Gly Thr Lys Leu Glu Ile Lys
            100                 105                 110

<210> SEQ ID NO 685
<211> LENGTH: 5
<212> TYPE: PRT
<213> ORGANISM: Artificial Sequence
<220> FEATURE:
<223> OTHER INFORMATION: 49G10-F4 HVR-H1

<400> SEQUENCE: 685

Asn Tyr Trp Met Gln
1               5

<210> SEQ ID NO 686
<211> LENGTH: 17
<212> TYPE: PRT
<213> ORGANISM: Artificial Sequence
<220> FEATURE:
<223> OTHER INFORMATION: 49G10-F4 HVR-H2

<400> SEQUENCE: 686

Glu Ile Asp Pro Ser Asp Ser Tyr Thr Asn Tyr Asn Gln Asn Phe Lys
1               5                   10                  15

Asp

<210> SEQ ID NO 687
<211> LENGTH: 12
<212> TYPE: PRT
<213> ORGANISM: Artificial Sequence
<220> FEATURE:
<223> OTHER INFORMATION: 49G10-F4 HVR-H3

<400> SEQUENCE: 687

Arg Trp Tyr Ile Asn Ser Val Arg Tyr Phe Asp Val
1               5                   10

<210> SEQ ID NO 688
<211> LENGTH: 16
<212> TYPE: PRT
<213> ORGANISM: Artificial Sequence
<220> FEATURE:
<223> OTHER INFORMATION: 49G10-F4 HVR-L1

<400> SEQUENCE: 688

Arg Ser Ser Gln Ser Ile Val His Ser Asn Gly Asn Ile Tyr Leu Glu
1               5                   10                  15

<210> SEQ ID NO 689
<211> LENGTH: 7
<212> TYPE: PRT
<213> ORGANISM: Artificial Sequence
<220> FEATURE:
<223> OTHER INFORMATION: 49G10-F4 HVR-L2

<400> SEQUENCE: 689

Lys Val Ser Asn Arg Phe Ser
1               5

<210> SEQ ID NO 690
<211> LENGTH: 9
<212> TYPE: PRT
<213> ORGANISM: Artificial Sequence
<220> FEATURE:
<223> OTHER INFORMATION: 49G10-F4 HVR-L3

-continued

<400> SEQUENCE: 690

Phe Gln Gly Ala His Val Pro Phe Thr
1               5

<210> SEQ ID NO 691
<211> LENGTH: 122
<212> TYPE: PRT
<213> ORGANISM: Artificial Sequence
<220> FEATURE:
<223> OTHER INFORMATION: 65B1-A2 Heavy Chain Variable Region (VH)

<400> SEQUENCE: 691

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Thr Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Thr Thr Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Gln Gly Gly Phe Ile Thr Thr Ala Tyr Tyr Ala Met Asp Tyr Trp
            100                 105                 110

Gly Gln Gly Thr Ser Val Thr Val Ser Ser
        115                 120

<210> SEQ ID NO 692
<211> LENGTH: 112
<212> TYPE: PRT
<213> ORGANISM: Artificial Sequence
<220> FEATURE:
<223> OTHER INFORMATION: 65B1-A2 Light Chain Variable Region (VL)

<400> SEQUENCE: 692

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

<210> SEQ ID NO 693
<211> LENGTH: 5
<212> TYPE: PRT
<213> ORGANISM: Artificial Sequence
<220> FEATURE:
<223> OTHER INFORMATION: 65B1-A2 HVR-H1

<400> SEQUENCE: 693

Thr Tyr Gly Val His
1               5

<210> SEQ ID NO 694
<211> LENGTH: 16
<212> TYPE: PRT
<213> ORGANISM: Artificial Sequence
<220> FEATURE:
<223> OTHER INFORMATION: 65B1-A2 HVR-H2

<400> SEQUENCE: 694

Val Ile Trp Ser Asp Gly Ser Thr Thr Tyr Asn Ser Ala Leu Lys Ser
1               5                   10                  15

<210> SEQ ID NO 695
<211> LENGTH: 14
<212> TYPE: PRT
<213> ORGANISM: Artificial Sequence
<220> FEATURE:
<223> OTHER INFORMATION: 65B1-A2 HVR-H3

<400> SEQUENCE: 695

Gln Gly Gly Phe Ile Thr Thr Ala Tyr Tyr Ala Met Asp Tyr
1               5                   10

<210> SEQ ID NO 696
<211> LENGTH: 17
<212> TYPE: PRT
<213> ORGANISM: Artificial Sequence
<220> FEATURE:
<223> OTHER INFORMATION: 65B1-A2 HVR-L1

<400> SEQUENCE: 696

Lys Ser Ser Gln Ser Leu Leu Asn Ser Arg Thr Arg Lys Asn Tyr Leu
1               5                   10                  15

Ala

<210> SEQ ID NO 697
<211> LENGTH: 7
<212> TYPE: PRT
<213> ORGANISM: Artificial Sequence
<220> FEATURE:
<223> OTHER INFORMATION: 65B1-A2 HVR-L2

<400> SEQUENCE: 697

Trp Ala Ser Thr Arg Glu Ser
1               5

<210> SEQ ID NO 698
<211> LENGTH: 8
<212> TYPE: PRT
<213> ORGANISM: Artificial Sequence
<220> FEATURE:
<223> OTHER INFORMATION: 65B1-A2 HVR-L3

<400> SEQUENCE: 698

Lys Gln Ser Tyr Asn Leu Tyr Thr
1               5

ANTI-TAU ANTIBODIES AND METHODS OF USE

CROSS-REFERENCE TO RELATED APPLICATIONS

This application is a continuation of International Application No. PCT/US2017/064855, filed Dec. 6, 2017, which claims the benefit of priority of U.S. Provisional Application No. 62/431,183, filed Dec. 7, 2016, which is incorporated by reference herein in its entirety for any purpose.

FIELD OF THE INVENTION

The present invention relates to anti-Tau antibodies and methods of using the same.

BACKGROUND

Neurofibrillary tangles and neuropil threads (NTs) are the major neuropathological hallmarks of Alzheimer's Disease (AD). NTs are composed of the microtubule-associated Tau protein that has undergone post-translational modifications including phosphorylation, and develop by aggregation of hyperphosphorylated Tau conformers. AD shares this pathology with many neurodegenerative tauopathies, in particularly with certain types of frontotemporal dementia (FTD). Tau protein appears to be a major player in the cognitive demise in AD and related neurodegenerative tauopathies.

Therapeutic approaches that target Tau protein are scarce and comprise mainly inhibitors of the kinases that are thought to increase the phosphorylation of Tau to pathological levels, and compounds that block the cytoplasmic aggregation of hyper-phosphorylated Tau protein. These approaches suffer various draw-backs of specificity and efficacy. There is a need for additional therapeutic agents that target the pathological protein conformers that are known or presumed to cause neurodegenerative disorders.

SUMMARY

The invention provides anti-Tau antibodies and methods of using the same.

In some embodiments, an isolated antibody that binds to human Tau is provided, wherein the antibody binds to monomeric Tau, oligomeric Tau, non-phosphorylated Tau, and phosphorylated Tau. In some embodiments, the antibody binds an epitope within amino acids 2 to 24 of mature human Tau. In some embodiments, the antibody is a monoclonal antibody. In some embodiments, the antibody is a human, humanized, or chimeric antibody. In some embodiments, the antibody is an antibody fragment that binds human Tau. In some embodiments, the human Tau comprises the sequence of SEQ ID NO: 2.

In some embodiments, the antibody comprises:
a) HVR-H1 comprising the amino acid sequence of SEQ ID NO: 605; HVR-H2 comprising the amino acid sequence of SEQ ID NO: 606; and HVR-H3 comprising the amino acid sequence of SEQ ID NO: 607; or
b) HVR-H1 comprising the amino acid sequence of SEQ ID NO: 613; HVR-H2 comprising the amino acid sequence of SEQ ID NO: 614; and HVR-H3 comprising the amino acid sequence of SEQ ID NO: 615;
c) HVR-H1 comprising the amino acid sequence of SEQ ID NO: 621; HVR-H2 comprising the amino acid sequence of SEQ ID NO: 622; and HVR-H3 comprising the amino acid sequence of SEQ ID NO: 623;
d) HVR-H1 comprising the amino acid sequence of SEQ ID NO: 629; HVR-H2 comprising the amino acid sequence of SEQ ID NO: 630; and HVR-H3 comprising the amino acid sequence of SEQ ID NO: 631;
e) HVR-H1 comprising the amino acid sequence of SEQ ID NO: 637; HVR-H2 comprising the amino acid sequence of SEQ ID NO: 638; and HVR-H3 comprising the amino acid sequence of SEQ ID NO: 639;
f) HVR-H1 comprising the amino acid sequence of SEQ ID NO: 645; HVR-H2 comprising the amino acid sequence of SEQ ID NO: 646; and HVR-H3 comprising the amino acid sequence of SEQ ID NO: 647;
g) HVR-H1 comprising the amino acid sequence of SEQ ID NO: 653; HVR-H2 comprising the amino acid sequence of SEQ ID NO: 654; and HVR-H3 comprising the amino acid sequence of SEQ ID NO: 655;
h) HVR-H1 comprising the amino acid sequence of SEQ ID NO: 661; HVR-H2 comprising the amino acid sequence of SEQ ID NO: 662; and HVR-H3 comprising the amino acid sequence of SEQ ID NO: 663;
i) HVR-H1 comprising the amino acid sequence of SEQ ID NO: 669; HVR-H2 comprising the amino acid sequence of SEQ ID NO: 670; and HVR-H3 comprising the amino acid sequence of SEQ ID NO: 671;
j) HVR-H1 comprising the amino acid sequence of SEQ ID NO: 677; HVR-H2 comprising the amino acid sequence of SEQ ID NO: 678; and HVR-H3 comprising the amino acid sequence of SEQ ID NO: 679;
k) HVR-H1 comprising the amino acid sequence of SEQ ID NO: 685; HVR-H2 comprising the amino acid sequence of SEQ ID NO: 686; and HVR-H3 comprising the amino acid sequence of SEQ ID NO: 687; or
l) HVR-H1 comprising the amino acid sequence of SEQ ID NO: 693; HVR-H2 comprising the amino acid sequence of SEQ ID NO: 694; and HVR-H3 comprising the amino acid sequence of SEQ ID NO: 695.

In some embodiments, the antibody comprises:
a) HVR-L1 comprising the amino acid sequence of SEQ ID NO: 608; HVR-L2 comprising the amino acid sequence of SEQ ID NO: 609; and HVR-L3 comprising the amino acid sequence of SEQ ID NO: 610;
b) HVR-L1 comprising the amino acid sequence of SEQ ID NO: 616; HVR-L2 comprising the amino acid sequence of SEQ ID NO: 617; and HVR-L3 comprising the amino acid sequence of SEQ ID NO: 618;
c) HVR-L1 comprising the amino acid sequence of SEQ ID NO: 624; HVR-L2 comprising the amino acid sequence of SEQ ID NO: 625; and HVR-L3 comprising the amino acid sequence of SEQ ID NO: 626;
d) HVR-L1 comprising the amino acid sequence of SEQ ID NO: 632; HVR-L2 comprising the amino acid sequence of SEQ ID NO: 633; and HVR-L3 comprising the amino acid sequence of SEQ ID NO: 634;
e) HVR-L1 comprising the amino acid sequence of SEQ ID NO: 640; HVR-L2 comprising the amino acid sequence of SEQ ID NO: 641; and HVR-L3 comprising the amino acid sequence of SEQ ID NO: 642;
f) HVR-L1 comprising the amino acid sequence of SEQ ID NO: 648; HVR-L2 comprising the amino acid sequence of SEQ ID NO: 649; and HVR-L3 comprising the amino acid sequence of SEQ ID NO: 650 g) HVR-L1 comprising the amino acid sequence of SEQ ID NO: 656; HVR-L2 comprising the amino acid sequence of SEQ ID NO: 657; and HVR-L3 comprising the amino acid sequence of SEQ ID NO: 658;

h) HVR-L1 comprising the amino acid sequence of SEQ ID NO: 664; HVR-L2 comprising the amino acid sequence of SEQ ID NO: 665; and HVR-L3 comprising the amino acid sequence of SEQ ID NO: 666;
i) HVR-L1 comprising the amino acid sequence of SEQ ID NO: 672; HVR-L2 comprising the amino acid sequence of SEQ ID NO: 673; and HVR-L3 comprising the amino acid sequence of SEQ ID NO: 674;
j) HVR-L1 comprising the amino acid sequence of SEQ ID NO: 680; HVR-L2 comprising the amino acid sequence of SEQ ID NO: 681; and HVR-L3 comprising the amino acid sequence of SEQ ID NO: 682;
k) HVR-L1 comprising the amino acid sequence of SEQ ID NO: 688; HVR-L2 comprising the amino acid sequence of SEQ ID NO: 689; and HVR-L3 comprising the amino acid sequence of SEQ ID NO: 690; or
l) HVR-L1 comprising the amino acid sequence of SEQ ID NO: 696; HVR-L2 comprising the amino acid sequence of SEQ ID NO: 697; and HVR-L3 comprising the amino acid sequence of SEQ ID NO: 698.

In some embodiments, the antibody comprises:
a) HVR-H1 comprising the amino acid sequence of SEQ ID NO: 605; HVR-H2 comprising the amino acid sequence of SEQ ID NO: 606; HVR-H3 comprising the amino acid sequence of SEQ ID NO: 607; HVR-L1 comprising the amino acid sequence of SEQ ID NO: 608; HVR-L2 comprising the amino acid sequence of SEQ ID NO: 609; and HVR-L3 comprising the amino acid sequence of SEQ ID NO: 610;
b) HVR-H1 comprising the amino acid sequence of SEQ ID NO: 613; HVR-H2 comprising the amino acid sequence of SEQ ID NO: 614; HVR-H3 comprising the amino acid sequence of SEQ ID NO: 615; HVR-L1 comprising the amino acid sequence of SEQ ID NO: 616; HVR-L2 comprising the amino acid sequence of SEQ ID NO: 617; and HVR-L3 comprising the amino acid sequence of SEQ ID NO: 618;
c) HVR-H1 comprising the amino acid sequence of SEQ ID NO: 621; HVR-H2 comprising the amino acid sequence of SEQ ID NO: 622; HVR-H3 comprising the amino acid sequence of SEQ ID NO: 623; HVR-L1 comprising the amino acid sequence of SEQ ID NO: 624; HVR-L2 comprising the amino acid sequence of SEQ ID NO: 625; and HVR-L3 comprising the amino acid sequence of SEQ ID NO: 626;
d) HVR-H1 comprising the amino acid sequence of SEQ ID NO: 629; HVR-H2 comprising the amino acid sequence of SEQ ID NO: 630; HVR-H3 comprising the amino acid sequence of SEQ ID NO: 631; HVR-L1 comprising the amino acid sequence of SEQ ID NO: 632; HVR-L2 comprising the amino acid sequence of SEQ ID NO: 633; and HVR-L3 comprising the amino acid sequence of SEQ ID NO: 634;
e) HVR-H1 comprising the amino acid sequence of SEQ ID NO: 637; HVR-H2 comprising the amino acid sequence of SEQ ID NO: 638; HVR-H3 comprising the amino acid sequence of SEQ ID NO: 639; HVR-L1 comprising the amino acid sequence of SEQ ID NO: 640; HVR-L2 comprising the amino acid sequence of SEQ ID NO: 641; and HVR-L3 comprising the amino acid sequence of SEQ ID NO: 642; or
f) HVR-H1 comprising the amino acid sequence of SEQ ID NO: 645; HVR-H2 comprising the amino acid sequence of SEQ ID NO: 646; HVR-H3 comprising the amino acid sequence of SEQ ID NO: 647; HVR-L1 comprising the amino acid sequence of SEQ ID NO: 648; HVR-L2 comprising the amino acid sequence of SEQ ID NO: 649; and HVR-L3 comprising the amino acid sequence of SEQ ID NO: 650
g) HVR-H1 comprising the amino acid sequence of SEQ ID NO: 653; HVR-H2 comprising the amino acid sequence of SEQ ID NO: 654; HVR-H3 comprising the amino acid sequence of SEQ ID NO: 655; HVR-L1 comprising the amino acid sequence of SEQ ID NO: 656; HVR-L2 comprising the amino acid sequence of SEQ ID NO: 657; and HVR-L3 comprising the amino acid sequence of SEQ ID NO: 658;
h) HVR-H1 comprising the amino acid sequence of SEQ ID NO: 661; HVR-H2 comprising the amino acid sequence of SEQ ID NO: 662; HVR-H3 comprising the amino acid sequence of SEQ ID NO: 663; HVR-L1 comprising the amino acid sequence of SEQ ID NO: 664; HVR-L2 comprising the amino acid sequence of SEQ ID NO: 665; and HVR-L3 comprising the amino acid sequence of SEQ ID NO: 666;
i) HVR-H1 comprising the amino acid sequence of SEQ ID NO: 669; HVR-H2 comprising the amino acid sequence of SEQ ID NO: 670; HVR-H3 comprising the amino acid sequence of SEQ ID NO: 671; HVR-L1 comprising the amino acid sequence of SEQ ID NO: 672; HVR-L2 comprising the amino acid sequence of SEQ ID NO: 673; and HVR-L3 comprising the amino acid sequence of SEQ ID NO: 674;
j) HVR-H1 comprising the amino acid sequence of SEQ ID NO: 677; HVR-H2 comprising the amino acid sequence of SEQ ID NO: 678; HVR-H3 comprising the amino acid sequence of SEQ ID NO: 679; HVR-L1 comprising the amino acid sequence of SEQ ID NO: 680; HVR-L2 comprising the amino acid sequence of SEQ ID NO: 681; and HVR-L3 comprising the amino acid sequence of SEQ ID NO: 682;
k) HVR-H1 comprising the amino acid sequence of SEQ ID NO: 685; HVR-H2 comprising the amino acid sequence of SEQ ID NO: 686; HVR-H3 comprising the amino acid sequence of SEQ ID NO: 687; HVR-L1 comprising the amino acid sequence of SEQ ID NO: 688; HVR-L2 comprising the amino acid sequence of SEQ ID NO: 689; and HVR-L3 comprising the amino acid sequence of SEQ ID NO: 690; or
l) HVR-H1 comprising the amino acid sequence of SEQ ID NO: 693; HVR-H2 comprising the amino acid sequence of SEQ ID NO: 694; HVR-H3 comprising the amino acid sequence of SEQ ID NO: 695; HVR-L1 comprising the amino acid sequence of SEQ ID NO: 696; HVR-L2 comprising the amino acid sequence of SEQ ID NO: 697; and HVR-L3 comprising the amino acid sequence of SEQ ID NO: 698.

In some embodiments, the antibody comprises:
a) a heavy chain variable region (VH) comprising a sequence that is at least 95% identical to SEQ ID NO: 603;
b) a light chain variable region (VL) comprising a sequence that is at least 95% identical to SEQ ID NO: 604;
c) a VH as in (a) and a VL as in (b);
d) a heavy chain variable region (VH) comprising a sequence that is at least 95% identical to SEQ ID NO: 611;
e) a light chain variable region (VL) comprising a sequence that is at least 95% identical to SEQ ID NO: 612;
f) a VH as in (d) and a VL as in (e);

g) a heavy chain variable region (VH) comprising a sequence that is at least 95% identical to SEQ ID NO: 619;
h) a light chain variable region (VL) comprising a sequence that is at least 95% identical to SEQ ID NO: 620;
i) a VH as in (g) and a VL as in (h);
j) a heavy chain variable region (VH) comprising a sequence that is at least 95% identical to SEQ ID NO: 627;
k) a light chain variable region (VL) comprising a sequence that is at least 95% identical to SEQ ID NO: 628;
l) a VH as in (j) and a VL as in (k);
m) a heavy chain variable region (VH) comprising a sequence that is at least 95% identical to SEQ ID NO: 635;
n) a light chain variable region (VL) comprising a sequence that is at least 95% identical to SEQ ID NO: 636;
o) a VH as in (m) and a VL as in (n);
p) a heavy chain variable region (VH) comprising a sequence that is at least 95% identical to SEQ ID NO: 643;
q) a light chain variable region (VL) comprising a sequence that is at least 95% identical to SEQ ID NO: 644;
r) a VH as in (p) and a VL as in (q) s) a heavy chain variable region (VH) comprising a sequence that is at least 95% identical to SEQ ID NO: 651;
t) a light chain variable region (VL) comprising a sequence that is at least 95% identical to SEQ ID NO: 652;
u) a VH as in (s) and a VL as in (t);
v) a heavy chain variable region (VH) comprising a sequence that is at least 95% identical to SEQ ID NO: 659;
w) a light chain variable region (VL) comprising a sequence that is at least 95% identical to SEQ ID NO: 660;
x) a VH as in (v) and a VL as in (w);
y) a heavy chain variable region (VH) comprising a sequence that is at least 95% identical to SEQ ID NO: 667;
z) a light chain variable region (VL) comprising a sequence that is at least 95% identical to SEQ ID NO: 668;
aa) a VH as in (y) and a VL as in (z);
bb) a heavy chain variable region (VH) comprising a sequence that is at least 95% identical to SEQ ID NO: 675;
cc) a light chain variable region (VL) comprising a sequence that is at least 95% identical to SEQ ID NO: 676;
dd) a VH as in (bb) and a VL as in (cc);
ee) a heavy chain variable region (VH) comprising a sequence that is at least 95% identical to SEQ ID NO: 683;
ff) a light chain variable region (VL) comprising a sequence that is at least 95% identical to SEQ ID NO: 684;
gg) a VH as in (ee) and a VL as in (ff); or
hh) a heavy chain variable region (VH) comprising a sequence that is at least 95% identical to SEQ ID NO: 691;
ii) a light chain variable region (VL) comprising a sequence that is at least 95% identical to SEQ ID NO: 692;
jj) a VH as in (hh) and a VL as in (ii).

In some embodiments, the antibody comprises:
a) a heavy chain variable region (VH) comprising the sequence of SEQ ID NO: 603;
b) a light chain variable region (VL) comprising the sequence of SEQ ID NO: 604;
c) a VH as in (a) and a VL as in (b);
d) a heavy chain variable region (VH) comprising the sequence of SEQ ID NO: 611;
e) a light chain variable region (VL) comprising the sequence of SEQ ID NO: 612;
f) a VH as in (d) and a VL as in (e);
g) a heavy chain variable region (VH) comprising the sequence of SEQ ID NO: 619;
h) a light chain variable region (VL) comprising the sequence of SEQ ID NO: 620;
i) a VH as in (g) and a VL as in (h);
j) a heavy chain variable region (VH) comprising the sequence of SEQ ID NO: 627;
k) a light chain variable region (VL) comprising the sequence of SEQ ID NO: 628; 1) a VH as in (j) and a VL as in (k);
m) a heavy chain variable region (VH) comprising the sequence of SEQ ID NO: 635;
n) a light chain variable region (VL) comprising the sequence of SEQ ID NO: 636;
o) a VH as in (m) and a VL as in (n);
p) a heavy chain variable region (VH) comprising the sequence of SEQ ID NO: 643;
q) a light chain variable region (VL) comprising the sequence of SEQ ID NO: 644;
r) a VH as in (p) and a VL as in (q) s) a heavy chain variable region (VH) comprising the sequence of SEQ ID NO: 651;
t) a light chain variable region (VL) comprising the sequence of SEQ ID NO: 652;
u) a VH as in (s) and a VL as in (t);
v) a heavy chain variable region (VH) comprising the sequence of SEQ ID NO: 659;
w) a light chain variable region (VL) comprising the sequence of SEQ ID NO: 660;
x) a VH as in (v) and a VL as in (w);
y) a heavy chain variable region (VH) comprising the sequence of SEQ ID NO: 667;
z) a light chain variable region (VL) comprising the sequence of SEQ ID NO: 668;
aa) a VH as in (y) and a VL as in (z);
bb) a heavy chain variable region (VH) comprising the sequence of SEQ ID NO: 675;
cc) a light chain variable region (VL) comprising the sequence of SEQ ID NO: 676;
dd) a VH as in (bb) and a VL as in (cc);
ee) a heavy chain variable region (VH) comprising the sequence of SEQ ID NO: 683;
ff) a light chain variable region (VL) comprising the sequence of SEQ ID NO: 684;
gg) a VH as in (ee) and a VL as in (ff); or
hh) a heavy chain variable region (VH) comprising the sequence of SEQ ID NO: 691;
ii) a light chain variable region (VL) comprising the sequence of SEQ ID NO: 692;
jj) a VH as in (hh) and a VL as in (ii).

In some embodiments, the antibody comprises HVR-H1 comprising the amino acid sequence of SEQ ID NO: 605;

HVR-H2 comprising the amino acid sequence of SEQ ID NO: 606; HVR-H3 comprising the amino acid sequence of SEQ ID NO: 607; HVR-L1 comprising the amino acid sequence of SEQ ID NO: 608; HVR-L2 comprising the amino acid sequence of SEQ ID NO: 609; and HVR-L3 comprising the amino acid sequence of SEQ ID NO: 610.

In some embodiments, the antibody comprises HVR-H1 comprising the amino acid sequence of SEQ ID NO: 613; HVR-H2 comprising the amino acid sequence of SEQ ID NO: 614; HVR-H3 comprising the amino acid sequence of SEQ ID NO: 615; HVR-L1 comprising the amino acid sequence of SEQ ID NO: 616; HVR-L2 comprising the amino acid sequence of SEQ ID NO: 617; and HVR-L3 comprising the amino acid sequence of SEQ ID NO: 618.

In some embodiments, the antibody comprises HVR-H1 comprising the amino acid sequence of SEQ ID NO: 621; HVR-H2 comprising the amino acid sequence of SEQ ID NO: 622; HVR-H3 comprising the amino acid sequence of SEQ ID NO: 623; HVR-L1 comprising the amino acid sequence of SEQ ID NO: 624; HVR-L2 comprising the amino acid sequence of SEQ ID NO: 625; and HVR-L3 comprising the amino acid sequence of SEQ ID NO: 626.

In some embodiments, the antibody comprises HVR-H1 comprising the amino acid sequence of SEQ ID NO: 629; HVR-H2 comprising the amino acid sequence of SEQ ID NO: 630; HVR-H3 comprising the amino acid sequence of SEQ ID NO: 631; HVR-L1 comprising the amino acid sequence of SEQ ID NO: 632; HVR-L2 comprising the amino acid sequence of SEQ ID NO: 633; and HVR-L3 comprising the amino acid sequence of SEQ ID NO: 634.

In some embodiments, the antibody comprises HVR-H1 comprising the amino acid sequence of SEQ ID NO: 637; HVR-H2 comprising the amino acid sequence of SEQ ID NO: 638; HVR-H3 comprising the amino acid sequence of SEQ ID NO: 639; HVR-L1 comprising the amino acid sequence of SEQ ID NO: 640; HVR-L2 comprising the amino acid sequence of SEQ ID NO: 641; and HVR-L3 comprising the amino acid sequence of SEQ ID NO: 642.

In some embodiments, the antibody comprises HVR-H1 comprising the amino acid sequence of SEQ ID NO: 645; HVR-H2 comprising the amino acid sequence of SEQ ID NO: 646; HVR-H3 comprising the amino acid sequence of SEQ ID NO: 647; HVR-L1 comprising the amino acid sequence of SEQ ID NO: 648; HVR-L2 comprising the amino acid sequence of SEQ ID NO: 649; and HVR-L3 comprising the amino acid sequence of SEQ ID NO: 650.

In some embodiments, the antibody comprises HVR-H1 comprising the amino acid sequence of SEQ ID NO: 653; HVR-H2 comprising the amino acid sequence of SEQ ID NO: 654; HVR-H3 comprising the amino acid sequence of SEQ ID NO: 655; HVR-L1 comprising the amino acid sequence of SEQ ID NO: 656; HVR-L2 comprising the amino acid sequence of SEQ ID NO: 657; and HVR-L3 comprising the amino acid sequence of SEQ ID NO: 658.

In some embodiments, the antibody comprises HVR-H1 comprising the amino acid sequence of SEQ ID NO: 661; HVR-H2 comprising the amino acid sequence of SEQ ID NO: 662; HVR-H3 comprising the amino acid sequence of SEQ ID NO: 663; HVR-L1 comprising the amino acid sequence of SEQ ID NO: 664; HVR-L2 comprising the amino acid sequence of SEQ ID NO: 665; and HVR-L3 comprising the amino acid sequence of SEQ ID NO: 666.

In some embodiments, the antibody comprises HVR-H1 comprising the amino acid sequence of SEQ ID NO: 669; HVR-H2 comprising the amino acid sequence of SEQ ID NO: 670; HVR-H3 comprising the amino acid sequence of SEQ ID NO: 671; HVR-L1 comprising the amino acid sequence of SEQ ID NO: 672; HVR-L2 comprising the amino acid sequence of SEQ ID NO: 673; and HVR-L3 comprising the amino acid sequence of SEQ ID NO: 674.

In some embodiments, the antibody comprises HVR-H1 comprising the amino acid sequence of SEQ ID NO: 677; HVR-H2 comprising the amino acid sequence of SEQ ID NO: 678; HVR-H3 comprising the amino acid sequence of SEQ ID NO: 679; HVR-L1 comprising the amino acid sequence of SEQ ID NO: 680; HVR-L2 comprising the amino acid sequence of SEQ ID NO: 681; and HVR-L3 comprising the amino acid sequence of SEQ ID NO: 682.

In some embodiments, the antibody comprises HVR-H1 comprising the amino acid sequence of SEQ ID NO: 685; HVR-H2 comprising the amino acid sequence of SEQ ID NO: 686; HVR-H3 comprising the amino acid sequence of SEQ ID NO: 687; HVR-L1 comprising the amino acid sequence of SEQ ID NO: 688; HVR-L2 comprising the amino acid sequence of SEQ ID NO: 689; and HVR-L3 comprising the amino acid sequence of SEQ ID NO: 690.

In some embodiments, the antibody comprises HVR-H1 comprising the amino acid sequence of SEQ ID NO: 693; HVR-H2 comprising the amino acid sequence of SEQ ID NO: 694; HVR-H3 comprising the amino acid sequence of SEQ ID NO: 695; HVR-L1 comprising the amino acid sequence of SEQ ID NO: 696; HVR-L2 comprising the amino acid sequence of SEQ ID NO: 697; and HVR-L3 comprising the amino acid sequence of SEQ ID NO: 698.

In some embodiments, the antibody comprises a heavy chain variable region comprising the amino acid sequence of SEQ ID NO: 603 and a light chain variable region comprising the amino acid sequence of SEQ ID NO: 604.

In some embodiments, the antibody comprises a heavy chain variable region comprising the amino acid sequence of SEQ ID NO: 611 and a light chain variable region comprising the amino acid sequence of SEQ ID NO: 612.

In some embodiments, the antibody comprises a heavy chain variable region comprising the amino acid sequence of SEQ ID NO: 619 and a light chain variable region comprising the amino acid sequence of SEQ ID NO: 620.

In some embodiments, the antibody comprises a heavy chain variable region comprising the amino acid sequence of SEQ ID NO: 627 and a light chain variable region comprising the amino acid sequence of SEQ ID NO: 628.

In some embodiments, the antibody comprises a heavy chain variable region comprising the amino acid sequence of SEQ ID NO: 635 and a light chain variable region comprising the amino acid sequence of SEQ ID NO: 636.

In some embodiments, the antibody comprises a heavy chain variable region comprising the amino acid sequence of SEQ ID NO: 643 and a light chain variable region comprising the amino acid sequence of SEQ ID NO: 644.

In some embodiments, the antibody comprises a heavy chain variable region comprising the amino acid sequence of SEQ ID NO: 651 and a light chain variable region comprising the amino acid sequence of SEQ ID NO: 652.

In some embodiments, the antibody comprises a heavy chain variable region comprising the amino acid sequence of SEQ ID NO: 659 and a light chain variable region comprising the amino acid sequence of SEQ ID NO: 660.

In some embodiments, the antibody comprises a heavy chain variable region comprising the amino acid sequence of SEQ ID NO: 667 and a light chain variable region comprising the amino acid sequence of SEQ ID NO: 668.

In some embodiments, the antibody comprises a heavy chain variable region comprising the amino acid sequence of SEQ ID NO: 675 and a light chain variable region comprising the amino acid sequence of SEQ ID NO: 676.

In some embodiments, the antibody comprises a heavy chain variable region comprising the amino acid sequence of SEQ ID NO: 683 and a light chain variable region comprising the amino acid sequence of SEQ ID NO: 684.

In some embodiments, the antibody comprises a heavy chain variable region comprising the amino acid sequence of SEQ ID NO: 691 and a light chain variable region comprising the amino acid sequence of SEQ ID NO: 692.

In some embodiments, an isolated antibody that binds to human Tau is provided, wherein the antibody binds an epitope within amino acids 19-33, 19-42, 28-44, 37-44, 37-51, 64-78, 73-87, 91-105, 100-114, 109-123, 118-132, 154-168, 172-177, 190-204, 217-231, 397-411, 421-429, or 422-429 of mature human Tau. In some embodiments, an isolated antibody that binds to human Tau is provided, wherein the antibody binds an epitope within amino acids 37-44, 64-78, 73-87, 91-105, 190-204, 421-429, or 422-429 of mature human Tau.

In some embodiments, an isolated antibody that binds human Tau is provided, wherein the antibody binds each of monomeric Tau, phosphorylated Tau, non-phosphorylated Tau, and oligomeric Tau with a $K_D$ of less than 400 nM, less than 100 nM, less than 75 nM, or less than 50 nM. In some embodiments, the antibody binds cynomolgus monkey Tau.

In some embodiments, an isolated nucleic acid is provided, wherein the isolated nucleic acid encodes an antibody described herein. In some embodiments, a host cell is provided, wherein the host cell comprises an isolated nucleic acid that encodes an antibody described herein. In some embodiments, a method of producing an antibody is provided, comprising culturing the host cell under conditions suitable for producing the antibody.

In some embodiments, an immunoconjugate is provided, wherein the immunoconjugate comprises an isolated antibody described herein and a therapeutic agent. In some embodiments, a labeled antibody is provided, comprising an antibody described herein and a detectable label.

In some embodiments, a pharmaceutical composition is provided, comprising an isolated antibody described herein and a pharmaceutically acceptable carrier.

In some embodiments, a method of treating a Tau protein associated disease is provided, comprising administering to an individual with a Tau protein associated disease an antibody described herein or a pharmaceutical composition comprising an antibody described herein. In some embodiments, the Tau protein associated disease is a tauopathy. In some embodiments, the tauopathy is a neurodegenerative tauopathy. In some embodiments, the tauopathy is selected from Alzheimer's Disease, amyotrophic lateral sclerosis, Parkinson's disease, Creutzfeldt-Jacob disease, Dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotetemporal dementia, frontotemporal dementia with parkinsonism linked to chromosome 17, Hallevorden-Spatz disease, multiple system atrophy, Niemann-Pick disease type C, Pallido-ponto-nigral degeneration, Pick's disease, progressive subcortical gliosis, progressive supranuclear palsy, Subacute sclerosing panencephalitis, Tangle only dementia (or tangle predominant dementia), Postencephalitic Parkinsonism, and Myotonic dystrophy. In some embodiments, the tauopathy is Alzheimer's disease or progressive supranuclear palsy. In some embodiments, the Tau protein associated disease is selected from PART (primary age-related Tauopathy), tangle predominant dementia, subacute sclerosis panencephalopathy, chronic traumatic encephalopathy (CTE), white matter tauopathy with globular glial inclusions, Lewy body dementia (LBD), mild cognitive impairment (MCI), glaucoma, familial British dementia, familiar Danish dementia, Guadeloupean Parkinsonism, neurodegeneration with brain iron accumulation, SLC9A6-related mental retardation, multiple sclerosis, HIV-related dementia, senile cardiac amyloidosis, and Huntington's disease.

In some embodiments, a method of retaining or increasing cognitive memory capacity or slowing memory loss in an individual is provided, comprising administering an antibody described herein or a pharmaceutical composition comprising an antibody described herein.

In some embodiments, a method of reducing the level of Tau protein, non-phosphorylated Tau protein, phosphorylated Tau protein, or hyperphosphorylated Tau protein in an individual is provided, comprising administering an antibody described herein or a pharmaceutical composition comprising an antibody described herein.

In some embodiments, an isolated antibody described herein is provided for use as a medicament. In some embodiments, an isolated antibody described herein is provided for use in treating a tauopathy in an individual. In some embodiments, the tauopathy is a neurodegenerative tauopathy. In some embodiments, the tauopathy is selected from Alzheimer's Disease, amyotrophic lateral sclerosis, Parkinson's disease, Creutzfeldt-Jacob disease, Dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotetemporal dementia, frontotemporal dementia with parkinsonism linked to chromosome 17, Hallevorden-Spatz disease, multiple system atrophy, Niemann-Pick disease type C, Pallido-ponto-nigral degeneration, Pick's disease, progressive subcortical gliosis, progressive supranuclear palsy, Subacute sclerosing panencephalitis, Tangle only dementia (or tangle predominant dementia), Postencephalitic Parkinsonism, and Myotonic dystrophy. In some embodiments, the tauopathy is Alzheimer's disease or progressive supranuclear palsy. In some embodiments, the Tau protein associated disease is selected from PART (primary age-related Tauopathy), tangle predominant dementia, subacute sclerosis panencephalopathy, chronic traumatic encephalopathy (CTE), white matter tauopathy with globular glial inclusions, Lewy body dementia (LBD), mild cognitive impairment (MCI), glaucoma, familial British dementia, familiar Danish dementia, Guadeloupean Parkinsonism, neurodegeneration with brain iron accumulation, SLC9A6-related mental retardation, multiple sclerosis, HIV-related dementia, senile cardiac amyloidosis, and Huntington's disease.

In some embodiments, an isolated antibody described herein is provided for use in retaining or increasing cognitive memory capacity or slowing memory loss in an individual. In some embodiments, an isolated antibody described herein is provided for use in reducing the level of Tau protein, phosphorylated Tau protein, non-phosphorylated Tau protein, or hyperphosphorylated Tau protein in an individual.

In some embodiments, use of an antibody described herein is provided for manufacture of a medicament for treating a Tau protein associated disease in an individual. In some embodiments, the Tau protein associate disease is a tauopathy. In some embodiments, the tauopathy is a neurodegenerative tauopathy. In some embodiments, the tauopathy is selected from Alzheimer's Disease, amyotrophic lateral sclerosis, Parkinson's disease, Creutzfeldt-Jacob disease, Dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotetemporal dementia, frontotemporal dementia with parkinsonism linked to chromosome 17, Hallevorden-Spatz disease, multiple system atrophy, Niemann-Pick disease type C, Pallido-ponto-nigral degeneration, Pick's disease, progressive subcortical gliosis, progressive supranuclear palsy, Subacute sclerosing panencephalitis, Tangle only dementia (or tangle predominant dementia), Postencephalitic Parkinsonism, and Myotonic dystrophy. In some embodiments, the tauopathy is Alzheimer's disease or progressive supranuclear palsy. In some embodiments, the Tau protein associated disease is selected from PART (primary age-related Tauopathy), tangle predominant dementia, subacute sclerosis panencephalopathy, chronic traumatic encephalopathy (CTE), white matter tauopathy with globular glial inclusions, Lewy body dementia (LBD), mild cognitive impairment (MCI), glaucoma, familial British dementia, familiar Danish dementia, Guadeloupean Parkinsonism, neurodegeneration with brain iron accumulation, SLC9A6-related mental retardation, multiple sclerosis, HIV-related dementia, senile cardiac amyloidosis, and Huntington's disease.

In some embodiments, use of an antibody described herein is provided for manufacture of a medicament for retaining or increasing cognitive memory capacity or slowing memory loss in an individual.

In any of the embodiments described herein, a method or use may comprise administering an antibody described herein in combination with at least one additional therapy. Non-limiting examples of additional therapies include neurological drugs, corticosteroids, antibiotics, antiviral agents, and other therapeutic agents. Such other therapeutic agents include, but are not limited to, other anti-Tau antibodies, antibodies against amyloid-beta, antibodies against beta-secretase 1 ("BACE1"), and inhibitors of beta-secretase 1.

In some embodiments, a method of detecting neurofibrillary tangles, neuropil threads, or dystrophic neuritis is provided, comprising contacting a sample with an antibody described herein. In some embodiments, methods of detecting Tau in a sample are provided, comprising contacting the sample with an antibody provided herein.

In some embodiments, methods of predicting whether a subject will respond to treatment with a therapeutic anti-Tau antibody are provided, comprising detecting Tau in a sample from the subject with a detection anti-Tau antibody, wherein the detection anti-Tau antibody binds an epitope within amino acids 1-15, 10-24, 19-33, 19-42, 28-42, 28-44, 37-44, or 37-51 of mature human Tau. In some such embodiments, if the level of Tau detected in the sample is greater than a control level of Tau, the subject is predicted to respond to treatment with a therapeutic anti-Tau antibody.

In some embodiments, methods of selecting a patient for treatment with a therapeutic anti-Tau antibody are provided, comprising detecting Tau in a sample from the subject with a detection anti-Tau antibody, wherein the detection anti-Tau antibody binds an epitope within amino acids 1-15, 10-24, 19-33, 19-42, 28-42, 28-44, 37-44, or 37-51 of mature human Tau. In some such embodiments, if the level of Tau detected in the sample is greater than a control level of Tau, the subject is selected for treatment with a therapeutic anti-Tau antibody.

In some embodiments, methods of monitoring treatment with a therapeutic anti-Tau antibody are provided, comprising detecting Tau in a sample from a subject undergoing treatment with a detection anti-Tau antibody, wherein the detection anti-Tau antibody binds an epitope within amino acids 1-15, 10-24, 19-33, 19-42, 28-42, 28-44, 37-44, or 37-51 of mature human Tau. In some such embodiments, an increase in Tau in a second sample from a subject taken at a later time point during treatment, compared to the level of Tau in a first sample from a subject taken at an earlier time point during treatment or prior to start of treatment, indicates that the treatment is effective. In some embodiments, the detection anti-Tau antibody does not compete with the therapeutic anti-Tau antibody for binding to Tau.

In some embodiments, the therapeutic anti-Tau antibody binds to an epitope within amino acids 2-24 of mature human Tau. In some embodiments, the detection anti-Tau antibody does not compete with the therapeutic anti-Tau antibody for binding to Tau. In some embodiments, the detection anti-Tau antibody is an antibody selected from Table 4 or Table 31. In some embodiments, the detection anti-Tau antibody is an antibody provided herein. In some embodiments, the detection anti-Tau antibody is selected from 15C6-A7, 63H3-D8, 123E9-A1, 64B9-F12, 7A11C12, 231G3F10, 63H3-D8, 64B9-F12, and 72E12-H9. In some embodiments, the detection anti-Tau antibody binds an epitope within amino acids 37-44 of mature human Tau.

In some embodiments, methods of selecting a patient for treatment with a therapeutic anti-Tau antibody are provided, comprising detecting Tau in a sample from the subject with a detection anti-Tau antibody, wherein the detection anti-Tau antibody binds a 2N isoform of mature human Tau. In some embodiments, if the level of a 2N isoform detected in the sample is greater than a control level of the 2N isoform, the subject is selected for treatment with a therapeutic anti-Tau antibody. In some embodiments, if the 2N isoform is detected in the sample, the subject is selected for treatment with a therapeutic anti-Tau antibody. In some embodiments, methods of monitoring the progression of cognitive impairment in a subject with a tauopathy are provided, comprising detecting Tau in a sample from the subject with a detection anti-Tau antibody, wherein the detection anti-Tau antibody binds a 2N isoform of mature human Tau. In some such embodiments, an increase in the level of 2N isoform of mature human Tau indicates a progression of cognitive impairment. In some embodiments, methods of monitoring treatment with a therapeutic anti-Tau antibody are provided, comprising detecting Tau in a sample from a subject undergoing treatment with a detection anti-Tau antibody, wherein the detection anti-Tau antibody binds a 2N isoform of mature human Tau. In some embodiments, a decrease in the level of 2N isoform of mature human Tau indicates that the treatment is effective. In some embodiments, the detection antibody binds an epitope within amino acids 64-78, 73-87, 82-96, 91-105, 100-114, 109-123, 118-132, 136-150, 154-168, 163-177, 172-177, 190-204, 421-429, or 422-429 of mature human Tau. In some embodiments, the detection antibody is an antibody selected from Table 4 or Table 31. In some embodiments, the detection antibody binds an epitope within amino acids 73-87, 91-105, 64-78, 190-204, 421-429, or 422-429. In some embodiments, the detection antibody is selected from 30A1C9, 211G6-B6, 77D1-D2, 71H8-D6, and 307H3E8. In some embodiments, the detection antibody binds an epitope within amino acids 64-78 or 109-123. In some embodiments, the detection antibody is selected from 30D12-B5, 49G10-F4, and 65B1-A2.

In some embodiments, the sample is a brain sample, a cerebrospinal fluid sample, or a blood sample.

BRIEF DESCRIPTION OF THE FIGURES

FIG. 5. Sensorgrams showing 37D3-H9 binding as a Fab (left panel) and as an IgG (right panel) to human Tau monomer covalently coupled to a Biacore chip surface. A 1:1 binding model has been applied and is shown as an overlay. The x-axis indicates time (units=seconds). The y-axis indicated Resonance Units (RU).

FIG. 6. Overlaid sensorgrams showing binding of hu37D3-H9.v5 samples t=0 (left panel) and t=2 weeks (right panel) to human Tau monomer at 3.1, 6.3, 12.5, 25, 25, 50 and 100 nM. A 1:1 binding model has been applied and is also shown in this figure. The x-axis indicates time (units=seconds). The y-axis indicated Resonance Units (RU).

FIG. 7. Binding of hu37D3-H9.v5 and hu37D3-H9.v5 N28D to monomeric Tau individually (left panel shows hu37D3-H9.v5 and middle panel shows hu37D3-H9.v5 N28D) and mixed at a 1:1 ratio (right panel). The x-axis indicates time (units=seconds). The y-axis indicated Resonance Units (RU).

FIG. 8A-D. Affinity, stability index and sequences of the ninety 37D3-H9 variants screened for potential improved stability. For clarity, values obtained with an unstressed control antibody (hu37D3-H9.v5 hIgGi) run at the beginning, middle and end of each experiment are shown in both sections of the table.

FIG. 15. Comparison of human and cynomolgus monkey Tau sequences. The epitope for antibody 37D3-H9 is indicated.

FIG. 18 shows an alignment of the kappa 1 light chain variable regions of hu37D3-H9.v1, hu37D3-H9.v39, hu37D3-H9.v40, and hu37D3-H9.v41.

FIG. 25 shows the Tau 0N/1N/2N isoform selectivity of certain antibodies, and the vaccine used to generate each antibody. Antibodies binding in the N-terminal region of Tau, spanning the region encoded by exons 1 to 4 were assayed for selectivity for or against human Tau isoforms. ELISAs were performed using 0N-, 1N-, and 2N-Tau, to verify human Tau isoform binding selectivity.

DETAILED DESCRIPTION OF EMBODIMENTS OF THE INVENTION

I. Definitions

Figure 1A:
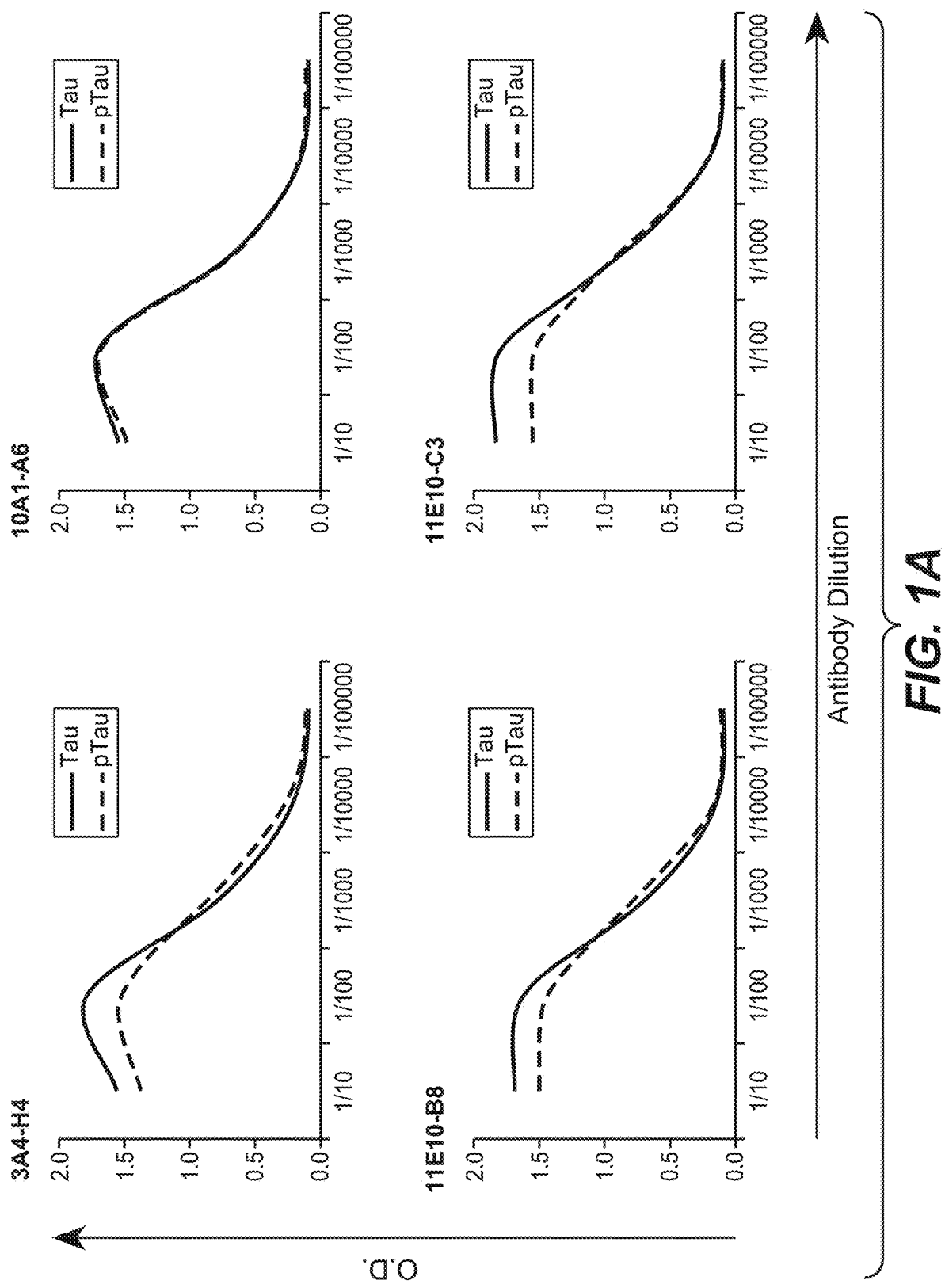
FIG. 1A-F. Binding of antibodies to hyperphosphorylated Tau (pTau) was compared to non-phosphorylated Tau using an ELISA. Results are expressed in optical densities (O.D.).
Figure 1B:
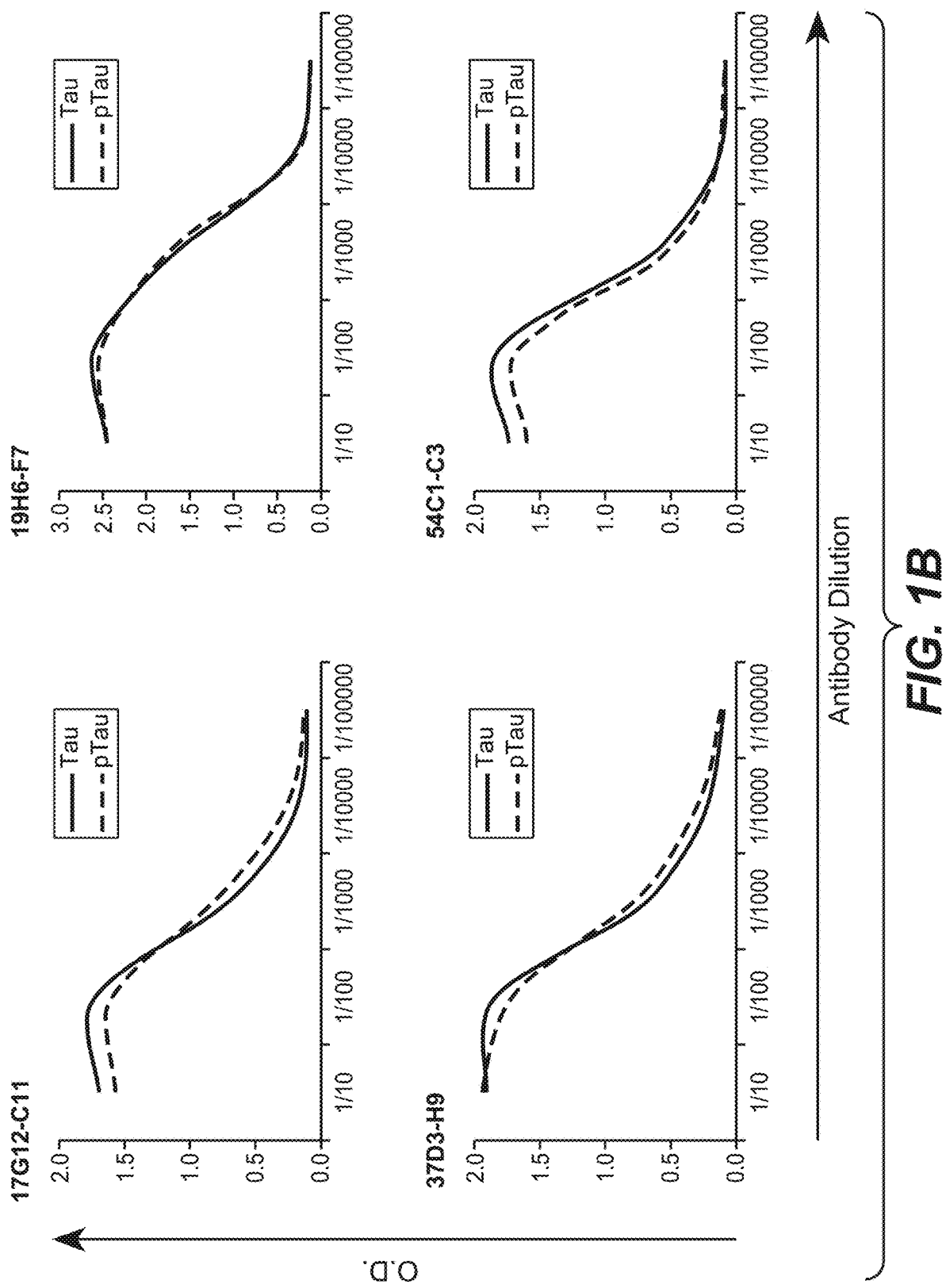
Figure 1C:
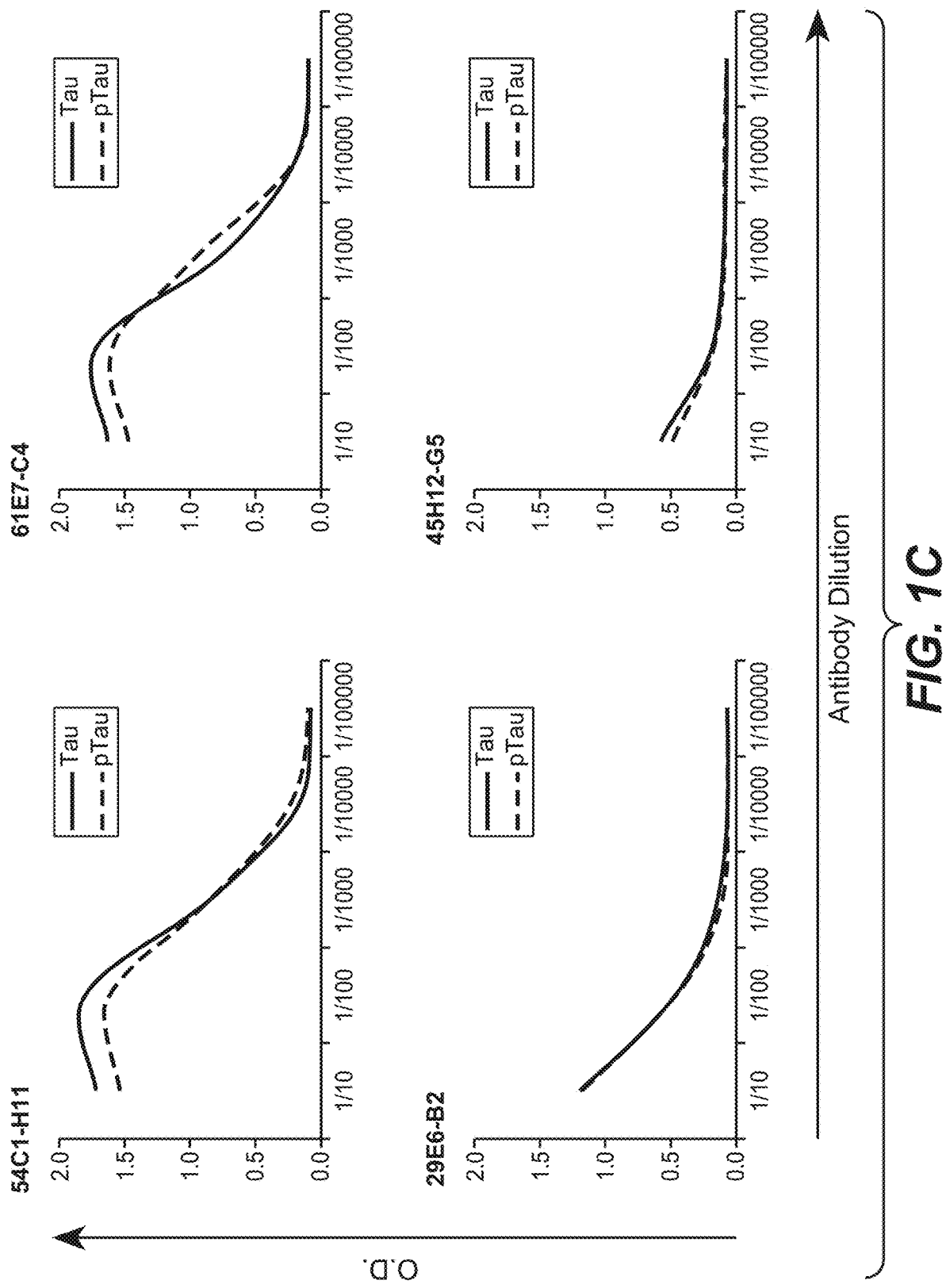
Figure 1D:
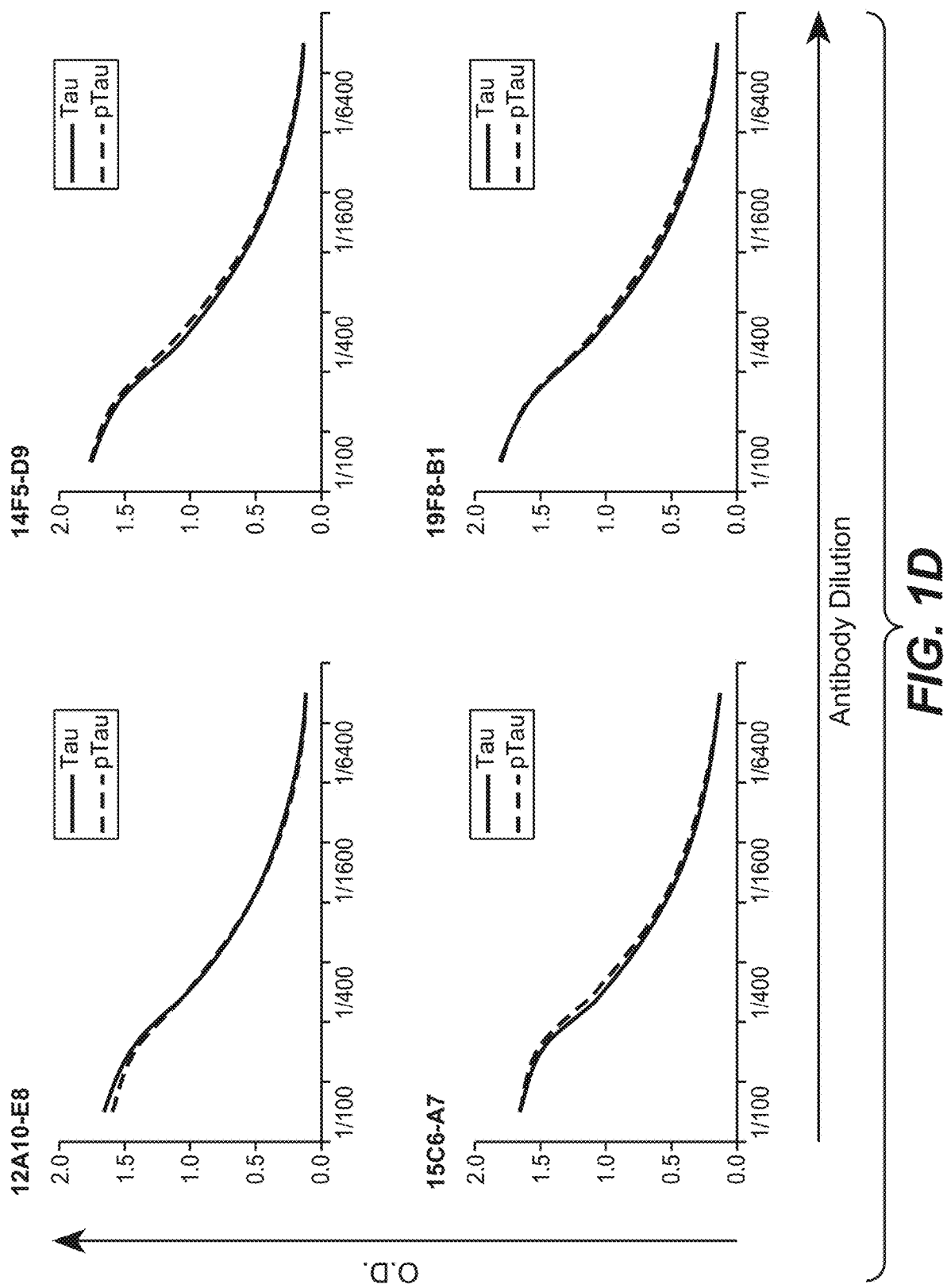
Figure 1E:
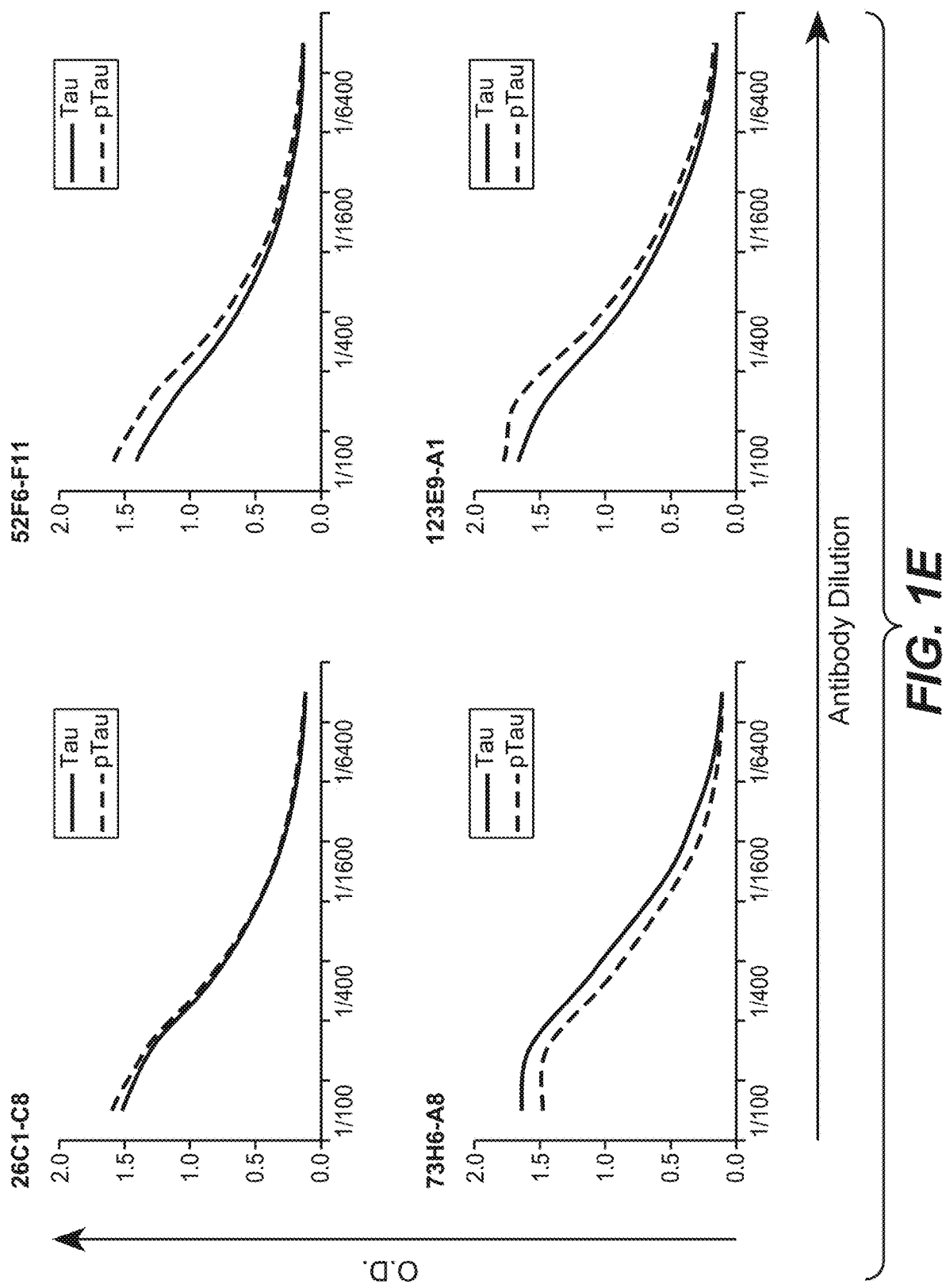
Figure 1F:
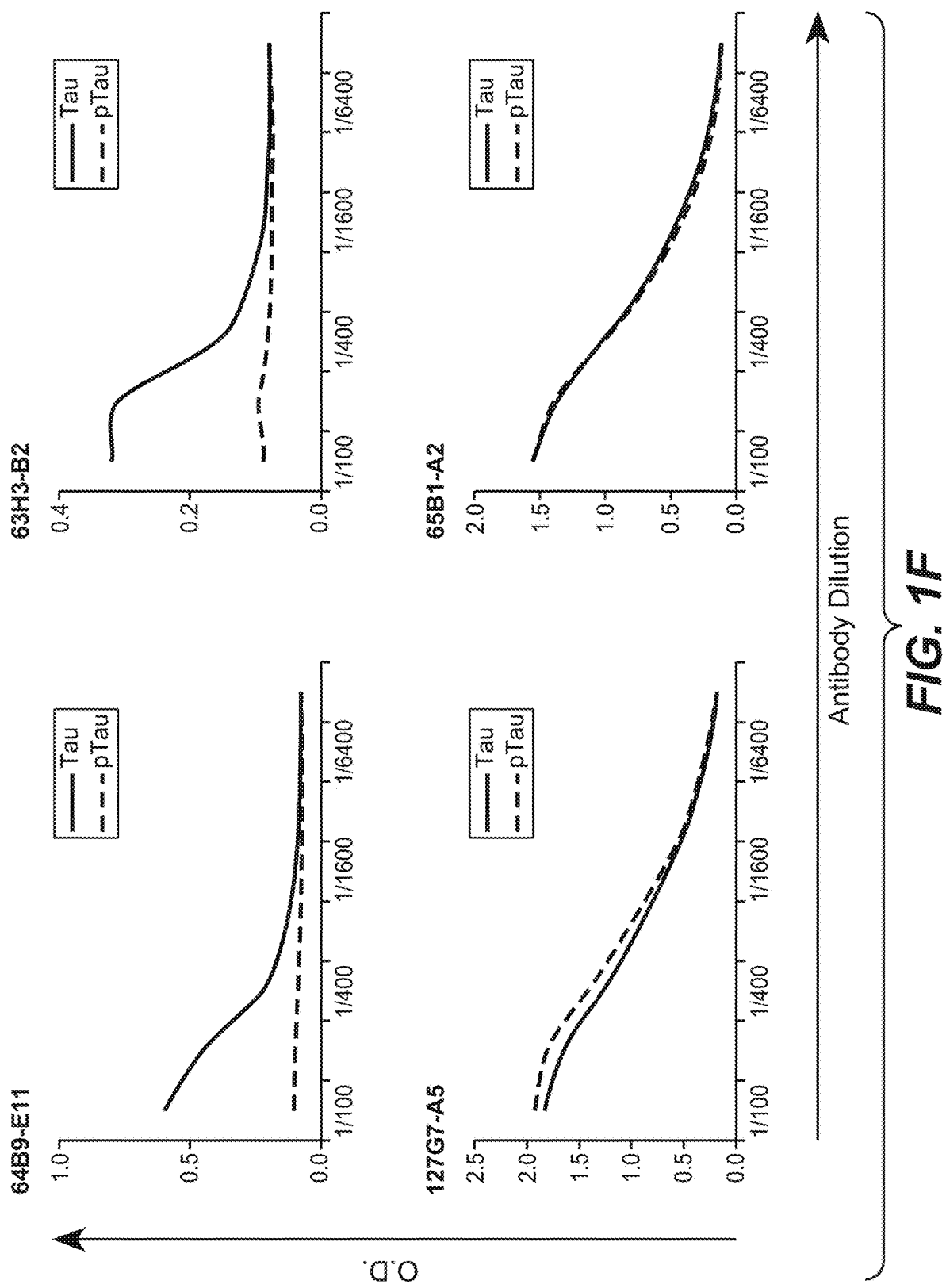

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-Tau antibody" and "an antibody that binds to Tau" refer to an antibody that is capable of binding Tau with sufficient affinity such that the antibody is useful as a diagnostic and/or therapeutic agent in targeting Tau. In some embodiments, the extent of binding of an anti-Tau antibody to an unrelated, non-Tau protein is less than about 10% of the binding of the antibody to Tau as measured, e.g., by a radioimmunoassay (RIA). In certain embodiments, an antibody that binds to Tau has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-Tau antibody binds to an epitope of Tau that is conserved among Tau from different species. The term "anti-Tau antibody" and "antibody that binds to Tau," as used herein, refers to an antibody that binds monomeric Tau, oligomeric Tau, and/or phosphorylated Tau, unless specifically indicated otherwise. In some such embodiments, the anti-Tau antibody binds to monomeric Tau, oligomeric Tau, non-phosphorylated Tau, and phosphorylated Tau with comparable affinities, such as with affinities that differ by no more than 50-fold from one another. In some embodiments, an antibody that binds monomeric Tau, oligomeric Tau, non-phosphorylated Tau, and phosphorylated Tau is referred to as a "pan-Tau antibody."

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In some embodiments, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In some embodiments, for the VL, the subgroup is subgroup kappa I as in Kabat et al., supra. In some embodiments, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-Tau antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "Tau," as used herein, refers to any native Tau protein from any vertebrate source, including mammals such as primates (e.g., humans) and rodents (e.g., mice and rats), unless otherwise indicated. The term encompasses "full-length," unprocessed Tau as well as any form of Tau that results from processing in the cell. The term also encompasses naturally occurring variants of Tau, e.g., splice variants or allelic variants.

The term "pTau," as used herein, refers to Tau in which a serine, a threonine or a tyrosine residue is phosphorylated by a protein kinase by the addition of a covalently bound phosphate group. In some embodiments, pTau is phosphorylated on a serine or on a threonine residue. In some embodiments, pTau is phosphorylated on Serine at position 409 and/or Serine at position 404. In some embodiments, pTau is phosphorylated on Serine at position 409.

The terms "soluble Tau" or "soluble Tau protein," as used herein, refer to proteins consisting of both completely solubilized Tau protein/peptide monomers or of Tau-like peptides/proteins, or of modified or truncated Tau peptides/proteins or of other derivates of Tau peptides/proteins monomers, and of Tau protein oligomers. "Soluble Tau" excludes particularly neurofibrillary tangles (NFT).

The term "insoluble Tau," as used herein, refers to multiple aggregated monomers of Tau peptides or proteins, or of Tau-like peptides/proteins, or of modified or truncated Tau peptides/proteins or of other derivates of Tau peptides/proteins forming oligomeric or polymeric structures which are insoluble both in vitro in aqueous medium and in vivo in the mammalian or human body more particularly in the brain, but particularly to multiple aggregated monomers of Tau or of modified or truncated Tau peptides/proteins or of derivatives thereof, which are insoluble in the mammalian or human body more particularly in the brain, respectively. "Insoluble Tau" particularly includes neurofibrillary tangles (NFT).

The terms "monomeric Tau" or "monoTau" or "Tau monomer", as used herein, refer to completely solubilized Tau proteins without aggregated complexes in aqueous medium.

The terms "aggregated Tau", "oligomeric Tau" and "Tau oligomer," as used herein, refer to multiple aggregated monomers of Tau peptides or proteins, or of Tau-like peptides/proteins, or of modified or truncated Tau peptides/proteins or of other derivates of Tau peptides/proteins forming oligomeric or polymeric structures which are insoluble or soluble both in vitro in aqueous medium and in vivo in the mammalian or human body more particularly in the brain, but particularly to multiple aggregated monomers of Tau or of modified or truncated Tau peptides/proteins or of derivatives thereof, which are insoluble or soluble in the mammalian or human body more particularly in the brain, respectively.

The terms "pTau PHF", "PHF", and "paired helical filaments," are used herein synonymously, refer to pairs of filaments wound into helices with a periodicity of 160 nm visible on electron microscopy. Width varies between 10 and 22 nm. PHF are the predominant structures in neurofibrillary tangles of Alzheimer's Disease (AD) and neuropil threads. PHF may also be seen in some but not all dystrophic neurites associated with neuritic plaques. The major component of PHF is a hyperphosphorylated form of microtubule-associated protein tau. PHF may be partially composed of disulfide-linked antiparallel hyper-phosphorylated Tau proteins. PHF Tau may be truncated of its C-terminal 20 amino acid residues. The mechanisms underlying PHF formation are uncertain but hyper-phosphorylation of Tau may disengage it from microtubules, increasing the soluble pool of Tau from which PHF can be formed inside neurons.

The "2N isoform" of Tau refers to an isoform of Tau that includes exon 2 and exon 3.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "early Alzheimer's Disease" or "early AD" as used herein (e.g., a "patient diagnosed with early AD" or a "patient suffering from early AD") includes patients with mild cognitive impairment, such as a memory deficit, due to AD and patients having AD biomarkers, for example amyloid positive patients.

The term "mild Alzheimer's Disease" or "mild AD" as used herein (e.g., a "patient diagnosed with mild AD") refers to a stage of AD characterized by an MMSE score of 20 to 26.

The term "mild to moderate Alzheimer's Disease" or "mild to moderate AD" as used herein encompasses both mild and moderate AD, and is characterized by an MMSE score of 18 to 26.

The term "moderate Alzheimer's Disease" or "moderate AD" as used herein (e.g., a "patient diagnosed with moderate AD") refers to a stage of AD characterized by an MMSE score of 18 to 19.

The term "MMSE" refers to the Mini Mental State Examination, which provides a score between 1 and 30. See Folstein, et al., 1975, J. Psychiatr. Res. 12:189-98. Scores of 26 and lower are generally considered to be indicative of a deficit. The lower the numerical score on the MMSE, the greater the tested patient's deficit or impairment relative to another individual with a lower score. An increase in MMSE score may be indicative of improvement in the patient's condition, whereas a decrease in MMSE score may denote worsening in the patient's condition.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

Antibodies that bind Tau are provided. In some embodiments, an antibody of the invention binds Tau binds monomeric Tau, oligomeric Tau, non-phosphorylated Tau, and phosphorylated Tau. In some embodiments, an antibody of the invention binds to an epitope within amino acids 2-24 of mature human Tau. In some embodiments, an antibody of the invention binds to an epitope within Tau amino acids 2-24 and binds monomeric Tau, oligomeric Tau, non-phosphorylated Tau, and phosphorylated Tau. In some embodiments, an antibody binds an epitope of human Tau having, or consisting of, the sequence AEPRQEFEVMEDHAG-TYGLGDRK (SEQ ID NO: 2). In some embodiments, an antibody binds an epitope of cynomolgus monkey Tau having, or consisting of, the sequence AEPRQEFDVMED-HAGTYGLGDRK (SEQ ID NO: 4). In some embodiments, an antibody binds an epitope of human Tau having, or consisting of, the sequence AEPRQEFEVMEDHAGTYGL-GDRK (SEQ ID NO: 2) and an epitope of cynomolgus monkey Tau having, or consisting of, the sequence AEPRQEFDVMEDHAGTYGLGDRK (SEQ ID NO: 4). In some embodiments, an antibody of the invention binds to an epitope within amino acids 19-33, 19-42, 37-51, 100-114, 109-123, 118-132, or 172-177 of mature human Tau. In some embodiments, an antibody of the invention binds to an epitope within amino acids 37-44, 64-78, 73-87, 91-105, 190-204, 421-429, or 422-429 of mature human Tau. In some embodiments, an antibody of the invention binds to an epitope within amino acids 19-33, 19-42, 37-51, 100-114, 109-123, 118-132, or 172-177 of mature human Tau and binds monomeric Tau, oligomeric Tau, non-phosphorylated Tau, and phosphorylated Tau. In some embodiments, an antibody of the invention binds to an epitope within amino acids 37-44, 64-78, 73-87, 91-105, 190-204, 421-429, or 422-429 of mature human Tau and binds monomeric Tau, oligomeric Tau, non-phosphorylated Tau, and phosphorylated Tau.

Antibodies of the invention are useful, e.g., for the diagnosis or treatment of neurodegenerative diseases.

A. Exemplary Anti-Tau Antibodies

In some embodiments, an anti-Tau antibody comprises:
a) HVR-H1 comprising the amino acid sequence of SEQ ID NO: 605; HVR-H2 comprising the amino acid sequence of SEQ ID NO: 606; and HVR-H3 comprising the amino acid sequence of SEQ ID NO: 607; or
b) HVR-H1 comprising the amino acid sequence of SEQ ID NO: 613; HVR-H2 comprising the amino acid sequence of SEQ ID NO: 614; and HVR-H3 comprising the amino acid sequence of SEQ ID NO: 615;
c) HVR-H1 comprising the amino acid sequence of SEQ ID NO: 621; HVR-H2 comprising the amino acid sequence of SEQ ID NO: 622; and HVR-H3 comprising the amino acid sequence of SEQ ID NO: 623;
d) HVR-H1 comprising the amino acid sequence of SEQ ID NO: 629; HVR-H2 comprising the amino acid sequence of SEQ ID NO: 630; and HVR-H3 comprising the amino acid sequence of SEQ ID NO: 631;
e) HVR-H1 comprising the amino acid sequence of SEQ ID NO: 637; HVR-H2 comprising the amino acid sequence of SEQ ID NO: 638; and HVR-H3 comprising the amino acid sequence of SEQ ID NO: 639;
f) HVR-H1 comprising the amino acid sequence of SEQ ID NO: 645; HVR-H2 comprising the amino acid sequence of SEQ ID NO: 646; and HVR-H3 comprising the amino acid sequence of SEQ ID NO: 647;
g) HVR-H1 comprising the amino acid sequence of SEQ ID NO: 653; HVR-H2 comprising the amino acid sequence of SEQ ID NO: 654; and HVR-H3 comprising the amino acid sequence of SEQ ID NO: 655;
h) HVR-H1 comprising the amino acid sequence of SEQ ID NO: 661; HVR-H2 comprising the amino acid sequence of SEQ ID NO: 662; and HVR-H3 comprising the amino acid sequence of SEQ ID NO: 663;
i) HVR-H1 comprising the amino acid sequence of SEQ ID NO: 669; HVR-H2 comprising the amino acid sequence of SEQ ID NO: 670; and HVR-H3 comprising the amino acid sequence of SEQ ID NO: 671;
j) HVR-H1 comprising the amino acid sequence of SEQ ID NO: 677; HVR-H2 comprising the amino acid sequence of SEQ ID NO: 678; and HVR-H3 comprising the amino acid sequence of SEQ ID NO: 679;
k) HVR-H1 comprising the amino acid sequence of SEQ ID NO: 685; HVR-H2 comprising the amino acid sequence of SEQ ID NO: 686; and HVR-H3 comprising the amino acid sequence of SEQ ID NO: 687; or
l) HVR-H1 comprising the amino acid sequence of SEQ ID NO: 693; HVR-H2 comprising the amino acid sequence of SEQ ID NO: 694; and HVR-H3 comprising the amino acid sequence of SEQ ID NO: 695.

In some embodiments, an anti-Tau antibody comprises:
a) HVR-L1 comprising the amino acid sequence of SEQ ID NO: 608; HVR-L2 comprising the amino acid sequence of SEQ ID NO: 609; and HVR-L3 comprising the amino acid sequence of SEQ ID NO: 610;
b) HVR-L1 comprising the amino acid sequence of SEQ ID NO: 616; HVR-L2 comprising the amino acid sequence of SEQ ID NO: 617; and HVR-L3 comprising the amino acid sequence of SEQ ID NO: 618;
c) HVR-L1 comprising the amino acid sequence of SEQ ID NO: 624; HVR-L2 comprising the amino acid sequence of SEQ ID NO: 625; and HVR-L3 comprising the amino acid sequence of SEQ ID NO: 626;
d) HVR-L1 comprising the amino acid sequence of SEQ ID NO: 632; HVR-L2 comprising the amino acid sequence of SEQ ID NO: 633; and HVR-L3 comprising the amino acid sequence of SEQ ID NO: 634;
e) HVR-L1 comprising the amino acid sequence of SEQ ID NO: 640; HVR-L2 comprising the amino acid sequence of SEQ ID NO: 641; and HVR-L3 comprising the amino acid sequence of SEQ ID NO: 642;
f) HVR-L1 comprising the amino acid sequence of SEQ ID NO: 648; HVR-L2 comprising the amino acid sequence of SEQ ID NO: 649; and HVR-L3 comprising the amino acid sequence of SEQ ID NO: 650
g) HVR-L1 comprising the amino acid sequence of SEQ ID NO: 656; HVR-L2 comprising the amino acid sequence of SEQ ID NO: 657; and HVR-L3 comprising the amino acid sequence of SEQ ID NO: 658;
h) HVR-L1 comprising the amino acid sequence of SEQ ID NO: 664; HVR-L2 comprising the amino acid sequence of SEQ ID NO: 665; and HVR-L3 comprising the amino acid sequence of SEQ ID NO: 666;
i) HVR-L1 comprising the amino acid sequence of SEQ ID NO: 672; HVR-L2 comprising the amino acid sequence of SEQ ID NO: 673; and HVR-L3 comprising the amino acid sequence of SEQ ID NO: 674;
j) HVR-L1 comprising the amino acid sequence of SEQ ID NO: 680; HVR-L2 comprising the amino acid sequence of SEQ ID NO: 681; and HVR-L3 comprising the amino acid sequence of SEQ ID NO: 682;
k) HVR-L1 comprising the amino acid sequence of SEQ ID NO: 688; HVR-L2 comprising the amino acid sequence of SEQ ID NO: 689; and HVR-L3 comprising the amino acid sequence of SEQ ID NO: 690; or
l) HVR-L1 comprising the amino acid sequence of SEQ ID NO: 696; HVR-L2 comprising the amino acid sequence of SEQ ID NO: 697; and HVR-L3 comprising the amino acid sequence of SEQ ID NO: 698.

In some embodiments, an anti-Tau antibody comprises:
a) HVR-H1 comprising the amino acid sequence of SEQ ID NO: 605; HVR-H2 comprising the amino acid sequence of SEQ ID NO: 606; HVR-H3 comprising the amino acid sequence of SEQ ID NO: 607; HVR-L1 comprising the amino acid sequence of SEQ ID NO: 608; HVR-L2 comprising the amino acid sequence of SEQ ID NO: 609; and HVR-L3 comprising the amino acid sequence of SEQ ID NO: 610;

b) HVR-H1 comprising the amino acid sequence of SEQ ID NO: 613; HVR-H2 comprising the amino acid sequence of SEQ ID NO: 614; HVR-H3 comprising the amino acid sequence of SEQ ID NO: 615; HVR-L1 comprising the amino acid sequence of SEQ ID NO: 616; HVR-L2 comprising the amino acid sequence of SEQ ID NO: 617; and HVR-L3 comprising the amino acid sequence of SEQ ID NO: 618;
c) HVR-H1 comprising the amino acid sequence of SEQ ID NO: 621; HVR-H2 comprising the amino acid sequence of SEQ ID NO: 622; HVR-H3 comprising the amino acid sequence of SEQ ID NO: 623; HVR-L1 comprising the amino acid sequence of SEQ ID NO: 624; HVR-L2 comprising the amino acid sequence of SEQ ID NO: 625; and HVR-L3 comprising the amino acid sequence of SEQ ID NO: 626;
d) HVR-H1 comprising the amino acid sequence of SEQ ID NO: 629; HVR-H2 comprising the amino acid sequence of SEQ ID NO: 630; HVR-H3 comprising the amino acid sequence of SEQ ID NO: 631; HVR-L1 comprising the amino acid sequence of SEQ ID NO: 632; HVR-L2 comprising the amino acid sequence of SEQ ID NO: 633; and HVR-L3 comprising the amino acid sequence of SEQ ID NO: 634;
e) HVR-H1 comprising the amino acid sequence of SEQ ID NO: 637; HVR-H2 comprising the amino acid sequence of SEQ ID NO: 638; HVR-H3 comprising the amino acid sequence of SEQ ID NO: 639; HVR-L1 comprising the amino acid sequence of SEQ ID NO: 640; HVR-L2 comprising the amino acid sequence of SEQ ID NO: 641; and HVR-L3 comprising the amino acid sequence of SEQ ID NO: 642;
f) HVR-H1 comprising the amino acid sequence of SEQ ID NO: 645; HVR-H2 comprising the amino acid sequence of SEQ ID NO: 646; HVR-H3 comprising the amino acid sequence of SEQ ID NO: 647; HVR-L1 comprising the amino acid sequence of SEQ ID NO: 648; HVR-L2 comprising the amino acid sequence of SEQ ID NO: 649; and HVR-L3 comprising the amino acid sequence of SEQ ID NO: 650
g) HVR-H1 comprising the amino acid sequence of SEQ ID NO: 653; HVR-H2 comprising the amino acid sequence of SEQ ID NO: 654; HVR-H3 comprising the amino acid sequence of SEQ ID NO: 655; HVR-L1 comprising the amino acid sequence of SEQ ID NO: 656; HVR-L2 comprising the amino acid sequence of SEQ ID NO: 657; and HVR-L3 comprising the amino acid sequence of SEQ ID NO: 658;
h) HVR-H1 comprising the amino acid sequence of SEQ ID NO: 661; HVR-H2 comprising the amino acid sequence of SEQ ID NO: 662; HVR-H3 comprising the amino acid sequence of SEQ ID NO: 663; HVR-L1 comprising the amino acid sequence of SEQ ID NO: 664; HVR-L2 comprising the amino acid sequence of SEQ ID NO: 665; and HVR-L3 comprising the amino acid sequence of SEQ ID NO: 666;
i) HVR-H1 comprising the amino acid sequence of SEQ ID NO: 669; HVR-H2 comprising the amino acid sequence of SEQ ID NO: 670; HVR-H3 comprising the amino acid sequence of SEQ ID NO: 671; HVR-L1 comprising the amino acid sequence of SEQ ID NO: 672; HVR-L2 comprising the amino acid sequence of SEQ ID NO: 673; and HVR-L3 comprising the amino acid sequence of SEQ ID NO: 674;
j) HVR-H1 comprising the amino acid sequence of SEQ ID NO: 677; HVR-H2 comprising the amino acid sequence of SEQ ID NO: 678; HVR-H3 comprising the amino acid sequence of SEQ ID NO: 679; HVR-L1 comprising the amino acid sequence of SEQ ID NO: 680; HVR-L2 comprising the amino acid sequence of SEQ ID NO: 681; and HVR-L3 comprising the amino acid sequence of SEQ ID NO: 682;
k) HVR-H1 comprising the amino acid sequence of SEQ ID NO: 685; HVR-H2 comprising the amino acid sequence of SEQ ID NO: 686; HVR-H3 comprising the amino acid sequence of SEQ ID NO: 687; HVR-L1 comprising the amino acid sequence of SEQ ID NO: 688; HVR-L2 comprising the amino acid sequence of SEQ ID NO: 689; and HVR-L3 comprising the amino acid sequence of SEQ ID NO: 690; or
l) HVR-H1 comprising the amino acid sequence of SEQ ID NO: 693; HVR-H2 comprising the amino acid sequence of SEQ ID NO: 694; HVR-H3 comprising the amino acid sequence of SEQ ID NO: 695; HVR-L1 comprising the amino acid sequence of SEQ ID NO: 696; HVR-L2 comprising the amino acid sequence of SEQ ID NO: 697; and HVR-L3 comprising the amino acid sequence of SEQ ID NO: 698.

In some embodiments, an anti-Tau antibody comprises at least one, two, three, four, five, or six HVRs selected from (a) HVR-H1 comprising an amino acid sequence selected from SEQ ID NOs: 12, 22, 282, 292, and 342; (b) HVR-H2 comprising an amino acid sequence selected from SEQ ID NOs: 13, 23, 283, 293, and 343; (c) HVR-H3 comprising an amino acid sequence selected from SEQ ID NOs: 14, 24, 284, 294, and 344; (d) HVR-L1 comprising an amino acid sequence selected from SEQ ID NOs: 15, 25, 285, 295, 345, and 468 to 556; (e) HVR-L2 comprising an amino acid sequence selected from SEQ ID NOs: 16, 26, 286, 296, and 346; and (f) HVR-L3 comprising an amino acid sequence selected from SEQ ID NOs: 17, 27, 287, 297, and 347.

In some embodiments, an anti-Tau antibody comprises at least one, two, three, four, five, or six HVRs selected from (a) HVR-H1 comprising the amino acid sequence of SEQ ID NO: 342; (b) HVR-H2 comprising the amino acid sequence of SEQ ID NO: 343; (c) HVR-H3 comprising the amino acid sequence of SEQ ID NO: 344; (d) HVR-L1 comprising the amino acid sequence of SEQ ID NO: 345; (e) HVR-L2 comprising the amino acid sequence of SEQ ID NO: 346; and (f) HVR-L3 comprising the amino acid sequence of SEQ ID NO: 347.

In some embodiments, an anti-Tau antibody comprises at least one, two, three, four, five, or six HVRs selected from (a) HVR-H1 comprising an amino acid sequence selected from SEQ ID NOs: 72 and 302; (b) HVR-H2 comprising an amino acid sequence selected from SEQ ID NOs: 73 and 303; (c) HVR-H3 comprising an amino acid sequence selected from SEQ ID NOs: 74 and 304; (d) HVR-L1 comprising an amino acid sequence selected from SEQ ID NOs: 75 and 305; (e) HVR-L2 comprising an amino acid sequence selected from SEQ ID NOs: 76 and 306; and (f) HVR-L3 comprising an amino acid sequence selected from SEQ ID NOs: 77 and 307.

In some embodiments, an anti-Tau antibody comprises at least one, two, three, four, five, or six HVRs selected from (a) HVR-H1 comprising an amino acid sequence selected from SEQ ID NOs: 82, 312, 322, and 332; (b) HVR-H2 comprising an amino acid sequence selected from SEQ ID NOs: 83, 313, 323, and 333; (c) HVR-H3 comprising an amino acid sequence selected from SEQ ID NOs: 84, 314, 324, and 334; (d) HVR-L1 comprising an amino acid sequence selected from SEQ ID NOs: 85, 315, 325, and 335; (e) HVR-L2 comprising an amino acid sequence selected from SEQ ID NOs: 86, 316, 326, and 336; and (f) HVR-L3 comprising an amino acid sequence selected from SEQ ID NOs: 87, 317, 327, and 337.

In some embodiments, an anti-Tau antibody comprises at least one, two, three, four, five, or six HVRs selected from (a) HVR-H1 comprising the amino acid sequence of SEQ ID NO: 32; (b) HVR-H2 comprising the amino acid sequence of SEQ ID NO: 33; (c) HVR-H3 comprising the amino acid sequence of SEQ ID NO: 34; (d) HVR-L1 comprising the amino acid sequence of SEQ ID NO: 35; (e) HVR-L2 comprising the amino acid sequence of SEQ ID NO: 36; and (f) HVR-L3 comprising the amino acid sequence of SEQ ID NO: 37.

In some embodiments, an anti-Tau antibody comprises at least one, two, three, four, five, or six HVRs selected from (a) HVR-H1 comprising the amino acid sequence of SEQ ID NO: 42; (b) HVR-H2 comprising the amino acid sequence of SEQ ID NO: 43; (c) HVR-H3 comprising the amino acid sequence of SEQ ID NO: 44; (d) HVR-L1 comprising the amino acid sequence of SEQ ID NO: 45; (e) HVR-L2 comprising the amino acid sequence of SEQ ID NO: 46; and (f) HVR-L3 comprising the amino acid sequence of SEQ ID NO: 47.

In some embodiments, an anti-Tau antibody comprises at least one, two, three, four, five, or six HVRs selected from (a) HVR-H1 comprising the amino acid sequence of SEQ ID NO: 52; (b) HVR-H2 comprising the amino acid sequence of SEQ ID NO: 53; (c) HVR-H3 comprising the amino acid sequence of SEQ ID NO: 54; (d) HVR-L1 comprising the amino acid sequence of SEQ ID NO: 55; (e) HVR-L2 comprising the amino acid sequence of SEQ ID NO: 56; and (f) HVR-L3 comprising the amino acid sequence of SEQ ID NO: 57.

In some embodiments, an anti-Tau antibody comprises at least one, two, three, four, five, or six HVRs selected from (a) HVR-H1 comprising the amino acid sequence of SEQ ID NO: 62; (b) HVR-H2 comprising the amino acid sequence of SEQ ID NO: 63; (c) HVR-H3 comprising the amino acid sequence of SEQ ID NO: 64; (d) HVR-L1 comprising the amino acid sequence of SEQ ID NO: 65; (e) HVR-L2 comprising the amino acid sequence of SEQ ID NO: 66; and (f) HVR-L3 comprising the amino acid sequence of SEQ ID NO: 67.

In some embodiments, an anti-Tau antibody comprises at least one, two, three, four, five, or six HVRs selected from (a) HVR-H1 comprising the amino acid sequence of SEQ ID NO: 72; (b) HVR-H2 comprising the amino acid sequence of SEQ ID NO: 73; (c) HVR-H3 comprising the amino acid sequence of SEQ ID NO: 74; (d) HVR-L1 comprising the amino acid sequence of SEQ ID NO: 75; (e) HVR-L2 comprising the amino acid sequence of SEQ ID NO: 76; and (f) HVR-L3 comprising the amino acid sequence of SEQ ID NO: 77.

In some embodiments, an anti-Tau antibody comprises at least one, two, three, four, five, or six HVRs selected from (a) HVR-H1 comprising the amino acid sequence of SEQ ID NO: 82; (b) HVR-H2 comprising the amino acid sequence of SEQ ID NO: 83; (c) HVR-H3 comprising the amino acid sequence of SEQ ID NO: 84; (d) HVR-L1 comprising the amino acid sequence of SEQ ID NO: 85; (e) HVR-L2 comprising the amino acid sequence of SEQ ID NO: 86; and (f) HVR-L3 comprising the amino acid sequence of SEQ ID NO: 87.

In some embodiments, an anti-Tau antibody comprises at least one, two, three, four, five, or six HVRs selected from (a) HVR-H1 comprising the amino acid sequence of SEQ ID NO: 92; (b) HVR-H2 comprising the amino acid sequence of SEQ ID NO: 93; (c) HVR-H3 comprising the amino acid sequence of SEQ ID NO: 94; (d) HVR-L1 comprising the amino acid sequence of SEQ ID NO: 95; (e) HVR-L2 comprising the amino acid sequence of SEQ ID NO: 96; and (f) HVR-L3 comprising the amino acid sequence of SEQ ID NO: 97.

In some embodiments, an anti-Tau antibody comprises at least one, two, three, four, five, or six HVRs selected from (a) HVR-H1 comprising the amino acid sequence of SEQ ID NO: 102; (b) HVR-H2 comprising the amino acid sequence of SEQ ID NO: 103; (c) HVR-H3 comprising the amino acid sequence of SEQ ID NO: 104; (d) HVR-L1 comprising the amino acid sequence of SEQ ID NO: 105; (e) HVR-L2 comprising the amino acid sequence of SEQ ID NO: 106; and (f) HVR-L3 comprising the amino acid sequence of SEQ ID NO: 107.

In some embodiments, an anti-Tau antibody comprises at least one, two, three, four, five, or six HVRs selected from (a) HVR-H1 comprising the amino acid sequence of SEQ ID NO: 112; (b) HVR-H2 comprising the amino acid sequence of SEQ ID NO: 113; (c) HVR-H3 comprising the amino acid sequence of SEQ ID NO: 114; (d) HVR-L1 comprising the amino acid sequence of SEQ ID NO: 115; (e) HVR-L2 comprising the amino acid sequence of SEQ ID NO: 116; and (f) HVR-L3 comprising the amino acid sequence of SEQ ID NO: 117.

In some embodiments, an anti-Tau antibody comprises at least one, two, three, four, five, or six HVRs selected from (a) HVR-H1 comprising the amino acid sequence of SEQ ID NO: 122; (b) HVR-H2 comprising the amino acid sequence of SEQ ID NO: 123; (c) HVR-H3 comprising the amino acid sequence of SEQ ID NO: 124; (d) HVR-L1 comprising the amino acid sequence of SEQ ID NO: 125; (e) HVR-L2 comprising the amino acid sequence of SEQ ID NO: 126; and (f) HVR-L3 comprising the amino acid sequence of SEQ ID NO: 127.

In some embodiments, an anti-Tau antibody comprises at least one, two, three, four, five, or six HVRs selected from (a) HVR-H1 comprising the amino acid sequence of SEQ ID NO: 132; (b) HVR-H2 comprising the amino acid sequence of SEQ ID NO: 133; (c) HVR-H3 comprising the amino acid sequence of SEQ ID NO: 134; (d) HVR-L1 comprising the amino acid sequence of SEQ ID NO: 135; (e) HVR-L2 comprising the amino acid sequence of SEQ ID NO: 136; and (f) HVR-L3 comprising the amino acid sequence of SEQ ID NO: 137.

In some embodiments, an anti-Tau antibody comprises at least one, two, three, four, five, or six HVRs selected from (a) HVR-H1 comprising the amino acid sequence of SEQ ID NO: 142; (b) HVR-H2 comprising the amino acid sequence of SEQ ID NO: 143; (c) HVR-H3 comprising the amino acid sequence of SEQ ID NO: 144; (d) HVR-L1 comprising the amino acid sequence of SEQ ID NO: 145; (e) HVR-L2 comprising the amino acid sequence of SEQ ID NO: 146; and (f) HVR-L3 comprising the amino acid sequence of SEQ ID NO: 147.

In some embodiments, an anti-Tau antibody comprises at least one, two, three, four, five, or six HVRs selected from (a) HVR-H1 comprising the amino acid sequence of SEQ ID NO: 152; (b) HVR-H2 comprising the amino acid sequence of SEQ ID NO: 153; (c) HVR-H3 comprising the amino acid sequence of SEQ ID NO: 154; (d) HVR-L1 comprising the amino acid sequence of SEQ ID NO: 155; (e) HVR-L2 comprising the amino acid sequence of SEQ ID NO: 156; and (f) HVR-L3 comprising the amino acid sequence of SEQ ID NO: 157.

In some embodiments, an anti-Tau antibody comprises at least one, two, three, four, five, or six HVRs selected from (a) HVR-H1 comprising the amino acid sequence of SEQ ID NO: 162; (b) HVR-H2 comprising the amino acid sequence of SEQ ID NO: 163; (c) HVR-H3 comprising the amino acid sequence of SEQ ID NO: 164; (d) HVR-L1 comprising the amino acid sequence of SEQ ID NO: 165; (e) HVR-L2 comprising the amino acid sequence of SEQ ID NO: 166; and (f) HVR-L3 comprising the amino acid sequence of SEQ ID NO: 167.

In some embodiments, an anti-Tau antibody comprises at least one, two, three, four, five, or six HVRs selected from (a) HVR-H1 comprising the amino acid sequence of SEQ ID NO: 172; (b) HVR-H2 comprising the amino acid sequence of SEQ ID NO: 173; (c) HVR-H3 comprising the amino acid sequence of SEQ ID NO: 174; (d) HVR-L1 comprising the amino acid sequence of SEQ ID NO: 175; (e) HVR-L2 comprising the amino acid sequence of SEQ ID NO: 176; and (f) HVR-L3 comprising the amino acid sequence of SEQ ID NO: 177.

In some embodiments, an anti-Tau antibody comprises at least one, two, three, four, five, or six HVRs selected from (a) HVR-H1 comprising the amino acid sequence of SEQ ID NO: 182; (b) HVR-H2 comprising the amino acid sequence of SEQ ID NO: 183; (c) HVR-H3 comprising the amino acid sequence of SEQ ID NO: 184; (d) HVR-L1 comprising the amino acid sequence of SEQ ID NO: 185; (e) HVR-L2 comprising the amino acid sequence of SEQ ID NO: 186; and (f) HVR-L3 comprising the amino acid sequence of SEQ ID NO: 187.

In some embodiments, an anti-Tau antibody comprises at least one, two, three, four, five, or six HVRs selected from (a) HVR-H1 comprising the amino acid sequence of SEQ ID NO: 192; (b) HVR-H2 comprising the amino acid sequence of SEQ ID NO: 193; (c) HVR-H3 comprising the amino acid sequence of SEQ ID NO: 194; (d) HVR-L1 comprising the amino acid sequence of SEQ ID NO: 195; (e) HVR-L2 comprising the amino acid sequence of SEQ ID NO: 196; and (f) HVR-L3 comprising the amino acid sequence of SEQ ID NO: 197.

In some embodiments, an anti-Tau antibody comprises at least one, two, three, four, five, or six HVRs selected from (a) HVR-H1 comprising the amino acid sequence of SEQ ID NO: 202; (b) HVR-H2 comprising the amino acid sequence of SEQ ID NO: 203; (c) HVR-H3 comprising the amino acid sequence of SEQ ID NO: 204; (d) HVR-L1 comprising the amino acid sequence of SEQ ID NO: 205; (e) HVR-L2 comprising the amino acid sequence of SEQ ID NO: 206; and (f) HVR-L3 comprising the amino acid sequence of SEQ ID NO: 207.

In some embodiments, an anti-Tau antibody comprises at least one, two, three, four, five, or six HVRs selected from (a) HVR-H1 comprising the amino acid sequence of SEQ ID NO: 212; (b) HVR-H2 comprising the amino acid sequence of SEQ ID NO: 213; (c) HVR-H3 comprising the amino acid sequence of SEQ ID NO: 214; (d) HVR-L1 comprising the amino acid sequence of SEQ ID NO: 215; (e) HVR-L2 comprising the amino acid sequence of SEQ ID NO: 216; and (f) HVR-L3 comprising the amino acid sequence of SEQ ID NO: 217.

In some embodiments, an anti-Tau antibody comprises at least one, two, three, four, five, or six HVRs selected from (a) HVR-H1 comprising the amino acid sequence of SEQ ID NO: 222; (b) HVR-H2 comprising the amino acid sequence of SEQ ID NO: 223; (c) HVR-H3 comprising the amino acid sequence of SEQ ID NO: 224; (d) HVR-L1 comprising the amino acid sequence of SEQ ID NO: 225; (e) HVR-L2 comprising the amino acid sequence of SEQ ID NO: 226; and (f) HVR-L3 comprising the amino acid sequence of SEQ ID NO: 227.

In some embodiments, an anti-Tau antibody comprises at least one, two, three, four, five, or six HVRs selected from (a) HVR-H1 comprising the amino acid sequence of SEQ ID NO: 232; (b) HVR-H2 comprising the amino acid sequence of SEQ ID NO: 233; (c) HVR-H3 comprising the amino acid sequence of SEQ ID NO: 234; (d) HVR-L1 comprising the amino acid sequence of SEQ ID NO: 235; (e) HVR-L2 comprising the amino acid sequence of SEQ ID NO: 236; and (f) HVR-L3 comprising the amino acid sequence of SEQ ID NO: 237.

In some embodiments, an anti-Tau antibody comprises at least one, two, three, four, five, or six HVRs selected from (a) HVR-H1 comprising the amino acid sequence of SEQ ID NO: 242; (b) HVR-H2 comprising the amino acid sequence of SEQ ID NO: 243; (c) HVR-H3 comprising the amino acid sequence of SEQ ID NO: 244; (d) HVR-L1 comprising the amino acid sequence of SEQ ID NO: 245; (e) HVR-L2 comprising the amino acid sequence of SEQ ID NO: 246; and (f) HVR-L3 comprising the amino acid sequence of SEQ ID NO: 247.

In some embodiments, an anti-Tau antibody comprises at least one, two, three, four, five, or six HVRs selected from (a) HVR-H1 comprising the amino acid sequence of SEQ ID NO: 252; (b) HVR-H2 comprising the amino acid sequence of SEQ ID NO: 253; (c) HVR-H3 comprising the amino acid sequence of SEQ ID NO: 254; (d) HVR-L1 comprising the amino acid sequence of SEQ ID NO: 255; (e) HVR-L2 comprising the amino acid sequence of SEQ ID NO: 256; and (f) HVR-L3 comprising the amino acid sequence of SEQ ID NO: 257.

In some embodiments, an anti-Tau antibody comprises at least one, two, three, four, five, or six HVRs selected from (a) HVR-H1 comprising the amino acid sequence of SEQ ID NO: 262; (b) HVR-H2 comprising the amino acid sequence of SEQ ID NO: 263; (c) HVR-H3 comprising the amino acid sequence of SEQ ID NO: 264; (d) HVR-L1 comprising the amino acid sequence of SEQ ID NO: 265; (e) HVR-L2 comprising the amino acid sequence of SEQ ID NO: 266; and (f) HVR-L3 comprising the amino acid sequence of SEQ ID NO: 267.

In some embodiments, an anti-Tau antibody comprises at least one, two, three, four, five, or six HVRs selected from (a) HVR-H1 comprising the amino acid sequence of SEQ ID NO: 272; (b) HVR-H2 comprising the amino acid sequence of SEQ ID NO: 273; (c) HVR-H3 comprising the amino acid sequence of SEQ ID NO: 274; (d) HVR-L1 comprising the amino acid sequence of SEQ ID NO: 275; (e) HVR-L2 comprising the amino acid sequence of SEQ ID NO: 276; and (f) HVR-L3 comprising the amino acid sequence of SEQ ID NO: 277.

In some embodiments, an anti-Tau antibody comprises at least one, two, three, four, five, or six HVRs selected from (a) HVR-H1 comprising the amino acid sequence of SEQ ID NO: 282; (b) HVR-H2 comprising the amino acid sequence of SEQ ID NO: 283; (c) HVR-H3 comprising the amino acid sequence of SEQ ID NO: 284; (d) HVR-L1 comprising the amino acid sequence of SEQ ID NO: 285; (e) HVR-L2 comprising the amino acid sequence of SEQ ID NO: 286; and (f) HVR-L3 comprising the amino acid sequence of SEQ ID NO: 287.

In some embodiments, an anti-Tau antibody comprises at least one, two, three, four, five, or six HVRs selected from (a) HVR-H1 comprising the amino acid sequence of SEQ ID NO: 292; (b) HVR-H2 comprising the amino acid sequence of SEQ ID NO: 293; (c) HVR-H3 comprising the amino acid sequence of SEQ ID NO: 294; (d) HVR-L1 comprising the amino acid sequence of SEQ ID NO: 295; (e) HVR-L2 comprising the amino acid sequence of SEQ ID NO: 296; and (f) HVR-L3 comprising the amino acid sequence of SEQ ID NO: 297.

In some embodiments, an anti-Tau antibody comprises at least one, two, three, four, five, or six HVRs selected from (a) HVR-H1 comprising the amino acid sequence of SEQ ID NO: 302; (b) HVR-H2 comprising the amino acid sequence of SEQ ID NO: 303; (c) HVR-H3 comprising the amino acid sequence of SEQ ID NO: 304; (d) HVR-L1 comprising the amino acid sequence of SEQ ID NO: 305; (e) HVR-L2 comprising the amino acid sequence of SEQ ID NO: 306; and (f) HVR-L3 comprising the amino acid sequence of SEQ ID NO: 307.

In some embodiments, an anti-Tau antibody comprises at least one, two, three, four, five, or six HVRs selected from (a) HVR-H1 comprising the amino acid sequence of SEQ ID NO: 312; (b) HVR-H2 comprising the amino acid sequence of SEQ ID NO: 313; (c) HVR-H3 comprising the amino acid sequence of SEQ ID NO: 314; (d) HVR-L1 comprising the amino acid sequence of SEQ ID NO: 315; (e) HVR-L2 comprising the amino acid sequence of SEQ ID NO: 316; and (f) HVR-L3 comprising the amino acid sequence of SEQ ID NO: 317.

In some embodiments, an anti-Tau antibody comprises at least one, two, three, four, five, or six HVRs selected from (a) HVR-H1 comprising the amino acid sequence of SEQ ID NO: 322; (b) HVR-H2 comprising the amino acid sequence of SEQ ID NO: 323; (c) HVR-H3 comprising the amino acid sequence of SEQ ID NO: 324; (d) HVR-L1 comprising the amino acid sequence of SEQ ID NO: 325; (e) HVR-L2 comprising the amino acid sequence of SEQ ID NO: 326; and (f) HVR-L3 comprising the amino acid sequence of SEQ ID NO: 327.

In some embodiments, an anti-Tau antibody comprises at least one, two, three, four, five, or six HVRs selected from (a) HVR-H1 comprising the amino acid sequence of SEQ ID NO: 332; (b) HVR-H2 comprising the amino acid sequence of SEQ ID NO: 333; (c) HVR-H3 comprising the amino acid sequence of SEQ ID NO: 334; (d) HVR-L1 comprising the amino acid sequence of SEQ ID NO: 335; (e) HVR-L2 comprising the amino acid sequence of SEQ ID NO: 336; and (f) HVR-L3 comprising the amino acid sequence of SEQ ID NO: 337.

In some embodiments, an anti-Tau antibody comprises at least one, two, or three HVRs selected from (a) HVR-H1 comprising an amino acid sequence selected from SEQ ID NOs: 12, 22, 282, 292, and 342; (b) HVR-H2 comprising an amino acid sequence selected from SEQ ID NOs: 13, 23, 283, 293, and 343; and (c) HVR-H3 comprising an amino acid sequence selected from SEQ ID NOs: 14, 24, 284, 294, and 344. In some embodiments, an anti-Tau antibody comprises (a) HVR-H1 comprising an amino acid sequence selected from SEQ ID NOs: 12, 22, 282, 292, and 342; (b) HVR-H2 comprising an amino acid sequence selected from SEQ ID NOs: 13, 23, 283, 293, and 343; and (c) HVR-H3 comprising an amino acid sequence selected from SEQ ID NOs: 14, 24, 284, 294, and 344.

In some embodiments, an anti-Tau antibody comprises (a) HVR-H1 comprising the amino acid sequence of SEQ ID NO: 342; (b) HVR-H2 comprising the amino acid sequence of SEQ ID NO: 343; and (c) HVR-H3 comprising the amino acid sequence of SEQ ID NO: 344. In some embodiments, an anti-Tau antibody comprises at least one, two, or three HVRs selected from (a) HVR-H1 comprising the amino acid sequence of SEQ ID NO: 342; (b) HVR-H2 comprising the amino acid sequence of SEQ ID NO: 343; and (c) HVR-H3 comprising the amino acid sequence of SEQ ID NO: 344.

In some embodiments, an anti-Tau antibody comprises at least one, two, or three HVRs selected from (a) HVR-H1 comprising an amino acid sequence selected from SEQ ID NOs: 72 and 302; (b) HVR-H2 comprising an amino acid sequence selected from SEQ ID NOs: 73 and 303; and (c) HVR-H3 comprising an amino acid sequence selected from SEQ ID NOs: 74 and 304. In some embodiments, an anti-Tau antibody comprises (a) HVR-H1 comprising an amino acid sequence selected from SEQ ID NOs: 72 and 302; (b) HVR-H2 comprising an amino acid sequence selected from SEQ ID NOs: 73 and 303; and (c) HVR-H3 comprising an amino acid sequence selected from SEQ ID NOs: 74 and 304.

In some embodiments, an anti-Tau antibody comprises at least one, two, or three HVRs selected from (a) HVR-H1 comprising an amino acid sequence selected from SEQ ID NOs: 82, 312, 322, and 332; (b) HVR-H2 comprising an amino acid sequence selected from SEQ ID NOs: 83, 313, 323, and 333; and (c) HVR-H3 comprising an amino acid sequence selected from SEQ ID NOs: 84, 314, 324, and 334. In some embodiments, an anti-Tau antibody comprises (a) HVR-H1 comprising an amino acid sequence selected from SEQ ID NOs: 82, 312, 322, and 332; (b) HVR-H2 comprising an amino acid sequence selected from SEQ ID NOs: 83, 313, 323, and 333; and (c) HVR-H3 comprising an amino acid sequence selected from SEQ ID NOs: 84, 314, 324, and 334.

In some embodiments, an anti-Tau antibody comprises at least one, two, or three HVRs selected from (a) HVR-H1 comprising the amino acid sequence of SEQ ID NO: 32; (b) HVR-H2 comprising the amino acid sequence of SEQ ID NO: 33; and (c) HVR-H3 comprising the amino acid sequence of SEQ ID NO: 34. In some embodiments, an anti-Tau antibody comprises (a) HVR-H1 comprising the amino acid sequence of SEQ ID NO: 32; (b) HVR-H2 comprising the amino acid sequence of SEQ ID NO: 33; and (c) HVR-H3 comprising the amino acid sequence of SEQ ID NO: 34.

In some embodiments, an anti-Tau antibody comprises at least one, two, or three HVRs selected from (a) HVR-H1 comprising the amino acid sequence of SEQ ID NO: 42; (b) HVR-H2 comprising the amino acid sequence of SEQ ID NO: 43; and (c) HVR-H3 comprising the amino acid sequence of SEQ ID NO: 44. In some embodiments, an anti-Tau antibody comprises (a) HVR-H1 comprising the amino acid sequence of SEQ ID NO: 42; (b) HVR-H2 comprising the amino acid sequence of SEQ ID NO: 43; and (c) HVR-H3 comprising the amino acid sequence of SEQ ID NO: 44.

In some embodiments, an anti-Tau antibody comprises at least one, two, or three HVRs selected from (a) HVR-H1 comprising the amino acid sequence of SEQ ID NO: 52; (b) HVR-H2 comprising the amino acid sequence of SEQ ID NO: 53; and (c) HVR-H3 comprising the amino acid sequence of SEQ ID NO: 54. In some embodiments, an anti-Tau antibody comprises (a) HVR-H1 comprising the amino acid sequence of SEQ ID NO: 52; (b) HVR-H2 comprising the amino acid sequence of SEQ ID NO: 53; and (c) HVR-H3 comprising the amino acid sequence of SEQ ID NO: 54.

In some embodiments, an anti-Tau antibody comprises at least one, two, or three HVRs selected from (a) HVR-H1 comprising the amino acid sequence of SEQ ID NO: 62; (b) HVR-H2 comprising the amino acid sequence of SEQ ID NO: 63; and (c) HVR-H3 comprising the amino acid sequence of SEQ ID NO: 64. In some embodiments, an anti-Tau antibody comprises (a) HVR-H1 comprising the amino acid sequence of SEQ ID NO: 62; (b) HVR-H2 comprising the amino acid sequence of SEQ ID NO: 63; and (c) HVR-H3 comprising the amino acid sequence of SEQ ID NO: 64.

In some embodiments, an anti-Tau antibody comprises at least one, two, or three HVRs selected from (a) HVR-H1 comprising the amino acid sequence of SEQ ID NO: 72; (b) HVR-H2 comprising the amino acid sequence of SEQ ID NO: 73; and (c) HVR-H3 comprising the amino acid sequence of SEQ ID NO: 74. In some embodiments, an anti-Tau antibody comprises (a) HVR-H1 comprising the amino acid sequence of SEQ ID NO: 72; (b) HVR-H2 comprising the amino acid sequence of SEQ ID NO: 73; and (c) HVR-H3 comprising the amino acid sequence of SEQ ID NO: 74.

In some embodiments, an anti-Tau antibody comprises at least one, two, or three HVRs selected from (a) HVR-H1 comprising the amino acid sequence of SEQ ID NO: 82; (b) HVR-H2 comprising the amino acid sequence of SEQ ID NO: 83; and (c) HVR-H3 comprising the amino acid sequence of SEQ ID NO: 84. In some embodiments, an anti-Tau antibody comprises (a) HVR-H1 comprising the amino acid sequence of SEQ ID NO: 82; (b) HVR-H2 comprising the amino acid sequence of SEQ ID NO: 83; and (c) HVR-H3 comprising the amino acid sequence of SEQ ID NO: 84.

In some embodiments, an anti-Tau antibody comprises at least one, two, or three HVRs selected from (a) HVR-H1 comprising the amino acid sequence of SEQ ID NO: 92; (b) HVR-H2 comprising the amino acid sequence of SEQ ID NO: 93; and (c) HVR-H3 comprising the amino acid sequence of SEQ ID NO: 94. In some embodiments, an anti-Tau antibody comprises (a) HVR-H1 comprising the amino acid sequence of SEQ ID NO: 92; (b) HVR-H2 comprising the amino acid sequence of SEQ ID NO: 93; and (c) HVR-H3 comprising the amino acid sequence of SEQ ID NO: 94.

In some embodiments, an anti-Tau antibody comprises at least one, two, or three HVRs selected from (a) HVR-H1 comprising the amino acid sequence of SEQ ID NO: 102; (b) HVR-H2 comprising the amino acid sequence of SEQ ID NO: 103; and (c) HVR-H3 comprising the amino acid sequence of SEQ ID NO: 104. In some embodiments, an anti-Tau antibody comprises (a) HVR-H1 comprising the amino acid sequence of SEQ ID NO: 102; (b) HVR-H2 comprising the amino acid sequence of SEQ ID NO: 103; and (c) HVR-H3 comprising the amino acid sequence of SEQ ID NO: 104.

In some embodiments, an anti-Tau antibody comprises at least one, two, or three HVRs selected from (a) HVR-H1 comprising the amino acid sequence of SEQ ID NO: 112; (b) HVR-H2 comprising the amino acid sequence of SEQ ID NO: 113; and (c) HVR-H3 comprising the amino acid sequence of SEQ ID NO: 114. In some embodiments, an anti-Tau antibody comprises (a) HVR-H1 comprising the amino acid sequence of SEQ ID NO: 112; (b) HVR-H2 comprising the amino acid sequence of SEQ ID NO: 113; and (c) HVR-H3 comprising the amino acid sequence of SEQ ID NO: 114.

In some embodiments, an anti-Tau antibody comprises at least one, two, or three HVRs selected from (a) HVR-H1 comprising the amino acid sequence of SEQ ID NO: 122; (b) HVR-H2 comprising the amino acid sequence of SEQ ID NO: 123; and (c) HVR-H3 comprising the amino acid sequence of SEQ ID NO: 124. In some embodiments, an anti-Tau antibody comprises (a) HVR-H1 comprising the amino acid sequence of SEQ ID NO: 122; (b) HVR-H2 comprising the amino acid sequence of SEQ ID NO: 123; and (c) HVR-H3 comprising the amino acid sequence of SEQ ID NO: 124.

In some embodiments, an anti-Tau antibody comprises at least one, two, or three HVRs selected from (a) HVR-H1 comprising the amino acid sequence of SEQ ID NO: 132; (b) HVR-H2 comprising the amino acid sequence of SEQ ID NO: 133; and (c) HVR-H3 comprising the amino acid sequence of SEQ ID NO: 134. In some embodiments, an anti-Tau antibody comprises (a) HVR-H1 comprising the amino acid sequence of SEQ ID NO: 132; (b) HVR-H2 comprising the amino acid sequence of SEQ ID NO: 133; and (c) HVR-H3 comprising the amino acid sequence of SEQ ID NO: 134.

In some embodiments, an anti-Tau antibody comprises at least one, two, or three HVRs selected from (a) HVR-H1 comprising the amino acid sequence of SEQ ID NO: 142; (b) HVR-H2 comprising the amino acid sequence of SEQ ID NO: 143; and (c) HVR-H3 comprising the amino acid sequence of SEQ ID NO: 144. In some embodiments, an anti-Tau antibody comprises (a) HVR-H1 comprising the amino acid sequence of SEQ ID NO: 142; (b) HVR-H2 comprising the amino acid sequence of SEQ ID NO: 143; and (c) HVR-H3 comprising the amino acid sequence of SEQ ID NO: 144.

In some embodiments, an anti-Tau antibody comprises at least one, two, or three HVRs selected from (a) HVR-H1 comprising the amino acid sequence of SEQ ID NO: 152; (b) HVR-H2 comprising the amino acid sequence of SEQ ID NO: 153; and (c) HVR-H3 comprising the amino acid sequence of SEQ ID NO: 154. In some embodiments, an anti-Tau antibody comprises (a) HVR-H1 comprising the amino acid sequence of SEQ ID NO: 152; (b) HVR-H2 comprising the amino acid sequence of SEQ ID NO: 153; and (c) HVR-H3 comprising the amino acid sequence of SEQ ID NO: 154.

In some embodiments, an anti-Tau antibody comprises at least one, two, or three HVRs selected from (a) HVR-H1 comprising the amino acid sequence of SEQ ID NO: 162; (b) HVR-H2 comprising the amino acid sequence of SEQ ID NO: 163; and (c) HVR-H3 comprising the amino acid sequence of SEQ ID NO: 164. In some embodiments, an anti-Tau antibody comprises (a) HVR-H1 comprising the amino acid sequence of SEQ ID NO: 162; (b) HVR-H2 comprising the amino acid sequence of SEQ ID NO: 163; and (c) HVR-H3 comprising the amino acid sequence of SEQ ID NO: 164.

In some embodiments, an anti-Tau antibody comprises at least one, two, or three HVRs selected from (a) HVR-H1 comprising the amino acid sequence of SEQ ID NO: 172; (b) HVR-H2 comprising the amino acid sequence of SEQ ID NO: 173; and (c) HVR-H3 comprising the amino acid sequence of SEQ ID NO: 174. In some embodiments, an anti-Tau antibody comprises (a) HVR-H1 comprising the amino acid sequence of SEQ ID NO: 172; (b) HVR-H2 comprising the amino acid sequence of SEQ ID NO: 173; and (c) HVR-H3 comprising the amino acid sequence of SEQ ID NO: 174.

In some embodiments, an anti-Tau antibody comprises at least one, two, or three HVRs selected from (a) HVR-H1 comprising the amino acid sequence of SEQ ID NO: 182; (b) HVR-H2 comprising the amino acid sequence of SEQ ID NO: 183; and (c) HVR-H3 comprising the amino acid sequence of SEQ ID NO: 184. In some embodiments, an anti-Tau antibody comprises (a) HVR-H1 comprising the amino acid sequence of SEQ ID NO: 182; (b) HVR-H2 comprising the amino acid sequence of SEQ ID NO: 183; and (c) HVR-H3 comprising the amino acid sequence of SEQ ID NO: 184.

In some embodiments, an anti-Tau antibody comprises at least one, two, or three HVRs selected from (a) HVR-H1 comprising the amino acid sequence of SEQ ID NO: 192; (b) HVR-H2 comprising the amino acid sequence of SEQ ID NO: 193; and (c) HVR-H3 comprising the amino acid sequence of SEQ ID NO: 194. In some embodiments, an anti-Tau antibody comprises (a) HVR-H1 comprising the amino acid sequence of SEQ ID NO: 192; (b) HVR-H2 comprising the amino acid sequence of SEQ ID NO: 193; and (c) HVR-H3 comprising the amino acid sequence of SEQ ID NO: 194.

In some embodiments, an anti-Tau antibody comprises at least one, two, or three HVRs selected from (a) HVR-H1 comprising the amino acid sequence of SEQ ID NO: 202; (b) HVR-H2 comprising the amino acid sequence of SEQ ID NO: 203; and (c) HVR-H3 comprising the amino acid sequence of SEQ ID NO: 204. In some embodiments, an anti-Tau antibody comprises (a) HVR-H1 comprising the amino acid sequence of SEQ ID NO: 202; (b) HVR-H2 comprising the amino acid sequence of SEQ ID NO: 203; and (c) HVR-H3 comprising the amino acid sequence of SEQ ID NO: 204.

In some embodiments, an anti-Tau antibody comprises at least one, two, or three HVRs selected from (a) HVR-H1 comprising the amino acid sequence of SEQ ID NO: 212; (b) HVR-H2 comprising the amino acid sequence of SEQ ID NO: 213; and (c) HVR-H3 comprising the amino acid sequence of SEQ ID NO: 214. In some embodiments, an anti-Tau antibody comprises (a) HVR-H1 comprising the amino acid sequence of SEQ ID NO: 212; (b) HVR-H2 comprising the amino acid sequence of SEQ ID NO: 213; and (c) HVR-H3 comprising the amino acid sequence of SEQ ID NO: 214.

In some embodiments, an anti-Tau antibody comprises at least one, two, or three HVRs selected from (a) HVR-H1 comprising the amino acid sequence of SEQ ID NO: 222; (b) HVR-H2 comprising the amino acid sequence of SEQ ID NO: 223; and (c) HVR-H3 comprising the amino acid sequence of SEQ ID NO: 224. In some embodiments, an anti-Tau antibody comprises (a) HVR-H1 comprising the amino acid sequence of SEQ ID NO: 222; (b) HVR-H2 comprising the amino acid sequence of SEQ ID NO: 223; and (c) HVR-H3 comprising the amino acid sequence of SEQ ID NO: 224.

In some embodiments, an anti-Tau antibody comprises at least one, two, or three HVRs selected from (a) HVR-H1 comprising the amino acid sequence of SEQ ID NO: 232; (b) HVR-H2 comprising the amino acid sequence of SEQ ID NO: 233; and (c) HVR-H3 comprising the amino acid sequence of SEQ ID NO: 234. In some embodiments, an anti-Tau antibody comprises (a) HVR-H1 comprising the amino acid sequence of SEQ ID NO: 232; (b) HVR-H2 comprising the amino acid sequence of SEQ ID NO: 233; and (c) HVR-H3 comprising the amino acid sequence of SEQ ID NO: 234.

In some embodiments, an anti-Tau antibody comprises at least one, two, or three HVRs selected from (a) HVR-H1 comprising the amino acid sequence of SEQ ID NO: 242; (b) HVR-H2 comprising the amino acid sequence of SEQ ID NO: 243; and (c) HVR-H3 comprising the amino acid sequence of SEQ ID NO: 244. In some embodiments, an anti-Tau antibody comprises (a) HVR-H1 comprising the amino acid sequence of SEQ ID NO: 242; (b) HVR-H2 comprising the amino acid sequence of SEQ ID NO: 243; and (c) HVR-H3 comprising the amino acid sequence of SEQ ID NO: 244.

In some embodiments, an anti-Tau antibody comprises at least one, two, or three HVRs selected from (a) HVR-H1 comprising the amino acid sequence of SEQ ID NO: 252; (b) HVR-H2 comprising the amino acid sequence of SEQ ID NO: 253; and (c) HVR-H3 comprising the amino acid sequence of SEQ ID NO: 254. In some embodiments, an anti-Tau antibody comprises (a) HVR-H1 comprising the amino acid sequence of SEQ ID NO: 252; (b) HVR-H2 comprising the amino acid sequence of SEQ ID NO: 253; and (c) HVR-H3 comprising the amino acid sequence of SEQ ID NO: 254.

In some embodiments, an anti-Tau antibody comprises at least one, two, or three HVRs selected from (a) HVR-H1 comprising the amino acid sequence of SEQ ID NO: 262; (b) HVR-H2 comprising the amino acid sequence of SEQ ID NO: 263; and (c) HVR-H3 comprising the amino acid sequence of SEQ ID NO: 264. In some embodiments, an anti-Tau antibody comprises (a) HVR-H1 comprising the amino acid sequence of SEQ ID NO: 262; (b) HVR-H2 comprising the amino acid sequence of SEQ ID NO: 263; and (c) HVR-H3 comprising the amino acid sequence of SEQ ID NO: 264.

In some embodiments, an anti-Tau antibody comprises at least one, two, or three HVRs selected from (a) HVR-H1 comprising the amino acid sequence of SEQ ID NO: 272; (b) HVR-H2 comprising the amino acid sequence of SEQ ID NO: 273; and (c) HVR-H3 comprising the amino acid sequence of SEQ ID NO: 274. In some embodiments, an anti-Tau antibody comprises (a) HVR-H1 comprising the amino acid sequence of SEQ ID NO: 272; (b) HVR-H2 comprising the amino acid sequence of SEQ ID NO: 273; and (c) HVR-H3 comprising the amino acid sequence of SEQ ID NO: 274.

In some embodiments, an anti-Tau antibody comprises at least one, two, or three HVRs selected from (a) HVR-H1 comprising the amino acid sequence of SEQ ID NO: 282; (b) HVR-H2 comprising the amino acid sequence of SEQ ID NO: 283; and (c) HVR-H3 comprising the amino acid sequence of SEQ ID NO: 284. In some embodiments, an anti-Tau antibody comprises (a) HVR-H1 comprising the amino acid sequence of SEQ ID NO: 282; (b) HVR-H2 comprising the amino acid sequence of SEQ ID NO: 283; and (c) HVR-H3 comprising the amino acid sequence of SEQ ID NO: 284.

In some embodiments, an anti-Tau antibody comprises at least one, two, or three HVRs selected from (a) HVR-H1 comprising the amino acid sequence of SEQ ID NO: 292; (b) HVR-H2 comprising the amino acid sequence of SEQ ID NO: 293; and (c) HVR-H3 comprising the amino acid sequence of SEQ ID NO: 294. In some embodiments, an anti-Tau antibody comprises (a) HVR-H1 comprising the amino acid sequence of SEQ ID NO: 292; (b) HVR-H2 comprising the amino acid sequence of SEQ ID NO: 293; and (c) HVR-H3 comprising the amino acid sequence of SEQ ID NO: 294.

In some embodiments, an anti-Tau antibody comprises at least one, two, or three HVRs selected from (a) HVR-H1 comprising the amino acid sequence of SEQ ID NO: 302; (b) HVR-H2 comprising the amino acid sequence of SEQ ID NO: 303; and (c) HVR-H3 comprising the amino acid sequence of SEQ ID NO: 304. In some embodiments, an anti-Tau antibody comprises (a) HVR-H1 comprising the amino acid sequence of SEQ ID NO: 302; (b) HVR-H2 comprising the amino acid sequence of SEQ ID NO: 303; and (c) HVR-H3 comprising the amino acid sequence of SEQ ID NO: 304.

In some embodiments, an anti-Tau antibody comprises at least one, two, or three HVRs selected from (a) HVR-H1 comprising the amino acid sequence of SEQ ID NO: 312; (b) HVR-H2 comprising the amino acid sequence of SEQ ID NO: 313; and (c) HVR-H3 comprising the amino acid sequence of SEQ ID NO: 314. In some embodiments, an anti-Tau antibody comprises (a) HVR-H1 comprising the amino acid sequence of SEQ ID NO: 312; (b) HVR-H2 comprising the amino acid sequence of SEQ ID NO: 313; and (c) HVR-H3 comprising the amino acid sequence of SEQ ID NO: 314.

In some embodiments, an anti-Tau antibody comprises at least one, two, or three HVRs selected from (a) HVR-H1 comprising the amino acid sequence of SEQ ID NO: 322; (b) HVR-H2 comprising the amino acid sequence of SEQ ID NO: 323; and (c) HVR-H3 comprising the amino acid sequence of SEQ ID NO: 324. In some embodiments, an anti-Tau antibody comprises (a) HVR-H1 comprising the amino acid sequence of SEQ ID NO: 322; (b) HVR-H2 comprising the amino acid sequence of SEQ ID NO: 323; and (c) HVR-H3 comprising the amino acid sequence of SEQ ID NO: 324.

In some embodiments, an anti-Tau antibody comprises at least one, two, or three HVRs selected from (a) HVR-H1 comprising the amino acid sequence of SEQ ID NO: 332; (b) HVR-H2 comprising the amino acid sequence of SEQ ID NO: 333; and (c) HVR-H3 comprising the amino acid sequence of SEQ ID NO: 334. In some embodiments, an anti-Tau antibody comprises (a) HVR-H1 comprising the amino acid sequence of SEQ ID NO: 332; (b) HVR-H2 comprising the amino acid sequence of SEQ ID NO: 333; and (c) HVR-H3 comprising the amino acid sequence of SEQ ID NO: 334.

In some embodiments, an anti-Tau antibody comprises at least one, two, or three HVRs selected from (a) HVR-L1 comprising an amino acid sequence selected from SEQ ID NOs: 15, 25, 285, 295, 345, and 468 to 556; (b) HVR-L2 comprising an amino acid sequence selected from SEQ ID NOs: 16, 26, 286, 296, and 346; and (c) HVR-L3 comprising an amino acid sequence selected from SEQ ID NOs: 17, 27, 287, 297, and 347. In some embodiments, an anti-Tau antibody comprises (a) HVR-L1 comprising an amino acid sequence selected from SEQ ID NOs: 15, 25, 285, 295, 345, and 468 to 556; (b) HVR-L2 comprising an amino acid sequence selected from SEQ ID NOs: 16, 26, 286, 296, and 346; and (c) HVR-L3 comprising an amino acid sequence selected from SEQ ID NOs: 17, 27, 287, 297, and 347.

In some embodiments, an anti-Tau antibody comprises at least one, two, or three HVRs selected from (a) HVR-L1 comprising the amino acid sequence of SEQ ID NO: 345; (b) HVR-L2 comprising the amino acid sequence of SEQ ID NO: 346; and (c) HVR-L3 comprising the amino acid sequence of SEQ ID NO: 347. In some embodiments, an anti-Tau antibody comprises (a) HVR-L1 comprising the amino acid sequence of SEQ ID NO: 345; (b) HVR-L2 comprising the amino acid sequence of SEQ ID NO: 346; and (c) HVR-L3 comprising the amino acid sequence of SEQ ID NO: 347.

In some embodiments, an anti-Tau antibody comprises at least one, two, or three HVRs selected from (a) HVR-L1 comprising an amino acid sequence selected from SEQ ID NOs: 75 and 305; (b) HVR-L2 comprising an amino acid sequence selected from SEQ ID NOs: 76 and 306; and (c) HVR-L3 comprising an amino acid sequence selected from SEQ ID NOs: 77 and 307. In some embodiments, an anti-Tau antibody comprises (a) HVR-L1 comprising an amino acid sequence selected from SEQ ID NOs: 75 and 305; (b) HVR-L2 comprising an amino acid sequence selected from SEQ ID NOs: 76 and 306; and (c) HVR-L3 comprising an amino acid sequence selected from SEQ ID NOs: 77 and 307.

In some embodiments, an anti-Tau antibody comprises at least one, two, or three HVRs selected from (a) HVR-L1 comprising an amino acid sequence selected from SEQ ID NOs: 85, 315, 325, and 335; (b) HVR-L2 comprising an amino acid sequence selected from SEQ ID NOs: 86, 316, 326, and 336; and (c) HVR-L3 comprising an amino acid sequence selected from SEQ ID NOs: 87, 317, 327, and 337. In some embodiments, an anti-Tau antibody comprises (a) HVR-L1 comprising an amino acid sequence selected from SEQ ID NOs: 85, 315, 325, and 335; (b) HVR-L2 comprising an amino acid sequence selected from SEQ ID NOs: 86, 316, 326, and 336; and (c) HVR-L3 comprising an amino acid sequence selected from SEQ ID NOs: 87, 317, 327, and 337.

In some embodiments, an anti-Tau antibody comprises at least one, two, or three HVRs selected from (a) HVR-L1 comprising the amino acid sequence of SEQ ID NO: 35; (b) HVR-L2 comprising the amino acid sequence of SEQ ID NO: 36; and (c) HVR-L3 comprising the amino acid sequence of SEQ ID NO: 37. In some embodiments, an anti-Tau antibody comprises (a) HVR-L1 comprising the amino acid sequence of SEQ ID NO: 35; (b) HVR-L2 comprising the amino acid sequence of SEQ ID NO: 36; and (c) HVR-L3 comprising the amino acid sequence of SEQ ID NO: 37.

In some embodiments, an anti-Tau antibody comprises at least one, two, or three HVRs selected from (a) HVR-L1 comprising the amino acid sequence of SEQ ID NO: 45; (b) HVR-L2 comprising the amino acid sequence of SEQ ID NO: 46; and (c) HVR-L3 comprising the amino acid sequence of SEQ ID NO: 47. In some embodiments, an anti-Tau antibody comprises (a) HVR-L1 comprising the amino acid sequence of SEQ ID NO: 45; (b) HVR-L2 comprising the amino acid sequence of SEQ ID NO: 46; and (c) HVR-L3 comprising the amino acid sequence of SEQ ID NO: 47.

In some embodiments, an anti-Tau antibody comprises at least one, two, or three HVRs selected from (a) HVR-L1 comprising the amino acid sequence of SEQ ID NO: 55; (b) HVR-L2 comprising the amino acid sequence of SEQ ID NO: 56; and (c) HVR-L3 comprising the amino acid sequence of SEQ ID NO: 57. In some embodiments, an anti-Tau antibody comprises (a) HVR-L1 comprising the amino acid sequence of SEQ ID NO: 55; (b) HVR-L2 comprising the amino acid sequence of SEQ ID NO: 56; and (c) HVR-L3 comprising the amino acid sequence of SEQ ID NO: 57.

In some embodiments, an anti-Tau antibody comprises at least one, two, or three HVRs selected from (a) HVR-L1 comprising the amino acid sequence of SEQ ID NO: 65; (b) HVR-L2 comprising the amino acid sequence of SEQ ID NO: 66; and (c) HVR-L3 comprising the amino acid sequence of SEQ ID NO: 67. In some embodiments, an anti-Tau antibody comprises (a) HVR-L1 comprising the amino acid sequence of SEQ ID NO: 65; (b) HVR-L2 comprising the amino acid sequence of SEQ ID NO: 66; and (c) HVR-L3 comprising the amino acid sequence of SEQ ID NO: 67.

In some embodiments, an anti-Tau antibody comprises at least one, two, or three HVRs selected from (a) HVR-L1 comprising the amino acid sequence of SEQ ID NO: 75; (b) HVR-L2 comprising the amino acid sequence of SEQ ID NO: 76; and (c) HVR-L3 comprising the amino acid sequence of SEQ ID NO: 77. In some embodiments, an anti-Tau antibody comprises (a) HVR-L1 comprising the amino acid sequence of SEQ ID NO: 75; (b) HVR-L2 comprising the amino acid sequence of SEQ ID NO: 76; and (c) HVR-L3 comprising the amino acid sequence of SEQ ID NO: 77.

In some embodiments, an anti-Tau antibody comprises at least one, two, or three HVRs selected from (a) HVR-L1 comprising the amino acid sequence of SEQ ID NO: 85; (b) HVR-L2 comprising the amino acid sequence of SEQ ID NO: 86; and (c) HVR-L3 comprising the amino acid sequence of SEQ ID NO: 87. In some embodiments, an anti-Tau antibody comprises (a) HVR-L1 comprising the amino acid sequence of SEQ ID NO: 85; (b) HVR-L2 comprising the amino acid sequence of SEQ ID NO: 86; and (c) HVR-L3 comprising the amino acid sequence of SEQ ID NO: 87.

In some embodiments, an anti-Tau antibody comprises at least one, two, or three HVRs selected from (a) HVR-L1 comprising the amino acid sequence of SEQ ID NO: 95; (b) HVR-L2 comprising the amino acid sequence of SEQ ID NO: 96; and (c) HVR-L3 comprising the amino acid sequence of SEQ ID NO: 97. In some embodiments, an anti-Tau antibody comprises (a) HVR-L1 comprising the amino acid sequence of SEQ ID NO: 95; (b) HVR-L2 comprising the amino acid sequence of SEQ ID NO: 96; and (c) HVR-L3 comprising the amino acid sequence of SEQ ID NO: 97.

In some embodiments, an anti-Tau antibody comprises at least one, two, or three HVRs selected from (a) HVR-L1 comprising the amino acid sequence of SEQ ID NO: 105; (b) HVR-L2 comprising the amino acid sequence of SEQ ID NO: 106; and (c) HVR-L3 comprising the amino acid sequence of SEQ ID NO: 107. In some embodiments, an anti-Tau antibody comprises (a) HVR-L1 comprising the amino acid sequence of SEQ ID NO: 105; (b) HVR-L2 comprising the amino acid sequence of SEQ ID NO: 106; and (c) HVR-L3 comprising the amino acid sequence of SEQ ID NO: 107.

In some embodiments, an anti-Tau antibody comprises at least one, two, or three HVRs selected from (a) HVR-L1 comprising the amino acid sequence of SEQ ID NO: 115; (b) HVR-L2 comprising the amino acid sequence of SEQ ID NO: 116; and (c) HVR-L3 comprising the amino acid sequence of SEQ ID NO: 117. In some embodiments, an anti-Tau antibody comprises (a) HVR-L1 comprising the amino acid sequence of SEQ ID NO: 115; (b) HVR-L2 comprising the amino acid sequence of SEQ ID NO: 116; and (c) HVR-L3 comprising the amino acid sequence of SEQ ID NO: 117.

In some embodiments, an anti-Tau antibody comprises at least one, two, or three HVRs selected from (a) HVR-L1 comprising the amino acid sequence of SEQ ID NO: 125; (b) HVR-L2 comprising the amino acid sequence of SEQ ID NO: 126; and (c) HVR-L3 comprising the amino acid sequence of SEQ ID NO: 127. In some embodiments, an anti-Tau antibody comprises (a) HVR-L1 comprising the amino acid sequence of SEQ ID NO: 125; (b) HVR-L2 comprising the amino acid sequence of SEQ ID NO: 126; and (c) HVR-L3 comprising the amino acid sequence of SEQ ID NO: 127.

In some embodiments, an anti-Tau antibody comprises at least one, two, or three HVRs selected from (a) HVR-L1 comprising the amino acid sequence of SEQ ID NO: 135; (b) HVR-L2 comprising the amino acid sequence of SEQ ID NO: 136; and (c) HVR-L3 comprising the amino acid sequence of SEQ ID NO: 137. In some embodiments, an anti-Tau antibody comprises (a) HVR-L1 comprising the amino acid sequence of SEQ ID NO: 135; (b) HVR-L2 comprising the amino acid sequence of SEQ ID NO: 136; and (c) HVR-L3 comprising the amino acid sequence of SEQ ID NO: 137.

In some embodiments, an anti-Tau antibody comprises at least one, two, or three HVRs selected from (a) HVR-L1 comprising the amino acid sequence of SEQ ID NO: 145; (b) HVR-L2 comprising the amino acid sequence of SEQ ID NO: 146; and (c) HVR-L3 comprising the amino acid sequence of SEQ ID NO: 147. In some embodiments, an anti-Tau antibody comprises (a) HVR-L1 comprising the amino acid sequence of SEQ ID NO: 145; (b) HVR-L2 comprising the amino acid sequence of SEQ ID NO: 146; and (c) HVR-L3 comprising the amino acid sequence of SEQ ID NO: 147.

In some embodiments, an anti-Tau antibody comprises at least one, two, or three HVRs selected from (a) HVR-L1 comprising the amino acid sequence of SEQ ID NO: 155; (b) HVR-L2 comprising the amino acid sequence of SEQ ID NO: 156; and (c) HVR-L3 comprising the amino acid sequence of SEQ ID NO: 157. In some embodiments, an anti-Tau antibody comprises (a) HVR-L1 comprising the amino acid sequence of SEQ ID NO: 155; (b) HVR-L2 comprising the amino acid sequence of SEQ ID NO: 156; and (c) HVR-L3 comprising the amino acid sequence of SEQ ID NO: 157.

In some embodiments, an anti-Tau antibody comprises at least one, two, or three HVRs selected from (a) HVR-L1 comprising the amino acid sequence of SEQ ID NO: 165; (b) HVR-L2 comprising the amino acid sequence of SEQ ID NO: 166; and (c) HVR-L3 comprising the amino acid sequence of SEQ ID NO: 167. In some embodiments, an anti-Tau antibody comprises (a) HVR-L1 comprising the amino acid sequence of SEQ ID NO: 165; (b) HVR-L2 comprising the amino acid sequence of SEQ ID NO: 166; and (c) HVR-L3 comprising the amino acid sequence of SEQ ID NO: 167.

In some embodiments, an anti-Tau antibody comprises at least one, two, or three HVRs selected from (a) HVR-L1 comprising the amino acid sequence of SEQ ID NO: 175; (b) HVR-L2 comprising the amino acid sequence of SEQ ID NO: 176; and (c) HVR-L3 comprising the amino acid sequence of SEQ ID NO: 177. In some embodiments, an anti-Tau antibody comprises (a) HVR-L1 comprising the amino acid sequence of SEQ ID NO: 175; (b) HVR-L2 comprising the amino acid sequence of SEQ ID NO: 176; and (c) HVR-L3 comprising the amino acid sequence of SEQ ID NO: 177.

In some embodiments, an anti-Tau antibody comprises at least one, two, or three HVRs selected from (a) HVR-L1 comprising the amino acid sequence of SEQ ID NO: 185; (b) HVR-L2 comprising the amino acid sequence of SEQ ID NO: 186; and (c) HVR-L3 comprising the amino acid sequence of SEQ ID NO: 187. In some embodiments, an anti-Tau antibody comprises (a) HVR-L1 comprising the amino acid sequence of SEQ ID NO: 185; (b) HVR-L2 comprising the amino acid sequence of SEQ ID NO: 186; and (c) HVR-L3 comprising the amino acid sequence of SEQ ID NO: 187.

In some embodiments, an anti-Tau antibody comprises at least one, two, or three HVRs selected from (a) HVR-L1 comprising the amino acid sequence of SEQ ID NO: 195; (b) HVR-L2 comprising the amino acid sequence of SEQ ID NO: 196; and (c) HVR-L3 comprising the amino acid sequence of SEQ ID NO: 197. In some embodiments, an anti-Tau antibody comprises (a) HVR-L1 comprising the amino acid sequence of SEQ ID NO: 195; (b) HVR-L2 comprising the amino acid sequence of SEQ ID NO: 196; and (c) HVR-L3 comprising the amino acid sequence of SEQ ID NO: 197.

In some embodiments, an anti-Tau antibody comprises at least one, two, or three HVRs selected from (a) HVR-L1 comprising the amino acid sequence of SEQ ID NO: 205; (b) HVR-L2 comprising the amino acid sequence of SEQ ID NO: 206; and (c) HVR-L3 comprising the amino acid sequence of SEQ ID NO: 207. In some embodiments, an anti-Tau antibody comprises (a) HVR-L1 comprising the amino acid sequence of SEQ ID NO: 205; (b) HVR-L2 comprising the amino acid sequence of SEQ ID NO: 206; and (c) HVR-L3 comprising the amino acid sequence of SEQ ID NO: 207.

In some embodiments, an anti-Tau antibody comprises at least one, two, or three HVRs selected from (a) HVR-L1 comprising the amino acid sequence of SEQ ID NO: 215; (b) HVR-L2 comprising the amino acid sequence of SEQ ID NO: 216; and (c) HVR-L3 comprising the amino acid sequence of SEQ ID NO: 217. In some embodiments, an anti-Tau antibody comprises (a) HVR-L1 comprising the amino acid sequence of SEQ ID NO: 215; (b) HVR-L2 comprising the amino acid sequence of SEQ ID NO: 216; and (c) HVR-L3 comprising the amino acid sequence of SEQ ID NO: 217.

In some embodiments, an anti-Tau antibody comprises at least one, two, or three HVRs selected from (a) HVR-L1 comprising the amino acid sequence of SEQ ID NO: 225; (b) HVR-L2 comprising the amino acid sequence of SEQ ID NO: 226; and (c) HVR-L3 comprising the amino acid sequence of SEQ ID NO: 227. In some embodiments, an anti-Tau antibody comprises (a) HVR-L1 comprising the amino acid sequence of SEQ ID NO: 225; (b) HVR-L2 comprising the amino acid sequence of SEQ ID NO: 226; and (c) HVR-L3 comprising the amino acid sequence of SEQ ID NO: 227.

In some embodiments, an anti-Tau antibody comprises at least one, two, or three HVRs selected from (a) HVR-L1 comprising the amino acid sequence of SEQ ID NO: 235; (b) HVR-L2 comprising the amino acid sequence of SEQ ID NO: 236; and (c) HVR-L3 comprising the amino acid sequence of SEQ ID NO: 237. In some embodiments, an anti-Tau antibody comprises (a) HVR-L1 comprising the amino acid sequence of SEQ ID NO: 235; (b) HVR-L2 comprising the amino acid sequence of SEQ ID NO: 236; and (c) HVR-L3 comprising the amino acid sequence of SEQ ID NO: 237.

In some embodiments, an anti-Tau antibody comprises at least one, two, or three HVRs selected from (a) HVR-L1 comprising the amino acid sequence of SEQ ID NO: 245; (b) HVR-L2 comprising the amino acid sequence of SEQ ID NO: 246; and (c) HVR-L3 comprising the amino acid sequence of SEQ ID NO: 247. In some embodiments, an anti-Tau antibody comprises (a) HVR-L1 comprising the amino acid sequence of SEQ ID NO: 245; (b) HVR-L2 comprising the amino acid sequence of SEQ ID NO: 246; and (c) HVR-L3 comprising the amino acid sequence of SEQ ID NO: 247.

In some embodiments, an anti-Tau antibody comprises at least one, two, or three HVRs selected from (a) HVR-L1 comprising the amino acid sequence of SEQ ID NO: 255; (b) HVR-L2 comprising the amino acid sequence of SEQ ID NO: 256; and (c) HVR-L3 comprising the amino acid sequence of SEQ ID NO: 257. In some embodiments, an anti-Tau antibody comprises (a) HVR-L1 comprising the amino acid sequence of SEQ ID NO: 255; (b) HVR-L2 comprising the amino acid sequence of SEQ ID NO: 256; and (c) HVR-L3 comprising the amino acid sequence of SEQ ID NO: 257.

In some embodiments, an anti-Tau antibody comprises at least one, two, or three HVRs selected from (a) HVR-L1 comprising the amino acid sequence of SEQ ID NO: 265; (b) HVR-L2 comprising the amino acid sequence of SEQ ID NO: 266; and (c) HVR-L3 comprising the amino acid sequence of SEQ ID NO: 267. In some embodiments, an anti-Tau antibody comprises (a) HVR-L1 comprising the amino acid sequence of SEQ ID NO: 265; (b) HVR-L2 comprising the amino acid sequence of SEQ ID NO: 266; and (c) HVR-L3 comprising the amino acid sequence of SEQ ID NO: 267.

In some embodiments, an anti-Tau antibody comprises at least one, two, or three HVRs selected from (a) HVR-L1 comprising the amino acid sequence of SEQ ID NO: 275; (b) HVR-L2 comprising the amino acid sequence of SEQ ID NO: 276; and (c) HVR-L3 comprising the amino acid sequence of SEQ ID NO: 277. In some embodiments, an anti-Tau antibody comprises (a) HVR-L1 comprising the amino acid sequence of SEQ ID NO: 275; (b) HVR-L2 comprising the amino acid sequence of SEQ ID NO: 276; and (c) HVR-L3 comprising the amino acid sequence of SEQ ID NO: 277.

In some embodiments, an anti-Tau antibody comprises at least one, two, or three HVRs selected from (a) HVR-L1 comprising the amino acid sequence of SEQ ID NO: 285; (b) HVR-L2 comprising the amino acid sequence of SEQ ID NO: 286; and (c) HVR-L3 comprising the amino acid sequence of SEQ ID NO: 287. In some embodiments, an anti-Tau antibody comprises (a) HVR-L1 comprising the amino acid sequence of SEQ ID NO: 285; (b) HVR-L2 comprising the amino acid sequence of SEQ ID NO: 286; and (c) HVR-L3 comprising the amino acid sequence of SEQ ID NO: 287.

In some embodiments, an anti-Tau antibody comprises at least one, two, or three HVRs selected from (a) HVR-L1 comprising the amino acid sequence of SEQ ID NO: 295; (b) HVR-L2 comprising the amino acid sequence of SEQ ID NO: 296; and (c) HVR-L3 comprising the amino acid sequence of SEQ ID NO: 297. In some embodiments, an anti-Tau antibody comprises (a) HVR-L1 comprising the amino acid sequence of SEQ ID NO: 295; (b) HVR-L2 comprising the amino acid sequence of SEQ ID NO: 296; and (c) HVR-L3 comprising the amino acid sequence of SEQ ID NO: 297.

In some embodiments, an anti-Tau antibody comprises at least one, two, or three HVRs selected from (a) HVR-L1 comprising the amino acid sequence of SEQ ID NO: 305; (b) HVR-L2 comprising the amino acid sequence of SEQ ID NO: 306; and (c) HVR-L3 comprising the amino acid sequence of SEQ ID NO: 307. In some embodiments, an anti-Tau antibody comprises (a) HVR-L1 comprising the amino acid sequence of SEQ ID NO: 305; (b) HVR-L2 comprising the amino acid sequence of SEQ ID NO: 306; and (c) HVR-L3 comprising the amino acid sequence of SEQ ID NO: 307.

In some embodiments, an anti-Tau antibody comprises at least one, two, or three HVRs selected from (a) HVR-L1 comprising the amino acid sequence of SEQ ID NO: 315; (b) HVR-L2 comprising the amino acid sequence of SEQ ID NO: 316; and (c) HVR-L3 comprising the amino acid sequence of SEQ ID NO: 317. In some embodiments, an anti-Tau antibody comprises (a) HVR-L1 comprising the amino acid sequence of SEQ ID NO: 315; (b) HVR-L2 comprising the amino acid sequence of SEQ ID NO: 316; and (c) HVR-L3 comprising the amino acid sequence of SEQ ID NO: 317.

In some embodiments, an anti-Tau antibody comprises at least one, two, or three HVRs selected from (a) HVR-L1 comprising the amino acid sequence of SEQ ID NO: 325; (b) HVR-L2 comprising the amino acid sequence of SEQ ID NO: 326; and (c) HVR-L3 comprising the amino acid sequence of SEQ ID NO: 327. In some embodiments, an anti-Tau antibody comprises (a) HVR-L1 comprising the amino acid sequence of SEQ ID NO: 325; (b) HVR-L2 comprising the amino acid sequence of SEQ ID NO: 326; and (c) HVR-L3 comprising the amino acid sequence of SEQ ID NO: 327.

In some embodiments, an anti-Tau antibody comprises at least one, two, or three HVRs selected from (a) HVR-L1 comprising the amino acid sequence of SEQ ID NO: 335; (b) HVR-L2 comprising the amino acid sequence of SEQ ID NO: 336; and (c) HVR-L3 comprising the amino acid sequence of SEQ ID NO: 337. In some embodiments, an anti-Tau antibody comprises (a) HVR-L1 comprising the amino acid sequence of SEQ ID NO: 335; (b) HVR-L2 comprising the amino acid sequence of SEQ ID NO: 336; and (c) HVR-L3 comprising the amino acid sequence of SEQ ID NO: 337.

In some embodiments, an anti-Tau antibody comprises (a) HVR-H1 comprising an amino acid sequence selected from SEQ ID NOs: 12, 22, 282, 292, and 342; (b) HVR-H2 comprising an amino acid sequence selected from SEQ ID NOs: 13, 23, 283, 293, and 343; (c) HVR-H3 comprising an amino acid sequence selected from SEQ ID NOs: 14, 24, 284, 294, and 344; (d) HVR-L1 comprising an amino acid sequence selected from SEQ ID NOs: 15, 25, 285, 295, 345, and 468 to 556; (e) HVR-L2 comprising an amino acid sequence selected from SEQ ID NOs: 16, 26, 286, 296, and 346; and (f) HVR-L3 comprising an amino acid sequence selected from SEQ ID NOs: 17, 27, 287, 297, and 347.

In some embodiments, an anti-Tau antibody comprises (a) HVR-H1 comprising the amino acid sequence of SEQ ID NO: 342; (b) HVR-H2 comprising the amino acid sequence of SEQ ID NO: 343; (c) HVR-H3 comprising the amino acid sequence of SEQ ID NO: 344; (d) HVR-L1 comprising the amino acid sequence of SEQ ID NO: 345; (e) HVR-L2 comprising the amino acid sequence of SEQ ID NO: 346; and (f) HVR-L3 comprising the amino acid sequence of SEQ ID NO: 347.

In some embodiments, an anti-Tau antibody comprises (a) HVR-H1 comprising an amino acid sequence selected from SEQ ID NOs: 72 and 302; (b) HVR-H2 comprising an amino acid sequence selected from SEQ ID NOs: 73 and 303; (c) HVR-H3 comprising an amino acid sequence selected from SEQ ID NOs: 74 and 304; (d) HVR-L1 comprising an amino acid sequence selected from SEQ ID NOs: 75 and 305; (e) HVR-L2 comprising an amino acid sequence selected from SEQ ID NOs: 76 and 306; and (f) HVR-L3 comprising an amino acid sequence selected from SEQ ID NOs: 77 and 307.

In some embodiments, an anti-Tau antibody comprises (a) HVR-H1 comprising an amino acid sequence selected from SEQ ID NOs: 82, 312, 322, and 332; (b) HVR-H2 comprising an amino acid sequence selected from SEQ ID NOs: 83, 313, 323, and 333; (c) HVR-H3 comprising an amino acid sequence selected from SEQ ID NOs: 84, 314, 324, and 334; (d) HVR-L1 comprising an amino acid sequence selected from SEQ ID NOs: 85, 315, 325, and 335; (e) HVR-L2 comprising an amino acid sequence selected from SEQ ID NOs: 86, 316, 326, and 336; and (f) HVR-L3 comprising an amino acid sequence selected from SEQ ID NOs: 87, 317, 327, and 337.

In some embodiments, an anti-Tau antibody comprises (a) HVR-H1 comprising the amino acid sequence of SEQ ID NO: 32; (b) HVR-H2 comprising the amino acid sequence of SEQ ID NO: 33; (c) HVR-H3 comprising the amino acid sequence of SEQ ID NO: 34; (d) HVR-L1 comprising the amino acid sequence of SEQ ID NO: 35; (e) HVR-L2 comprising the amino acid sequence of SEQ ID NO: 36; and (f) HVR-L3 comprising the amino acid sequence of SEQ ID NO: 37.

In some embodiments, an anti-Tau antibody comprises (a) HVR-H1 comprising the amino acid sequence of SEQ ID NO: 42; (b) HVR-H2 comprising the amino acid sequence of SEQ ID NO: 43; (c) HVR-H3 comprising the amino acid sequence of SEQ ID NO: 44; (d) HVR-L1 comprising the amino acid sequence of SEQ ID NO: 45; (e) HVR-L2 comprising the amino acid sequence of SEQ ID NO: 46; and (f) HVR-L3 comprising the amino acid sequence of SEQ ID NO: 47.

In some embodiments, an anti-Tau antibody comprises (a) HVR-H1 comprising the amino acid sequence of SEQ ID NO: 52; (b) HVR-H2 comprising the amino acid sequence of SEQ ID NO: 53; (c) HVR-H3 comprising the amino acid sequence of SEQ ID NO: 54; (d) HVR-L1 comprising the amino acid sequence of SEQ ID NO: 55; (e) HVR-L2 comprising the amino acid sequence of SEQ ID NO: 56; and (f) HVR-L3 comprising the amino acid sequence of SEQ ID NO: 57.

In some embodiments, an anti-Tau antibody comprises (a) HVR-H1 comprising the amino acid sequence of SEQ ID NO: 62; (b) HVR-H2 comprising the amino acid sequence of SEQ ID NO: 63; (c) HVR-H3 comprising the amino acid sequence of SEQ ID NO: 64; (d) HVR-L1 comprising the amino acid sequence of SEQ ID NO: 65; (e) HVR-L2 comprising the amino acid sequence of SEQ ID NO: 66; and (f) HVR-L3 comprising the amino acid sequence of SEQ ID NO: 67.

In some embodiments, an anti-Tau antibody comprises (a) HVR-H1 comprising the amino acid sequence of SEQ ID NO: 72; (b) HVR-H2 comprising the amino acid sequence of SEQ ID NO: 73; (c) HVR-H3 comprising the amino acid sequence of SEQ ID NO: 74; (d) HVR-L1 comprising the amino acid sequence of SEQ ID NO: 75; (e) HVR-L2 comprising the amino acid sequence of SEQ ID NO: 76; and (f) HVR-L3 comprising the amino acid sequence of SEQ ID NO: 77.

In some embodiments, an anti-Tau antibody comprises (a) HVR-H1 comprising the amino acid sequence of SEQ ID NO: 82; (b) HVR-H2 comprising the amino acid sequence of SEQ ID NO: 83; (c) HVR-H3 comprising the amino acid sequence of SEQ ID NO: 84; (d) HVR-L1 comprising the amino acid sequence of SEQ ID NO: 85; (e) HVR-L2 comprising the amino acid sequence of SEQ ID NO: 86; and (f) HVR-L3 comprising the amino acid sequence of SEQ ID NO: 87.

In some embodiments, an anti-Tau antibody comprises (a) HVR-H1 comprising the amino acid sequence of SEQ ID NO: 92; (b) HVR-H2 comprising the amino acid sequence of SEQ ID NO: 93; (c) HVR-H3 comprising the amino acid sequence of SEQ ID NO: 94; (d) HVR-L1 comprising the amino acid sequence of SEQ ID NO: 95; (e) HVR-L2 comprising the amino acid sequence of SEQ ID NO: 96; and (f) HVR-L3 comprising the amino acid sequence of SEQ ID NO: 97.

In some embodiments, an anti-Tau antibody comprises (a) HVR-H1 comprising the amino acid sequence of SEQ ID NO: 102; (b) HVR-H2 comprising the amino acid sequence of SEQ ID NO: 103; (c) HVR-H3 comprising the amino acid sequence of SEQ ID NO: 104; (d) HVR-L1 comprising the amino acid sequence of SEQ ID NO: 105; (e) HVR-L2 comprising the amino acid sequence of SEQ ID NO: 106; and (f) HVR-L3 comprising the amino acid sequence of SEQ ID NO: 107.

In some embodiments, an anti-Tau antibody comprises (a) HVR-H1 comprising the amino acid sequence of SEQ ID NO: 112; (b) HVR-H2 comprising the amino acid sequence of SEQ ID NO: 113; (c) HVR-H3 comprising the amino acid sequence of SEQ ID NO: 114; (d) HVR-L1 comprising the amino acid sequence of SEQ ID NO: 115; (e) HVR-L2 comprising the amino acid sequence of SEQ ID NO: 116; and (f) HVR-L3 comprising the amino acid sequence of SEQ ID NO: 117.

In some embodiments, an anti-Tau antibody comprises (a) HVR-H1 comprising the amino acid sequence of SEQ ID NO: 122; (b) HVR-H2 comprising the amino acid sequence of SEQ ID NO: 123; (c) HVR-H3 comprising the amino acid sequence of SEQ ID NO: 124; (d) HVR-L1 comprising the amino acid sequence of SEQ ID NO: 125; (e) HVR-L2 comprising the amino acid sequence of SEQ ID NO: 126; and (f) HVR-L3 comprising the amino acid sequence of SEQ ID NO: 127.

In some embodiments, an anti-Tau antibody comprises (a) HVR-H1 comprising the amino acid sequence of SEQ ID NO: 132; (b) HVR-H2 comprising the amino acid sequence of SEQ ID NO: 133; (c) HVR-H3 comprising the amino acid sequence of SEQ ID NO: 134; (d) HVR-L1 comprising the amino acid sequence of SEQ ID NO: 135; (e) HVR-L2 comprising the amino acid sequence of SEQ ID NO: 136; and (f) HVR-L3 comprising the amino acid sequence of SEQ ID NO: 137.

In some embodiments, an anti-Tau antibody comprises (a) HVR-H1 comprising the amino acid sequence of SEQ ID NO: 142; (b) HVR-H2 comprising the amino acid sequence of SEQ ID NO: 143; (c) HVR-H3 comprising the amino acid sequence of SEQ ID NO: 144; (d) HVR-L1 comprising the amino acid sequence of SEQ ID NO: 145; (e) HVR-L2 comprising the amino acid sequence of SEQ ID NO: 146; and (f) HVR-L3 comprising the amino acid sequence of SEQ ID NO: 147.

In some embodiments, an anti-Tau antibody comprises (a) HVR-H1 comprising the amino acid sequence of SEQ ID NO: 152; (b) HVR-H2 comprising the amino acid sequence of SEQ ID NO: 153; (c) HVR-H3 comprising the amino acid sequence of SEQ ID NO: 154; (d) HVR-L1 comprising the amino acid sequence of SEQ ID NO: 155; (e) HVR-L2 comprising the amino acid sequence of SEQ ID NO: 156; and (f) HVR-L3 comprising the amino acid sequence of SEQ ID NO: 157.

In some embodiments, an anti-Tau antibody comprises (a) HVR-H1 comprising the amino acid sequence of SEQ ID NO: 162; (b) HVR-H2 comprising the amino acid sequence of SEQ ID NO: 163; (c) HVR-H3 comprising the amino acid sequence of SEQ ID NO: 164; (d) HVR-L1 comprising the amino acid sequence of SEQ ID NO: 165; (e) HVR-L2 comprising the amino acid sequence of SEQ ID NO: 166; and (f) HVR-L3 comprising the amino acid sequence of SEQ ID NO: 167.

In some embodiments, an anti-Tau antibody comprises (a) HVR-H1 comprising the amino acid sequence of SEQ ID NO: 172; (b) HVR-H2 comprising the amino acid sequence of SEQ ID NO: 173; (c) HVR-H3 comprising the amino acid sequence of SEQ ID NO: 174; (d) HVR-L1 comprising the amino acid sequence of SEQ ID NO: 175; (e) HVR-L2 comprising the amino acid sequence of SEQ ID NO: 176; and (f) HVR-L3 comprising the amino acid sequence of SEQ ID NO: 177.

In some embodiments, an anti-Tau antibody comprises (a) HVR-H1 comprising the amino acid sequence of SEQ ID NO: 182; (b) HVR-H2 comprising the amino acid sequence of SEQ ID NO: 183; (c) HVR-H3 comprising the amino acid sequence of SEQ ID NO: 184; (d) HVR-L1 comprising the amino acid sequence of SEQ ID NO: 185; (e) HVR-L2 comprising the amino acid sequence of SEQ ID NO: 186; and (f) HVR-L3 comprising the amino acid sequence of SEQ ID NO: 187.

In some embodiments, an anti-Tau antibody comprises (a) HVR-H1 comprising the amino acid sequence of SEQ ID NO: 192; (b) HVR-H2 comprising the amino acid sequence of SEQ ID NO: 193; (c) HVR-H3 comprising the amino acid sequence of SEQ ID NO: 194; (d) HVR-L1 comprising the amino acid sequence of SEQ ID NO: 195; (e) HVR-L2 comprising the amino acid sequence of SEQ ID NO: 196; and (f) HVR-L3 comprising the amino acid sequence of SEQ ID NO: 197.

In some embodiments, an anti-Tau antibody comprises (a) HVR-H1 comprising the amino acid sequence of SEQ ID NO: 202; (b) HVR-H2 comprising the amino acid sequence of SEQ ID NO: 203; (c) HVR-H3 comprising the amino acid sequence of SEQ ID NO: 204; (d) HVR-L1 comprising the amino acid sequence of SEQ ID NO: 205; (e) HVR-L2 comprising the amino acid sequence of SEQ ID NO: 206; and (f) HVR-L3 comprising the amino acid sequence of SEQ ID NO: 207.

In some embodiments, an anti-Tau antibody comprises (a) HVR-H1 comprising the amino acid sequence of SEQ ID NO: 212; (b) HVR-H2 comprising the amino acid sequence of SEQ ID NO: 213; (c) HVR-H3 comprising the amino acid sequence of SEQ ID NO: 214; (d) HVR-L1 comprising the amino acid sequence of SEQ ID NO: 215; (e) HVR-L2 comprising the amino acid sequence of SEQ ID NO: 216; and (f) HVR-L3 comprising the amino acid sequence of SEQ ID NO: 217.

In some embodiments, an anti-Tau antibody comprises (a) HVR-H1 comprising the amino acid sequence of SEQ ID NO: 222; (b) HVR-H2 comprising the amino acid sequence of SEQ ID NO: 223; (c) HVR-H3 comprising the amino acid sequence of SEQ ID NO: 224; (d) HVR-L1 comprising the amino acid sequence of SEQ ID NO: 225; (e) HVR-L2 comprising the amino acid sequence of SEQ ID NO: 226; and (f) HVR-L3 comprising the amino acid sequence of SEQ ID NO: 227.

In some embodiments, an anti-Tau antibody comprises (a) HVR-H1 comprising the amino acid sequence of SEQ ID NO: 232; (b) HVR-H2 comprising the amino acid sequence of SEQ ID NO: 233; (c) HVR-H3 comprising the amino acid sequence of SEQ ID NO: 234; (d) HVR-L1 comprising the amino acid sequence of SEQ ID NO: 235; (e) HVR-L2 comprising the amino acid sequence of SEQ ID NO: 236; and (f) HVR-L3 comprising the amino acid sequence of SEQ ID NO: 237.

In some embodiments, an anti-Tau antibody comprises (a) HVR-H1 comprising the amino acid sequence of SEQ ID NO: 242; (b) HVR-H2 comprising the amino acid sequence of SEQ ID NO: 243; (c) HVR-H3 comprising the amino acid sequence of SEQ ID NO: 244; (d) HVR-L1 comprising the amino acid sequence of SEQ ID NO: 245; (e) HVR-L2 comprising the amino acid sequence of SEQ ID NO: 246; and (f) HVR-L3 comprising the amino acid sequence of SEQ ID NO: 247.

In some embodiments, an anti-Tau antibody comprises (a) HVR-H1 comprising the amino acid sequence of SEQ ID NO: 252; (b) HVR-H2 comprising the amino acid sequence of SEQ ID NO: 253; (c) HVR-H3 comprising the amino acid sequence of SEQ ID NO: 254; (d) HVR-L1 comprising the amino acid sequence of SEQ ID NO: 255; (e) HVR-L2 comprising the amino acid sequence of SEQ ID NO: 256; and (f) HVR-L3 comprising the amino acid sequence of SEQ ID NO: 257.

In some embodiments, an anti-Tau antibody comprises (a) HVR-H1 comprising the amino acid sequence of SEQ ID NO: 262; (b) HVR-H2 comprising the amino acid sequence of SEQ ID NO: 263; (c) HVR-H3 comprising the amino acid sequence of SEQ ID NO: 264; (d) HVR-L1 comprising the amino acid sequence of SEQ ID NO: 265; (e) HVR-L2 comprising the amino acid sequence of SEQ ID NO: 266; and (f) HVR-L3 comprising the amino acid sequence of SEQ ID NO: 267.

In some embodiments, an anti-Tau antibody comprises (a) HVR-H1 comprising the amino acid sequence of SEQ ID NO: 272; (b) HVR-H2 comprising the amino acid sequence of SEQ ID NO: 273; (c) HVR-H3 comprising the amino acid sequence of SEQ ID NO: 274; (d) HVR-L1 comprising the amino acid sequence of SEQ ID NO: 275; (e) HVR-L2 comprising the amino acid sequence of SEQ ID NO: 276; and (f) HVR-L3 comprising the amino acid sequence of SEQ ID NO: 277.

In some embodiments, an anti-Tau antibody comprises (a) HVR-H1 comprising the amino acid sequence of SEQ ID NO: 282; (b) HVR-H2 comprising the amino acid sequence of SEQ ID NO: 283; (c) HVR-H3 comprising the amino acid sequence of SEQ ID NO: 284; (d) HVR-L1 comprising the amino acid sequence of SEQ ID NO: 285; (e) HVR-L2 comprising the amino acid sequence of SEQ ID NO: 286; and (f) HVR-L3 comprising the amino acid sequence of SEQ ID NO: 287.

In some embodiments, an anti-Tau antibody comprises (a) HVR-H1 comprising the amino acid sequence of SEQ ID NO: 292; (b) HVR-H2 comprising the amino acid sequence of SEQ ID NO: 293; (c) HVR-H3 comprising the amino acid sequence of SEQ ID NO: 294; (d) HVR-L1 comprising the amino acid sequence of SEQ ID NO: 295; (e) HVR-L2 comprising the amino acid sequence of SEQ ID NO: 296; and (f) HVR-L3 comprising the amino acid sequence of SEQ ID NO: 297.

In some embodiments, an anti-Tau antibody comprises (a) HVR-H1 comprising the amino acid sequence of SEQ ID NO: 302; (b) HVR-H2 comprising the amino acid sequence of SEQ ID NO: 303; (c) HVR-H3 comprising the amino acid sequence of SEQ ID NO: 304; (d) HVR-L1 comprising the amino acid sequence of SEQ ID NO: 305; (e) HVR-L2 comprising the amino acid sequence of SEQ ID NO: 306; and (f) HVR-L3 comprising the amino acid sequence of SEQ ID NO: 307.

In some embodiments, an anti-Tau antibody comprises (a) HVR-H1 comprising the amino acid sequence of SEQ ID NO: 312; (b) HVR-H2 comprising the amino acid sequence of SEQ ID NO: 313; (c) HVR-H3 comprising the amino acid sequence of SEQ ID NO: 314; (d) HVR-L1 comprising the amino acid sequence of SEQ ID NO: 315; (e) HVR-L2 comprising the amino acid sequence of SEQ ID NO: 316; and (f) HVR-L3 comprising the amino acid sequence of SEQ ID NO: 317.

In some embodiments, an anti-Tau antibody comprises (a) HVR-H1 comprising the amino acid sequence of SEQ ID NO: 322; (b) HVR-H2 comprising the amino acid sequence of SEQ ID NO: 323; (c) HVR-H3 comprising the amino acid sequence of SEQ ID NO: 324; (d) HVR-L1 comprising the amino acid sequence of SEQ ID NO: 325; (e) HVR-L2 comprising the amino acid sequence of SEQ ID NO: 326; and (f) HVR-L3 comprising the amino acid sequence of SEQ ID NO: 327.

In some embodiments, an anti-Tau antibody comprises (a) HVR-H1 comprising the amino acid sequence of SEQ ID NO: 332; (b) HVR-H2 comprising the amino acid sequence of SEQ ID NO: 333; (c) HVR-H3 comprising the amino acid sequence of SEQ ID NO: 334; (d) HVR-L1 comprising the amino acid sequence of SEQ ID NO: 335; (e) HVR-L2 comprising the amino acid sequence of SEQ ID NO: 336; and (f) HVR-L3 comprising the amino acid sequence of SEQ ID NO: 337.

In any of the above embodiments, an anti-Tau antibody is humanized. In some embodiments, an anti-Tau antibody comprises HVRs as in any of the above embodiments, and further comprises an acceptor human framework, e.g. a human immunoglobulin framework or a human consensus framework.

In another aspect, an anti-Tau antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 603, 611, 619, 627, 635, 643, 651, 659, 667, 675, 683, or 691. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Tau antibody comprising that sequence retains the ability to bind to Tau. In certain embodiments, a total of 1 to 10 amino acids have been substituted, inserted and/or deleted in SEQ ID NO: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 603, 611, 619, 627, 635, 643, 651, 659, 667, 675, 683, or 691. In certain embodiments, substitutions, insertions, or deletions occur in regions outside the HVRs (i.e., in the FRs). Optionally, the anti-Tau antibody comprises the VH sequence in SEQ ID NO: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 603, 611, 619, 627, 635, 643, 651, 659, 667, 675, 683, or 691, including post-translational modifications of that sequence. In a particular embodiment, the VH comprises one, two or three HVRs selected from: (a) HVR-H1 comprising the amino acid sequence of SEQ ID NO: 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 605, 613, 621, 629, 637, 645, 653, 661, 669, 677, 685, or 693, (b) HVR-H2 comprising the amino acid sequence of SEQ ID NO: 13, 23, 33, 43, 53, 63, 73, 83, 93, 100, 113, 123, 133, 143, 153, 163, 173, 183, 193, 203, 213, 223, 233, 243, 253, 263, 273, 283, 293, 303, 313, 323, 333, 343, 606, 614, 622, 630, 638, 646, 654, 662, 670, 678, 686, or 694, and (c) HVR-H3 comprising the amino acid sequence of SEQ ID NO: 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 607, 615, 623, 631, 638, 647, 655, 663, 671, 679, 687, or 695.

In another aspect, an anti-Tau antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 604, 612, 620, 628, 636, 644, 652, 660, 668, 676, 684, or 692. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Tau antibody comprising that sequence retains the ability to bind to Tau. In certain embodiments, a total of 1 to 10 amino acids have been substituted, inserted and/or deleted in SEQ ID NO: 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 604, 612, 620, 628, 636, 644, 652, 660, 668, 676, 684, or 692. In certain embodiments, substitutions, insertions, or deletions occur in regions outside the HVRs (i.e., in the FRs). Optionally, the anti-Tau antibody comprises the VL sequence in SEQ ID NO: 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 604, 612, 620, 628, 636, 644, 652, 660, 668, 676, 684, or 692, including post-translational modifications of that sequence. In a particular embodiment, the VL comprises one, two or three HVRs selected from: (a) HVR-L1 comprising the amino acid sequence of SEQ ID NO: 15, 25, 35, 45, 55, 65, 75, 85, 95, 105, 115, 125, 135, 145, 155, 165, 175, 185, 195, 205, 215, 225, 235, 245, 255, 265, 275, 285, 295, 305, 315, 325, 335, 345, 608, 616, 624, 632, 640, 648, 656, 664, 672, 680, 688, or 696; (b) HVR-L2 comprising the amino acid sequence of SEQ ID NO: 16, 26, 36, 46, 56, 66, 76, 86, 96, 106, 116, 126, 136, 146, 156, 166, 176, 186, 196, 206, 216, 226, 236, 246, 266, 266, 276, 286, 296, 306, 316, 326, 336, 346, 609, 617, 625, 633, 641, 649, 657, 665, 673, 681, 689, or 697; and (c) HVR-L3 comprising the amino acid sequence of SEQ ID NO: 17, 27, 37, 47, 57, 67, 77, 87, 97, 107, 117, 127, 137, 147, 157, 167, 177, 187, 197, 207, 217, 227, 237, 247, 267, 277, 277, 287, 297, 307, 317, 327, 337, 347, 610, 618, 626, 634, 642, 650, 658, 666, 674, 682, 690, or 698.

In some embodiments, an anti-Tau antibody comprises:
a) a heavy chain variable region (VH) comprising a sequence that is at least 95% identical to SEQ ID NO: 603;
b) a light chain variable region (VL) comprising a sequence that is at least 95% identical to SEQ ID NO: 604;
c) a VH as in (a) and a VL as in (b);
d) a heavy chain variable region (VH) comprising a sequence that is at least 95% identical to SEQ ID NO: 611;
e) a light chain variable region (VL) comprising a sequence that is at least 95% identical to SEQ ID NO: 612;
f) a VH as in (d) and a VL as in (e);
g) a heavy chain variable region (VH) comprising a sequence that is at least 95% identical to SEQ ID NO: 619;
h) a light chain variable region (VL) comprising a sequence that is at least 95% identical to SEQ ID NO: 620;
i) a VH as in (g) and a VL as in (h);
j) a heavy chain variable region (VH) comprising a sequence that is at least 95% identical to SEQ ID NO: 627;
k) a light chain variable region (VL) comprising a sequence that is at least 95% identical to SEQ ID NO: 628; 1) a VH as in (j) and a VL as in (k);
m) a heavy chain variable region (VH) comprising a sequence that is at least 95% identical to SEQ ID NO: 635;
n) a light chain variable region (VL) comprising a sequence that is at least 95% identical to SEQ ID NO: 636;
o) a VH as in (m) and a VL as in (n); or p) a heavy chain variable region (VH) comprising a sequence that is at least 95% identical to SEQ ID NO: 643;
q) a light chain variable region (VL) comprising a sequence that is at least 95% identical to SEQ ID NO: 644;
r) a VH as in (p) and a VL as in (q);
s) a heavy chain variable region (VH) comprising a sequence that is at least 95% identical to SEQ ID NO: 651;
t) a light chain variable region (VL) comprising a sequence that is at least 95% identical to SEQ ID NO: 652;
u) a VH as in (s) and a VL as in (t);
v) a heavy chain variable region (VH) comprising a sequence that is at least 95% identical to SEQ ID NO: 659;
w) a light chain variable region (VL) comprising a sequence that is at least 95% identical to SEQ ID NO: 660;
x) a VH as in (v) and a VL as in (w);
y) a heavy chain variable region (VH) comprising a sequence that is at least 95% identical to SEQ ID NO: 667;
z) a light chain variable region (VL) comprising a sequence that is at least 95% identical to SEQ ID NO: 668;
aa) a VH as in (y) and a VL as in (z);
bb) a heavy chain variable region (VH) comprising a sequence that is at least 95% identical to SEQ ID NO: 675;
cc) a light chain variable region (VL) comprising a sequence that is at least 95% identical to SEQ ID NO: 676;
dd) a VH as in (bb) and a VL as in (cc);
ee) a heavy chain variable region (VH) comprising a sequence that is at least 95% identical to SEQ ID NO: 683;
ff) a light chain variable region (VL) comprising a sequence that is at least 95% identical to SEQ ID NO: 684;
gg) a VH as in (ee) and a VL as in (ff); or hh) a heavy chain variable region (VH) comprising a sequence that is at least 95% identical to SEQ ID NO: 691;
ii) a light chain variable region (VL) comprising a sequence that is at least 95% identical to SEQ ID NO: 692;
jj) a VH as in (hh) and a VL as in (ii).

In some embodiments, an anti-Tau antibody comprises:
a) a heavy chain variable region (VH) comprising the sequence of SEQ ID NO: 603;

b) a light chain variable region (VL) comprising the sequence of SEQ ID NO: 604;
c) a VH as in (a) and a VL as in (b);
d) a heavy chain variable region (VH) comprising the sequence of SEQ ID NO: 611;
e) a light chain variable region (VL) comprising the sequence of SEQ ID NO: 612;
f) a VH as in (d) and a VL as in (e);
g) a heavy chain variable region (VH) comprising the sequence of SEQ ID NO: 619;
h) a light chain variable region (VL) comprising the sequence of SEQ ID NO: 620;
i) a VH as in (g) and a VL as in (h);
j) a heavy chain variable region (VH) comprising the sequence of SEQ ID NO: 627;
k) a light chain variable region (VL) comprising the sequence of SEQ ID NO: 628; 1) a VH as in (j) and a VL as in (k);
m) a heavy chain variable region (VH) comprising the sequence of SEQ ID NO: 635;
n) a light chain variable region (VL) comprising the sequence of SEQ ID NO: 636;
o) a VH as in (m) and a VL as in (n); or p) a heavy chain variable region (VH) comprising the sequence of SEQ ID NO: 643;
q) a light chain variable region (VL) comprising the sequence of SEQ ID NO: 644;
r) a VH as in (p) and a VL as in (q);
s) a heavy chain variable region (VH) comprising the sequence of SEQ ID NO: 651;
t) a light chain variable region (VL) comprising the sequence of SEQ ID NO: 652;
u) a VH as in (s) and a VL as in (t);
v) a heavy chain variable region (VH) comprising the sequence of SEQ ID NO: 659;
w) a light chain variable region (VL) comprising the sequence of SEQ ID NO: 660;
x) a VH as in (v) and a VL as in (w);
y) a heavy chain variable region (VH) comprising the sequence of SEQ ID NO: 667;
z) a light chain variable region (VL) comprising the sequence of SEQ ID NO: 668;
aa) a VH as in (y) and a VL as in (z);
bb) a heavy chain variable region (VH) comprising the sequence of SEQ ID NO: 675;
cc) a light chain variable region (VL) comprising the sequence of SEQ ID NO: 676;
dd) a VH as in (bb) and a VL as in (cc);
ee) a heavy chain variable region (VH) comprising the sequence of SEQ ID NO: 683;
ff) a light chain variable region (VL) comprising the sequence of SEQ ID NO: 684;
gg) a VH as in (ee) and a VL as in (ff); or
hh) a heavy chain variable region (VH) comprising the sequence of SEQ ID NO: 691;
ii) a light chain variable region (VL) comprising the sequence of SEQ ID NO: 692;
jj) a VH as in (hh) and a VL as in (ii).

In another aspect, an anti-Tau antibody is provided, wherein the antibody comprises a VH as in any of the embodiments provided above, and a VL as in any of the embodiments provided above. In some embodiments, the antibody comprises the VH and VL sequences in SEQ ID NO: 280 and SEQ ID NO: 281, respectively, including post-translational modifications of those sequences. In some embodiments, the antibody comprises the VH and VL sequences in SEQ ID NO: 290 and SEQ ID NO: 291, respectively, including post-translational modifications of those sequences. In some embodiments, the antibody comprises the VH and VL sequences in SEQ ID NO: 300 and SEQ ID NO: 301, respectively, including post-translational modifications of those sequences. In some embodiments, the antibody comprises the VH and VL sequences in SEQ ID NO: 310 and SEQ ID NO: 311, respectively, including post-translational modifications of those sequences. In some embodiments, the antibody comprises the VH and VL sequences in SEQ ID NO: 320 and SEQ ID NO: 321, respectively, including post-translational modifications of those sequences. In some embodiments, the antibody comprises the VH and VL sequences in SEQ ID NO: 330 and SEQ ID NO: 331, respectively, including post-translational modifications of those sequences. In some embodiments, the antibody comprises the VH and VL sequences in SEQ ID NO: 340 and SEQ ID NO: 341, respectively, including post-translational modifications of those sequences.

In some embodiments, the antibody comprises a heavy chain variable region comprising the amino acid sequence of SEQ ID NO: 603 and a light chain variable region comprising the amino acid sequence of SEQ ID NO: 604, including post-translational modifications of those sequences.

In some embodiments, the antibody comprises a heavy chain variable region comprising the amino acid sequence of SEQ ID NO: 611 and a light chain variable region comprising the amino acid sequence of SEQ ID NO: 612, including post-translational modifications of those sequences.

In some embodiments, the antibody comprises a heavy chain variable region comprising the amino acid sequence of SEQ ID NO: 619 and a light chain variable region comprising the amino acid sequence of SEQ ID NO: 620, including post-translational modifications of those sequences.

In some embodiments, the antibody comprises a heavy chain variable region comprising the amino acid sequence of SEQ ID NO: 627 and a light chain variable region comprising the amino acid sequence of SEQ ID NO: 628, including post-translational modifications of those sequences.

In some embodiments, the antibody comprises a heavy chain variable region comprising the amino acid sequence of SEQ ID NO: 635 and a light chain variable region comprising the amino acid sequence of SEQ ID NO: 636, including post-translational modifications of those sequences.

In some embodiments, the antibody comprises a heavy chain variable region comprising the amino acid sequence of SEQ ID NO: 643 and a light chain variable region comprising the amino acid sequence of SEQ ID NO: 644, including post-translational modifications of those sequences.

In some embodiments, the antibody comprises a heavy chain variable region comprising the amino acid sequence of SEQ ID NO: 651 and a light chain variable region comprising the amino acid sequence of SEQ ID NO: 652.

In some embodiments, the antibody comprises a heavy chain variable region comprising the amino acid sequence of SEQ ID NO: 659 and a light chain variable region comprising the amino acid sequence of SEQ ID NO: 660.

In some embodiments, the antibody comprises a heavy chain variable region comprising the amino acid sequence of SEQ ID NO: 667 and a light chain variable region comprising the amino acid sequence of SEQ ID NO: 668.

In some embodiments, the antibody comprises a heavy chain variable region comprising the amino acid sequence of SEQ ID NO: 675 and a light chain variable region comprising the amino acid sequence of SEQ ID NO: 676.

In some embodiments, the antibody comprises a heavy chain variable region comprising the amino acid sequence of SEQ ID NO: 683 and a light chain variable region comprising the amino acid sequence of SEQ ID NO: 684.

In some embodiments, the antibody comprises a heavy chain variable region comprising the amino acid sequence of SEQ ID NO: 691 and a light chain variable region comprising the amino acid sequence of SEQ ID NO: 692.

In some embodiments, an anti-Tau antibody is provided, wherein the antibody comprises a heavy chain comprising the amino acid sequence of SEQ ID NO: 348 or SEQ ID NO: 602 and a light chain comprising the amino acid sequence of SEQ ID NO: 349. In some embodiments, an anti-Tau antibody is provided, wherein the antibody comprises a heavy chain consisting of the amino acid sequence of SEQ ID NO: 348 or SEQ ID NO: 602 and a light chain consisting of the amino acid sequence of SEQ ID NO: 349.

In a further aspect, the invention provides an antibody that binds to the same epitope as an anti-Tau antibody provided herein. For example, in certain embodiments, an antibody is provided that binds to the same epitope as an antibody selected from 15C6-A7, 63H3-D8, 123E9-A1, 64B9-F12, 231G3F10, 7A11C12, 30A1C9, 211G6-B6, 77D1-D2, 71H8-D6, 307H3E8, 63H3-D8, 64B9-F12, 72E12-H9, 30D12-B5, 49G10-F4, and 65B1-A2. In certain embodiments, an antibody is provided that binds to the same epitope of human Tau as an antibody selected from 15C6-A7, 63H3-D8, 123E9-A1, 64B9-F12, 231G3F10, 30A1C9, 211G6-B6, 77D1-D2, 71H8-D6, 307H3E8, 63H3-D8, 64B9-F12, 72E12-H9, 30D12-B5, 49G10-F4, and 65B-A2, but does not compete with antibody hu37D3-H9.v28.A4. In certain embodiments, an antibody is provided that binds to an epitope within a fragment of Tau consisting of amino acids 2-24 of SEQ ID NO: 2. In certain embodiments, an antibody is provided that binds to an epitope within a fragment of Tau consisting of amino acids 7-24 of SEQ ID NO: 2. In certain embodiments, an antibody is provided that binds to an epitope within a fragment of Tau consisting of amino acids 7-20 of SEQ ID NO: 2. In certain embodiments, an antibody is provided that binds to an epitope within a fragment of Tau consisting of amino acids 10-24 of SEQ ID NO: 2. In certain embodiments, an antibody is provided that binds to an epitope within a fragment of Tau consisting of amino acids 7-21 of SEQ ID NO: 2. In certain embodiments, an antibody is provided that binds to an epitope within a fragment of Tau consisting of amino acids 8-22 of SEQ ID NO: 2. In certain embodiments, an antibody is provided that binds to an epitope within a fragment of Tau consisting of amino acids 11-25 of SEQ ID NO: 2. In certain embodiments, an antibody is provided that binds to one or more, or all, of the following fragments of Tau: 2-24, 7-24, 7-20, 10-24, 7-21, 8-22, and 11-25. In some embodiments, an antibody is provided that binds to a peptide having the sequence of SEQ ID NO: 593, but does not bind to a peptide having the sequence of SEQ ID NO: 596 or SEQ ID NO: 597.

In a further aspect of the invention, an anti-Tau antibody according to any of the above embodiments is a monoclonal antibody, including a chimeric, humanized or human antibody. In one embodiment, an anti-Tau antibody is an antibody fragment, e.g., a Fv, Fab, Fab', scFv, diabody, or F(ab')$_2$ fragment. In another embodiment, the antibody is a full length antibody, e.g., an intact IgG1 or IgG4 antibody or other antibody class or isotype as defined herein.

In a further aspect, an anti-Tau antibody according to any of the above embodiments may incorporate any of the features, singly or in combination, as described in Sections 1-7 below: 1. Antibody Affinity In certain embodiments, an antibody provided herein has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In some embodiments, $K_D$ is measured by a radiolabeled antigen binding assay (RIA). In some embodiments, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 resonance units (RU). In some embodiments, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 pM) before injection at a flow rate of 5 µl/minute to achieve approximately 10 resonance units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio koff/kon. See, e.g., Chen et al., *J. Mol. Biol.* 293:865-881 (1999). If the on-rate exceeds 106 $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO M spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. Nat. Med. 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for Tau and the other is for any other antigen. In certain embodiments, one of the binding specificities is for Tau and the other is for amyloid beta. In certain embodiments, bispecific antibodies may bind to two different epitopes of Tau. Bispecific antibodies may also be used to localize cytotoxic agents to cells which express Tau. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bispecific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to Tau as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |

TABLE 1-continued

| Original Residue | Exemplary Substitutions | Preferred Substitutions |
|---|---|---|
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.
Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g.

complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In some embodiments, isolated nucleic acid encoding an anti-Tau antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In some embodiments, the host cell is eukaryotic, e.g. a Chinese Hamster Ovary (CHO) cell or lymphoid cell (e.g., Y0, NS0, Sp20 cell). In some embodiments, a method of making an anti-Tau antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-Tau antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N. Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NSO and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-Tau antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with an antibody described herein for binding to Tau. In certain embodiments, such a competing antibody binds to the same epitope (e.g., a linear or a conformational epitope) that is bound by 15C6-A7, 63H3-D8, 64B9-F12, 123E9-A1, 7A11C12, 231G3F10, 30A1C9, 211G6-B6, 77D1-D2, 71H8-D6, 307H3E8, 63H3-D8, 64B9-F12, 72E12-H9, 30D12-B5, 49G10-F4, and 65B1-A2. In some embodiments, an antibody binds to an epitope within amino acids 1-51 of mature human Tau but does not compete with antibody hu37D3-H9.v28.A4. In some embodiments, an antibody binds to an epitope within amino acids 1-15, 10-24, 19-33, 19-42, 28-42, 28-44, 37-44, or 37-51 of mature human Tau but does not compete with antibody hu37D3-H9.v28.A4. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized Tau (such as monomeric Tau) is incubated in a solution comprising a first labeled antibody that binds to Tau (e.g., any antibody described herein, such as hu37D3-H9.v28.A4) and a second unlabeled antibody that is being tested for its ability to compete with the first antibody for binding to Tau. The second antibody may be present in a hybridoma supernatant. As a control, immobilized Tau is incubated in a solution comprising the first labeled antibody but not the second unlabeled antibody. After incubation under conditions permissive for binding of the first antibody to Tau, excess unbound antibody is removed, and the amount of label associated with immobilized Tau is measured. If the amount of label associated with immobilized Tau is substantially reduced in the test sample relative to the control sample, then that indicates that the second antibody is competing with the first antibody for binding to Tau. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-Tau (e.g., pan-Tau) antibodies thereof having biological activity. Biological activity may include, e.g., binding of such antibodies to multiple forms of Tau (e.g., monomeric Tau, oligomeric Tau, non-phosphorylated Tau, and phosphorylated Tau) and reducing the level of Tau protein (e.g., total Tau, total soluble Tau, soluble non-phosphorylated Tau, soluble phosphorylated Tau, total insoluble Tau, insoluble non-phosphorylated Tau, insoluble phosphorylated Tau, hyperphosphorylated Tau, or paired helical filaments containing hyperphosphorylated Tau, in the brain, e.g., in the brain cortex and/or hippocampus). Antibodies having such biological activity in vivo and/or in vitro are also provided.

In certain embodiments, an antibody of the invention is tested for such biological activity. For example, an animal model of tauopathy, such as a Tau transgenic mice (e.g., P301L), can be used to detect binding of anti-Tau antibodies to brain sections, and for example, to neurofibrillary tangles in the brains of the transgenic mice. Further, an animal model of tauopathy, such as a Tau transgenic mice (e.g., P301L), can be treated with anti-Tau antibodies and experimental techniques known in the art can be used to assess whether such treatment reduces the level of Tau protein (e.g., total Tau, total soluble Tau, soluble phosphorylated Tau, soluble non-phosphorylated Tau, total insoluble Tau, insoluble phosphorylated Tau, insoluble non-phosphorylated Tau, hyperphosphorylated Tau, or paired helical filaments containing hyperphosphorylated Tau) in the mouse brain (e.g., in the brain cortex and/or hippocampus).

D. Immunoconjugates

The invention also provides immunoconjugates comprising an anti-Tau antibody herein conjugated to one or more other therapeutic agents or radioactive isotopes.

In another embodiment, an immunoconjugate comprises an antibody as described herein conjugated to a radioactive atom to form a radioconjugate. A variety of radioactive isotopes are available for the production of radioconjugates. Examples include At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triamine-pentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-Tau antibodies provided herein is useful for detecting the presence of Tau in a biological sample. The term "detecting" as used herein encompasses quantitative or qualitative detection. In certain embodiments, a biological sample comprises a cell or tissue, such as cerebrospinal fluid, a cell or tissue of the brain (e.g., brain cortex or hippocampus), or blood. In some embodiments, a biological sample is cerebrospinal fluid.

In some embodiments, an anti-Tau antibody for use in a method of diagnosis or detection is provided. In a further aspect, a method of detecting the presence of Tau in a biological sample is provided. In certain embodiments, the method comprises contacting the biological sample with an anti-Tau antibody as described herein under conditions permissive for binding of the anti-Tau antibody to Tau, and detecting whether a complex is formed between the anti-Tau antibody and Tau. Such method may be an in vitro or in vivo method. Further, the complex formed between the anti-Tau antibody and Tau in a test biological sample can be compared to the complex formed in a control biological sample (e.g., a biological sample from a healthy subject or subjects). The amount of the complex formed between the anti-Tau antibody and Tau in a test biological sample can also be quantified and compared to the amount of the complex formed in a control biological sample (e.g., a biological sample from a healthy subject or subjects) or to the average amount of the complex known to be formed in healthy subjects.

In some embodiments, an anti-Tau antibody is used to select subjects eligible for therapy with an anti-Tau antibody, e.g. where Tau is a biomarker for selection of patients. For example, in some embodiments, an anti-Tau (e.g., pan-Tau) antibody is used to detect whether the subject has a Tau protein disease or disorder, or whether the subject is at high risk (or predisposed to) a Tau protein disease or disorder.

Exemplary diseases or disorders that may be diagnosed using an antibody of the invention include Tau protein associated diseases or disorders, and diseases or disorders caused by or associated with the formation of neurofibrillary tangles or neuropil threads. In some embodiments, diseases or disorders that may be diagnosed using an antibody of the invention include Tau protein associated diseases or disorders that are manifested in an impairment or loss of cognitive functions including reasoning, situational judgement, memory capacity, learning, and/or special navigation. In particular, diseases or disorders that may be diagnosed using an antibody of the invention include tauopathies such as neurodegenerative tauopathies. Exemplary diseases or disorders that may be diagnosed using an antibody of the invention include, but are not limited to, Alzheimer's Disease, Creutzfeldt-Jacob disease, Dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia, frontotemporal dementia with parkinsonism linked to chromosome 17, Hallevorden-Spatz disease, multiple system atrophy, Niemann-Pick disease type C, Pallido-ponto-nigral degeneration, Pick's disease, progressive subcortical gliosis, progressive supranuclear palsy, Subacute sclerosing panencephalitis, Tangle only dementia (or tangle predominant dementia), Postencephalitic Parkinsonism, and Myotonic dystrophy. In some embodiments, a disorder that may be diagnosed using an antibody of the invention is Alzheimer's Disease (AD). In some embodiments, the Tau protein associated disease is selected from PART (primary age-related Tauopathy), tangle predominant dementia, subacute sclerosis panencephalopathy, chronic traumatic encephalopathy (CTE), white matter tauopathy with globular glial inclusions, Lewy body dementia (LBD), mild cognitive impairment (MCI), glaucoma, familial British dementia, familiar Danish dementia, Guadeloupean Parkinsonism, neurodegeneration with brain iron accumulation, SLC9A6-related mental retardation, multiple sclerosis, HIV-related dementia, senile cardiac amyloidosis, and Huntington's disease.

In certain embodiments, labeled anti-Tau antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In some instances, due to the extensive fragmentation of Tau protein, diagnostic assays that detect the Tau mid-domain (e.g., amino acids 159-224) may not accurately reflect the abundance of the N-terminal region of Tau. Thus, in some embodiments, methods of detecting Tau in a sample from a subject comprises detecting Tau with an antibody that binds to the N-terminal region of Tau. Such antibodies may be desirable, for example, to more accurately determine the abundance of the N-terminal region of Tau in a sample from a subject. In some embodiments, using an anti-Tau antibody that binds the N-terminal region of Tau may allow for a more accurate prediction of which patients are likely to respond to treatment with an anti-Tau antibody that binds the N-terminal region of Tau, in contrast to existing Tau diagnostics that detect the mid-domain of Tau. In some embodiments, the anti-Tau antibody used for detection does not compete with the therapeutic anti-Tau antibody used for treatment. In some such embodiments, the anti-Tau antibody used for detection binds an epitope within amino acids 1-15, 10-24, 19-33, 19-42, 28-42, 28-44, 37-44, or 37-51 of mature human Tau. By using a non-competing antibody for detection, in some embodiments, a more accurate measurement of therapeutic antibody target engagement may be made.

It is believed that the level of the 2N isoforms of Tau may be prognostic for (1) the abundance of fibrillary CNS Tau pathology, and (2) the rate of progression of cognitive impairment. Thus, in some embodiments, an anti-Tau antibody that binds to the 2N isoforms of Tau may be useful for monitoring the progression of disease and/or monitoring treatment.

F. Pharmaceutical Formulations

Pharmaceutical formulations of an anti-Tau antibody as described herein are prepared by mixing such antibody having the desired degree of purity with one or more optional pharmaceutically acceptable carriers, diluents, and/or excipients (*Remington's Pharmaceutical Sciences* 16th edition, Osol, A. Ed. (1980)), in the form of lyophilized formulations or aqueous solutions. Pharmaceutically acceptable carriers, diluents, and excipients are generally nontoxic to recipients at the dosages and concentrations employed, and include, but are not limited to: sterile water, buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-Tau antibodies provided herein may be used in therapeutic methods.

In one aspect, an anti-Tau antibody for use as a medicament is provided. In further aspects, an anti-Tau antibody for use in treating a Tau protein associated disease or disorder is provided. In some embodiments, an anti-Tau antibody for use in treating diseases or disorders caused by or associated with the formation of neurofibrillary tangles or neuropil threads is provided. In particular embodiments, an anti-Tau antibody for use in treating a tauopathy such as a neurodegenerative tauopathy is provided. Exemplary Tau protein associated diseases or disorders that can be treated that can be treated with anti-tau antibodies include, without limitation, Alzheimer's Disease, amyotrophic lateral sclerosis, Parkinson's disease, Creutzfeldt-Jacob disease, Dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia, frontotemporal dementia with parkinsonism linked to chromosome 17, Hallevorden-Spatz disease, multiple system atrophy, Niemann-Pick disease type C, Pallido-ponto-nigral degeneration, Pick's disease, progressive subcortical gliosis, progressive supranuclear palsy, Subacute sclerosing panencephalitis, Tangle only dementia (or tangle predominant dementia), Postencephalitic Parkinsonism, and Myotonic dystrophy. In some embodiments, Tau protein associated diseases or disorders that can be treated that can be treated with anti-tau antibodies include PART (primary age-related Tauopathy), tangle predominant dementia, subacute sclerosis panencephalopathy, chronic traumatic encephalopathy (CTE), white matter tauopathy with globular glial inclusions, Lewy body dementia (LBD), mild cognitive impairment (MCI), glaucoma, familial British dementia, familiar Danish dementia, Guadeloupean Parkinsonism, neurodegeneration with brain iron accumulation, SLC9A6-related mental retardation, multiple sclerosis, HIV-related dementia, senile cardiac amyloidosis, and Huntington's disease. In some embodiments, an anti-Tau antibody for use in treating Alzheimer's Disease (AD) is provided herein. In some embodiments, an anti-Tau antibody for use in treating moderate AD, mild to moderate AD, mild AD, early AD, or prodromal AD is provided herein. Further, Tau protein associated diseases or disorders that can be treated with an anti-Tau antibody include diseases or disorders that are manifested in an impairment or loss of a cognitive function such as reasoning, situational judgement, memory capacity, learning, and/or special navigation. In certain embodiments, an anti-Tau antibody for use in a method of treatment is provided. In certain embodiments, the invention provides an anti-Tau antibody for use in a method of treating an individual, having any one of the Tau associated diseases or disorders described above, comprising administering to the individual an effective amount of the anti-Tau antibody. In one such embodiment, the method further comprises administering to the individual an effective amount of at least one additional therapeutic agent, e.g., as described below.

In some embodiments, the antibody of the invention is used to treat an individual having an MMSE score of between 20 and 30, between 20 and 26, between 24 and 30, between 21 and 26, between 22 and 26, between 22 and 28, between 23 and 26, between 24 and 26, or between 25 and 26. In some embodiments, the patient has an MMSE score between 22 and 26. As used herein, an MMSE score between two numbers includes the numbers at each end of the range. For example, an MMSE score between 22 and 26 includes MMSE scores of 22 and 26.

In some embodiments, the antibodies of the invention are used to treat an individual who is 'tau positive,' e.g., a patient having brain tau deposits that are typical of Tau protein associated disorders, e.g., a patient having a positive Tau PET scan.

In further embodiments, the invention provides an anti-Tau antibody for use in reducing the levels of Tau protein (e.g., total Tau, total soluble Tau, soluble phosphorylated Tau, total insoluble Tau, insoluble phosphorylated Tau, hyperphosphorylated Tau, or paired helical filaments containing hyperphosphorylated Tau) in an individual. For example such reduction can occur in the brain (e.g., in the brain cortex and/or hippocampus). In some embodiments, the invention provides an anti-Tau antibody for use in reducing the levels of phosphorylated Tau. In some embodiments, the invention provides an anti-Tau antibody for use in reducing the levels of insoluble Tau (e.g., insoluble phosphorylated Tau). In some embodiments, the invention provides an anti-Tau antibody for use in reducing the levels of hyperphosphorylated Tau. In some embodiments, the invention provides an anti-Tau antibody for use in reducing the levels of paired helical filaments (e.g., paired helical filaments containing hyperphosphorylated Tau) in a brain tissue (e.g., in the brain cortex and/or hippocampus). In certain embodiments, the invention provides an anti-Tau antibody for use in a method of reducing the levels of Tau protein (e.g., total Tau, total soluble Tau, soluble phosphorylated Tau, total insoluble Tau, insoluble phosphorylated Tau, hyperphosphorylated Tau, or paired helical filaments containing hyperphosphorylated Tau) in the brain (e.g., in the brain cortex and/or hippocampus) in an individual comprising administering to the individual an effective amount of the anti-Tau antibody to reduce the levels of Tau protein. An "individual" according to any of the above embodiments is a mammal, preferably a human.

In some embodiments, the invention provides an anti-Tau antibody for use in modulating the levels of Tau protein (e.g., total Tau, total soluble Tau, soluble phosphorylated Tau, total insoluble Tau, insoluble phosphorylated Tau, hyperphosphorylated Tau, or paired helical filaments containing hyperphosphorylated Tau), for example, in the brain (e.g., in the brain cortex and/or hippocampus) of an individual.

In a further aspect, the invention provides for the use of an anti-Tau antibody in the manufacture or preparation of a medicament. In some embodiments, the medicament is for treatment of a Tau protein associated disease or disorder. The Tau protein associated disease or disorder can be a disease or disorders caused by or associated with the formation of neurofibrillary tangles or neuropil threads. In particular embodiments, the medicament is for treatment of a tauopathy such as a neurodegenerative tauopathy. In specific embodiments, the medicament is for treatment of diseases or disorders selected from the group consisting of: Alzheimer's Disease (AD), Creutzfeldt-Jacob disease, Dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia, frontotemporal dementia with parkinsonism linked to chromosome 17, Hallevorden-Spatz disease, multiple system atrophy, Niemann-Pick disease type C, Pallido-ponto-nigral degeneration, Pick's disease, progressive subcortical gliosis, progressive supranuclear palsy, Subacute sclerosing panencephalitis, Tangle only dementia (or tangle predominant dementia), Postencephalitic Parkinsonism, and Myotonic dystrophy. In some embodiments, the medicament is for treating PART (primary age-related Tauopathy), tangle predominant dementia, subacute sclerosis panencephalopathy, chronic traumatic encephalopathy (CTE), white matter tauopathy with globular glial inclusions, Lewy body dementia (LBD), mild cognitive impairment (MCI), glaucoma, familial British dementia, familiar Danish dementia, Guadeloupean Parkinsonism, neurodegeneration with brain iron accumulation, SLC9A6-related mental retardation, multiple sclerosis, HIV-related dementia, senile cardiac amyloidosis, or Huntington's disease. In some embodiments, the medicament is for treatment of AD. In particular embodiments, the medicament is for treatment of a Tau associated disease or disorder that is manifested in an impairment or loss of a cognitive function such as reasoning, situational judgement, memory capacity, learning, or special navigation. In a further embodiment, the medicament is for use in a method of treating one of the above-listed diseases (e.g., a tauopathy such as AD) comprising administering to an individual having such disease an effective amount of the medicament. In one such embodiment, the method further comprises administering to the individual an effective amount of at least one additional therapeutic agent, e.g., as described below.

In a further embodiment, the medicament is for reducing the levels of Tau protein (e.g., total Tau, total soluble Tau, soluble non-phorphorylated Tau, soluble phosphorylated Tau, total insoluble Tau, insoluble phosphorylated Tau, insoluble non-phorphorylated Tau, hyperphosphorylated Tau, or paired helical filaments containing hyperphosphorylated Tau). For example, such reducing of Tau protein can be observed in the brain (e.g., in the brain cortex and/or hippocampus) or in cerebrospinal fluid of an individual. In some embodiments, the medicament is for reducing the levels of paired helical filaments. In a further embodiment, the medicament is for use in a method of reducing the levels of Tau protein (e.g., total Tau, total soluble Tau, soluble phosphorylated Tau, total insoluble Tau, insoluble phosphorylated Tau, hyperphosphorylated Tau, or paired helical filaments containing hyperphosphorylated Tau) in an individual comprising administering to the individual an effective amount of the medicament to reducing the levels of Tau protein. An "individual" according to any of the above embodiments is a mammal, preferably, a human.

In a further aspect, the invention provides a method for treating a Tau protein associated disease or disorder. Tau protein associated disease or disorder that can be treated in accordance with the methods provided herein include diseases or disorders caused by or associated with the formation of neurofibrillary tangles or neuropil threads. In particular embodiments, the invention provides a method for treating a tauopathy such as a neurodegenerative tauopathy. In specific embodiments, the invention provides a method for treating a disease or disorder selected from the group consisting of: Alzheimer's Disease, Creutzfeldt-Jacob disease, Dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotetemporal dementia, frontotemporal dementia with parkinsonism linked to chromosome 17, Hallevorden-Spatz disease, multiple system atrophy, Niemann-Pick disease type C, Pallido-ponto-nigral degeneration, Pick's disease, progressive subcortical gliosis, progressive supranuclear palsy, Subacute sclerosing panencephalitis, Tangle only dementia (or tangle predominant dementia), Postencephalitic Parkinsonism, and Myotonic dystrophy. In some embodiments, methods of treating a Tau protein associated disease selected from PART (primary age-related Tauopathy), tangle predominant dementia, subacute sclerosis panencephalopathy, chronic traumatic encephalopathy (CTE), white matter tauopathy with globular glial inclusions, Lewy body dementia (LBD), mild cognitive impairment (MCI), glaucoma, familial British dementia, familial Danish dementia, Guadeloupean Parkinsonism, neurodegeneration with brain iron accumulation, SLC9A6-related mental retardation, multiple sclerosis, HIV-related dementia, senile cardiac amyloidosis, and Huntington's disease are provided. In some embodiments, the invention provides a method for treating Alzheimer's Disease (AD). In particular embodiments, the invention provides a method for treating a Tau protein associated disease or disorder that is manifested in an impairment or loss of a cognitive function such as reasoning, situational judgement, memory capacity, learning, or special navigation. In some embodiments, the method comprises administering to an individual, having any one of the diseases or disorders described above, an effective amount of an anti-Tau antibody. In one such embodiment, the method further comprises administering to the individual an effective amount of at least one additional therapeutic agent, e.g., as described below. In some embodiments, the method comprises administering to an individual having one of the diseases described herein an effective amount of an anti-Tau antibody. In one such embodiment, the method further comprises administering to the individual an effective amount of at least one additional therapeutic agent, as described below. An "individual" according to any of the above embodiments may be a human.

In a further aspect, the invention provides a method for reducing the levels of Tau protein (e.g., total Tau, total soluble Tau, soluble phosphorylated Tau, total insoluble Tau, insoluble phosphorylated Tau, hyperphosphorylated Tau, or paired helical filaments containing hyperphosphorylated Tau) in an individual. For example, such reducing of the levels of Tau protein can be observed in the brain (e.g., brain cortex and/or hippocampus) or cerebrospinal fluid of an individual. In some embodiments, the invention provides a method for reducing the levels of paired helical filaments. In some embodiments, the method comprises administering to the individual an effective amount of an anti-Tau antibody to reduce the levels of Tau protein. In some embodiments, an "individual" is a human.

In some aspects, the invention provides a method for alleviating one or more symptoms of a Tau protein associated disease or disorder; or an anti-Tau antibody or a medicament comprising anti-Tau antibody for alleviating one or more symptoms of a Tau protein associated disease or disorder (such as any of the diseases or disorders described herein, for example, AD). In some aspects, the invention provides a method for reducing the number of symptoms or the severity of one or more symptoms of a Tau protein associated disease or disorder; or an anti-Tau antibody or a medicament comprising anti-Tau antibody for reducing the number of symptoms or the severity of one or more symptoms of a Tau protein associated disease or disorder (such as any of the diseases or disorders described herein, for example, AD). In a particular embodiment, the symptom of a Tau protein associated disease or disorder is an impairment in cognition. In a specific embodiment, the symptom of a Tau protein associated disease or disorder is an impairment in learning and/or memory. In a specific embodiment, the symptom of a Tau protein associated disease or disorder is a long-term memory loss. In a specific embodiment, the symptom of a Tau protein associated disease or disorder is dementia. In some embodiments, the symptom of a Tau protein associated disease or disorder is confusion, irritability, aggression, mood swings, or a language impairment. In some embodiments, the symptom of a Tau protein associated disease or disorder is an impairment or loss of one or more cognitive functions such as reasoning, situational judgment, memory capacity, and/or learning. The methods provided herein comprise administration of an amount (e.g., therapeutically effective amount) of an anti-Tau antibody to an individual (e.g., who displays one or more symptoms of a Tau protein associated disease or disorder).

In specific aspects, the invention provides a method for retaining or increasing cognitive memory capacity, or for slowing down memory loss associated with a Tau protein associated disease or disorder; or an anti-Tau antibody or a medicament comprising anti-Tau antibody for retaining or increasing cognitive memory capacity or for slowing down memory loss associated with a Tau protein associated disease or disorder (such as any of the diseases or disorders described herein, for example, AD). The methods provided herein comprise administration of an amount (e.g., therapeutically effective amount) of an anti-Tau antibody to an individual (e.g., who displays one or more symptoms of memory loss or a decrease of memory capacity).

In some aspects, the invention provides a method for decreasing the rate of progression of a Tau protein associated disease or disorder; or an anti-Tau antibody or a medicament comprising anti-Tau antibody for decreasing the rate of progression of a Tau protein associated disease or disorder (such as any of the diseases or disorders described herein, for example, AD). The methods provided herein comprise administration of an amount (e.g., therapeutically effective amount) of an anti-Tau antibody to an individual (e.g., who displays one or more symptoms of a Tau protein associated disease or disorder).

In some aspects, the invention provides a method for preventing the development of a Tau protein associated disease or disorder; or an anti-Tau antibody or a medicament comprising anti-Tau antibody for preventing the development of a Tau protein associated disease or disorder (such as any of the diseases or disorders described herein, for example, AD). The methods provided herein comprise administration of an amount (e.g., therapeutically effective amount) of an anti-Tau antibody to an individual (e.g., who is at risk of a Tau protein associated disease or disorder).

In some aspects, the invention provides a method for delaying the development of a Tau protein associated disease or disorder; or an anti-Tau antibody or a medicament comprising anti-Tau antibody for delaying the development of a Tau protein associated disease or disorder (such as any of the diseases or disorders described herein, for example, AD). The methods provided herein comprise administration of an amount (e.g., therapeutically effective amount) of an anti-Tau antibody to an individual (e.g., who displays one or more symptoms of a Tau protein associated disease or disorder).

In a further aspect, the invention provides pharmaceutical formulations comprising any of the anti-Tau antibodies provided herein, e.g., for use in any of the above therapeutic methods. In some embodiments, a pharmaceutical formulation comprises any of the anti-Tau antibodies provided herein and a pharmaceutically acceptable carrier. In another embodiment, a pharmaceutical formulation comprises any of the anti-Tau antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent.

For example, the composition according to the invention may be administered in combination with other compositions comprising an additional therapeutic agent, such as a biologically active substance or compound such as, for example, a known compound used in the medication of tauopathies and/or of amyloidoses, a group of diseases and disorders associated with amyloid or amyloid-like protein such as the amyloid 3 protein involved in Alzheimer's Disease.

Generally, the other biologically active compound may include neuron-transmission enhancers, psychotherapeutic drugs, acetylcholine esterase inhibitors, calcium-channel blockers, biogenic amines, benzodiazepine tranquilizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, serotonergic receptor antagonists, or other therapeutic agents. In particular, the biologically active agent or compound may comprise at least one compound selected from compounds against oxidative stress, anti-apoptotic compounds, metal chelators, inhibitors of DNA repair such as pirenzepine and metabolites, 3-amino-1-propanesulfonic acid (3APS), 1,3-propanedisulfonate (1,3PDS), secretase activators, beta- and gamma-secretase inhibitors, tau proteins, anti-Tau antibodies (including, but not limited to, antibodies disclosed in WO2012049570, WO2014028777, WO2014165271, WO2014100600, WO2015200806, U.S. Pat. Nos. 8,980,270, and 8,980,271), neurotransmitter, beta-sheet breakers, antiinflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine and other drugs and nutritive supplements such as, for example, vitamin B 12, cysteine, a precursor of acetylcholine, lecithin, choline, Ginkgo biloba, acyetyl-L-carnitine, idebenone, propentofylline, or a xanthine derivative, together with a binding peptide according to the invention including antibodies, particularly monoclonal antibodies and active fragments thereof, and, optionally, a pharmaceutically acceptable carrier and/or a diluent and/or an excipient and instructions for the treatment of diseases.

In some embodiments, an antibody of the invention may be administered in combination with a neurological drug. Such neurological drugs include, but are not limited to, an antibody or other binding molecule (including, but not limited to a small molecule, a peptide, an aptamer, or other protein binder) that specifically binds to a target selected from: beta secretase, presenilin, amyloid precursor protein or portions thereof, amyloid beta peptide or oligomers or fibrils thereof, death receptor 6 (DR6), receptor for advanced glycation endproducts (RAGE), parkin, and huntingtin; an NMDA receptor antagonist (i.e., memantine), a monoamine depletor (i.e., tetrabenazine); an ergoloid mesylate; an anticholinergic antiparkinsonism agent (i.e., procyclidine, diphenhydramine, trihexylphenidyl, benztropine, biperiden and trihexyphenidyl); a dopaminergic antiparkinsonism agent (i.e., entacapone, selegiline, pramipexole, bromocriptine, rotigotine, selegiline, ropinirole, rasagiline, apomorphine, carbidopa, levodopa, pergolide, tolcapone and amantadine); a tetrabenazine; an anti-inflammatory (including, but not limited to, a nonsteroidal anti-inflammatory drug (i.e., indomethicin and other compounds listed above); a hormone (i.e., estrogen, progesterone and leuprolide); a vitamin (i.e., folate and nicotinamide); a dimebolin; a homotaurine (i.e., 3-aminopropanesulfonic acid; 3APS); a serotonin receptor activity modulator (i.e., xaliproden); an, an interferon, and a glucocorticoid or corticosteroid. The term "corticosteroid" includes, but is not limited to, fluticasone (including fluticasone propionate (FP)), beclometasone, budesonide, ciclesonide, mometasone, flunisolide, betamethasone and triamcinolone. "Inhalable corticosteroid" means a corticosteroid that is suitable for delivery by inhalation. Exemplary inhalable corticosteroids are fluticasone, beclomethasone dipropionate, budenoside, mometasone furoate, ciclesonide, flunisolide, and triamcinolone acetonide.

In some embodiments, one or more anti-amyloid beta (anti-Abeta) antibodies may be administered with an anti-Tau antibody provided herein. Non-limiting examples of such anti-Abeta antibodies include crenezumab, solanezumab, bapineuzumab, aducanumab, gantenerumab, and BAN-2401 (Biogen, Eisai Co., Ltd.). In some embodiments, one or more beta-amyloid aggregation inhibitors may be administered with an anti-Tau antibody provided herein. Nonlimiting exemplary beta-amyloid aggregation inhibitors include ELND-005 (also referred to as AZD-103 or scyllo-inositol), tramiprosate, and PTI-80 (Exebryl-1®; Proteo-Tech). In some embodiments, one or more BACE inhibitors may be administered with an anti-Tau antibody provided herein. Non-limiting examples of such BACE inhibitors include E-2609 (Biogen, Eisai Co., Ltd.), AZD3293 (also known as LY3314814; AstraZeneca, Eli Lilly & Co.), MK-8931 (verubecestat), and JNJ-54861911 (Janssen, Shionogi Pharma). In some embodiments, one or more Tau inhibitors may be administered with an anti-Tau antibody provided herein. Non-limiting examples of such Tau inhibitors include methylthioninium, LMTX (also known as leuco-methylthioninium or Trx-0237; TauRx Therapeutics Ltd.), Rember™ (methylene blue or methylthioninium chloride [MTC]; Trx-0014; TauRx Therapeutics Ltd), PBT2 (Prana Biotechnology), and PTI-51-CH3 (TauPro™; ProteoTech). In some embodiments, one or more other anti-Tau antibodies may be administered with an anti-Tau antibody provided herein. Non-limiting examples of such other anti-Tau antibodies include BMS-986168 (Bristol-Myers Squibb) and C2N-8E12 (AbbVie, C2N Diagnostics, LLC). In some embodiments, a general misfolding inhibitor, such as NPT088 (NeuroPhage Pharmaceuticals), may be administered with an anti-Tau antibody provided herein.

In some embodiments, the composition according to the invention may comprise niacin or memantine together with a chimeric antibody or a humanized antibody according to the invention including antibodies, particularly monoclonal antibodies and active fragments thereof, and, optionally, a pharmaceutically acceptable carrier and/or a diluent and/or an excipient.

In some embodiments, compositions are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with the chimeric antibody or the humanized antibody according to the invention or active fragments thereof, and, optionally, a pharmaceutically acceptable carrier and/or a diluent and/or an excipient.

Other compounds that can be suitably used in compositions in addition to chimeric antibody or humanized antibody according to the invention, are those disclosed, for example, in WO 2004/058258 (see especially pages 16 and 17) including therapeutic drug targets (page 36-39), alkanesulfonic acids and alkanolsulfuric acid (pages 39-51), cholinesterase inhibitors (pages 51-56), NMDA receptor antagonists (pages 56-58), estrogens (pages 58-59), non-steroidal anti-inflammatory drugs (pages 60-61), antioxidants (pages 61-62), peroxisome proliferators-activated receptors (PPAR) agonists (pages 63-67), cholesterol-lowering agents (pages 68-75); amyloid inhibitors (pages 75-77), amyloid formation inhibitors (pages 77-78), metal chelators (pages 78-79), anti-psychotics and anti-depressants (pages 80-82), nutritional supplements (pages 83-89) and compounds increasing the availability of biologically active substances in the brain (see pages 89-93) and prodrugs (pages 93 and 94), which document is incorporated herein by reference, but especially the compounds mentioned on the pages indicated above.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In some embodiments, administration of the anti-Tau antibody and administration of an additional therapeutic agent occur within about one month, or within about one, two or three weeks, or within about one, two, three, four, five, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 pg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 pg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-Tau antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-Tau antibody.

III. Examples

The following are examples of methods and compositions of the invention. It is understood that various other embodiments may be practiced, given the general description provided above.

Example 1: Generation of Tau for Immunization

Generation of Monomeric Recombinant Tau

The recombinant human Tau construct, 2N4R isoform (amino acids 2-441), was fused to a N-terminal His-tag to facilitate purification and characterization. See, e.g., FIG. 15. The fusion construct was cloned into the pET52b vector (Novagen) and expressed in E. coli. Cells were harvested and lysed under denaturing condition using 7M guanidinium chloride overnight at 4° C. with stirring. Cell debris was pelleted at 40,000 rpm for 1 hour. The recombinant, His-tagged protein was isolated by nickel affinity chromatography (Ni Sepharose excel affinity resin, GE Healthcare Life Sciences) followed by size-exclusion chromatography (Superdex 200 resin, GE Healthcare Life Sciences) under denaturing condition. Guanidinium chloride was removed by dialyzing the recovered protein into 20 mM MES, 50 mM NaCl, and 1 mM TCEP at pH 6.8. The His-tag was subsequently removed using TEV protease, followed by final purification using cation exchange chromatography (Mono S column, GE Healthcare Life Sciences) to remove the cleaved His-tag. The purification buffer contained 0.1% Triton x-114 (v/v) to remove endotoxin. Purified protein was exchanged into PBS with 1 mM TCEP. The purity and monomeric state were analyzed by SDS-PAGE and SEC-MALLS. Identity was confirmed by mass spectrometry. Protein concentration was determined by UV absorption at 280 nm. The final product was free of endotoxin (<0.5 EU/mg), as determined by Kinetic Limulus Amebocyte Lysate (LAL) assay.

Generation of Phosphorylated Tau

Phosphorylated Tau was generated using the Tau 2-441 construct prepared using the method described above. The protein construct was phosphorylated using 0.5 µM PKA kinase (Life Technologies), which phosphorylates serine 409, among other residues. The reaction mixture was incubated with 1 mM ATP, 5 mM $MgCl_2$, at room temperature for 72 hours. Phosphorylation was confirmed by mass spectrometry. Size-exclusion chromatography (Superdex 75, GE Healthcare Life Sciences) was used to remove the kinase. The purity, monomeric state, and endotoxin level of the phosphorylated protein preparation were analyzed substantially as described above.

In Vitro Oligomerization of Monomeric Tau

Oligomeric Tau was generated using the monomeric Tau 2-441 construct. The monomeric protein was first exchanged into 20 mM N,N-Bis(2-hydroxyethyl)-2-aminoethanesulfonic acid (BES), 25 mM NaCl, pH 7.4, followed by oligomeriztion using 75 pM arachidonic acid (Cayman Chemicals) and 18 kDa Heparin (Sigma Aldrich), at equimolar concentration with protein at 37° C. for 3 days. Oligomerization was confirmed by thioflavin T fluorescence assay, dynamic light scattering (DLS), and analytical size-exclusion chromatography. Oligomeric Tau is in some instances referred to as "oligoTau."

Example 2: Generation of Anti-Tau Antibodies

Methods

Generation of Hybridomas

Female C57BL/6JOlaHsd (C57BL/6) and BALB/c OlaHsd (Balb/c) wild-type mice (Harlan, USA) were received at 9 weeks of age. Tau knock-out mice (B6.129-Mapttm1Hnd/J; The Jackson Laboratory, USA) were received at 6 and 9 weeks of age. Vaccinations started at 12 to 15 weeks of age. Mice were vaccinated with oligomerized human Tau. Before vaccination, the oligoTau was mixed with one of two adjuvants used in this study, Ribi Adjuvant System (Ribi; Sigma-Aldrich, Switzerland) at 50% v/v, or a combination of CpG single-stranded synthetic DNA oligodeoxynucleotides (CpG; Microsynth, Switzerland) and aluminium hydroxide (Al; Brenntag, Switzerland). Ribi is 2% squalene oil-in-water emulsion containing monophosphoryl lipid A (isolated from Salmonella minnesota) and synthetic trehalose dicorynomycolate (isolated from the cord factor of the Tubercle bacillus) in squalene oil, 0.2% Tween-80, and water.

Mice were vaccinated by subcutaneous injection (s.c.), except groups D and G, which received a combination of intraperitoneal (i.p.) and hock administrations. Mice in group D were administered 50 pg of oligoTau i.p. and 10 µg of oligoTau as hock injection. Mice in group G were administered 8 µg of oligoTau i.p. and 2 µg of oligoTau as hock injection. See Table 2.

For vaccinations containing CpG and Al (CpG/Al) as adjuvant, each injection of 200 µL contained 60 µg (30 nmol) CpG, 1 mg Al, and 50 µg oligoTau. For all study groups, mice were injected on days 0, 14, 35, and 56. Mice used for myeloma fusion (Nanotools, Germany) were additionally vaccinated with three daily booster injections of oligoTau (50 µg per i.p. injection) without adjuvant added.

TABLE 2

Mice and vaccination protocols

| Study group | Mouse strain | Total oligoTau dose (µg/injection) | Adjuvant | Vaccination route |
|---|---|---|---|---|
| A | C57BL/6 | 50 | CpG/Al | s.c. |
| B | C57BL/6 | 50 | Ribi | s.c. |
| C | Balb/c | 50 | CpG/Al | s.c. |
| D | Balb/c | 60 | CpG/Al | hock + i.p. |
| E | Balb/c | 5 | CpG/Al | s.c. |
| F | Balb/c | 50 | Ribi | s.c. |
| G | Tau knock-out | 10 | Ribi | hock + i.p. |

Mice were bled and sacrificed one day following the last of three booster injections, and splenocytes were fused with myeloma cells to generate antibody producing hybridomas.

Selection of Hybridomas for Subcloning

For fusions, mice were divided into three groups, for a total of 10 fusions (2 fusions in one group, four fusions in the second group, and four fusions in the third group), generating 299 hybridomas. Viable hybridomas were grown using serum-containing selection media, and the best hybridomas were then selected for subcloning, using ELISA assays for full-length human Tau and oligoTau binding as described below. Following limiting dilution, the final hybridomas were then grown in serum-free medium and media was collected from stable colonies for antibody screening and selection.

ELISA Screening Assays

Serum-free supernatants were harvested from stable hybridomas. The supernatants containing antibodies of interest were then screened by ELISA assays to characterize antibody properties and select antibodies for further development. The ELISA assays were used to determine the following: binding to full-length human Tau (flTau; Signal-Chem, Canada), binding to hyperphosphorylated flTau (Genentech, USA), binding to oligomeric versus monomeric preparations of flTau, binding to 0N4R, 1N4R and 2N4R Tau isoforms (rPeptide, USA), and binding to certain antibody Tau epitope(s). Briefly, 96-well MaxiSorp ELISA plates (Nunc, Denmark) were coated with one of the targets as shown in Table 3.

TABLE 3

Targets used for the ELISA screening assays.

| Assay | ELISA setup | Target |
|---|---|---|
| Binding to flTau | Indirect ELISA | Full-length human Tau (flTau) coated at 1 µg/mL |
| Binding to pTau | Indirect ELISA | Full-length human Tau phosphorylated in vitro using 4 kinases (GSK3β, Cdk5, PKA, and CK1δ; hyper-phosphorylated Tau or pTau) purified and coated at 1 µg/mL |
| Epitope mapping | Indirect ELISA | Biotinylated 15-mer peptides spanning the 441 amino acids (aa) of human Tau with 9 aa offset and 6 aa overlap coated at 10 µg/mL on a streptavidin 96-well plate |
| Binding to oligoTau | Capture ELISA | AVI-tag biotinylated oligomeric and monomeric flTau captured in solution by anti-IgG immobilized antibodies being tested |
| Binding to human Tau isoforms | Indirect ELISA | 0N4R Tau, 1N4R Tau and 2N4R Tau coated at 1 µg/mL |

Coating was done overnight in phosphate-buffered saline (PBS) at 4° C. Plates were washed thoroughly with 0.05% Tween-20/PBS and then blocked with 1% bovine serum albumin (BSA) in 0.05% Tween-20/PBS for 1 hr at 37° C. The antibody contained in the hybridoma supernatant was then added at the indicated dilutions, and incubated for 2 hrs at 37° C. after which the plates were washed as described previously.

For the indirect ELISAs, an AP-conjugated anti-mouse IgG secondary antibody (Jackson ImmunoResearch Laboratories, United Kingdom) was added at 1/6000 dilution in 0.05% Tween-20/PBS for 2 hr at 37° C. After the final wash, plates were incubated with p-nitrophenyl phosphate disodium hexahydrate (pNPP; Sigma-Aldrich, Switzerland) phosphatase substrate solution, and read at 405 nm using an ELISA plate reader (Tecan, Switzerland). Results are expressed as optical densities (O.D.).

For the oligoTau and monoTau capture ELISAs, antibodies contained in serum-free sterile hybridoma supernatants were immobilized on an anti-IgG coated plate at 500-fold dilution, followed by the incubation of oligoTau or monoTau, both with site-specific biotinylation via an AVI-tag. The target incubations started at 5 µg/mL and then were diluted 8- or 16-fold. Streptavidin-HRP and ABTS substrate was used for signal quantitation in a plate reader (Tecan, Switzerland). Results are expressed as O.D.

Affinity Estimates

Affinity of non-purified antibodies in serum-free hybridoma supernatants was estimated by surface plasmon resonance using a Biacore T-100 instrument (GE Healthcare, United Kingdom). Antibodies were immobilized onto an anti-IgG biosensor chip, and flTau (SignalChem, Canada) was used as the target analyte. Kinetic analysis was done using a 1:1 Langmuir fit model.

SDS-PAGE and Western-Blot Assays

The binding of selected panTau antibodies to Tau in human brain was tested in a Western-blot (WB) using brain lysates from three AD and two age-matched non-AD control donors (Tissue Solutions, United Kingdom). The lysates were processed to obtain a detergent-free soluble Tau fraction. Processed lysates were loaded onto 4-12% bis-tris gels (Novex, Life Technologies, Switzerland) and transferred onto Immobilon PVDF membranes and blotted with antibodies being tested with and an IRDye 800CW goat anti-mouse secondary antibody (Li-Cor, USA).

ELISA Assay Using Human Brain Lysates or Recombinant Human Tau Isoforms

To assess the binding of selected antibodies to non-denatured human Tau in AD and control brain lysates, or to recombinant Tau isoforms 0N4R, 1N4R and 2N4R (rPeptide, USA), antibodies from hybridoma supernatants, or a negative and positive control antibodies, were immobilized on a 96-well plate as described above. Tau in soluble human brain lysates from AD or age-matched control subjects (400 µg/mL protein; all from Tissue Solutions, United Kingdom) or recombinant Tau isoforms (1 µg/mL) were then captured and detection was performed using a polyclonal rabbit panTau antibody (AbCam, United Kingdom) followed by an Fc-γ fragment specific anti-rabbit IgG-AP (Jackson ImmunoResearch, USA). Brain lysate from Tau knock-out mouse was used as a negative sample control. Plates were incubated with pNPP (Sigma-Aldrich) phosphatase substrate solution, and read at 405 nm using an ELISA plate reader (Tecan, Switzerland). Results are expressed as optical densities (O.D.).

Sequencing of Antibody Hybridomas

Hybridoma cell lysates were supplied to Antitope (Antitope, United Kingdom) for variable region gene sequencing. Briefly, RT-PCR was performed using degenerate primer pools for murine signal sequences together with constant region primers for each of IgG variable heavy (VH), IgM VH, Ig kappa variable light (KVL) and Ig λ VL chains. Heavy chain V-region mRNA was amplified using a set of six degenerate primer pools (HA to HF) specific for VH signal sequences together with either IgM or IgG-specific constant region primers. The light chain V-region mRNA was amplified using a set of eight signal sequence-specific degenerate primer pools, seven for the κ cluster (KA to KG) and one for the λ cluster (LA), together with either κ or λ constant region primers. The PCR products obtained from successful amplification were purified, cloned into a 'TA' cloning vector (pGEM-T Easy, Promega), transformed into E. coli and individual colonies sequenced. The nucleotide and amino acid sequences of the antibody VH and VL regions were determined with the sequences for 27 antibody hybridomas.

Results

Selection of Hybridomas for Subcloning

Hybridomas that were generated from each of the three rounds of fusions, a total of 299 hybridomas derived from ten fusions, were initially assayed for binding to flTau, with selected hybridomas additionally assayed for binding to pTau and oligomerized Tau. The aim was to select antibodies that bind equally well to Tau and to Tau modified post-translationally, such as phosphorylated or oligomeric Tau. For this, assays were run on hybridomas to select for the best panTau properties. To determine antibody binding region and the specific Tau epitope, the binding region was first determined using different Tau fragments and then a library of 15-mer overlapping Tau peptides spanning the full 441 amino acids (aa) sequence of the longest human Tau isoform. A group of antibodies binding to pre-determined regions of Tau were intentionally avoided with the aim to maximize binding to different post-translationally modified forms of Tau and to all the six different human Tau isoforms present in humans.

The three fusion series resulted in the generation of 133 subcloned stable hybridomas that were screened for the best panTau properties. A combination of different screening assays was used to narrow down the number of antibody hybridomas having the preferred properties for a panTau antibody. For comparing flTau and pTau binding, 90 hybridomas were assayed with the results of 24 hybridomas shown in FIG. 1A-F. As an initial screen had been performed using Tau fragments to avoid selecting antibodies binding to regions of Tau known to have high density of residues that are phosphorylated in Alzheimer's disease (AD) and other tauopathies, most antibodies tested bound to both flTau and pTau with similar binding properties as determined by this ELISA.

In some embodiments, it is desirable that a panTau antibody bind to both monomeric and oligomeric forms of Tau without a strong preference to one or the other. A capture ELISA was set up to determine if antibodies bound to both monomeric and oligomeric forms of flTau. An ELISA run in capture mode preserves the oligomer conformation of pre-oligomerized Tau and the monomeric state of monoTau better than when run as a direct or indirect ELISA with the targets immobilized onto an ELISA plate.

Each assay was run by directly comparing the binding of the two forms of Tau to all 90 antibodies tested. Antibodies known to have preferred binding to either oligoTau or that do not discriminate between the two forms of Tau were used as controls in each assay. The results of 18 hybridomas are shown in FIG. 2A-E.

Mapping the epitopes is important for selecting antibodies with good panTau properties, as antibodies that bind to regions with high density of potential pTau residues (Ser, Thr, and Tyr) can be avoided. Binding to all six isoforms of human Tau was also used as a selection criterion for a panTau antibody. The panTau epitopes of antibodies that had been initially selected were verified and determined with improved accuracy using a library of 49 peptides each having 15 amino acids (aa) spanning the full length of human Tau, with an overlap of 6 aa residues and an offset of 9 aa. The residue numbers are based on the longest isoform of human Tau (441 aa). Non-purified antibodies were used at high 1/10 dilution to verify binding versus no binding to all peptides. Screening of antibodies from 112 hybridomas previously selected by ELISA indicated binding to 20 different Tau epitopes (Table 4).

TABLE 4

Tau epitopes for antibodies

| Antibody | Tau epitope (aa) |
|---|---|
| 14F5-D9 | 1-15 |
| 94B2-B12 | 1-15 |
| 94B2-C1 | 1-15 |
| 10A1-A6 | 10-24 |
| 10A1-D8 | 10-24 |
| 11E10-B8 | 10-24 |
| 17G12-C11 | 10-24 |
| 17G12-D5 | 10-24 |
| 19H6-A1 | 10-24 |
| 19H6-F7 | 10-24 |
| 19H6-G8 | 10-24 |
| 37D3-H12 | 10-24 |
| 37D3-H9 | 10-24 |
| 37E8-B4 | 10-24 |
| 37E8-C2 | 10-24 |
| 3A4-H4 | 10-24 |
| 3H10-E12(A) | 10-24 |
| 3H10-G12 | 10-24 |
| 44B7-A9 | 10-24 |
| 44B7-B1 | 10-24 |
| 54C1-H11 | 10-24 |
| 61E7-B11 | 10-24 |
| 61H10-B4 | 10-24 |
| 61H10-H3 | 10-24 |
| 127G7-A5 | 10-24 |
| 127G7-E7 | 10-24 |
| 115A4-A3 | 10-24 |
| 115A4-B1 | 10-24 |
| 125B11-B6 | 10-24 |
| 73C8-A5 | 10-24 |
| 73C8-G4 | 10-24 |
| 76B4-D9 | 10-24 |
| 76B4-H7 | 10-24 |
| 123E9-B3 | 19-33 |
| 15C6-A7 | 19-33 |
| 19F8-B1 | 19-33 |
| 24A11-D5 | 19-33 |
| 63H3-B2 | 19-33 |
| 63H3-D8 | 19-33 |
| 64B9-E11 | 19-33 |
| 64B9-F12 | 19-33 |
| 45D2-C9 | 19-33 |
| 45D2-F4 | 19-33 |
| 72E12-B2 | 19-33 |
| 72G10-A7 | 19-33 |
| 72G10-B6 | 19-33 |
| 123E9-A1 | 19-42 |
| 19F8-C11 | 19-42 |
| 7A11-C12 | 19-42 |
| 89F4-A2 | 28-42 |
| 89F4-A1 | 28-44 |
| 12A10-E8 | 37-51 |
| 55E7-B12 | 37-51 |
| 72E12-H9 | 37-51 |
| 55E7-F11 | 37-51 |
| 30D12-B5 | 64-78 |
| 21C1-D8 | 64-78 |
| 21C1-G6 | 64-78 |
| 30D12-F6 | 64-78 |
| 31A3-A4 | 64-78 |
| 31A3-A7 | 64-78 |
| 77D1-D2 | 64-78 |
| 77D1-E6 | 64-78 |
| 30A1-C9 | 73-87 |
| 30A1-D11 | 73-87 |
| 28F5-G8 | 82-96 |
| 28F5-H8 | 82-96 |
| 33G9-A11 | 100-114 |
| 33G9-B9 | 100-114 |
| 52F2-E12 | 100-114 |
| 52F2-E8 | 100-114 |
| 52F6-B3 | 100-114 |

TABLE 4-continued

Tau epitopes for antibodies

| Antibody | Tau epitope (aa) |
|---|---|
| 52F6-F11 | 100-114 |
| 56D3-C8 | 100-114 |
| 56D3-E9 | 100-114 |
| 70B10-B6B2 | 100-114 |
| 70B10-B6G12 | 100-114 |
| 78E4-D11 | 100-114 |
| 78E4-G4 | 100-114 |
| 30G1-B2 | 109-123 |
| 30G1-C11 | 109-123 |
| 49G10-F4 | 109-123 |
| 49G10-H1 | 109-123 |
| 65B1-A2 | 109-123 |
| 65B1-A7 | 109-123 |
| 73H6-B8 | 109-123 |
| 113F5-A8 | 109-123 |
| 113F5-F7 | 109-123 |
| 125B11-H3 | 109-123 |
| 26C1-B11 | 118-132 |
| 26C1-C8 | 118-132 |
| 74H10-A3 | 118-132 |
| 74H10-C3 | 118-132 |
| 78F3-B2 | 118-132 |
| 78F3-E7C6 | 118-132 |
| 78F3-E7H7 | 118-132 |
| 126H12-G6 | 136-150 |
| 126H12-H7 | 136-150 |
| 22G7-C9 | 154-168 |
| 22G7-G9 | 154-168 |
| 111B8-C4 | 163-177 |
| 111B8-F10 | 163-177 |
| 66F5-A1 | 172-177 |
| 66F5-F2 | 172-177 |
| 71H8-A1 | 190-204 |
| 71H8-D6 | 190-204 |
| 83E10-D10 | 190-204 |
| 83E10-D6 | 190-204 |
| 126F11-B3 | 217-231 |
| 126F11-G11 | 217-231, 335-357 |
| 93A8-C9 | 397-411 |
| 93A8-D2 | 397-411 |

Human Tau Isoform Selectivity

Figure 26:
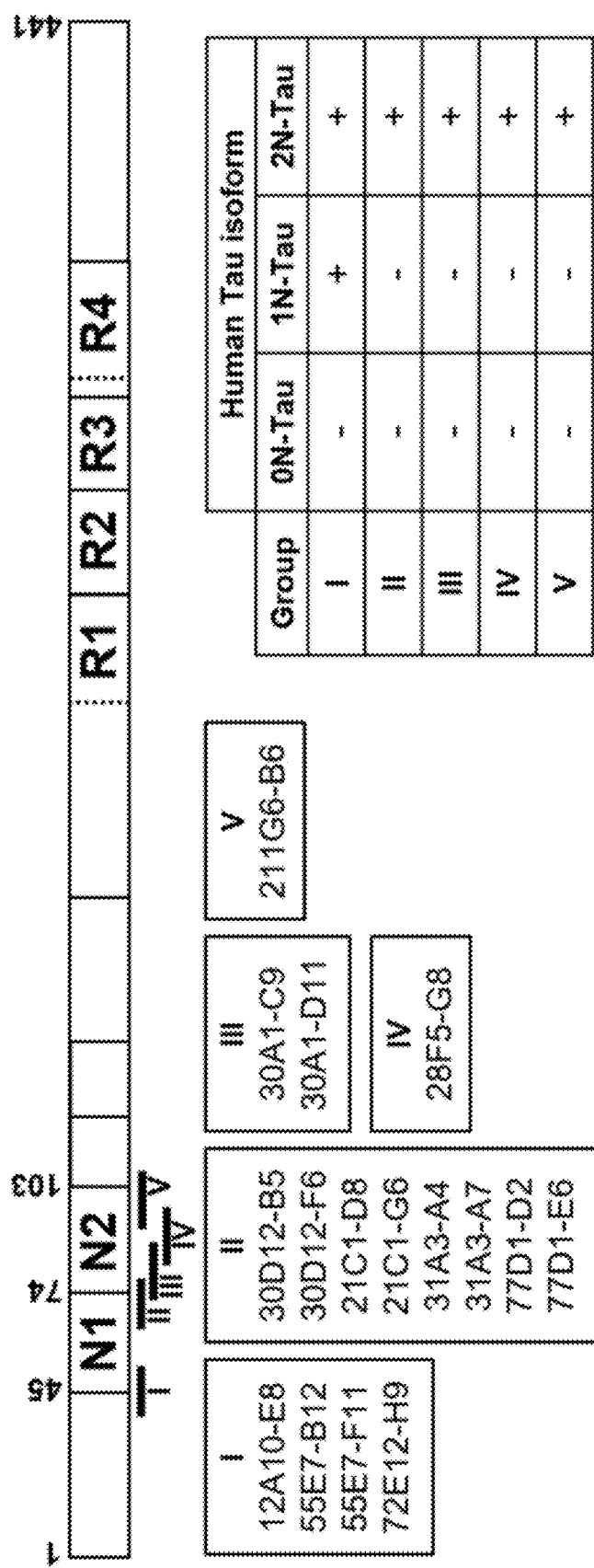
FIG. 26 shows epitope grouping of antibodies that binds in the N-terminal region of Tau. Antibodies are divided into five groups indicated as I to V, with epitopes mapped to residues 37-51 (Group I), 64-78 (Group II), 73-87 (Group III), 82-96 (Group IV), or 91-105 (Group VI). The table specifies the Tau isoforms these antibodies are selective for (+) and against (−).

Antibodies with epitopes mapped to the region of Tau encoded by exons 1 to 4 were assayed for binding selectivity for or against three human Tau isoforms. Indirect or sandwich ELISAs were performed using 0N-, 1N-, and 2N-Tau to verify human Tau isoform binding selectivity (FIGS. 25 and 26). As indicated by the assigned epitopes, antibodies binding to residues 37-51 (12A10-E8, 55E7-B12, 55E7-F11, and 72E12-H9) are selective for isoforms that are either 1N- or 2N-Tau, whereas antibodies binding to residues 64-78 (30D12-B5, 30D12-F6, 21C1-D8, 21C1-G6, 31A3-A4, 31A3-A7, 77D1-D2, and 77D1-E6), 73-87 (30A1-C9, and 30A1-D11), 82-96 (28F5-G8), or 91-105 (211G6-B6) are selective for 2N-Tau. None of these antibodies bound to 0N-Tau. All other antibodies mapped to epitopes in the region bound to all three isoforms of human Tau.

For affinity measurements to flTau, antibodies were measured using SPR on a Biacore instrument, with the $K_D$s determined. Biacore affinity measurements were done by immobilizing antibodies on an anti-IgG chip and using flTau as the target analyte. Results for certain antibodies are shown in Table 5. Of the antibodies measured for affinity to flTau, 47 antibodies had affinities better than 20 nM, of which 35 antibodies had $K_D$s under 5 nM with antibody 37D3-H9 having a $K_D$ (affinity) of 1 nM.

TABLE 5

Affinity for flTau

| Antibody | $K_D$ (nM) |
|---|---|
| 37D3-H9 | 1 |
| 54C1-H11 | 1.5 |
| 123E9-A1 | 1.8 |
| 9462-C1 | 1.9 |
| 24A11-D5 | 2 |
| 113F5-F7 | 2.4 |
| 89F4-A1 | 2.9 |
| 19F8-B1 | 2.9 |
| 61E7-C4 | 3.3 |
| 126F11-G11 | 4.2 |
| 26C1-C8 | 4.3 |
| 93A8-D2 | 4.3 |
| 37E8-B4 | 4.4 |
| 61E7-B11 | 4.8 |
| 125B11-H3 | 6 |
| 54C1-C3 | 6.8 |
| 94B2-B12 | 4.5 |
| 127G7-A5 | 3 |
| 63H3-D8 | 0.5 |
| 64B9-F12 | 2 |
| 7A11-C12 | 0.5 |
| 12A10-E8 | 0.8 |
| 52F6-B3 | 11 |
| 49G10-F4 | 1 |
| 65B1-A2 | 0.8 |
| 74H10-A3 | 4 |
| 83E10-D6 | 0.4 |
| 126F11-B3 | 2.2 |
| 231G3-F10 | 0.2 |
| 3A4-H4 | 7.8 |
| 52F6-F11 | 8.4 |
| 3A4-A12 | 10.1 |
| 44B7-B1 | 14.7 |
| 3H10-E12 | 19.4 |
| 10A1-D8 | 19.6 |
| 52F2-E8 | 26 |
| 19H6-F7 | 39 |
| 34H4-F5 | 43 |
| 19H6-A1 | 56 |
| 34H4-B10 | 69 |
| 17G12-C11 | 118 |
| 45H12-C4 | 139 |
| 17G12-D5 | 161 |
| 61H10-H3 | 177 |
| 11E10-C3 | 399 |
| 72E12-H9 | 2 |
| 30D12-B5 | 2 |
| 77D1-D2 | 0.5 |
| 30A1-C9 | 0.6 |
| 28F5-G8 | 1 |
| 33G9-A11 | 14 |
| 74H10-C3 | 8 |
| 78F3-E7H7 | 6.7 |
| 22G7-C9 | 36 |
| 71H8-D6 | 0.8 |
| 83E10-D10 | 0.4 |
| 211G6-B6 | 4.7 |
| 307H3-E8 | 1 |

Figure 3:
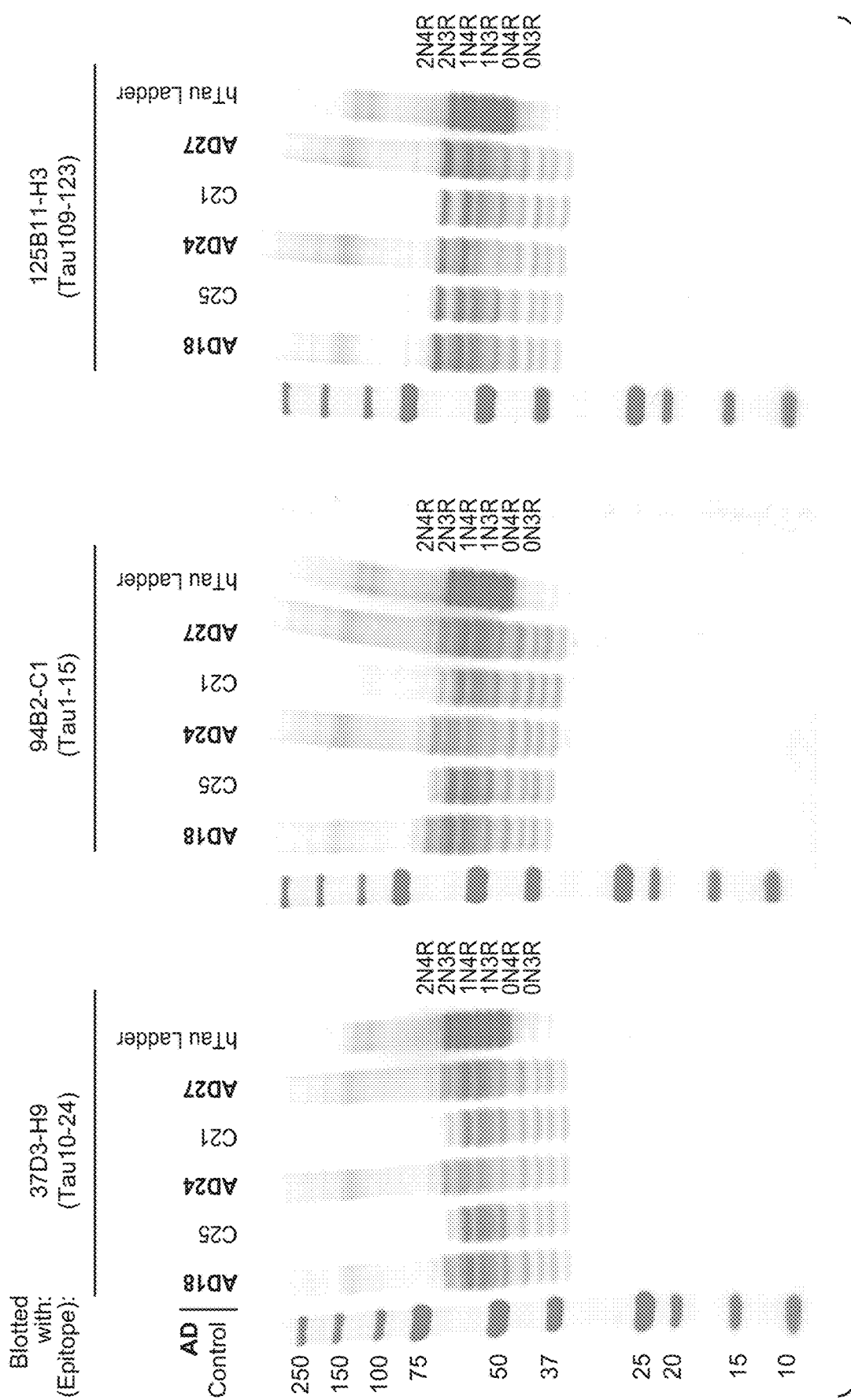
FIG. 3. The three panTau antibodies tested show binding to soluble Tau in brain lysates from Alzheimer's disease (AD) and matched control donors using a Western blot (WB) assay. Protein extracts from AD and control brain lysates, and six isoforms of recombinant human Tau, were run on SDS-PAGE and membranes blotted with three panTau antibodies (37D3-H9, 94B2-C1, and 125B11-H3). Lanes with AD samples are labeled as AD18, AD24, and AD27, and lanes with control samples are labeled as C25 and C21. The lanes run with six isoforms of recombinant human Tau are labeled as hTau ladder.

To verify the binding of selected antibodies to all six isoforms of human Tau, an SDS-PAGE was run with a recombinant Tau ladder containing all six isoforms and Western-blot (WB) done using three selected Tau antibodies. All three panTau antibodies bind to all six Tau isoforms (FIG. 3). Furthermore, brain homogenates from three AD and two age-matched controls were simultaneously run for comparison. As expected, and based on the mapped epitopes, all three antibodies tested in this assay showed binding to all six Tau isoforms. The difference observed in band patterns between human AD and control donors may represent the greater phosphorylation and/or SDS-stable Tau aggregates that would be expected to be present in AD subjects.

Figure 4A:
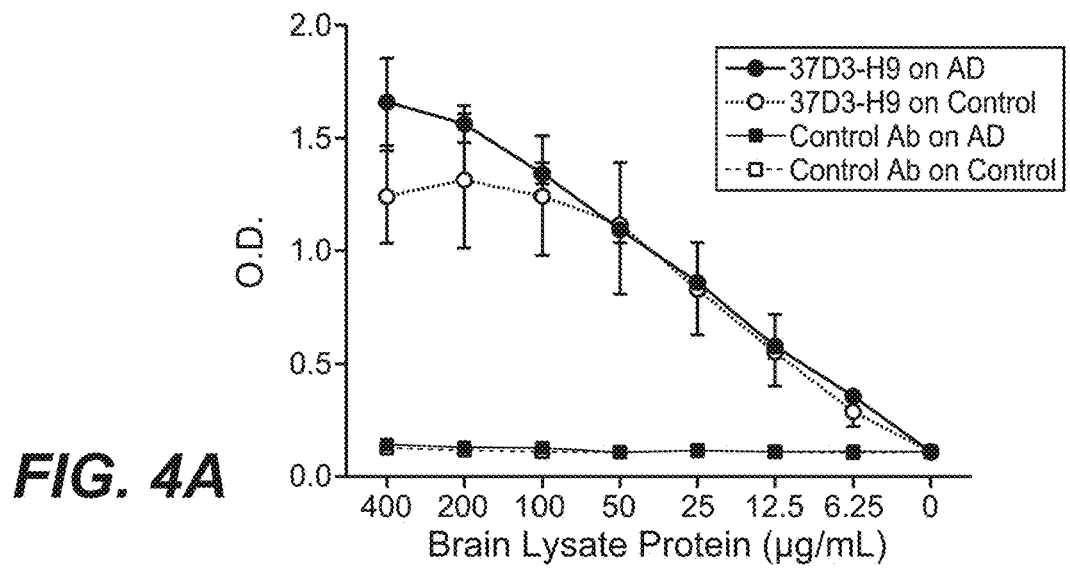
FIG. 4A-C. PanTau antibodies show binding to soluble Tau in brain lysates from AD and matched control donors using a Tau capture ELISA. Data is shown for three panTau antibodies, 37D3-H9, 94B2-C1, and 125B11-H3. Results are expressed in optical densities (O.D.), with mean values ±SD, N=2.
Figure 4B:
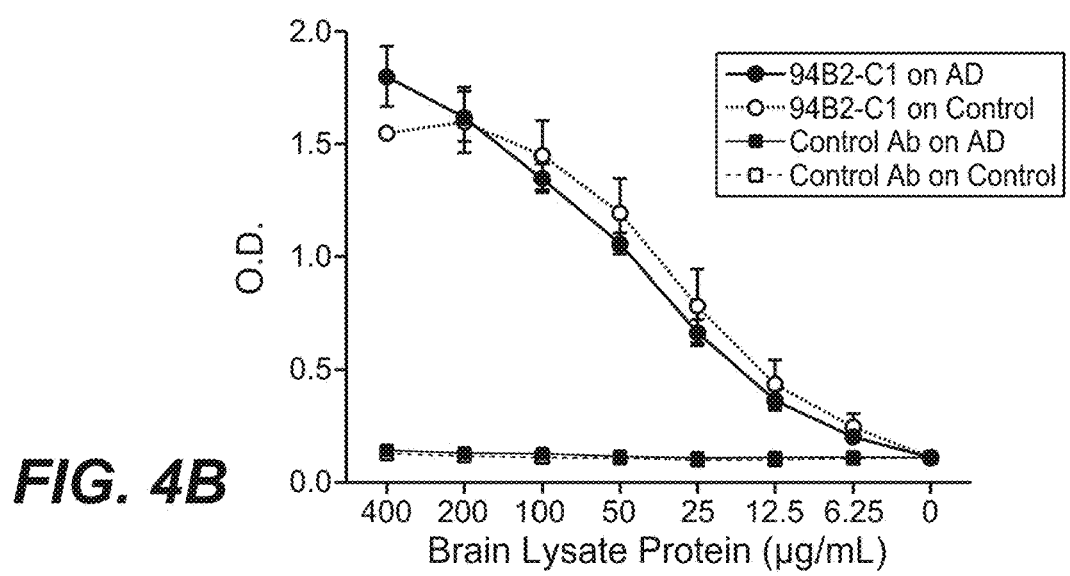
Figure 4C:
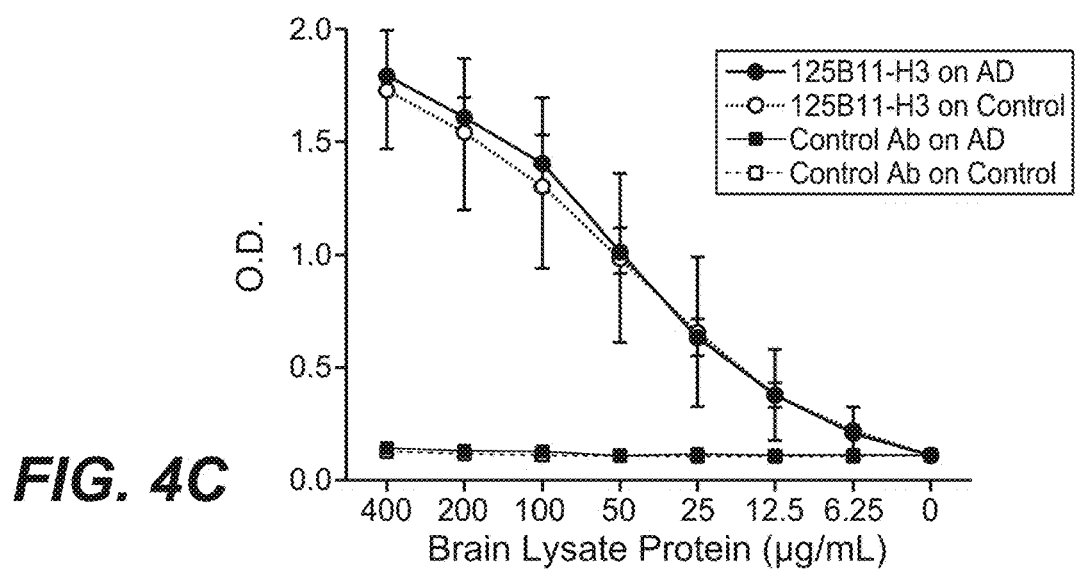

Human Alzheimer's disease (AD) and control samples were additionally run in a non-denaturing ELISA capture assay to verify binding to Tau in human brains. Samples lysates processed for soluble Tau from two AD and two non-AD age-matched control subjects were run at 8 dilutions testing three antibodies (FIG. 4A-C).

Antibody variable chain sequences were determined for 27 hybridomas (Antitope, United Kingdom). Protein sequences for certain heavy and light chain variable domains and hypervariable regions (HVRs) are shown in the Table of Sequences.

Example 3: Characterization Anti-Tau Antibodies

Antibody heavy and light chains were constructed via gene synthesis and subcloning of the resulting DNA into murine IgG2a (heavy chain) and murine kappa (light chain) mammalian expression vectors. Antibodies were expressed in CHO or 293T cells by transient co-transfection of the heavy chain and light chain plasmids and were purified with affinity resin MabSelectSure (GE Healthcare Life Sciences). Purified recombinant antibodies were screened for binding to Tau monomer protein on a Biacore T200 surface plasmon resonance instrument using a mouse IgG capture kit and a Series S CM5 chip. Antibodies in mIgG2a format diluted in 10 mM HEPES pH7.4, 150 mM NaCl, 0.05% Tween 20 (running buffer, HBSP) were captured for 30 or 45 seconds at a concentration of 1 µg/ml (antibodies 26C1, 94B2-C1, 52F6-F11.v1, 52F6-F11.v2, 11E10-B8, 55E7-F11, 125B1-H3, 123E9-A1, 30G1-B2, 66F5-A1, 89F4-A1, 93A8-D2 and 126F11-G11) or for 70 or 150 seconds at a concentration of 0.1 µg/ml (antibodies 19H6-F7, 3A4-H4, 54C1-H11 and 37D3-H9) using a flow rate of 10 µl/min. Binding of Tau monomer in HBSP was monitored at 25° C. using a flow rate of 30 µl/min and concentrations of 16, 31, 63, 125, 125, 250 and 500 nM for antibodies 26C1 and 94B2; 16, 31, 63, 125, 125, 250, 500 and 1000 nM for antibodies 52F6-F11.v1 and 52F6-F11.v2; 6, 19, 56, 56, 167 and 500 nM for antibodies 11E10-B8, 55E7-F11 and 125B11-H3; 5, 16, 49, 148, 148, 444, 1333 and 4000 nM for antibodies 123E9-A1, 30G1-B2, 66F5-A1, 89F4-A1, 93A8-D2 and 126F11-G11; 0.4, 1.6, 6.3, 2.5, 100 and 400 nM for 19H6-F7; and 0.2, 0.8, 4, 4, 20 and 100 nM for 3A4-H4, 54C1-H11 and 37D3-H9. Association and dissociation times were monitored for 180-480 seconds and for 300-600 seconds respectively. Antibody 37D3-H9 was selected for further analysis due to the high affinity (Table 6) and the absence of NXS/T glycosylation motifs in the CDRs.

TABLE 6

$K_D$ (nM) of murine antibodies to human Tau monomer.
Data shown represent output of a 1:1 binding model.

| Antibody | $K_D$ (nM) | $k_{on}$ (1/Ms) | $k_{off}$ (1/s) |
|---|---|---|---|
| 26C1 | 17 | $4 \times 10^4$ | $7 \times 10^{-4}$ |
| 94B2-C1 | 6 | $5 \times 10^4$ | $3 \times 10^{-4}$ |
| 54C1-H11 | 0.6 | $3 \times 10^5$ | $2 \times 10^{-4}$ |
| 3A4-H4 | 12 | $3 \times 10^4$ | $3 \times 10^{-4}$ |
| 37D3-H9 | 1.6 | $1 \times 10^5$ | $1 \times 10^{-4}$ |
| 19H6-F7 | 10 | $2 \times 10^5$ | $2 \times 10^{-3}$ |
| 11E10-B8 | 108 | $2 \times 10^5$ | $2 \times 10^{-2}$ |
| 55E7-F11 | 171 | $2 \times 10^5$ | $4 \times 10^{-2}$ |
| 125B11-H3 | 5 | $5 \times 10^4$ | $3 \times 10^{-4}$ |
| 123E9-A1 | 52 | $4 \times 10^5$ | $2 \times 10^{-2}$ |
| 30G1-B2 | 20 | $4 \times 10^5$ | $8 \times 10^{-3}$ |
| 66F5-A1 | 105 | $8 \times 10^4$ | $8 \times 10^{-3}$ |
| 89F4-A1 | 27 | $3 \times 10^5$ | $7 \times 10^{-3}$ |
| 93A8-D2 | 6 | $3 \times 10^5$ | $2 \times 10^{-3}$ |

TABLE 6-continued $K_D$ (nM) of murine antibodies to human Tau monomer.
Data shown represent output of a 1:1 binding model.

| Antibody | $K_D$ (nM) | $k_{on}$ (1/Ms) | $k_{off}$ (1/s) |
|---|---|---|---|
| 126F11-G11 | 3 | $2 \times 10^6$ | $4 \times 10^{-3}$ |
| 52F6-F11.v1 | 15 | $5 \times 10^4$ | $7 \times 10^{-4}$ |
| 52F6-F11.v2 | 5 | $7 \times 10^4$ | $4 \times 10^{-4}$ |

37D3-H9 Demonstrates Avidity when Binding to Tau Protein

Human monomer Tau protein was covalently coupled to a Biacore Series S CM5 chip using the Biacore Amine Coupling Kit (GE Life Sciences), resulting in immobilization to a level of approximately 128 RU. Direct binding of 37D3-H9 in both Fab and IgG formats was monitored using the single-cycle kinetics experimental format with five association periods of 300s each and antibody concentrations of 1, 2, 4, 8 and 16 nM (IgG) or 5, 10, 20, 40 and 80 nM (Fab). Dissociation was monitored for 7200 seconds (Fab) or for 14400 seconds (IgG). A value for the dissociation rate was calculated by fitting a 1:1 binding model to the data. Calculated dissociation rates were $5.0 \times 10^{-4}$ for 37D3-H9 Fab and $1.1 \times 10^{-5}$ for 37D3-H9 IgG, a 45-fold difference. FIG. 5 illustrates the difference in the dissociation rates of Fab (left panel) and IgG (right panel), indicating that 37D3-H9 IgG is demonstrating avidity.

Example 4: Humanization of Anti-Tau Antibodies

Antibody 37D3-H9 was humanized by grafting the antibody CDRs and selected variable region framework residues onto human antibody consensus frameworks (Dennis, M. S. (2010). CDR repair: A novel approach to antibody humanization. In Current Trends in Monoclonal Antibody Development and Manufacturing, S. J. Shire, W. Gombotz, K. Bechtold-Peters and J. Andya, eds. (Springer, New York), pp. 9-28). Grafting onto consensus VH3, Vκ2 and Vκ1 frameworks was assessed. The heavy chain graft included murine residue at position 49 (Kabat numbering system). The Vκ2 graft included murine residues in framework positions 2 and 4. The Vκ1 graft included murine residues in framework positions 2, 4 and 43. Humanized variants were constructed by gene synthesis and subcloning into human IgG1 or IgG4 and Kappa chain mammalian expression vectors. Antibodies were expressed by co-transfection of the heavy and light chain plasmids into CHO cells and purified with affinity resin MabSelect Sure. Humanized variants were screened for affinity to human Tau monomer using the Biacore human IgG capture kit, a Series S CM5 chip and a Biacore T200 instrument. Antibodies were diluted to 2 µg/ml and captured for 15 seconds at 10 µl/min. Association and dissociation of 100, 33, 11 and 3.7 nM human Tau monomer in 10 mM HEPES pH7.4, 150 mM NaCl, 0.05% Tween 20 (running buffer, HBSP) was monitored for 180 seconds and 600 seconds respectively at a flow rate of 30 µl/min. A 1:1 binding model was applied to the results (Table 7).

TABLE 7

Affinity screening of humanized variants for monomeric human Tau

| Antibody variant | Light chain framework | $K_D$ (nM) |
|---|---|---|
| hu37D3-H9.v1 | Kappa1 | 4.1 |
| hu37D3-H9.v2 | Kappa1 | 5.6 |
| hu37D3-H9.v3 | Kappa1 | 8.8 |

TABLE 7-continued

Affinity screening of humanized variants for monomeric human Tau

| Antibody variant | Light chain framework | $K_D$ (nM) |
|---|---|---|
| hu37D3-H9.v4 | Kappa1 | 8.2 |
| hu37D3-H9.v5 | Kappa2 | 1.9 |
| hu37D3-H9.v6 | Kappa2 | 3.5 |
| hu37D3-H9.v7 | Kappa2 | 27.0 |
| hu37D3-H9.v8 | Kappa2 | 10.2 |
| hu37D3-H9.v9 | Kappa2 | 13.2 |
| hu37D3-H9.v10 | Kappa2 | 14.3 |
| hu37D3-H9.v11 | Kappa2 | 74.8 |
| hu37D3-H9.v12 | Kappa2 | 21.6 |
| hu37D3-H9.v13 | Kappa2 | 9.0 |
| hu37D3-H9.v14 | Kappa2 | 10.8 |
| hu37D3-H9.v15 | Kappa2 | 19.0 |
| hu37D3-H9.v16 | Kappa2 | 27.2 |
| hu37D3-H9.v17 | Kappa2 | 8.1 |
| hu37D3-H9.v18 | Kappa2 | 13.4 |
| hu37D3-H9.v19 | Kappa2 | 55.7 |
| hu37D3-H9.v20 | Kappa2 | 36.9 |
| hu37D3-H9.v21 | Kappa2 | 38.1 |
| hu37D3-H9.v22 | Kappa2 | 36.6 |
| hu37D3-H9.v23 | Kappa2 | 81.1 |
| hu37D3-H9.v24 | Kappa2 | 56.6 |

Antibody variants hu37D3-H9.v1, hu37D3-H9.v2, hu37D3-H9.v5 and hu37D3-H9.v6 were characterized further by surface plasmon resonance with additional antibody concentrations and longer association/dissociation times. These variants were analyzed with a broader range of human Tau monomer concentrations (1.2, 3.7, 11.1, 11.1, 33.3, 100 nM) and increased association (300 seconds) and dissociation (1200 seconds) periods. A 1:1 binding model was applied to the results (Table 8).

TABLE 8

Detailed analysis of binding kinetics of selected variants to human Tau by surface plasmon resonance

| Antibody variant | Light chain framework | $K_D$ (nM) |
|---|---|---|
| hu37D3-H9.v1 | Kappa1 | 1.1 nM, 1.0 nM |
| hu37D3-H9.v2 | Kappa1 | 1.2 nM |
| hu37D3-H9.v5 | Kappa2 | 0.8 nM |
| hu37D3-H9.v6 | Kappa2 | 1.4 nM |

A YTE (M252Y/S254T/T256E) mutation was incorporated into certain IgG4 antibodies. Fc Receptor-neonate (FcRn) binding domain mutations such as M252Y, S254T and T256E (YTE) have been described to increase FcRn binding and thus increase the half-life of antibodies. See U.S. Published Patent Application No. 2003/0190311 and Dall'Acqua et al., *J. Biol. Chem.* 281:23514-23524 (2006).

Antibody 125B11-H3 was humanized onto VH3 and Vκ1 consensus frameworks. The heavy chain graft included murine residues at position 78 (Kabat numbering system). The Vκ1 graft included murine residues in framework positions 43 and 87. The light chain of 113F5-F7 was also humanized onto the Vκ1 framework, with additional murine residues at framework positions 43 and 87. Humanized variant heavy chains (125B11) and light chains (125B11 and 113F5-F7) were co-transfected in multiple combinations and purified in 96-well format as described above. Humanized variants were then screened for affinity for human Tau monomer using the Biacore human IgG capture kit, a Series S CM5 chip and a Biacore T200 instrument. Antibodies were diluted to 2 μg/ml and captured for 15 seconds at 10 μl/min. Association and dissociation of 0, 100 and 500 nM human Tau monomer in HBSP was monitored for 180s and 300s respectively at a flow rate of 40 μl/min. A 1:1 binding model was applied to the results (Table 9).

TABLE 9

Screening of 125B11-H3 and 113F5-F7 humanization variants by surface plasmon resonance

| Screening $K_D$ (nM) | | 125B11 heavy chain humanization variant | | | | | |
|---|---|---|---|---|---|---|---|
| | | HC1 | HC2 | HC3 | HC4 | HC5 | HC6 |
| 125B11 light | LC1 | 16, 19 | 18 | 18 | 15 | 85 | — |
| chain | LC2 | 20 | 20 | 19 | 14 | —* | NT |
| humanization | LC3 | 21 | 23 | 20 | 15 | — | — |
| variant | LC4 | 23 | 22 | 20 | 17 | >100 | >100 |
| 113F5-F7 light | LC1 | 57 | 61 | 54 | 44 | — | — |
| chain | LC2 | 67 | 68 | 55 | 47 | — | — |
| humanization | LC3 | 61 | 64 | 54 | 47 | >100 | — |
| variant | LC4 | 71 | 77 | 65 | 51 | — | — |

*Minimal binding to Tau monomer.
NT, not tested.

Variants hu125B11.v17 (HC3+LC1), hu125B11.v26 (HC4+LC2) and hu125B11.v28 (HC4+LC4) were selected for high-resolution kinetic analysis based on the affinity screen (Table 10). Antibody 94B2-C1 was humanized onto VH1 and Vκ2 frameworks. The heavy chain graft also included murine residues at position 28, 29, 67, 69, 71, and 73 (Kabat numbering system). The Vκ2 graft also included murine residues in framework positions 2, 36, and 46. Combinations of eight heavy chains and eight light chains were expressed, purified and screened by surface plasmon resonance (SPR) as described for 125B11 above. Results of the SPR screen are shown in Table 11. Variant hu94B2.v105 (heavy chain variant 94B2.HCl, light chain variant 94B2.LC13) was selected for detailed SPR characterization (Table 11).

TABLE 10

Kinetic data for selected humanized anti-Tau antibody variants

| Antibody | Isotype | $K_D$ (nM) | $k_{on}$ (1/Ms) | $k_{off}$ (1/s) |
|---|---|---|---|---|
| hu125B11.v17 | hIgG1 | 10.5 | $0.8 \times 10^5$ | $0.8 \times 10^{-3}$ |
| hu125B11.v26 | hIgG1 | 9.5 | $0.7 \times 10^5$ | $0.7 \times 10^{-3}$ |
| hu125B11.v28 | hIgG1 | 10.2 | $0.7 \times 10^5$ | $0.7 \times 10^{-3}$ |
| hu94B2.v105 | hIgG1 | 3.7 | $0.8 \times 10^5$ | $0.3 \times 10^{-3}$ |

TABLE 11

Screening of 94B2 humanization variants by surface plasmon resonance

| Screening $K_D$ (nM) | | LC9 | LC10 | LC11 | LC12 | LC13 | LC14 | LC15 | LC16 |
|---|---|---|---|---|---|---|---|---|---|
| 94B2 Heavy | HC1 | 3.8* | § | 91.5 | § | 4.1¶ | § | 104.0 | § |
| Chain | HC2 | 5.7 | § | 89.6 | § | 7.4 | NT | 99.6 | § |
| humanization | HC3 | 2.0 | § | 69.3 | § | 3.8 | § | 64.1 | § |
| variant: | HC4 | 61.9 | § | § | § | 64.1 | § | § | § |
| | HC5 | 2.7 | § | 62.6 | § | 4.0 | § | 72.6 | § |
| | HC6 | 0.9 | § | 70.1 | § | 3.0 | § | 74.1 | § |
| | HC7 | 52.9 | § | § | § | 57.8 | § | § | § |
| | HC8 | 1.0 | § | 44.3 | § | 2.4 | § | 51.5 | § |

*Mean of n = 3 repeats.
¶hu94B2.v105.
§ Minimal binding to Tau monomer observed.

NT, not tested.

Example 5: Stability Analysis of Humanized Anti-Tau Antibodies

Identification of Chemical Instability

Antibody samples were thermally stressed to mimic stability over the shelf life of the product. Samples were buffer exchanged into 20 mM Acetate buffer, pH 5.5, or phosphate buffer, pH 7.4, and diluted to a concentration of 1 mg/ml. One ml of sample was stressed at 40° C. for 2 weeks and a second was stored at −70° C. as a control. Both samples were then digested using trypsin to create peptides that could be analyzed using liquid chromatography (LC)—mass spectrometry (MS) analysis. For each peptide in the sample retention time, from the LC as well as high resolution accurate mass and peptide ion fragmentation information (amino acid sequence information) were acquired in the MS. Extracted ion chromatograms (XIC) were taken for peptides of interest (native and modified peptide ions) from the data sets at a window of +10 ppm and peaks were integrated to determine area. Relative percentages of modification were calculated for each sample by taking the (area of the modified peptide) divided by (area of the modified peptide plus the area of the native peptide) multiplied by 100. These relative percentages were then compared between the control (t=0) and the stressed (t=2 weeks) samples. Percentages shown represent the control (t=0) value subtracted from the stressed (t=2 weeks) value. Deamidation analysis of antibodies hu37D3-H9.v1 and hu37D3-H9.v5 led to the observation that the sequence $N^{28}G^{29}N^{30}$ (Kabat numbering) within the light chain CDR-1 was susceptible to deamidation. The increase in deamidated $N^{28}G^{29}N^{30}$ was found to be 16.5% for hu37D3-H9.v1 and 11% for hu37D3-H9.v5.

Impact of Deamidation on Antibody Binding to Antigen

To assess the impact of $N^{28}$ deamidation on the affinity for human Tau, it was desirable to obtain two samples with widely separated $N^{28}$ deamidation status. Hu37D3-H9.v5 hIgG4.S228P was incubated at 40° C. for two weeks at a concentration of 1 mg/ml in Phosphate Buffered Saline, pH 7.4. Deamidation of the $N^{28}G^{29}$ motif was measured using LC-MS/MS. The t=2 week stressed sample had a 43.1% increase deamidation relative to the t=0 unstressed sample. The stressed and unstressed antibodies were analyzed for Tau binding by surface plasmon resonance (Biacore) using the GE Biacore human IgG capture kit and a Series S CM5 chip. The hIgG were diluted to 2 μg/ml in 10 mM HEPES pH7.4, 150 mM NaCl, 0.05% Tween 20 (running buffer, HBSP) and captured at a flow rate of 10 μl/min for 15 seconds (t0 sample) or 17 seconds (t2 sample). Kinetic data was collected for Human Tau monomer injected at concentrations of 0, 3.1, 6.3, 12.5, 25, 25, 50 & 100 nM in HBSP, using a flow rate of 30 μl/min, a 300 s association phase and an 1800 s dissociation phase. Between cycles the surface was regenerated using a 30 second injection of 3M Magnesium Chloride at 10 μl/min. A 1:1 binding model was fitted to the data using instrument defaults, including local fitting of the "RI" parameter. Results shown in FIG. 6 and Table 12 demonstrate that although the stressed antibody immobilized at greater levels than the unstressed antibody in this experiment, the magnitude of the Tau binding signal (as represented by the magnitude of the parameter Rmax) was noticeably lower. After normalizing the Rmax value for the differences in capture level, the stressed (t=2 weeks) sample appeared to show approximately half the total Tau binding capacity of the unstressed sample (indicated by a 56% reduction in the Normalized Rmax). The calculated affinity did not appear to change: in this analysis the difference in $K_D$ between the t=0 and the t=2 weeks samples was less than 2% ($K_D$=0.7 nM for t=0 and t=2 weeks). The results are consistent with the t=2 weeks sample containing a significantly reduced population of high affinity antibody.

TABLE 12

Relative binding of stressed and unstressed hu37D3-H9.v5 samples to monomeric Tau by surface plasmon resonance

| hu37D3-H9.v5 hIgG4.S228P sample | Ligand Level (RU) | Rmax (RU) | Normalized Rmax (=Rmax/ Ligand Level) | Change in Normalized Rmax |
|---|---|---|---|---|
| Control (t = 0) | 102.9 | 47.7 | 0.46 | N/A |
| Stressed (t = 2 weeks) | 146.8 | 30.2 | 0.21 | −56% |

Impact of Deamidation on Antibody Binding to Antigen and Calculation of "Normalized Rmax"

Given that asparagine deamidation is expected to result in aspartic acid and iso-aspartic acid products (Bischoff R. & Kolbe H. V. J. (1994). *J. Chromat.* 5, 662, p 261-278) the impact of replacing $N^{28}$ with $D^{28}$ (variant hu37D3-H9.v5 N28D) on affinity for human Tau monomer was analyzed. Affinity was assessed at 25° C. using a Biacore T200 instrument, the GE Biacore human IgG capture kit and a CM5 Series S chip. The hIgG were diluted to 2 μg/ml in 10 mM HEPES pH7.4, 150 mM NaCl, 0.05% Tween 20 (running buffer, HBSP) and captured at a flow rate of 10 μl/min for 22 seconds. Kinetic data was collected for human Tau monomer injected at concentrations of 0, 6.3, 12.5, 25, 25, 50, 100, 200, and 400 nM in HBSP, using a flow rate of 30 µl/min, a 300 second association phase and a 600 second dissociation phase. Between cycles the surface was regenerated using a 30 second injection of 3M Magnesium Chloride at 10 µl/min. A 1:1 binding model was fitted to the data and affinities for hu37D3-H9.v5 and hu37D3-H9.v5.3 (also referred to herein as hu37D3-H9.v5 N28D) calculated using kinetic analysis. Parameters used for the 1:1 fitting included the Instrument default of local fitting for the "RI" parameter. The results are shown in FIG. 7 and Table 13.

Calculated $K_D$ for the hu37D3-H9.v5 N28D variant was $160 \times 10^{-9}$ M, compared to $1.5 \times 10^{-9}$ M (mean, n=4 intra-experiment determinations) for hu37D3-H9.v5 analyzed under the same conditions. Therefore, conversion of $N^{28}$ to $D^{28}$ causes >100-fold reduction in affinity. Given the comparatively low affinity of the hu37D3-H9.v5 N28D variant, and the comparatively rapid kinetics, we reasoned that the kinetics analysis of a mixture of the $N^{28}$ and $D^{28}$ variants would be dominated by the higher affinity population, and that presence of the lower affinity variants might be reflected by a reduction in the Normalized Rmax. To validate this reasoning, the Tau-binding profile of antibody variants hu37D3-H9.v5 and hu37D3-H9.v5 N28D were compared to that of the two antibodies mixed together in equal quantities. Compared to hu37D3-H9.v5 alone, a 1:1 mix of hu37D3-H9.v5 and hu37D3-H9.v5 N28D resulted in a 45% reduction in Normalized Rmax (Table 13). We concluded that changes in Normalized Rmax upon thermal stress may be indicative of a reduced population of high affinity antibody in the stressed sample. We reasoned that changes in Normalized Rmax could therefore be used to screen variants of hu37D3-H9 for improved stability.

TABLE 13

Changes in Normalized Rmax observed upon thermal stress of hu37D3-H9.v5 and upon mixing of hu37D3-H9.v5 with anticipated deamidation product hu37D3-H9.v5 N28D

| Sample | $K_D$ (nM) | Rmax (RU) | Decrease in Normalized Rmax compared to Reference* | Comments |
|---|---|---|---|---|
| hu37D3-H9.v5 hIgG1 | 1.5 ± 0.2 | 76.1 ± 0.4 | Reference | Mean +/− Standard Deviation of four intra-experiment analyses |
| hu37D3-H9.v5 N28D hIgG1 | 160 | 81.0 | 4% | |
| hu37D3-H9.v5 & hu37D3-H9.v5 N28D hIgG1 | 2.0 | 46.4 | 45% | Two antibodies mixed at a 1:1 ratio |
| hu37D3-H9.v5 hIgG4.S228P, t = 0 | 1.5 | 68.8 | 3% | Control for Stressed sample |
| hu37D3-H9.v5 hIgG4.S228P, t = 2 weeks | 1.5 | 33.4 | 54% | Stressed sample |

*Normalized Rmax = Rmax (RU)/Ligand Level (RU). Normalized Rmax for reference antibody = 0.33 (mean of four intra-experiment determinations, standard deviation < 0.01).

Antibody Optimization and Selection

Ninety 37D3-H9 variants were assessed by Biacore to compare their functional stability with or without a two-week 40° C. thermal stress period. The variants included most single mutations of the $N^{28}G^{29}N^{30}T^{31}$ motif, double mutants containing the G29A mutation, double mutations of Asn-28 and Tyr-32 that might functionally replace these to hydrogen-bonded residues, as well as all possible permutations of residues 2, 4, 33, and 93 as either the residues present in the original 37D3-H9 antibody or the corresponding germline residue variant. In addition, mutations were tested in the context of residue 1 being Asp or Glu, which does not impact affinity or stability of the Asn-28 residue.

Antibodies were expressed by transient transfection of Expi293 cells in 96-well format and automated purification performed on a Tecan freedom EVO 200 liquid handling system with a 500 µL MCA96 head. Briefly, IgGs in 1 mL culture were captured using tip columns that were custom packed with 20 µL MabSelect SuRe resin (Glygen Corp & GE Healthcare). After washing with 1×PBS pH 7.4, IgGs were eluted into 160 µL of 50 mM phosphoric acid pH 3 and neutralized with 12 µL of 20×PBS pH 11. MabSelect SuRe tip columns were stripped in 0.1 M NaOH and regenerated with 1×PBS pH 7.4 for consecutive use of up to 15 times. Purified antibodies in 96-well format were normalized to 0.1 mg/ml using a Hamilton Star liquid handling robot. The "pre-stress" samples were kept at approximately 4° C. and the "post-stress" samples were incubated at 40° C. for two weeks in a PCR machine. Functional stability of the variants was compared by running surface plasmon resonance kinetics experiments with the "pre-stress" and "post-stress" antibody preps. The antibodies were assessed using a human antibody capture CM5 Series S chip generated using the GE Biacore human IgG capture kit and a Biacore T200 instrument. Antibodies diluted to 2 µg/ml were immobilized using a 15 second injection time and 10 µl/min flow rate. Binding to Tau monomer at 0 nM, 26.5 nM and 265 nM, at 25° C., using a flow rate of 40 µl/min, was monitored for a 180 second association phase followed by a 300 second dissociation phase. Samples were run in 10 mM HEPES pH7.4, 150 mM NaCl, 0.05% Tween 20 (HBSP) using a multi-cycle kinetics format. Data was analyzed using BIAevaluation software, fitting a 1:1 binding model. The resulting affinity ($K_D$) values are shown in FIG. 8A-D. A Stability Index was also calculated, using the rationale that affinity-compromised antibodies (due for example to deamidation of key residues) are expected to contribute equally to the IgG capture level ("Ligand Level") but to contribute less to the measured Tau binding, and that this would be reflected in the experimentally derived value for Rmax. To account for variations in the amount of each antibody captured, Rmax was normalized for the antibody capture level (as measured by "Ligand Level", Response Units immobilized during antibody capture). Thus Normalized Rmax is calculated as the experimental Rmax (units=RU) divided by the "Ligand Level" (Evaluation output representing the RU captured during the hIgG capture step, units=RU), and Stability Index is calculated here as Normalized Rmax (post-stress) divided by Normalized Rmax (pre-stress).

Figure 9:
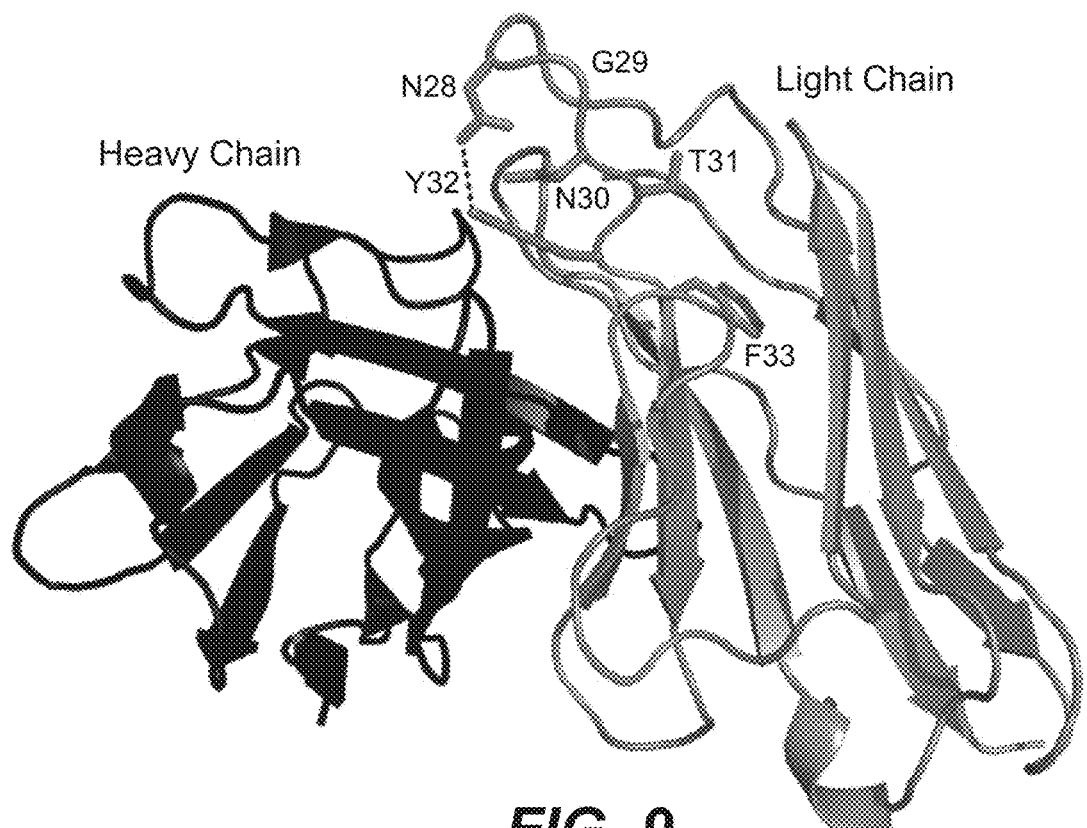
FIG. 9. Structural model of the 37D3-H9 Fv region showing the positions of residues 28-33 (NGNTYF motif) of the light chain and relative positions of residues 28 and 33. Note that residue 33, mutated in hu37D3.v28.A4 to Leu, is not nearby the unstable Asn-28 residue. The dotted line shows a hydrogen bond between residues Asn-28 and Tyr-32. Figure generated using MOE software package (Chemical Computing Group).

Selected antibodies were expressed by transient transfection of CHO cells and purified. The antibodies were then stressed for two weeks at 1 mg/ml and deamidation analyzed by LC-MS/MS, using RCM tryptic peptide mapping with DTT reduction, IAA capping and pH 8.2 digestion. Results (Table 14) demonstrated that variant hu37D3-H9.v28.A4 had reduced susceptibility to deamidation on the $N^{28}G^{29}N^{30}$ motif. The reduced deamidation of the hu37D3-H9.v28.A4 was unexpected, as the residue is not located in the immediate vicinity of the Asn-28 residue (FIG. 9) and it is not clear how the F33L mutation might stabilize Asn-28.

TABLE 14

Stability of the hu37D3-H9.v28.A4 variants in stress tests for deamidation

| Antibody | | Thermal Stress Conditions | Increase in deamidation of light chain $N^{28}G^{29}N^{30}$ |
|---|---|---|---|
| hu37D3-H9.v1 | hIgG1 | 40° C. in Acetate Buffer, pH 5.5 | 16.5% |
| hu37D3-H9.v5 | hIgG1 | 40° C. in Acetate Buffer, pH 5.5 | 11% |
| hu37D3-H9.v28.A4 | hIgG1 | 40° C. in Acetate Buffer, pH 5.5 | $N^{28}$: 2.8% $N^{30}$: 0.2% |
| | | 37° C. in PBS pH 7.4 | $N^{28}$: 5.3% $N^{30}$: ND |
| | hIgG4.S228P.YTE | 40° C. in Acetate Buffer, pH 5.5 | $N^{28}$: 0% $N^{30}$: 0% |
| | | 37° C. in PBS pH 7.4 | $N^{28}$: 10.4% $N^{30}$: 2.0% |

Example 6: Humanized Anti-Tau Antibody Selection and Characterization

Antibody Selection and Characterization: Binding to Human Tau Protein

Affinity of selected antibodies was assessed at 25° C. using a Biacore T200 instrument, the GE Biacore human IgG capture kit and a CM5 Series S chip. The hIgG were diluted to 0.25 µg/ml in 10 mM HEPES pH7.4, 150 mM NaCl, 0.05% Tween 20 (running buffer, HBSP) and captured at a flow rate of 10 µl/min for 150 seconds. Kinetic data was collected for Human Tau monomer injected at concentrations of 0, 0.4, 1.2, 3.7, 11, 11, 33 and 100 nM in HBSP, using a flow rate of 30 µl/min, a 300 second association phase and a 600 second dissociation phase. Between cycles the surface was regenerated using two sequential 30 second injections of 3M MgCl at 10 µl/min. Data was fit to a 1:1 binding model (Table 15).

TABLE 15

Kinetic data for selected humanized anti-Tau antibody variants

| Antibody | Isotype | $K_D$ (nM) | $k_{on}$ (1/Ms) | $k_{off}$ (1/s) |
|---|---|---|---|---|
| hu37D3-H9.v28.A4 | hIgG1 | 1.5 | $6.9 \times 10^5$ | $1.1 \times 10^{-3}$ |
| hu37D3-H9.v5 | hIgG1 | 1.0 | $7.5 \times 10^5$ | $0.8 \times 10^{-3}$ |
| hu37D3-H9.v5 | hIgG4.S228P | 1.3 | $7.1 \times 10^5$ | $0.9 \times 10^{-3}$ |
| hu37D3-H9.v1 | hIgG4.S228P | 2.0 | $6.7 \times 10^5$ | $1.3 \times 10^{-3}$ |

Antibody Characterization. Binding to Human Tau Protein in hIgG4.S228P. YTE Format Affinity was assessed at 25° C. using a Biacore T200 instrument, the GE Biacore human FAb capture kit and a CM5 Series S chip. The hIgG were diluted to 0.5 µg/ml in 10 mM HEPES pH7.4, 150 mM NaCl, 0.05% Tween 20 (running buffer, HBSP) and captured at a flow rate of 10 µl/min for 180 seconds. Kinetic data was collected for Human Tau monomer injected at concentrations of 0, 0.4, 1.2, 3.7, 11, 11, 33 and 100 nM in HBSP, using a flow rate of 30 µl/min, a 300 second association phase and a 600 second dissociation phase. Between cycles the surface was regenerated using two sequential 60 second injections of 10 mM Glycine pH 2.1. Data was fit to a 1:1 binding model. Kinetic data are shown in Table 16.

TABLE 16

Binding kinetics of hu37D3-H9.v28.A4 hIgG4.S228P.YTE to monomeric human Tau by surface plasmon resonance

| Antibody | Antibody preparation | $K_D$ (nM) | $k_{on}$ (1/Ms) | $k_{off}$ (1/s) |
|---|---|---|---|---|
| hu37D3-H9.v28.A4 | Prep 1 | 1.4 | $6 \times 10^5$ | $9 \times 10^{-4}$ |
| hIgG4.S228P.YTE | Prep 2 | 1.4 | $6 \times 10^5$ | $9 \times 10^{-4}$ |

Antibody Characterization: Binding to Cynomolgus Monkey Tau Protein

Affinity was assessed at 25° C. using a Biacore T200 instrument, the GE Biacore human IgG capture kit and a CM5 Series S chip. The hIgG were diluted to 2 µg/ml in 10 mM HEPES pH7.4, 150 mM NaCl, 0.05% Tween 20 (running buffer, HBSP) and captured at a flow rate of 10 µl/min for 15 seconds. Kinetic data was collected for Human Tau monomer injected at a minimum of five different non-zero concentrations between 1.2 and 100 nM, with one replicate concentration. Kinetics were assessed using a flow rate of 30 µl/min, a 300 second association phase and a 600 second dissociation phase. Between cycles a 30 second regeneration injection of 3M Magnesium Chloride was performed at a flow rate of 10 µl/min. The results were fit to a 1:1 binding model. Kinetic data are shown in Table 17.

TABLE 17

Affinity of humanized anti-Tau antibodies for monomeric cynomolgus monkey Tau

| Antibody | Ligand Level (RU) | Rmax (RU) | $K_D$ (nM) | $k_{on}$ (1/Ms) | $k_{off}$ (1/s) |
|---|---|---|---|---|---|
| hu37D3.v28.A4 | 113.9 | 62.6 | 0.7 | $17 \times 10^5$ | $1 \times 10^{-3}$ |
| hu37D3.v28.F1 | 126.9 | 61.2 | 1.3 | $12 \times 10^5$ | $2 \times 10^{-3}$ |
| hu37D3.v28.A12 | 162.6 | 85.2 | 1.0 | $17 \times 10^5$ | $2 \times 10^{-3}$ |
| hu37D3.v29.2 | 168.6 | 86.0 | 1.4 | $17 \times 10^5$ | $2 \times 10^{-3}$ |
| hu37D3-H9.v5 | 125.1 | 55.5 | 0.6 | $15 \times 10^5$ | $1 \times 10^{-3}$ |
| hu37D3-H9.v1 | 130.2 | 51.7 | 0.8 | $20 \times 10^5$ | $1 \times 10^{-3}$ |

Humanized antibodies hu37D3.v28.A4 and hu37D3.v28.F1 also bind to phosphorylated Tau (pTau).

Example 7: Pharmacokinetics of Anti-Tau Antibody

To evaluate the pharmacokinetics of the anti-Tau 37D3-H9 mIgG2a antibody in vivo, C57BL/6 mice were administered a single intravenous (IV) or intraperitoneal (IP) bolus injection at a dose of 10 mg/kg to conscious mice. At various time points up to 28 days post-dose, plasma samples were collected to determined anti-Tau antibody concentrations.

The concentrations of the dosed antibody in mouse plasma were measured with a generic ELISA using a mouse anti-muIgG2a antibody coat, followed by adding plasma samples starting at a dilution of 1:100, and finished by adding a mouse anti-muIgG2a-biotin conjugate, and then streptavidin conjugated to horseradish peroxidase for detection. The assay had a standard curve range of 1.56-200 ng/mL and a limit of detection of 0.16 µg/mL. Results below this limit of detection were reported as less than reportable (LTR).

Figure 10:
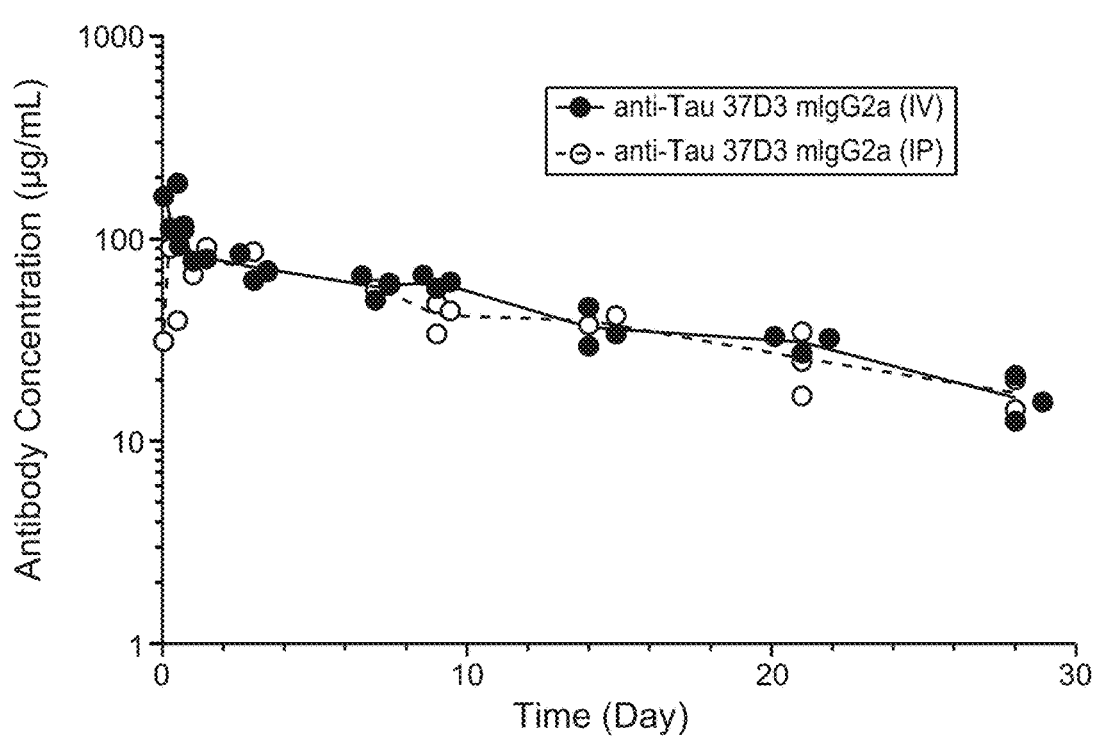
FIG. 10 shows pharmacokinetics of anti-Tau antibody 37D3-H9 in mice following a single 10 mg/kg intravenous or intraperitoneal injection.

FIG. 10 shows the results of the pharmacokinetic analysis for anti-Tau 37D3-H9 mIgG2a. Anti-Tau 37D3-H9 mIgG2a had similar exposure and clearance in wild-type C57BL/6 mice as isotype control antibodies, with a clearance of 6.31 mL/day/kg.

To evaluate the pharmacokinetics of anti-Tau 94B2-C1 mIgG2a and anti-tau 125B 1-H3 mIgG2a in vivo, a single IP bolus injection of antibody was administered at a dose of 10 mg/kg to conscious C57BL/6 mice. At various time points up to 28 days post-dose, plasma samples were collected to determined anti-Tau antibody concentrations.

The concentrations of the dosed antibody in mouse plasma and was measured with a generic ELISA using a mouse anti-muIgG2a antibody coat, followed by adding plasma samples starting at a dilution of 1:100, and finished by adding a mouse anti-muIgG2a-biotin conjugate, and then streptavidin conjugated to horseradish peroxidase for detection. The assay had a standard curve range of 0.78-100 ng/mL and a limit of detection of 0.078 µg/mL. The concentrations were also measured with a specific ELISA using recombinant Tau as the coat, followed by adding plasma samples starting at a dilution of 1:10, and finished by adding goat anti-mIgG2a conjugated to horseradish peroxidase for detection. The assay had a standard curve range of 0.078-10 ng/mL and a limit of detection of 0.0008 µg/mL. Results below this limit of detection were reported as less than reportable (LTR).

Figure 16:
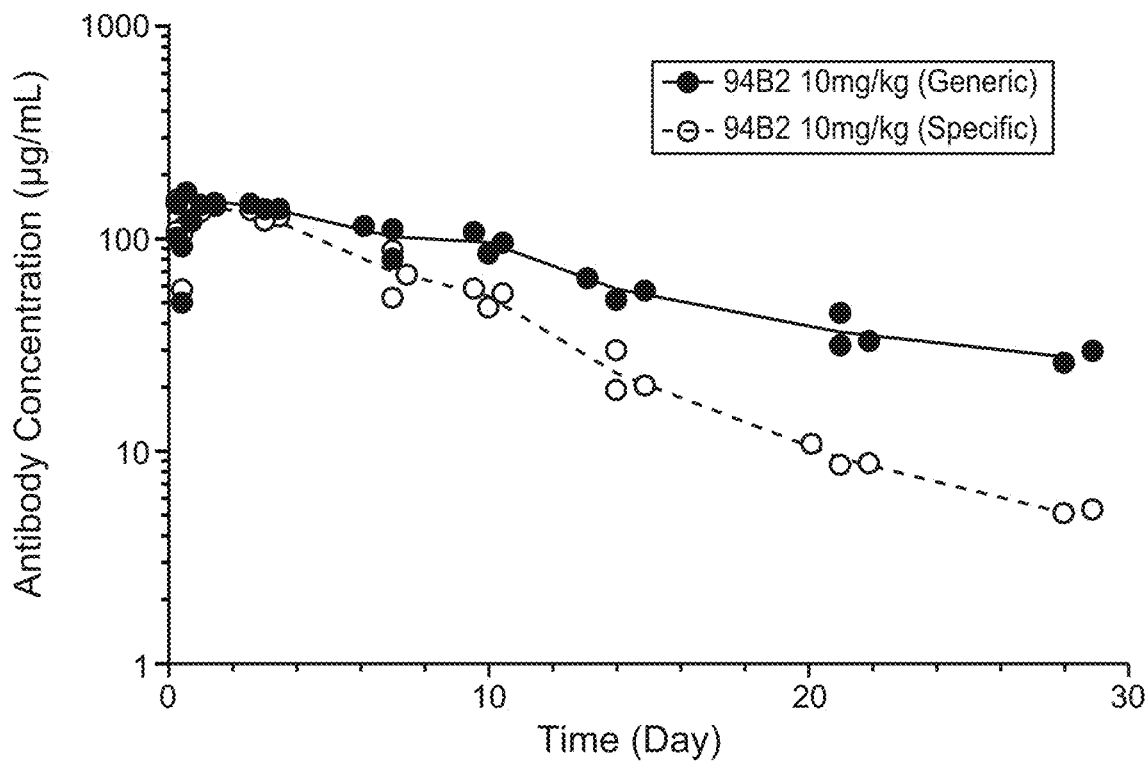
FIG. 16 shows pharmacokinetics of anti-Tau antibody 94B2-C1 in mice following a single 10 mg/kg intravenous or intraperitoneal injection.
Figure 17:
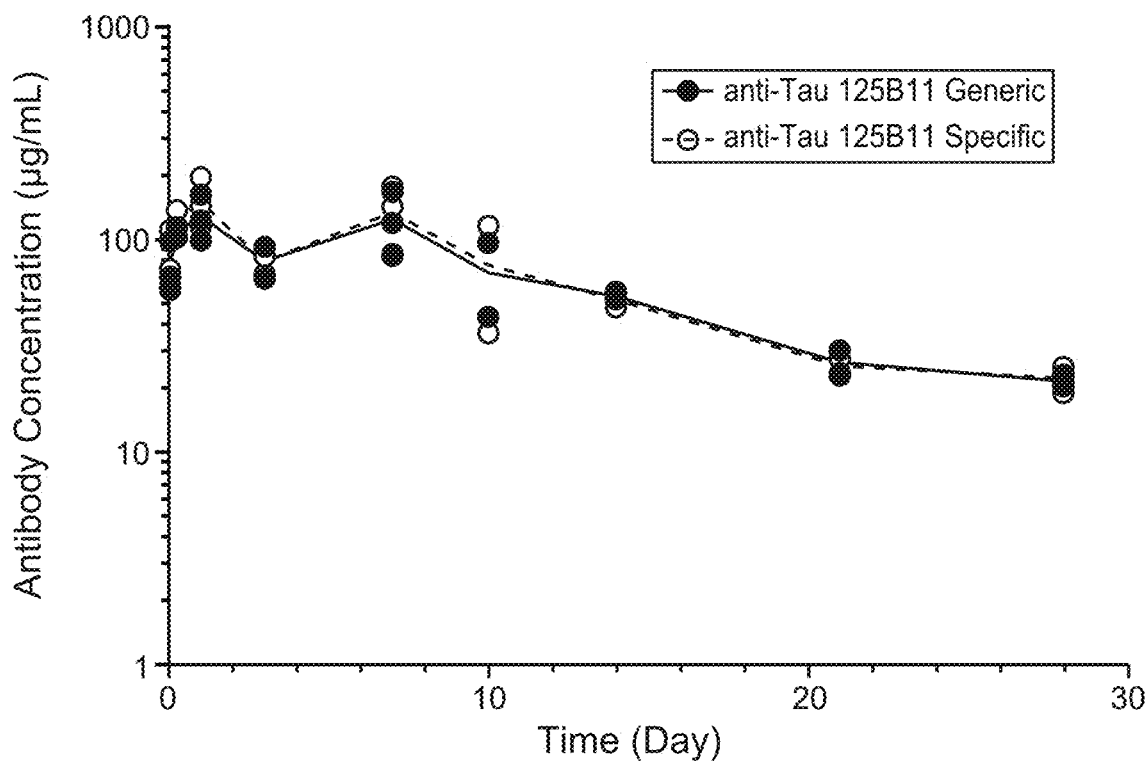
FIG. 17 shows pharmacokinetics of anti-Tau antibody 125B11-H3 in mice following a single 10 mg/kg intravenous or intraperitoneal injection.

The results of those experiments are shown in FIGS. 16 and 17. Anti-Tau 94B2 mIgG2a had similar exposure and clearance in wild-type C57BL/6 mice as an isotype control antibody when concentrations were analyzed using a generic assay, but lower exposure and faster clearance when concentrations were analyzed using a specific assay. See FIG. 16. The clearance determined by the generic assay was 4.06 mL/day/kg and that determined by the specific assay was 7.53 mL/day/kg. These results suggest that the antibody may undergo in vivo changes over time that compromise its ability to recognize its target. Anti-Tau 125B 1-H3 mIgG2a had similar exposure and clearance in wild-type C57BL/6 mice as an isotype control antibody, regardless of which assay generated the concentrations. See FIG. 17. The clearance determined by the generic assay is 4.96 mL/day/kg and that determined by the specific assay is 4.90 mL/day/kg.

Table 18 shows the pharmacokinetic parameters for anti-Tau antibodies 37D3-H9, 94B2-C1, and 125B11-H3 in mice.

TABLE 18

Pharmacokinetic parameters for anti-Tau antibodies

| | Administration Route | Assay | Cmax (µg/mL) | AUCinf (µg/mL*day) | CL or CL/F (mL/day/kg) |
|---|---|---|---|---|---|
| 37D3-H9 | IV | Generic | 185 | 1590 | 6.31 |
| | IP | Generic | 107 | 1680 | 6.76 |
| 94B2-C1 | IP | Generic | 151 | 2460 | 4.06 |
| | IP | Specific | 141 | 1330 | 4.91 |
| 125B11-H3 | IP | Generic | 127 | 2020 | 4.96 |
| | IP | Specific | 151 | 2040 | 4.90 |

To evaluate the pharmacokinetics of hu37D3.v28.A4 hIgG4.S228P and hu37D3.v28.A4 hIgG4-S228P.YTE antibodies in vivo, cynomolgus monkeys (*Macaca fascicularis*) were administered a single IV bolus injection at a dose of 1 mg/kg to conscious moneys. At various time points up to 49 days post-dose, plasma samples were collected to determined anti-Tau antibody concentrations.

The concentrations of the dosed antibody in monkey plasma and was measured with a generic ELISA using a sheep anti-human IgG antibody coat, followed by adding plasma samples starting at a dilution of 1:100, and finished by adding goat anti-human IgG conjugated to horseradish peroxidase for detection. The assay had a standard curve range of 0.156-20 ng/mL and a limit of detection of 0.02 µg/mL. Results below this limit of detection were reported as less than reportable (LTR).

Figure 11:
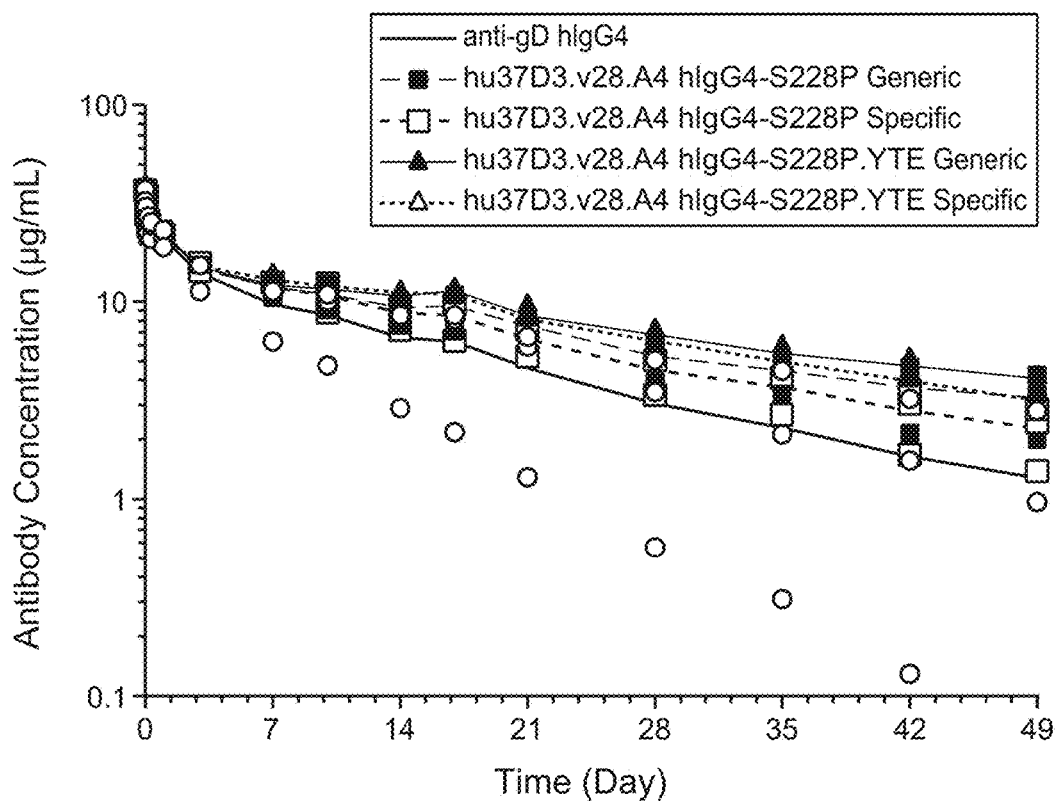
FIG. 11 shows pharmacokinetics of hu37D3.v28.A4 hIgG4-S228P and hu37D3.v28.A4 hIgG4-S228P.YTE in cynomolgus monkeys following a single IV bolus injection at a dose of 1 mg/kg.

FIG. 11 shows the results of the pharmacokinetic analysis for hu37D3.v28.A4 hIgG4.S228P and hu37D3.v28.A4 hIgG4-S228P.YTE. In FIG. 11, each set of datapoints represents one animal and the lines represent the average for all animals in the antibody and assay group. Table 19 shows the pharmacokinetic parameters for hu37D3.v28.A4 hIgG4.S228P and hu37D3.v28.A4 hIgG4-S228P.YTE in cynomolgus monkeys.

TABLE 19

Pharmacokinetic parameters for hu37D3.v28.A4 hIgG4.S228P and hu37D3.v28.A4 hIgG4-S228P.YTE in cynomolgus monkeys

| Antibody | Assay | Cmax (µg/mL) | AUCinf (day*µg/ mL) | CL (mL/ day/kg) | Vss (mL/kg) |
|---|---|---|---|---|---|
| anti-gD hIgG4 | Generic | 34.6 | 386 | 2.66 | 55.5 |
| hu37D3.v28.A4 hIgG4.S228P | Generic | 35.7 ± 2.59 | 559 ± 209 | 1.97 ± 0.743 | 71.9 ± 16.0 |
| | Specific | 35.4 ± 1.37 | 419 ± 89.9 | 2.47 ± 0.581 | 60.8 ± 3.49 |
| hu37D3.v28.A4 hIgG4.S228P.YTE | Generic | 34.5 ± 5.23 | 578 ± 43.5 | 1.74 ± 0.125 | 60.5 ± 1.87 |
| | Specific | 33.5 ± 2.72 | 520 ± 39.0 | 1.93 ± 0.139 | 56.5 ± 4.90 |

Example 8: Further Epitope Characterization of Anti-Tau Antibody

Following a comparison of 37D3-H9 binding to biotinylated Tau monomer and biotinylated peptide (MAPT_10-24), binding of 37D3-H9 to additional biotinylated peptides was also assessed. Nunc maxisorp 96-well microplates were coated at 4° C. for >12 hours with Neutravidin diluted to 2 µg/ml in 50 mM Sodium Carbonate Buffer, pH 9.6. All subsequent incubations were performed at room temperature. After coating, plates were blocked with Superblock™ (PBS) Blocking Buffer (Thermo Fisher Scientific) for two hours then washed thoroughly with PBS, 0.05% Polysorbate 20. Wells were then exposed to biotinylated Tau peptides (Table 20) or Avi-tag biotinylated Tau monomer at 1 µg/ml for one hour and washed as previously. Peptides were synthesized using standard solid-phase Fmoc chemistry (see, e.g., Fmoc solid phase peptide synthesis: A practical approach; Chan, W. C., White, P. D., Eds.; Oxford University Press: New York, 2000). Antibodies 37D3-H9 mIgG2a and hu37D3-H9.v5 hIgG1, serially diluted from 500 nM to 50 pM in 90% Superblock™ (PBS) Blocking Buffer, were allowed to bind biotinylated-Tau coated wells for 90 minutes. Wells were washed as previously and bound antibody detected with peroxidase-conjugated secondary antibody (Invitrogen/Life Technologies) diluted 1/1000 in Superblock™ Blocking Buffer (Rabbit anti-Mouse IgG or Goat Anti-Human IgG (H+L) respectively). After twenty minutes wells were washed as previously and signal developed with TMB Microwell 2-Component Substrate (KPL). Reactions were stopped by addition of 1M Phosphoric Acid and absorbance at 450 nm was measured with a SpectraMax M2 platereader.

TABLE 20

Peptide Sequences

| MAPT sequence | Peptide sequence | SEQ ID NO: |
|---|---|---|
| MAPT(10-24) | VMEDHAGTYGLGDRK | 592 |
| MAPT(2-24) | AEPRQEFEVMEDHAGTYGLGDRK | 593 |
| MAPT(2-34) | AEPRQEFEVMEDHAGTYGLGDRKDQGGYTMHQD | 594 |
| MAPT(10-44) | VMEDHAGTYGLGDRKDQGGYTMHQDQEGDTDAGLK | 595 |

Figure 12B:
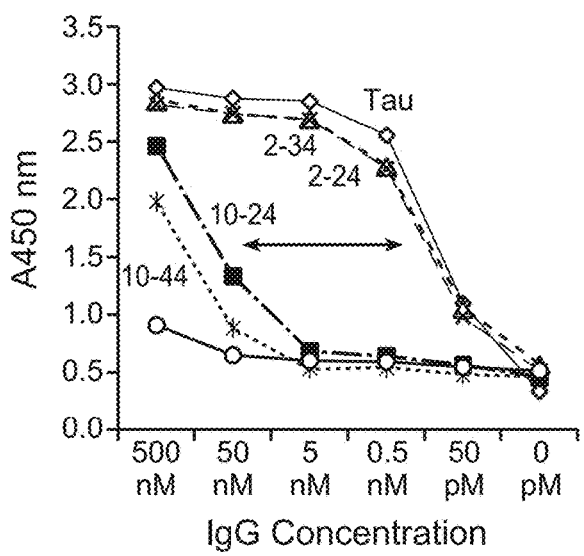
FIG. 12A-C. Binding of certain anti-Tau antibodies to Tau fragments. (A) Binding of certain anti-Tau antibodies to Tau fragments 1-15, 10-24, 19-33, 28-42, 37-51, and 46-60 is shown. (B) Binding of antibody 37D3-H9 mIgG2a to Tau fragments 10-44, 10-24, 2-24, 2-34, and full-length Tau. (C) Binding of antibody hu37D3-H9.v5 hIgG1 to Tau fragments 10-44, 10-24, 2-24, 2-34, and full-length Tau.
Figure 12C:
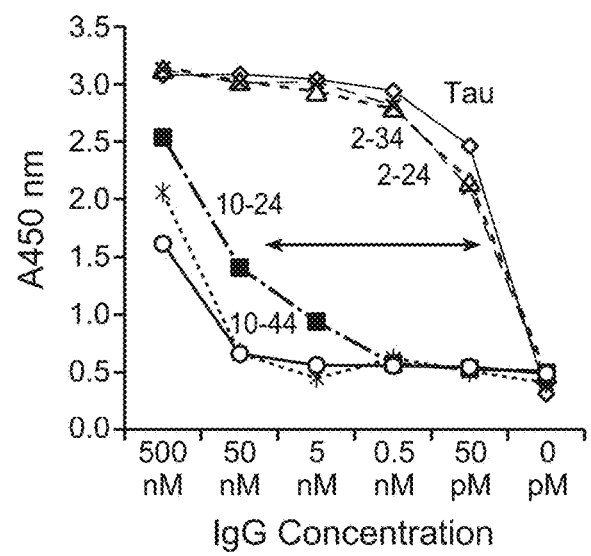
Figure 12A:
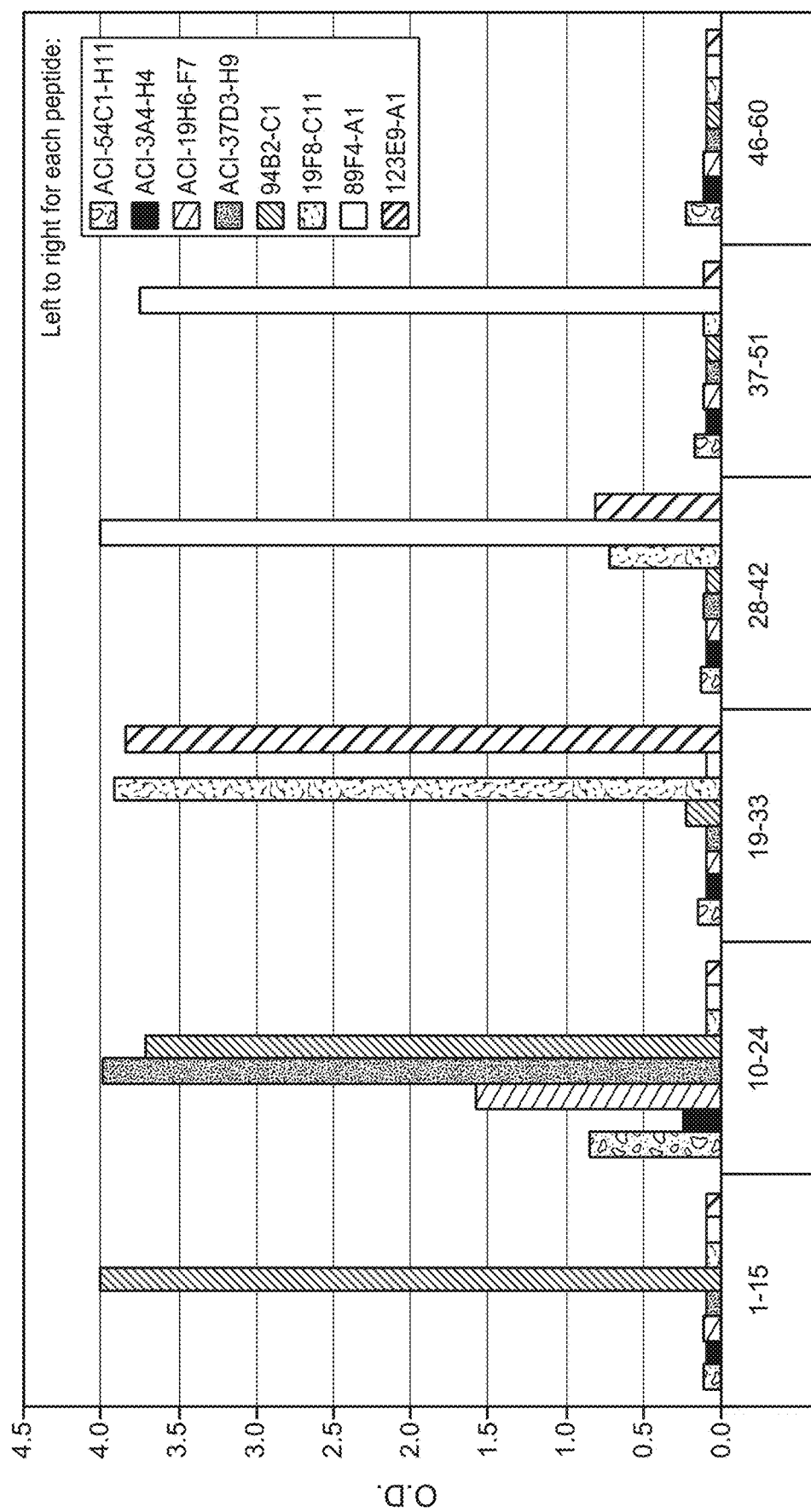

The results of that experiment are shown in FIG. 12. FIG. 12A shows binding of each of the indicated antibodies for the indicated peptides. Antibodies 37D3-H9 and 94B2-C1 both showed strong binding to fragment 10-24 in that experiment, and antibody 94B2-C1 also showed strong binding to fragment 1-15. Antibodies 19F8-C11 and 123E9-A1 showed strong binding to fragment 19-33, while antibody 89F4-A1 showed strong binding to fragments 28-42 and 37-51. See FIG. 12A. Antibodies 37D3-H9 mIgG2a and hu37D3-H9.v5 hIgG1 both showed strong binding to Tau fragments 2-24 and 2-34 and weaker binding to fragment 10-24. See FIGS. 12B and 12C. These results suggest that antibodies 37D3-H9 mIgG2a and hu37D3-H9.v5 hIgG1 bind an epitope of Tau within amino acids 2-24 of the mature protein.

In an alanine scanning substitution experiment, mutations Y18A and L20A were found to abrogate binding by murine antibody 37D3-H9 to a Tau fragment (fragment 2-21), suggesting that the antibody contacts these Tau residues. Using a series of 15mer offset peptides, it was found that murine antibody 37D3-H9 showed similar binding to fragment 9-23 as to fragment 10-24, and also showed moderate binding to fragments 7-21, 8-22, and 11-25.

Example 9: Cell-Based Characterization of 37D3-H9 Humanized Antibodies

Methods
Primary Hippocampal and Microglial Culture and Hippocampal-Microglial Co-Culture Dissociated primary hippocampal neurons were prepared from embryonic day 16-17 wild-type C57BL/6N mice. Cells were plated onto PDL/laminin-coated 8-well chamber slides (Biocoat, 354688 Corning) at 25,000 cells/well. Cells were plated and maintained in NbActiv4 (BrainBits) and half of the media was replaced twice a week. Recombinant tau and antibodies were applied to the culture at 18 cell divisions.

For microglial culture, cortices and hippocampi from postnatal day 1-2 C57BL/6N mice were dissociated and grown in 10% FBS in DMEM in 225 mm$^2$ culture flasks for 10-12 days. The culture flasks were gently shaken to dissociate microglia and the cells in 10% FBS in DMEM were replated onto either PDL/laminin-coated 8-well chamber slides at 30,000 cells/well for imaging or uncoated 48-well plates (3548, Corning) at 100,000 cells/well for cytokine assay. 4-5 hours after plating, cells were switched to serum-free low-glucose DMEM and maintained overnight before treatment with recombinant tau and antibodies.

Hippocampal-microglial co-cultures were prepared by replating microglia dissociated from 225 mm$^2$ culture flasks onto 18 DIV primary hippocampal neurons in 8-well slide chambers (12,500 microglia and 25,000 neurons per one well). Co-cultures were treated with recombinant tau and antibodies 4 hours after microglia plating.

In Vitro Treatment of Recombinant Tau and Antibodies

For 18 DIV hippocampal cultures or hippocampal-microglial co-cultures, recombinant human oligomeric tau and antibodies (500 nM each at 1:1 ratio) or controls were pre-incubated in neuron culture medium (conditioned medium from 18 DIV hippocampal culture:fresh NbActiv4 at 1:1) for 1 hour at 37° C. before they were added to the cells. Cells were incubated with the tau-antibody mix or control in the media for 72 hours (hippocampal culture) or 48 hours (hippocampal-microglial co-culture). Cells were washed with PBS three times before fixation.

For microglia culture, recombinant human oligomeric tau and antibodies or controls were pre-incubated at 125 nM each (immunocytochemistry/imaging) or 250 nM each (cytokine assay) in low-glucose DMEM in the absence of serum for 1 hour at 37° C. prior to the addition to the cells. For immunocytochemistry/imaging, cells were incubated with the tau-antibody mix or controls for 10 minutes and washed three times with PBS before fixation. For cytokine assay, cells were incubated with the tau-antibody mix or control for 24 hours and medium of each well was collected for cytokine assay.

Immunocytochemistry, Imaging, and Quantification

Cells were fixed with 4% paraformaldehyde in PBS for 15 min and permeabilized with 0.1% Triton X-100 in PBS for 10 minutes. 10% donkey serum was used for blocking and cells were incubated with primary antibodies in PBS overnight at 4° C., followed by incubation with Alexa-fluorophore-labeled secondary antibodies against appropriate species developed in donkey (Invitrogen). Primary antibodies used were anti-tau (DAKO), rabbit anti-human tau developed against the human tau N-terminal region spanning amino acids 11-24, anti-MAP2 (ab5392, Abcam), and anti-Iba-1 (ab5076, Abcam). The slides were mounted with Prolong Gold DAPI (P36935, Invitrogen) and no. 1 coverslips.

Confocal fluorescent imaging was performed with a LSM780 (Carl Zeiss, Inc.) using Zen 2010 software (Carl Zeiss, Inc.). For imaging of hippocampal cultures and hippocampal-microglial co-cultures, 5 z-stack images at 0.98 µm intervals were collected using Plan Apochromat 20×/0.8 M27 objective lens. For the MAP2 fragmentation assay, a maximum intensity z projection was created for the image stack and analyzed using Metamorph (Molecular Devices, Sunnyvale, Calif.). A median filter and nearest neighbor deconvolution were used for noise reduction. Neurite and cell body lengths were analyzed using the neurite outgrowth module followed by morphological processing. Fragments less than 15 pixels (6.225 µm) were normalized to total signal length to obtain a measure of MAP2 fragmentation.

Microglia were imaged with ca-Plan Apochromat 100×/1.46 M27 objective. Quantification of recombinant tau uptake in the cells was performed with Image J (1.43u, 64-bit, National Institute of Health). ROIs of cell area were drawn manually using Iba-1 signal as a reference. Area and integrated intensity of tau immunoreactivity of ROI were measured to obtain tau immunoreactivity normalized to area. All analyses were performed blinded to experimental conditions.

Results

Figure 13A:
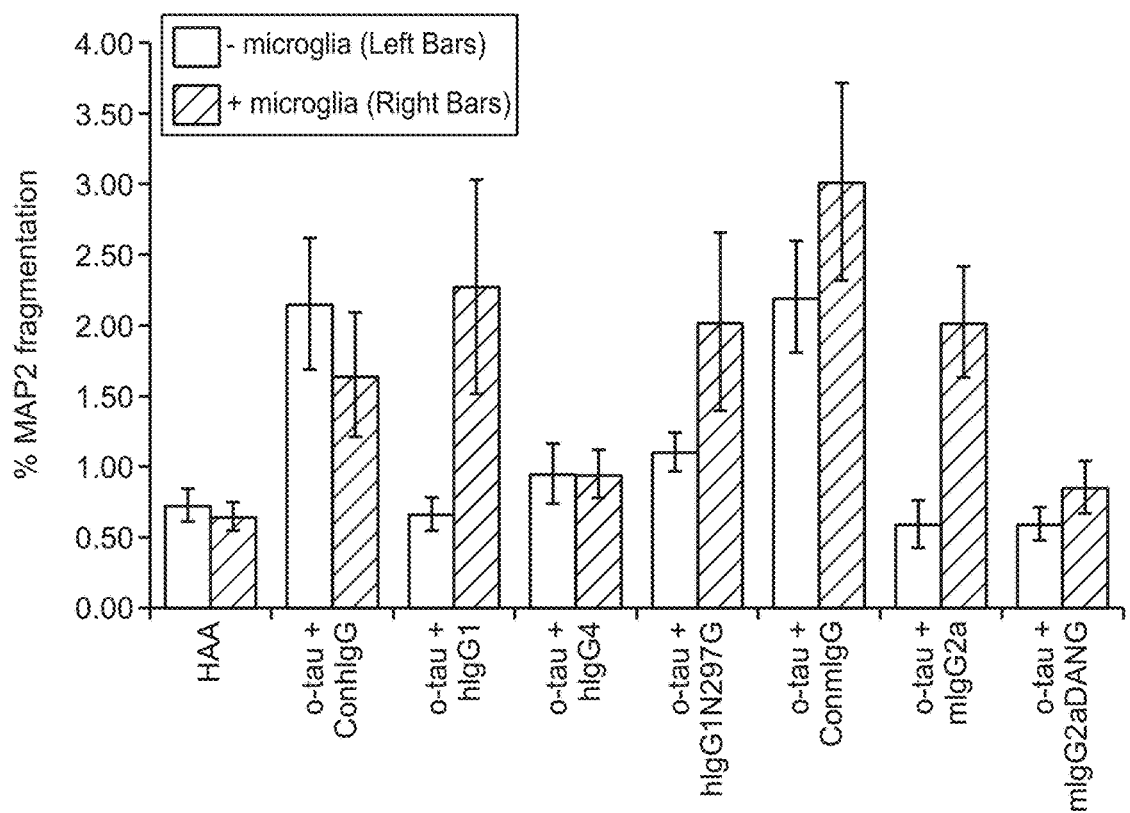
FIG. 13A-B. Effect of effector function on Tau toxicity in neuron-microglia co-cultures. (A) Percent MAP2 fragmentation in co-cultures contacted with various antibodies and oligomeric Tau. (B) Images of neurons (top panels) and neuron-microglia co-cultures (bottom panels) contacted with various antibodies and oligomeric Tau.
Figure 13B:
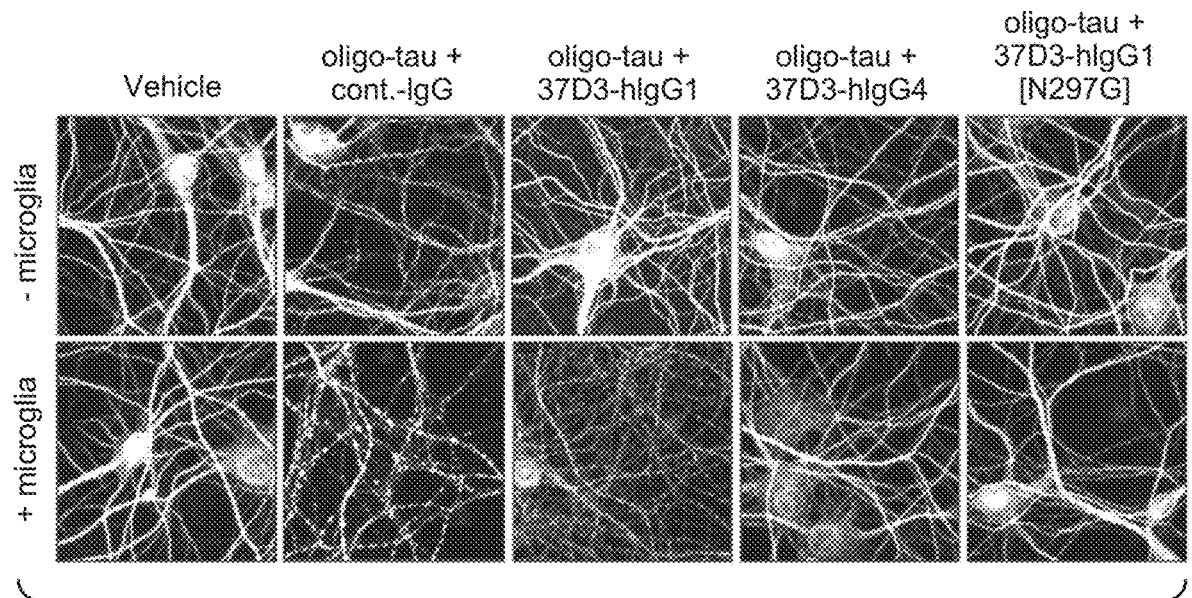

The results of the experiment are shown in FIG. 13. As shown in FIG. 13A, antibodies with full effector function were not protective against Tau toxicity in the neuron-microglia co-cultures. FIG. 13B shows images of neuron-microglia co-cultures contacted with oligomeric Tau and antibodies (bottom panels). Antibody 37D3-H9 hIgG4 and hu37D3-H9 hIgG1 (N297G), which lack effector function, were protective against Tau toxicity, while 37D3-H9 hIgG1 was not.

Example 10: Dose-Dependent Reduction of Tau Pathology in Tau Tg Mice Administered 37D3-H9 IgG2a or 37D3-H9 IgG2a DANG Transgenic mice expressing human Tau P301L under the Thy1 promoter (Tau P301L-Tg) were maintained on a C57BL/6N (Charles River) background. Tau P301L-Tg and wild type littermate mice were assigned to treatment groups and dosed once weekly intraperitoneally (i.p.) with either IgG2a-control (anti-gp120) at 30 mg/kg, anti-tau 37D3-H9 WT IgG2a at 3, 10 or 30 mg/kg, anti-tau 37D3-H9 DANG IgG2a at 3, 10 or 30 mg/kg. DANG refers to D265A/N297G mutations in IgG2a, which abrogate effector function. All antibody-dosing solutions were prepared in 10 mM histidine pH 5.8, 6% sucrose, 0.02% Tween 20 at a concentration of 10 mg/ml. Treatment started at 13 weeks of age. The mouse groups in the in vivo study were males and staggered into 3 cohorts. In addition, 3 TauP301L-Tg mice were harvested at age 3 months without undergoing any treatment in order to determine the baseline level of pathology at the time of treatment initiation.

To harvest tissue, mice were anesthetized with 2.5% tribromoethanol (0.5 ml per 25 g body weight) and transcardially perfused with PBS. Brains were harvested and bisected. Right hemispheres were fixed in 4% paraformaldehyde overnight at 4° C. then transferred to phosphate buffered saline prior to processing for immunohistochemistry. Left hemispheres were sub-dissected on ice then frozen at −80° C. for biochemical analysis. Tail clips were taken from all mice to confirm genotypes.

Hemibrains were multiply embedded into a gelatin matrix using MultiBrain® blocks (NeuroScience Associates, Knoxville, Tenn.) and sectioned coronally at 25 μm thickness. Within each block, the brain position was randomized relative to genotype and treatment. Free-floating sections of individual mouse hemibrains or of MultiBrain® blocks were stained as previously described (Le Pichon et al., 2013, PLoS One, 8(4): e62342), but with washes in PBS instead of Tris buffered saline and primary antibody incubations at 4° C. instead of room temperature. Primary antibody was rabbit anti-pTau212/214 (generated in-house; 0.01 μg/ml). To avoid high background staining, in the case of mouse primary antibodies that were subtype specific, we used the corresponding subtype-specific secondary antibody (eg. Biotinylated anti-mouse IgG3, Bethyl A90-111B).

Immunohistochemically stained slides were imaged using the Leica SCN400 (Leica Microsystems; Buffalo Grove, Ill.) whole slide scanning system at 200× magnification with a resolution of 0.5 μm/pixel. Regions of interest (ROIs) were manually drawn on 4 matched hippocampal levels per animal, and the amount of staining in these ROIs was quantified in an automated fashion using the two endpoints described below. All image analysis was performed blind to genotype and treatment groups. For positive pixel area analysis for quantitation of IHC stains, digital images of antibody-labeled brain sections were analyzed as previously described (Le Pichon et al., 2013). The percent area stained was calculated by normalizing the total positive pixels to the total pixel area of the ROI. The integrated intensity was calculated using the Beer-Lambert law, absorbance=−log (transmitted light intensity/incident light intensity), for the positive pixel areas only.

Figure 14:
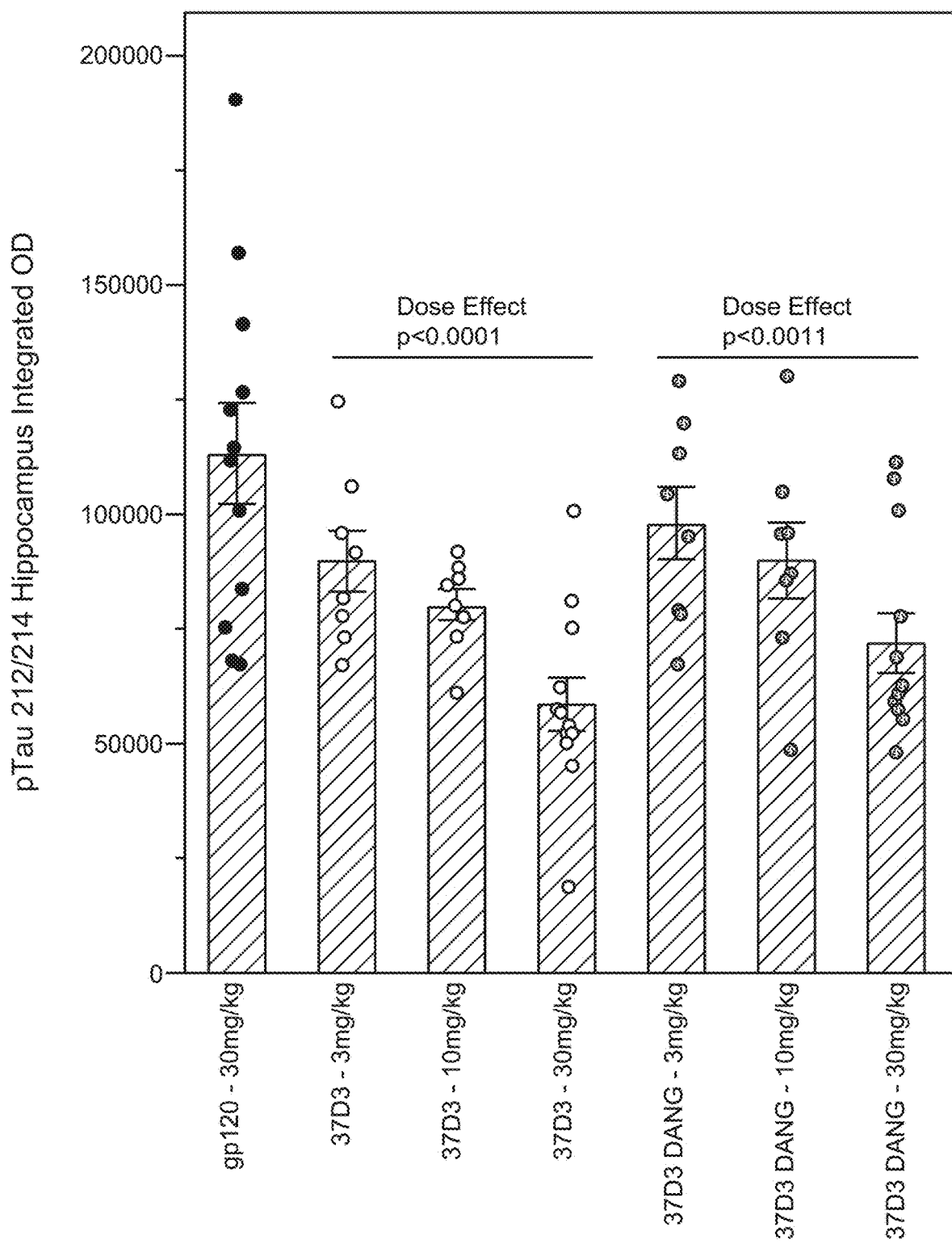
FIG. 14. pTau212/214 levels in the hippocampus of mice administered anti-tau 37D3-H9 WT IgG2a or anti-tau 37D3-H9 DANG IgG2.

The results of that experiment are shown in FIG. 14. Administration of anti-tau 37D3-H9 WT IgG2a or anti-tau 37D3-H9 DANG IgG2a resulted in a dose-dependent reduction of pTau212/214 in the hippocampus.

Example 11: Humanized 37D3-H9 Kappa 1 Variants

Figure 18:
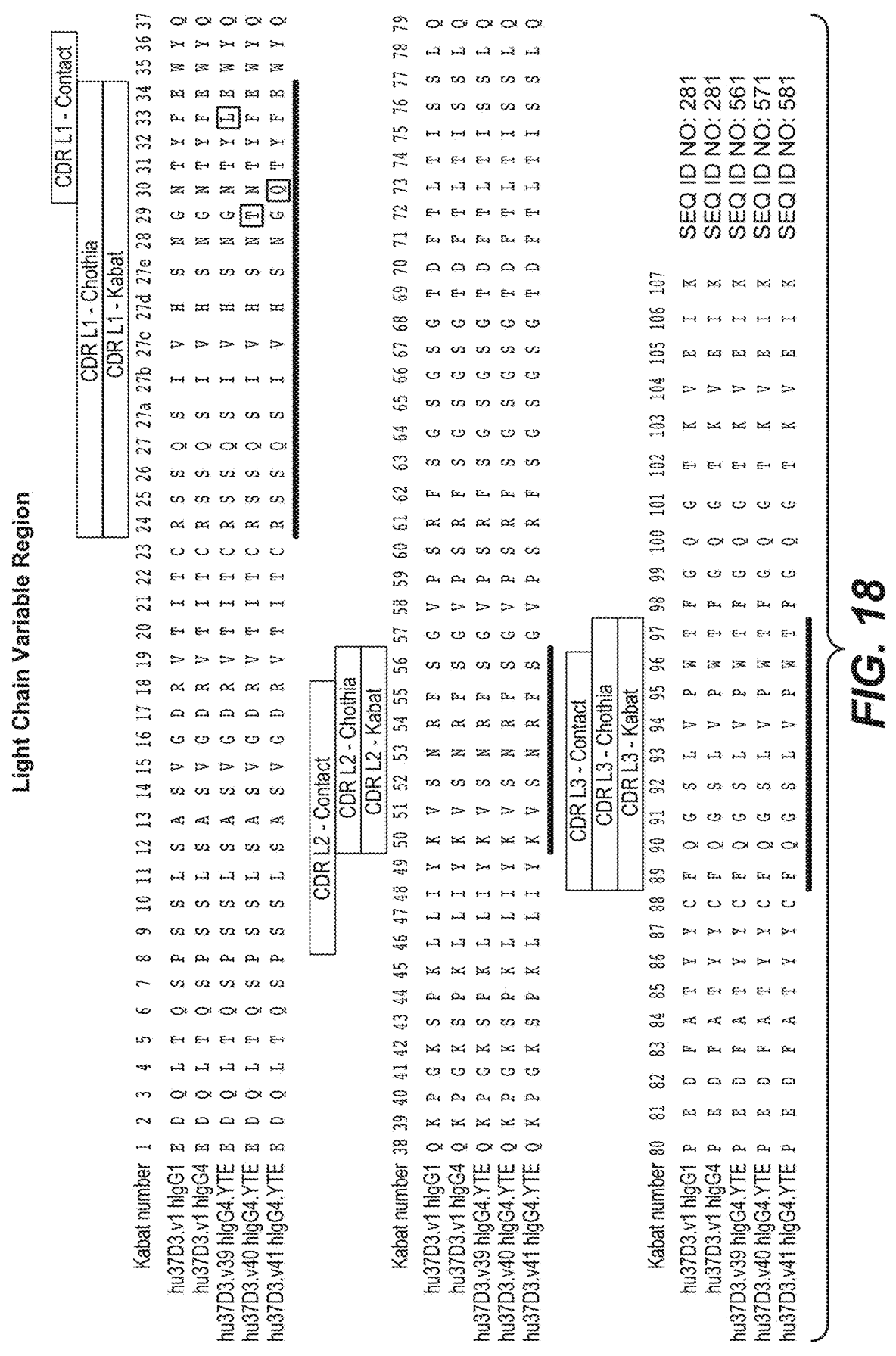

Humanized antibody variants based on hu37D3-H9.v1, which has a kappa 1 light chain, were made and tested for $N^{28}$ stability. An alignment of the light chain variable region of the three variants tested with hu37D3-H9.v1 is shown in FIG. 18. The three variants differ from each other in the light chain variable region: hu37D3.v39 contains the mutation F33L, hu37D3.v40 contains the mutation G29T and hu37D3.v41 contains the mutation N30Q.

Antibody samples were thermally stressed, as follows. Samples were buffer exchanged into 20 mM histidine acetate, 240 mM sucrose, pH 5.5 and diluted to a concentration of 1 mg/ml. One ml of sample was stressed at 40° C. for 2 weeks and a second was stored at −70° C. as a control. Both samples were then digested using trypsin to create peptides that could be analyzed using liquid chromatography (LC)—mass spectrometry (MS) analysis. For each peptide in the sample retention time, from the LC as well as high resolution accurate mass and peptide ion fragmentation information (amino acid sequence information) were acquired in the MS. Extracted ion chromatograms (XIC) were taken for peptides of interest (native and modified peptide ions) from the data sets at a window of +10 ppm and peaks were integrated to determine area. Relative percentages of modification were calculated for each sample by taking the (area of the modified peptide) divided by (area of the modified peptide plus the area of the native peptide) multiplied by 100. These relative percentages were then compared between the control (t=0) and the stressed (t=2 weeks) samples. Percentages shown represent the control (t=0) value subtracted from the stressed (t=2 weeks) value. The results are shown in Table 21. The results demonstrate that the F33L mutation is effective for reducing deamidation in a kappa 1 humanized light chains.

TABLE 21

Stability of the hu37D3-H9.v1 variants in stress tests for deamidation.

| Antibody | | Increase in deamidation of light chain $N^{28}G^{29}N^{30}$ |
|---|---|---|
| hu37D3.v39 | hIgG4.S228P.YTE | $N^{28}$: 2.7% |
| | | $N^{30}$: No significant increase detected |
| hu37D3.v40 | hIgG4.S228P.YTE | $N^{28}$: 12.1% |
| | | $N^{30}$: 3.9% |
| hu37D3.v41 | hIgG4.S228P.YTE | $N^{28}$: 6.0% |
| | | $N^{30}$: Residue replaced with glutamine |

Affinity of the humanized antibody variants was measured at 25° C. using a Biacore T200 instrument, the GE Biacore human FAb capture kit, and a CM5 Series S chip. Antibodies were diluted to 1 μg/ml in HBSP (10 mM HEPES pH7.4, 150 mM NaCl, 0.05% Tween 20) and captured at a flow rate of 10 μl/min for 180 seconds. Kinetic data were collected for human Tau monomer injected at 1.2, 3.7, 11, 33 and 100 nM in HBSP using the Single Cycle Kinetics methodology and a flow rate of 30 μl/min. Each concentration of Tau monomer was injected for a period of 3 minutes and dissociation was monitored for ten minutes. Between cycles, the surface was regenerated with two sequential one-minute injections of 10 mM glycine pH2.1. Data was fit to a 1:1 binding model using BIAEvaluation software. Each antibody was analyzed twice within the experiment; data in Table 22 are shown as mean±range.

TABLE 22

Affinities of hu37D3-H9.v1 variants for monomeric Tau

|  | $K_D$ (nM) | $k_{on}$ (1/Ms) | $K_{off}$ (1/s) |
|---|---|---|---|
| hu37D3.v1 hIgG1 | 2.3 ± 0.3 | 6 ± 0.5 × $10^5$ | 1 ± 0.1 × $10^{-3}$ |
| hu37D3.v1 hIgG4 | 2.3 ± 0.3 | 6 ± 0.2 × $10^5$ | 1 ± 0.1 × $10^{-3}$ |
| hu37D3.v39 hIgG4.YTE | 1.9 ± 0.2 | 6 ± 0.6 × $10^5$ | 1 ± 0.02 × $10^{-3}$ |
| hu37D3.v40 hIgG4.YTE | 4.4 ± 0.5 | 8 ± 0.9 × $10^5$ | 3 ± 0.02 × $10^{-3}$ |
| hu37D3.v41 hIgG4.YTE | 5.4 ± 0.3 | 9 ± 1.2 × $10^5$ | 5 ± 0.3 × $10^{-3}$ |

Example 12: Pharmacokinetics and Pharmacodynamics of hu37D3.v28.A4 hIgG4-S228P and hu37D3.v28.A4 hIgG4-S228P.YTE in Cynomolgus Monkeys To evaluate the pharmacokinetics and pharmacodynamics of hu37D3.v28.A4 hIgG4.S228P and hu37D3.v28.A4 hIgG4-S228P.YTE antibodies in vivo, five conscious cynomolgus monkeys (*Macaca fascicularis*) per group were administered a single IV bolus injection at a dose of 50 mg/kg in the first phase. Anti-gD hIgG4 was used as a control, also at a dose of 50 mg/kg. At various time points up to 35 days post-dose, plasma and CSF samples were collected to determine anti-Tau antibody concentrations. After the final sample collection, the animals were allowed to recover for 63-64 days before initiation of the second phase. In the second phase, the 15 animals from the first phase, plus 3 additional animals, were divided into two groups; the first group (n=9) was administered antibody hu37D3.v28.A4 hIgG4.S228P and the second group (n=9) was administered hu37D3.v28.A4 hIgG4-S228P.YTE antibody, both at 50 mg/kg. Brains of 4 or 5 animals per group were harvested at 2 days and 10 days post-dose.

Human IgG4 antibodies in cynomolgus monkey plasma, CSF, and brain homogenate (described below) were measured with an ELISA using a sheep anti-human IgG monkey adsorbed antibody coat, followed by adding plasma samples starting at a dilution of 1:100, CSF samples starting at a dilution of 1:20, or brain homogenate samples starting at a dilution of 1:10, and finished by adding a goat anti-human IgG antibody conjugated to horseradish peroxidase monkey adsorbed for detection. Color was developed using 3,3',5,5'-tetramethylbenzidine and neutralized using 1M phosphoric acid. Samples were read at 450/620 nm. The assay has a standard curve range of 0.156-20 ng/mL and a limit of detection of 0.02 ug/mL for plasma, 0.003 µg/mL for CSF, and 0.002 µg/mL for brain homogenate. Results below this concentration were reported as less than reportable (LTR).

Figure 19A:
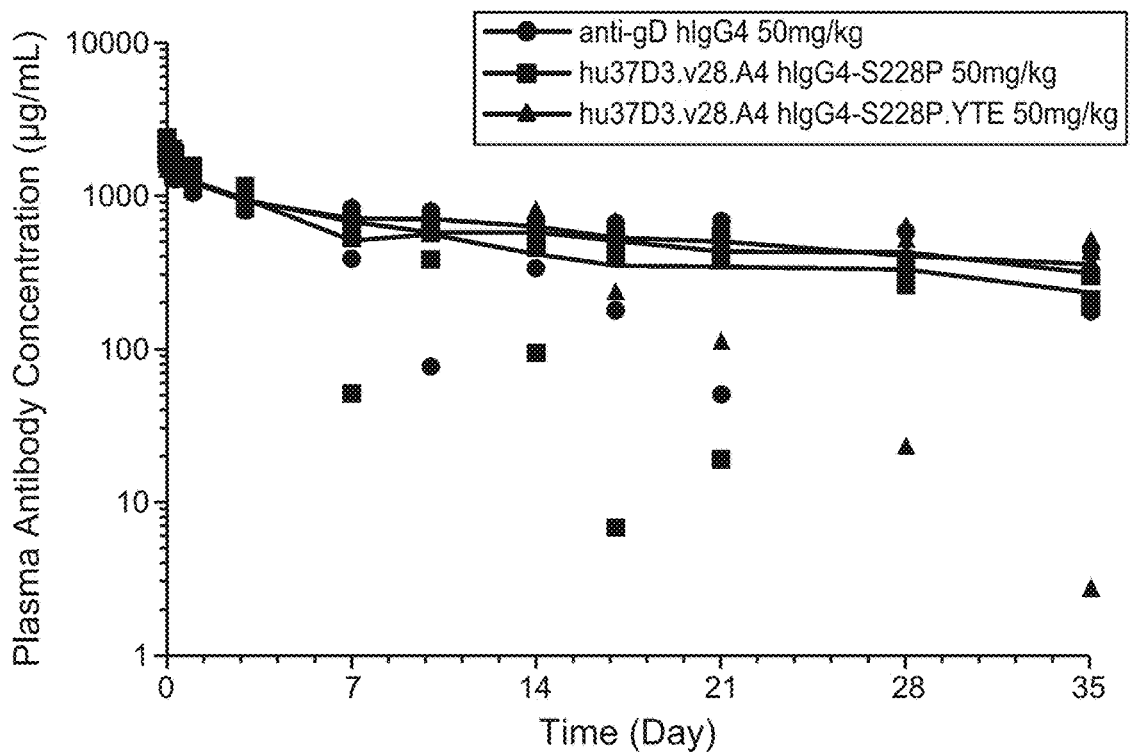
FIG. 19A-B show plasma antibody concentration (A) and CSF antibody concentration (B) in cynomolgus monkeys following a single IV injection of the indicated antibody at 50 mg/kg.
Figure 19B:
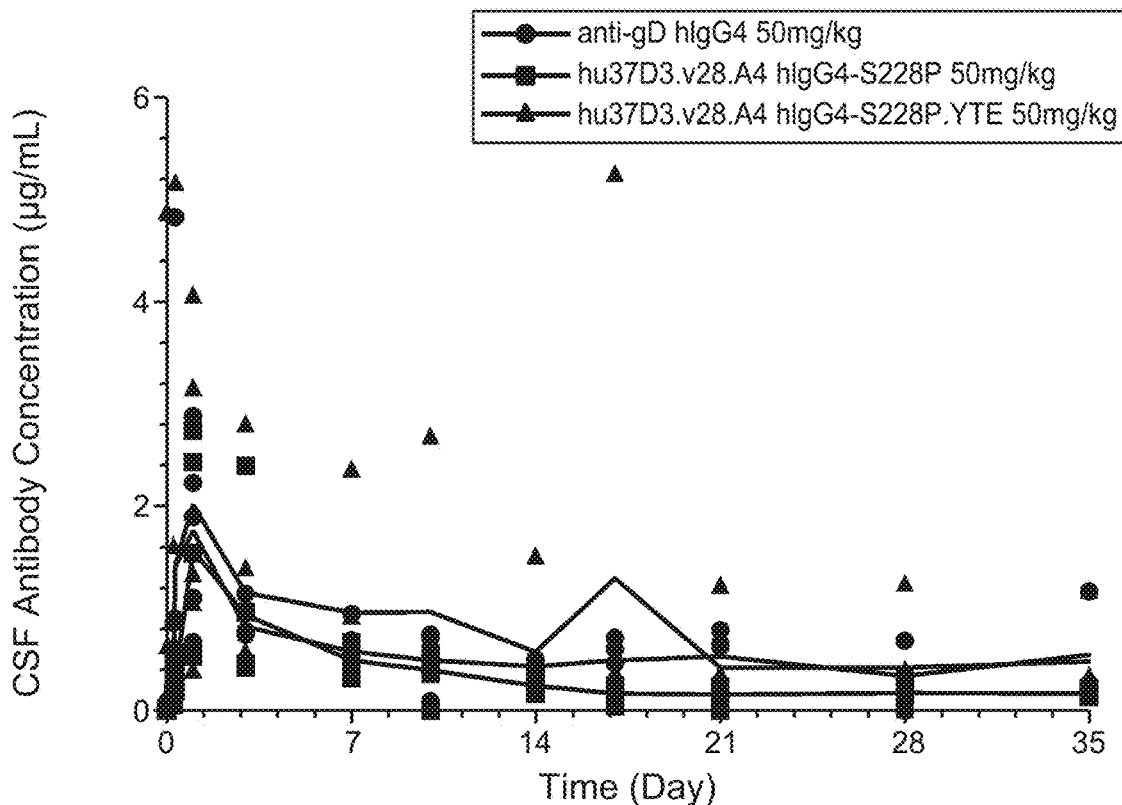

The results of the pharmacokinetic analysis are shown in FIG. 19A (plasma) and 19B (CSF), and in Tables 23 and 24. Animals that were suspected of being anti-therapeutic antibody positive (ATA+) were excluded from the analysis. These data show that introducing the YTE mutations in the Fc region of hu37D3.v28.A4 hIgG4.S228P slowed the peripheral and CSF clearance rates of the antibody by about two fold.

TABLE 23

Mean (±SD) plasma clearance and $C_{max}$ estimates following single IV bolus dose

| Antibody | Plasma clearance (mL/day/kg) | $C_{max}$ (µg/mL) |
|---|---|---|
| anti-gD hIgG4 | 1.67 ± 0.415 | 1950 ± 174 |
| hu37D3.v28.A4 hIgG4.S228P | 2.09 ± 0.229 | 1970 ± 144 |
| hu37D3.v28.A4 hIgG4-S228P.YTE | 1.12 ± 0.233 | 1850 ± 156 |

TABLE 24

Mean (±SD) CSF $C_{max}$ estimates following single IV bolus dose

| Antibody | $C_{max}$ (µg/mL) |
|---|---|
| anti-gD hIgG4 | 1.39 ± 0.751 |
| hu37D3.v28.A4 hIgG4.5228P | 0.910 ± 0.552 |
| hu37D3.v28.A4 hIgG4-5228P.YTE | 2.51 ± 1.93 |

The brain concentration of the antibodies at 2 and 10 days post-injection was determined as follows. Brain tissue was weighed and then homogenized in 1% NP-40 in phosphate-buffered saline containing cOmplete™, Mini, EDTA-free protease inhibitor cocktail tablets. The homogenized brain samples were then rotated at 4° C. for 1 hour before spinning at 14,000 rpm for 20 minutes. The supernatant was isolated for brain antibody measurement by ELISA, as described above. The results of that experiment are shown in FIGS. 21A-D. The concentration of antibody hu37D3.v28.A4 hIgG4-S228P.YTE in the brain, and the ratio of brain:plasma concentration for antibody hu37D3.v28.A4 hIgG4-S228P.YTE trended higher than antibody hu37D3.v28.A4 hIgG4.S228P.

The pharmacodynamics response in plasma was also determined. The concentration of total Tau in K2EDTA plasma was determined using an electrochemiluminescence (ECL) immunoassay (Roche Professional Diagnostics (RPD), Penzberg, Germany). The Elecsys® immunoassay is validated for the quantification of total Tau in human CSF, and because of the similarity between human and cynomolgus monkey Tau, was considered acceptable for the measurement of cynomolgus monkey Tau in CSF and plasma. The assay captures and detects amino acids 159-224 of human and cynomolgus monkey Tau, a region present in all known isoforms, independent of phosphorylation state. The lower detection limit (LDL) of the assay is 1.01 µg/mL. The assay is tolerant to 15.0 mg/mL of hu37D3.v28.A4 hIgG4-S228P.YTE.

Figure 20:
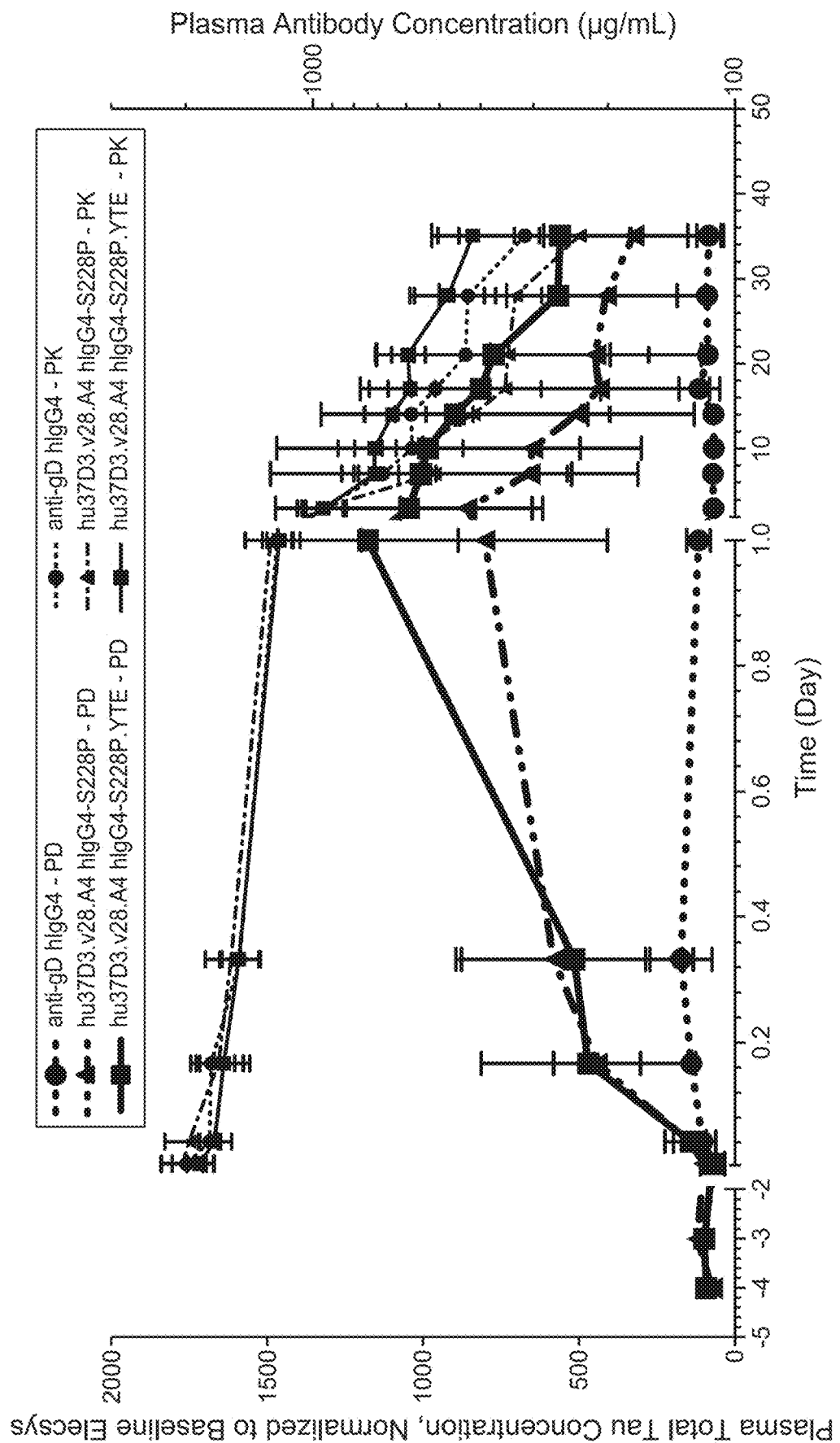
FIG. 20 shows plasma total Tau concentration and plasma antibody concentration in cynomolgus monkeys following a single IV injection of the indicated antibody at 50 mg/kg.
Figure 21A:
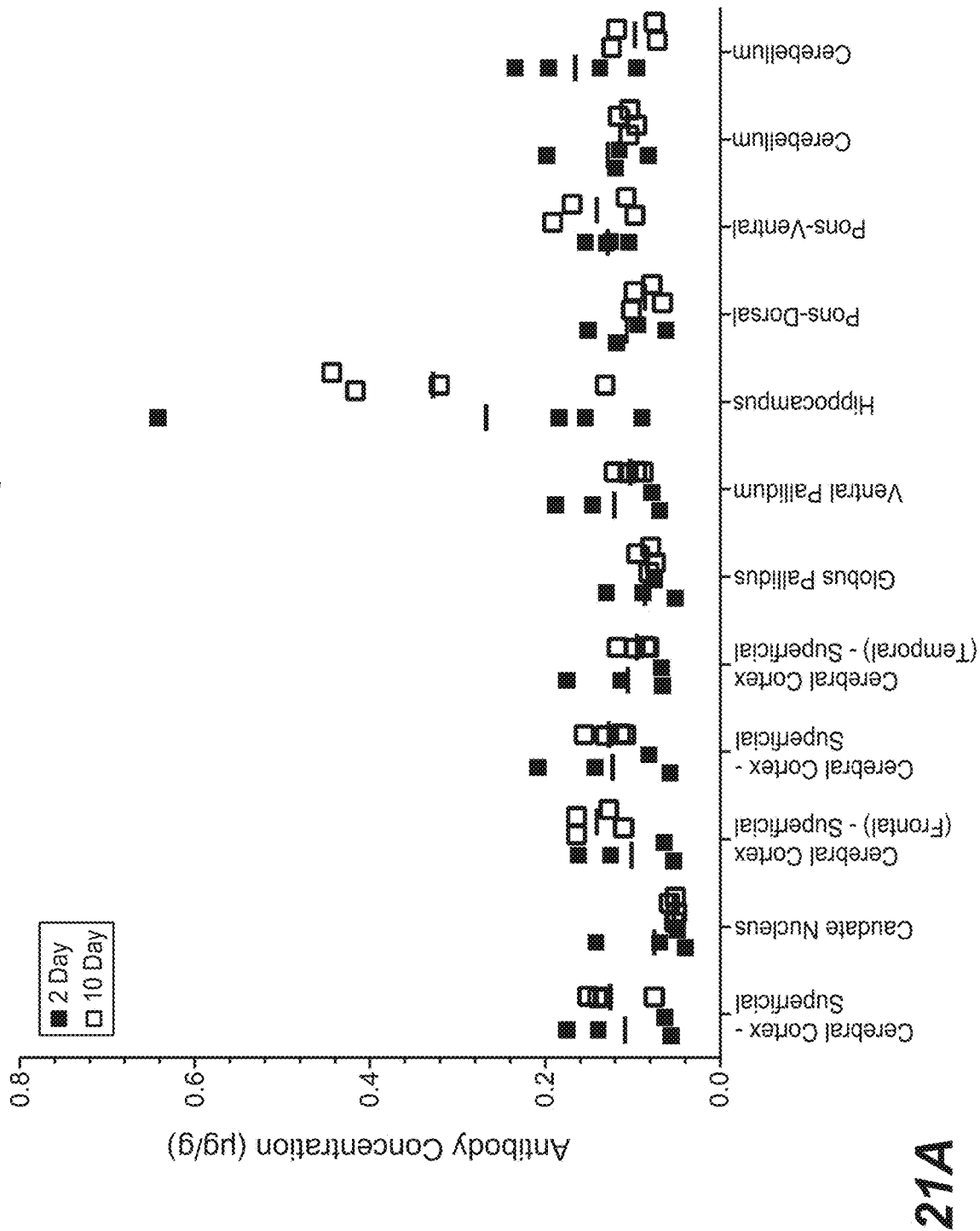
FIGS. 21A-D show antibody concentration in various regions of cynomolgus monkey brain 2 days and 10 days following a single IV injection of hu37D3.v28.A4 hIgG4-S228P (A) and hu37D3.v28.A4 hIgG4-S228P.YTE (B) at 50 mg/kg; average antibody concentration in brain (C); % brain:plasma antibody concentration (D).
Figure 21B:
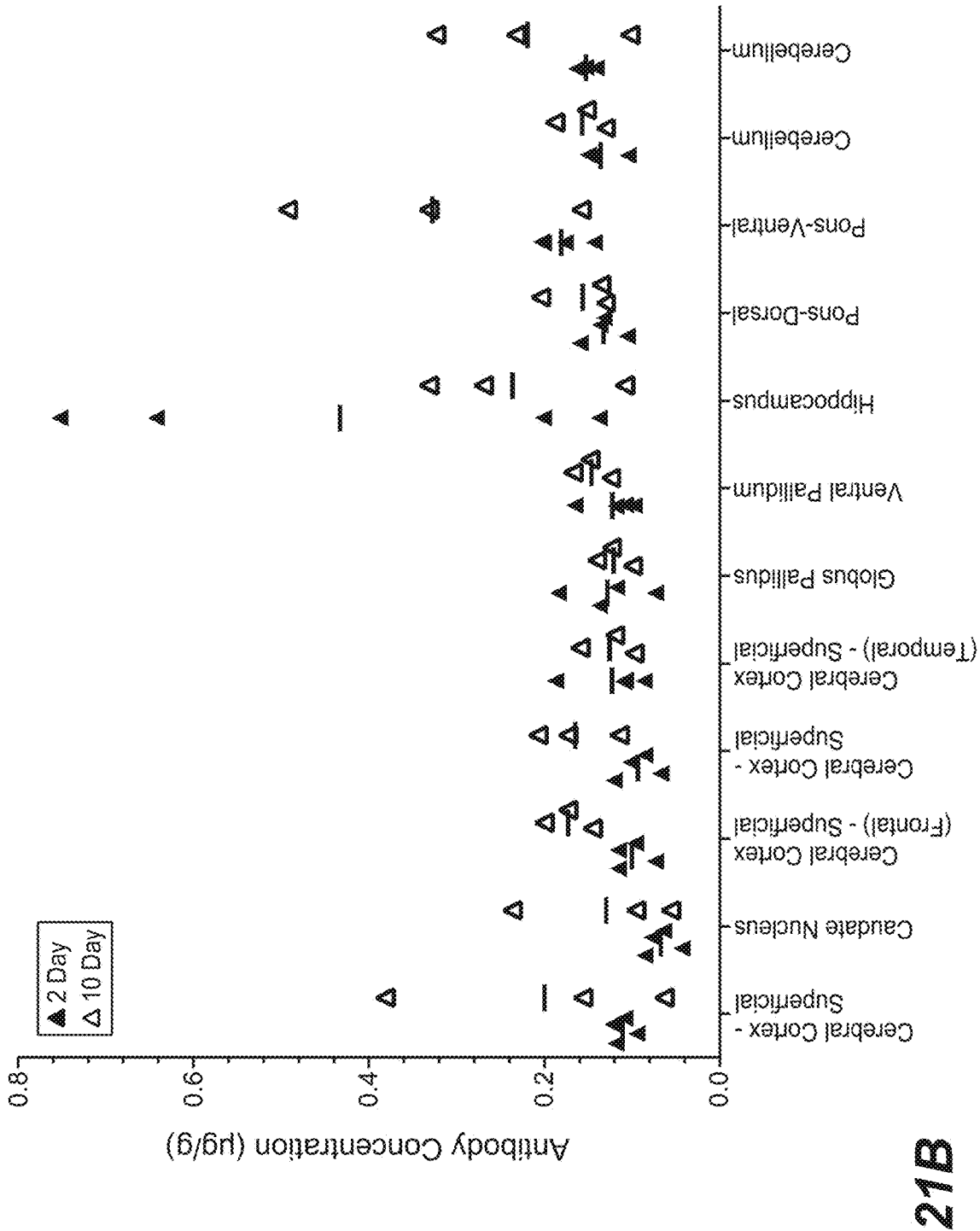
Figure 21C:
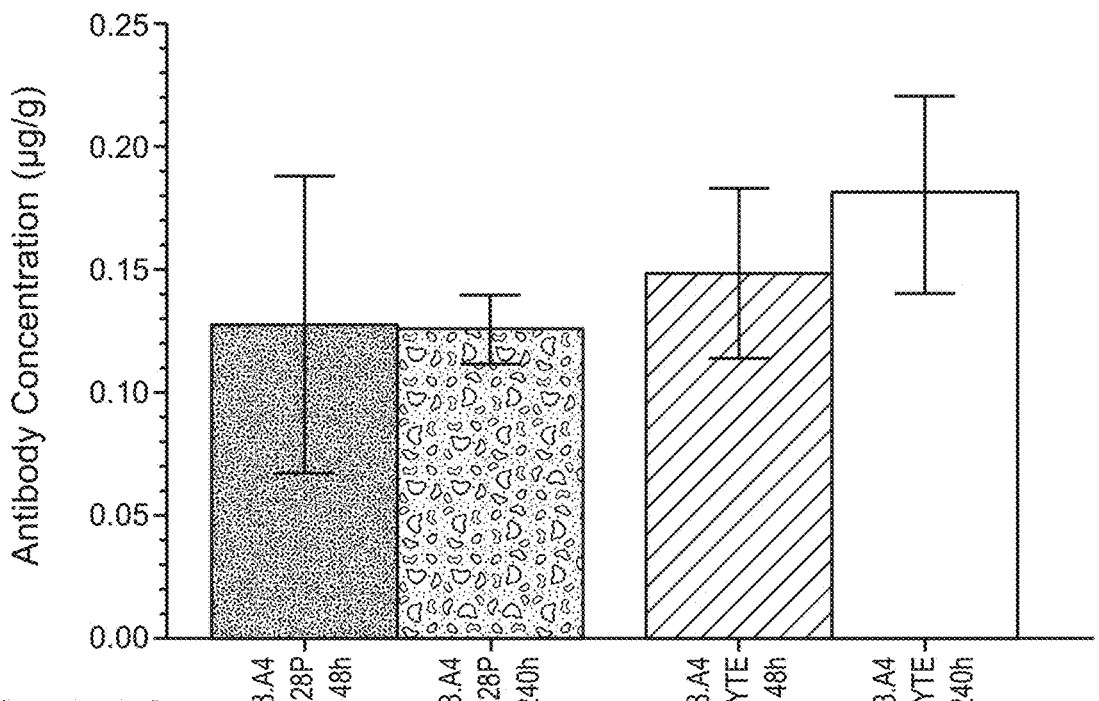
Figure 21D:
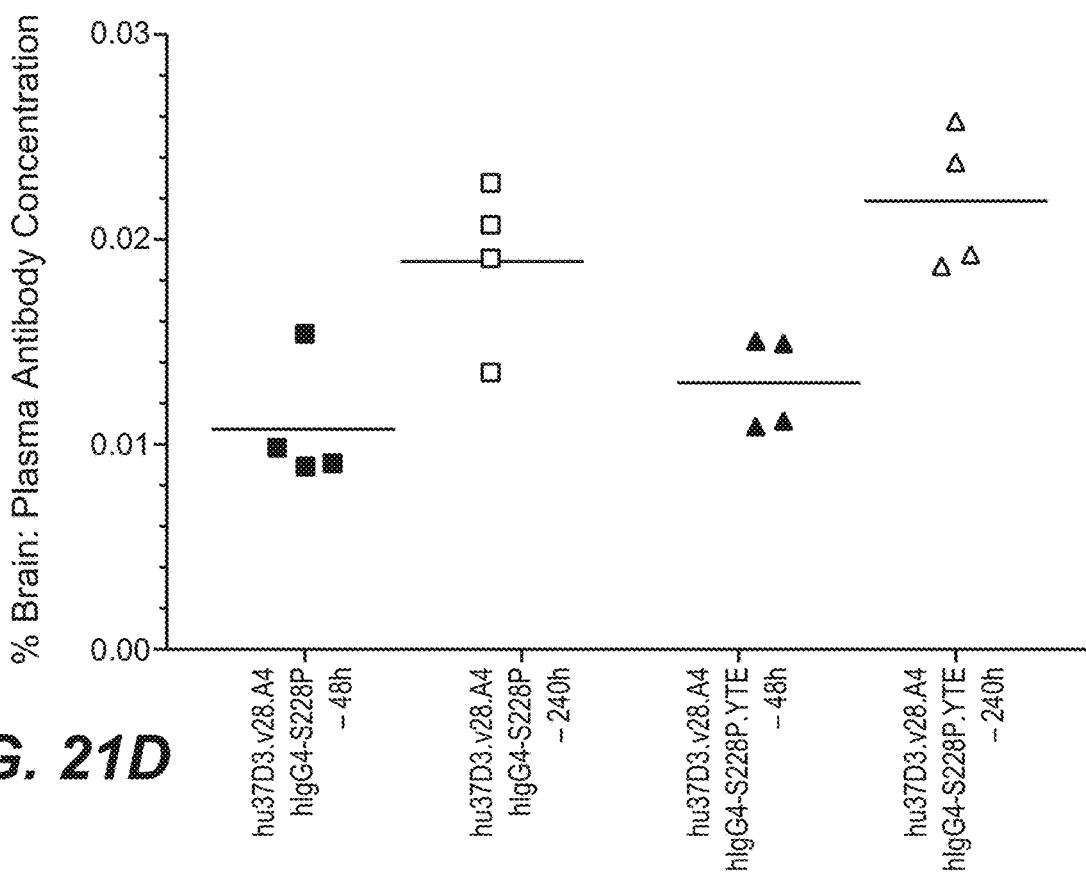

The results of the pharmacodynamic analysis are shown in FIG. 20. There were 3 animals per group after excluding animals suspected of being ATA+, and another animal that lacked baseline values. Surprisingly, within the first day of dosing, plasma Tau levels rise to a greater degree in the animals treated with the YTE variant versus the non-YTE variant. Further, that result is not predicted from the pharmacokinetics response (FIG. 20), as the PK is similar between the variants at the early time points. A more robust response is sustained in the animals treated with the YTE variant for the entire duration of sampling.

Example 13: Pharmacokinetics and Pharmacodynamics of hu37D3.v28.A4 hIgG4-S228P.YTE in Cynomolgus Monkey Brain To assess antibody pharmacokinetics in brain, twelve conscious cynomolgus monkeys (*Macaca fascicularis*) per group were administered a single IV bolus injection of hu37D3.v28.A4 hIgG4-S228P.YTE at a dose of 50 mg/kg. Anti-gD hIgG4 was used as a control, also at a dose of 50 mg/kg. At various time points up to 42 days post-dose, plasma samples were collected to determine anti-Tau antibody concentrations. In addition, at various time points up to 42 days, 2 monkeys were sacrificed and brain and CSF concentrations of antibody were determined.

Antibody concentrations were determined substantially as described in Example 12.

Figure 22A:
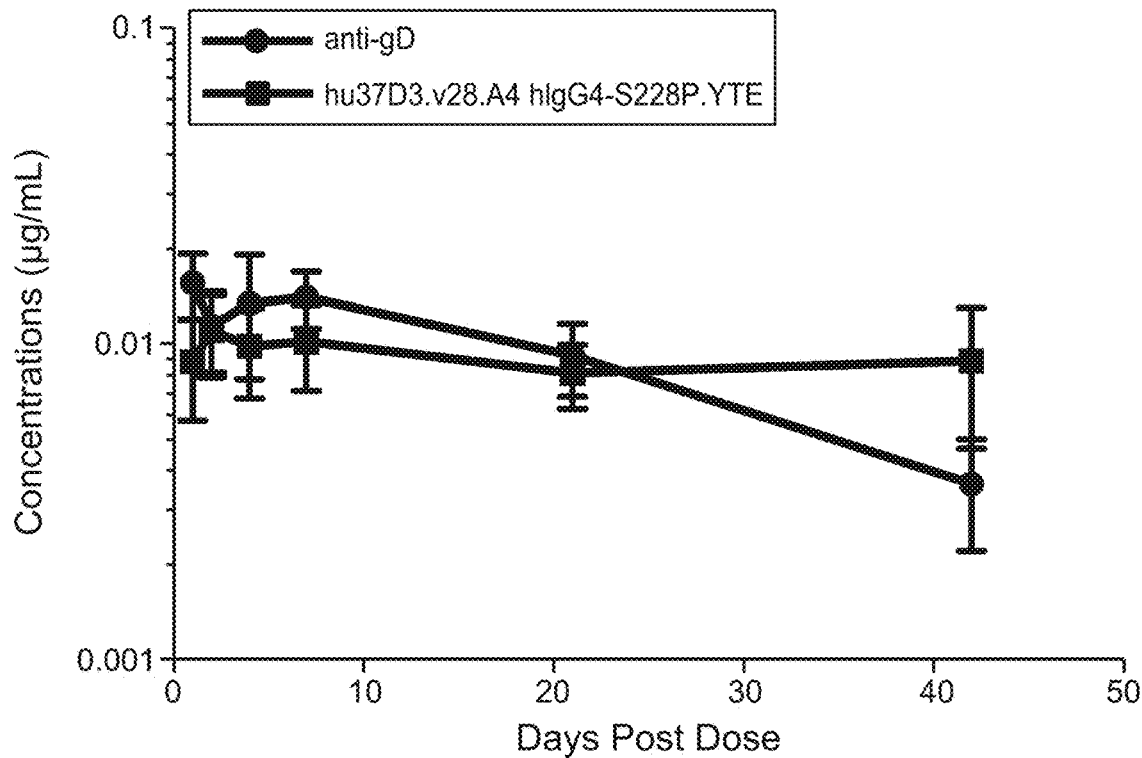
FIGS. 22A-B show the concentration of antibody in cynomolgus monkey brain at various time points following a single IV injection of the indicated antibody at 50 mg/kg, plotted in logarithmic (A) and linear (B) scale.
Figure 22B:
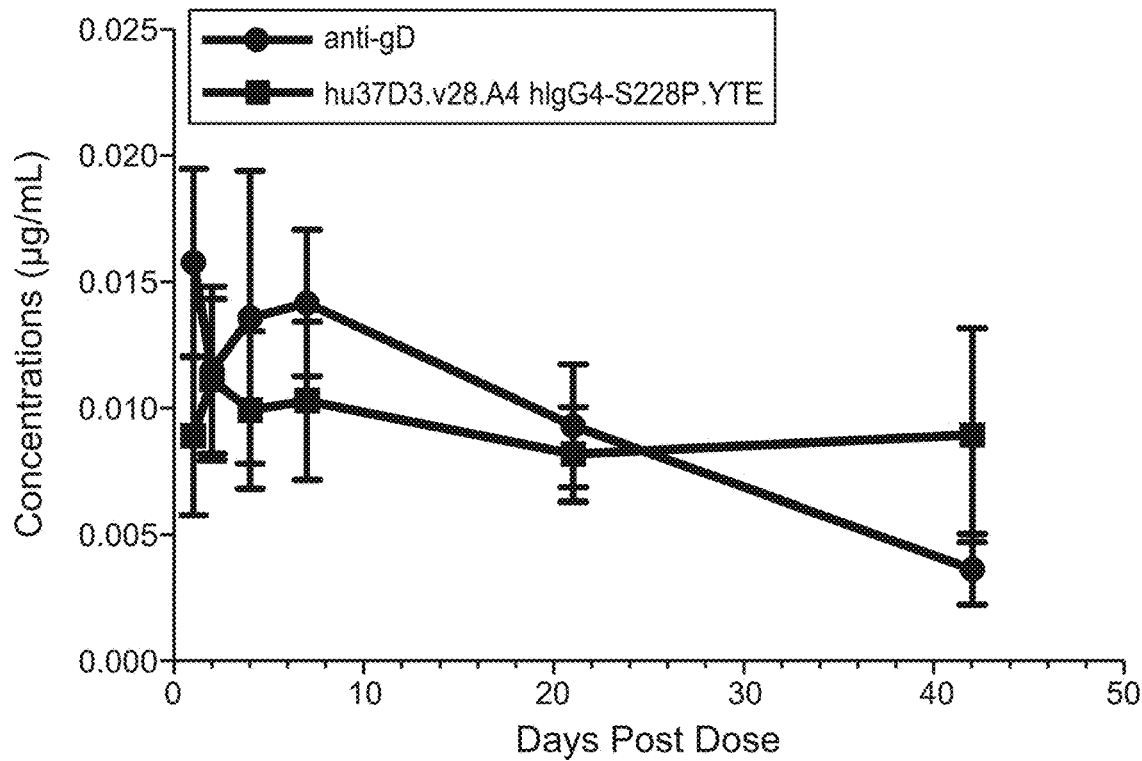

FIG. 22A-B show the concentration of antibody in cynomolgus monkey brain at various time points post-dose, plotted in logarithmic (A) and linear (B) scale. Table 25 shows the brain concentration parameters. PGP-45

TABLE 25

Mean (±SD) brain PK parameter estimates following single IV bolus dose

| Group | Cmax (µg/ml) | AUCall (day*µg/ml) |
|---|---|---|
| anti-gD hIgG4 | 0.175 ± 0.02 | 4.26 ± 0.35 |
| hu37D3.v28.A4 hIgG4-S228P.YTE | 0.12. ± 0.03 | 3.88 ± 0.89 |

The hu37D3.v28.A4 hIgG4-S228P.YTE antibody showed increased brain concentration at the terminal timepoint, compared to anti-gD.

Figure 23A:
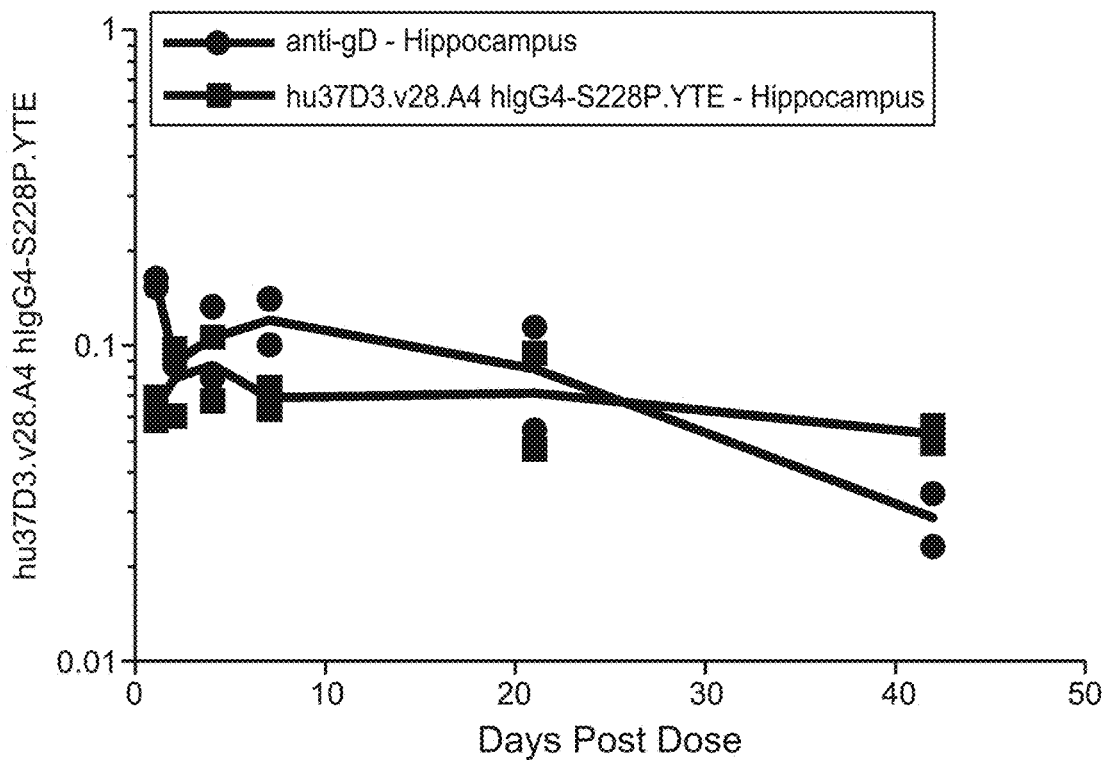
FIGS. 23A-E show show the concentration of antibody in the hippocampus (A), cerebellum (B), frontal cortex (C), CSF (D), and plasma (E) of cynomolgus monkeys at various time points following a single IV injection of the indicated antibody at 50 mg/kg.
Figure 23B:
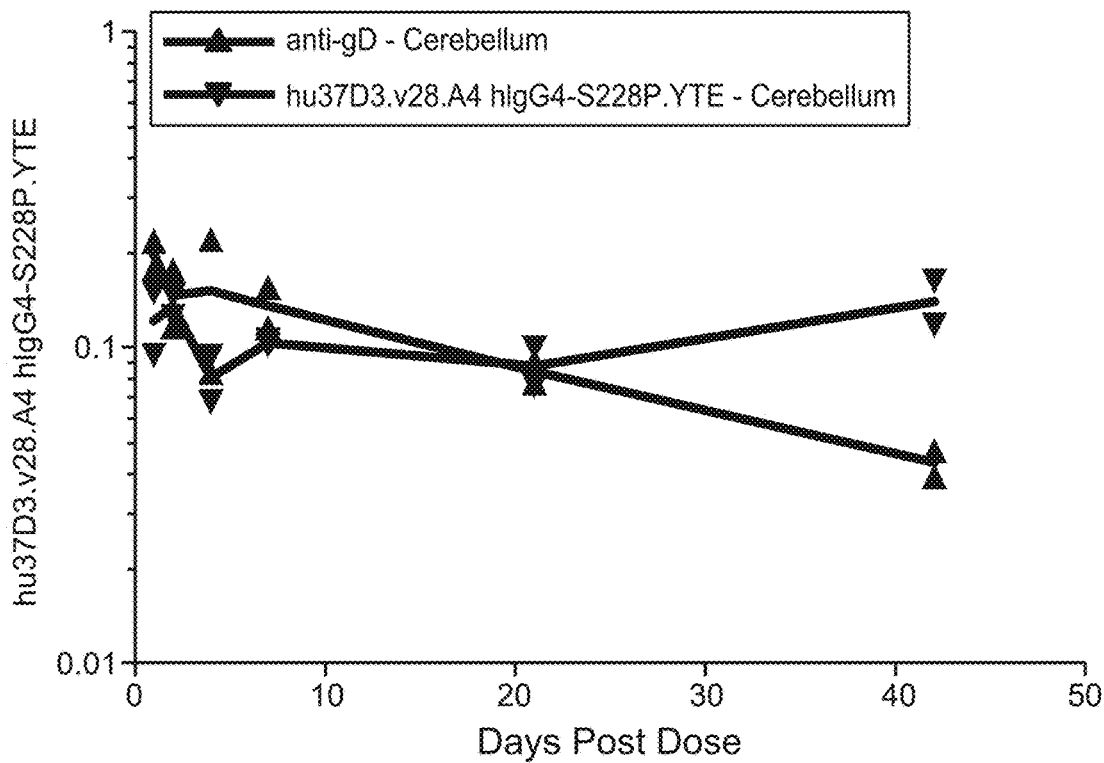
Figure 23C:
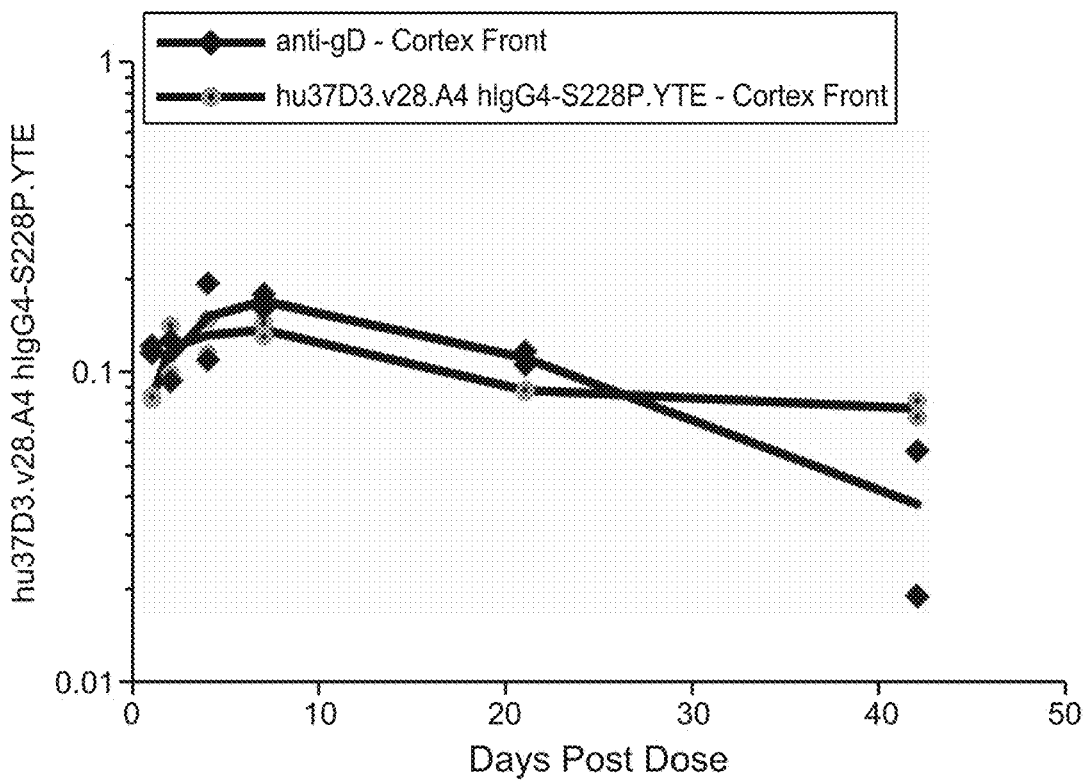

The concentration of the antibodies in various regions of the brain, including hippocampus, cerebellum, and frontal cortex, was also determined. FIG. 23A-C and Tables 26 to 28 show the results of that analysis.

TABLE 26

Mean hippocampus PK parameter estimates following single IV bolus dose

| Group | Cmax (µg/ml) | AUCall (day*µg/ml) |
|---|---|---|
| anti-gD hIgG4 | 0.159 | 3.95 |
| hu37D3.v28.A4 hIgG4-S228P.YTE | 0.087 | 2.87 |

TABLE 27

Mean cerebellum PK parameter estimates following single IV bolus dose

| Group | Cmax (µg/ml) | AUCall (day*µg/ml) |
|---|---|---|
| anti-gD hIgG4 | 0.196 | 4.30 |
| hu37D3.v28.A4 hIgG4-S228P.YTE | 0.139 | 4.56 |

TABLE 28

Mean frontal cortex PK parameter estimates following singe IV bolus dose

| Group | Cmax (µg/ml) | AUCall (day*µg/ml) |
|---|---|---|
| anti-gD hIgG4 | 0.17 | 4.65 |
| hu37D3.v28.A4 hIgG4-S228P.YTE | 0.138 | 4.22 |

The results of that experiment show exposure of various regions of the brain to antibody hu37D3.v28.A4 hIgG4-S228P.YTE following a single IV injection. Overall exposures in brain were comparable across the two groups, however, similar to the observations in plasma, there was about a two-fold increase in antibody concentrations in the brain at the terminal timepoint in animals dosed with antibody hu37D3.v28.A4 hIgG4-S228P.YTE, compared to anti-gD. See FIG. 23. These results suggest maintenance of higher trough (terminal) concentrations in brain after dosing with the YTE antibody.

Figure 23D:
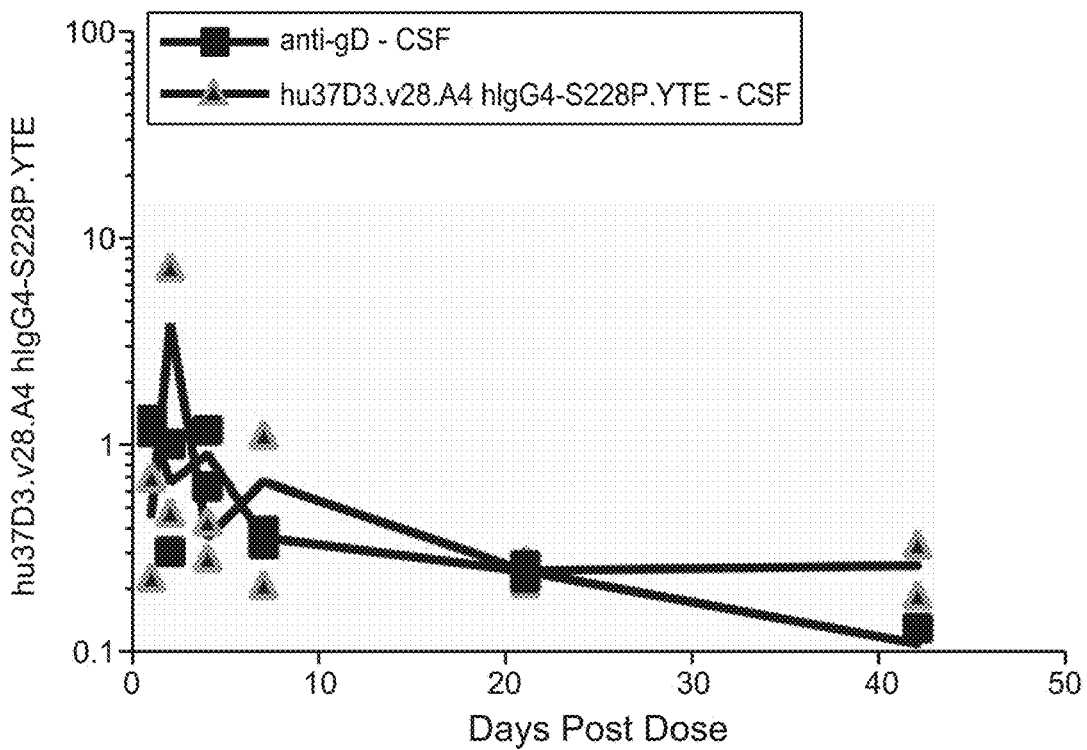
Figure 23E:
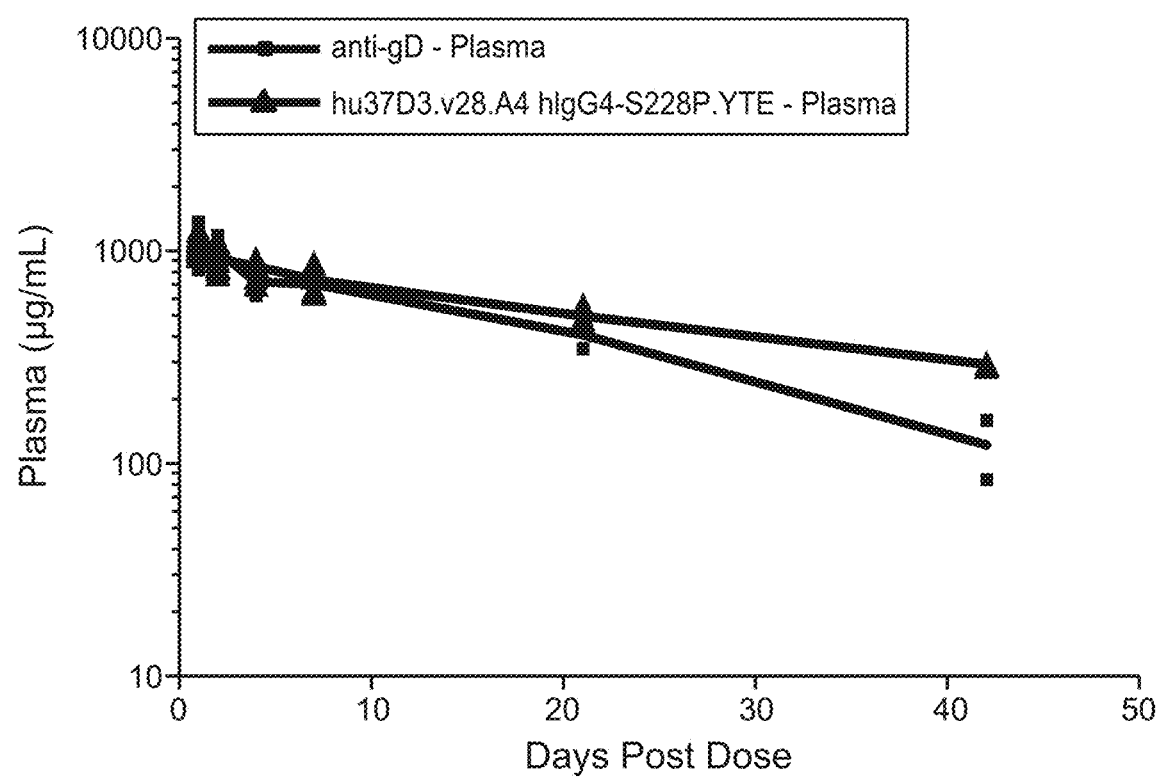

The concentration of the antibodies in CSF and plasma over time was also determined. FIGS. 23D (CSF) and 23E (plasma) and Tables 29 and 30 show the results of that analysis.

TABLE 29

Mean CSF PK parameter estimates following single IV bolus dose

| Group | Cmax (µg/ml) | AUCall (day*µg/ml) |
|---|---|---|
| anti-gD hIgG4 | 1.270 | 18.400 |
| hu37D3.v28.A4 hIgG4-S228P.YTE | 3.980 | 21.100 |

TABLE 30

Mean plasma PK parameter estimates following single IV bolus dose

| Group | Cmax (µg/ml) | Tmax Day | AUCall (day*µg/ml) | Terminal (Day 43) µg/mL |
|---|---|---|---|---|
| anti-gD hIgG4 | 0.175 ± 0.02 | 2 | 4.26 ± 0.35 | 36.3 ± 14.1 |
| hu37D3.v28.A4 hIgG4-S228P.YTE | 0.12. ± 0.03 | 3 | 3.88 ± 0.89 | 89.4 ± 42.3 |

Again, similar to the plasma and brain pharmacokinetics, there was about a two-fold increased antibody concentration in CSF and plasma at the terminal timepoint in animals dosed with antibody hu37D3.v28.A4 hIgG4-S228P.YTE, compared to anti-gD. See FIG. 23.

Using the collected plasma samples from the cynomolgus monkeys, the plasma pharmacodynamics of antibody hu37D3.v28.A4 hIgG4-S228P.YTE and control antibody following a single IV 50 mg/kg dose were assessed. Plasma Tau was quantitated using the Elecsys® immunoassay discussed in Example 12.

Figure 24A:
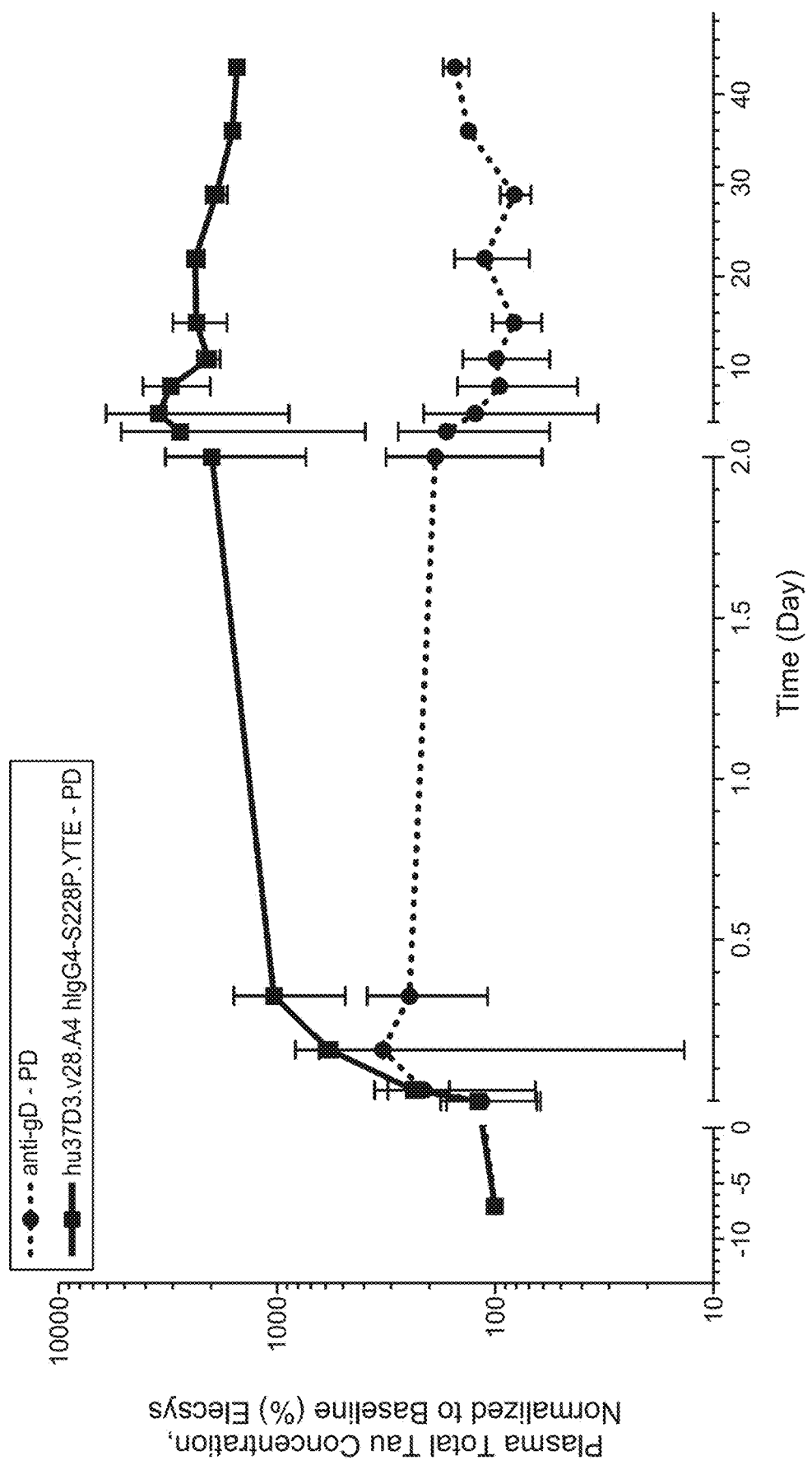
FIGS. 24A-B show average (A) and individual (B) plasma total Tau concentration over time in cynomolgus monkeys following a single IV injection of the indicated antibody at 50 mg/kg.
Figure 24B:
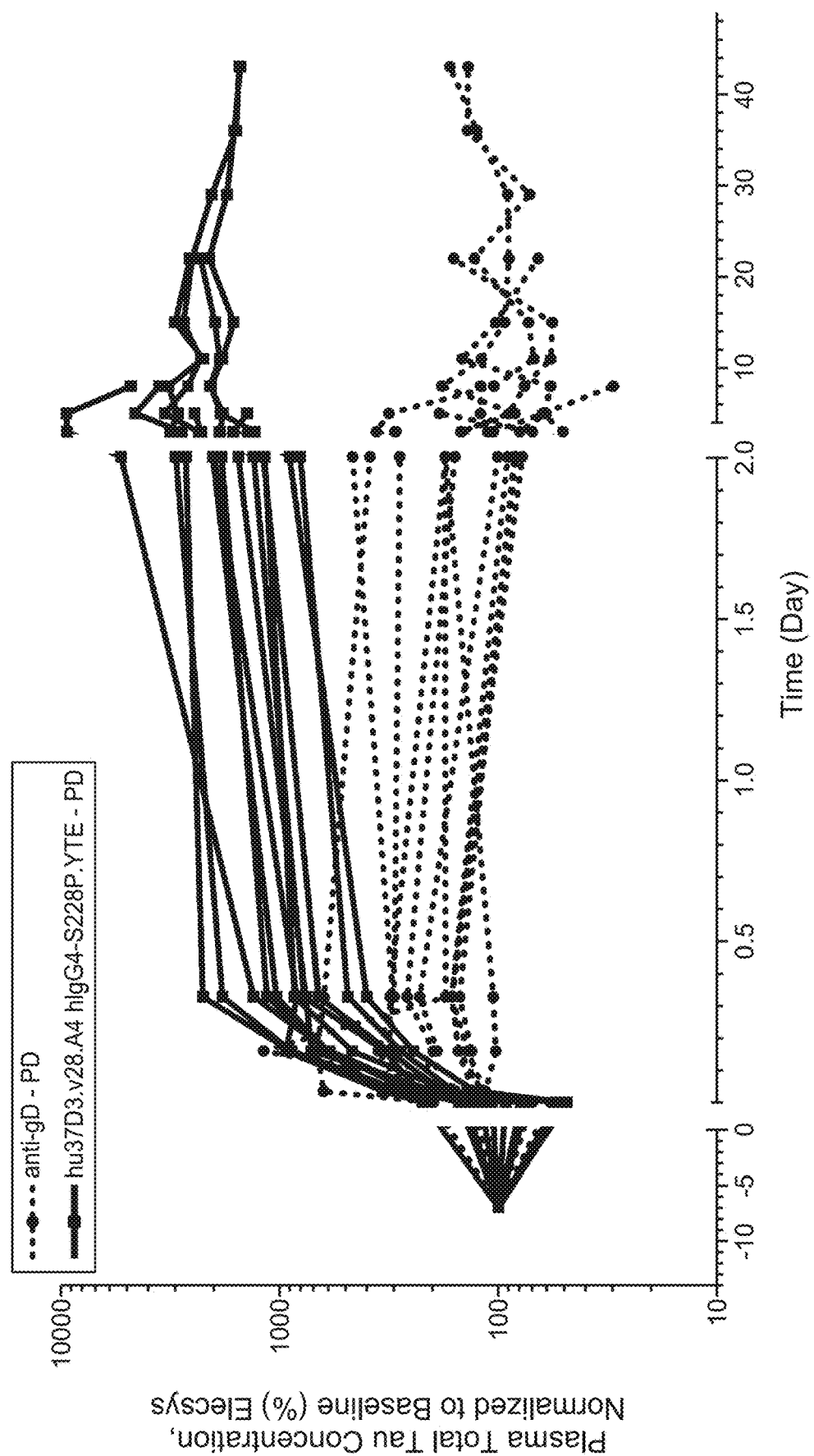

The results of the pharmacodynamics analysis are shown in FIG. 24A-B. FIG. 24A shows the mean total plasma Tau concerntration, normalized to baseline. FIG. 24B shows the total plasma Tau concerntration in individual monkeys in the study, normalized to baseline. Similar to the results observed in Example 12, administration of antibody hu37D3.v28.A4 hIgG4-S228P.YTE resulted in significantly increased plasma Tau levels. While not intending to be bound by any particular theory, these data suggest that hu37D3.v28.A4 hIgG4-S228P.YTE binds to Tau in the brain, and consequently Tau is cleared from the brain into the periphery. These results are consistent with target engagement in the brain by hu37D3.v28.A4 hIgG4-S228P.YTE.

Example 14: Vaccination of Mice with Liposomal Vaccine Containing a Full-Length Tau Protein as Antigen The liposomal vaccine with full-length human Tau-441 (flTau, SignalChem, Canada) as antigen was used for antibody generation. Briefly, DMPC, DMPG lipids (both by Lipoid AG, Switzerland), cholesterol and monophosphoryl lipid A (both by Avanti Polar Lipids, USA) at a molar ratio 9:1:7:0.05, respectively, were solubilized in EtOH at 60° C. for 30 min. An identical batch was additionally manufactured but without adjuvant for boost vaccinations. Multilamellar liposomes were extruded (EmulsiFlex-C5, Avestin, Germany) through polycarbonate Whatman filters with a pore size of 0.08 μm. The flTau protein used as the antigen was reduced with TCEP (Sigma-Aldrich, Switzerland) at a TCEP/protein molar ratio of 100:1 for 30 min at room temperature. The flTau was further coupled to DSPE-PEG (2000)maleimide lipid (Avanti Polar Lipids) at a lipid/protein molar ratio of 30:1 at ambient temperature for 4h. The coupled product was incubated with preformed liposomes for 15h at 37° C. Liposomes were further subjected to ultrafiltration and diafiltration in PBS pH 7.4, sterile filtered by passing through 0.2 m polyethersulfone (PES) membrane syringe filters, and stored at 5° C. until administration.

For the vaccinations, female C57BL/6JOlaHsd (C57BL/6) wild-type mice (Harlan, USA) were bled and heparinized plasma prepared, and then vaccinated with the liposomal vaccine described above starting at 10 weeks of age. Vaccinations were performed by subcutaneous injection (s.c.) on days 0, 5, 8, 21, and 35 with additional bleeds done on days 14, 28, and 35. Prior to fusion, mice were boosted three times with an adjuvant-free preparation of the vaccine on days 55, 56, and 57. Mice were sacrificed and fusion with myeloma cells done on day 58. Splenocytes from four mice were used for fusions, with cells used individually from two mice and pooled from two mice for a total of three separate fusions. For screening fusion products, a 1:8 supernatant dilution was run using Luminex bead-based multiplex technology (Luminex, The Netherlands), capturing IgGs with anti-mouse IgG-Fc antibodies specific for the IgG1, IgG2a, IgG2b, IgG2c, and IgG3 subclasses (Jackson ImmunoResearch, USA). Binding to beads conjugated to flTau and, optionally, to one of the following Tau fragments: Tau50-391, Tau99-441, Tau151-421, Tau151-441, or Tau231-441 (all by SignalChem) identified 183 hits. Subcloning was done by limiting dilution for 50 hybridomas selected from the initial round of screening for best binders to flTau and, optionally, to one of the above Tau fragments. Following limiting dilution, the final hybridomas were then adapted to serum-free medium and media was collected from stable colonies for antibody screening and selection. Antibodies 211G6-B6, 231G3F10, and 307H3E8 were identified from this screen.

Figure 2A:
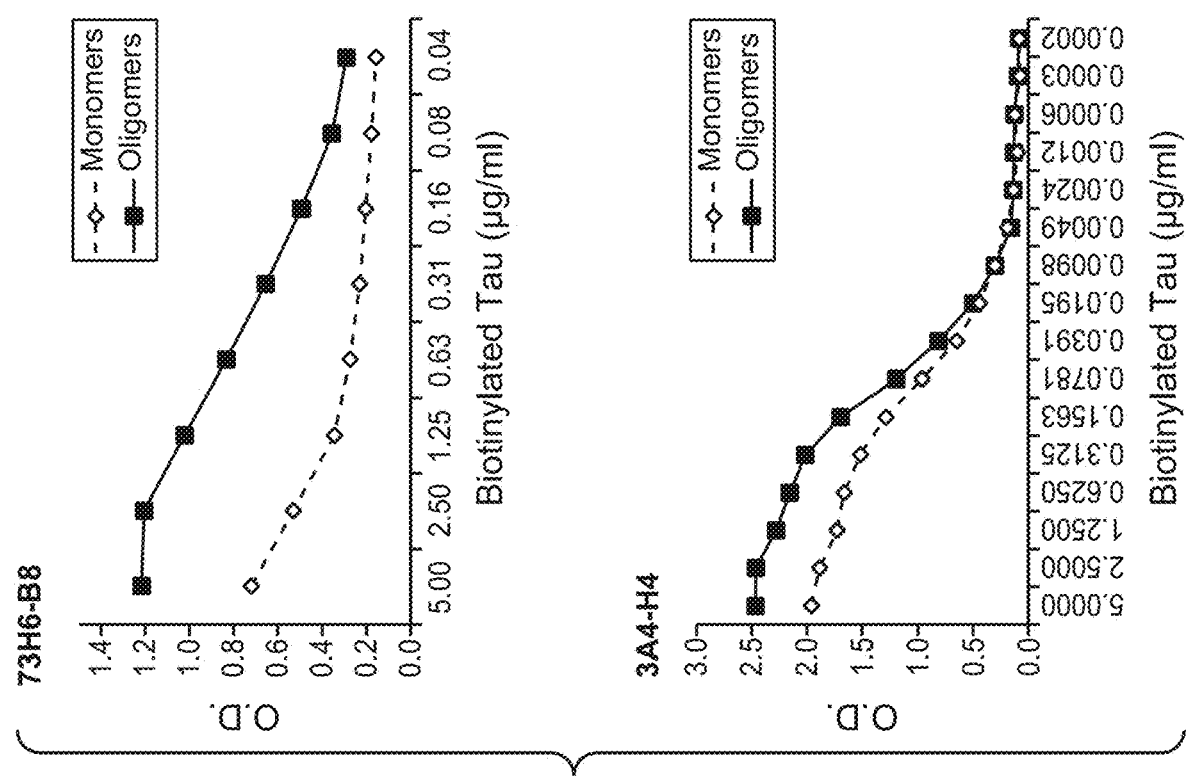
FIG. 2A-E. Binding of antibodies to oligomeric Tau was assessed using an oligo- and monoTau capture ELISA. Results are expressed in optical densities (O.D.).
Figure 2B:
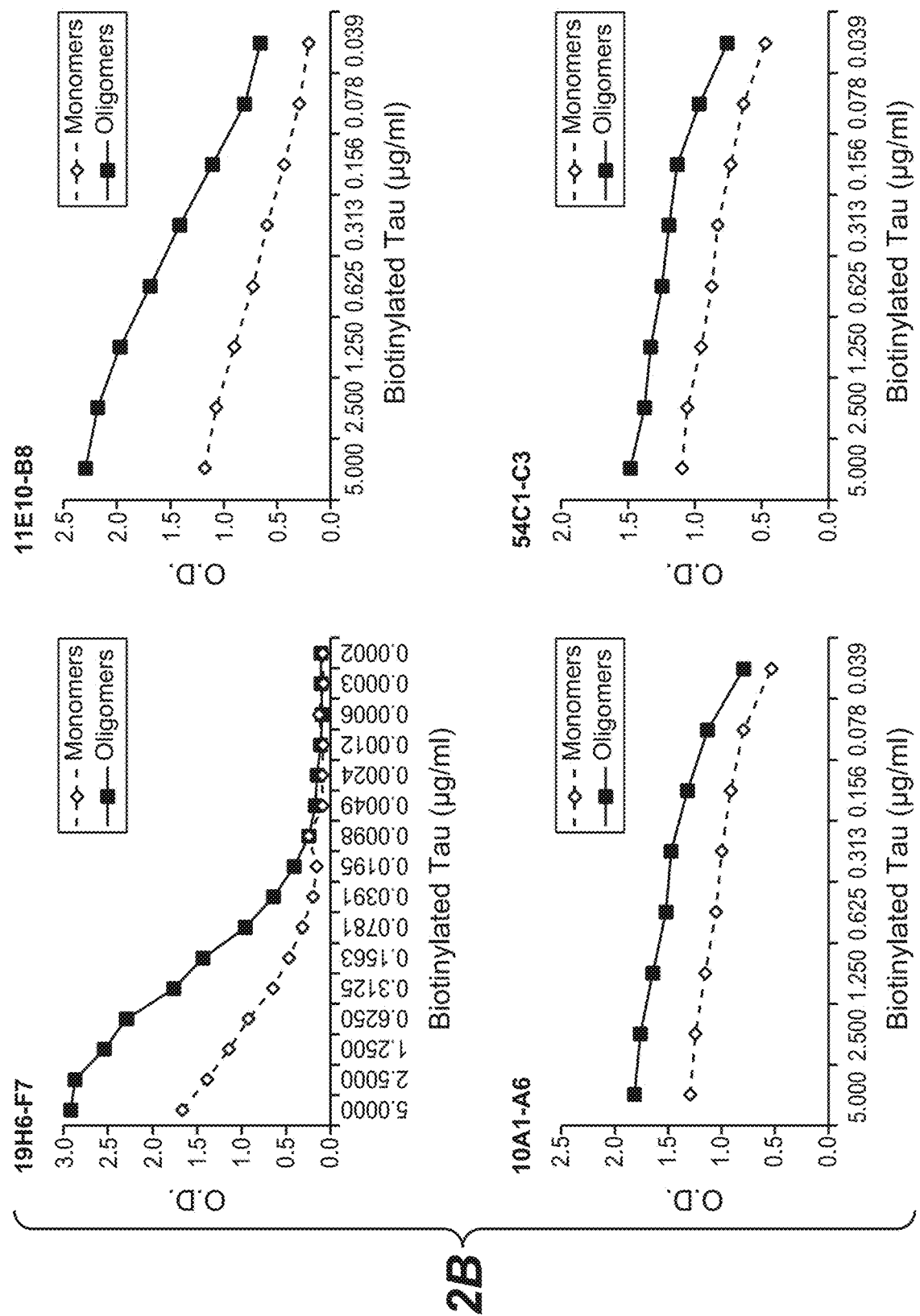
Figure 2C:
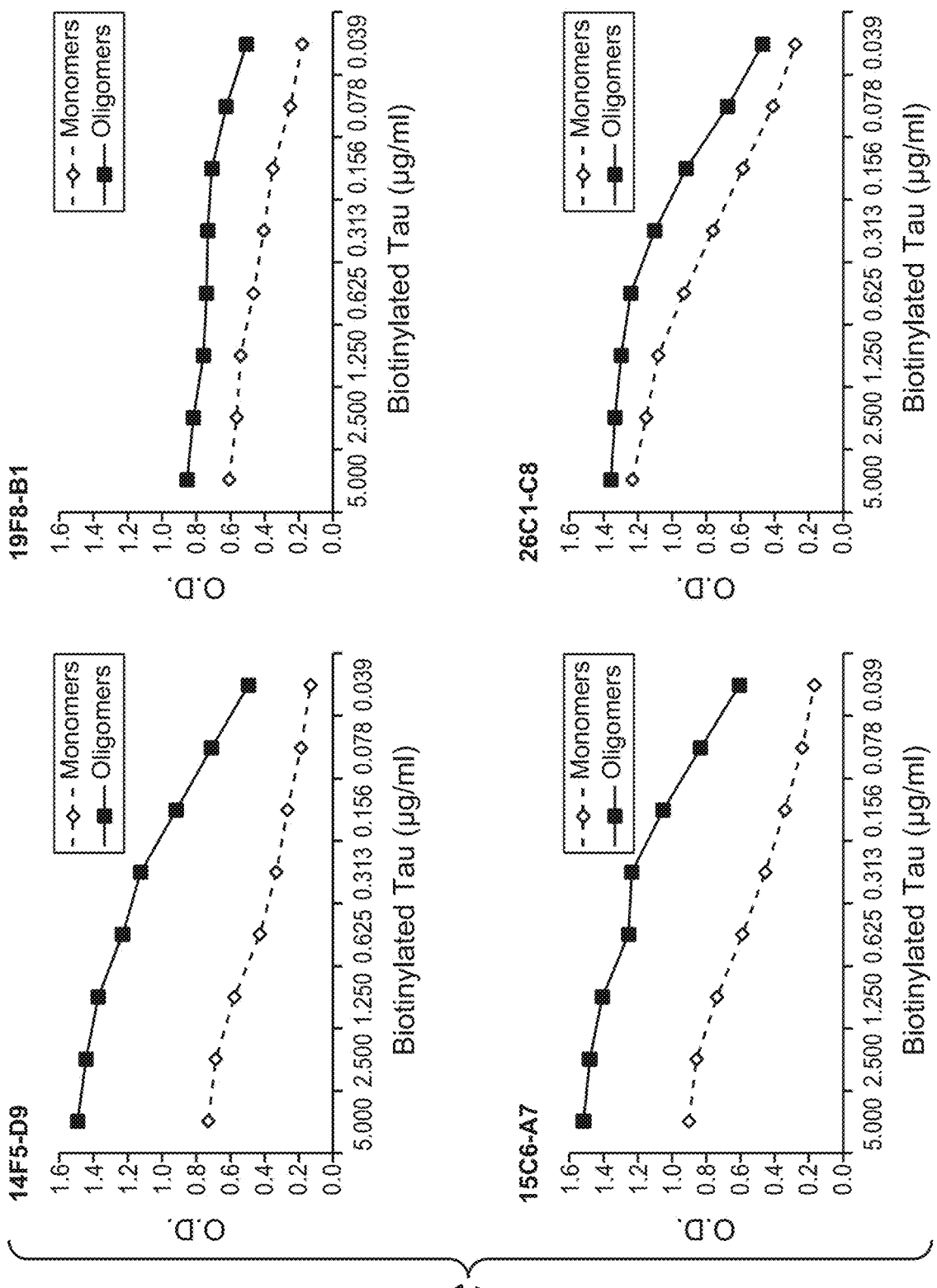
Figure 2D:
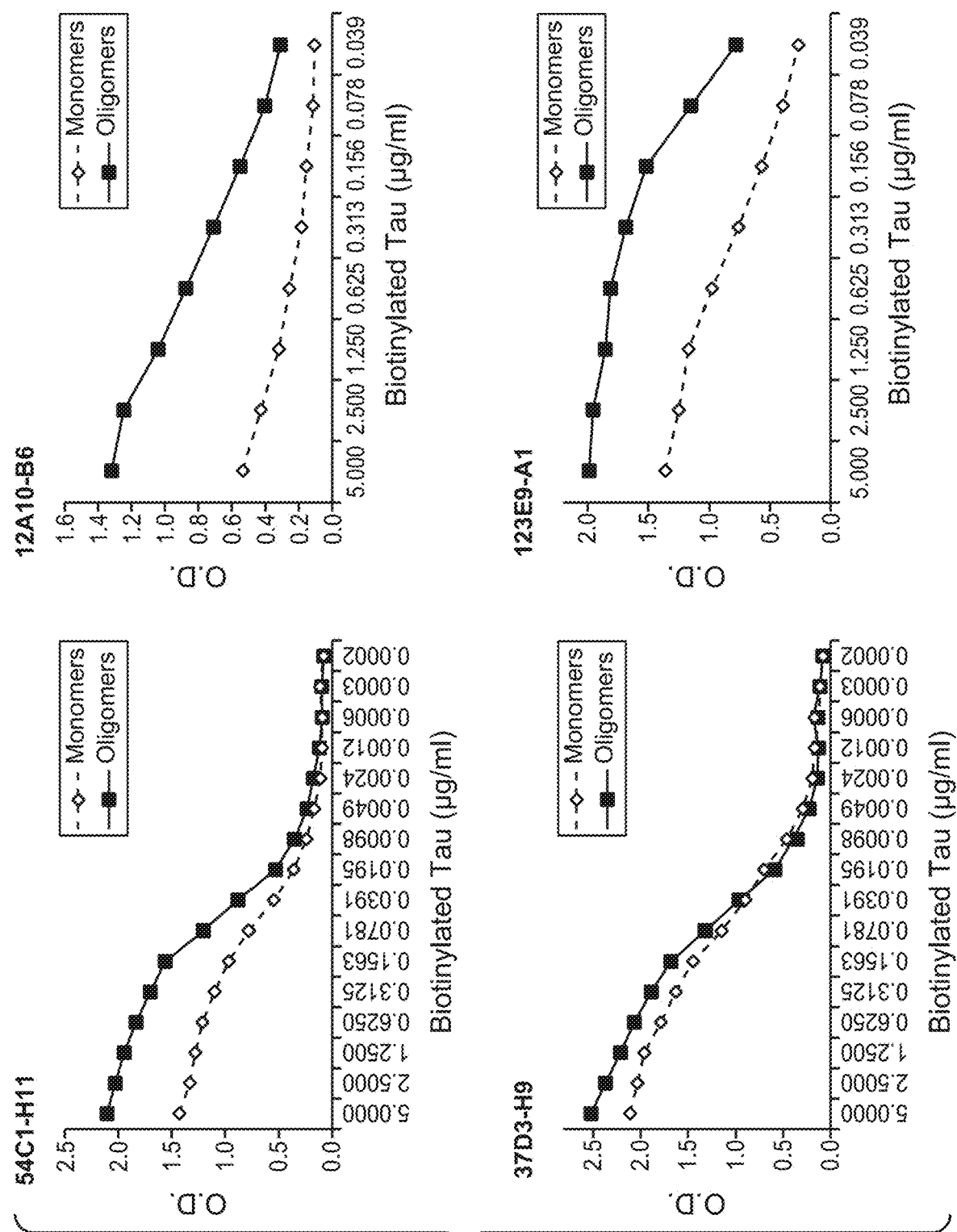
Figure 2E:
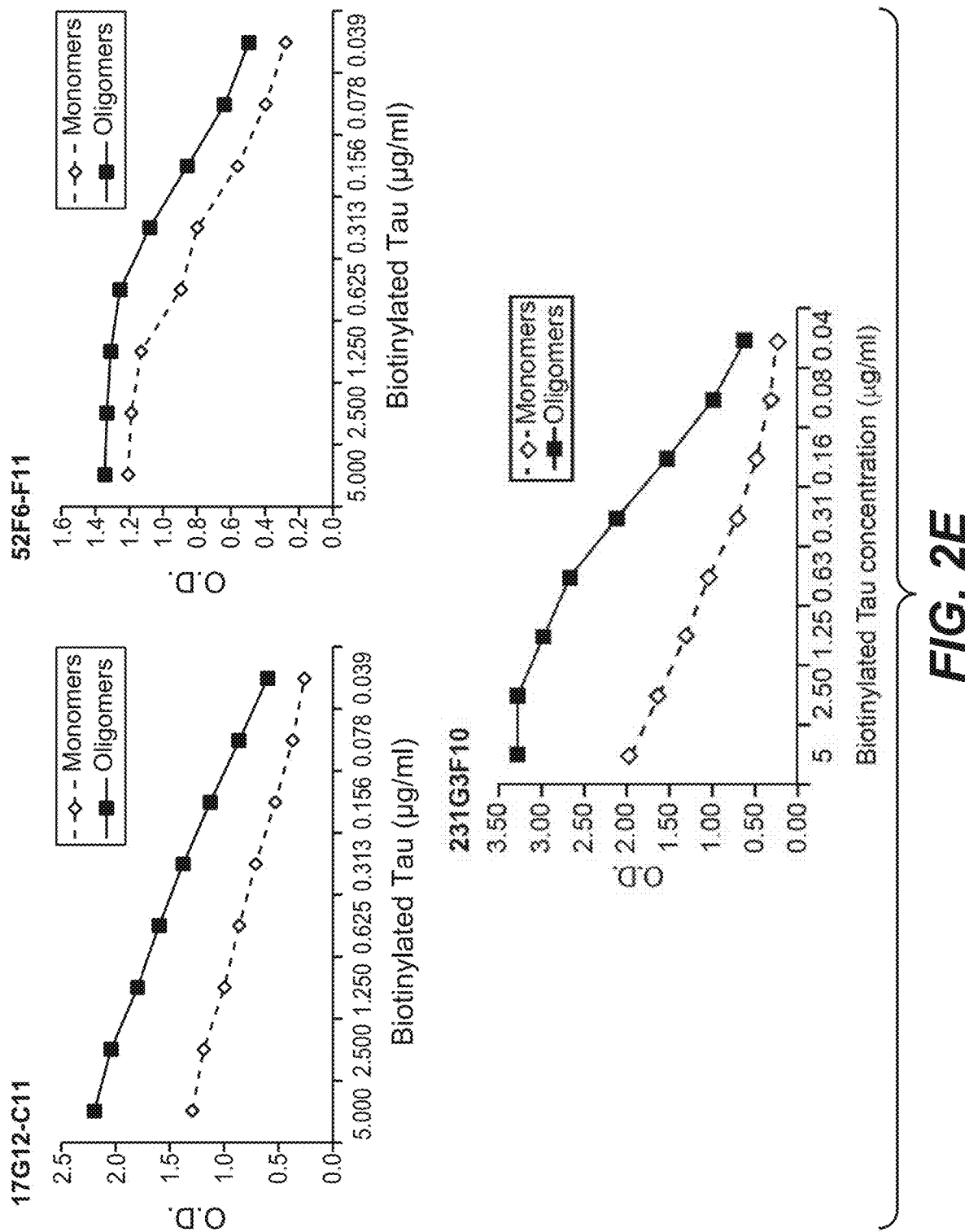

FIG. 2E shows binding of antibody 231G3F10 to monomeric and oligomeric Tau.

Epitope mapping was carried out substantially as described in Example 2. Table 31 lists the epitopes for the 211G6-B6, 231G3F10, and 307H3E8 antibodies. Table 5 shows the $K_D$ values for antibodies 211G6-B6, 231G3F10, and 307H3E8.

TABLE 31

Epitope mapping of antibodies generated with liposomal vaccine

| Antibody | Epitope |
|---|---|
| 211G6-B6 | 91-105 (exon 3) |
| 231G3F10 | 37-44 |
| 307H3E8 | 421-429, 422-429 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Table of Sequences

| SEQ ID NO | Description | Sequence |
|---|---|---|
| 2 | Human Tau epitope (2-24) | AEPRQEFEVMEDHAGTYGLGDRK |
| 4 | Cynomolgus monkey Tau epitope (2-24) | AEPRQEFDVMEDHAGTYGLGDRK |
| 10 | 37D3-H9 heavy chain variable region (VH) | EVQLVESGGD LAKPGGSLKL SCTASGLIFR SYGMSWVRQT PDKRLEWVAT INSGGTYTYY PDSVKGRFTI SRDNAKNTLY LQMSSLKSED TAMYYCANSY SGAMDYWGQG TSVTVSS |
| 11 | 37D3-H9 light chain variable region (VL) | DDLLTQTPLS LPVSLGDPAS ISCRSSQSIV HSNGNTYFEW YLQKPGQSPK LLIYKVSNRF SGVPDRFSGS GSGTDFTLKI SRVEAEDLGV YYCFQGSLVP WTFGGGTKLE IK |
| 12 | 37D3-H9 HVR-H1 | SYGMS |
| 13 | 37D3-H9 HVR-H2 | TINSGGTYTYYPDSVKG |
| 14 | 37D3-H9 HVR-H3 | SYSGAMDY |
| 15 | 37D3-H9 HVR-L1 | RSSQSIVHSNGNTYFE |
| 16 | 37D3-H9 HVR-L2 | KVSNRFS |
| 17 | 37D3-H9 HVR-L3 | FQGSLVPWT |

| SEQ ID NO | Description | Sequence |
|---|---|---|
| 20 | 37D3-H9b heavy chain variable region (VH) | EVQLVESGGD LAKPGGSLKL SCTASGLIFR SYGMSWVRQT PDKRLEWVAT INSGGTYTYY PDSVKGRFTI SRDNAKNTLY LQMSSLKSED TAMYYCANSY SGAMDYWGQG TSVTVSS |
| 21 | 37D3-H9b light chain variable region (VL) | EDLLTQTPLS LPVSLGDPAS ISCRSSQSIV HSNGNTYFEW YLQKPGQSPK LLIYKVSNRF SGVPDRFSGS GSGTDFTLKI SRVEAEDLGV YYCFQGSLVP WTFGGGTKLE IK |
| 22 | 37D3-H9b HVR-H1 | SYGMS |
| 23 | 37D3-H9b HVR-H2 | TINSGGTYTYYPDSVKG |
| 24 | 37D3-H9b HVR-H3 | SYSGAMDY |
| 25 | 37D3-H9b HVR-L1 | RSSQSIVHSNGNTYFE |
| 26 | 37D3-H9b HVR-L2 | KVSNRFS |
| 27 | 37D3-H9b HVR-L3 | FQGSLVPWT |
| 30 | 11E10-B8 heavy chain variable region (VH) | EVQLVESGGD LVKPGGSLKL SCAASGFTFR SYGMSWVRQT PDKRLEWVAT ISGGGSYTYY PDSVKGRFTI SRDNAKNTLY LQMSSLKSED TAMYYCAVSY DGAMDYWGQG TSVTVSS |
| 31 | 11E10-B8 light chain variable region (VL) | DVLMTQTPLS LPVSLGDQAS ISCRSSQSIV HSNGNTYLEW YLQKPGQSPK LLIYKVSNRF SGVPDRFSGS GSGTDFTLKI SRVEAEDLGL YYCFQGSHVP WTFGGGTKLE IK |
| 32 | 11E10-B8 HVR-H1 | SYGMS |
| 33 | 11E10-B8 HVR-H2 | TISGGGSYTYYPDSVKG |
| 34 | 11E10-B8 HVR-H3 | SYDGAMDY |
| 35 | 11E10-B8 HVR-L1 | RSSQSIVHSNGNTYLE |
| 36 | 11E10-B8 HVR-L2 | KVSNRFS |
| 37 | 11E10-B8 HVR-L3 | FQGSHVPWT |
| 40 | 54C1-H11 and 61E7-C4 heavy chain variable region (VH) | EVQLVESGGD LVKPGGSLKV SCVASGFTFR SYGMSWVRQT PDKRLDWVAT ISSGGNYTYY PDSVKGRFTI SRDNAKNTLY LQMSSLKSED TAMYYCASSY SGAMDYWGQG TSVTVSS |
| 41 | 54C1-H11 and 61E7-C4 light chain variable region (VL) | DTVMTQSPLS LPVSLGDQAS ISCRSSQSIV HSNGNTYLEW YLQKPGQSPK LLIYTVSNRF SGVPDRFSGS GSGTDFTLKI SRVEAEDLGV YYCFQGSHVP WTFGGGTKLE IK |
| 42 | 54C1-H11 and 61E7-C4 HVR-H1 | SYGMS |
| 43 | 54C1-H11 and 61E7-C4 HVR-H2 | TISSGGNYTYYPDSVKG |
| 44 | 54C1-H11 and 61E7-C4 HVR-H3 | SYSGAMDY |
| 45 | 54C1-H11 and 61E7-C4 HVR-L1 | RSSQSIVHSNGNTYLE |
| 46 | 54C1-H11 and 61E7-C4 HVR-L2 | TVSNRFS |
| 47 | 54C1-H11 and 61E7-C4 HVR-L3 | FQGSHVPWT |
| 50 | 3A4-H4 heavy chain variable region (VH) | EVQLVESGGD LVKPGGSLKL SCAASGFTFS SYGMSWVRQT PDKRLEWVAT ISSGGTYTYY PDSVKGRFTI SRDNAKNTLY LQMSSLKSED TAMYFCATSY DGAMDYWGQG TSVTVSS |

Table of Sequences

| SEQ ID NO | Description | Sequence |
|---|---|---|
| 51 | 3A4-H4 light chain variable region (VL) | DVLMTQTPLS LPVSLGDQAS ISCRSSQNIV HSNGNTYLEW YLQKPGQSPK LLIYKVSNRF SGVPDRFSGS GSGTDFTLKI SRVEAEDLGV YYCFQGTLVP WTFGGGTKLE IK |
| 52 | 3A4-H4 HVR-H1 | SYGMS |
| 53 | 3A4-H4 HVR-H2 | TISSGGTYTYYPDSVKG |
| 54 | 3A4-H4 HVR-H3 | SYDGAMDY |
| 55 | 3A4-H4 HVR-L1 | RSSQNIVHSNGNTYLE |
| 56 | 3A4-H4 HVR-L2 | KVSNRFS |
| 57 | 3A4-H4 HVR-L3 | FQGTLVPWT |
| 60 | 19H6-F7 heavy chain variable region (VH) | EVQLVESGGD LVKPGGSLKL SCAASGFTFS SYGMSWVRQT PDKRLEWVAT ISSGGTYTYY PDSVKGRFTI SRDNAKNTLY LQMSSLKSED TAMYYCAPSY DGAMDYWGQG TSVTVSS |
| 61 | 19H6-F7 light chain variable region (VL) | DVLMTQTPLS LPVSLGDQAS ISCRSSQSIV HSNGNTYLEW YLQKPGQSPK LLIYKVSNRF SGVPDRFSGS GSGTDFTLKI SRVEAEDLGV YYCFQGSLVP WTFGGGTKLE IK |
| 62 | 19H6-F7 HVR-H1 | SYGMS |
| 63 | 19H6-F7 HVR-H2 | TISSGGTYTYYPDSVKG |
| 64 | 19H6-F7 HVR-H3 | SYDGAMDY |
| 65 | 19H6-F7 HVR-L1 | RSSQSIVHSNGNTYLE |
| 66 | 19H6-F7 HVR-L2 | KVSNRFS |
| 67 | 19H6-F7 HVR-L3 | FQGSLVPWT |
| 70 | 94B2-C1 heavy chain variable region (VH) | EVQLQQSGPE LVKPGASMKI SCKASGYSLT GYTMNWVKQS HGKNLEWIGL ISPYNGVTSY NQKFKGKATL TVDKSSNTAY MELLSLTFED SAVYYCARQG AYWGQGTLVT VSA |
| 71 | 94B2-C1 light chain variable region (VL) | DVVMTQTPLT LSVTIGQPAS ISCKSSQSLL DSDGKTYLNW LLQRPGQSPK RLIYLVSKLD SGVPDRFTGS GSGTDFTLKI SRVEAEDLGV YYCWQGTHFP WTFGGGTKLE IK |
| 72 | 94B2-C1 HVR-H1 | GYTMN |
| 73 | 94B2-C1 HVR-H2 | LISPYNGVTSYNQKFKG |
| 74 | 94B2-C1 HVR-H3 | QGAY |
| 75 | 94B2-C1 HVR-L1 | KSSQSLLDSDGKTYLN |
| 76 | 94B2-C1 HVR-L2 | LVSKLDS |
| 77 | 94B2-C1 HVR-L3 | WQGTHFPWT |
| 80 | 125B11-H3 heavy chain variable region (VH) | EVKLEESGGG LVQPGGSMKL SCVASRFIFS NYWMNWVRQS PEKGLEWVAQ IRLKSDNYAT HYAESVKGRF TISRDDSKSS VYLQMNNLRA EDTGIYYCTG GTTYWGQGTT LTVSS |
| 81 | 125B11-H3 light chain variable region (VL) | DIVMTQSQKF LSTSVGDRVN ITCKASQNVG TAVAWYQQKP GQSPGLLIYS ASIRYTGVPD RFTGNGSGTD FTLTISDMQS EDLADYFCQQ FRTYPYTFGG GTKLEIK |
| 82 | 125B11-H3 HVR-H1 | NYWMN |
| 83 | 125B11-H3 HVR-H2 | QIRLKSDNYA THYAESVKG |
| 84 | 125B11-H3 HVR-H3 | GTTY |

| SEQ ID NO | Description | Sequence |
|---|---|---|
| 85 | 125B11-H3 HVR-L1 | KASQNVGTAVA |
| 86 | 125B11-H3 HVR-L2 | SASIRYT |
| 87 | 125B11-H3 HVR-L3 | QQFRTYPYT |
| 90 | 113F5-F7 heavy chain variable region (VH) | EVKLEESGGG LVQPGGSMRL SCVASEFTFS NYWMNWIRQS PEKGLEWVAQ IRLKSDNYAT HYAESVKGRF TISRDASNFS VYLQMNNLRA EDTGIYYCTG GTSYWGQGTT LTVSS |
| 91 | 113F5-F7 light chain variable region (VL) | DIVMTQSQKI MSTSVGDRVS ITCKASQNVG TAVAWYQQRP GHSPKLLIYS ASRRFSGVPD RFTGSGSGTD FTLTIINVQS EDLADYFCQQ FSTYPYTFGV GTKLEIK |
| 92 | 113F5-F7 HVR-H1 | NYWMN |
| 93 | 113F5-F7 HVR-H2 | QIRLKSDNYATHYAESVKG |
| 94 | 113F5-F7 HVR-H3 | GTSY |
| 95 | 113F5-F7 HVR-L1 | KASQNVGTAVA |
| 96 | 113F5-F7 HVR-L2 | SASRRFS |
| 97 | 113F5-F7 HVR-L3 | 44FsTYPYT |
| 100 | 26C1-B11 heavy chain variable region (VH) | EVHLQQSGAE LVRSGASVKL SCTASGFNIK DYYMYWVKQR PEQGLEWIGW IDPENGDTEY FPKFQGKATM TADTSSKTAY LQLSSLTSED TAVYYCNAWR ARATNSALDY WGQGTSVTVS S |
| 101 | 26C1-B11 light chain variable region (VL) | DVVMTQTPLT LSVTIGQPAS ISCKSSQSLL DSDGKTYLNW LLRRPGQSPK RLIYLVSKLD SGVPDRFTGS GSGTDFTLKI SRVEAEDLGV YYCWQGTHFP WTFGGGTKLE IK |
| 102 | 26C1-B11 HVR-H1 | DYYMY |
| 103 | 26C1-B11 HVR-H2 | WIDPENGDTE YFPKFQG |
| 104 | 26C1-B11 HVR-H3 | WRARATNSAL DY |
| 105 | 26C1-B11 HVR-L1 | KSSQSLLDSD GKTYLN |
| 106 | 26C1-B11 HVR-L2 | LVSKLDS |
| 107 | 26C1-B11 HVR-L3 | WQGTHFPWT |
| 110 | 26C1-C8 heavy chain variable region (VH) | EVHLQQSGAE LVRSGASVKL SCTASGFNIK DYYMYWVKQR PEQGLEWIGW IDPENGDTEY FPKFQGKATM TADTSSKTAY LQLSSLTSED TAVYYCNAWR ARATNSALDY WGQGTSVTVS S |
| 111 | 26C1-C8 light chain variable region (VL) | DVVMTQTPLT LSVTIGQPAS ISCKSSQSLL DSDGKTYLNW LLRRPGQSPK RLIYLVSKLD SGVPDRFTGS GSGTDFTLKI SRVEAEDLGV YYCWQGTHFP WTFGGGTKLE IK |
| 112 | 26C1-C8 HVR-H1 | DYYMY |
| 113 | 26C1-C8 HVR-H2 | WIDPENGDTE YFPKFQG |
| 114 | 26C1-C8 HVR-H3 | WRARATNSAL DY |
| 115 | 26C1-C8 HVR-L1 | KSSQSLLDSD GKTYLN |
| 116 | 26C1-C8 HVR-L2 | LVSKLDS |
| 117 | 26C1-C8 HVR-L3 | WQGTHFPWT |
| 120 | 30G1-B2 heavy chain variable region (VH) | QVQLQQSGAE LVRPGASVTL SCKASGYTFT DYEMYWVKQT PVHGLEWIGA IDPETGDTAY NQKFKGKATL TADKSSNTAY MELRSLTSED SAVYYCIRQY GNWFPYWGQG TLVTVSA |

Table of Sequences

| SEQ ID NO | Description | Sequence |
|---|---|---|
| 121 | 30G1-B2 light chain variable region (VL) | DVVMTQTPLS LPVSLGDQAS ISCRSSQSLV HANGNTYLHW FLQKPGLSPK LLIYKVSNRF SGVPDRFSGG GSGTDFTLKI TRLEAEDLGV YFCSQSTHVP FTFGSGTKLE IK |
| 122 | 30G1-B2 HVR-H1 | DYEMY |
| 123 | 30G1-B2 HVR-H2 | AIDPETGDTAYNQKFKG |
| 124 | 30G1-B2 HVR-H3 | QYGNWFPY |
| 125 | 30G1-B2 HVR-L1 | RSSQSLVHANGNTYLH |
| 126 | 30G1-B2 HVR-L2 | KVSNRFS |
| 127 | 30G1-B2 HVR-L3 | SQSTHVPFT |
| 130 | 66F5-A1 heavy chain variable region (VH) | QVQLQQSGAE LVRPGASVTL SCKASGYTFI DYEMNWVKQT PVHGLEWIGA IDPENGGTAY NQKFKGKAIV TADKSSSTAY MELRSLTSED SAVYYCSGPH FDYWGQGTTL TVSS |
| 131 | 66F5-A1 light chain variable region (VL) | DIVMTQSPSS LAMSVGQKVT MSCKSSQSLL NSSTQKNYLA WYQQKPGQSP KLLVYFASTR ESGVPDRFIG SGSGTDFTLT ISSVQAEDLA DYFCQQHYST PYTFGGGTKL EIK |
| 132 | 66F5-A1 HVR-H1 | DYEMN |
| 133 | 66F5-A1 HVR-H2 | AIDPENGGTA YNQKFKG |
| 134 | 66F5-A1 HVR-H3 | PHFDY |
| 135 | 66F5-A1 HVR-L1 | KSSQSLLNSS TQKNYLA |
| 136 | 66F5-A1 HVR-L2 | FASTRES |
| 137 | 66F5-A1 HVR-L3 | QQHYSTPYT |
| 140 | 123E9-A1 heavy chain variable region (VH) | EVQLQQSGPE LVKPGASVKM SCKASGYTFT DYYMKWVKQS HGKSLEWIGD IDPNNGGTSY NQKFKGKATL TVDKSSSTAY MQLNSLTSED SAVYYCARSA GFGDSFSFWG LGTLVTVSA |
| 141 | 123E9-A1 light chain variable region (VL) | DVLMTQTPLS LPVSLGDQAS ISCRSSQSIV HSNGNTYLEW YLQKPGQSPK LLIYKVSNRF SGVPDRFSGS GSGTDFTLKI SRVEAEDLGF YYCFQGSHVP PTFGGGTKLE IK |
| 142 | 123E9-A1 HVR-H1 | DYYMK |
| 143 | 123E9-A1 HVR-H2 | DIDPNNGGTSYNQKFKG |
| 144 | 123E9-A1 HVR-H3 | SAGFGDSFSF |
| 145 | 123E9-A1 HVR-L1 | RSSQSIVHSNGNTYLE |
| 146 | 123E9-A1 HVR-L2 | KVSNRFS |
| 147 | 123E9-A1 HVR-L3 | FQGSHVPPT |
| 150 | 15C6-A7 heavy chain variable region (VH) | EVQLQQSGPE LVKPGASVMM TCKASGYTFT DYYMKWVKQS NGKSLEWIGD LDPYTGGANY NQKFKGKATL TVDKSSSTAY MHLNSLTSED SAVYYCARSR GYGDSFAYWG QGTLVTVSA |
| 151 | 15C6-A7 light chain variable region (VL) | DVLMTQTPLS LPVSLGDQAS ISCRSSQNIV HSNGNTYLEW YLQKPGQSPK LLIYKVSNRF SGVPDKFSGS GSGTDFTLKI SRVEAEDLGV YFCFQGSHVP PTFGGGTKLE IK |
| 152 | 15C6-A7 HVR-H1 | DYYMK |
| 153 | 15C6-A7 HVR-H2 | DLDPYTGGAN YNQKFKG |
| 154 | 15C6-A7 HVR-H3 | SRGYGDSFAY |
| 155 | 15C6-A7 HVR-L1 | RSSQNIVHSN GNTYLE |

Table of Sequences

| SEQ ID NO | Description | Sequence |
|---|---|---|
| 156 | 15C6-A7 HVR-L2 | KVSNRFS |
| 157 | 15C6-A7 HVR-L3 | FQGSHVPPT |
| 160 | 19F8-B1 heavy chain variable region (VH) | EVQLQQSGPE LVKPGASVKM SCKASGYTFT DYYMKWVKQS HGKSLEWIGD LNPNNGGTLY NQKFKGQATL TVDKSSSTAY MQFNSLTSED SAVYYCARSA GYGDSFAYWG QGTLVTVSA |
| 161 | 19F8-B1 light chain variable region (VL) | DVLMTQTPLS LPVSLGDQAS ISCRSSQNIV HSNGNTYLEW YLQKPGQSPK LLIYKVSNRF SGVPDRFSGS GSGTDFTLKI SRVEAEDLGI YFCFQGSHVP PTFGGGTKLE IK |
| 162 | 19F8-B1 HVR-H1 | DYYMK |
| 163 | 19F8-B1 HVR-H2 | DLNPNNGGTL YNQKFKG |
| 164 | 19F8-B1 HVR-H3 | SAGYGDSFAY |
| 165 | 19F8-B1 HVR-L1 | RSSQNIVHSN GNTYLE |
| 166 | 19F8-B1 HVR-L2 | KVSNRFS |
| 167 | 19F8-B1 HVR-L3 | FQGSHVPPT |
| 170 | 24A11-D5 heavy chain variable region (VH) | EVQLQQSGPE LVKPGASVKM SCKASGYTFT DYYMKWVKQS HGKSLEWIGD LNPKNGGIIY NQKFKGQATL TVDKSSSTAY MQLNSLTSED SAVFYCARSG GYGDSFAYWG QGTLVTVSA |
| 171 | 24A11-D5 light chain variable region (VL) | DVLMTQTPLS LPVSLGDQAS ISCRSSQNIV HSNGNTYLEW YLQKPGQSPK LLIYKVSNRF SGVPDRFSGS GSGTDFTLKI SRVEAEDLGI YFCFQGSHVP PTFGGGTKLE IK |
| 172 | 24A11-D5 HVR-H1 | DYYMK |
| 173 | 24A11-D5 HVR-H2 | DLNPKNGGII YNQKFKG |
| 174 | 24A11-D5 HVR-H3 | SGGYGDSFAY |
| 175 | 24A11-D5 HVR-L1 | RSSQNIVHSN GNTYLE |
| 176 | 24A11-D5 HVR-L2 | KVSNRFS |
| 177 | 24A11-D5 HVR-L3 | FQGSHVPPT |
| 180 | 126F11-G11 heavy chain variable region (VH) | EVQLQQSGAE LVRPGASVKL SCTASGFNIK DDYMHWVKQR PEQGLEWIGW IDPENGDTEY ASKFQGKATI TTDTSSNTAY LQLSSLTSED TAVYYCLDFA YGYWGQGTTL TVSS |
| 181 | 126F11-G11 light chain variable region (VL) | DVLMTQTPLS LPVSLGDQAS ISCRSSQSIV HSNGNTYLEW YLQKPGQSPK LLIYKVSNRF SGVPDRFSGS GSGTDFTLKI SRVEAEDLGV YYCFQGSHVP PAFGGGTKLE IK |
| 182 | 126F11-G11 HVR-H1 | DDYMH |
| 183 | 126F11-G11 HVR-H2 | WIDPENGDTE YASKFQG |
| 184 | 126F11-G11 HVR-H3 | FAYGY |
| 185 | 126F11-G11 HVR-L1 | RSSQSIVHSN GNTYLE |
| 186 | 126F11-G11 HVR-L2 | KVSNRFS |
| 187 | 126F11-G11 HVR-L3 | FQGSHVPPA |
| 190 | 89F4-A1 heavy chain variable region (VH) | EVQLVESGGG LVQPKGSLKL SCAASGFTFN TYAMNWVRQA PGKGLEWVAR IRSKSNNYAA YFADSVKDRF TISRDDSQTM LYLQMNNLKS EDTAMYYCVS GGNYVPFAYW GQGTLVTVSA |

| Table of Sequences | | |
|---|---|---|
| SEQ ID NO | Description | Sequence |
| 191 | 89F4-A1 light chain variable region (VL) | NIMMTQSPSS LAVSAGEKVT MSCKSSQSVF YSSEQRNYLA WYQQKPGQSP KLLISWASTR ESGVPDRFTG SGSGTDFTLT ISSVQGEDLA VYYCHQYLSS FTFGSGTKLE IK |
| 192 | 89F4-A1 HVR-H1 | TYAMN |
| 193 | 89F4-A1 HVR-H2 | RIRSKSNNYA AYFADSVKD |
| 194 | 89F4-A1 HVR-H3 | GGNYVPFAY |
| 195 | 89F4-A1 HVR-L1 | KSSQSVFYSS EQRNYLA |
| 196 | 89F4-A1 HVR-L2 | WASTRES |
| 197 | 89F4-A1 HVR-L3 | HQYLSSFT |
| 200 | 93A8-D2 heavy chain variable region (VH) | EVQLQQSGPV LVKPGASVKM SCKASGYTFT DYYVNWVKQS HGKGLEWIGL INPNNGRTSY NQNFNDKATL TVDKSSSTAF MDLNSLTSED SAVYYCTREG GTGYWGQGTT LSVSS |
| 201 | 93A8-D2 light chain variable region (VL) | DVVMTQTPLT LSVTIGQPAS ISCKSSQSLL DSDGKTYLNW LLQRPGQSPR RLIYLVSKLD SGVPDRFTGS GSGTDFTLKI SRVAAEDLGV YYCWQGTHFP RTFGGGTKLE IK |
| 202 | 93A8-D2 HVR-H1 | DYYVN |
| 203 | 93A8-D2 HVR-H2 | LINPNNGRTSYNQNFND |
| 204 | 93A8-D2 HVR-H3 | EGGTGY |
| 205 | 93A8-D2 HVR-L1 | KSSQSLLDSDGKTYLN |
| 206 | 93A8-D2 HVR-L2 | LVSKLDS |
| 207 | 93A8-D2 HVR-L3 | WQGTHFPRT |
| 210 | 14F5-D9 heavy chain variable region (VH) | EVKLVESGGG LVQPGGSLRL SCATSGFTFS DFYMEWVRQS PGKRLEWIAA SKNKANDYTT EYNASVKDRF FVSRDTSQSI LYLQMNALRA EDTAIYYCAR DALGTVFAYW GQGTLVTVSA |
| 211 | 14F5-D9 light chain variable region (VL) | DVVMTQTPLS LPVSLGDQAS ISCRSSQSLV HSNGNTYLHW YLQKPGQSPK LLIYKVFNRF SGVPDRFSGS GSGTDFTLKI SRVEAEDLGV YFCSQSTLVP LTFGAGTKLE LK |
| 212 | 14F5-D9 HVR-H1 | DFYME |
| 213 | 14F5-D9 HVR-H2 | ASKNKANDYT TEYNASVKD |
| 214 | 14F5-D9 HVR-H3 | DALGTVFAY |
| 215 | 14F5-D9 HVR-L1 | RSSQSLVHSN GNTYLH |
| 216 | 14F5-D9 HVR-L2 | KVFNRFS |
| 217 | 14F5-D9 HVR-L3 | SQSTLVPLT |
| 220 | 73H6-B8 heavy chain variable region (VH) | QVQLKESGPG LVAPSQSLSI TCTISGFSLT SYGVHWVRQP PGKGLEWLVV IWSDGSTTYN SALKSRLSIS KDNSKSQVFL KMNSLQTDDT AMYYCARQGG FITTAYYAMD YWGQGTSVTV SS |
| 221 | 73H6-B8 light chain variable region (VL) | DIVMSQSPSS LAVSAGEKVT MSCKSSQSLL NSRTRKNYLA WYQQKPGQSP KLLIYWASTR ESGVPDRFTG SGSGTDFTLT ISSVQAEDLA VYYCKQSYNL YTFGGGTKLE IK |
| 222 | 73H6-B8 HVR-H1 | SYGVH |
| 223 | 73H6-B8 HVR-H2 | VIWSDGSTTY NSALKS |
| 224 | 73H6-B8 HVR-H3 | QGGFITTAYY ANDY |
| 225 | 73H6-B8 HVR-L1 | KSSQSLLNSR TRKNYLA |

-continued

| Table of Sequences | | |
|---|---|---|
| SEQ ID NO | Description | Sequence |
| 226 | 73H6-B8 HVR-L2 | WASTRES |
| 227 | 73H6-B8 HVR-L3 | KQSYNLYT |
| 230 | 22G7-C9 heavy chain variable region (VH) | QIQLVQSGPE LKKPGETVKI SCKASGYTFT DCSIHWVKQA PGEGLKWMGW INTETGEPSY ADDFKGRFAF SLETSASTAF LQINNLKSED TASYFCGTAY YRYDGALDYW GQGTSVTVSS |
| 231 | 22G7-C9 light chain variable region (VL) | DIVLTQSPAS LAVSLGQRAT ISCRASQSVS TSSYSYMHWF QQKPGQPPKL LIKYASNLES GVPARFSGSG SGTDFTLNIH PVEEEDTATY YCQHSWELPW TFGGGTKLEI K |
| 232 | 22G7-C9 HVR-H1 | DCSIH |
| 233 | 22G7-C9 HVR-H2 | WINTETGEPS YADDFKG |
| 234 | 22G7-C9 HVR-H3 | AYYRYDGALD Y |
| 235 | 22G7-C9 HVR-L1 | RASQSVSTSS YSYMH |
| 236 | 22G7-C9 HVR-L2 | YASNLES |
| 237 | 22G7-C9 HVR-L3 | QHSWELPWT |
| 240 | 7A11-C12 heavy chain variable region (VH) | QIQLVQSGPD LKKPGETVKI SCKASGYTFT NYGMNWVKQA PGKGLKWMGW INTNTGEPTY AEEFKGRFAF SLETSASTAY LQIDNLKNED TATYFCARGT VSFPYWGQGT LVTVSA |
| 241 | 7A11-C12 light chain variable region (VL) | DVVMSQTPLS LPVSLGDHAS ISCRSSQNLV HSDGNTYLHW YLQKPGQSPK LLIYKVSNRF SGVPDRFSGS GSGTDFTLKI SRVEAEDLGV YFCSQSTHVI FTFGSGTKLE IK |
| 242 | 7A11-C12 HVR-H1 | NYGMN |
| 243 | 7A11-C12 HVR-H2 | WINTNTGEPT YAEEFKG |
| 244 | 7A11-C12 HVR-H3 | GTVSFPY |
| 245 | 7A11-C12 HVR-L1 | RSSQNLVHSD GNTYLH |
| 246 | 7A11-C12 HVR-L2 | KVSNRFS |
| 247 | 7A11-C12 HVR-L3 | SQSTHVIFT |
| 250 | 12A10-E8 heavy chain variable region (VH) | QIQLVQSGPE LKKPGETVKI SCKASGYTFT NYGMNWVKQA PGKGLKWMGW INMYTGEPTY GDDFKGRFVF SLETSVSTVY LQINNLKKED TATFFCARGG RPDYWGQGTS VTVSS |
| 251 | 12A10-E8 light chain variable region (VL) | DVLMTQTPLS LPVSLGDQAS ISCRSSQSIV HSNGNTYLEW YLQKPGQSPK LLIYKVFNRF SGVPDRFSGS GSGTDFTLKI NRVEAEDLGV YYCLQGSHVP YTFGGGTKLE IK |
| 252 | 12A10-E8 HVR-H1 | NYGMN |
| 253 | 12A10-E8 HVR-H2 | WINMYTGEPT YGDDFKG |
| 254 | 12A10-E8 HVR-H3 | GGRPDY |
| 255 | 12A10-E8 HVR-L1 | RSSQSIVHSN GNTYLE |
| 256 | 12A10-E8 HVR-L2 | KVFNRFS |
| 257 | 12A10-E8 HVR-L3 | LQGSHVPYT |
| 260 | 55E7-F11 heavy chain variable region (VH) | EVKLEESGGG LVQPGGSMKL SCVASGFTFS NYWMNWVRQS PEKGLEWVAQ IRLKSDNYAT HYAESVKGRF TISRDDSKSS VYLQMNNLRA EDTGIYYCAG YFYGGYFDVW GTGTTVTVSS |
| 261 | 55E7-F11 light chain variable region (VL) | ELVLTQSPTT MAASPGKKIT ITCSASSSIS SNYLHWYQQK PGFSPKLLIY RTSNLASGVP ARFSGSGSGT SYSLTIGTME AEDVATYYCQ QGSSLPFTFG SGTKLEIK |
| 262 | 55E7-F11 HVR-H1 | NYWMN |

| SEQ ID NO | Description | Sequence |
|---|---|---|
| 263 | 55E7-F11 HVR-H2 | QIRLKSDNYA THYAESVKG |
| 264 | 55E7-F11 HVR-H3 | YFYGGYFDV |
| 265 | 55E7-F11 HVR-L1 | SASSSISSNY LH |
| 266 | 55E7-F11 HVR-L2 | RTSNLAS |
| 267 | 55E7-F11 HVR-L3 | QQGSSLPFT |
| 270 | 52F6-F11 heavy chain variable region (VH) | QVQLQQSGTE LAKPGASVKL SCKASGYTFT HYWMHWIKQR PGQGLEWIGY IYPTNDYTKY NQNFRDKATL TADESSNSAY MQLNSLTYED SAVYYCARAG NRVFDFWGQG TTLTVSS |
| 271 | 52F6-F11 light chain variable region (VL) | QAVVTQESAL TTSPGETVTL TCRSSTGAVT TSNFANWVQE KPDHLFTGLI GGTNNRAPGV PARFSGSLIG DKAALTITGA QTEDEAIYFC ALWYSNLWVF GGGTKLTVL |
| 272 | 52F6-F11 HVR-H1 | HYWMH |
| 273 | 52F6-F11 HVR-H2 | YIYPTNDYTK YNQNFRD |
| 274 | 52F6-F11 HVR-H3 | AGNRVFDF |
| 275 | 52F6-F11 HVR-L1 | RSSTGAVTTS NFAN |
| 276 | 52F6-F11 HVR-L2 | GTNNRAP |
| 277 | 52F6-F11 HVR-L3 | ALWYSNLWV |
| 280 | Hu37D3-H9.v1 heavy chain variable region (VH) | EVQLVESGGG LVQPGGSLRL SCAASGLIFR SYGMSWVRQA PGKGLEWVAT INSGGTYTYY PDSVKGRFTI SRDNSKNTLY LQMNSLRAED TAVYYCANSY SGAMDYWGQG TLVTVSS |
| 281 | Hu37D3-H9.v1 light chain variable region (VL) | EDQLTQSPSS LSASVGDRVT ITCRSSQSIV HSNGNTYFEW YQQKPGKSPK LLIYKVSNRF SGVPSRFSGS GSGTDFTLTI SSLQPEDFAT YYCFQGSLVP WTFGQGTKVE IK |
| 282 | Hu37D3-H9.v1 HVR-H1 | SYGMS |
| 283 | Hu37D3-H9.v1 HVR-H2 | TINSGGTYTYYPDSVKG |
| 284 | Hu37D3-H9.v1 HVR-H3 | SYSGAMDY |
| 285 | Hu37D3-H9.v1 HVR-L1 | RSSQSIVHSNGNTYFE |
| 286 | Hu37D3-H9.v1 HVR-L2 | KVSNRFS |
| 287 | Hu37D3-H9.v1 HVR-L3 | FQGSLVPWT |
| 288 | Hu37D3-H9.v1 IgG1 heavy chain | EVQLVESGGG LVQPGGSLRL SCAASGLIFR SYGMSWVRQA PGKGLEWVAT INSGGTYTYY PDSVKGRFTI SRDNSKNTLY LQMNSLRAED TAVYYCANSY SGAMDYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 289 | Hu37D3-H9.v1 IgG1 light chain | EDQLTQSPSS LSASVGDRVT ITCRSSQSIV HSNGNTYFEW YQQKPGKSPK LLIYKVSNRF SGVPSRFSGS GSGTDFTLTI SSLQPEDFAT YYCFQGSLVP WTFGQGTKVE IKRTVAAPSV FIFPPSDEQL KSGTASVVCL LNNFYPREAK VQWKVDNALQ |

-continued

| SEQ ID NO | Description | Sequence |
|---|---|---|
| | | SGNSQESVTE QDSKDSTYSL SSTLTLSKAD YEKHKVYACE VTHQGLSSPV TKSFNRGEC |
| 290 | Hu37D3-H9.v5 heavy chain variable region (VH) | EVQLVESGGG LVQPGGSLRL SCAASGLIFR SYGMSWVRQA PGKGLEWVAT INSGGTYTYY PDSVKGRFTI SRDNSKNTLY LQMNSLRAED TAVYYCANSY SGAMDYWGQG TLVTVSS |
| 291 | Hu37D3-H9.v5 light chain variable region (VL) | EDVLTQTPLS LPVTPGQPAS ISCRSSQSIV HSNGNTYFEW YLQKPGQSPQ LLIYKVSNRF SGVPDRFSGS GSGTDFTLKI SRVEAEDVGV YYCFQGSLVP WTFGQGTKVE IK |
| 292 | Hu37D3-H9.v5 HVR-H1 | SYGMS |
| 293 | Hu37D3-H9.v5 HVR-H2 | TINSGGTYTYYPDSVKG |
| 294 | Hu37D3-H9.v5 HVR-H3 | SYSGAMDY |
| 295 | Hu37D3-H9.v5 HVR-L1 | RSSQSIVHSNGNTYFE |
| 296 | Hu37D3-H9.v5 HVR-L2 | KVSNRFS |
| 297 | Hu37D3-H9.v5 HVR-L3 | FQGSLVPWT |
| 300 | Hu94B2.v105 heavy chain variable region (VH) | EVQLVQSGAE VKKPGASVKV SCKASGYSLT GYTMNWVRQA PGQGLEWIGL ISPYNGVTSY NQKFKGRATL TVDKSTSTAY LELSSLRSED TAVYYCARQG AYWGQGTLVT VSS |
| 301 | Hu94B2.v105 light chain variable region (VL) | DIVMTQTPLS LPVTPGQPAS ISCKSSQSLL DSDGKTYLNW LLQKPGQSPQ RLIYLVSKLD SGVPDRFSGS GSGTDFTLKI SRVEAEDVGV YYCWQGTHFP WTFGQGTKVE IK |
| 302 | Hu94B2.v105 HVR-H1 | GYTMN |
| 303 | Hu94B2.v105 HVR-H2 | LISPYNGVTSYNQKFKG |
| 304 | Hu94B2.v105 HVR-H3 | QGAY |
| 305 | Hu94B2.v105 HVR-L1 | KSSQSLLDSDGKTYLN |
| 306 | Hu94B2.v105 HVR-L2 | LVSKLDS |
| 307 | Hu94B2.v105 HVR-L3 | WQGTHFPWT |
| 310 | hu125B11.v17 heavy chain variable region (VH) | EVQLVESGGG LVQPGGSLRL SCAASRFIFS NYWMNWVRQA PGKGLEWVAQ IRLKSDNYAT HYAESVKGRF TISRDDSKNT LYLQMNSLRA EDTAVYYCTG GTTYWGQGTL VTVSS |
| 311 | hu125B11.v17 light chain variable region (VL) | DIQMTQSPSS LSASVGDRVT ITCKASQNVG TAVAWYQQKP GKSPKLLIYS ASIRYTGVPS RFSGSGSGTD FTLTISSLQP EDFATYFCQQ FRTYPYTFGQ GTKVEIK |
| 312 | hu125B11.v17 HVR-H1 | NYWMN |
| 313 | hu125B11.v17 HVR-H2 | QIRLKSDNYATHYAESVKG |
| 314 | hu125B11.v17 HVR-H3 | GTTY |

-continued

| SEQ ID NO | Description | Sequence |
|---|---|---|
| 315 | hu125B11.v17 HVR-L1 | KASQNVGTAVA |
| 316 | hu125B11.v17 HVR-L2 | SASIRYT |
| 317 | hu125B11.v17 HVR-L3 | QQFRTYPYT |
| 320 | hu125B11.v26 heavy chain variable region (VH) | EVQLVESGGG LVQPGGSLRL SCAASRFIFS NYWMNWVRQA PGKGLEWVAQ IRLKSDNYAT HYAESVKGRF TISRDNSKNT LYLQMNSLRA EDTAVYYCTG GTTYWGQGTL VTVSS |
| 321 | hu125B11.v26 light chain variable region (VL) | DIQMTQSPSS LSASVGDRVT ITCKASQNVG TAVAWYQQKP GKAPKLLIYS ASIRYTGVPS RFSGSGSGTD FTLTISSLQP EDFATYFCQQ FRTYPYTFGQ GTKVEIK |
| 322 | hu125B11.v26 HVR-H1 | NYWMN |
| 323 | hu125B11.v26 HVR-H2 | QIRLKSDNYATHYAESVKG |
| 324 | hu125B11.v26 HVR-H3 | GTTY |
| 325 | hu125B11.v26 HVR-L1 | KASQNVGTAVA |
| 326 | hu125B11.v26 HVR-L2 | SASIRYT |
| 327 | hu125B11.v26 HVR-L3 | QQFRTYPYT |
| 330 | hu125B11.v28 heavy chain variable region (VH) | EVQLVESGGG LVQPGGSLRL SCAASRFIFS NYWMNWVRQA PGKGLEWVAQ IRLKSDNYAT HYAESVKGRF TISRDNSKNT LYLQMNSLRA EDTAVYYCTG GTTYWGQGTL VTVSS |
| 331 | hu125B11.v28 light chain variable region (VL) | DIQMTQSPSS LSASVGDRVT ITCKASQNVG TAVAWYQQKP GKAPKLLIYS ASIRYTGVPS RFSGSGSGTD FTLTISSLQP EDFATYYCQQ FRTYPYTFGQ GTKVEIK |
| 332 | hu125B11.v28 HVR-H1 | NYWMN |
| 333 | hu125B11.v28 HVR-H2 | QIRLKSDNYATHYAESVKG |
| 334 | hu125B11.v28 HVR-H3 | GTTY |
| 335 | hu125B11.v28 HVR-L1 | KASQNVGTAVA |
| 336 | hu125B11.v28 HVR-L2 | SASIRYT |
| 337 | hu125B11.v28 HVR-L3 | QQFRTYPYT |
| 340 | Hu37D3-H9.v28.A4 heavy chain variable region (VH) | EVQLVESGGG LVQPGGSLRL SCAASGLIFR SYGMSWVRQA PGKGLEWVAT INSGGTYTYY PDSVKGRFTI SRDNSKNTLY LQMNSLRAED TAVYYCANSY SGAMDYWGQG TLVTVSS |
| 341 | Hu37D3-H9.v28.A4 light chain variable region (VL) | DDVLTQTPLS LPVTPGQPAS ISCRSSQSIV HSNGNTYLEW YLQKPGQSPQ LLIYKVSNRF SGVPDRFSGS GSGTDFTLKI SRVEAEDVGV YYCFQGSLVP WTFGQGTKVE IK |

Table of Sequences

| SEQ ID NO | Description | Sequence |
|---|---|---|
| 342 | Hu37D3-H9.v28.A4 HVR-H1 | SYGMS |
| 343 | Hu37D3-H9.v28.A4 HVR-H2 | TINSGGTYTYYPDSVKG |
| 344 | Hu37D3-H9.v28.A4 HVR-H3 | SYSGAMDY |
| 345 | Hu37D3-H9.v28.A4 HVR-L1 | RSSQSIVHSNGNTYLE |
| 346 | Hu37D3-H9.v28.A4 HVR-L2 | KVSNRFS |
| 347 | Hu37D3-H9.v28.A4 HVR-L3 | FQGSLVPWT |
| 348 | Hu37D3-H9.v28.A4 IgG4-S228P.YTE heavy chain | EVQLVESGGG LVQPGGSLRL SCAASGLIFR SYGMSWVRQA PGKGLEWVAT INSGGTYTYY PDSVKGRFTI SRDNSKNTLY LQMNSLRAED TAVYYCANSY SGAMDYWGQG TLVTVSSAST KGPSVFPLAP CSRSTSESTA ALGCLVKDYF PEPVTVSWNS GALTSGVHTF PAVLQSSGLY SLSSVVTVPS SSLGTKTYTC NVDHKPSNTK VDKRVESKYG PPCPPCPAPE FLGGPSVFLF PPKPKDTLYI TREPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV SLTCLVKGFY PSDIAVEWES NGQPENNYKT TPPVLDSDGS FFLYSRLTVD KSRWQEGNVF SCSVMHEALH NHYTQKSLSL SLGK |
| 602 | Hu37D3-H9.v28.A4 IgG4-S228P.YTE des-K heavy chain | EVQLVESGGG LVQPGGSLRL SCAASGLIFR SYGMSWVRQA PGKGLEWVAT INSGGTYTYY PDSVKGRFTI SRDNSKNTLY LQMNSLRAED TAVYYCANSY SGAMDYWGQG TLVTVSSAST KGPSVFPLAP CSRSTSESTA ALGCLVKDYF PEPVTVSWNS GALTSGVHTF PAVLQSSGLY SLSSVVTVPS SSLGTKTYTC NVDHKPSNTK VDKRVESKYG PPCPPCPAPE FLGGPSVFLF PPKPKDTLYI TREPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV SLTCLVKGFY PSDIAVEWES NGQPENNYKT TPPVLDSDGS FFLYSRLTVD KSRWQEGNVF SCSVMHEALH NHYTQKSLSL SLG |
| 349 | Hu37D3-H9.v28.A4 IgG4-S228P.YTE light chain | DDVLTQTPLS LPVTPGQPAS ISCRSSQSIV HSNGNTYLEW YLQKPGQSPQ LLIYKVSNRF SGVPDRFSGS GSGTDFTLKI SRVEAEDVGV YYCFQGSLVP WTFGQGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 442 | hu125B11-H3.LC1 | DIQMTQSPSS LSASVGDRVT ITCKASQNVG TAVAWYQQKP GKSPKLLIYS ASIRYTGVPS RFSGSGSGTD FTLTISSLQP EDFATYFCQQ FRTYPYTFGQ GTKVEIK |
| 443 | hu125B11-H3.LC2 | DIQMTQSPSS LSASVGDRVT ITCKASQNVG TAVAWYQQKP GKAPKLLIYS ASIRYTGVPS RFSGSGSGTD FTLTISSLQP EDFATYFCQQ FRTYPYTFGQ GTKVEIK |
| 444 | hu125B11-H3.LC3 | DIQMTQSPSS LSASVGDRVT ITCKASQNVG TAVAWYQQKP GKSPKLLIYS ASIRYTGVPS RFSGSGSGTD FTLTISSLQP EDFATYYCQQ FRTYPYTFGQ GTKVEIK |
| 445 | hu125B11-H3.LC4 | DIQMTQSPSS LSASVGDRVT ITCKASQNVG TAVAWYQQKP GKAPKLLIYS ASIRYTGVPS RFSGSGSGTD FTLTISSLQP EDFATYYCQQ FRTYPYTFGQ GTKVEIK |
| 446 | hu125B11-H3.HC1 | EVQLVESGGG LVQPGGSLRL SCAASRFIFS NYWMNWVRQA PGKGLEWVAQ IRLKSDNYAT HYAESVKGRF TISRDDSKNT VYLQMNSLRA EDTAVYYCTG GTTYWGQGTL VTVSS |
| 447 | hu125B11-H3.HC2 | EVQLVESGGG LVQPGGSLRL SCAASRFIFS NYWMNWVRQA PGKGLEWVAQ IRLKSDNYAT HYAESVKGRF TISRDNSKNT VYLQMNSLRA EDTAVYYCTG GTTYWGQGTL VTVSS |

Table of Sequences

| SEQ ID NO | Description | Sequence |
|---|---|---|
| 448 | hu125B11-H3.HC3 | EVQLVESGGG LVQPGGSLRL SCAASRFIFS NYWMNWVRQA PGKGLEWVAQ IRLKSDNYAT HYAESVKGRF TISRDDSKNT LYLQMNSLRA EDTAVYYCTG GTTYWGQGTL VTVSS |
| 449 | hu125B11-H3.HC4 | EVQLVESGGG LVQPGGSLRL SCAASRFIFS NYWMNWVRQA PGKGLEWVAQ IRLKSDNYAT HYAESVKGRF TISRDNSKNT LYLQMNSLRA EDTAVYYCTG GTTYWGQGTL VTVSS |
| 450 | hu125B11-H3.HC5 | EVQLVESGGG LVQPGGSLRL SCAASRFIFS NYYMNWVRQA PGKGLEWVAQ IRLKSDNYAT HYAESVKGRF TISRDDSKNT VYLQMNSLRA EDTAVYYCTG GTTYWGQGTL VTVSS |
| 451 | hu125B11-H3.HC6 | EVQLVESGGG LVQPGGSLRL SCAASRFIFS NYFMNWVRQA PGKGLEWVAQ IRLKSDNYAT HYAESVKGRF TISRDDSKNT VYLQMNSLRA EDTAVYYCTG GTTYWGQGTL VTVSS |
| 452 | Hu94B2.HC1 | EVQLVQSGAE VKKPGASVKV SCKASGYSLT GYTMNWVRQA PGQGLEWIGL ISPYNGVTSY NQKFKGRATL TVDKSTSTAY LELSSLRSED TAVYYCARQG AYWGQGTLVT VSS |
| 453 | Hu94B2.HC2 | EVQLVQSGAE VKKPGASVKV SCKASGYSLT GYTMNWVRQA PGQGLEWIGL ISPYNGVTSY NQKFKGRVTL TVDKSTSTAY LELSSLRSED TAVYYCARQG AYWGQGTLVT VSS |
| 454 | Hu94B2.HC3 | EVQLVQSGAE VKKPGASVKV SCKASGYSLT GYTMNWVRQA PGQGLEWIGL ISPYNGVTSY NQKFKGRATI TVDKSTSTAY LELSSLRSED TAVYYCARQG AYWGQGTLVT VSS |
| 455 | Hu94B2.HC4 | EVQLVQSGAE VKKPGASVKV SCKASGYSLT GYTMNWVRQA PGQGLEWIGL ISPYNGVTSY NQKFKGRATL TRDKSTSTAY LELSSLRSED TAVYYCARQG AYWGQGTLVT VSS |
| 456 | Hu94B2.HC5 | EVQLVQSGAE VKKPGASVKV SCKASGYSLT GYTMNWVRQA PGQGLEWIGL ISPYNGVTSY NQKFKGRATL TVDTSTSTAY LELSSLRSED TAVYYCARQG AYWGQGTLVT VSS |
| 457 | Hu94B2.HC6 | EVQLVQSGAE VKKPGASVKV SCKASGYSLT GYTMNWVRQA PGQGLEWIGL ISPYNGVTSY NQKFKGRVTI TVDKSTSTAY LELSSLRSED TAVYYCARQG AYWGQGTLVT VSS |
| 458 | Hu94B2.HC7 | EVQLVQSGAE VKKPGASVKV SCKASGYSLT GYTMNWVRQA PGQGLEWIGL ISPYNGVTSY NQKFKGRVTI TRDKSTSTAY LELSSLRSED TAVYYCARQG AYWGQGTLVT VSS |
| 459 | Hu94B2.HC8 | EVQLVQSGAE VKKPGASVKV SCKASGYSLT GYTMNWVRQA PGQGLEWIGL ISPYNGVTSY NQKFKGRVTI TVDTSTSTAY LELSSLRSED TAVYYCARQG AYWGQGTLVT VSS |
| 460 | Hu94B2.LC9 | DVVMTQTPLS LPVTPGQPAS ISCKSSQSLL DSDGKTYLNW LLQKPGQSPQ RLIYLVSKLD SGVPDRFSGS GSGTDFTLKI SRVEAEDVGV YYCWQGTHFP WTFGQGTKVE IK |
| 461 | Hu94B2.LC10 | DVVMTQTPLS LPVTPGQPAS ISCKSSQSLL DSDGKTYLNW LLQKPGQSPQ LLIYLVSKLD SGVPDRFSGS GSGTDFTLKI SRVEAEDVGV YYCWQGTHFP WTFGQGTKVE IK |
| 462 | Hu94B2.LC11 | DVVMTQTPLS LPVTPGQPAS ISCKSSQSLL DSDGKTYLNW YLQKPGQSPQ RLIYLVSKLD SGVPDRFSGS GSGTDFTLKI SRVEAEDVGV YYCWQGTHFP WTFGQGTKVE IK |
| 463 | Hu94B2.LC12 | DVVMTQTPLS LPVTPGQPAS ISCKSSQSLL DSDGKTYLNW YLQKPGQSPQ LLIYLVSKLD SGVPDRFSGS GSGTDFTLKI SRVEAEDVGV YYCWQGTHFP WTFGQGTKVE IK |
| 464 | Hu94B2.LC13 | DIVMTQTPLS LPVTPGQPAS ISCKSSQSLL DSDGKTYLNW LLQKPGQSPQ RLIYLVSKLD SGVPDRFSGS GSGTDFTLKI SRVEAEDVGV YYCWQGTHFP WTFGQGTKVE IK |
| 465 | Hu94B2.LC14 | DIVMTQTPLS LPVTPGQPAS ISCKSSQSLL DSDGKTYLNW LLQKPGQSPQ LLIYLVSKLD SGVPDRFSGS GSGTDFTLKI SRVEAEDVGV YYCWQGTHFP WTFGQGTKVE IK |

| SEQ ID NO | Description | Sequence |
|---|---|---|
| 466 | Hu94B2.LC15 | DIVMTQTPLS LPVTPGQPAS ISCKSSQSLL DSDGKTYLNW YLQKPGQSPQ RLIYLVSKLD SGVPDRFSGS GSGTDFTLKI SRVEAEDVGV YYCWQGTHFP WTFGQGTKVE IK |
| 467 | Hu94B2.LC16 | DIVMTQTPLS LPVTPGQPAS ISCKSSQSLL DSDGKTYLNW YLQKPGQSPQ LLIYLVSKLD SGVPDRFSGS GSGTDFTLKI SRVEAEDVGV YYCWQGTHFP WTFGQGTKVE IK |
| 468 | Hu37D3-H9.v5.1 HVR-L1 | RSSQSIVHSNANTYFE |
| 469 | Hu37D3-H9.v5.2 HVR-L1 | RSSQSIVHSSGNTYFE |
| 470 | Hu37D3-H9.v5.3 HVR-L1 | RSSQSIVHSDGNTYFE |
| 471 | Hu37D3-H9.v5.4 HVR-L1 | RSSQSIVHSQGNTYFE |
| 472 | Hu37D3-H9.v5.5 HVR-L1 | RSSQSIVHSEGNTYFE |
| 473 | Hu37D3-H9.v5.6 HVR-L1 | RSSQSIVHSAGNTYFE |
| 474 | Hu37D3-H9.v5.7 HVR-L1 | RSSQSIVHSNGDTYFE |
| 475 | Hu37D3-H9.v5.8 HVR-L1 | RSSQSIVHSNGQTYFE |
| 476 | Hu37D3-H9.v5.9 HVR-L1 | RSSQSIVHSNGETYFE |
| 477 | Hu37D3-H9.v5.10 HVR-L1 | RSSQSIVHSNGATYFE |
| 478 | Hu37D3-H9.v5.11 HVR-L1 | RSSQSIVHSNGSTYFE |
| 479 | Hu37D3.v28 HVR-L1 | RSSQSIVHSNGNTYFE |
| 480 | Hu37D3.v28.A2 HVR-L1 | RSSQSIVHSNGNTYFE |
| 481 | Hu37D3.v28.A4 HVR-L1 | RSSQSIVHSNGNTYLE |
| 482 | Hu37D3.v28.A6 HVR-L1 | RSSQSIVHSNGNTYLE |
| 483 | Hu37D3.v28.A8 HVR-L1 | RSSQSIVHSNGNTYFE |
| 484 | Hu37D3.v28.A10 HVR-L1 | RSSQSIVHSNGNTYFE |
| 485 | Hu37D3.v28.A12 HVR-L1 | RSSQSIVHSNGNTYLE |
| 486 | Hu37D3.v28.A14 HVR-L1 | RSSQSIVHSNGNTYLE |
| 487 | Hu37D3.v28.A16 HVR-L1 | RSSQSIVHSNGNTYFE |
| 488 | Hu37D3.v28.A18 HVR-L1 | RSSQSIVHSNGNTYFE |
| 489 | Hu37D3.v28.A20 HVR-L1 | RSSQSIVHSNGNTYLE |

-continued

| SEQ ID NO | Description | Sequence |
|---|---|---|
| 490 | Hu37D3.v28.A22 HVR-L1 | RSSQSIVHSNGNTYLE |
| 491 | Hu37D3.v28.A24 HVR-L1 | RSSQSIVHSNGNTYFE |
| 492 | Hu37D3.v28.A26 HVR-L1 | RSSQSIVHSNGNTYFE |
| 493 | Hu37D3.v28.A28 HVR-L1 | RSSQSIVHSNGNTYLE |
| 494 | Hu37D3.v28.A30 HVR-L1 | RSSQSIVHSNGNTYLE |
| 495 | Hu37D3.v28.B1 HVR-L1 | RSSQSIVHSIGNTFFE |
| 496 | Hu37D3.v28.B2 HVR-L1 | RSSQSIVHSMGNTFFE |
| 497 | Hu37D3.v28.B3 HVR-L1 | RSSQSIVHSQGNTWFE |
| 498 | Hu37D3.v28.B4 HVR-L1 | RSSQSIVHSQGNTHFE |
| 499 | Hu37D3.v28.B6 HVR-L1 | RSSQSIVHSDGNTRFE |
| 500 | Hu37D3.v28.B7 HVR-L1 | RSSQSIVHSDGNTKFE |
| 501 | Hu37D3.v28.B8 HVR-L1 | RSSQSIVHSEGNTRFE |
| 502 | Hu37D3.v28.C1 HVR-L1 | RSSQSIVHSNNNTYFE |
| 503 | Hu37D3.v28.C2 HVR-L1 | RSSQSIVHSNDNTYFE |
| 504 | Hu37D3.v28.D1 HVR-L1 | RSSQSIVHANGNTYFE |
| 505 | Hu37D3.v28.E1 HVR-L1 | RSSQSIVNSNGNTYFE |
| 506 | Hu37D3.v28.E2 HVR-L1 | RSSQSIVQSNGNTYFE |
| 507 | Hu37D3.v28.E3 HVR-L1 | RSSQSIVDSDGNTYFE |
| 508 | Hu37D3.v28.F1 HVR-L1 | RSSQSIVHSNTNTYFE |
| 509 | Hu37D3.v28.F2 HVR-L1 | RSSQSIVHTNGNTYFE |
| 510 | Hu37D3.v28.F3 HVR-L1 | RSSQSIVHTNANTYFE |
| 511 | Hu37D3.v28.51 HVR-L1 | RSSQSIVHSHGNTYFE |
| 512 | Hu37D3.v28.52 HVR-L1 | RSSQSIVHSKGNTYFE |
| 513 | Hu37D3.v28.53 HVR-L1 | RSSQSIVHSRGNTYFE |

-continued

Table of Sequences

| SEQ ID NO | Description | Sequence |
|---|---|---|
| 514 | Hu37D3.v28.54 HVR-L1 | RSSQSIVHSLGNTYFE |
| 515 | Hu37D3.v28.55 HVR-L1 | RSSQSIVHSNQNTYFE |
| 516 | Hu37D3.v28.56 HVR-L1 | RSSQSIVHSNYNTYFE |
| 517 | Hu37D3.v28.57 HVR-L1 | RSSQSIVHSNFNTYFE |
| 518 | Hu37D3.v29.1 HVR-L1 | RSSQSIVHSNGDTYFE |
| 519 | Hu37D3.v29.2 HVR-L1 | RSSQSIVHSNGQTYFE |
| 520 | Hu37D3.v29.3 HVR-L1 | RSSQSIVHSNGETYFE |
| 521 | Hu37D3.v29.4 HVR-L1 | RSSQSIVHSNGATYFE |
| 522 | Hu37D3.v29.5 HVR-L1 | RSSQSIVHSNGHTYFE |
| 523 | Hu37D3.v29.6 HVR-L1 | RSSQSIVHSNGKTYFE |
| 524 | Hu37D3.v29.7 HVR-L1 | RSSQSIVHSNGLTYFE |
| 525 | Hu37D3.v29.8 HVR-L1 | RSSQSIVHSNADTYFE |
| 526 | Hu37D3.v29.9 HVR-L1 | RSSQSIVHSNAQTYFE |
| 527 | Hu37D3.v29.10 HVR-L1 | RSSQSIVHSNAETYFE |
| 528 | Hu37D3.v29.11 HVR-L1 | RSSQSIVHSNAATYFE |
| 529 | Hu37D3.v29.12 HVR-L1 | RSSQSIVHSNAHTYFE |
| 530 | Hu37D3.v29.13 HVR-L1 | RSSQSIVHSNAKTYFE |
| 531 | Hu37D3.v29.14 HVR-L1 | RSSQSIVHSNALTYFE |
| 532 | Hu37D3-H9.v30.1 HVR-L1 | RSSQSIVHSGGNTYFE |
| 533 | Hu37D3-H9.v30.2 HVR-L1 | RSSQSIVHSTGNTYFE |
| 534 | Hu37D3-H9.v30.3 HVR-L1 | RSSQSIVHSVGNTYFE |
| 535 | Hu37D3-H9.v30.4 HVR-L1 | RSSQSIVHSLGNTYFE |
| 536 | Hu37D3-H9.v30.5 HVR-L1 | RSSQSIVHSIGNTYFE |
| 537 | Hu37D3-H9.v30.6 HVR-L1 | RSSQSIVHSPGNTYFE |

-continued

| SEQ ID NO | Description | Sequence |
|---|---|---|
| 538 | Hu37D3-H9.v30.7 HVR-L1 | RSSQSIVHSFGNTYFE |
| 539 | Hu37D3-H9.v30.8 HVR-L1 | RSSQSIVHSYGNTYFE |
| 540 | Hu37D3-H9.v30.9 HVR-L1 | RSSQSIVHSHGNTYFE |
| 541 | Hu37D3-H9.v30.10 HVR-L1 | RSSQSIVHSKGNTYFE |
| 542 | Hu37D3-H9.v30.11 HVR-L1 | RSSQSIVHSRGNTYFE |
| 543 | Hu37D3-H9.v31.1 HVR-L1 | RSSQSIVHSNAGTYFE |
| 544 | Hu37D3-H9.v31.2 HVR-L1 | RSSQSIVHSNAVTYFE |
| 545 | Hu37D3-H9.v31.3 HVR-L1 | RSSQSIVHSNAITYFE |
| 546 | Hu37D3-H9.v31.4 HVR-L1 | RSSQSIVHSNAPTYFE |
| 547 | Hu37D3-H9.v31.5 HVR-L1 | RSSQSIVHSNAFTYFE |
| 548 | Hu37D3-H9.v31.6 HVR-L1 | RSSQSIVHSNAYTYFE |
| 549 | Hu37D3-H9.v31.7 HVR-L1 | RSSQSIVHSNARTYFE |
| 550 | Hu37D3-H9.v31.8 HVR-L1 | RSSQSIVHSNANVYFE |
| 551 | Hu37D3-H9.v31.9 HVR-L1 | RSSQSIVHSNANIYFE |
| 552 | Hu37D3-H9.v31.10 HVR-L1 | RSSQSIVHSNANPYFE |
| 553 | Hu37D3-H9.v31.11 HVR-L1 | RSSQSIVHSNANFYFE |
| 554 | Hu37D3-H9.v31.12 HVR-L1 | RSSQSIVHSNANYYFE |
| 555 | Hu37D3-H9.v31.13 HVR-L1 | RSSQSIVHSNANNYFE |
| 556 | Hu37D3-H9.v31.14 HVR-L1 | RSSQSIVHSNANRYFE |
| 557 | Human Tau 7-24 peptide | EFEVMEDHAGTYGLGDRK |
| 558 | Human Tau 7-20 peptide | EFEVMEDHAGTYGL |
| 560 | Hu37D3.v39 heavy chain variable region (VH) | EVQLVESGGG LVQPGGSLRL SCAASGLIFR SYGMSWVRQA PGKGLEWVAT INSGGTYTYY PDSVKGRFTI SRDNSKNTLY LQMNSLRAED TAVYYCANSY SGAMDYWGQG TLVTVSS |
| 561 | Hu37D3.v39 light chain variable region (VL) | EDQLTQSPSS LSASVGDRVT ITCRSSQSIV HSNGNTYLEW YQQKPGKSPK LLIYKVSNRF SGVPSRFSGS GSGTDFTLTI SSLQPEDFAT YYCFQGSLVP WTFGQGTKVE IK |

| SEQ ID NO | Description | Sequence |
|---|---|---|
| 562 | Hu37D3.v39 HVR-H1 | SYGMS |
| 563 | Hu37D3.v39 HVR-H2 | TINSGGTYTYYPDSVKG |
| 564 | Hu37D3.v39 HVR-H3 | SYSGAMDY |
| 565 | Hu37D3.v39 HVR-L1 | RSSQSIVHSNGNTYLE |
| 566 | Hu37D3.v39 HVR-L2 | KVSNRFS |
| 567 | Hu37D3.v39 HVR-L3 | FQGSLVPWT |
| 568 | Hu37D3.v39 IgG4-S228P.YTE heavy chain | EVQLVESGGG LVQPGGSLRL SCAASGLIFR SYGMSWVRQA PGKGLEWVAT INSGGTYTYY PDSVKGRFTI SRDNSKNTLY LQMNSLRAED TAVYYCANSY SGAMDYWGQG TLVTVSSAST KGPSVFPLAP CSRSTSESTA ALGCLVKDYF PEPVTVSWNS GALTSGVHTF PAVLQSSGLY SLSSVVTVPS SSLGTKTYTC NVDHKPSNTK VDKRVESKYG PPCPPCPAPE FLGGPSVFLF PPKPKDTLYI TREPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV SLTCLVKGFY PSDIAVEWES NGQPENNYKT TPPVLDSDGS FFLYSRLTVD KSRWQEGNVF SCSVMHEALH NHYTQKSLSL SLGK |
| 569 | Hu37D3.v39 IgG4-S228P.YTE light chain | EDQLTQSPSS LSASVGDRVT ITCRSSQSIV HSNGNTYLEW YQQKPGKSPK LLIYKVSNRF SGVPSRFSGS GSGTDFTLTI SSLQPEDFAT YYCFQGSLVP WTFGQGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 570 | Hu37D3.v40 heavy chain variable region (VH) | EVQLVESGGG LVQPGGSLRL SCAASGLIFR SYGMSWVRQA PGKGLEWVAT INSGGTYTYY PDSVKGRFTI SRDNSKNTLY LQMNSLRAED TAVYYCANSY SGAMDYWGQG TLVTVSS |
| 571 | Hu37D3.v40 light chain variable region (VL) | EDQLTQSPSS LSASVGDRVT ITCRSSQSIV HSNTNTYFEW YQQKPGKSPK LLIYKVSNRF SGVPSRFSGS GSGTDFTLTI SSLQPEDFAT YYCFQGSLVP WTFGQGTKVE IK |
| 572 | Hu37D3.v40 HVR-H1 | SYGMS |
| 573 | Hu37D3.v40 HVR-H2 | TINSGGTYTYYPDSVKG |
| 574 | Hu37D3.v40 HVR-H3 | SYSGAMDY |
| 575 | Hu37D3.v40 HVR-L1 | RSSQSIVHSNTNTYFE |
| 576 | Hu37D3.v40 HVR-L2 | KVSNRFS |
| 577 | Hu37D3.v40 HVR-L3 | FQGSLVPWT |
| 578 | Hu37D3.v40 IgG4-S228P.YTE heavy chain | EVQLVESGGG LVQPGGSLRL SCAASGLIFR SYGMSWVRQA PGKGLEWVAT INSGGTYTYY PDSVKGRFTI SRDNSKNTLY LQMNSLRAED TAVYYCANSY SGAMDYWGQG TLVTVSSAST KGPSVFPLAP CSRSTSESTA ALGCLVKDYF PEPVTVSWNS GALTSGVHTF PAVLQSSGLY SLSSVVTVPS SSLGTKTYTC NVDHKPSNTK VDKRVESKYG PPCPPCPAPE FLGGPSVFLF PPKPKDTLYI TREPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV |

| SEQ ID NO | Description | Sequence |
|---|---|---|
| | | SLTCLVKGFY PSDIAVEWES NGQPENNYKT TPPVLDSDGS FFLYSRLTVD KSRWQEGNVF SCSVMHEALH NHYTQKSLSL SLGK |
| 579 | Hu37D3.v40 IgG4-S228P.YTE light chain | EDQLTQSPSS LSASVGDRVT ITCRSSQSIV HSNTNTYFEW YQQKPGKSPK LLIYKVSNRF SGVPSRFSGS GSGTDFTLTI SSLQPEDFAT YYCFQGSLVP WTFGQGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 580 | Hu37D3.v41 heavy chain variable region (VH) | EVQLVESGGG LVQPGGSLRL SCAASGLIFR SYGMSWVRQA PGKGLEWVAT INSGGTYTYY PDSVKGRFTI SRDNSKNTLY LQMNSLRAED TAVYYCANSY SGAMDYWGQG TLVTVSS |
| 581 | Hu37D3.v41 light chain variable region (VL) | EDQLTQSPSS LSASVGDRVT ITCRSSQSIV HSNGQTYFEW YQQKPGKSPK LLIYKVSNRF SGVPSRFSGS GSGTDFTLTI SSLQPEDFAT YYCFQGSLVP WTFGQGTKVE IK |
| 582 | Hu37D3.v41 HVR-H1 | SYGMS |
| 583 | Hu37D3.v41 HVR-H2 | TINSGGTYTYYPDSVKG |
| 584 | Hu37D3.v41 HVR-H3 | SYSGAMDY |
| 585 | Hu37D3.v41 HVR-L1 | RSSQSIVHSNGQTYFE |
| 586 | Hu37D3.v41 HVR-L2 | KVSNRFS |
| 587 | Hu37D3.v41 HVR-L3 | FQGSLVPWT |
| 588 | Hu37D3.v41 IgG4-S228P.YTE heavy chain | EVQLVESGGG LVQPGGSLRL SCAASGLIFR SYGMSWVRQA PGKGLEWVAT INSGGTYTYY PDSVKGRFTI SRDNSKNTLY LQMNSLRAED TAVYYCANSY SGAMDYWGQG TLVTVSSAST KGPSVFPLAP CSRSTSESTA ALGCLVKDYF PEPVTVSWNS GALTSGVHTF PAVLQSSGLY SLSSVVTVPS SSLGTKTYTC NVDHKPSNTK VDKRVESKYG PPCPPCPAPE FLGGPSVFLF PPKPKDTLYI TREPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV SLTCLVKGFY PSDIAVEWES NGQPENNYKT TPPVLDSDGS FFLYSRLTVD KSRWQEGNVF SCSVMHEALH NHYTQKSLSL SLGK |
| 589 | Hu37D3.v41 IgG4-S228P.YTE light chain | EDQLTQSPSS LSASVGDRVT ITCRSSQSIV HSNGQTYFEW YQQKPGKSPK LLIYKVSNRF SGVPSRFSGS GSGTDFTLTI SSLQPEDFAT YYCFQGSLVP WTFGQGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 590 | Hu37D3-H9.v1 IgG4-S228P heavy chain | EVQLVESGGG LVQPGGSLRL SCAASGLIFR SYGMSWVRQA PGKGLEWVAT INSGGTYTYY PDSVKGRFTI SRDNSKNTLY LQMNSLRAED TAVYYCANSY SGAMDYWGQG TLVTVSSAST KGPSVFPLAP CSRSTSESTA ALGCLVKDYF PEPVTVSWNS GALTSGVHTF PAVLQSSGLY SLSSVVTVPS SSLGTKTYTC NVDHKPSNTK VDKRVESKYG PPCPPCPAPE FLGGPSVFLF PPKPKDTLMI SRTPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV SLTCLVKGFY PSDIAVEWES NGQPENNYKT TPPVLDSDGS FFLYSRLTVD KSRWQEGNVF SCSVMHEALH NHYTQKSLSL SLGK |
| 591 | Hu37D3-H9.v1 IgG4 light chain | EDQLTQSPSS LSASVGDRVT ITCRSSQSIV HSNGNTYFEW YQQKPGKSPK LLIYKVSNRF SGVPSRFSGS GSGTDFTLTI SSLQPEDFAT YYCFQGSLVP WTFGQGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |

Table of Sequences

| SEQ ID NO | Description | Sequence |
|---|---|---|
| 592 | MAPT(10-24) | VMEDHAGTYGLGDRK |
| 593 | MAPT(2-24) | AEPRQEFEVMEDHAGTYGLGDRK |
| 594 | MAPT(2-34) | AEPRQEFEVMEDHAGTYGLGDRKDQGGYTMHQD |
| 595 | MAPT(10-44) | VMEDHAGTYGLGDRKDQGGYTMHQDQEGDTDAGLK |
| 596 | MAPT(2-24)Y18A | AEPRQEFEVMEDHAGTAGLGDRK |
| 597 | MAPT(2-24)L20A | AEPRQEFEVMEDHAGTYGAGDRK |
| 598 | hu113F5-F7.LC1 | DIQMTQSPSS LSASVGDRVT ITCKASQNVG TAVAWYQQKP GKSPKLLIYS ASRRFSGVPS RFSGSGSGTD FTLTISSLQP EDFATYFCQQ FSTYPYTFGQ GTKVEIK |
| 599 | hu113F5-F7.LC2 | DIQMTQSPSS LSASVGDRVT ITCKASQNVG TAVAWYQQKP GKAPKLLIYS ASRRFSGVPS RFSGSGSGTD FTLTISSLQP EDFATYFCQQ FSTYPYTFGQ GTKVEIK |
| 600 | hu113F5-F7.LC3 | DIQMTQSPSS LSASVGDRVT ITCKASQNVG TAVAWYQQKP GKSPKLLIYS ASRRFSGVPS RFSGSGSGTD FTLTISSLQP EDFATYYCQQ FSTYPYTFGQ GTKVEIK |
| 601 | hu113F5-F7.LC4 | DIQMTQSPSS LSASVGDRVT ITCKASQNVG TAVAWYQQKP GKAPKLLIYS ASRRFSGVPS RFSGSGSGTD FTLTISSLQP EDFATYYCQQ FSTYPYTFGQ GTKVEIK |
| 603 | 231G3F10 Heavy Chain Variable Region | EVRLVESGGG LVQPKGSLKL SCAASGFSFN TYAMNWVRQA PGKGLEWVAR IRSKRNNFAT YYADSVKDRF TISRDDSKSM LYLQMNNLKT EDTAMYYCVR WGYDDPYAMD YWGQGTSVTV SS |
| 604 | 231G3F10 Light Chain Variable Region | NIMMTQSPSS LAVSAGEKVT MSCKSSQSVL YSSNQKNYLA WYQQKPGQSP KLLIYWASAR ESGVPDRFTG SGSGTDFTLT ISSVQAEDLA VYYCHQYFSS FTFGSGTKLE IK |
| 605 | 231G3F10 HVR-H1 | TYAMN |
| 606 | 231G3F10 HVR-H2 | RIRSKRNNFATYYADSVKD |
| 607 | 231G3F10 HVR-H3 | WGYDDPYAMDY |
| 608 | 231G3F10 HVR-L1 | KSSQSVLYSSNQKNYLA |
| 609 | 231G3F10 HVR-L2 | WASAREs |
| 610 | 231G3F10 HVR-L3 | HQYFSSFT |
| 611 | 30A1C9 Heavy Chain Variable Region | GVQLQQSGPE LVKPGASVKI SCKTSGYTFT EYTMHWMKQS HGKSLEWIGG IDPNTGNTNY NQKFKGKATL TVDKSSSTAY MDLRSLTSED SAVYYFYGSG YWGQGTILTV SS |
| 612 | 30A1C9 Light Chain Variable Region | DVLMTQSPLS LPVSLGDQAS ISCRSSQSIV HSNGNTYLEW FLQKPGQSPK LLIYKVSNRF SGVPDRFSGS GSGTDFTLKI SRVEAEDLGV YYCFQASHVP RTFGGGTKLE IK |
| 613 | 30A1C9 HVR-H1 | EYTMH |
| 614 | 30A1C9 HVR-H2 | GIDPNTGNTNYNQKFKG |
| 615 | 30A1C9 HVR-H3 | SGY |
| 616 | 30A1C9 HVR-L1 | RSSQSIVHSNGNTYLE |
| 617 | 30A1C9 HVR-L2 | KVSNRFS |
| 618 | 30A1C9 HVR-L3 | FQASHVPRT |
| 619 | 211G6-B6 Heavy Chain Variable Region | QVQLKESGPG LVAPSQSLSI TCTVSGFSLT SYAISWVRQP PGKGLEWLGV IWTGGGTNYN SALKSRLSIT KDNSKNQVFF RMNSLQTDDT ARYYCARKKL YDYDGGYFFD YWGQGTTLTV SS |

-continued

| Table of Sequences | | |
|---|---|---|
| SEQ ID NO | Description | Sequence |
| 620 | 211G6-B6 Light Chain Variable Region | DIVMSQSPSS LAMSVGEKVT MSCKSNQSLL YSSNQKNYLA WYQQKPGQSP KLLIYWASTR ESGVPDRFTG SGSGTDFTLT ISSVKAEDLA VYYCHQYYSY PWTFGGGTKL EIK |
| 621 | 211G6-B6 HVR-H1 | SYAIS |
| 622 | 211G6-B6 HVR-H2 | VIWTGGGTNYNSALKS |
| 623 | 211G6-B6 HVR-H3 | KKLYDYDGGYFFDY |
| 624 | 211G6-B6 HVR-L1 | KSNQSLLYSSNQKNYLA |
| 625 | 211G6-B6 HVR-L2 | WASTRES |
| 626 | 211G6-B6 HVR-L3 | HQYYSYPWT |
| 627 | 77D1-D2 Heavy Chain Variable Region | EVQLQQSVAE LVRPGASVTL SCTSSGFNIK NTYMHWVIQR PEQGLEWIGK IDPAIVNTKY APKFQGKATI TADTSSNTAY LQLSSLTSED TGIYYCAEGA LLYWGLGTSV TVSS |
| 628 | 77D1-D2 Light Chain Variable Region | DVVMTQTPLS LSVTIGQPAS ISCKSSQSLL HSNGKTYLNW LQQRPGQAPK LLMYLVSKVD PGIPDRFSGS GSETDFTLKI SRVEAEDLGV YYCFQGTYYP HTFGGGTKLE IK |
| 629 | 77D1-D2 HVR-H1 | NTYMH |
| 630 | 77D1-D2 HVR-H2 | KIDPAIVNTKYAPKFQG |
| 631 | 77D1-D2 HVR-H3 | GALLY |
| 632 | 77D1-D2 HVR-L1 | KSSQSLLHSNGKTYLN |
| 633 | 77D1-D2 HVR-L2 | LVSKVDP |
| 634 | 77D1-D2 HVR-L3 | FQGTYYPHT |
| 635 | 71H8-D6 and 83E10-D6 Heavy Chain Variable Region | EVQLQQSGAE LVRSGASVKL SCTASGFNIK DYYIQWVKQR PEQGLEWIGW IDPENGDTDY APKFQGKATM TADTSSNTAY LQFSSLTSED TAVYYCNRGW GYWGQGTTLT VSS |
| 636 | 71H8-D6 and 83E10-D6 Light Chain Variable Region | DVVMTQTPLT LPITLGQPAS ISCKSSQSLL HSDGKTYLSW LLQRPGQSPK RLIYLVSELD SGVPDRFTGS GSGTDFTLKI SRVEAEDLGL YYCWQGTHFP QTFGGGTKLE IK |
| 637 | 71H8-D6 and 83E10-D6 HVR-H1 | DYYIQ |
| 638 | 71H8-D6 and 83E10-D6 HVR-H2 | WIDPENGDTDYAPKFQG |
| 639 | 71H8-D6 and 83E10-D6 HVR-H3 | GWGY |
| 640 | 71H8-D6 and 83E10-D6 HVR-L1 | KSSQSLLHSDGKTYLS |
| 641 | 71H8-D6 and 83E10-D6 HVR-L2 | LVSELDS |
| 642 | 71H8-D6 and 83E10-D6 HVR-L3 | WQGTHFPQT |
| 643 | 307H3E8 Heavy Chain Variable Region | EVKFEESGGG LVQPGGSMKL SCVASGFTFS NYWMNWVRQS PEKGLEWVAQ IRLKSDNHAT HYAESVKGRF TISRDDSKST VYLQMNNLGA EDTGIYFCTE GGAYFDYWGQ GTTLTVSS |
| 644 | 307H3E8 Light Chain Variable Region | DVVMTQTPLS LPVSLGDQAS ISCRSSQNLV HSNGNTYFHW YLQKPGQSPK LLIYKVSNRF SGVPDRFSGS GSGTDFTLKI SRVEAEDLGV YVCSQSTHVP PTFGGGTKLE IK |
| 645 | 307H3E8 HVR-H1 | NYWMN |

| SEQ ID NO | Description | Sequence |
|---|---|---|
| 646 | 307H3E8 HVR-H2 | QIRLKSDNHATHYAESVKG |
| 647 | 307H3E8 HVR-H3 | GGAYFDY |
| 648 | 307H3E8 HVR-L1 | RSSQNLVHSNGNTYFH |
| 649 | 307H3E8 HVR-L2 | KVSNRFS |
| 650 | 307H3E8 HVR-L3 | SQSTHVPPT |
| 651 | 63H3-D8 Heavy Chain Variable Region | QIQLVQSGPE LKKPGETVKI SCKASGYTFT SHGMSWVKQA PGKGLKWMGW INTYSGVPTY ADDFKGRFAF SLETSASTAY LQINNLKNED TATYFCARSE LSWFAYWGQG TLVTVSA |
| 652 | 63H3-D8 Light Chain Variable Region | DIVMTQSPAT LSVTPGDRVS LSCRASQSIS DYLHWYQQKS HESPRLLIKY ASQSISGIPS RFSGSGSGSD FTLSINSVEP EDVGVYYCQN GHSFPYTFGG GTKLEIK |
| 653 | 63H3-D8 HVR-H1 | SHGMS |
| 654 | 63H3-D8 HVR-H2 | WINTYSGVPTYADDFKG |
| 655 | 63H3-D8 HVR-H3 | SELSWFAY |
| 656 | 63H3-D8 HVR-L1 | RASQSISDYLH |
| 657 | 63H3-D8 HVR-L2 | YASQSIS |
| 658 | 63H3-D8 HVR-L3 | QNGHSFPYT |
| 659 | 64B9-F12 Heavy Chain Variable Region (VH) | QIQLVQSGPELRKPGETVKISCKASGYTFTTYGMSWVKQAPGEGLK WMGWINTYSGMPTYADDFKGRFAFSLETSARTAYLQINNLKNEDTA TYFCARSELSWFAYWGQGTLVTVSA |
| 660 | 64B9-F12 Light Chain Variable Region (VL) | DIVMTQSPATLSVTPGDRVSLSCRASQSISDYLHWYQQKSHESPRL LIKYASQSISGIPSRFSGSGSGSDFTLSINSVEPEDVGVYYCQNGH NFPYTFGGGTKLEIK |
| 661 | 64B9-F12 HVR-H1 | TYGMS |
| 662 | 64B9-F12 HVR-H2 | WINTYSGMPTYADDFKG |
| 663 | 64B9-F12 HVR-H3 | SELSWFAY |
| 664 | 64B9-F12 HVR-L1 | RASQSISDYLH |
| 665 | 64B9-F12 HVR-L2 | YASQSIS |
| 666 | 64B9-F12 HVR-L3 | QNGHNFPYT |
| 667 | 72E12-H9 Heavy Chain Variable Region (VH) | EVKLEESGGGLVQPGGSMKLSCVASGFTFSNYWMNWVRQSPEKGL EWVAQI RLKSDNYATHYAESVKGRFTISRDDSKSSVYLQMNNLRAEDT-GIY YCAGYFYGGYFDVWGTGTTVTVSS |
| 668 | 72E12-H9 Light Chain Variable Region (VL) | ELVLTQSPTTMAASPGKKITITCSASSSISSNYLHWYQQKPGFSP KLLIYRTSNLASGVPARFSGSGSGTSYSLTIGTMEAEDVATYYCQ QGSSLPFTFGSGTKLEIK |
| 669 | 72E12-H9 HVR-H1 | NYWMN |
| 670 | 72E12-H9 HVR-H2 | QIRLKSDNYATHYAESVKG |
| 671 | 72E12-H9 HVR-H3 | YFYGGYFDV |
| 672 | 72E12-H9 HVR-L1 | SASSSISSNYLH |
| 673 | 72E12-H9 HVR-L2 | RTSNLAS |
| 674 | 72E12-H9 HVR-L3 | QQGSSLPFT |

Table of Sequences

| SEQ ID NO | Description | Sequence |
|---|---|---|
| 675 | 30D12-B5 Heavy Chain Variable Region (VH) | EVQLQQSGAELVKPGASVKLSCTTSGFNIKDTYMHWVKQRPEQGLE WIGGIDPANGNTKYDPKFQGKATITADTSSNTAYLQLSSLTSEDTA VYYCAHGNFVYWGQGTLVTVSA |
| 676 | 30D12-B5 Light Chain Variable Region (VL) | DVVMTQTPLSLSVTIGQPASISCKSSQSLLYSNGKTYLNWFQQRPG QAPKHLMYQVSKLDPGIPDRFSGSGSETDFTLKISRVEAEDLGVYY CLQGTYYPLTFGAGTNLELK |
| 677 | 30D12-B5 HVR-H1 | DTYMH |
| 678 | 30D12-B5 HVR-H2 | GIDPANGNTKYDPKFQG |
| 679 | 30D12-B5 HVR-H3 | GN |
| 680 | 30D12-B5 HVR-L1 | KSSQSLLYSNGKTYLN |
| 681 | 30D12-B5 HVR-L2 | QVSKLDP |
| 682 | 30D12-B5 HVR-L3 | LQGTYYPLT |
| 683 | 49G10-F4 Heavy Chain Variable Region (VH) | QVQLQQPGAELVQPGASVKLSCKASGYTFTNYWMQWIKQRPGQGLE WIGEIDPSDSYTNYNQNFKDKATLTVDTSSRTAYMQLSSLTSEDSA VYYCTRRWYI NSVRYFDVWGTGTTVTVSA |
| 684 | 49G10-F4 Light Chain Variable Region (VL) | DVLMTQTPLSLSASLGDQASISCRSSQSIVHSNGNIYLEWYLQKPG QSPKLLIYKVSNRFSGVSDRFSGSGSGTDFTLKISRVEAEDLGVYY CFQGAHVPFT FGAGTKLEIK |
| 685 | 49G10-F4 HVR-H1 | NYWMQ |
| 686 | 49G10-F4 HVR-H2 | EIDPSDSYTNYNQNFKD |
| 687 | 49G10-F4 HVR-H3 | RWYINSVRYFDV |
| 688 | 49G10-F4 HVR-L1 | RSSQSIVHSNGNIYLE |
| 689 | 49G10-F4 HVR-L2 | KVSNRFS |
| 690 | 49G10-F4 HVR-L3 | FQGAHVPFT |
| 691 | 65B1-A2 Heavy Chain Variable Region (VH) | QVQLKESGPGLVAPSQSLSITCTISGFSLTTYGVHWVRQPPGKGLE WLVVIWSDGSTTYNSALKSRLSISKDNSKSQVFLKMNSLQTDDTAM YYCARQGGFITTAYYAMDYWGQGTSVTVSS |
| 692 | 65B1-A2 Light Chain Variable Region (VL) | DIVMSQSPSSLAVSAGEKVTMSCKSSQSLLNSRTRKNYLAWYQQKP GQSPKLLIYWASTRESGVPDRFTGSGSGTDFTLTISSVQAEDLAVY YCKQSYNLYTFGGGTKLEIK |
| 693 | 65B1-A2 HVR-H1 | TYGVH |
| 694 | 65B1-A2 HVR-H2 | VIWSDGSTTYNSALKS |
| 695 | 65B1-A2 HVR-H3 | QGGFITTAYYAMDY |
| 696 | 65B1-A2 HVR-L1 | KSSQSLLNSRTRKNYLA |
| 697 | 65B1-A2 HVR-L2 | WASTRES |
| 698 | 65B1-A2 HVR-L3 | KQSYNLYT |

What is claimed is:

1. An isolated antibody that binds to human Tau, wherein the antibody comprises:
   a) HVR-H1 comprising the amino acid sequence of SEQ ID NO: 605; HVR-H2 comprising the amino acid sequence of SEQ ID NO: 606; HVR-H3 comprising the amino acid sequence of SEQ ID NO: 607; HVR-L1 comprising the amino acid sequence of SEQ ID NO: 608; HVR-L2 comprising the amino acid sequence of SEQ ID NO: 609; and HVR-L3 comprising the amino acid sequence of SEQ ID NO: 610;
   b) HVR-H1 comprising the amino acid sequence of SEQ ID NO: 613; HVR-H2 comprising the amino acid sequence of SEQ ID NO: 614; HVR-H3 comprising the amino acid sequence of SEQ ID NO: 615; HVR-L1 comprising the amino acid sequence of SEQ ID NO: 616; HVR-L2 comprising the amino acid sequence of SEQ ID NO: 617; and HVR-L3 comprising the amino acid sequence of SEQ ID NO: 618;
   c) HVR-H1 comprising the amino acid sequence of SEQ ID NO: 621; HVR-H2 comprising the amino acid sequence of SEQ ID NO: 622; HVR-H3 comprising the amino acid sequence of SEQ ID NO: 623; HVR-L1 comprising the amino acid sequence of SEQ ID NO: 624; HVR-L2 comprising the amino acid sequence of SEQ ID NO: 625; and HVR-L3 comprising the amino acid sequence of SEQ ID NO: 626;
   d) HVR-H1 comprising the amino acid sequence of SEQ ID NO: 629; HVR-H2 comprising the amino acid sequence of SEQ ID NO: 630; HVR-H3 comprising the amino acid sequence of SEQ ID NO: 631; HVR-L1 comprising the amino acid sequence of SEQ ID NO: 632; HVR-L2 comprising the amino acid sequence of SEQ ID NO: 633; and HVR-L3 comprising the amino acid sequence of SEQ ID NO: 634;
   e) HVR-H1 comprising the amino acid sequence of SEQ ID NO: 637; HVR-H2 comprising the amino acid sequence of SEQ ID NO: 638; HVR-H3 comprising the amino acid sequence of SEQ ID NO: 639; HVR-L1 comprising the amino acid sequence of SEQ ID NO: 640; HVR-L2 comprising the amino acid sequence of SEQ ID NO: 641; and HVR-L3 comprising the amino acid sequence of SEQ ID NO: 642;
   f) HVR-H1 comprising the amino acid sequence of SEQ ID NO: 645; HVR-H2 comprising the amino acid sequence of SEQ ID NO: 646; HVR-H3 comprising the amino acid sequence of SEQ ID NO: 647; HVR-L1 comprising the amino acid sequence of SEQ ID NO: 648; HVR-L2 comprising the amino acid sequence of SEQ ID NO: 649; and HVR-L3 comprising the amino acid sequence of SEQ ID NO: 650;
   g) HVR-H1 comprising the amino acid sequence of SEQ ID NO: 653; HVR-H2 comprising the amino acid sequence of SEQ ID NO: 654; HVR-H3 comprising the amino acid sequence of SEQ ID NO: 655; HVR-L1 comprising the amino acid sequence of SEQ ID NO: 656; HVR-L2 comprising the amino acid sequence of SEQ ID NO: 657; and HVR-L3 comprising the amino acid sequence of SEQ ID NO: 658;
   h) HVR-H1 comprising the amino acid sequence of SEQ ID NO: 661; HVR-H2 comprising the amino acid sequence of SEQ ID NO: 662; HVR-H3 comprising the amino acid sequence of SEQ ID NO: 663; HVR-L1 comprising the amino acid sequence of SEQ ID NO: 664; HVR-L2 comprising the amino acid sequence of SEQ ID NO: 665; and HVR-L3 comprising the amino acid sequence of SEQ ID NO: 666;
   i) HVR-H1 comprising the amino acid sequence of SEQ ID NO: 669; HVR-H2 comprising the amino acid sequence of SEQ ID NO: 670; HVR-H3 comprising the amino acid sequence of SEQ ID NO: 671; HVR-L1 comprising the amino acid sequence of SEQ ID NO: 672; HVR-L2 comprising the amino acid sequence of SEQ ID NO: 673; and HVR-L3 comprising the amino acid sequence of SEQ ID NO: 674;
   j) HVR-H1 comprising the amino acid sequence of SEQ ID NO: 677; HVR-H2 comprising the amino acid sequence of SEQ ID NO: 678; HVR-H3 comprising the amino acid sequence of SEQ ID NO: 679; HVR-L1 comprising the amino acid sequence of SEQ ID NO: 680; HVR-L2 comprising the amino acid sequence of SEQ ID NO: 681; and HVR-L3 comprising the amino acid sequence of SEQ ID NO: 682;
   k) HVR-H1 comprising the amino acid sequence of SEQ ID NO: 685; HVR-H2 comprising the amino acid sequence of SEQ ID NO: 686; HVR-H3 comprising the amino acid sequence of SEQ ID NO: 687; HVR-L1 comprising the amino acid sequence of SEQ ID NO: 688; HVR-L2 comprising the amino acid sequence of SEQ ID NO: 689; and HVR-L3 comprising the amino acid sequence of SEQ ID NO: 690; or
   l) HVR-H1 comprising the amino acid sequence of SEQ ID NO: 693; HVR-H2 comprising the amino acid sequence of SEQ ID NO: 694; HVR-H3 comprising the amino acid sequence of SEQ ID NO: 695; HVR-L1 comprising the amino acid sequence of SEQ ID NO: 696; HVR-L2 comprising the amino acid sequence of SEQ ID NO: 697; and HVR-L3 comprising the amino acid sequence of SEQ ID NO: 698.

2. The antibody of claim 1, wherein the antibody comprises:
   a) a heavy chain variable region (VH) comprising a sequence that is at least 95% identical to SEQ ID NO: 603;
   b) a light chain variable region (VL) comprising a sequence that is at least 95% identical to SEQ ID NO: 604;
   c) a VH as in (a) and a VL as in (b);
   d) a heavy chain variable region (VH) comprising a sequence that is at least 95% identical to SEQ ID NO: 611;
   e) a light chain variable region (VL) comprising a sequence that is at least 95% identical to SEQ ID NO: 612;
   f) a VH as in (d) and a VL as in (e);
   g) a heavy chain variable region (VH) comprising a sequence that is at least 95% identical to SEQ ID NO: 619;
   h) a light chain variable region (VL) comprising a sequence that is at least 95% identical to SEQ ID NO: 620;
   i) a VH as in (g) and a VL as in (h);
   j) a heavy chain variable region (VH) comprising a sequence that is at least 95% identical to SEQ ID NO: 627;
   k) a light chain variable region (VL) comprising a sequence that is at least 95% identical to SEQ ID NO: 628;
   l) a VH as in (j) and a VL as in (k);
   m) a heavy chain variable region (VH) comprising a sequence that is at least 95% identical to SEQ ID NO: 635;

n) a light chain variable region (VL) comprising a sequence that is at least 95% identical to SEQ ID NO: 636;
o) a VH as in (m) and a VL as in (n);
p) a heavy chain variable region (VH) comprising a sequence that is at least 95% identical to SEQ ID NO: 643;
q) a light chain variable region (VL) comprising a sequence that is at least 95% identical to SEQ ID NO: 644;
r) a VH as in (p) and a VL as in (q);
s) a heavy chain variable region (VH) comprising a sequence that is at least 95% identical to SEQ ID NO: 651;
t) a light chain variable region (VL) comprising a sequence that is at least 95% identical to SEQ ID NO: 652;
u) a VH as in (s) and a VL as in (t);
v) a heavy chain variable region (VH) comprising a sequence that is at least 95% identical to SEQ ID NO: 659;
w) a light chain variable region (VL) comprising a sequence that is at least 95% identical to SEQ ID NO: 660;
x) a VH as in (v) and a VL as in (w);
y) a heavy chain variable region (VH) comprising a sequence that is at least 95% identical to SEQ ID NO: 667;
z) a light chain variable region (VL) comprising a sequence that is at least 95% identical to SEQ ID NO: 668;
aa) a VH as in (y) and a VL as in (z);
bb) a heavy chain variable region (VH) comprising a sequence that is at least 95% identical to SEQ ID NO: 675;
cc) a light chain variable region (VL) comprising a sequence that is at least 95% identical to SEQ ID NO: 676;
dd) a VH as in (bb) and a VL as in (cc);
ee) a heavy chain variable region (VH) comprising a sequence that is at least 95% identical to SEQ ID NO: 683;
ff) a light chain variable region (VL) comprising a sequence that is at least 95% identical to SEQ ID NO: 684;
gg) a VH as in (ee) and a VL as in (ff);
hh) a heavy chain variable region (VH) comprising a sequence that is at least 95% identical to SEQ ID NO: 691;
ii) a light chain variable region (VL) comprising a sequence that is at least 95% identical to SEQ ID NO: 692; or
jj) a VH as in (hh) and a VL as in (ii).

3. The antibody of claim 1, wherein the antibody comprises:
a) a heavy chain variable region (VH) comprising the sequence of SEQ ID NO: 603;
b) a light chain variable region (VL) comprising the sequence of SEQ ID NO: 604;
c) a VH as in (a) and a VL as in (b);
d) a heavy chain variable region (VH) comprising the sequence of SEQ ID NO: 611;
e) a light chain variable region (VL) comprising the sequence of SEQ ID NO: 612;
f) a VH as in (d) and a VL as in (e);
g) a heavy chain variable region (VH) comprising the sequence of SEQ ID NO: 619;
h) a light chain variable region (VL) comprising the sequence of SEQ ID NO: 620;
i) a VH as in (g) and a VL as in (h);
j) a heavy chain variable region (VH) comprising the sequence of SEQ ID NO: 627;
k) a light chain variable region (VL) comprising the sequence of SEQ ID NO: 628;
l) a VH as in (j) and a VL as in (k);
m) a heavy chain variable region (VH) comprising the sequence of SEQ ID NO: 635;
n) a light chain variable region (VL) comprising the sequence of SEQ ID NO: 636;
o) a VH as in (m) and a VL as in (n);
p) a heavy chain variable region (VH) comprising the sequence of SEQ ID NO: 643;
q) a light chain variable region (VL) comprising the sequence of SEQ ID NO: 644;
r) a VH as in (p) and a VL as in (q);
s) a heavy chain variable region (VH) comprising the sequence of SEQ ID NO: 651;
t) a light chain variable region (VL) comprising the sequence of SEQ ID NO: 652;
u) a VH as in (s) and a VL as in (t);
v) a heavy chain variable region (VH) comprising the sequence of SEQ ID NO: 659;
w) a light chain variable region (VL) comprising the sequence of SEQ ID NO: 660;
x) a VH as in (v) and a VL as in (w);
y) a heavy chain variable region (VH) comprising the sequence of SEQ ID NO: 667;
z) a light chain variable region (VL) comprising the sequence of SEQ ID NO: 668;
aa) a VH as in (y) and a VL as in (z);
bb) a heavy chain variable region (VH) comprising the sequence of SEQ ID NO: 675;
cc) a light chain variable region (VL) comprising the sequence of SEQ ID NO: 676;
dd) a VH as in (bb) and a VL as in (cc);
ee) a heavy chain variable region (VH) comprising the sequence of SEQ ID NO: 683;
ff) a light chain variable region (VL) comprising the sequence of SEQ ID NO: 684;
gg) a VH as in (ee) and a VL as in (ff);
hh) a heavy chain variable region (VH) comprising the sequence of SEQ ID NO: 691;
ii) a light chain variable region (VL) comprising the sequence of SEQ ID NO: 692; or
jj) a VH as in (hh) and a VL as in (ii).

4. The isolated antibody of claim 1, wherein the antibody binds each of monomeric Tau, phosphorylated Tau, non-phosphorylated Tau, and oligomeric Tau with a $K_D$ of less than 400 nM, less than 100 nM, less than 75 nM, or less than 50 nM.

5. The isolated antibody of claim 1, which binds cynomolgus monkey Tau.

6. An isolated nucleic acid that encodes the antibody of claim 1.

7. An isolated host cell comprising the nucleic acid of claim 6.

8. A method of producing an antibody comprising culturing the host cell of claim 7 under conditions suitable for producing the antibody.

9. An immunoconjugate comprising the isolated antibody of claim 1 and a second therapeutic agent.

10. A labeled antibody comprising the antibody of claim 1 and a detectable label.

11. A method of detecting Tau, neurofibrillary tangles, neuropil threads, and/or dystrophic neurites in a sample, comprising contacting the sample with the antibody of claim 1.

12. The isolated antibody of claim 1, wherein the antibody binds to monomeric Tau, oligomeric Tau, non-phosphorylated Tau, and phosphorylated Tau.

13. The isolated antibody of claim 1, which is a monoclonal antibody.

14. The isolated antibody of claim 13, wherein the antibody is an IgG1 or an IgG4 antibody.

15. The isolated antibody of claim 1, which is a mouse, humanized, or chimeric antibody.

16. The isolated antibody of claim 1, which is an antibody fragment that binds human Tau.

17. The isolated antibody of claim 1, wherein the human Tau comprises the sequence of SEQ ID NO: 2.

18. A method of selecting a patient for treatment with a therapeutic anti-Tau antibody, comprising detecting Tau in a sample from the subject with a detection anti-Tau antibody, wherein the detection anti-Tau antibody is an antibody comprising:
   a) HVR-H1 comprising the amino acid sequence of SEQ ID NO: 605; HVR-H2 comprising the amino acid sequence of SEQ ID NO: 606; HVR-H3 comprising the amino acid sequence of SEQ ID NO: 607; HVR-L1 comprising the amino acid sequence of SEQ ID NO: 608; HVR-L2 comprising the amino acid sequence of SEQ ID NO: 609; and HVR-L3 comprising the amino acid sequence of SEQ ID NO: 610 ;
   b) HVR-H1 comprising the amino acid sequence of SEQ ID NO: 653; HVR-H2 comprising the amino acid sequence of SEQ ID NO: 654; HVR-H3 comprising the amino acid sequence of SEQ ID NO: 655; HVR-L1 comprising the amino acid sequence of SEQ ID NO: 656; HVR-L2 comprising the amino acid sequence of SEQ ID NO: 657; and HVR-L3 comprising the amino acid sequence of SEQ ID NO: 658;
   c) HVR-H1 comprising the amino acid sequence of SEQ ID NO: 661; HVR-H2 comprising the amino acid sequence of SEQ ID NO: 662; HVR-H3 comprising the amino acid sequence of SEQ ID NO: 663; HVR-L1 comprising the amino acid sequence of SEQ ID NO: 664; HVR-L2 comprising the amino acid sequence of SEQ ID NO: 665; and HVR-L3 comprising the amino acid sequence of SEQ ID NO: 666; or
   d) HVR-H1 comprising the amino acid sequence of SEQ ID NO: 669; HVR-H2 comprising the amino acid sequence of SEQ ID NO: 670; HVR-H3 comprising the amino acid sequence of SEQ ID NO: 671; HVR-L1 comprising the amino acid sequence of SEQ ID NO: 672; HVR-L2 comprising the amino acid sequence of SEQ ID NO: 673; and HVR-L3 comprising the amino acid sequence of SEQ ID NO: 674.

19. A method of monitoring treatment with a therapeutic anti-Tau antibody, comprising detecting Tau in a sample from a subject undergoing treatment with a detection anti-Tau antibody, wherein the detection anti-Tau antibody is an antibody comprising:
   a) HVR-H1 comprising the amino acid sequence of SEQ ID NO: 605; HVR-H2 comprising the amino acid sequence of SEQ ID NO: 606; HVR-H3 comprising the amino acid sequence of SEQ ID NO: 607; HVR-L1 comprising the amino acid sequence of SEQ ID NO: 608; HVR-L2 comprising the amino acid sequence of SEQ ID NO: 609; and HVR-L3 comprising the amino acid sequence of SEQ ID NO: 610;
   b) HVR-H1 comprising the amino acid sequence of SEQ ID NO: 653; HVR-H2 comprising the amino acid sequence of SEQ ID NO: 654; HVR-H3 comprising the amino acid sequence of SEQ ID NO: 655; HVR-L1 comprising the amino acid sequence of SEQ ID NO: 656; HVR-L2 comprising the amino acid sequence of SEQ ID NO: 657; and HVR-L3 comprising the amino acid sequence of SEQ ID NO: 658;
   c) HVR-H1 comprising the amino acid sequence of SEQ ID NO: 661; HVR-H2 comprising the amino acid sequence of SEQ ID NO: 662; HVR-H3 comprising the amino acid sequence of SEQ ID NO: 663; HVR-L1 comprising the amino acid sequence of SEQ ID NO: 664; HVR-L2 comprising the amino acid sequence of SEQ ID NO: 665; and HVR-L3 comprising the amino acid sequence of SEQ ID NO: 666; or
   d) HVR-H1 comprising the amino acid sequence of SEQ ID NO: 669; HVR-H2 comprising the amino acid sequence of SEQ ID NO: 670; HVR-H3 comprising the amino acid sequence of SEQ ID NO: 671; HVR-L1 comprising the amino acid sequence of SEQ ID NO: 672; HVR-L2 comprising the amino acid sequence of SEQ ID NO: 673; and HVR-L3 comprising the amino acid sequence of SEQ ID NO: 674.

20. A method of selecting a patient for treatment with a therapeutic anti-Tau antibody, comprising detecting Tau in a sample from the patient with a detection anti-Tau antibody, wherein the detection anti-Tau antibody is an antibody comprising:
   a) HVR-H1 comprising the amino acid sequence of SEQ ID NO: 613; HVR-H2 comprising the amino acid sequence of SEQ ID NO: 614; HVR-H3 comprising the amino acid sequence of SEQ ID NO: 615; HVR-L1 comprising the amino acid sequence of SEQ ID NO: 616; HVR-L2 comprising the amino acid sequence of SEQ ID NO: 617; and HVR-L3 comprising the amino acid sequence of SEQ ID NO: 618;
   b) HVR-H1 comprising the amino acid sequence of SEQ ID NO: 621; HVR-H2 comprising the amino acid sequence of SEQ ID NO: 622; HVR-H3 comprising the amino acid sequence of SEQ ID NO: 623; HVR-L1 comprising the amino acid sequence of SEQ ID NO: 624; HVR-L2 comprising the amino acid sequence of SEQ ID NO: 625; and HVR-L3 comprising the amino acid sequence of SEQ ID NO: 626;
   c) HVR-H1 comprising the amino acid sequence of SEQ ID NO: 629; HVR-H2 comprising the amino acid sequence of SEQ ID NO: 630; HVR-H3 comprising the amino acid sequence of SEQ ID NO: 631; HVR-L1 comprising the amino acid sequence of SEQ ID NO: 632; HVR-L2 comprising the amino acid sequence of SEQ ID NO: 633; and HVR-L3 comprising the amino acid sequence of SEQ ID NO: 634;
   d) HVR-H1 comprising the amino acid sequence of SEQ ID NO: 637; HVR-H2 comprising the amino acid sequence of SEQ ID NO: 638; HVR-H3 comprising the amino acid sequence of SEQ ID NO: 639; HVR-L1 comprising the amino acid sequence of SEQ ID NO: 640; HVR-L2 comprising the amino acid sequence of SEQ ID NO: 641; and HVR-L3 comprising the amino acid sequence of SEQ ID NO: 642; or
   e) HVR-H1 comprising the amino acid sequence of SEQ ID NO: 677; HVR-H2 comprising the amino acid sequence of SEQ ID NO: 678; HVR-H3 comprising the amino acid sequence of SEQ ID NO: 679; HVR-L1 comprising the amino acid sequence of SEQ ID NO: 680; HVR-L2 comprising the amino acid sequence of SEQ ID NO: 681; and HVR-L3 comprising the amino acid sequence of SEQ ID NO: 682.

21. A method of monitoring the progression of cognitive impairment in a subject with a tauopathy, comprising detecting Tau in a sample from the subject with a detection anti-Tau antibody, wherein the detection anti-Tau antibody is an antibody comprising:
  a) HVR-H1 comprising the amino acid sequence of SEQ ID NO: 613; HVR-H2 comprising the amino acid sequence of SEQ ID NO: 614; HVR-H3 comprising the amino acid sequence of SEQ ID NO: 615; HVR-L1 comprising the amino acid sequence of SEQ ID NO: 616; HVR-L2 comprising the amino acid sequence of SEQ ID NO: 617; and HVR-L3 comprising the amino acid sequence of SEQ ID NO: 618;
  b) HVR-H1 comprising the amino acid sequence of SEQ ID NO: 621; HVR-H2 comprising the amino acid sequence of SEQ ID NO: 622; HVR-H3 comprising the amino acid sequence of SEQ ID NO: 623; HVR-L1 comprising the amino acid sequence of SEQ ID NO: 624; HVR-L2 comprising the amino acid sequence of SEQ ID NO: 625; and HVR-L3 comprising the amino acid sequence of SEQ ID NO: 626;
  c) HVR-H1 comprising the amino acid sequence of SEQ ID NO: 629; HVR-H2 comprising the amino acid sequence of SEQ ID NO: 630; HVR-H3 comprising the amino acid sequence of SEQ ID NO: 631; HVR-L1 comprising the amino acid sequence of SEQ ID NO: 632; HVR-L2 comprising the amino acid sequence of SEQ ID NO: 633; and HVR-L3 comprising the amino acid sequence of SEQ ID NO: 634;
  d) HVR-H1 comprising the amino acid sequence of SEQ ID NO: 637; HVR-H2 comprising the amino acid sequence of SEQ ID NO: 638; HVR-H3 comprising the amino acid sequence of SEQ ID NO: 639; HVR-L1 comprising the amino acid sequence of SEQ ID NO: 640; HVR-L2 comprising the amino acid sequence of SEQ ID NO: 641; and HVR-L3 comprising the amino acid sequence of SEQ ID NO: 642; or
  e) HVR-H1 comprising the amino acid sequence of SEQ ID NO: 677; HVR-H2 comprising the amino acid sequence of SEQ ID NO: 678; HVR-H3 comprising the amino acid sequence of SEQ ID NO: 679; HVR-L1 comprising the amino acid sequence of SEQ ID NO: 680; HVR-L2 comprising the amino acid sequence of SEQ ID NO: 681; and HVR-L3 comprising the amino acid sequence of SEQ ID NO: 682.

22. A method of monitoring treatment with a therapeutic anti-Tau antibody, comprising detecting Tau in a sample from a subject undergoing treatment with a detection anti-Tau antibody, wherein the detection anti-Tau antibody is an antibody comprising:
  a) HVR-H1 comprising the amino acid sequence of SEQ ID NO: 613; HVR-H2 comprising the amino acid sequence of SEQ ID NO: 614; HVR-H3 comprising the amino acid sequence of SEQ ID NO: 615; HVR-L1 comprising the amino acid sequence of SEQ ID NO: 616; HVR-L2 comprising the amino acid sequence of SEQ ID NO: 617; and HVR-L3 comprising the amino acid sequence of SEQ ID NO: 618;
  b) HVR-H1 comprising the amino acid sequence of SEQ ID NO: 621; HVR-H2 comprising the amino acid sequence of SEQ ID NO: 622; HVR-H3 comprising the amino acid sequence of SEQ ID NO: 623; HVR-L1 comprising the amino acid sequence of SEQ ID NO: 624; HVR-L2 comprising the amino acid sequence of SEQ ID NO: 625; and HVR-L3 comprising the amino acid sequence of SEQ ID NO: 626;
  c) HVR-H1 comprising the amino acid sequence of SEQ ID NO: 629; HVR-H2 comprising the amino acid sequence of SEQ ID NO: 630; HVR-H3 comprising the amino acid sequence of SEQ ID NO: 631; HVR-L1 comprising the amino acid sequence of SEQ ID NO: 632; HVR-L2 comprising the amino acid sequence of SEQ ID NO: 633; and HVR-L3 comprising the amino acid sequence of SEQ ID NO: 634;
  d) HVR-H1 comprising the amino acid sequence of SEQ ID NO: 637; HVR-H2 comprising the amino acid sequence of SEQ ID NO: 638; HVR-H3 comprising the amino acid sequence of SEQ ID NO: 639; HVR-L1 comprising the amino acid sequence of SEQ ID NO: 640; HVR-L2 comprising the amino acid sequence of SEQ ID NO: 641; and HVR-L3 comprising the amino acid sequence of SEQ ID NO: 642; or
  e) HVR-H1 comprising the amino acid sequence of SEQ ID NO: 677; HVR-H2 comprising the amino acid sequence of SEQ ID NO: 678; HVR-H3 comprising the amino acid sequence of SEQ ID NO: 679; HVR-L1 comprising the amino acid sequence of SEQ ID NO: 680; HVR-L2 comprising the amino acid sequence of SEQ ID NO: 681; and HVR-L3 comprising the amino acid sequence of SEQ ID NO: 682.

* * * * *